(12) United States Patent
Joung et al.

(10) Patent No.: US 10,273,271 B2
(45) Date of Patent: Apr. 30, 2019

(54) METHODS OF TRANSCRIPTION ACTIVATOR LIKE EFFECTOR ASSEMBLY

(71) Applicant: The General Hospital Corporation, Boston, MA (US)

(72) Inventors: J. Keith Joung, Winchester, MA (US); Jeffry D. Sander, Ankeny, IA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/156,574

(22) Filed: May 17, 2016

(65) Prior Publication Data
US 2016/0318978 A1 Nov. 3, 2016

Related U.S. Application Data

(63) Continuation of application No. 14/232,067, filed as application No. PCT/US2012/046451 on Jul. 12, 2012, now abandoned.
(Continued)

(51) Int. Cl.
C12N 9/22 (2006.01)
C12N 15/10 (2006.01)
(Continued)

(52) U.S. Cl.
CPC ............. *C07K 14/195* (2013.01); *C12N 9/22* (2013.01); *C12N 15/1093* (2013.01);
(Continued)

(58) Field of Classification Search
None
See application file for complete search history.

(56) References Cited

U.S. PATENT DOCUMENTS

| 4,603,044 A | 7/1986 | Geho et al. |
| 4,797,368 A | 1/1989 | Carter et al. |

(Continued)

FOREIGN PATENT DOCUMENTS

| EP | 1941060 | 7/2008 |
| EP | 2206723 | 7/2010 |

(Continued)

OTHER PUBLICATIONS

Alvarez and Curiel, "A phase I study of recombinant adenovirus vector-mediated intraperitoneal delivery of herpes simplex virus thymidine kinase (HSV-TK) gene and intravenous ganciclovir for previously treated ovarian and extraovarian cancer patients," Hum. Gene Ther., Mar. 1997, 5:597-613.

(Continued)

*Primary Examiner* — Addison D Ault
(74) *Attorney, Agent, or Firm* — Fish & Richardson P.C.

(57) ABSTRACT

The disclosure describes methods that include providing a first nucleic acid having a sequence encoding a first set comprising one or more transcription activator-like effector (TALE) repeat domains and/or one or more portions of one or more TALE repeat domains; contacting the first nucleic acid with a first enzyme, wherein the first enzyme creates a first ligatable end; providing a second nucleic acid having a sequence encoding a second set comprising one or more TALE repeat domains and/or one or more portions of one or more TALE repeat domains; contacting the second nucleic acid with a second enzyme, wherein the second enzyme creates a second ligatable end, and wherein the first and second ligatable ends are compatible; and ligating the first and second nucleic acids through the first and second ligatable ends to produce a first ligated nucleic acid, wherein the first ligated nucleic acid is linked to a solid support, and (Continued)

wherein the first ligated nucleic acid encodes a polypeptide comprising said first and second sets.

14 Claims, 31 Drawing Sheets

Specification includes a Sequence Listing.

Related U.S. Application Data

(60) Provisional application No. 61/610,212, filed on Mar. 13, 2012, provisional application No. 61/601,409, filed on Feb. 21, 2012, provisional application No. 61/508,366, filed on Jul. 15, 2011.

(51) Int. Cl.

| | |
|---|---|
| C12N 15/66 | (2006.01) |
| C12P 19/34 | (2006.01) |
| C40B 40/08 | (2006.01) |
| C40B 50/06 | (2006.01) |
| C12P 21/02 | (2006.01) |
| C07K 14/195 | (2006.01) |
| C12Q 1/6806 | (2018.01) |

(52) U.S. Cl.
CPC ............ *C12N 15/66* (2013.01); *C12P 19/34* (2013.01); *C12P 21/02* (2013.01); *C12Y 301/00* (2013.01); *C40B 40/08* (2013.01); *C40B 50/06* (2013.01); *C07K 2319/00* (2013.01); *C07K 2319/24* (2013.01); *C07K 2319/41* (2013.01); *C07K 2319/43* (2013.01); *C07K 2319/80* (2013.01); *C12Q 1/6806* (2013.01)

(56) References Cited

U.S. PATENT DOCUMENTS

| | | | |
|---|---|---|---|
| 4,957,773 | A | 9/1990 | Spencer et al. |
| 6,007,988 | A | 12/1999 | Choo et al. |
| 6,013,453 | A | 1/2000 | Choo et al. |
| 6,453,242 | B1 | 9/2002 | Eisenberg et al. |
| 6,492,117 | B1 | 12/2002 | Choo et al. |
| 6,503,717 | B2 | 1/2003 | Case et al. |
| 6,511,808 | B2 | 1/2003 | Wolffe et al. |
| 6,534,261 | B1 | 3/2003 | Cox, III et al. |
| 7,001,768 | B2 | 2/2006 | Wolfe et al. |
| 7,220,719 | B2 | 5/2007 | Case |
| 7,741,086 | B2 | 6/2010 | Shi |
| 7,914,796 | B2 | 3/2011 | Miller |
| 8,034,598 | B2 | 10/2011 | Miller |
| 8,071,370 | B2 | 12/2011 | Wolffe |
| 8,771,986 | B2 | 7/2014 | Miller |
| 8,962,281 | B2 | 2/2015 | Doyon |
| 2002/0106680 | A1 | 8/2002 | Shinmyo |
| 2002/0119498 | A1 | 8/2002 | Joung et al. |
| 2002/0160940 | A1 | 10/2002 | Case et al. |
| 2002/0164575 | A1 | 11/2002 | Case et al. |
| 2003/0083283 | A1 | 5/2003 | Bennett et al. |
| 2006/0115850 | A1 | 6/2006 | Schatz |
| 2008/0131962 | A1 | 6/2008 | Miller |
| 2009/0133158 | A1 | 5/2009 | Lahaye et al. |
| 2010/0132069 | A1 | 5/2010 | Lahaye et al. |
| 2011/0059502 | A1 | 3/2011 | Chalasani |
| 2011/0112040 | A1 | 5/2011 | Liu et al. |
| 2011/0301073 | A1 | 12/2011 | Gregory et al. |
| 2012/0064620 | A1 | 3/2012 | Bonas |
| 2012/0100569 | A1 | 4/2012 | Liu et al. |
| 2013/0323220 | A1 | 12/2013 | Joung et al. |
| 2014/0274812 | A1 | 9/2014 | Joung et al. |
| 2015/0267176 | A1 | 9/2015 | Joung et al. |
| 2015/0376626 | A1 | 12/2015 | Joung et al. |
| 2016/0010076 | A1 | 1/2016 | Joung et al. |
| 2016/0024523 | A1 | 1/2016 | Joung et al. |

FOREIGN PATENT DOCUMENTS

| | | |
|---|---|---|
| JP | 2003-501069 | 1/2003 |
| JP | 2003-531616 | 10/2003 |
| JP | 2013-529083 | 7/2013 |
| JP | 2015-527889 | 9/2015 |
| WO | WO 1991/016024 | 10/1991 |
| WO | WO 1991/017424 | 11/1991 |
| WO | WO 9319202 | 9/1993 |
| WO | WO 1993/024641 | 12/1993 |
| WO | WO 9517413 | 6/1995 |
| WO | WO 9810095 | 3/1998 |
| WO | WO 9947536 | 9/1999 |
| WO | WO 00/75368 | 12/2000 |
| WO | WO 2001/019981 | 3/2001 |
| WO | WO 2001/053480 | 7/2001 |
| WO | WO 0183732 | 11/2001 |
| WO | WO 2002/057308 | 7/2002 |
| WO | WO 2002/099084 | 12/2002 |
| WO | 2004/099366 | 11/2004 |
| WO | 2006/071608 | 7/2006 |
| WO | WO 2007/128982 | 11/2007 |
| WO | WO 2009/134409 | 11/2009 |
| WO | WO 2010/037001 | 4/2010 |
| WO | WO 2010/079430 | 7/2010 |
| WO | WO 2011/017293 | 2/2011 |
| WO | WO 2011/019385 | 2/2011 |
| WO | WO 2011/072246 | 6/2011 |
| WO | WO 2011/146121 | 11/2011 |
| WO | WO 2012/138939 | 10/2012 |
| WO | WO 2013/012674 | 1/2013 |
| WO | WO 2013/017950 | 2/2013 |

OTHER PUBLICATIONS

Anders and Huber, "Differential expression analysis for sequence count data," Genome Biol., 11(10):R106, Epub Oct. 27, 2010.

Arimondo et al., "Exploring the Cellular Activity of Camptothecin—Triple—Helix-Forming Oligonucleotide Conjugates," Mol. Cell. Biol., 26(1):324-33 (2006).

Arnould et al., "Engineering of large numbers of highly specific homing endonucleases that induce recombination on novel DNA targets," J Mol Biol., 355(3):443-458, Epub Nov. 15, 2005.

Arnould et al., "The I-CreI meganuclease and its engineered derivatives: applications from cell modification to gene therapy," Protein Eng Des Sel., 24(1-2):27-31, Epub Nov. 3, 2010.

Arora et al., "Residues 1-254 of anthrax toxin lethal factor are sufficient to cause cellular uptake of fused polypeptides," J. Biol. Chem., Feb. 1993, 268:3334-41.

Australian Office Action in Australian Application No. 2012284365, dated Jul. 29, 2016, 5 pages.

Bae et al., "Human zinc fingers as building blocks in the construction of artificial transcription factors," Nat Biotechnol., 21(3):275-280, Epub Feb. 18, 2003.

Bannister et al., "Histone methylation: Dynamic or static?," Cell, Jun. 28, 2002, 109(7): 801-806.

Batt, C.A., Chapter 14. Genetic Engineering of Food Proteins in Food Proteins and Their Applications, Damodaran, S., Ed. CRC Press, Mar. 12, 1997, p. 425.

Beerli and Barbas, "Engineering polydactyl zinc-finger transcription factors," Nat Biotechnol., 20(2):135-141, Feb. 2002.

Bello et al., "Hypermethylation of the DNA repair gene MGMT: association with TP53 G:C to A:T transitions in a series of 469 nervous system tumors," Mutat. Res., Oct. 2004, 554:23-32.

Berg, "Proposed structure for the zinc-binding domains from transcription factor IIIA and related proteins," Proc Natl Acad Sci U S A., 85(1):99-102, Jan. 1988.

Bergmann et al., "Epigenetic engineering shows H3K4me2 is required for HJURP targeting and CENP-A assembly on a synthetic-chuman kinetochore." The EMBO Journal, Jan. 2011, 30: 328-340.

(56) References Cited

OTHER PUBLICATIONS

Biancotto et al., "Histone modification therapy of cancer," Adv Genet., 70:341-386, 2010.
Blaese et al., "T lymphocyte-directed gene therapy for ADA-SCID: initial trial results after 4 years," Science, Oct. 1995, 270(5235):475-480.
Blancafort et al., "Designing transcription factor architectures for drug discovery," Mol Pharmacol., 66(6):1361-1371, Epub Aug. 31, 2004.
Boch et al., "Xanthomonas AvrBs3 family-type III effectors: discovery and function," Annu Rev Phytopathol., 48:419-436, 2010.
Boch, "TALEs of genome targeting," Nat Biotechnol., 29(2):135-136, Feb. 2011.
Bogdanove & Voytas, "TAL Effectors: Customizable Proteins for DNA Targeting," Science, 333:1843-1846 (2011).
Doyle, Computational and experimental analysis of TAL effector-DNA binding [dissertation], Jan. 2013, Iowa State University, Ames, Iowa, 162 pages.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dreidax et al., "Low p14ARF expression in neuroblastoma cells is associated with repressed histone mark status, and enforced expression induces growth arrest and apoptosis," Hum Mol Genet., 22(9):1735-1745, May 1, 2013.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Eisenschmidt et al., "Developing a programmed restriction endonuclease for highly specific DNA cleavage," Nucleic Acids Res., 33(22):7039-47 (2005).
El-Andaloussi et al., "Cell-penetrating peptides: mechanisms and applications," Curr. Pharm. Des., 2005, 11:3597-3611.
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elliot and O'Hare, "Intercellular trafficking and protein delivery by a herpesvirus structural protein," Cell, 88(2):223-233, Jan. 24, 1997.
Elrod-Erickson et al., "High-resolution structures of variant Zif268-DNA complexes: implications for understanding zinc finger-DNA recognition," Structure, 6(4):451-464, Apr. 15, 1998.
Endoh et al., "Cellular siRNA delivery using TatU1A and photo-induced RNA interference," Methods Mol. Biol., 2010, 623:271-281.
Entry for CDKN2A, cyclin-dependent kinase inhibitor 2A [*Homo sapiens* (human)], Gene ID: 1029, updated on May 29, 2016, and printed from http:www.ncbi.nlm.nih.gov/gene/1029 as pp. 1/9-9/9 pm May 31, 2016.
Ernst, J. et al., "Mapping and analysis of chromatin state dynamics in nine human cell types," Nature, 2011, 473:43-49.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
European Office Action in European Application No. 13845212, dated May 18, 2016, 1 page.
Evans et al., Binding, Regeneration of Plants, Plant Protoplasts, pp. 21-73 (1985).
Evans et al., Protoplasts Isolation and Culture, Handbook of Plant Cell Culture, pp. 124-176 (1983).
Extended European Search Report in European Application No. 12814750.1, dated Jun. 30, 2015, 13 pages.
Extended European Search Report in European Application No. 13797024, dated Mar. 15, 2016, 9 pages.
Extended European Search Report in European Application No. 13845212, dated Apr. 29, 2016, 6 pages.
Externded European Search Report in European Application No. 14749683, dated Sep. 9, 2016, 7 pages.
Fahraeus et al., "Inhibition of pRb phosphorylation and cell-cycle progression by a 20-residue peptide derived from p16CDKN2/INK4A," Curr Biol., 6(1):84-91, Jan. 1, 1996.
Foley et al., "Targeted mutagenesis in zebrafish using customized zinc-finger nucleases", Nature Protocols, Nature Publishing Group, Jan. 2009, 4(12):1855-1868.
Fonfara et al., "Creating highly specific nucleases by fusion of active restriction endonucleases and catalytically inactive homing endonucleases," Nucleic Acids Res., 40(2):847-860, Epub Sep. 29, 2011.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Futaki, "Oligoarginine vectors for intracellular delivery: design and cellular-uptake mechanisms," Biopolymers, 2006, 84:241-249.
Gao et al., "Hypermethylation of the RASSF1A gene in gliomas," Clin. Chim. Acta., Nov. 2004, 349:173-9.
Garcia-Bustos et al., "Nuclear protein localization," Biochim Biophys Acta., 1071(1):83-101, Mar. 7, 1991.
Garg et al., "Engineering synthetic TAL effectors with orthogonal target sites," Nucleic Acids Res., 40(15):7584-7595, Epub May 11, 2012.
Gavin et al., "Dimethylated lysine 9 of histone 3 is elevated in schizophrenia and exhibits a divergent response to histone deacetylase inhibitors in lymphocyte cultures," J. Psychiatry Neurosci., May 2009, 34(3):232-7.
Geibler et al., "Transcriptional Activators of Human Genes with Programmable DNA-Specificity ," PLoS One, 6:e19509 (2011).
GenBank Accession No. NM_001009999.2, "*Homo sapiens* lysine (K)-specific demethylase 1A (KDM1A), transcript variant 1, mRNA," Apr. 6, 2014, 6 pages.
GenBank Accession No. NP_055828.2, "Lysine-specific histone demethylase 1A isoform b [*Homo sapiens*]," Apr. 6, 2014, 4 pages.
GenBank Accesssion No. NM_015013.3, "*Homo sapiens* lysine (K)-specific demethylase 1A (KDM1A), transcript variant 2, mRNA," Apr. 6, 2014, 6 pages.
Gillies et al., "A tissue-specific transcription enhancer element is located in the major intron of a rearranged immunoglobulin heavy chain gene," Cell, 33(3):717-728, Jul. 1983.
Gong and Zhu, "Active DNA demethylation by oxidation and repair," Cell Research, 2011, 21:1649-1651.
Gossen and Bujard, "Tight control of gene expression in mammalian cells by tetracycline-responsive promoters," Proc Natl Acad Sci U S A., 89(12):5547-5551, Jun. 15, 1992.
Graef et al., "Proximity and orientation underlie signaling by the non-receptor tyrosine kinase ZAP70," Embo. J., 1997, 16(18):5618-5628.
Huang Shi, "Histone methyltransferases, diet nutrients and tumour suppressors," Nature Reviews. Cancer, Jun. 2002, 2(6): 469-7-476.
Humphrey et al., "Stable histone deacetylase complexes distinguished by the presence of SANT domain proteins CoREST/kiaa0071 and Mta-L1," Journal of Biological Chemistry, Mar. 2, 2001, 276(9): 6817-6824.
Inaba et al., "Generation of large numbers of dendritic cells from mouse bone marrow cultures supplemented with granulocyte/macrophage colony-stimulating factor," J Exp Med., 176(6):1693-1702, Dec. 1, 1992.
International Preliminary Report on Patentability in International Application No. PCT/US2013/043075, dated Dec. 2, 2014, 7 pages.
International Preliminary Report on Patentability in International Application No. PCT/US2014/015343, dated Aug. 20, 2015, 7 pages.
International Preliminary Report on Patentability in International Application No. PCT/US2013/064511, dated Apr. 23, 2015, 12 pages.

(56) References Cited

OTHER PUBLICATIONS

International Search Report and Written Opinion in International Application No. PCT/US2013/043075, dated Sep. 26, 2013, 10 pages.
International Search Report and Written Opinion in International Application No. PCT/US2014/015343, dated Jun. 3, 2014, 17 pages.
International Search Report and Written Opinion in International Application No. PCT/US2013/064511, dated Jan. 30, 2014, 8 pages.
Isalan et al., "A rapid, generally applicable method to engineer zinc fingers illustrated by targeting the HIV-1 promoter," Nat. Biotechnol., 19(7):656-660, Jul. 2001.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 2009, 8(11):1698-1710.
Jamieson et al., "In vitro selection of zinc fingers with altered DNA-binding specificity," Biochemistry, 33(19):5689-5695, May 17, 1994.
Japanese Office Action in Japanese Application No. 2014-520317, dated Apr. 5, 2016, 8 pages.
Jinek et al., "A programmable dual-RNA-guided DNA endonuclease in adaptive bacterial immunity," Science, 337(6096):816-821, Epub Jun. 28, 2012.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases"," Nat. Methods, Jan. 2010, 7:91-92.
Juillerat et al., "Comprehensive analysis of the specificity of transcription activator-like effector nucleases," Nucleic Acids Res., 42(8):5390-5402, Epub Feb. 24, 2014.
Jumlongras et al., "An evolutionarily conserved enhancer regulates Bmp4 expression in developing incisor and limb bud," PLoS One, 7(6):e38568, Epub Jun. 12, 2012.
Karmirantzou and Harnodrakas, "A Web-based classification system of DNA-binding protein families," Protein Eng. 14(7):465-472, Jul. 2001.
Sharma, "Schizophrenia, epigenetics and ligand-activated nuclear receptors: a framework for chromatin therapeutics," Schizophr. Res., Jan. 2005, 72:79-90.
Shi et al., "Histone demethylation mediated by the nuclear amine oxidase homolog LSD1," Cell, 119(7):941-953, Dec. 29, 2004.
Shi et al., "Metabolic enzymes and coenzymes in transcription—a direct link between metabolism and transcription?," Trends in Genetics: TIG, Sep. 20104, 20(9): 445-452.
Silva et al., "Meganucleases and other tools for targeted genome engineering: perspectives and challenges for gene therapy," Curr Gene Ther., 11(1):Feb. 11-27, 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Sipione et al., "Insulin expressing cells from differentiated embryonic stem cells are not beta cells," Diabetologia, 47(3):499-508. Epub Feb. 14, 2004.
Skinner et al., "Use of the Glu-Glu-Phe C-terminal epitope for rapid purification of the catalytic domain of normal and mutant ras GTPase-activating proteins," J. Biol. Chem., 1991, 266:14163-14166.
Stadler et al., "DNA-binding factors shape the mouse methylome at distal regulatory regions," Nature, 480(7378):490-495, Dec. 14, 2011.
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Stoddard, "Homing endonuclease structure and function," Q. Rev. Biophys., 38(1): 49-95, Epub Dec. 9, 2005.
Stott et al., "The alternative product from the human CDKN2A locus, p14(ARF), participates in a regulatory feedback loop with p53 and MDM2," EMBO J., 17(17):5001-5014, Sep. 1, 1998.
Streubel et al., "TAL effector RVD specificities and efficiencies," Nat Biotechnol., 30(7):593-595, Jul. 10, 2012.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA By MLL Partner TET1," Science, 324:930-935 (2009).
Tan et al., "Zinc-finger protein-targeted gene regulation: genomewide single-gene specificity," Proc Natl Acad Sci U S A., 100(21):11997-2002, Epub Sep. 26, 2003.
Tesson et al., "Knockout rats generated by embryo microinjection of TALENs," Nat. Biotechnol., 29:695-696 (2011).
Thiesen et al., "Conserved KRAB protein domain identified upstream from the zinc finger region of Kox 8," Nucleic Acids Res., 1991, 19:3996.
Thompson et al., "Engineering and Identifying Supercharged Proteins for Macromolecule Delivery into Mammalian Cells," Methods in Enzymology, 2012, 503:293-319.
Thurman et al., "The accessible chromatin landscape of the human genome," Nature, 489(7414):75-82, Sep. 6, 2012.
Tjong and Zhou, "DISPLAR: an accurate method for predicting DNA-binding sites on protein surfaces," Nucleic Acids Res., 35(5):1465-1477, Epub Feb. 6, 2007.
Topf et al., "Regional 'pro-drug' gene therapy: intravenous administration of an adenoviral vector expressing the *E. coli* cytosine deaminase gene and systemic administration of 5-fluorocytosine suppresses growth of hepatic metastasis of colon carcinoma," Gene Ther., Apr. 1998, 5:507-513.
Townsend et al., "High-frequency modification of plant genes using engineered zinc-finger nucleases," Nature: International Weekly Journal of Science, Nature Publishing Group, May 21, 2009, pp. 442-445.
Tratschin et al., "A human parvovirus, adeno-associated virus, as a eucalyotic vector: transient expression and encapsidation of the procaryotic gene for chloramphenicol acetyltransferase," Mol. Cell. Biol., Oct. 1984, 4:2072-81.
Tratschin et al., "Adeno-Associated Virus Vector for High-Frequency Integration, Expression, and Rescue of Genes in Mammalian Cells," Mol. Cell. Biol., Nov. 1985, 5:3251-60.
Tremblay et al., "Transcription activator-like effector proteins induce the expression of the frataxin gene," Hum Gene Ther., 23(8):883-890, Epub Jul. 20, 2012.
Uhlman, "An alternative approach in gene synthesis: use of long selpriming oligodeoxynucleotides for the construction of double-stranded DNA," Gene, Nov. 15, 1988, 71(15): 29-40.
Uhlmann et al., "Distinct methylation profiles of glioma subtypes," Int. J. Cancer, Aug. 2003, 106:52-9.
U.S. Final Office Action in U.S. Appl. No. 13/838,520, dated Jul. 15, 2015, 35 pages.
U.S. Non-Final Office Action in U.S. Appl. No. 13/838,520, dated Oct. 6, 2014, 38 pages.
U.S. Non-Final Office Action in U.S. Appl. No. 14/232,067, dated Nov. 17, 2015, 10 pages.
Valton et al., "Overcoming transcription activator-like effector (TALE) DNA binding domain sensitivity to cytosine methylation," J Biol Chem., 287(46):38427-38432, Epub Sep. 26, 2012.
Visel et al., "Genomic views of distant-acting enhancers," Nature, 461(7261):199-205, Sep. 10, 2009.
Vogelstein and Kinzler, "Cancer genes and the pathways they control," Nat. Med., Aug. 2004, 10:789-799.
Voytas and Joung, "Plant Science. DNA binding made easy," Science, Dec. 11, 2009, 326: 1491-1492.
Wagner et al., "Efficient and persistent gene transfer of AAV-CFTR in maxillary sinus," Lancet, Jun. 1998, 351:1702-1703.

(56) References Cited

OTHER PUBLICATIONS

Wang et al., "An integrated chip for the high-throughput synthesis of transcription activator-like effectors," Angew Chem Int Ed Engl., 51(34):8505-8508, Epub Jul. 23, 2012.
Wang et al., "Human PADA4 regulates histone arginine methylation levels via demethylimination," Science, Oct. 8, 2004, 306(5694): 279-283.
Wang et al., "pH-sensitive immunoliposomes mediate target-cell-specific delivery and controlled expression of a foreign gene in mouse," PNAS, Nov. 1987, 84:7851-7855.
Wang et al., "Positive and negative regulation of gene expression in eukaryotic cells with an inducible transcriptional regulator," Gene Ther., 4(5):432-441, May 1997.
Weising et al., "Foreign Genes in Plants: Transfer, Structure, Expression, and Applications," Ann. Rev. Genet., 1988, 22:421-477.
Welsh et al., "Adenovirus-mediated gene transfer for cystic fibrosis: Part A. Safety of dose and repeat administration in the nasal epithelium. Part B. Clinical efficacy in the maxillary sinus," Hum. Gene Ther., Feb. 1995, 6(2):205-218.
Whyte et al., "Enhancer decommissioning by LSD1 during embryonic stem cell differentiation," Nature, 482(7384):221-225, Feb. 1, 2012.
Widschwendter and Jones, "DNA methylation and breast carcinogenesis," Oncogene, Aug. 2002, 21:5462-82.
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wu et al., "Building zinc fingers by selection: toward a therapeutic application," Proc Natl Acad Sci U S A., 92(2):344-348, Jan. 17, 1995.
Wu et al., "Custom-designed zinc finger nucleases: what is next?" Cell Mol Life Sci., 64(22):2933-2944, Nov. 2007.
Wu, "The 5' ends of *Drosophila* heat shock genes in chromatin are hypersensitive to DNase I," Nature, 286(5776):854-860, Aug. 28, 1980.
Xie et al., "DNA hypomethylation within specific transposable element families associates with tissue-specific enhancer landscape," Nat Genet., 45(7):836-841, Epub May 26, 2013.
Xu et al., "Pioneer factor interactions and unmethylated CpG dinucleotides mark silent tissue-specific enhancers in embryonic stem cells," Proc Natl Acad Sci U S A., 104(30):12377-12382, Epub Jul. 18, 2007.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yoon and Brem, "Noncanonical transcript forms in yeast and their regulation during environmental stress," RNA, 16(6):1256-1267, Epub Apr. 26, 2010.
Yost et al., "Targets in epigenetics: inhibiting the methyl writers of the histone code," Curr Chem Genomics, 5(Suppl 1):72-84, Epub Aug. 22, 2011.
Zhang et al., "Efficient construction of sequence-specific TAL effectors for modulating mammalian transcription," Nat Biotechnol., 29(2):149-153, Epub Jan. 19, 2011.
Zhang et al., "Genome-wide identification of regulatory DNA elements and protein-binding footprints using signatures of open chromatin in *Arabidopsis*," Plant Cell., 24(7):2719-2731. Epub. Jul. 5, 2012.
Zhang et al., "Programmable Sequence-Specific Transcriptional Regulation of mammilian Genome Using Designer TAL Effectors," Nature Biotechnology, Feb. 2011, 29(2): 149-153.
Zhang et al., "Supplementary Information, Data S1, TET1 is a 5mC hydroxylase in vitro" from, "TET1 is a DNA-binding protein that modulates DNA methylation and gene transcription via hydroxylation of 5-methylcytosine," Cell Res., 6 pages, 2010.
Zhang et al., "Transcription activator-like effector nucleases enable efficient plant genome engineering," Plant Physiol., 161(1):20-27, Epub Nov. 2, 2012.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zheng S et al., "Correlations of partial and extensive methylation at the P14ARF locus with reduced MRNA expression in colorectal cancer cell lines and clinicopathological features in primary tumors," Carcinogenesis, Nov. 1, 2000, 21(11): 2057-2064.
Zitzewitz et al., "Probing the folding mechanism of a leucine zipper peptide by stopped-flA4:A48ism spectroscopy," Biochemistry, 34(39):12812-12819, Oct. 3, 1995.
Australian Office Action in Australian Application No. 2012284365, dated Jul. 29, 2016.
Bogdanove et al., "TAL effectors: finding plant genes for disease and defense," Curr. Opin. Plant Biol., 13:394-401 (2010).
Bonas et al., "Genetic and Structural Characterization of the Avirulence Gene AVR-BS3 From Xanthomonas-Campestris Pathovar Vesicatoria," Molecular and General Genetics, Jul. 1989, 218(1): 127-136.
Boyle et al., "High-resolution mapping and characterization of open chromatin across the genome," Cell., 132(2):311-322, Jan. 25, 2008.
Bulger and Groudine, "Functional and mechanistic diversity of distal transcription enhancers," Cell., 144(3):327-339, Feb. 4, 2011.
Bultmann et al., "Targeted transcriptional activation of silent oct4 pluripotency gene by combining designer TALEs and inhibition of epigenetic modifiers," Nucleic Acids Res., 40(12):5368-77. Epub Mar. 2, 2012.
Burnett et al., "Conditional macrophage ablation in transgenic mice expressing a Fas-based suicide gene," J. Leukoc. Biol., Apr. 2004, 75(4):612-623.
Calo and Wysocka, "Modification of enhancer chromatin: what, how, and why?" Mol Cell., Mar. 2013, 49(5):825-837.
Carbonetti et al., "Use of pertussis toxin vaccine molecule PT19K/129G to deliver peptide epitopes for stimulation of a cytotoxic T lymphocyte response," Abstr. Annu Meet. Am. Soc. Microbiol., 1995, 95:295.
Carey et al., "A mechanism for synergistic activation of a mammalian gene by GAL4 derivatives," Nature, 345(6273):361-364, May 24, 1990.
Caron et al., "Intracellular Delivery of a Tat-eGFP Fusion Protein into Muscle Cells," Mol Ther., Mar. 2001, 3:310-318.
Carroll et al., "Design, construction and in vitro testing of zinc finger nucleases," Nat Protoc., 1(3):1329-1341, 2006.
Carroll, "Progress and prospects: zinc-finger nucleases as gene therapy agents," Gene Ther., 15(22):1463-1468, Epub Sep. 11, 2008.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol Ther., 16(7):1200-1207, Epub Jun. 10, 2008.
Chaikind et al., "Targeted DNA Methylation Using an Artificially Bisected M.HhaI Fused to Zinc Fingers," PLoS ONE, 7(9):E44852 pp. 1-11 (2012).
Chase et al., "Histone methylation at H3K9: evidence for a restrictive epigenome in schizophrenia," Schizophr Res., 149(1-3):15-20, Epub Jun. 28, 2013.
Chen et al., "Crystal structure of human histone lysine-specific demethylase 1 (LSD1)," Proc Natl Acad Sci U S A., 103(38):13956-13961, Epub Sep. 6, 2006.
Chen et al., "Fusion protein linkers: property, design and functionality," Adv Drug Deliv Rev., 65(10):1357-1369, [author manuscript] Epub Sep. 29, 2012.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Chim et al., "Methylation profiling in multiple myeloma," Leuk. Res., Apr. 2004, 28:379-85.
Choo and Klug, "Toward a code for the interactions of zinc fingers with DNA: selection of randomized fingers displayed on phage," Proc Natl Acad Sci U S A., 91(23):11163-11167, Nov. 8, 1994.
Chylinski et al., "The tracrRNA and Cas9 families of type II CRISPR-Cas immunity systems," RNA Biol., 10(5):726-737, Epub Apr. 5, 2013.

(56) References Cited

OTHER PUBLICATIONS

Coffman et al., "Improved renal function in mouse kidney allografts lacking MHC class I antigens," J. Immunol., Jul. 1993, 151:425-35.
Cong et al., "Comprehensive interrogation of natural TALE DNA-binding modules and transcriptional repressor domains," Nat Commun., 3:968, [author manuscript] Jul. 24, 2012.
Cong et al., "Multiplex genome engineering using CRISPR/Cas systems," Science, 339(6121):819-823, Epub Jan. 3, 2013.
Consortium, The ENCODE Project, "An integrated encyclopedia of DNA elements in the human genome," Nature, Sep. 2012, 488:57-74.
Copeland et al., "Targeting genetic alterations in protein methyltransferases for personalized cancer therapeutics," Oncogene., 32(8):939-946, Epub Nov. 19, 2012.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Creyghton et al., "Histone H3K27ac separates active from poised enhancers and predicts developmental state," Proc Natl Acad Sci U S A., 107(50):21931-21936, Epub Nov. 24, 2010.
Cronican et al., "A Class of Human Proteins that Deliver Functional Proteins into Mammalian Cells In Vitro and In Vivo," Chem Biol., Jul. 2011, 18:833-838.
Cronican et al., "Potent Delivery of Functional Proteins into Mammalian Cells in Vitro and in Vivo Using a Supercharged Protein," ACS Chem. Biol., 2010, 5:747.
d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
De Zhu, "The altered DNA methylation pattern and its implications in liver cancer," Cell. Res., 2005, 15:272-80.
Derossi et al., "The Third Helix of the Antennapedia Homeodomain Translocates through Biological Membranes," J. Biol. Chem., Apr. 1994, 269:10444.
Deshayes et al., "Cell-penetrating peptides: tools for intracellular delivery of therapeutics," Cell. Mol. Life Sci., Aug. 2005, 62:1839-49.
Dhami et al., "Genomic approaches uncover increasing complexities in the regulatory landscape at the human SCL (TAL1) locus," PLoS One, 5(2):e9059, Feb. 5, 2010.
Donnelly et al., "Targeted delivery of peptide epitopes to class I major histocompatibility molecules by a modified Pseudomonas exotoxin," PNAS, Apr. 1993, 90:3530-34.
Doyle et al., "TAL Effector-Nucleotide Targeter (TALE-NT) 2.0: tools for TAL effector design and target prediction," Nucleic Acids Res., 40(Web Server issue):W117-W122, Epub Jun. 12, 2012.
European Office Action in European Application No. 13845212, dated May 18, 2016, 2 pages.
Extended European Search Report in European Application No. 12814750.1, dated Jun. 30, 2015, 6 pages.
Extended European Search Report in European Application No. 13797024, dated Mar. 15, 2016, 6 pages.
Extended European Search Report in European Application No. 13845212, dated Apr. 29, 2016, 7 pages.
Externded European Search Report in European Application No. 14749683, dated Sep. 9, 2016.
Gregory et al., "Selective DNA demethylation by fusion of TOG with a sequence-specific DNA-binding domain", EPIGENETICS, Apr. 2012, 7(4):344-349.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Gruen et al., "An in vivo selection system for homing endonuclease activity," Nucleic Acids Res., 30(7):e29, Apr. 1, 2002.
Guo et el., "Hydroxylation of 5-Methylcytosine by TET1 Promotes Active DNA Demethylation in the Adult Brain ," Cell, 145:423-434 (2011).
Hakimi et al., "A core-BRAF35 complex containing histone deacetylase mediates repression of neuronal-specific genes," Proceedings of the National Academy of Sciences of the United States of America, May 28, 2002, 99(11): 7420-7425.
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
He et al., "Tet-Mediated Formation of 5-Carboxylcytosine and Its Excision by TDG in Mammalian DNA," Science, 333:1303-1307 (2011).
Heintzman et al., "Histone modifications at human enhancers reflect global cell-type-specific gene expression," Nature, 459(7243):108-112, Epub Mar. 18, 2009.
Heppard et al., "Developmental and Growth Temperature Regulation of Two Different Microsomal [omega]-6 Desaturase Genes in Soybeans," Plant Physiol., 1996, 110:311-319.
Hermonat & Muzyczka, "Use of adeno-associated virus as a mammalian DNA cloning vector: Transduction of neomycin resistance into mammalian tissue culture cells," PNAS, Oct. 1984, 81:6466-70.
Hockemeyer et al., "Genetic engineering of human pluripotent cells using TALE nucleases," Nat. Biotechnol., 29:731-734 (2011).
Hoivik et al., "DNA methylation of intronic enhancers directs tissue-specific expression of steroidogenic factor 1/adrenal 4 binding protein (SF-1/Ad4BP)," Endocrinology, 152(5):2100-2112, Epub Feb. 22, 2011.
Hopp et al., "A Short Polypeptide Marker Sequence Useful for Recombinant Protein Identification and Purification," BioTechnology, Oct. 1988, 6:1204-10.
Hsu and Zhang, "Dissecting neural function using targeted genome engineering technologies," ACS Chem Neurosci., 3(8):603-610, Epub Jul. 19, 2012.
Huang et al., "Heritable gene targeting in zebrafish using customized TALENs," Nat. Biotechnol., 29:699-700 (2011).
Japanese Office Action in Japanese Application No. 2014-520317, dated Apr. 5, 2016.
Kearns et al., "Recombinant adeno-associated virus (AAV-CFTR) vectors do not integrate in a site-specific fashion in an immortalized epithelial cell line," Gene Ther., Sep. 1996, 9:748-55.
Kim et al., "Targeted genome editing in human cells with zinc finger nucleases constructed via modular assembly," Genome Res., 19(7):1279-1288, Epub May 21, 2009.
Kim et al., "Genome editing with modularly assembled zinc-finger nucleases," Nat. Methods, 7(2):91-92, Feb. 2010.
Klee et al., "Agrobacterium-Mediated Plant Transformation and its Further Applications to Plant Biology," Ann. Rev. Plant Phys., Jun. 1987, 38:467-486.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Ko et al., "Impaired hydroxylation of 5-methylcytosine in myeloid cancers with mutant TET2," Nature, Dec. 2010, 468(7325):839-843.
Kohn et al., "Engraftment of gene-modified umbilical cord blood cells in neonates with adenosine deaminase deficiency," Nat. Med., 1995, 1:1017-1023.
Koller et al., "Normal development of mice deficient in beta 2M, MHC class I proteins, and CD8+ T cells," Science, Jun. 1990, 248:1227-30.

(56) References Cited

OTHER PUBLICATIONS

Ku et al., "Genomewide analysis of PRC1 and PRC2 occupancy identifies two classes of bivalent domains," PLoS Genet., 4(10):e1000242, Epub Oct. 31, 2008.
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lawrence et al., "Supercharging Proteins Can Impart Unusual Resilience," J. Am. Chem. Soc., 2007, 129:10110-10112.
Lea et al., "Aberrant p16 methylation is a biomarker for tobacco exposure in cervical squamous cell carcinogenesis," Am. J. Obstet. Gynecol., 2004, 190:674-9.
Lee et al., "An essential role for CoREST in nucleosomal histone 3 lysine 4 demethylation," Nature, 437(7057):432-435, Epub Aug. 3, 2005.
Lee et al., "Three-dimensional solution structure of a single zinc finger DNA-binding domain," Science., 245(4918):635-637, Aug. 11, 1989.
Li et al., "DNA methylation in prostate cancer," Biochim. Biophys. Acta., Sep. 2004, 1704:87-102.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Transcription activator-like effector hybrids for conditional control and rewiring of chromosomal transgene expression," Sci Rep., 2:897, Epub Nov. 28, 2012.
Li et al., "TAL nucleases (TALNs): hybrid proteins composed of TAL effectors and FokI DNA-cleavage domain," Nucl Acids Res, 39:359-372 (2011).
Lin et al., "iDNA-Prot: identification of DNA binding proteins using random forest with grey model," PLoS One., 6(9):e24756, Epub Sep. 15, 2011.
Lin et al., "Inhibition of Nuclear Translocation of Transcription Factor NF-κB by a Synthetic Peptide Containing a Cell Membrane-permeable Motif and Nuclear Localization Sequence," J. Biol. Chem., 1995, 270:14255-58.
Lippow et al., "Creation of a type IIS restriction endonuclease with a long recognition sequence," Nucleic Acids Res., 37(9):3061-3073, May 2009.
Liu et al., "Regulation of an endogenous locus using a panel of designed zinc finger proteins targeted to accessible chromatin regions. Activation of vascular endothelial growth factor A," J Biol Chem., 276(14):11323-11334, Epub Jan. 5, 2001.
Liu et al., "Validated zinc finger protein designs for all 16 GNN DNA triplet targets," J. Biol. Chem., 277(6):3850-3856, Epub Nov. 28, 2001.
Loenarz and Schofield, Oxygenase Catalyzed 5-Methylcytosine Hydroxylation, Chemistry & Biology, Jun. 2009, 16:580-583.
Lund et al., "DNA Methylation Polymorphisms Precede Any Histological Sign of Atherosclerosis in Mice Lacking Apolipoprotein E," J. Biol. Chem., Jul. 2004, 279:29147-54.
Lutz-Freyerinuth et al., "Quantitative determination that one of two potential RNA-binding domains of the A protein component of the U1 small nuclear ribonucleoprotein complex binds with high affinity to stem-loop II of U1 RNA," PNAS, Aug. 1990, 87:6393-97.
Mabaera et al., "Developmental- and differentiation-specific patterns of human γ- and β-globin promoter DNA methylation," Blood, 110(4):1343-52 (2007).

Madrigal and Krajewski, "Current bioinformatic approaches to identify DNase I hypersensitive sites and genomic footprints from DNase-seq data," Front Genet., 3:230, eCollection 2012, Oct. 31, 2012.
Maeder et al., "Robust, synergistic regulation of human gene expression using TALE activators,"Nat Methods., 10(3):243-245, Epub Feb. 10, 2013.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "Targeted transcriptional repression using a chimeric TALE-SRDX repressor protein," Plant Mol Biol., 78(3):311-321, Epub Dec. 14, 2011.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock In and Sequence Modulation Mediated by a Psoralen-linked Triplex-forming Oligonucleotide," J Biol Chem., 283(17):11244-52 (2008).
Malech et al., "Prolonged production of NADPH oxidase-corrected granulocytes after gene therapy of chronic granulomatous disease," PNAS, Oct. 1997, 94:12133-38.
Mancini et al. "CpG methylation within the 5' regulatory region of the BRCA1 gene is tumor specific and includes a putative CREB binding site," Oncogene, 1998, 16:1161-9.
Mandecki et al., "A totally synthetic plasmid for general cloning, gene expression and mutagenesis in *Escherichia coli*," Gene, Sep. 28, 1990, 94(1):103-107.
Mandell and Barbas et al., "Zinc Finger Tools: custom DNA-binding domains for transcription factors and nucleases," Nucleic Acids Res., 34(Web Server issue):W516-W523, Jul. 1, 2006.
Markmann et al., "Indefinite survival of MHC class I-deficient murine pancreatic islet allografts," Transplantation, Dec. 1992, 54:1085-89.
Martin et al., "GAP domains responsible for ras p21-dependent inhibition of muscarinic atrial K+ channel currents," Science, Jan. 1992, 255:192-194.
Maurano et al., "Systematic localization of common disease-associated variation in regulatory DNA," Science, 337(6099):1190-1195, Epub Sep. 5, 2012.
McDaniell et al., "Heritable individual-specific and allele-specific chromatin signatures in humans," Science, 328(5975):235-239, [author manuscript] Epub Mar. 18, 2010.
McNaughton et al., "Mammalian cell penetration, siRNA transfection, and DNA transfection by supercharged proteins," PNAS, Apr. 2009, 106:6111.
Mendenhall et al., "Locus-specific editing of histone modifications at endogenous enhancers," Nat Biotechnol., 31(12):1133-1136, Epub Sep. 8, 2013.
Metzger et al., "LSD1 demethylates repressive histone marks to promote androgen-receptor-dependent transcription," Nature, 437(7057):436-439, 2005.
Miller et al., "Repetitive zinc-binding domains in the protein transcription factor IIIA from Xenopus oocytes," EMBO J., 4(6):1609-1614, Jun. 1985.
Moore et al., "Design of polyzinc finger peptides with structured linkers," Proc Natl Acad Sci USA, Feb. 2001, 98:1432-1436.
Moore et al., "Improved somatic mutagenesis in zebrafish using transcription activator-like effector nucleases (TALENs)," PLoS One, May 2012, 7(5):e37877.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Mussolino and Cathomen, "TALE nucleases: tailored genome engineering made easy," Curr Opin Biotechnol., 23(5):644-650, Epub Feb. 17, 2012.

(56) References Cited

OTHER PUBLICATIONS

Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Neering et al., "Transduction of primitive human hematopoietic cells with recombinant adenovirus vectors," Blood, 88(4):1147-1155, Aug. 15, 1996.
Ng et al., "In vivo epigenomic profiling of germ cells reveals germ cell molecular signatures," Dev Cell., 24(3):324-333, Epub Jan. 24, 2013.
Noonan and McCallion, "Genomics of long-range regulatory elements," Annu Rev Genomics Hum Genet., 11:1-23, 2010.
Novak et al., "Functional Characterization of Protease-treated Bacillus anthracis Protective Antigen," J. Biol. Chem., Aug. 1992, 267:17186-93.
Oligino et al., "Drug inducible transgene expression in brain using a herpes simplex virus vector," Gene Ther., 5(4):491-496, Apr. 1998.
Ong and Corees, "Enhancer function: new insights into the regulation of tissue-specific gene expression," Nat Rev Genet., 12(4):283-293, Epub Mar. 1, 2011.
Ovchinnikov et al., "PspXI, a novel restriction endonuclease that recognizes the unusual DNA sequence 5-VCTCGAGB-3," Bulletin of Biotechnology and Physico-chemical Biology, 2005, 1(1):18-24.
Paik W K et al., "Enzymatic Demethylation of Calf Thymus Histones," Biochemical and Biophysical Research Communications, 1973, 51(3): 781-788.
Palva et al., "Secretion of interferon by Bacillus subtilis," Gene, 22(2-3):229-235, May-Jun. 1983.
Paques et al., "Meganucleases and DNA double-strand break-induced recombination: persetives for gene thereapy," Current Gene Therapy, Bentham Science Publishers LTD, Feb. 1, 2007, 7(1):49-66.
Pavletich and Pabo, "Zinc finger-DNA recognition: crystal structure of a Zif268-DNA complex at 2.1 A," Science, 252(5007):809-817, May 10, 1991.
Perelle et al., "Characterization of Clostridium perfringens Iota-Toxin Genes and Expression in *Eschenichia coli*," Infect. Immun , Dec. 1993, 61:5147-56.
Perez-Pinera et al., "Synergistic and tunable human gene activation by combinations of synthetic transcription factors," Nat Methods., 10(3):239-342, Epub Feb. 3, 2013.
Perez-Quintero et al., "An Improved Method for TAL Effectors DNA-Binding Sites Prediction Reveals Functional Convergence in TAL Repertoires of Xanthomonas oryzae Strains," Jul. 2013, PLOS One vol. 8, No. 7, e68464, pp. 1-15, 2013.
Pingoud and Silva, "Precision genome surgery," Nat Biotechnol., 25(7):743-744, Jul. 2007.
Prochiantz, "Getting hydrophilic compounds into cells: lessons from homeopeptides," Curr. Opin. Neurobiol., Oct. 1996, 6:629-634.
Qi et al., "Repurposing CRISPR as an RNA-guided platform for sequence-specific control of gene expression," Cell, 152(5):1173-1183, Feb. 28, 2013.
Rada-Iglesias et al., "A unique chromatin signature uncovers early developmental enhancers in humans," Nature, 470(7333):279-283, Epub Dec. 15, 2010.
Ram et al., "Combinatorial patterning of chromatin regulators uncovered by genome-wide location analysis in human cells," Cell, 147(7):1628-1639, Dec. 23, 2011.
Ramirez et al., "Unexpected failure rates for modular assembly of engineered zinc fingers," Nat Methods., 5(5):374-375, May 2008.
Rebar and Pabo, "Zinc finger phage: affinity selection of fingers with new DNA-binding specificities," Science, 263(5147):671-673, Feb. 4, 1994.

Rendahl et al., "Regulation of gene expression in vivo following transduction by two separate rAAV vectors," Nat. Biotechnol., 16(8):757-761, Aug. 1998.
Reyon et al., "Engineering designer transcription activator-like effector nucleases (TALENs) by REAL or REAL-Fast assembly" Curr Protoc Mol Biol., Chapter 12:Unit 12.15, [author manuscript] Oct. 2012.
Rivenbank et al., "Epigenetic reprogramming of cancer cells via targeted DNA methylation," Epigenetics, Apr. 2012, 7(4): 350-360.
Rodenhiser and Mann, "Epigenetics and human disease: translating basic biology into clinical applications," CMAJ, 174(3):341-348 (2006).
Rohde et al., "Bisma—Fast and accurate bisulfite sequencing data analysis of individual clones from unique and repetitive sequences," BMC Bioinformatics, 11:230 12 pages (2010).
Rosenbloom et al., "ENCODE whole-genome data in the UCSC Genome Browser: update 2012," Nucleic Acids Res., 40(Database issue):D912-D917, Epub Nov. 9, 2011.
Rosenecker et al., "Adenovirus infection in cystic fibrosis patients: implications for the use of adenoviral vectors for gene transfer," Infection, 1996, 24(1)5-8.
Rothman, "Mechanisms of intracellular protein transport," Nature, 372(6501):55-63, Nov. 3, 1994.
Ruben et al., "Isolation of a rel-related human cDNA that potentially encodes the 65-кD subunit of NF-kappa B," Science, Mar. 1991, 251:1490-93.
Sabo et al, "Genome-scale mapping of DNase I sensitivity in vivo using tiling DNA microarrays," Nat Methods., 3(7):511-518, Jul. 2006.
Sabo et al., "Discovery of functional noncoding elements by digital analysis of chromatin structure," Proc Natl Acad Sci U S A., 101(48):16837-16842, Epub Nov. 18, 2004.
Sadowski et al., "GAL4-VP16 is an unusually potent transcriptional activator," Nature, Oct. 1988, 335:563-564.
Samulski et al., "Helper-Free Stocks of Recombinant Adeno-Associated Viruses: Normal Integration Does Not Require Viral Gene Expression," J. Virol., Sep. 1989, 63:3822-28.
Sander et al., "Targeted gene disruption in somatic zebrafish cells using engineered TALENs," Nat. Biotechnol., 29:697-698 (2011).
Sanjana et al., "A transcription activator-like effector toolbox for genome engineering," Nat Protoc., 7(1):171-192, Jan. 5, 2012.
Schleifman et al., "Triplex-mediated gene modification," Methods Mol. Biol., 435:175-190, 2008.
Schmidt et al., "Arginine-rich cell-penetrating peptides," FEBS Lett., May 2010, 584:1806-13.
Scholze & Boch, "TAL effectors are remote controls for gene activation," J. Curr. Opin. Microbiol, 14:47-53 (2011).
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Supplementary European Search Report issued in EP 12814750 dated Feb. 24, 2015, 3 pages.
Supplementary European Search Report issued in EP 13797024 dated Feb. 16, 2016, 3 pages.
Supplementary European Search Report issued in EP12814750 dated Feb. 24, 2015 (13 pages).
International Preliminary Report on Patentability in International Application No. PCT/US2012/046451, dated Jan. 21, 2014, 6 pages.
Akopian et al., "Chimeric recombinases with designed DNA sequence recognition," Proc Natl Acad Sci USA, Jul. 22, 2003;100(15):8688-91.
Aslanidis et al., "Ligation-independent cloning of PCR products (LIC-PCR)," Nucleic Acids Res., Oct. 25, 1990;18(20):6069-74.
Bibikova et al., "Enhancing gene targeting with designed zinc finger nucleases," Science, May 2, 2003;300(5620):764.
Bibikova et al., "Stimulation of homologous recombination through targeted cleavage by chimeric nucleases," Mol Cell Biol., Jan. 2001;21(1):289-97.

(56) References Cited

OTHER PUBLICATIONS

Boch et al., "Breaking the code of DNA binding specificity of TAL-type III effectors," Science, Dec. 11, 2009;326(5959):1509-12.
Briggs et al., "Iterative capped assembly: rapid and scalable synthesis of repeat-module DNA such as TAL effectors from individual monomers," Nucleic Acids Res., Aug. 2012;40(15):e117.
Cade et al., "Highly efficient generation of heritable zebrafish gene mutations using homo- and heterodimeric TALENs," Nucleic Acids Res., Sep. 2012;40(16):8001-10.
Cermak et al., "Efficient design and assembly of custom TALEN and other TAL effector-based constructs for DNA targeting," Nucleic Acids Res., Jul. 2011;39(12):e82.
Davis, "Transcriptional regulation by MAP kinases," Mol Reprod Dev., Dec. 1995 ;42(4):459-67.
Gu et al., "R gene expression induced by a type-III effector triggers disease resistance in rice," Nature, Jun. 23, 2005;435(7045):1122-5.
Joung et al., "A bacterial two-hybrid selection system for studying protein-DNA and protein-protein interactions," Proc Natl Acad Sci USA, Jun. 20, 2000;97(13):7382-7.
Kay et al., "A bacterial effector acts as a plant transcription factor and induces a cell size regulator," Science, Oct. 26, 2007;318(5850):648-51.
Kim et al., "Hybrid restriction enzymes: zinc finger fusions to Fok I cleavage domain," Proc Natl Acad Sci USA, Feb. 6, 1996;93(3):1156-60.
Li et al., "Modularly assembled designer TAL effector nucleases for targeted gene knockout and gene replacement in eukaryotes," Nucleic Acids Research, 39(14):6315-6325 (2011).
Maeder et al., "Oligomerized pool engineering (OPEN): an 'open-source' protocol for making customized zinc-finger arrays," Nat Protoc., 2009;4(10):1471-501.
Maeder et al., "Rapid "open-source" engineering of customized zinc-finger nucleases for highly efficient gene modification," Mol Cell., Jul. 25, 2008;31(2):294-301.
Moore et al., "Improved somatic mutagenesis in zebrafish using transcription activator-like effector nucleases (TALENs)," PLoS One., 2012;7(5):e37877, 9 pages.
Moscou and Bogdanove "A simple cipher governs DNA recognition by TAL effectors," Science, Dec. 11, 2009;326(5959):1501.
Orlando et al., "Zinc-finger nuclease-driven targeted integration into mammalian genomes using donors with limited chromosomal homology," Nucleic Acids Res., Aug. 2010;38(15):e152, 15 pages.
Porteus & Baltimore, "Chimeric nucleases stimulate gene targeting in human cells," Science. 2003. May 2;300(5620):763.
Reyon et al., "FLASH Assembly of TALENs Enables High-Throughput Genome Editing," Nat Biotechnol., May 2012;30(5):460-467.
Romer et al., "Plant pathogen recognition mediated by promoter activation of the pepper Bs3 resistance gene," Science, Oct. 26, 2007;318(5850):645-8.
Schonthal, "Regulation of gene expression by serine/threonine protein phosphatases," Semin Cancer Biol., Aug. 1995;6(4):239-48.
Schornack et al., "Gene-for-gene-mediated recognition of nuclear-targeted AvrBs3-like bacterial effector proteins," J Plant Physiol., Feb. 2006;163(3):256-72.
Sugio et al., "Two type III effector genes of Xanthomonas oryzae pv. oryzae control the induction of the host genes OsTFIIAgamma1 and OsTFX1 during bacterial blight of rice," Proc Natl Acad Sci USA, Jun. 19, 2007;104(25):10720-5.
Urnov et al., "Highly efficient endogenous human gene correction using designed zinc-finger nucleases" Nature, Jun. 2, 2005;435(7042):646-51
Van den Brulle et al., "A novel solid phase technology for high-throughput gene synthesis," BioTechniques, 45(3):340-343 (2008).
Weber et al., "Assembly of Designer TAL Effectors by Golden Gate Cloning," PLOS One, 6(5):e19722 (2011).
Wright et al., "Standardized reagents and protocols for engineering zinc finger nucleases by modular assembly," Nat Protoc., 2006;1(3):1637-52.

Xu et al., "Cytosine methylation targetted to pre-determined sequences," Nat Genet., Dec. 1997;17(4):376-8.
Yang et al., "Os8N3 is a host disease-susceptibility gene for bacterial blight of rice," Proc Natl Acad Sci USA, Jul. 5, 2006;103(27):10503-8.
Yeager, "Genome Editing in a FLASH ," BioTechniques, Apr. 4, 2012, 2 pages http://www.biotechniques.com/news/Genome-Editing-in-a-FLASH/biotechniques-329367.html.
International Search Report and Written Opinion dated Nov. 15, 2012 in international application No. PCT/US2012/046451, 8 pgs.
Miller J.C. et al. A TALE nuclease architecture for efficient genome editing. Nature Biotechnology, 2011, v.29, n,2, pp. 143-148.
Morbitzer R. et al. Assembly of custom TALE-type DNA binding domains by modular cloning. Nucleic Acids Research, 2011, v.39, n.13, pp. 5790-5799.
Li T. et al. TAL nucleases (TALNs): hybrid proteins composed of TAL effectors and Fok1 DNA-cleavage domain. Nucleic Acids Research, 2011, v.39, n.1, pp. 359-372.
Christian M. Targeting DNA double-strand breaks with TAL effector nucleases. Genetics, 2010, v.186, n.2, pp. 757-761.
Entry for CDKN2A, cyclin-dependent kinase inhibitor 2A [Homo sapiens (human)], Gene ID: 1029, updated on Oct. 31, 2016, and printed from http:www.ncbi.nlm.nih.gov/gene/1029 as pp. 1/9 on Nov. 1, 2016.
Huang, "Histone methyltransferases, diet nutrients and tumour suppressors," Nature Reviews. Cancer, Jun. 2002, 2(6): 469-7-476.
Paik et al., "Enzymatic Demethylation of Calf Thymus Histones," Biochemical and Biophysical Research Communications, 1973, 51(3): 781-788.
Perez-Quintero et al., "An Improved Method for TAL Effectors DNA-Binding Sites Prediction Reveals Functional Convergence in TAL Repertoires of Xanthomonas oryzae Strains," Jul. 2013, PLOS One, 8: e68464.
Rohde et al., "BISMA—Fast and accurate bisulfite sequencing data analysis of individual clones from unique and repetitive sequences," BMC Bioinformatics, 2010, 11:230 12 pages.
Zheng et al., "Correlations of partial and extensive methylation at the P14ARF locus with reduced MRNA expression in colorectal cancer cell lines and clinicopathological features in primary tumors," Carcinogenesis, Nov. 1, 2000, 21(11): 2057-2064.
Kondo et al., "Epigenetic changes in colorectal cancer," Cancer Metastasis Reviews, Jan. 2004, 23(1-2): 29-39.
Medenhall et al., "Identification of promoter targets of enhancers by epigenetic knockdown using TAL DNA binding proteins," Epigenetics & Chromatin, 2013, 6(Suppl): 1-2.
Office Action in U.S. Appl. No. 14/435,065, dated Jan. 26, 2017, 22 pages.
Office Action in U.S. Appl. No. 14/766,713, dated Jan. 26, 2017, 39 pages.
Office Action in Japanese Appliaction No. 2014-520317, dated Jan. 17, 2017, 6 pages (with English translation).
Office Action in U.S. Appl. No. 13/838,520, dated Feb. 24, 2017, 49 pages.
Office Action in European Application No. 12814750.1, dated Mar. 8, 2017, 7 pages.
European Office Action in European Application No. 13797024.0, dated Jul. 18, 2017, 9 pages.
Frauer et al., "Different Binding Properties and Function of CXXC Zinc Finger Domains in Dnmt1 and Tet1," PLOS One, Feb. 2011, 6: e16627.
Li et al. Regulatory mechanisms of tumor suppressor p16AINK4A and their relevance to cancer. Biochemistry, vol. 50, pp. 5566-5582, May 27, 2011.
Office Action in U.S. Appl. No. 14/435,065, dated Jul. 27, 2017.
Office Action in U.S. Appl. No. 14/766,713, dated Jul. 25, 2017.
Pekowska et al. H3K4 tri-methylation provides an epigenetic signature of active enhancers. The EMBO Journal, vol. 30, pp. 4198-4210, Aug. 16, 2011, including supplementary figures S1-S11, printed as pp. 1/13-13/13.
Sera et al. Zinc-finger-based artificial transcription factors and their applications. Advanced Drug Delivery Reviews, vol. 61, pp. 513-526, Apr. 2009.

(56) References Cited

OTHER PUBLICATIONS

Beerli et al., "Toward controlling gene expression at will: Specific regulation of the erbB-2/HER-2 promoter using polydactyl zinc finger proteins constructed from modular building blocks," PNAS, Dec. 1998, 95: 14628-14633.
European Office Action in Application No. 13797024.0, dated Mar. 16, 2018, 8 pages.
Extended European Search Report in Application No. 17205413.2, dated Mar. 23, 2018, 7 pages.
GEO Sample G5M1008573, Duke DnaseSeq HEK293T, Sep. 25, 2012, printed as pp. 1/2-282 from https://www.ncbi.nlrn.nih.gov/geo/query/acc.cgi?acc=GSM1008573. (Year: 2012).
Jia et al., "Cancer gene therapy targeting cellular apoptosis machinery," Cancer Treatment Reviews, 2012, 38:868-879.
Maeder et al, "Upregulation of the Pluripotency-Associated miRNA 302-367 Cluster 1 Using Engineered Transcription Activator-Like Effector(TALE) Activators," Molecular Therapy, 2012, 20:S193 499.
Office Action in Canadian Application No. 2,841,710, dated May 11, 2018, 4 pages.
Office Action in European Application No. 13845212.3, dated Feb. 15, 2018, 4 pages.
Office Action in Japanese Application No. 2015-557129, dated Dec. 19, 2017, 8 pages (with English translation).
Tani et al., "Updates on current advances in gene therapy," The West Indian Medical Journal, Mar. 2011, 60:188-194.
Verma and Weitzman, "Gene Therapy: Twenty-first century medicine," Annual Review of Biochemistry, 2005, 74:711-738.
Yan et al., "Drugging the undruggable: Transcription therapy for cancer," Biochinnica et Biophysica Acta, 2013, 1835: 76-85.
GenBank Accession No. FJ176909.1, "Xanthomonas oryzae pv. oryzae clone 041 avirulence/virulence factor repeat domain protein like gene, complete sequence," dated Sep. 30, 2008 [retrieved on Aug. 30, 2018]. Retrieved from the Internet: URL <https://www.ncbi.nlm.nih.gov/nuccore/FJ176909.1/>, 2 pages.
Office Action in Australian Application No. 2017204819, dated Sep. 7, 2018, 7 pages.
Office Action in Japanese Application No. 2017-136828, dated Sep. 11, 2018 (with English translation).

Archive of 376 pre-assembled TALE repeat units

```
TCGCGCGTTTCGGTGATGACGGTGAAAACCTCTGACACATGCAGCTCCCGGAGACGGTCACAGCTTGT
CTGTAAGCGGATGCCGGGAGCAGACAAGCCCGTCAGGGCGCGTCAGCGGGTGTTGGCGGGTGTCGGGG
CTGGCTTAACTATGCGGCATCAGAGCAGATTGTACTGAGAGTGCACCATATGCGGTGTGAAATACCGC
ACAGATGCGTAAGGAGAAAATACCGCATCAGGCGCCATTCGCCATTCAGGCTGCGCAACTGTTGGGAA
GGGCGATCGGTGCGGGCCTCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGGCCAGTGAATTCGAGCTCG
GTACCTCGCGAATGCATCTAGATATCGGATCCCGGGCCCGTCGACTGCAGAGGCCTGCATGCAAGCTT
GGCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCGTTG
CGCTCACTGCCCGCTTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCT
GGCGTTTTTCCATAGGCTCCGCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCTGCGCTCTGCTGA
AGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCATCTGGCC
CCAGTGCTGCAATGATACCGCGAGAgCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTT
ACATGATCCCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAGTGCCACCTGACGTCTAAGAA
ACCATTATTATCATGACATTAACCTATAAAAATAGGCGTATCACGAGGCCCTTTCGTC
(SEQ ID NO:1)
```

| Type | SEQUENCE | SEQ ID NO: |
|---|---|---|
| α/ε | LTP*D*QVVAIASNIGGKQALETVQRLLPVLCQ*D*HG | 2 |
| β | LTP*E*QVVAIASNIGGKQALETVQRLLPVLCQ*A*HG | 3 |
| γ | LTP*D*QVVAIASNIGGKQALETVQRLLPVLCQ*A*HG | 4 |
| δ | LTP*A*QVVAIASNIGGKQALETVQRLLPVLCQ*D*HG | 5 |

FIG 4B

| Type | SEQUENCE | SEQ ID NO: |
|---|---|---|
| α/ε | CTGACCCCAGACCAGGTAGTCGCAATCGCGTCGAACATTGG GGGAAAGCAAGCCCTGGAAACCGTGCAAAGGTTGTTGCCG GTCCTTTGTCAAGACCACGGC | 6 |
| Type β: | CTTACACCGGAGCAAGTCGTGGCCATTGCAAGCAACATCGG TGGCAAACAGGCTCTTGAGACGGTTCAGAGACTTCTCCCAG TTCTCTGTCAAGCCCACGGG | 7 |
| Type γ: | CTGACTCCCGATCAAGTTGTAGCGATTGCGTCGAACATTGGA GGGAAACAAGCATTGGAGACTGTCCAACGGCTCCTTCCCGT GTTGTGTCAAGCCCACGGT | 8 |
| Type δ: | TTGACGCCTGCACAAGTGGTCGCCATCGCCTCCAATATTGGCG GTAAGCAGGCGCTGGAAACAGTACAGCGCCTGCTGCCTGTACT GTGCCAGGATCATGGA | 9 |

GACGGATCGGGAGATCTCCCGATCCCCTATGGTCGACTCTCAGTACAATCTGCTCTGATGCCGCATAGTTAAGCCAGTA
TCTGCTCCCTGCTTGTGTGTTGGAGGTCGCTGAGTAGTGCGCGAGCAAAATTTAAGCTACAACAAGGCAAGGCTTGAC
CGACAATTGCATGAAGAATCTGCTTAGGGTTAGGCGTTTTGCGCTGCTTCGCGATGTACGGGCCAGATATACGCGTTG
ACATTGATTATTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGACGTATGTTCC
CATAGTAACGCCAATAGGGACTTTCCATTGACGTCAATGGGTGGACTATTTACGGTAAACTGCCCACTTGGCAGTACAT
CAAGTGTATCATATGCCAAGTACGCCCCCTATTGACGTCAATGACGGTAAATGGCCCGCCTGGCATTATGCCCAGTACA
TGACCTTATGGGACTTTCCTACTTGGCAGTACATCTACGTATTAGTCATCGCTATTACCATGGTGATGCGGTTTTGGCAG
TACATCAATGGGCGTGGATAGCGGTTTGACTCACGGGGATTTCCAAGTCTCCACCCCATTGACGTCAATGGGAGTTTG
TTTTGGCACCAAAATCAACGGGACTTTCCAAAATGTCGTAACAACTCCGCCCCATTGACGCAAATGGGCGGTAGGCGT
GTACGGTGGGAGGTCTATATAAGCAGAGCTCTCTGGCTAACTAGAGAACCCACTGCTTACTGGCTTATCGAAATTAAT
ACGACTCACTATAGGGAGACCCAAGCTGGCTAGCaccATGGACTACAAAGACCATGACGGTGATTATAAAGATCATGA
CATCGATTACAAGGATGACGATGACAAGATGGCCCCCAAGAAGAAGAGGAAGGTGGGCATTCACCGCGGGGTACCT
ATGGTGGACTTGAGGACACTCGGTTATTCGCAACAGCAACAGGAGAAAATCAAGCCTAAGGTCAGGAGCACCGTCGC
GCAACACCACGAGGCGCTTGTGGGGCATGGCTTCACTCATGCGCATATTGTCGCGCTTTCACAGCACCCTGCGGCGCT
TGGGACGGTGGCTGTCAAATACCAAGATATGATTGCGGCCCTGCCCGAAGCCACGCACGAGGCAATTGTAGGGGTCG
GTAAACAGTGGTCGGGAGCGCGAGCACTTGAGGCGCTGCTGACTGTGGCGGGTGAGCTTAGGGGGCCTCCGCTCCA
GCTCGACACCGGGCAGCTGCTGAAGATCGCGAAGAGAGGGGGAGTAACAGCGGTAGAGGCAGTGCACGCCTGGCG
CAATGCGCTCACCGGGGCCCCCTTGAACAGAGACGATTAATGCGTCTCGCTGACACCCGAACAGGTGGTCGCCATTGC
TXXXXXXXXXGGAGGACGGCCAGCCTTGGAGTCCATCGTAGCCCAATTGTCCAGGCCCGATCCCGCGTTGGCTGCGTT
AACGAATGACCATCTGGTGGCGTTGGCATGTCTTGGTGGACGACCCGCGCTCGATGCAGTCAAAAAGGGTCTGCCTCA
TGCTCCCGCATTGATCAAAAGAACCAACCGGCGGATTCCCGAGAGAACTTCCCATCGAGTCGCGGGATCCCAACTAGT
CAAAAGTGAACTGGAGGAGAAGAAATCTGAACTTCGTCATAAATTGAAATATGTGCCTCATGAATATATTGAATTAAT
TGAAATTGCCAGAAATTCCACTCAGGATAGAATTCTTGAAATGAAGGTAATGGAATTTTTTATGAAAGTTTATGGATAT
AGAGGTAAACATTTGGGTGGATCAAGGAAACCGGACGGAGCAATTTATACTGTCGGATCTCCTATTGATTACGGTGTG
ATCGTGGATACTAAAGCTTATAGCGGAGGTTATAATCTGCCAATTGGCCAAGCAGATGAAATGCAACGATATGTCGAA
GAAAATCAAACACGAAACAAACATATCAACCCTAATGAATGGTGGAAAGTCTATCCATCTTCTGTAACGGAATTTAAGT
TTTTATTTGTGAGTGGTCACTTTAAAGGAAACTACAAAGCTCAGCTTACACGATTAAATCATATCACTAATTGTAATGGA
GCTGTTCTTAGTGTAGAAGAGCTTTTAATTGGTGGAGAAATGATTAAAGCCGGCACATTAACCTTAGAGGAAGTCAGA
CGGAAATTTAATAACGGCGAGATAAACTTTTAAGGGCCCTTCGAAGGTAAGCCTATCCCTAACCCTCTCCTCGGTCTCG
ATTCTACGCGTACCGGTCATCATCACCATCACCATTGAGTTTAAACCCGCTGATCAGCCTCGACTGTGCCTTCTAGTTGC
CAGCCATCTGTTGTTTGCCCCTCCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGGGCAGGACAGCAAGGGGG
AGGATTGGGAAGACAATAGCAGGCATGCTGGGGATGCGGTGGGCTCTATGGCTTCTGAGGCGGAAAGAACCAGCTG
GGGCTCTAGGGGGTATCCCCACGCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTTTCTCGCCACGTTCGCCGGCTTTCCC
CGTCAAGCTCTAAATCGGGGCATCCCTTTAGGGTTCCGATTTAGTGCTTTACGGCACCTCGACCCCAAAAAACTTGATT
AGGGTGATGGTTCACGTAGTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCTCGGTCTATTCTTTTGATTTATAAGGGATTTTGGGGA
TTTCGGCCTATTGGTTAAAAAATGAGCTGATTTAACAAAAATTTAACGCGAATTAATTCTGTGGAATGTGTGTCAGTTA
GGGTGTGGAAAGTCCCCAGGCTCCCCAGGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTC
(SEQ ID NO:10)

AGCAACCATAGTCCCGCCCCTAACTCCGCCCATCCCGCCCCTAACTCCGCCCAGTTCCGCCCATTCTCCGCCCCATGGC
TGACTAATTTTTTTTATTTATGCAGAGGCCGAGGCCGCCTCTGCCTCTGAGCTATTCCAGAAGTAGTGAGGAGGCTTT
TTTGGAGGCCTAGGCTTTTGCAAAAAGCTCCCGGGAGCTTGTATATCCATTTTCGGATCTGATCAGCACGTGTTGACA
ATTAATCATCGGCATAGTATATCGGCATAGTATAATACGACAAGGTGAGGAACTAAACCATGGCCAAGCCTTTGTCTC
AAGAAGAATCCACCCTCATTGAAAGAGCAACGGCTACAATCAACAGCATCCCCATCTCTGAAGACTACAGCGTCGCC
AGCGCAGCTCTCTCTAGCGACGGCCGCATCTTCACTGGTGTCAATGTATATCATTTTACTGGGGACCTTGTGCAGAA
CTCGTGGTGCTGGGCACTGCTGCTGCTGCGGCAGCTGGCAACCTGACTTGTATCGTCGCGATCGGAAATGAGAACA
GGGGCATCTTGAGCCCCTGCGGACGGTGTCGACAGGTGCTTCTCGATCTGCATCCTGGGATCAAAGCGATAGTGAA
GGACAGTGATGGACAGCCGACGGCAGTTGGGATTCGTGAATTGCTGCCCTCTGGTTATGTGTGGGAGGGCTAAGCA
CTTCGTGGCCGAGGAGCAGGACTGACACGTGCTACGAGATTTCGATTCCACCGCCGCCTTCTATGAAAGGTTGGGCT
TCGGAATCGTTTTCCGGGACGCCGGCTGGATGATCCTCCAGCGCGGGGATCTCATGCTGGAGTTCTTCGCCCACCCC
AACTTGTTTATTGCAGCTTATAATGGTTACAAATAAAGCAATAGCATCACAAATTTCACAAATAAAGCATTTTTTCAC
TGCATTCTAGTTGTGGTTTGTCCAAACTCATCAATGTATCTTATCATGTCTGTATACCGTCGACCTCTAGCTAGAGCTT
GGCGTAATCATGGTCATAGCTGTTTCCTGTGTGAAATTGTTATCCGCTCACAATTCCACACAACATACGAGCCGGAAG
CATAAAGTGTAAAGCCTGGGGTGCCTAATGAGTGAGCTAACTCACATTAATTGCGTTGCGCTCACTGCCCGCTTTCCA
GTCGGGAAACCTGTCGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATCGACGCTC
AAGTCAGAGGTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGACCGAGTTGCTCTTGCC
CGGCGTCAATACGGGATAATACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAATGCCGCAAAAAAGGGAATAAGGGCGA
CACGGAAATGTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCACCTGACGT
C                (SEQ ID NO:11)

14 of 30 sequences mutated. (46%)

| Sequence | Δ SIZE | SEQ ID NO: |
|---|---|---|
| CTACGGCGTGCAGTGCTTCAGCCGGCTACCCCGACCACATGAAGCAGCACGACTTCTTCAAGGACTACGTCCGAAGGCTACGTCCAGGAGCGCACCATCTCTTCAAGGA | WT | 12 |
| CTACGGCGTGCAGTGCTTCAGCCGCTACCCGA---CATGAAGCAGCACGACTTCTTCAAGGACTACGTCCGAAGGCTACGTCCAGGAGCGCACCATCTCTTCAAGGA | Δ3 (3X) | 13 |
| CTACGGCGTGCAGTGCTTCAGCCG-------AAGCAGCACGACTTCTTCAAGGACTACGTCCGAAGGCTACGTCCAGGAGCGCACCATCTCTTCAAGGA | Δ16 | 14 |
| CTACGGCGTGCAGTGCTTCAGCCGCTAC---------------GACTTCTTCAAGGACTACGTCCGAAGGCTACGTCCAGGAGCGCACCATCTCTTCAAGGA | Δ21 | 15 |
| CTACGGCGTGCAGTGCTTCAGCCGC--------------ACGACTTCTCCAGTCCGCATGCCCGAAGGCTACNTCCAGGAGCGCACCATCTCTTCAAGGA | Δ22 | 16 |
| CTACGGCGTGCAGTGCTTCAGC----------------------ACTTCAAGTCCGCATGCCCGAAGGCTACGTCCAGGAGCGCACCATCTCTTCAAGGA | Δ30 (Δ31 and +1) | 17 |
| CTACGGCGTGCAGTGCAG-----------------------------CACGACTTCTTCAAGTCCGCATGCCCGAAGGCTACGTCCAGGAGCGCACCATCTCTTCAAGGA | Δ33 | 18 |
| CTACGGCGTGCAGTGCAG-----------------------------CACGACTTCTTCAAGTCCGCATGCCCGAAGGCTACGTCCAGGAGCGCACCATCTCTTCAAGGA | Δ33 | 19 |
| CTACGGCGTGCAGTGCAGTT-------------------------------------GCCCGAAGGCTACGTCCAGGAGCGCACCATCTCTTCAAGGA | Δ51 | 20 |
| CTACGGCGTGCAGTGCTTCAGCC--------------------------------------GCTACGTCCAGGAGCGCACCATCTCTTCAAGGA | Δ54 | 21 |
| CTACG---------------------------------------------------------CCATGCCCGAAGGCTACGTCCAGGAGCGCACCATCTCTTCAAGGA | Δ60 | 22 |
| CTACGGCGTGCAGTGCTT---------------------------------------------------------------CTTCAAGGA | Δ84 | 23 |
| CTACGGCGTGCAGTGCTTCAGCCGGCTACCCCGACCACACCACATGAAGCAGCACGACTTCTTCAAGTCCGCATGCCCGAAGGCTACGTCCAGGAGCGCACCATCTCTTCAAGGA | +2 | 24 |

FIG. 8

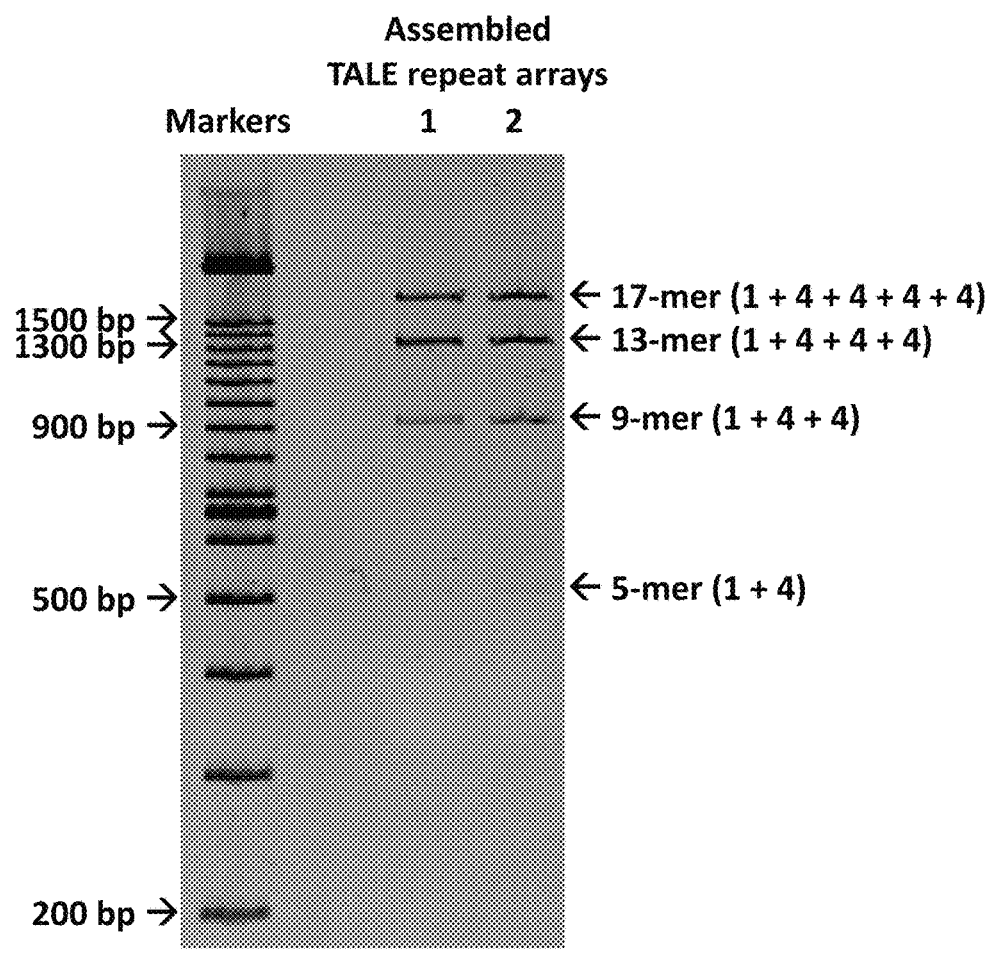

FIG. 11A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGAACAATAATGGGGGAAAGCAAG
CCCTGGAAACCGTGCAAAGGTTGTTGCCGGTCCTTTGTCAAGACCACGGCCTTACACCGGAGCAAGTCGTGGCCA
TTGCATCCCACGACGGTGGCAAACAGGCTCTTGAGACGGTTCAGAGACTTCTCCCAGTTCTCTGTCAAGCCCACGG
GCTGACTCCCGATCAAGTTGTAGCGATTGCGTCGAACATTGGAGGGAAACAAGCATTGGAGACTGTCCAACGGCT
CCTTCCCGTGTTGTGTCAAGCCCACGGTTTGACGCCTGCACAAGTGGTCGCCATCGCCAACAACAACGGCGGTAAG
CAGGCGCTGGAAACAGTACAGCGCCTGCTGCCTGTACTGTGCCAGGATCATGGACTGACCCCAGACCAGGTAGTC
GCAATCGCGTCAAACGGAGGGGGAAAGCAAGCCCTGGAAACCGTGCAAAGGTTGTTGCCGGTCCTTTGTCAAGA
CCACGGCCTTACACCGGAGCAAGTCGTGGCCATTGCAAATAATAACGGTGGCAAACAGGCTCTTGAGACGGTTCA
GAGACTTCTCCCAGTTCTCTGTCAAGCCCACGGGCTGACTCCCGATCAAGTTGTAGCGATTGCGTCGCATGACGGA
GGGAAACAAGCATTGGAGACTGTCCAACGGCTCCTTCCCGTGTTGTGTCAAGCCCACGGTTTGACGCCTGCACAA
GTGGTCGCCATCGCCTCGAATGGCGGCGGTAAGCAGGCGCTGGAAACAGTACAGCGCCTGCTGCCTGTACTGTGC
CAGGATCATGGACTGACCCCAGACCAGGTAGTCGCAATCGCGTCAAACGGAGGGGGAAAGCAAGCCCTGGAAAC
CGTGCAAAGGTTGTTGCCGGTCCTTTGTCAAGACCACGGCCTTACACCGGAGCAAGTCGTGGCCATTGCATCCCAC
GACGGTGGCAAACAGGCTCTTGAGACGGTTCAGAGACTTCTCCCAGTTCTCTGTCAAGCCCACGGGCTGACTCCCG
ATCAAGTTGTAGCGATTGCGTCGAACATTGGAGGGAAACAAGCATTGGAGACTGTCCAACGGCTCCTTCCCGTGT
TGTGTCAAGCCCACGGTTTGACGCCTGCACAAGTGGTCGCCATCGCCAACAACAACGGCGGTAAGCAGGCGCTGG
AAACAGTACAGCGCCTGCTGCCTGTACTGTGCCAGGATCATGGACTGACCCCAGACCAGGTAGTCGCAATCGCGT
CACATGACGGGGGAAAGCAAGCCCTGGAAACCGTGCAAAGGTTGTTGCCGGTCCTTTGTCAAGACCACGGCCTTA
CACCGGAGCAAGTCGTGGCCATTGCATCCCACGACGGTGGCAAACAGGCTCTTGAGACGGTTCAGAGACTTCTCC
CAGTTCTCTGTCAAGCCCACGGGCTGACTCCCGATCAAGTTGTAGCGATTGCGAATAACATGGAGGGAAACAAG
CATTGGAGACTGTCCAACGGCTCCTTCCCGTGTTGTGTCAAGCCCACGGTCTGACACCCGAACAGGTGGTCGCCAT
TGCTTCCCACGACGGAGGACGGCCAGCCTTGGAGTCCATCGTAGCCCAATTGTCCAGGCCCGATCCCGCGTTGGCT
GCGTTAACGAATGACCATCTGGTGGCGTTGGCATGTCTTGGTGGACGACCCGCGCTCGATGCAGTCAAAAAGGGT
CTGCCTCATGCTCCCGCATTGATCAAAAGAACCAACCGGCGGATTCCCGAGAGAACTTCCCATCGAGTCGCGGGAT
CC
(SEQ ID NO:25)

FIG. 11B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIANNNGGKQALETVQRLLPVLCQDHGLTPEQVVAIASHDGGKQALE
TVQRLLPVLCQAHGLTPDQVVAIASNIGGKQALETVQRLLPVLCQAHGLTPAQVVAIANNNGGKQALETVQRLLPVLC
QDHGLTPDQVVAIASNGGGKQALETVQRLLPVLCQDHGLTPEQVVAIANNNGGKQALETVQRLLPVLCQAHGLTPDQ
VVAIASHDGGKQALETVQRLLPVLCQAHGLTPAQVVAIASNGGGKQALETVQRLLPVLCQDHGLTPDQVVAIASNGG
GKQALETVQRLLPVLCQDHGLTPEQVVAIASHDGGKQALETVQRLLPVLCQAHGLTPDQVVAIASNIGGKQALETVQR
LLPVLCQAHGLTPAQVVAIANNNGGKQALETVQRLLPVLCQDHGLTPDQVVAIASHDGGKQALETVQRLLPVLCQDH
GLTPEQVVAIASHDGGKQALETVQRLLPVLCQAHGLTPDQVVAIANNNGGKQALETVQRLLPVLCQAHGLTPEQVVAI
ASHDGGRPALESIVAQLSRPDPALAALTNDHLVALACLGGRPALDAVKKGLPHAPALIKRTNRRIPERTSHRVAGS
(SEQ ID NO:26)

FIG. 12A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGAACAATAATGGGGGAAAGCAAG
CCCTGGAAACCGTGCAAAGGTTGTTGCCGGTCCTTTGTCAAGACCACGGCCTTACACCGGAGCAAGTCGTGGCCA
TTGCATCCCACGACGGTGGCAAACAGGCTCTTGAGACGGTTCAGAGACTTCTCCCAGTTCTCTGTCAAGCCCACGG
GCTGACTCCCGATCAAGTTGTAGCGATTGCGTCGAACATTGGAGGGAAACAAGCATTGGAGACTGTCCAACGGCT
CCTTCCCGTGTTGTGTCAAGCCCACGGTTTGACGCCTGCACAAGTGGTCGCCATCGCCAACAACAACGGCGGTAAG
CAGGCGCTGGAAACAGTACAGCGCCTGCTGCCTGTACTGTGCCAGGATCATGGACTGACCCCAGACCAGGTAGTC
GCAATCGCGTCAAACGGAGGGGGAAAGCAAGCCCTGGAAACCGTGCAAAGGTTGTTGCCGGTCCTTTGTCAAGA
CCACGGCCTTACACCGGAGCAAGTCGTGGCCATTGCAAATAATAACGGTGGCAAACAGGCTCTTGAGACGGTTCA
GAGACTTCTCCCAGTTCTCTGTCAAGCCCACGGGCTGACTCCCGATCAAGTTGTAGCGATTGCGTCGCATGACGGA
GGGAAACAAGCATTGGAGACTGTCCAACGGCTCCTTCCCGTGTTGTGTCAAGCCCACGGTTTGACGCCTGCACAA
GTGGTCGCCATCGCCTCGAATGGCGGCGGTAAGCAGGCGCTGGAAACAGTACAGCGCCTGCTGCCTGTACTGTGC
CAGGATCATGGACTGACCCCAGACCAGGTAGTCGCAATCGCGTCAAACGGAGGGGGAAAGCAAGCCCTGGAAAC
CGTGCAAAGGTTGTTGCCGGTCCTTTGTCAAGACCACGGCCTTACACCGGAGCAAGTCGTGGCCATTGCATCCCAC
GACGGTGGCAAACAGGCTCTTGAGACGGTTCAGAGACTTCTCCCAGTTCTCTGTCAAGCCCACGGGCTGACTCCCG
ATCAAGTTGTAGCGATTGCGTCGAACATTGGAGGGAAACAAGCATTGGAGACTGTCCAACGGCTCCTTCCCGTGT
TGTGTCAAGCCCACGGTTTGACGCCTGCACAAGTGGTCGCCATCGCCAACAACAACGGCGGTAAGCAGGCGCTGG
AAACAGTACAGCGCCTGCTGCCTGTACTGTGCCAGGATCATGGACTGACCCCAGACCAGGTAGTCGCAATCGCGT
CACATGACGGGGGAAAGCAAGCCCTGGAAACCGTGCAAAGGTTGTTGCCGGTCCTTTGTCAAGACCACGGCCTTA
CACCGGAGCAAGTCGTGGCCATTGCATCCCACGACGGTGGCAAACAGGCTCTTGAGACGGTTCAGAGACTTCTCC
CAGTTCTCTGTCAAGCCCACGGGCTGACTCCCGATCAAGTTGTAGCGATTGCGAATAACAATGGAGGGAAACAAG
CATTGGAGACTGTCCAACGGCTCCTTCCCGTGTTGTGTCAAGCCCACGGTTTGACGCCTGCACAAGTGGTCGCCAT
CGCCAGCCATGATGGCGGTAAGCAGGCGCTGGAAACAGTACAGCGCCTGCTGCCTGTACTGTGCCAGGATCATG
GACTGACACCCGAACAGGTGGTCGCCATTGCTTCTAATGGGGGAGGACGGCCAGCCTTGGAGTCCATCGTAGCCC
AATTGTCCAGGCCCGATCCCGCGTTGGCTGCGTTAACGAATGACCATCTGGTGGCGTTGGCATGTCTTGGTGGAC
GACCCGCGCTCGATGCAGTCAAAAAGGGTCTGCCTCATGCTCCCGCATTGATCAAAAGAACCAACCGGCGGATTC
CCGAGAGAACTTCCCATCGAGTCGCGGGATCC (SEQ ID NO:27)

FIG. 12B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIANNNGGKQALETVQRLLPVLCQDHGLTPEQVVAIASHDGGKQALE
TVQRLLPVLCQAHGLTPDQVVAIASNIGGKQALETVQRLLPVLCQAHGLTPAQVVAIANNNGGKQALETVQRLLPVLC
QDHGLTPDQVVAIASNGGGKQALETVQRLLPVLCQDHGLTPEQVVAIANNNGGKQALETVQRLLPVLCQAHGLTPDQ
VVAIASHDGGKQALETVQRLLPVLCQAHGLTPAQVVAIASNGGGKQALETVQRLLPVLCQDHGLTPDQVVAIASNGG
GKQALETVQRLLPVLCQDHGLTPEQVVAIASHDGGKQALETVQRLLPVLCQAHGLTPDQVVAIASNIGGKQALETVQR
LLPVLCQAHGLTPAQVVAIANNNGGKQALETVQRLLPVLCQDHGLTPDQVVAIASHDGGKQALETVQRLLPVLCQDH
GLTPEQVVAIASHDGGKQALETVQRLLPVLCQAHGLTPDQVVAIANNNGGKQALETVQRLLPVLCQAHGLTPAQVVAI
ASHDGGKQALETVQRLLPVLCQDHGLTPEQVVAIASNGGGRPALESIVAQLSRPDPALAALTNDHLVALACLGGRPAL
DAVKKGLPHAPALIKRTNRRIPERTSHRVAGS
(SEQ ID NO:28)

FIG. 13A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGTCAAACGGAGGGGGAAAGCAAG
CCCTGGAAACCGTGCAAAGGTTGTTGCCGGTCCTTTGTCAAGACCACGGCCTTACACCGGAGCAAGTCGTGGCCA
TTGCAAATAATAACGGTGGCAAACAGGCTCTTGAGACGGTTCAGAGACTTCTCCCAGTTCTCTGTCAAGCCCACGG
GCTGACTCCCGATCAAGTTGTAGCGATTGCGTCGAACATTGGAGGGAAACAAGCATTGGAGACTGTCCAACGGCT
CCTTCCCGTGTTGTGTCAAGCCCACGGTTTGACGCCTGCACAAGTGGTCGCCATCGCCTCCAATATTGGCGGTAAG
CAGGCGCTGGAAACAGTACAGCGCCTGCTGCCTGTACTGTGCCAGGATCATGGACTGACCCCAGACCAGGTAGTC
GCAATCGCGAACAATAATGGGGGAAAGCAAGCCCTGGAAACCGTGCAAAGGTTGTTGCCGGTCCTTTGTCAAGAC
CACGGCCTTACACCGGAGCAAGTCGTGGCCATTGCAAGCAACATCGGTGGCAAACAGGCTCTTGAGACGGTTCAG
AGACTTCTCCCAGTTCTCTGTCAAGCCCACGGGCTGACTCCCGATCAAGTTGTAGCGATTGCGTCGAACATTGGAG
GGAAACAAGCATTGGAGACTGTCCAACGGCTCCTTCCCGTGTTGTGTCAAGCCCACGGTTTGACGCCTGCACAAGT
GGTCGCCATCGCCAACAACAACGGCGGTAAGCAGGCGCTGGAAACAGTACAGCGCCTGCTGCCTGTACTGTGCCA
GGATCATGGACTGACCCCAGACCAGGTAGTCGCAATCGCGTCAAACGGAGGGGGAAAGCAAGCCCTGGAAACCG
TGCAAAGGTTGTTGCCGGTCCTTTGTCAAGACCACGGCCTTACACCGGAGCAAGTCGTGGCCATTGCATCCCACGA
CGGTGGCAAACAGGCTCTTGAGACGGTTCAGAGACTTCTCCCAGTTCTCTGTCAAGCCCACGGGCTGACTCCCGAT
CAAGTTGTAGCGATTGCGAATAACAATGGAGGGAAACAAGCATTGGAGACTGTCCAACGGCTCCTTCCCGTGTTG
TGTCAAGCCCACGGTTTGACGCCTGCACAAGTGGTCGCCATCGCCTCGAATGGCGGCGGTAAGCAGGCGCTGGAA
ACAGTACAGCGCCTGCTGCCTGTACTGTGCCAGGATCATGGACTGACCCCAGACCAGGTAGTCGCAATCGCGAAC
AATAATGGGGGAAAGCAAGCCCTGGAAACCGTGCAAAGGTTGTTGCCGGTCCTTTGTCAAGACCACGGCCTTACA
CCGGAGCAAGTCGTGGCCATTGCATCCCACGACGGTGGCAAACAGGCTCTTGAGACGGTTCAGAGACTTCTCCCA
GTTCTCTGTCAAGCCCACGGGCTGACTCCCGATCAAGTTGTAGCGATTGCGTCCAACGGTGGAGGGAAACAAGCA
TTGGAGACTGTCCAACGGCTCCTTCCCGTGTTGTGTCAAGCCCACGGTTTGACGCCTGCACAAGTGGTCGCCATCG
CCAACAACAACGGCGGTAAGCAGGCGCTGGAAACAGTACAGCGCCTGCTGCCTGTACTGTGCCAGGATCATGGAC
TGACACCCGAACAGGTGGTCGCCATTGCTTCCCACGACGGAGGACGGCCAGCCTTGGAGTCCATCGTAGCCCAAT
TGTCCAGGCCCGATCCCGCGTTGGCTGCGTTAACGAATGACCATCTGGTGGCGTTGGCATGTCTTGGTGGACGAC
CCGCGCTCGATGCAGTCAAAAAGGGTCTGCCTCATGCTCCCGCATTGATCAAAAGAACCAACCGGCGGATTCCCG
AGAGAACTTCCCATCGAGTCGCGGGATCC
(SEQ ID NO:29)

FIG. 13B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIASNGGGKQALETVQRLLPVLCQDHGLTPEQVVAIANNNGGKQALE
TVQRLLPVLCQAHGLTPDQVVAIASNIGGKQALETVQRLLPVLCQAHGLTPAQVVAIASNIGGKQALETVQRLLPVLCQ
DHGLTPDQVVAIANNNGGKQALETVQRLLPVLCQDHGLTPEQVVAIASNIGGKQALETVQRLLPVLCQAHGLTPDQV
VAIASNIGGKQALETVQRLLPVLCQAHGLTPAQVVAIANNNGGKQALETVQRLLPVLCQDHGLTPDQVVAIASNGGGK
QALETVQRLLPVLCQDHGLTPEQVVAIASHDGGKQALETVQRLLPVLCQAHGLTPDQVVAIANNNGGKQALETVQRLL
PVLCQAHGLTPAQVVAIASNGGGKQALETVQRLLPVLCQDHGLTPDQVVAIANNNGGKQALETVQRLLPVLCQDHGL
TPEQVVAIASHDGGKQALETVQRLLPVLCQAHGLTPDQVVAIASNGGGKQALETVQRLLPVLCQAHGLTPAQVVAIAN
NNGGKQALETVQRLLPVLCQDHGLTPEQVVAIASHDGGRPALESIVAQLSRPDPALAALTNDHLVALACLGGRPALDA
VKKGLPHAPALIKRTNRRIPERTSHRVAGS
(SEQ ID NO:30)

FIG. 14A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGAACAATAATGGGGGAAAGCAAG
CCCTGGAAACCGTGCAAAGGTTGTTGCCGGTCCTTTGTCAAGACCACGGCCTTACACCGGAGCAAGTCGTGGCCA
TTGCAAGCAACATCGGTGGCAAACAGGCTCTTGAGACGGTTCAGAGACTTCTCCCAGTTCTCTGTCAAGCCCACGG
GCTGACTCCCGATCAAGTTGTAGCGATTGCGTCGAACATTGGAGGGAAACAAGCATTGGAGACTGTCCAACGGCT
CCTTCCCGTGTTGTGTCAAGCCCACGGTTTGACGCCTGCACAAGTGGTCGCCATCGCCAACAACAACGGCGGTAAG
CAGGCGCTGGAAACAGTACAGCGCCTGCTGCCTGTACTGTGCCAGGATCATGGACTGACCCCAGACCAGGTAGTC
GCAATCGCGTCGAACATTGGGGGAAAGCAAGCCCTGGAAACCGTGCAAAGGTTGTTGCCGGTCCTTTGTCAAGAC
CACGGCCTTACACCGGAGCAAGTCGTGGCCATTGCAAGCAACATCGGTGGCAAACAGGCTCTTGAGACGGTTCAG
AGACTTCTCCCAGTTCTCTGTCAAGCCCACGGGCTGACTCCCGATCAAGTTGTAGCGATTGCGAATAACAATGGAG
GGAAACAAGCATTGGAGACTGTCCAACGGCTCCTTCCCGTGTTGTGTCAAGCCCACGGTTTGACGCCTGCACAAGT
GGTCGCCATCGCCTCGAATGGCGGCGGTAAGCAGGCGCTGGAAACAGTACAGCGCCTGCTGCCTGTACTGTGCCA
GGATCATGGACTGACCCCAGACCAGGTAGTCGCAATCGCGTCACATGACGGGGAAAGCAAGCCCTGGAAACCG
TGCAAAGGTTGTTGCCGGTCCTTTGTCAAGACCACGGCCTTACACCGGAGCAAGTCGTGGCCATTGCAAATAATAA
CGGTGGCAAACAGGCTCTTGAGACGGTTCAGAGACTTCTCCCAGTTCTCTGTCAAGCCCACGGGCTGACTCCCGAT
CAAGTTGTAGCGATTGCGTCCAACGGTGGAGGGAAACAAGCATTGGAGACTGTCCAACGGCTCCTTCCCGTGTTG
TGTCAAGCCCACGGTTTGACGCCTGCACAAGTGGTCGCCATCGCCAACAACAACGGCGGTAAGCAGGCGCTGGAA
ACAGTACAGCGCCTGCTGCCTGTACTGTGCCAGGATCATGGACTGACCCCAGACCAGGTAGTCGCAATCGCGTCA
CATGACGGGGAAAGCAAGCCCTGGAAACCGTGCAAAGGTTGTTGCCGGTCCTTTGTCAAGACCACGGCCTTACA
CCGGAGCAAGTCGTGGCCATTGCAAGCAATGGGGGTGGCAAACAGGCTCTTGAGACGGTTCAGAGACTTCTCCCA
GTTCTCTGTCAAGCCCACGGGCTGACTCCCGATCAAGTTGTAGCGATTGCGAATAACAATGGAGGGAAACAAGCA
TTGGAGACTGTCCAACGGCTCCTTCCCGTGTTGTGTCAAGCCCACGGTTTGACGCCTGCACAAGTGGTCGCCATCG
CCAGCCATGATGGCGGTAAGCAGGCGCTGGAAACAGTACAGCGCCTGCTGCCTGTACTGTGCCAGGATCATGGAC
TGACACCCGAACAGGTGGTCGCCATTGCTTCTAATGGGGGAGGACGGCCAGCCTTGGAGTCCATCGTAGCCCAAT
TGTCCAGGCCCGATCCCGCGTTGGCTGCGTTAACGAATGACCATCTGGTGGCGTTGGCATGTCTTGGTGGACGAC
CCGCGCTCGATGCAGTCAAAAAGGGTCTGCCTCATGCTCCCGCATTGATCAAAAGAACCAACCGGCGGATTCCCG
AGAGAACTTCCCATCGAGTCGCGGGATCC
(SEQ ID NO:31)

FIG. 14B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIANNNGGKQALETVQRLLPVLCQDHGLTPEQVVAIASNIGGKQALET
VQRLLPVLCQAHGLTPDQVVAIASNIGGKQALETVQRLLPVLCQAHGLTPAQVVAIANNNGGKQALETVQRLLPVLCQ
DHGLTPDQVVAIASNIGGKQALETVQRLLPVLCQDHGLTPEQVVAIASNIGGKQALETVQRLLPVLCQAHGLTPDQVV
AIANNNGGKQALETVQRLLPVLCQAHGLTPAQVVAIASNGGGKQALETVQRLLPVLCQDHGLTPDQVVAIASHDGGK
QALETVQRLLPVLCQDHGLTPEQVVAIANNNGGKQALETVQRLLPVLCQAHGLTPDQVVAIASNGGGKQALETVQRL
LPVLCQAHGLTPAQVVAIANNNGGKQALETVQRLLPVLCQDHGLTPDQVVAIASHDGGKQALETVQRLLPVLCQDHG
LTPEQVVAIASNGGGKQALETVQRLLPVLCQAHGLTPDQVVAIANNNGGKQALETVQRLLPVLCQAHGLTPAQVVAIA
SHDGGKQALETVQRLLPVLCQDHGLTPEQVVAIASNGGGRPALESIVAQLSRPDPALAALTNDHLVALACLGGRPALD
AVKKGLPHAPALIKRTNRRIPERTSHRVAGS
(SEQ ID NO:32)

FIG. 15A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGAGTAACAGCGGTAGAGGCAGTGCACGCCTGGCGCAATGC
GCTCACCGGGGCCCCCTTGAACCTGACCCCAGACCAGGTAGTCGCAATCGCGTCACATGACGGGGGAAAGCAAGC
CCTGGAAACCGTGCAAAGGTTGTTGCCGGTCCTTTGTCAAGACCACGGCCTTACACCGGAGCAAGTCGTGGCCATT
GCAAATAATAACGGTGGCAAACAGGCTCTTGAGACGGTTCAGAGACTTCTCCCAGTTCTCTGTCAAGCCCACGGG
CTGACTCCCGATCAAGTTGTAGCGATTGCGTCGAACATTGGAGGGAAACAAGCATTGGAGACTGTCCAACGGCTC
CTTCCCGTGTTGTGTCAAGCCCACGGTTTGACGCCTGCACAAGTGGTCGCCATCGCCAACAACAACGGCGGTAAGC
AGGCGCTGGAAACAGTACAGCGCCTGCTGCCTGTACTGTGCCAGGATCATGGACTGACCCCAGACCAGGTAGTCG
CAATCGCGTCACATGACGGGGGAAAGCAAGCCCTGGAAACCGTGCAAAGGTTGTTGCCGGTCCTTTGTCAAGACC
ACGGCCTTACACCGGAGCAAGTCGTGGCCATTGCAAGCAATGGGGGTGGCAAACAGGCTCTTGAGACGGTTCAG
AGACTTCTCCCAGTTCTCTGTCAAGCCCACGGGCTGACTCCCGATCAAGTTGTAGCGATTGCGAATAACAATGGAG
GGAAACAAGCATTGGAGACTGTCCAACGGCTCCTTCCCGTGTTGTGTCAAGCCCACGGTTTGACGCCTGCACAAGT
GGTCGCCATCGCCTCCAATATTGGCGGTAAGCAGGCGCTGGAAACAGTACAGCGCCTGCTGCCTGTACTGTGCCA
GGATCATGGACTGACCCCAGACCAGGTAGTCGCAATCGCGTCGAACATTGGGGAAAGCAAGCCCTGGAAACCG
TGCAAAGGTTGTTGCCGGTCCTTTGTCAAGACCACGGCCTTACACCGGAGCAAGTCGTGGCCATTGCAAATAATAA
CGGTGGCAAACAGGCTCTTGAGACGGTTCAGAGACTTCTCCCAGTTCTCTGTCAAGCCCACGGGCTGACTCCCGAT
CAAGTTGTAGCGATTGCGAATAACAATGGAGGGAAACAAGCATTGGAGACTGTCCAACGGCTCCTTCCCGTGTTG
TGTCAAGCCCACGGTTTGACGCCTGCACAAGTGGTCGCCATCGCCAACAACAACGGCGGTAAGCAGGCGCTGGAA
ACAGTACAGCGCCTGCTGCCTGTACTGTGCCAGGATCATGGACTGACCCCAGACCAGGTAGTCGCAATCGCGTCA
CATGACGGGGGAAAGCAAGCCCTGGAAACCGTGCAAAGGTTGTTGCCGGTCCTTTGTCAAGACCACGGCCTTACA
CCGGAGCAAGTCGTGGCCATTGCAAGCAACATCGGTGGCAAACAGGCTCTTGAGACGGTTCAGAGACTTCTCCCA
GTTCTCTGTCAAGCCCACGGGCTGACTCCCGATCAAGTTGTAGCGATTGCGTCCAACGGTGGAGGGAAACAAGCA
TTGGAGACTGTCCAACGGCTCCTTCCCGTGTTGTGTCAAGCCCACGGTCTGACACCCGAACAGGTGGTCGCCATTG
CTTCCCACGACGGAGGACGGCCAGCCTTGGAGTCCATCGTAGCCCAATTGTCCAGGCCCGATCCCGCGTTGGCTG
CGTTAACGAATGACCATCTGGTGGCGTTGGCATGTCTTGGTGGACGACCCGCGCTCGATGCAGTCAAAAAGGGTC
TGCCTCATGCTCCCGCATTGATCAAAAGAACCAACCGGCGGATTCCCGAGAGAACTTCCCATCGAGTCGCGGGATC
C
(SEQ ID NO: 33)

FIG. 15B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIASHDGGKQALETVQRLLPVLCQDHGLTPEQVVAIANNNGGKQALE
TVQRLLPVLCQAHGLTPDQVVAIASNIGGKQALETVQRLLPVLCQAHGLTPAQVVAIANNNGGKQALETVQRLLPVLC
QDHGLTPDQVVAIASHDGGKQALETVQRLLPVLCQDHGLTPEQVVAIASNGGGKQALETVQRLLPVLCQAHGLTPDQ
VVAIANNNGGKQALETVQRLLPVLCQAHGLTPAQVVAIASNIGGKQALETVQRLLPVLCQDHGLTPDQVVAIASNIGG
KQALETVQRLLPVLCQDHGLTPEQVVAIANNNGGKQALETVQRLLPVLCQAHGLTPDQVVAIANNNGGKQALETVQR
LLPVLCQAHGLTPAQVVAIANNNGGKQALETVQRLLPVLCQDHGLTPDQVVAIASHDGGKQALETVQRLLPVLCQDH
GLTPEQVVAIASNIGGKQALETVQRLLPVLCQAHGLTPDQVVAIASNGGGKQALETVQRLLPVLCQAHGLTPEQVVAIA
SHDGGRPALESIVAQLSRPDPALAALTNDHLVALACLGGRPALDAVKKGLPHAPALIKRTNRRIPERTSHRVAGS
(SEQ ID NO:34)

FIG. 16A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGTCACATGACGGGGGAAAGCAAGC
CCTGGAAACCGTGCAAAGGTTGTTGCCGGTCCTTTGTCAAGACCACGGCCTTACACCGGAGCAAGTCGTGGCCATT
GCAAATAATAACGGTGGCAAACAGGCTCTTGAGACGGTTCAGAGACTTCTCCCAGTTCTCTGTCAAGCCCACGGG
CTGACTCCCGATCAAGTTGTAGCGATTGCGTCGAACATTGGAGGGAAACAAGCATTGGAGACTGTCCAACGGCTC
CTTCCCGTGTTGTGTCAAGCCCACGGTTTGACGCCTGCACAAGTGGTCGCCATCGCCAACAACAACGGCGGTAAGC
AGGCGCTGGAAACAGTACAGCGCCTGCTGCCTGTACTGTGCCAGGATCATGGACTGACCCCAGACCAGGTAGTCG
CAATCGCGTCACATGACGGGGGAAAGCAAGCCCTGGAAACCGTGCAAAGGTTGTTGCCGGTCCTTTGTCAAGACC
ACGGCCTTACACCGGAGCAAGTCGTGGCCATTGCAAGCAATGGGGGTGGCAAACAGGCTCTTGAGACGGTTCAG
AGACTTCTCCCAGTTCTCTGTCAAGCCCACGGGCTGACTCCCGATCAAGTTGTAGCGATTGCGAATAACAATGGAG
GGAAACAAGCATTGGAGACTGTCCAACGGCTCCTTCCCGTGTTGTGTCAAGCCCACGGTTTGACGCCTGCACAAGT
GGTCGCCATCGCCTCCAATATTGGCGGTAAGCAGGCGCTGGAAACAGTACAGCGCCTGCTGCCTGTACTGTGCCA
GGATCATGGACTGACCCCAGACCAGGTAGTCGCAATCGCGTCGAACATTGGGGGAAAGCAAGCCCTGGAAACCG
TGCAAAGGTTGTTGCCGGTCCTTTGTCAAGACCACGGCCTTACACCGGAGCAAGTCGTGGCCATTGCAAATAATAA
CGGTGGCAAACAGGCTCTTGAGACGGTTCAGAGACTTCTCCCAGTTCTCTGTCAAGCCCACGGGCTGACTCCCGAT
CAAGTTGTAGCGATTGCGAATAACAATGGAGGGAAACAAGCATTGGAGACTGTCCAACGGCTCCTTCCCGTGTTG
TGTCAAGCCCACGGTTTGACGCCTGCACAAGTGGTCGCCATCGCCAACAACAACGGCGGTAAGCAGGCGCTGGAA
ACAGTACAGCGCCTGCTGCCTGTACTGTGCCAGGATCATGGACTGACCCCAGACCAGGTAGTCGCAATCGCGTCA
CATGACGGGGGAAAGCAAGCCCTGGAAACCGTGCAAAGGTTGTTGCCGGTCCTTTGTCAAGACCACGGCCTTACA
CCGGAGCAAGTCGTGGCCATTGCAAGCAACATCGGTGGCAAACAGGCTCTTGAGACGGTTCAGAGACTTCTCCCA
GTTCTCTGTCAAGCCCACGGGCTGACTCCCGATCAAGTTGTAGCGATTGCGTCCAACGGTGGAGGGAAACAAGCA
TTGGAGACTGTCCAACGGCTCCTTCCCGTGTTGTGTCAAGCCCACGGTTTGACGCCTGCACAAGTGGTCGCCATCG
CCAGCCATGATGGCGGTAAGCAGGCGCTGGAAACAGTACAGCGCCTGCTGCCTGTACTGTGCCAGGATCATGGAC
TGACACCCGAACAGGTGGTCGCCATTGCTAATAATAACGGAGGACGGCCAGCCTTGGAGTCCATCGTAGCCCAAT
TGTCCAGGCCCGATCCCGCGTTGGCTGCGTTAACGAATGACCATCTGGTGGCGTTGGCATGTCTTGGTGGACGAC
CCGCGCTCGATGCAGTCAAAAAGGGTCTGCCTCATGCTCCCGCATTGATCAAAAGAACCAACCGGCGGATTCCCG
AGAGAACTTCCCATCGAGTCGCGGGATCC
(SEQ ID NO:35)

FIG. 16B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIASHDGGKQALETVQRLLPVLCQDHGLTPEQVVAIANNNGGKQALE
TVQRLLPVLCQAHGLTPDQVVAIASNIGGKQALETVQRLLPVLCQAHGLTPAQVVAIANNNGGKQALETVQRLLPVLC
QDHGLTPDQVVAIASHDGGKQALETVQRLLPVLCQDHGLTPEQVVAIASNGGGKQALETVQRLLPVLCQAHGLTPDQ
VVAIANNNGGKQALETVQRLLPVLCQAHGLTPAQVVAIASNIGGKQALETVQRLLPVLCQDHGLTPDQVVAIASNIGG
KQALETVQRLLPVLCQDHGLTPEQVVAIANNNGGKQALETVQRLLPVLCQAHGLTPDQVVAIANNNGGKQALETVQR
LLPVLCQAHGLTPAQVVAIANNNGGKQALETVQRLLPVLCQDHGLTPDQVVAIASHDGGKQALETVQRLLPVLCQDH
GLTPEQVVAIASNIGGKQALETVQRLLPVLCQAHGLTPDQVVAIASNGGGKQALETVQRLLPVLCQAHGLTPAQVVAIA
SHDGGKQALETVQRLLPVLCQDHGLTPEQVVAIANNNGGRPALESIVAQLSRPDPALAALTNDHLVALACLGGRPALD
AVKKGLPHAPALIKRTNRRIPERTSHRVAGS                    (SEQ ID NO:36)

FIG. 17A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGTCAAACGGAGGGGGAAAGCAAG
CCCTGGAAACCGTGCAAAGGTTGTTGCCGGTCCTTTGTCAAGACCACGGCCTTACACCGGAGCAAGTCGTGGCCA
TTGCAAATAATAACGGTGGCAAACAGGCTCTTGAGACGGTTCAGAGACTTCTCCCAGTTCTCTGTCAAGCCCACGG
GCTGACTCCCGATCAAGTTGTAGCGATTGCGTCCAACGGTGGAGGGAAACAAGCATTGGAGACTGTCCAACGGCT
CCTTCCCGTGTTGTGTCAAGCCCACGGTTTGACGCCTGCACAAGTGGTCGCCATCGCCAACAACAACGGCGGTAAG
CAGGCGCTGGAAACAGTACAGCGCCTGCTGCCTGTACTGTGCCAGGATCATGGACTGACCCCAGACCAGGTAGTC
GCAATCGCGTCACATGACGGGGGAAAGCAAGCCCTGGAAACCGTGCAAAGGTTGTTGCCGGTCCTTTGTCAAGAC
CACGGCCTTACACCGGAGCAAGTCGTGGCCATTGCATCCCACGACGGTGGCAAACAGGCTCTTGAGACGGTTCAG
AGACTTCTCCCAGTTCTCTGTCAAGCCCACGGGCTGACTCCCGATCAAGTTGTAGCGATTGCGTCGCATGACGGAG
GGAAACAAGCATTGGAGACTGTCCAACGGCTCCTTCCCGTGTTGTGTCAAGCCCACGGTTTGACGCCTGCACAAGT
GGTCGCCATCGCCAGCCATGATGGCGGTAAGCAGGCGCTGGAAACAGTACAGCGCCTGCTGCCTGTACTGTGCCA
GGATCATGGACTGACCCCAGACCAGGTAGTCGCAATCGCGTCGAACATTGGGGGAAAGCAAGCCCTGGAAACCG
TGCAAAGGTTGTTGCCGGTCCTTTGTCAAGACCACGGCCTTACACCGGAGCAAGTCGTGGCCATTGCAAATAATAA
CGGTGGCAAACAGGCTCTTGAGACGGTTCAGAGACTTCTCCCAGTTCTCTGTCAAGCCCACGGGCTGACTCCCGAT
CAAGTTGTAGCGATTGCGAATAACAATGGAGGGAAACAAGCATTGGAGACTGTCCAACGGCTCCTTCCCGTGTTG
TGTCAAGCCCACGGTTTGACGCCTGCACAAGTGGTCGCCATCGCCTCCAATATTGGCGGTAAGCAGGCGCTGGAA
ACAGTACAGCGCCTGCTGCCTGTACTGTGCCAGGATCATGGACTGACCCCAGACCAGGTAGTCGCAATCGCGTCA
AACGGAGGGGGAAAGCAAGCCCTGGAAACCGTGCAAAGGTTGTTGCCGGTCCTTTGTCAAGACCACGGCCTTAC
ACCGGAGCAAGTCGTGGCCATTGCAAATAATAACGGTGGCAAACAGGCTCTTGAGACGGTTCAGAGACTTCTCCC
AGTTCTCTGTCAAGCCCACGGGCTGACTCCCGATCAAGTTGTAGCGATTGCGTCCAACGGTGGAGGGAAACAAGC
ATTGGAGACTGTCCAACGGCTCCTTCCCGTGTTGTGTCAAGCCCACGGTTTGACGCCTGCACAAGTGGTCGCCATC
GCCTCGAATGGCGGCGGTAAGCAGGCGCTGGAAACAGTACAGCGCCTGCTGCCTGTACTGTGCCAGGATCATGG
ACTGACACCCGAACAGGTGGTCGCCATTGCTAATAATAACGGAGGACGGCCAGCCTTGGAGTCCATCGTAGCCCA
ATTGTCCAGGCCCGATCCCGCGTTGGCTGCGTTAACGAATGACCATCTGGTGGCGTTGGCATGTCTTGGTGGACG
ACCCGCGCTCGATGCAGTCAAAAAGGGTCTGCCTCATGCTCCCGCATTGATCAAAAGAACCAACCGGCGGATTCCC
GAGAGAACTTCCCATCGAGTCGCGGATCC          (SEQ ID NO:37)

FIG. 17B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIASNGGGKQALETVQRLLPVLCQDHGLTPEQVVAIANNNGGKQALE
TVQRLLPVLCQAHGLTPDQVVAIASNGGGKQALETVQRLLPVLCQAHGLTPAQVVAIANNNGGKQALETVQRLLPVLC
QDHGLTPDQVVAIASHDGGKQALETVQRLLPVLCQDHGLTPEQVVAIASHDGGKQALETVQRLLPVLCQAHGLTPDQ
VVAIASHDGGKQALETVQRLLPVLCQAHGLTPAQVVAIASHDGGKQALETVQRLLPVLCQDHGLTPDQVVAIASNIGG
KQALETVQRLLPVLCQDHGLTPEQVVAIANNNGGKQALETVQRLLPVLCQAHGLTPDQVVAIANNNGGKQALETVQR
LLPVLCQAHGLTPAQVVAIASNIGGKQALETVQRLLPVLCQDHGLTPDQVVAIASNGGGKQALETVQRLLPVLCQDHG
LTPEQVVAIANNNGGKQALETVQRLLPVLCQAHGLTPDQVVAIASNGGGKQALETVQRLLPVLCQAHGLTPAQVVAIA
SNGGGKQALETVQRLLPVLCQDHGLTPEQVVAIANNNGGRPALESIVAQLSRPDPALAALTNDHLVALACLGGRPALD
AVKKGLPHAPALIKRTNRRIPERTSHRVAGS          (SEQ ID NO:38)

FIG. 18A

TCTAGAGCTAGCACCATGGACTACAAAGACCATGACGGTGATTATAAAGATCATGACATCGATTACAAGGATGAC
GATGACAAGATGGCCCCCAAGAAGAAGAGGAAGGTGGGCATTCACCGCGGGGTACCTATGGTGGACTTGAGGAC
ACTCGGTTATTCGCAACAGCAACAGGAGAAAATCAAGCCTAAGGTCAGGAGCACCGTCGCGCAACACCACGAGG
CGCTTGTGGGGCATGGCTTCACTCATGCGCATATTGTCGCGCTTTCACAGCACCCTGCGGCGCTTGGGACGGTGGC
TGTCAAATACCAAGATATGATTGCGGCCCTGCCCGAAGCCACGCACGAGGCAATTGTAGGGGTCGGTAAACAGTG
GTCGGGAGCGCGAGCACTTGAGGCGCTGCTGACTGTGGCGGGTGAGCTTAGGGGGCCTCCGCTCCAGCTCGACA
CCGGGCAGCTGCTGAAGATCGCGAAGAGAGGGGGAGTAACAGCGGTAGAGGCAGTGCACGCCTGGCGCAATGC
GCTCACCGGGGCCCCCTTGAACCTGACCCCAGACCAGGTAGTCGCAATCGCGAACAATAATGGGGGAAAGCAAG
CCCTGGAAACCGTGCAAAGGTTGTTGCCGGTCCTTTGTCAAGACCACGGCCTTACACCGGAGCAAGTCGTGGCCA
TTGCAAGCAATGGGGGTGGCAAACAGGCTCTTGAGACGGTTCAGAGACTTCTCCCAGTTCTCTGTCAAGCCCACG
GGCTGACTCCCGATCAAGTTGTAGCGATTGCGAATAACAATGGAGGGAAACAAGCATTGGAGACTGTCCAACGGC
TCCTTCCCGTGTTGTGTCAAGCCCACGGTTTGACGCCTGCACAAGTGGTCGCCATCGCCAGCCATGATGGCGGTAA
GCAGGCGCTGGAAACAGTACAGCGCCTGCTGCCTGTACTGTGCCAGGATCATGGACTGACCCCAGACCAGGTAGT
CGCAATCGCGTCACATGACGGGGGAAAGCAAGCCCTGGAAACCGTGCAAAGGTTGTTGCCGGTCCTTTGTCAAGA
CCACGGCCTTACACCGGAGCAAGTCGTGGCCATTGCATCCCACGACGGTGGCAAACAGGCTCTTGAGACGGTTCA
GAGACTTCTCCCAGTTCTCTGTCAAGCCCACGGGCTGACTCCCGATCAAGTTGTAGCGATTGCGTCGCATGACGGA
GGGAAACAAGCATTGGAGACTGTCCAACGGCTCCTTCCCGTGTTGTGTCAAGCCCACGGTTTGACGCCTGCACAA
GTGGTCGCCATCGCCTCCAATATTGGCGGTAAGCAGGCGCTGGAAACAGTACAGCGCCTGCTGCCTGTACTGTGC
CAGGATCATGGACTGACCCCAGACCAGGTAGTCGCAATCGCGAACAATAATGGGGGAAAGCAAGCCCTGGAAAC
CGTGCAAAGGTTGTTGCCGGTCCTTTGTCAAGACCACGGCCTTACACCGGAGCAAGTCGTGGCCATTGCAAATAAT
AACGGTGGCAAACAGGCTCTTGAGACGGTTCAGAGACTTCTCCCAGTTCTCTGTCAAGCCCACGGGCTGACTCCCG
ATCAAGTTGTAGCGATTGCGTCGAACATTGGAGGGAAACAAGCATTGGAGACTGTCCAACGGCTCCTTCCCGTGT
TGTGTCAAGCCCACGGTTTGACGCCTGCACAAGTGGTCGCCATCGCCTCGAATGGCGGCGGTAAGCAGGCGCTGG
AAACAGTACAGCGCCTGCTGCCTGTACTGTGCCAGGATCATGGACTGACCCCAGACCAGGTAGTCGCAATCGCGA
ACAATAATGGGGGAAAGCAAGCCCTGGAAACCGTGCAAAGGTTGTTGCCGGTCCTTTGTCAAGACCACGGCCTTA
CACCGGAGCAAGTCGTGGCCATTGCAAGCAATGGGGGTGGCAAACAGGCTCTTGAGACGGTTCAGAGACTTCTCC
CAGTTCTCTGTCAAGCCCACGGGCTGACTCCCGATCAAGTTGTAGCGATTGCGTCCAACGGTGGAGGGAAACAAG
CATTGGAGACTGTCCAACGGCTCCTTCCCGTGTTGTGTCAAGCCCACGGTTTGACGCCTGCACAAGTGGTCGCCAT
CGCCAACAACAACGGCGGTAAGCAGGCGCTGGAAACAGTACAGCGCCTGCTGCCTGTACTGTGCCAGGATCATG
GACTGACACCCGAACAGGTGGTCGCCATTGCTTCCCACGACGGAGGACGGCCAGCCTTGGAGTCCATCGTAGCCC
AATTGTCCAGGCCCGATCCCGCGTTGGCTGCGTTAACGAATGACCATCTGGTGGCGTTGGCATGTCTTGGTGGAC
GACCCGCGCTCGATGCAGTCAAAAAGGGTCTGCCTCATGCTCCCGCATTGATCAAAAGAACCAACCGGCGGATTC
CCGAGAGAACTTCCCATCGAGTCGCGGGATCC         (SEQ ID NO:39)

FIG. 18B

MDYKDHDGDYKDHDIDYKDDDDKMAPKKKRKVGIHRGVPMVDLRTLGYSQQQQEKIKPKVRSTVAQHHEALVGHG
FTHAHIVALSQHPAALGTVAVKYQDMIAALPEATHEAIVGVGKQWSGARALEALLTVAGELRGPPLQLDTGQLLKIAKR
GGVTAVEAVHAWRNALTGAPLNLTPDQVVAIANNNGGKQALETVQRLLPVLCQDHGLTPEQVVAIASNGGGKQALE
TVQRLLPVLCQAHGLTPDQVVAIANNNGGKQALETVQRLLPVLCQAHGLTPAQVVAIASHDGGKQALETVQRLLPVLC
QDHGLTPDQVVAIASHDGGKQALETVQRLLPVLCQDHGLTPEQVVAIASHDGGKQALETVQRLLPVLCQAHGLTPDQ
VVAIASHDGGKQALETVQRLLPVLCQAHGLTPAQVVAIASNIGGKQALETVQRLLPVLCQDHGLTPDQVVAIANNNGG
KQALETVQRLLPVLCQDHGLTPEQVVAIANNNGGKQALETVQRLLPVLCQAHGLTPDQVVAIASNIGGKQALETVQRL
LPVLCQAHGLTPAQVVAIASNGGGKQALETVQRLLPVLCQDHGLTPDQVVAIANNNGGKQALETVQRLLPVLCQDHG
LTPEQVVAIASNGGGKQALETVQRLLPVLCQAHGLTPDQVVAIASNGGGKQALETVQRLLPVLCQAHGLTPAQVVAIA
NNNGGKQALETVQRLLPVLCQDHGLTPEQVVAIASHDGGRPALESIVAQLSRPDPALAALTNDHLVALACLGGRPALD
AVKKGLPHAPALIKRTNRRIPERTSHRVAGS            (SEQ ID NO:40)

| SEQUENCE | Δ SIZE | SEQ ID NO: |
|---|---|---|
| AXIN2 | | |
| TAL2200/TAL2201 | | |
| Mutations in 2 of 83 sequences ≈ 2.4% | | |
| TTCCAGACTCAGTGGGAAGAGAGCTCCCTCACCTGAGTAGCGCTATGTTGGTGACTTGCCTCCCGGACCCCAGCAGCAGCTTCCGTGA | WT | 301. |
| TTCCAGACTCAGTGGGAAGAGAGCTCCCTCACCATGA---------TTGCCTCCCGGACCCCAGCAGCAGCTTCCGTGA | Δ8 | 302. |
| TTCCAGACTCAGTGGGAAGAGAGCTCCCTCA-------------------------------CCCGGACCCCAGCAGCAGCTTCCGTGA | Δ31 | 303. |
| BRCA1 | | |
| TAL2384/TAL2385 | | |
| Mutations in 7 of 14 sequences ≈ 50.0% | | |
| GGCGTGGGAGAGTGGATTTCCGAAGCTGACAGATGGTATTCTTTTGACGGGGGTAGGGCGGAACCTGAGAGGCGTAAGGCGTTGTG | WT | 304. |
| GGCGTGGGAGAGTGGATTTCCGAAGCTGACAGAT-----------------GGGTAGGGCGGAACCTGAGAGGCGTAAGGCGTTGTG | Δ17 | 305. |
| GGCGTGGGAGAGTGGATTTCCGAAGCTGACAGA-----------------------GGGGCGGAACCTGAGAGGCGTAAGGCGTTGTG | Δ23 | 306. |
| GGCGTGGGAGAGTGGATTTCCGAAGCTGACAGA---------------------------GGAACCTGAGAGGCGTAAGGCGTTGTG | Δ27 | 307. |
| GGCGTGGGAGAGTGGATTTCCGAAGCTGACAGATG-------------------------------GGTAAGGCGTTGTG | Δ38 | 308. |
| GGCGTGGGAGAGTGGATTTCCGAAGCTGACAGATG--------------------------------GGTAAGGCGTTGTG | Δ39 | 309. |
| AGTGGATTTCCGAAGCTGACAGATG------/-------tgtgaagaagaGGCTGGTCATGAGGTCAGGAGTCC | Δ183 (Δ193 +10) | 310. |
| CGCTCAGGAGGCCTTCACCCTCTGCTCGGGTAAAGG-----/-------AACTGGAATATGCCTTGAGGGGG | Δ235 | 311. |
| CHD7 | | |
| TAL2238/TAL2239 | | |
| Mutations in 4 of 81 sequences ≈ 4.9% | | |
| CCTGAGCTGTGGTTTGGAGGAGCCGTGTTGTTGGAAGAAGAATGATGAGTCTTTTTGGCGAGGATGGGAATATTT | WT | 312. |
| CCTGAGCTGTGGTTTGGAGGAGCCGTGTGTTGTTGGAAGAAGATCa-------GAATGATGAGTCTTTTTGGCGAGGATGGGAATATTT | Δ9 (Δ11 +2) | 313. |
| CCTGAGCTGTGGTTTGGAGGAGCCGTGTTGTTGGAAGAAGATG-------GAATGATGAGTCTTTTTGGCGAGGATGGGAATATTT | Δ10 | 314. |
| CCTGAGCTGTGGTTTGGAGGAGCCGTGTTGTTGGAAGAAGAT---------------------GGCGAGGATGGGAATATTT | Δ28 | 315. |
| TAAAGAAATATGGAATGACAT--------/------AAAATCCAGTAAATCCTATG | Δ199 | 316. |

FIG. 21A

CDC73
TAL2202/TAL2203
Mutations in 9 of 37 sequences ≈ 24.3%

| SEQUENCE | Δ SIZE | SEQ ID NO: |
|---|---|---|
| GAGGGGGGGGAAGATGCGGACGTGCTTAGCGTCCTGCGACAGTACAACATCCAGAAGAAGGAGATTGTGGTGAAGGGAGACGAAGTG | WT | 317. |
| GAGGGGGGGGAAGATGCGGACGTGCTTAGCGTCCTGCGACAGTACA-------GAAGAAGGAGATTGTGGTGAAGGGAGACGAAGTG | Δ7 | 318. |
| GAGGGGGGGGAAGATGGCGGACGTGCTTAGCGTCCTGCGACAGTACAAC------GAAGAAGGAGATTGTGGTGAAGGGAGACGAAGTG | Δ8 | 319. |
| GAGGGGGGGGAAGATGGCGGACGTGCTTAGCGTCCTGCGACA-------TCCAGAAGAAGGAGATTGTGGTGAAGGGAGACGAAGTG | Δ8 | 320. |
| GAGGGGGGGGAAGATGGCGGACGTGCTGCTTAGCGTCCTGCGACAG-------AAGAAGGAGATTGTGGTGAAGGGAGACGAAGTG | Δ12 (2x) | 321. |
| GAGGGGGGGGAAGATGGCGGACGTGCCTGCTTAGCGTCCTGCGACAGT--------ATTGTGGTGAAGGGAGACGAAGTG | Δ20 | 322. |
| GAGGGGGGGGAAGATGGCGGACGTGCTTAGCGTCCTGCGACAG-------TTGTGGTGAAGGGAGACGAAGTG | Δ22 | 323. |
| GAGGGGGGGGAAGAATGGCGGACGTGCTGCTTAGCGTCCTGCGACAGTACCAACATCCAGAAGAAGGAGATTGTGGTGAAGGGAGACGAA | +3 | 324. |
| AGGGGCGAGGCGACAAGAAGAAGAAGAAGGAGGCAGG---------/---------ATTGTGTGAAGGGAGACGAAGTG | Δ101 | 325. |

CYLD
TAL2386/TAL2387
Mutations in 10 of 44 ≈ 22.7%

| SEQUENCE | Δ SIZE | SEQ ID NO: |
|---|---|---|
| TTAGTATTTGAAGTTAATATCACATGGTTCAGCTTATGGAGCCAAGAAAAAGTCACTTCACCCTACTGGGAAGAGAGCGGATTTTT | WT | 326. |
| TTAGTATTTGAAGTTAATATCACATCACAA--------AAGTCACTTCACCCTACTGGGAAGAGCGGATTTTT | Δ9 | 327. |
| TTAGTATTTGAAGTTAATATCACATCACAA-------------------GTCACTTCACCCTACTGGGAAGAGCGGATTTTT | Δ29 | 328. |
| TTAGTATTTGAAGTTAATATCACAATA-----------------TCACCCTACTGGGAAGAGCGGATTTTT | Δ41 | 329. |
| TTAGTATTTGAAGTTAATA----------------------------CCCTACTGGGAAGAGCGGATTTTT | Δ48 | 330. |
| T----------------------------------AAGTCACTTCACCCTACTGGGAAGAGAGCGGATTTTT | Δ52 | 331. |
| TTAGTATT-----------------------------------CCCTACTGGGAAGAGCGGATTTTT | Δ55 | 332. |
| TTAGTATTTGAAGTT--------------------------------GAAGAGCGGATTTTT | Δ57 | 333. |
| TTAGTATTTGAA-----------------------------------CGGATTTTT | Δ66 | 334. |
| TTAG------------------------------------- | Δ84 | 335. |
| TAATATCACAATGAGTTCtcagggcacaccaggcccaggggaccaccaggccctgggtaagcatgcagtccaggtggacatcagg tgccaggggAAAAGTCACTTCACCCTA | +62 (Δ18 + 80) | 336. |

FIG. 21B

| SEQUENCE | Δ SIZE | SEQ ID NO: |
|---|---|---|
| NCOR2 | | |
| TAL2284/TAL2285 | | |
| Mutations in 7 of 88 ≈ 8.0% | | |
| TCCACACAGCCTGTGGCACAGACGTGGAGGGCCACTGAGCCCGCTACCCGCCCACAGCCTTTCCTACCCAGTGCAGATGCCCGGA | WT | 337. |
| TCCACACAGCCTGTGGCACAGACGTGGAGGGCCACTGAGCCCGCTA-CCGCCCACAGCCCTTTCCTACCCAGTGCAGATGCCCGGA | Δ1 | 338. |
| TCCACACAGCCTGTGGCACAGACGTGGAGGGCCACTGAGCCCGC--------CCCACAGCCTTTCCTACCCAGTGCAGATGCCCGGA | Δ7 | 339. |
| TCCACACAGCCTGTGGCACAGACGTGGAGGGCCACTGAGC------------CCCACAGCCTTTCCTACCCAGTGCAGATGCCCGGA | Δ12 | 340. |
| TCCACAC--------------------------------------------------------------AGATGCCCGGA | Δ69 | 341. |
| CCCCACCACC----------------------/--------------TTTCCTACCCAGTGCAGATGCCCGGA | Δ70 | 342. |
| GCTTATTGCGGC----------------/-----------CTTTCTCCTGGGAGCCAGGCT | Δ213 | 343. |
| TCCACACAGCCTGTGGCACAGACGTGGAGGGCCACTGAGCCCGCCCCACAGCCTTTCCTACCCAGTGCAGATCGCCC | +3 | 344. |
| JAK2 | | |
| TAL2406/TAL2407 | | |
| Mutations in 13 of 21 sequences ≈ 61.9% | | |
| TTTCTCTTACAGGCAAATGTTCTGAAAAAGACTCTGC[ATG]GAATGGCCTGCCTTACGATGACAGAAATGGAGGGAACATCCACCTCT | WT | 345. |
| TTTCTCTTACAGGCAAATGTTCTGAAAAAGACTCTGCATG-----GGGCCTGCCTTACGATGACAGAAATGGAGGGAACATCCACCTCT | Δ4 | 346. |
| TTTCTCTTACAGGCAAATGTTCTGAAAAAGACTCTGCATG--------GGCCTGCCTTACGATGACAGAAATGGAGGGAACATCCACCTCT | Δ5 | 347. |
| TTTCTCTTACAGGCAAATGTTCTGAAAAAGACTCTGCATG----------GCCTGCCTTACGATGACAGAAATGGAGGGAACATCCACCTCT | Δ6 | 348. |
| TTTCTCTTACAGGCAAATGTTCTGAAAAAGACTCTGCA--------TTACGATGACAGAAATGGAGGGAACATCCACCTCT | Δ8 | 349. |
| TTTCTCTTACAGGCAAATGTTCTGAAAAAGACTCTGC--------------GCCTGCCTTACGATGACAGAAATGGAGGGAACATCCACCTCT | Δ15 (2x) | 350. |
| TTTCTCTTACAGGCAAATGTTCTGAAAAAGACTCTGCATGGG--------------------AATGACAGAAATGGAGGGAACATCCACCTCT | Δ24 | 351. |
| TTTCTCTTACAGGCAAATGTTCTGAAAAAGACTCTGCAC------------------------GATGACAGAAATGGAGGGAACATCCACCTCT | Δ25 | 352. |
| TTTCTCTTACAGGCAAATGTTCTGAAAAAGACTCTG--------------------------CAGAAATGGAGGGAACATCCACCTCT | Δ26 | 353. |
| TTTCTCTTACAGGC------------------------------------------ATGGAGGGAACATCCACCTCT | Δ53 | 354. |
| T-----------------------------------------------------ACGATGACAGAAATGGAGGGAACATCCACCTCT | Δ54 | 355. |
| TTTCTCTTACAGGCAAATGTTCTGAAAAAGACTCTGCATGG-------agtaagtCTTACGATGACAGAAATGGAGGGAACATCCACCTCT | Δ4 (Δ11 +7) | 356. |
| CGGAGGTTTGCTGCAaacagagaaatt------------/--------CGATGACAGAAATGGAGGGAACATCCACCTCT | Δ288 (Δ301 +13) | 357. |

FIG. 21C

| SEQUENCE | Δ SIZE | SEQ ID NO: |
|---|---|---|
| MYCN TAL2280/TAL2281 Mutations in 12 of 35 sequences ≈ 34.3% | | |
| CGGGAGGCGAGCCGGAGCTGCTCGAGCGTCGGGCCATGCCGGGGCCATGATCTGAAGAACCCAGAGACCTCGAGTTTGACTCGCTACA | WT | 358 |
| CGGGAGGCGAGCCGGAGCTGCTCGAGCGTCGGG------CGCATGATCTGCAGAACCCAGAGACCTCGAGTTTGACTCGCTACA | Δ6 (Δ8 +2) | 359 |
| CGGGAGGCGAGCCGATGCCGAGCTGCTCGTCCACGTC--------CGGGCATGATCTGCAGAACCCAGAGACCTCGAGTTTGACTCGCTACA | Δ8 | 360 |
| CGGGAGGCGAGCCGATGCCGAGCTGCTCGTCCACGTC----------ATCTGCAAGAACCCAGAGACCTCGAGTTTGACTCGCTACA | Δ10 | 361 |
| CGGGAGGCGAGCCGAGCCGAGCTGCTCCAGCGTCCACCAT-----------CTGCAAGAACCCAGAGACCTCGAGTTTGACTCGCTACA | Δ11 | 362 |
| CGGGAGGCGAGCCGAGCCGATGCCGAGCTGCTCCACGTCCA------------TGATCTGCAAGAACCCAGAGACCTCGAGTTTGACTCGCTACA | Δ12 | 363 |
| CGGGAGGCGAGCCGAGCCGATGCCGAGCTGCTGTCCACGTCCAC-------------CAAGAACCCAGAGACCTCGAGTTTGACTCGCTACA | Δ18 | 364 |
| CGGGAGGCGAGCCGAGCCGATGCCGAGCTGCTC---------------ATGATCTGCAAGAACCCAGAGACCTCGAGTTTGACTCGCTACA | Δ19 | 365 |
| AAGGAAGCACCCCGGTCTTAA----------------------------------AGACCTCGAGTTTGACTCGCTACA | Δ100 | 366 |
| AGTGTTGGAGGTCGGCGCGCCCCCG-------------------------------GGCATGATCTGCAAGAACCCAGACCTCGAGTTT | Δ122 | 367 |
| AAGGAAGCACCCCGGTATTAA--------------------------------------ACGAAGATGACT | Δ141 | 368 |
| GAGGCCGAGCCGATGCCGAGCCGATGCCGATCTGGTGACGCTGCTCCAGTTGCAGGGAGAGGCGGCCTCTCCCGGCGACCCCTCTCCGCGGCGC CCCTGCCATTTCCCGGGAACACAGGGCTCAGCCCCCCTTTGTTAGTGCTCGTATGTCTTGCCTGGGAGCATTTGAGGCAGTGCTAGG GGCAGAGAGGTCCTGTTTCCCCCAAGTCTTGATCTGCAAGAACCCA | +160 (Δ29 +189) (2x) | 369 |
| NBN TAL2408/TAL2409 Mutations in 12 of 20 sequences ≈ 60% | | |
| TGCACGTCGGCTCGGCCCAGCTCGAGGAGCCTGAGCCGGACCGATTGGAAACTCTGCTGCCCGGCGGGCCCGGCAGGAGGTAAGGGCAGAAGGGAA | WT | 370 |
| TGCACGTCGGCTCGGCCCAGCTCCAGCCTCCAGCCCGGACCGATGTCGG-----GCTGCCCGCCTCGGCCAGGAGGTAAGGGCAGGAGGGCAGAAGGGAA | Δ5 | 371 |
| TGCACGTCGGCTCGGCCCAGCTCGAGCCCCAGCCCGGACCGATGTG--------CTGCCCGCCGCGGGCCGGCAGGAGGTAAGGGCAGGAGGGCAGAAGGGAA | Δ7 | 372 |
| TGCACGTCGGCTCGGCCCAGCTCGAGCCCCAGCCTGAGGAGCCGGACGACGATGTGGAAACTG-----GCCCGGCAGGAGGTAAGGGCAGGAGGGCAGAAGGGAA | Δ13 | 373 |
| TGCACGTCGGCTCGGCCCAGCTCGAGCCCCAGCCCGGACCGGACCGATGTGACT-----CCCGGCGGGCCGGCAGGAGGTAAGGGCAGGAGGGCAGAAGGGAA | Δ17 (Δ19 and +2) | 374 |
| TGCACGTCGGCTCGGCCCAGCTCGAGCCCCAGCCCGGACCGATGTGA-------------CCCGGCGGGCCCGGCAGGAGGTAAGGGCAGGAGGGCAGAAGGGAA | Δ19 | 375 |
| TGCACGTCGGCTCGGCCCAGCTCGAGCCCCAGCCCGGACCGATGTG-----------------CAGGAGGTAAGGGCAGGAGGGCAGAAGGGAA | Δ28 | 376 |
| TGCACGTCGGCTCGGCCCAGCTCGAGCCCCAGCCCGGACCGATGTGAAA-------------GTAAGGGCAGGAGGGCAGAAGGGAA | Δ28 | 377 |
| TGCACGTCGGCTCGGCCCAGCTCGAGCCCCAGCCCGGACCGGACCG-------------------GCAGGAGGTAAGGGCAGGAGGGCAGAAGGGAA | Δ30 | 378 |
| TGCACGTCGGCTCGGCCCAGCTCGAGCCCCAGCCCGGACCGGA-----------------------AGGAGGAGGTAAGGGCAGGAGGGCAGAAGGGAA | Δ35 | 379 |
| TGCACGTCGGCTCGGCCC-----------------------------------CCGCGCGGGCCCGGCAGGAGGTAAGGGCAGGAGGGCAGAAGGGAA | Δ39 | 380 |
| TGCACGTCGGCTCGGCCCCAGCC----------------------------------GGCAGGAGGTAAGGGCAGGAGGGCAGAAGGGAA | Δ45 | 381 |
| GCTCCCCGGGAGCGCGCACGTCCCGGAGCCCAT--------------------------GCCTGCGGGTGATTCCTGCG | Δ183 | 382 |

SEQUENCE LISTING

<160> NUMBER OF SEQ ID NOS: 439

<210> SEQ ID NO 1
<211> LENGTH: 2710
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tatcggatcc cgggcccgtc gactgcagag gcctgcatgc aagcttggcg    480
taatcatggt catagctgtt tcctgtgtga aattgttatc cgctcacaat tccacacaac    540
atacgagccg gaagcataaa gtgtaaagcc tggggtgcct aatgagtgag ctaactcaca    600
ttaattgcgt tgcgctcact gcccgctttc cagtcgggaa acctgtcgtg ccagctgcat    660
taatgaatcg gccaacgcgc ggggagaggc ggtttgcgta ttgggcgctc ttccgcttcc    720
tcgctcactg actcgctgcg ctcggtcgtt cggctgcggc gagcggtatc agctcactca    780
aaggcggtaa tacggttatc cacagaatca ggggataacg caggaaagaa catgtgagca    840
aaaggccagc aaaaggccag gaaccgtaaa aaggccgcgt tgctggcgtt tttccatagg    900
ctccgccccc ctgacgagca tcacaaaaat cgacgctcaa gtcagaggtg gcgaaacccg    960
acaggactat aaagatacca ggcgtttccc cctggaagct ccctcgtgcg ctctcctgtt   1020
ccgaccctgc cgcttaccgg atacctgtcc gcctttctcc cttcgggaag cgtggcgctt   1080
tctcatagct cacgctgtag gtatctcagt tcggtgtagg tcgttcgctc caagctgggc   1140
tgtgtgcacg aaccccccgt tcagcccgac cgctgcgcct tatccggtaa ctatcgtctt   1200
gagtccaacc cggtaagaca cgacttatcg ccactggcag cagccactgg taacaggatt   1260
agcagagcga ggtatgtagg cggtgctaca gagttcttga agtggtggcc taactacggc   1320
tacactagaa gaacagtatt tggtatctgc gctctgctga agccagttac cttcggaaaa   1380
agagttggta gctcttgatc cggcaaacaa accaccgctg gtagcggtgg tttttttgtt   1440
tgcaagcagc agattacgcg cagaaaaaaa ggatctcaag aagatccttt gatcttttct   1500
acggggtctg acgctcagtg gaacgaaaac tcacgttaag ggattttggt catgagatta   1560
tcaaaaagga tcttcaccta gatccttttaa aattaaaaat gaagttttaa atcaatctaa   1620
agtatatatg agtaaacttg gtctgacagt taccaatgct taatcagtga ggcacctatc   1680
tcagcgatct gtctatttcg ttcatccata gttgcctgac tccccgtcgt gtagataact   1740
acgatacggg agggcttacc atctggcccc agtgctgcaa tgataccgcg agagccacgc   1800
tcaccggctc cagatttatc agcaataaac cagccagccg gaagggccga gcgcagaagt   1860
ggtcctgcaa ctttatccgc ctccatccag tctattaatt gttgccggga agctagagta   1920
agtagttcgc cagttaatag tttgcgcaac gttgttgcca ttgctacagg catcgtggtg   1980
tcacgctcgt cgtttggtat ggcttcattc agctccggtt cccaacgatc aaggcgagtt   2040
acatgatccc ccatgttgtg caaaaaagcg gttagctcct tcggtcctcc gatcgttgtc   2100
agaagtaagt tggccgcagt gttatcactc atggttatgg cagcactgca taattctctt   2160
actgtcatgc catccgtaag atgcttttct gtgactggtg agtactcaac caagtcattc   2220
tgagaatagt gtatgcggcg accgagttgc tcttgcccgg cgtcaatacg ggataatacc   2280
gcgccacata gcagaacttt aaaagtgctc atcattggaa aacgttcttc ggggcgaaaa   2340
ctctcaagga tcttaccgct gttgagatcc agttcgatgt aacccactcg tgcacccaac   2400
tgatcttcag catcttttac tttcaccagc gtttctgggt gagcaaaaac aggaaggcaa   2460
aatgccgcaa aaaagggaat aagggcgaca cggaaatgtt gaatactcat actcttcctt   2520
tttcaatatt attgaagcat ttatcagggt tattgtctca tgagcggata catatttgaa   2580
tgtatttaga aaaataaaca ataggggtt ccgcgcacat ttccccgaaa agtgccacct   2640
```

```
gacgtctaag aaaccattat tatcatgaca ttaacctata aaataggcg tatcacgagg    2700 cccttccgtc                                                         2710
```

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 6
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ctgaccccag accaggtagt cgcaatcgcg tcgaacattg ggggaaagca agccctggaa      60
accgtgcaaa ggttgttgcc ggtcctttgt caagaccacg gc                        102

<210> SEQ ID NO 7
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cttacaccgg agcaagtcgt ggccattgca agcaacatcg gtggcaaaca ggctcttgag      60
acggttcaga gacttctccc agttctctgt caagcccacg gg                        102

<210> SEQ ID NO 8
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ctgactcccg atcaagttgt agcgattgcg tcgaacattg gagggaaaca agcattggag      60
actgtccaac ggctccttcc cgtgttgtgt caagcccacg gt                        102

<210> SEQ ID NO 9
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ttgacgcctg cacaagtggt cgccatcgcc tccaatattg gcggtaagca ggcgctggaa      60
acagtacagc gcctgctgcc tgtactgtgc caggatcatg ga                        102

<210> SEQ ID NO 10
<211> LENGTH: 3269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1483)..(1491)
<223> OTHER INFORMATION: a, c, t, g, unknown or other

<400> SEQUENCE: 10
gacggatcgg gagatctccc gatcccctat ggtcgactct cagtacaatc tgctctgatg      60

-continued

| | |
|---|---|
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| accatggact acaaagacca tgacggtgat tataaagatc atgacatcga ttacaaggat | 960 |
| gacgatgaca agatggcccc caagaagaag aggaaggtgg gcattcaccg cggggtacct | 1020 |
| atggtggact tgaggacact cggttattcg caacagcaac aggagaaaat caagcctaag | 1080 |
| gtcaggagca ccgtcgcgca acaccacgag gcgcttgtgg ggcatggctt cactcatgcg | 1140 |
| catattgtcg cgctttcaca gcaccctgcg gcgcttggga cggtggctgt caaataccaa | 1200 |
| gatatgattg cggccctgcc cgaagccacg cacgaggcaa ttgtaggggt cggtaaacag | 1260 |
| tggtcgggag cgcgagcact tgaggcgctg ctgactgtgg cgggtgagct tagggggcct | 1320 |
| ccgctccagc tcgacaccgg gcagctgctg aagatcgcga agagaggggg agtaacagcg | 1380 |
| gtagaggcag tgcacgcctg gcgcaatgcg ctcaccgggg ccccttgaa cagagacgat | 1440 |
| taatgcgtct cgctgacacc cgaacaggtg gtcgccattg ctnnnnnnnn nggaggacgg | 1500 |
| ccagccttgg agtccatcgt agcccaattg tccaggcccg atcccgcgtt ggctgcgtta | 1560 |
| acgaatgacc atctggtggc gttggcatgt cttggtggac gacccgcgct cgatgcagtc | 1620 |
| aaaaagggtc tgcctcatgc tcccgcattg atcaaaagaa ccaaccggcg gattcccgag | 1680 |
| agaacttccc atcgagtcgc gggatcccaa ctagtcaaaa gtgaactgga ggagaagaaa | 1740 |
| tctgaacttc gtcataaatt gaaatatgtg cctcatgaat atattgaatt aattgaaatt | 1800 |
| gccagaaatt ccactcagga tagaattctt gaaatgaagg taatggaatt ttttatgaaa | 1860 |
| gtttatggat atagaggtaa acatttgggt ggatcaagga aaccggacgg agcaatttat | 1920 |
| actgtcggat ctcctattga ttacggtgtg atcgtggata ctaaagctta tagcggaggt | 1980 |
| tataatctgc caattggcca agcagatgaa atgcaacgat atgtcgaaga aaatcaaaca | 2040 |
| cgaaacaaac atatcaaccc taatgaatgg tggaaagtct atccatcttc tgtaacggaa | 2100 |
| tttaagtttt tatttgtgag tggtcacttt aaaggaaact acaaagctca gcttacacga | 2160 |
| ttaaatcata tcactaattg taatggagct gttcttagtg tagaagagct tttaattggt | 2220 |
| ggagaaatga ttaaagccgg cacattaacc ttagaggaag tcagacggaa atttaataac | 2280 |
| ggcgagataa acttttaagg gcccttcgaa ggtaagccta tccctaaccc tctcctcggt | 2340 |
| ctcgattcta cgcgtaccgg tcatcatcac catcaccatt gagtttaaac ccgctgatca | 2400 |
| gcctcgactg tgccttctag ttgccagcca tctgttgttt gcccctcccc cgtgccttcc | 2460 |

```
ttgaccctgg aaggtgccac tcccactgtc ctttcctaat aaaatgagga aattgcatcg    2520
cattgtctga gtaggtgtca ttctattctg gggggtgggg tggggcagga cagcaagggg    2580
gaggattggg aagacaatag caggcatgct ggggatgcgg tgggctctat ggcttctgag    2640
gcggaaagaa ccagctgggg ctctaggggg tatccccacg cgccctgtag cggcgcatta    2700
agcgcggcgg gtgtggtggt tacgcgcagc gtgaccgcta cacttgccag cgccctagcg    2760
cccgctcctt tcgctttctt cccttccttt ctcgccacgt tcgccggctt tccccgtcaa    2820
gctctaaatc ggggcatccc tttagggttc cgatttagtg ctttacggca cctcgacccc    2880
aaaaaacttg attagggtga tggttcacgt agtgggccat cgccctgata gacggttttt    2940 cgcccttga cgttggagtc cacgttcttt aatagtggac tcttgttcca aactggaaca     3000
acactcaacc ctatctcggt ctattctttt gatttataag ggattttggg gatttcggcc    3060
tattggttaa aaaatgagct gatttaacaa aaatttaacg cgaattaatt ctgtggaatg    3120
tgtgtcagtt agggtgtgga aagtcccag gctccccagg caggcagaag tatgcaaagc     3180
atgcatctca attagtcagc aaccaggtgt ggaaagtccc caggctcccc agcaggcaga    3240
agtatgcaaa gcatgcatct caattagtc                                      3269

<210> SEQ ID NO 11
<211> LENGTH: 3178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
agcaaccata gtcccgcccc taactccgcc catcccgccc ctaactccgc ccagttccgc      60
ccattctccg ccccatggct gactaatttt ttttatttat gcagaggccg aggccgcctc     120
tgcctctgag ctattccaga agtagtgagg aggcttttt ggaggcctag gcttttgcaa      180
aaagctcccg ggagcttgta tatccatttt cggatctgat cagcacgtgt tgacaattaa     240
tcatcggcat agtatatcgg catagtataa tacgacaagg tgaggaacta aaccatggcc     300
aagcctttgt ctcaagaaga atccaccctc attgaaagag caacggctac aatcaacagc     360
atccccatct ctgaagacta cagcgtcgcc agcgcagctc tctctagcga cggccgcatc     420
ttcactggtg tcaatgtata tcatttact gggggacctt gtgcagaact cgtggtgctg      480
ggcactgctg ctgctgcggc agctggcaac ctgacttgta tcgtcgcgat cggaaatgag     540
aacaggggca tcttgagccc ctgcggacgg tgtcgacagg tgcttctcga tctgcatcct     600
gggatcaaag cgatagtgaa ggacagtgat ggacagccga cggcagttgg gattcgtgaa     660
ttgctgccct ctggttatgt gtgggagggc taagcacttc gtggccgagg agcaggactg     720
acacgtgcta cgagatttcg attccaccgc cgccttctat gaaaggttgg gcttcggaat     780
cgttttccgg gacgccggct ggatgatcct ccagcgcggg gatctcatgc tggagttctt     840
cgcccacccc aacttgttta ttgcagctta taatggttac aaataaagca atagcatcac     900
aaatttcaca aataaagcat ttttttcact gcattctagt tgtggtttgt ccaaactcat     960
caatgtatct tatcatgtct gtataccgtc gacctctagc tagagcttgg cgtaatcatg    1020
gtcatagctg tttcctgtgt gaaattgtta tccgctcaca attccacaca acatacgagc    1080
cggaagcata aagtgtaaag cctggggtgc ctaatgagtg agctaactca cattaattgc    1140
gttgcgctca ctgcccgctt tccagtcggg aaacctgtcg tgccagctgc attaatgaat    1200
```

-continued

```
cggccaacgc gcggggagag gcggtttgcg tattgggcgc tcttccgctt cctcgctcac    1260
tgactcgctg cgctcggtcg ttcggctgcg gcgagcggta tcagctcact caaaggcggt    1320
aatacggtta tccacagaat caggggataa cgcaggaaag aacatgtgag caaaaggcca    1380
gcaaaaggcc aggaaccgta aaaaggccgc gttgctggcg ttttttccata ggctccgccc    1440 ccctgacgag catcacaaaa atcgacgctc aagtcagagg tggcgaaacc cgacaggact    1500
ataaagatac caggcgtttc ccctggaag ctccctcgtg cgctctcctg ttccgaccct    1560
gccgcttacc ggatacctgt ccgcctttct cccttcggga agcgtggcgc tttctcaatg    1620
ctcacgctgt aggtatctca gttcggtgta ggtcgttcgc tccaagctgg gctgtgtgca    1680 cgaaccccc gttcagcccg accgctgcgc cttatccggt aactatcgtc ttgagtccaa    1740
cccggtaaga cacgacttat cgccactggc agcagccact ggtaacagga ttagcagagc    1800
gaggtatgta ggcggtgcta cagagttctt gaagtggtgg cctaactacg gctacactag    1860
aaggacagta tttggtatct gcgctctgct gaagccagtt accttcggaa aaagagttgg    1920
tagctcttga tccggcaaac aaaccaccgc tggtagcggt ggtttttttg tttgcaagca    1980
gcagattacg cgcagaaaaa aaggatctca agaagatcct ttgatctttt ctacggggtc    2040
tgacgctcag tggaacgaaa actcacgtta agggattttg gtcatgagat tatcaaaaag    2100
gatcttcacc tagatccttt taaattaaaa atgaagtttt aaatcaatct aaagtatata    2160
tgagtaaact tggtctgaca gttaccaatg cttaatcagt gaggcaccta tctcagcgat    2220
ctgtctattt cgttcatcca tagttgcctg actccccgtc gtgtagataa ctacgatacg    2280
ggagggctta ccatctggcc ccagtgctgc aatgataccg cgagacccac gctcaccggc    2340
tccagattta tcagcaataa accagccagc cggaagggcc gagcgcagaa gtggtcctgc    2400
aactttatcc gcctccatcc agtctattaa ttgttgccgg gaagctagag taagtagttc    2460
gccagttaat agtttgcgca acgttgttgc cattgctaca ggcatcgtgg tgtcacgctc    2520
gtcgtttggt atggcttcat tcagctccgg ttcccaacga tcaaggcgag ttacatgatc    2580
ccccatgttg tgcaaaaaag cggttagctc cttcggtcct ccgatcgttg tcagaagtaa    2640
gttggccgca gtgttatcac tcatggttat ggcagcactg cataattctc ttactgtcat    2700
gccatccgta agatgctttt ctgtgactgg tgagtactca accaagtcat tctgagaata    2760
gtgtatgcgg cgaccgagtt gctcttgccc ggcgtcaata cggataata ccgcgccaca    2820 tagcagaact ttaaaagtgc tcatcattgg aaaacgttct cggggcgaa aactctcaag    2880 gatcttaccg ctgttgagat ccagttcgat gtaacccact cgtgcaccca actgatcttc    2940
agcatctttt actttcacca gcgtttctgg gtgagcaaaa acaggaaggc aaaatgccgc    3000
aaaaaaggga ataagggcga cacggaaatg ttgaatactc atactcttcc tttttcaata    3060
ttattgaagc atttatcagg gttattgtct catgagcgga tacatatttg aatgtattta    3120
gaaaaataaa caatagggg ttccgcgcac atttccccga aaagtgccac ctgacgtc    3178
```

<210> SEQ ID NO 12
<211> LENGTH: 111
<212> TYPE: DNA
<213> ORGANISM: Homo sapiens

<400> SEQUENCE: 12

```
ctacggcgtg cagtgcttca gccgctaccc cgaccacatg aagcagcacg acttcttcaa    60
gtccgccatg cccgaaggct acgtccagga gcgcaccatc ttcttcaagg a              111
```

```
<210> SEQ ID NO 13
<211> LENGTH: 108
<212> TYPE: DNA
<213> ORGANISM: Homo sapiens

<400> SEQUENCE: 13
ctacggcgtg cagtgcttca gccgctaccc cgacatgaag cagcacgact tcttcaagtc      60
cgccatgccc gaaggctacg tccaggagcg caccatcttc ttcaagga                 108

<210> SEQ ID NO 14
<211> LENGTH: 95
<212> TYPE: DNA
<213> ORGANISM: Homo sapiens

<400> SEQUENCE: 14
ctacggcgtg cagtgcttca gccgaagcag cacgacttct tcaagtccgc catgcccgaa      60
ggctacgtcc aggagcgcac catcttcttc aagga                               95

<210> SEQ ID NO 15
<211> LENGTH: 90
<212> TYPE: DNA
<213> ORGANISM: Homo sapiens

<400> SEQUENCE: 15
ctacggcgtg cagtgcttca gccgctacga cttcttcaag tccgccatgc ccgaaggcta      60
cgtccaggag cgcaccatct tcttcaagga                                     90

<210> SEQ ID NO 16
<211> LENGTH: 89
<212> TYPE: DNA
<213> ORGANISM: Homo sapiens
<220> FEATURE:
<221> NAME/KEY: modified_base
<222> LOCATION: (61)..(61)
<223> OTHER INFORMATION: a, c, t, g, unknown or other

<400> SEQUENCE: 16
ctacggcgtg cagtgcttca gccgcacgac ttcttccagt ccgccatgcc cgaaggctac      60
ntccaggagc gcaccatctt cttcaagga                                      89

<210> SEQ ID NO 17
<211> LENGTH: 80
<212> TYPE: DNA
<213> ORGANISM: Homo sapiens

<400> SEQUENCE: 17
ctacggcgtg cagtgcttca gcacttcaag tccgccatgc ccgaaggcta cgtccaggag      60
cgcaccatct tcttcaagga                                                80

<210> SEQ ID NO 18
<211> LENGTH: 78
<212> TYPE: DNA
<213> ORGANISM: Homo sapiens

<400> SEQUENCE: 18
ctacggcgtg cagcacgact tcttcaagtc cgccatgccc gaaggctacg tccaggagcg      60
caccatcttc ttcaagga                                                  78

<210> SEQ ID NO 19
<211> LENGTH: 78
```

```
<212> TYPE: DNA
<213> ORGANISM: Homo sapiens

<400> SEQUENCE: 19
ctacggcgtg cagcacgact tcttcaagtc cgccatgccc gaaggctacg tccaggagcg    60
caccatcttc ttcaagga                                                  78

<210> SEQ ID NO 20
<211> LENGTH: 60
<212> TYPE: DNA
<213> ORGANISM: Homo sapiens

<400> SEQUENCE: 20
ctacggcgtg cagtgcttgc ccgaaggcta cgtccaggag cgcaccatct tcttcaagga    60

<210> SEQ ID NO 21
<211> LENGTH: 57
<212> TYPE: DNA
<213> ORGANISM: Homo sapiens

<400> SEQUENCE: 21
ctacggcgtg cagtgcttca gccgctacgt ccaggagcgc accatcttct tcaagga       57

<210> SEQ ID NO 22
<211> LENGTH: 51
<212> TYPE: DNA
<213> ORGANISM: Homo sapiens

<400> SEQUENCE: 22
ctacgccatg cccgaaggct acgtccagga gcgcaccatc ttcttcaagg a             51

<210> SEQ ID NO 23
<211> LENGTH: 27
<212> TYPE: DNA
<213> ORGANISM: Homo sapiens

<400> SEQUENCE: 23
ctacggcgtg cagtgcttct tcaagga                                        27

<210> SEQ ID NO 24
<211> LENGTH: 113
<212> TYPE: DNA
<213> ORGANISM: Homo sapiens

<400> SEQUENCE: 24
ctacggcgtg cagtgcttca gccgctaccc cgacaccaca tgaagcagca cgacttcttc    60
aagtccgcca tgcccgaagg ctacgtccag gagcgcacca tcttcttcaa gga          113

<210> SEQ ID NO 25
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tctagagcta gcaccatgga ctacaaagac catgacggtg attataaaga tcatgacatc    60
gattacaagg atgacgatga caagatggcc cccaagaaga agaggaaggt gggcattcac   120
cgcggggtac ctatggtgga cttgaggaca ctcggttatt cgcaacagca acaggagaaa   180
atcaagccta aggtcaggag caccgtcgcg caacaccacg aggcgcttgt ggggcatggc   240
```

```
ttcactcatg cgcatattgt cgcgctttca cagcaccctg cggcgcttgg gacggtggct      300
gtcaaatacc aagatatgat tgcggccctg cccgaagcca cgcacgaggc aattgtaggg      360
gtcggtaaac agtggtcggg agcgcgagca cttgaggcgc tgctgactgt ggcgggtgag      420 cttaggggc ctccgctcca gctcgacacc gggcagctgc tgaagatcgc gaagagaggg       480
ggagtaacag cggtagaggc agtgcacgcc tggcgcaatg cgctcaccgg gccccccttg      540
aacctgaccc cagaccaggt agtcgcaatc gcgaacaata atgggggaaa gcaagccctg      600
gaaaccgtgc aaaggttgtt gccggtcctt tgtcaagacc acggccttac accggagcaa      660
gtcgtggcca ttgcatccca cgacggtggc aaacaggctc ttgagacggt tcagagactt      720
ctcccagttc tctgtcaagc ccacgggctg actcccgatc aagttgtagc gattgcgtcg      780
aacattggag ggaaacaagc attggagact gtccaacggc tccttcccgt gttgtgtcaa      840
gcccacggtt tgacgcctgc acaagtggtc gccatcgcca acaacaacgg cggtaagcag      900
gcgctggaaa cagtacagcg cctgctgcct gtactgtgcc aggatcatgg actgacccca      960
gaccaggtag tcgcaatcgc gtcaaacgga gggggaaagc aagccctgga aaccgtgcaa     1020
aggttgttgc cggtcctttg tcaagaccac ggccttacac cggagcaagt cgtggccatt     1080
gcaaataata acgtggcaa acaggctctt gagacggttc agagacttct cccagttctc      1140
tgtcaagccc acgggctgac tcccgatcaa gttgtagcga ttgcgtcgca tgacggaggg     1200
aaacaagcat tggagactgt ccaacggctc cttcccgtgt tgtgtcaagc ccacggtttg     1260
acgcctgcac aagtggtcgc catcgcctcg aatggcggcg gtaagcaggc gctggaaaca     1320
gtacagcgcc tgctgcctgt actgtgccag gatcatggac tgaccccaga ccaggtagtc     1380
gcaatcgcgt caaacggagg gggaaagcaa gccctggaaa ccgtgcaaag gttgttgccg     1440
gtcctttgtc aagaccacgg ccttacaccg gagcaagtcg tggccattgc atcccacgac     1500
ggtggcaaac aggctcttga gacggttcag agacttctcc cagttctctg tcaagcccac     1560
gggctgactc ccgatcaagt tgtagcgatt gcgtcgaaca ttgagggaa caagcattg      1620 gagactgtcc aacggctcct tcccgtgttg tgtcaagccc acggtttgac gcctgcacaa     1680
gtggtcgcca tcgccaacaa caacggcggt aagcaggcgc tggaaacagt acagcgcctg     1740
ctgcctgtac tgtgccagga tcatggactg accccagacc aggtagtcgc aatcgcgtca     1800
catgacgggg gaaagcaagc cctggaaacc gtgcaaaggt tgttgccggt cctttgtcaa     1860
gaccacggcc ttacaccgga gcaagtcgtg gccattgcat cccacgacgg tggcaaacag     1920
gctcttgaga cggttcagag acttctccca gttctctgtc aagcccacgg ctgactccc     1980 gatcaagttg tagcgattgc gaataacaat ggagggaaac aagcattgga gactgtccaa     2040
cggctccttc ccgtgttgtg tcaagcccac ggtctgacac cgaacaggt ggtcgccatt      2100 gcttcccacg acggaggacg gccagccttg gagtccatcg tagcccaatt gtccaggccc     2160
gatcccgcgt tggctgcgtt aacgaatgac catctggtgg cgttggcatg tcttggtgga     2220
cgacccgcgc tcgatgcagt caaaaagggt ctgcctcatg ctcccgcatt gatcaaaaga     2280
accaaccggc ggattcccga gagaacttcc catcgagtcg cgggatcc                  2328
```

<210> SEQ ID NO 26
<211> LENGTH: 771
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
            35                  40                  45

Ser Gln Gln Gln Glu Lys Ile Lys Pro Lys Val Arg Ser Thr Val
50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Asn Asn Asn Gly Gly Lys
            180                 185                 190

Gln Ala Leu Glu Thr Val Gln Arg Leu Leu Pro Val Leu Cys Gln Asp
            195                 200                 205

His Gly Leu Thr Pro Glu Gln Val Val Ala Ile Ala Ser His Asp Gly
210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
            275                 280                 285

Asn Asn Asn Gly Gly Lys Gln Ala Leu Glu Thr Val Gln Arg Leu Leu
290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Asn Asn Asn Gly Gly Lys Gln Ala Leu Glu Thr Val
            355                 360                 365

Gln Arg Leu Leu Pro Val Leu Cys Gln Ala His Gly Leu Thr Pro Asp
            370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr

```
                        405                 410                 415
Pro Ala Gln Val Val Ala Ile Ala Ser Asn Gly Gly Lys Gln Ala
            420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser Asn Gly Gly Lys
    450                 455                 460
Gln Ala Leu Glu Thr Val Gln Arg Leu Leu Pro Val Leu Cys Gln Asp
465                 470                 475                 480
His Gly Leu Thr Pro Glu Gln Val Val Ala Ile Ala Ser His Asp Gly
                485                 490                 495
Gly Lys Gln Ala Leu Glu Thr Val Gln Arg Leu Leu Pro Val Leu Cys
            500                 505                 510
Gln Ala His Gly Leu Thr Pro Asp Gln Val Val Ala Ile Ala Ser Asn
            515                 520                 525
Ile Gly Gly Lys Gln Ala Leu Glu Thr Val Gln Arg Leu Leu Pro Val
    530                 535                 540
Leu Cys Gln Ala His Gly Leu Thr Pro Ala Gln Val Val Ala Ile Ala
545                 550                 555                 560
Asn Asn Asn Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser His Asp Gly Gly Lys Gln Ala Leu Glu Thr Val Gln Arg
            595                 600                 605
Leu Leu Pro Val Leu Cys Gln Asp His Gly Leu Thr Pro Glu Gln Val
    610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Asp
                645                 650                 655
Gln Val Val Ala Ile Ala Asn Asn Gly Gly Lys Gln Ala Leu Glu
            660                 665                 670
Thr Val Gln Arg Leu Leu Pro Val Leu Cys Gln Ala His Gly Leu Thr
            675                 680                 685
Pro Glu Gln Val Val Ala Ile Ala Ser His Asp Gly Gly Arg Pro Ala
    690                 695                 700
Leu Glu Ser Ile Val Ala Gln Leu Ser Arg Pro Asp Pro Ala Leu Ala
705                 710                 715                 720
Ala Leu Thr Asn Asp His Leu Val Ala Leu Ala Cys Leu Gly Gly Arg
                725                 730                 735
Pro Ala Leu Asp Ala Val Lys Lys Gly Leu Pro His Ala Pro Ala Leu
            740                 745                 750
Ile Lys Arg Thr Asn Arg Arg Ile Pro Glu Arg Thr Ser His Arg Val
            755                 760                 765
Ala Gly Ser
    770

<210> SEQ ID NO 27
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 27

```
tctagagcta gcaccatgga ctacaaagac catgacggtg attataaaga tcatgacatc    60
gattacaagg atgacgatga caagatggcc cccaagaaga gaggaaggt gggcattcac   120
cgcggggtac ctatggtgga cttgaggaca ctcggttatt cgcaacagca acaggagaaa   180
atcaagccta aggtcaggag caccgtcgcg caacaccacg aggcgcttgt ggggcatggc   240
ttcactcatg cgcatattgt cgcgctttca cagcaccctg cggcgcttgg gacggtggct   300
gtcaaatacc aagatatgat tgcggccctg cccgaagcca cgcacgaggc aattgtaggg   360
gtcggtaaac agtggtcggg agcgcgagca cttgaggcgc tgctgactgt ggcgggtgag   420
cttagggggc ctccgctcca gctcgacacc gggcagctgc tgaagatcgc gaagagaggg   480
ggagtaacag cggtagaggc agtgcacgcc tggcgcaatg cgctcaccgg gccccccttg   540
aacctgaccc cagaccaggt agtcgcaatc gcgaacaata tgggggaaa gcaagccctg   600
gaaaccgtgc aaaggttgtt gccggtcctt tgtcaagacc acggccttac accggagcaa   660
gtcgtggcca ttgcatccca cgacggtggc aaacaggctc ttgagacggt tcagagactt   720
ctcccagttc tctgtcaagc ccacgggctg actcccgatc aagttgtagc gattgcgtcg   780
aacattggag ggaaacaagc attggagact gtccaacggc tccttcccgt gttgtgtcaa   840
gcccacggtt tgacgcctgc acaagtggtc gccatcgcca acaacaacgg cggtaagcag   900
gcgctggaaa cagtacagcg cctgctgcct gtactgtgcc aggatcatgg actgacccca   960
gaccaggtag tcgcaatcgc gtcaaacgga ggggaaagc aagccctgga aaccgtgcaa  1020
aggttgttgc cggtcctttg tcaagaccac ggccttacac cggagcaagt cgtggccatt  1080
gcaaataata cggtggcaa acaggctctt gagacggttc agagacttct cccagttctc  1140
tgtcaagccc acgggctgac tcccgatcaa gttgtagcga ttgcgtcgca tgacggaggg  1200
aaacaagcat ggagactgt ccaacggctc cttcccgtgt tgtgtcaagc ccacggtttg  1260
acgcctgcac aagtggtcgc catcgcctcg aatggcggcg gtaagcaggc gctggaaaca  1320
gtacagcgcc tgctgcctgt actgtgccag gatcatggac tgaccccaga ccaggtagtc  1380
gcaatcgcgt caaacggagg gggaaagcaa gccctggaaa ccgtgcaaag gttgttgccg  1440
gtcctttgtc aagaccacgg ccttacaccg gagcaagtcg tggccattgc atcccacgac  1500
ggtggcaaac aggctcttga gacggttcag agacttctcc cagttctctg tcaagcccac  1560
gggctgactc ccgatcaagt tgtagcgatt gcgtcgaaca ttggagggaa caagcattg   1620
gagactgtcc aacggctcct tcccgtgttg tgtcaagccc acggtttgac gcctgcacaa  1680
gtggtcgcca tcgccaacaa caacggcggt aagcaggcgc tggaaacagt acagcgcctg  1740
ctgcctgtac tgtgccagga tcatggactg accccagacc aggtagtcgc aatcgcgtca  1800
catgacgggg gaaagcaagc cctggaaacc gtgcaaaggt tgttgccggt cctttgtcaa  1860
gaccacggcc ttacaccgga gcaagtcgtg ccattgcat cccacgacgg tggcaaacag  1920
gctcttgaga cggttcagag acttctccca gttctctgtc aagcccacgg gctgactccc  1980
gatcaagttg tagcgattgc gaataacaat ggagggaaac aagcattgga gactgtccaa  2040
cggctccttc ccgtgttgtg tcaagcccac ggtttgacgc ctgcacaagt ggtcgccatc  2100
gccagccatg atggcggtaa gcaggcgctg aaacagtac agcgcctgct gcctgtactg  2160
tgccaggatc atggactgac cccgaacag gtggtcgcca ttgcttctaa tgggggagga  2220
cggccagcct tggagtccat cgtagcccaa ttgtccaggc ccgatcccgc gttggctgcg  2280
```

```
ttaacgaatg accatctggt ggcgttggca tgtcttggtg gacgacccgc gctcgatgca    2340
gtcaaaaagg gtctgcctca tgctcccgca ttgatcaaaa gaaccaaccg gcggattccc    2400
gagagaactt cccatcgagt cgcgggatcc                                     2430
```

<210> SEQ ID NO 28
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Asn Asn Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Asn Asn Asn Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
                325                 330                 335
```

```
Leu Leu Pro Val Leu Cys Gln Asp His Gly Leu Thr Pro Glu Gln Val
            340                 345                 350

Val Ala Ile Ala Asn Asn Gly Gly Lys Gln Ala Leu Glu Thr Val
        355                 360                 365

Gln Arg Leu Leu Pro Val Leu Cys Gln Ala His Gly Leu Thr Pro Asp
370                 375                 380

Gln Val Ala Ile Ala Ser His Asp Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser Asn Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Gly Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
        530                 535                 540

Leu Cys Gln Ala His Gly Leu Thr Pro Ala Gln Val Val Ala Ile Ala
545                 550                 555                 560

Asn Asn Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Glu Gln Val
        610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Asn Asn Gly Gly Lys Gln Ala Leu Glu
            660                 665                 670

Thr Val Gln Arg Leu Leu Pro Val Leu Cys Gln Ala His Gly Leu Thr
            675                 680                 685

Pro Ala Gln Val Val Ala Ile Ala Ser His Asp Gly Gly Lys Gln Ala
        690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser Asn Gly Gly Gly Arg
                725                 730                 735

Pro Ala Leu Glu Ser Ile Val Ala Gln Leu Ser Arg Pro Asp Pro Ala
            740                 745                 750
```

Leu Ala Ala Leu Thr Asn Asp His Leu Val Ala Leu Ala Cys Leu Gly
            755                 760                 765

Gly Arg Pro Ala Leu Asp Ala Val Lys Lys Gly Leu Pro His Ala Pro
    770                 775                 780

Ala Leu Ile Lys Arg Thr Asn Arg Arg Ile Pro Glu Arg Thr Ser His
785                 790                 795                 800

Arg Val Ala Gly Ser
                805

<210> SEQ ID NO 29
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tctagagcta gcaccatgga ctacaaagac catgacggtg attataaaga tcatgacatc      60
gattacaagg atgacgatga caagatggcc cccaagaaga gaggaaggt gggcattcac     120
cgcggggtac ctatggtgga cttgaggaca ctcggttatt cgcaacagca acaggagaaa     180
atcaagccta aggtcaggag caccgtcgcg caacaccacg aggcgcttgt ggggcatggc     240
ttcactcatg cgcatattgt cgcgctttca cagcaccctg cggcgcttgg acggtggct      300
gtcaaatacc aagatatgat tgcggccctg cccgaagcca cgcacgaggc aattgtaggg     360
gtcggtaaac agtggtcggg agcgcgagca cttgaggcgc tgctgactgt ggcgggtgag     420
cttagggggc ctccgctcca gctcgacacc gggcagctgc tgaagatcgc gaagagaggg     480
ggagtaacag cggtagaggc agtgcacgcc tggcgcaatg cgctcaccgg gccccttg      540
aacctgaccc cagaccaggt agtcgcaatc gcgtcaaacg gagggggaaa gcaagccctg     600
gaaaccgtgc aaaggttgtt gccggtcctt tgtcaagacc acggccttac accggagcaa     660
gtcgtggcca ttgcaaataa taacggtggc aaacaggctc ttgagacggt tcagagactt     720
ctcccagttc tctgtcaagc ccacgggctg actcccgatc aagttgtagc gattgcgtcg     780
aacattggag ggaaacaagc attggagact gtccaacggc tccttcccgt gttgtgtcaa     840
gcccacggtt tgacgcctgc acaagtggtc gccatcgcct ccaatattgg cggtaagcag     900
gcgctggaaa cagtacagcg cctgctgcct gtactgtgcc aggatcatgg actgaccca      960
gaccaggtag tcgcaatcgc gaacaataat ggggaaagc aagccctgga accgtgcaa     1020
aggttgttgc cggtcctttg tcaagaccac ggccttacac cggagcaagt cgtggccatt    1080
gcaagcaaca tcggtggcaa acaggctctt gagacggttc agagacttct cccagttctc    1140
tgtcaagccc acgggctgac tcccgatcaa gttgtagcga ttgcgtcgaa cattggaggg    1200
aaacaagcat ggagactgt ccaacggctc cttcccgtgt tgtgtcaagc cacggtttg     1260
acgcctgcac aagtggtcgc catcgccaac aacaacggcg taagcaggc gctgaaaca     1320
gtacagcgcc tgctgcctgt actgtgccag gatcatggac tgaccccaga ccaggtagtc    1380
gcaatcgcgt caaacggagg gggaaagcaa gccctggaaa ccgtgcaaag gttgttgccg    1440
gtcctttgtc aagaccacgg ccttacaccg gagcaagtcg tggccattgc atcccacgac    1500
ggtggcaaac aggctcttga cggttcag agacttctcc cagttctctg tcaagcccac     1560
gggctgactc ccgatcaagt tgtagcgatt gcgaataaca atggagggaa acaagcattg    1620
gagactgtcc aacggctcct tcccgtgttg tgtcaagccc acggtttgac gcctgcacaa    1680

```
gtggtcgcca tcgcctcgaa tggcggcggt aagcaggcgc tggaaacagt acagcgcctg    1740
ctgcctgtac tgtgccagga tcatggactg accccagacc aggtagtcgc aatcgcgaac    1800
aataatgggg gaaagcaagc cctggaaacc gtgcaaaggt tgttgccggt cctttgtcaa    1860
gaccacggcc ttacaccgga gcaagtcgtg gccattgcat cccacgacgg tggcaaacag    1920
gctcttgaga cggttcagag acttctccca gttctctgtc aagcccacgg gctgactccc    1980
gatcaagttg tagcgattgc gtccaacggt ggagggaaac aagcattgga gactgtccaa    2040
cggctccttc ccgtgttgtg tcaagcccac ggtttgacgc ctgcacaagt ggtcgccatc    2100
gccaacaaca acggcggtaa gcaggcgctg aaacagtac agcgcctgct gcctgtactg    2160
tgccaggatc atggactgac acccgaacag gtggtcgcca ttgcttccca cgacggagga    2220
cggccagcct tggagtccat cgtagcccaa ttgtccaggc ccgatcccgc gttggctgcg    2280
ttaacgaatg accatctggt ggcgttggca tgtcttggtg gacgacccgc gctcgatgca    2340
gtcaaaaagg gtctgcctca tgctcccgca ttgatcaaaa gaaccaaccg gcggattccc    2400
gagagaactt cccatcgagt cgcgggatcc                                     2430
```

<210> SEQ ID NO 30
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Asn Asn Asn Gly
    210                 215                 220
```

-continued

```
Gly Lys Gln Ala Leu Glu Thr Val Gln Arg Leu Pro Val Leu Cys
225                 230                 235                 240

Gln Ala His Gly Leu Thr Pro Asp Gln Val Ala Ile Ala Ser Asn
            245                 250                 255

Ile Gly Gly Lys Gln Ala Leu Glu Thr Val Gln Arg Leu Pro Val
        260                 265                 270

Leu Cys Gln Ala His Gly Leu Thr Pro Ala Gln Val Val Ala Ile Ala
        275                 280                 285

Ser Asn Ile Gly Gly Lys Gln Ala Leu Glu Thr Val Gln Arg Leu Leu
        290                 295                 300

Pro Val Leu Cys Gln Asp His Gly Leu Thr Pro Asp Gln Val Val Ala
305                 310                 315                 320

Ile Ala Asn Asn Asn Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser Asn Ile Gly Gly Lys Gln Ala Leu Glu Thr Val
        355                 360                 365

Gln Arg Leu Leu Pro Val Leu Cys Gln Ala His Gly Leu Thr Pro Asp
370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Asn Asn Asn Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Gly Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser His Asp Gly
            485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Asn Asn
        515                 520                 525

Asn Gly Gly Lys Gln Ala Leu Glu Thr Val Gln Arg Leu Leu Pro Val
        530                 535                 540

Leu Cys Gln Ala His Gly Leu Thr Pro Ala Gln Val Val Ala Ile Ala
545                 550                 555                 560

Ser Asn Gly Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
            580                 585                 590

Ile Ala Asn Asn Asn Gly Gly Lys Gln Ala Leu Glu Thr Val Gln Arg
        595                 600                 605

Leu Leu Pro Val Leu Cys Gln Asp His Gly Leu Thr Pro Glu Gln Val
        610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Asp
```

|  | 645 |  |  |  | 650 |  |  |  | 655 |  |  |
|---|---|---|---|---|---|---|---|---|---|---|---|
| Gln | Val | Val | Ala | Ile | Ala | Ser | Asn | Gly | Gly | Gly | Lys | Gln | Ala | Leu | Glu |
|  |  |  | 660 |  |  |  |  | 665 |  |  |  | 670 |  |  |

Thr Val Gln Arg Leu Leu Pro Val Leu Cys Gln Ala His Gly Leu Thr
            675                 680                 685

Pro Ala Gln Val Val Ala Ile Ala Asn Asn Asn Gly Gly Lys Gln Ala
        690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser His Asp Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
                755                 760                 765

Gly Arg Pro Ala Leu Asp Ala Val Lys Lys Gly Leu Pro His Ala Pro
770                 775                 780

Ala Leu Ile Lys Arg Thr Asn Arg Arg Ile Pro Glu Arg Thr Ser His
785                 790                 795                 800

Arg Val Ala Gly Ser
            805

```
<210> SEQ ID NO 31
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
tctagagcta gcaccatgga ctacaaagac catgacggtg attataaaga tcatgacatc    60
gattacaagg atgacgatga caagatggcc cccaagaaga agaggaaggt gggcattcac   120
cgcggggtac ctatggtgga cttgaggaca ctcggttatt cgcaacagca acaggagaaa   180
atcaagccta aggtcaggag caccgtcgcg caacaccacg aggcgcttgt ggggcatggc   240
ttcactcatg cgcatattgt cgcgctttca cagcaccctg cggcgcttgg acggtggct   300 gtcaaatacc aagatatgat tgcggccctg cccgaagcca cgcacgaggc aattgtaggg   360
gtcggtaaac agtggtcggg agcgcgagca cttgaggcgc tgctgactgt ggcgggtgag   420 cttaggggc ctccgctcca gctcgacacc gggcagctgc tgaagatcgc gaagagaggg   480
ggagtaacag cggtagaggc agtgcacgcc tggcgcaatg cgctcaccgg gccccccttg   540
aacctgaccc cagaccaggt agtcgcaatc gcgaacaata tgggggaaa gcaagccctg   600 gaaaccgtgc aaaggttgtt gccggtcctt tgtcaagacc acggccttac accggagcaa   660
gtcgtggcca ttgcaagcaa catcggtggc aaacaggctc ttgagacggt tcagagactt   720
ctcccagttc tctgtcaagc ccacgggctg actcccgatc aagttgtagc gattgcgtcg   780
aacattggag ggaaacaagc attggagact gtccaacggc tccttcccgt gttgtgtcaa   840
gcccacggtt tgacgcctgc acaagtggtc gccatcgcca acaacaacgg cggtaagcag   900
gcgctggaaa cagtacagcg cctgctgcct gtactgtgcc aggatcatgg actgaccca   960 gaccaggtag tcgcaatcgc gtcgaacatt gggggaaagc aagccctgga aaccgtgcaa  1020
aggttgttgc cggtcctttg tcaagaccac ggccttacac cggagcaagt cgtggccatt  1080
```

```
gcaagcaaca tcggtggcaa acaggctctt gagacggttc agagacttct cccagttctc    1140
tgtcaagccc acgggctgac tcccgatcaa gttgtagcga ttgcgaataa caatggaggg    1200
aaacaagcat tggagactgt ccaacggctc cttcccgtgt tgtgtcaagc ccacggtttg    1260
acgcctgcac aagtggtcgc catcgcctcg aatggcggcg gtaagcaggc gctggaaaca    1320
gtacagcgcc tgctgcctgt actgtgccag gatcatggac tgaccccaga ccaggtagtc    1380
gcaatcgcgt cacatgacgg gggaaagcaa gccctggaaa ccgtgcaaag gttgttgccg    1440
gtcctttgtc aagaccacgg ccttacaccg gagcaagtcg tggccattgc aaataataac    1500
ggtggcaaac aggctcttga gacggttcag agacttctcc cagttctctg tcaagcccac    1560
gggctgactc ccgatcaagt tgtagcgatt gcgtccaacg gtgagggaa acaagcattg    1620 gagactgtcc aacggctcct tcccgtgttg tgtcaagccc acggtttgac gcctgcacaa    1680
gtggtcgcca tcgccaacaa caacggcggt aagcaggcgc tggaaacagt acagcgcctg    1740
ctgcctgtac tgtgccagga tcatggactg accccagacc aggtagtcgc aatcgcgtca    1800
catgacgggg gaaagcaagc cctggaaacc gtgcaaaggt tgttgccggt cctttgtcaa    1860
gaccacggcc ttacaccgga gcaagtcgtg gccattgcaa gcaatggggg tggcaaacag    1920
gctcttgaga cggttcagag acttctccca gttctctgtc aagcccacgg gctgactccc    1980
gatcaagttg tagcgattgc gaataacaat ggagggaaac aagcattgga gactgtccaa    2040
cggctccttc ccgtgttgtg tcaagcccac ggtttgacgc ctgcacaagt ggtcgccatc    2100
gccagccatg atggcggtaa gcaggcgctg aaacagtac agcgcctgct gcctgtactg    2160
tgccaggatc atggactgac cccgaacag gtggtcgcca ttgcttctaa tgggggagga    2220
cggccagcct tggagtccat cgtagcccaa ttgtccaggc ccgatcccgc gttggctgcg    2280
ttaacgaatg accatctggt ggcgttggca tgtcttggtg gacgaccggc gctcgatgca    2340
gtcaaaaagg gtctgcctca tgctcccgca ttgatcaaaa gaaccaaccg gcggattccc    2400
gagagaactt cccatcgagt cgcgggatcc                                     2430
```

<210> SEQ ID NO 32
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
```

```
                115                 120                 125
Leu Leu Thr Val Ala Gly Glu Leu Arg Gly Pro Pro Leu Gln Leu Asp
            130                 135                 140

Thr Gly Gln Leu Leu Lys Ile Ala Lys Arg Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Asn Asn Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Ala Ile Ala Ser Asn Ile Gly
        210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
            245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Asn Asn Asn Gly Gly Lys Gln Ala Leu Glu Thr Val Gln Arg Leu Leu
        290                 295                 300

Pro Val Leu Cys Gln Asp His Gly Leu Thr Pro Asp Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser Asn Ile Gly Gly Lys Gln Ala Leu Glu Thr Val
            355                 360                 365

Gln Arg Leu Leu Pro Val Leu Cys Gln Ala His Gly Leu Thr Pro Asp
370                 375                 380

Gln Val Val Ala Ile Ala Asn Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser Asn Gly Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser His Asp Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
            515                 520                 525

Gly Gly Gly Lys Gln Ala Leu Glu Thr Val Gln Arg Leu Leu Pro Val
        530                 535                 540
```

Leu Cys Gln Ala His Gly Leu Thr Pro Ala Gln Val Val Ala Ile Ala
545                 550                 555                 560

Asn Asn Asn Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
        580                 585                 590

Ile Ala Ser His Asp Gly Gly Lys Gln Ala Leu Glu Thr Val Gln Arg
    595                 600                 605

Leu Leu Pro Val Leu Cys Gln Asp His Gly Leu Thr Pro Glu Gln Val
610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Ala Gln Val Val Ala Ile Ala Ser His Asp Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser Asn Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
        755                 760                 765

Gly Arg Pro Ala Leu Asp Ala Val Lys Lys Gly Leu Pro His Ala Pro
    770                 775                 780

Ala Leu Ile Lys Arg Thr Asn Arg Arg Ile Pro Glu Arg Thr Ser His
785                 790                 795                 800

Arg Val Ala Gly Ser
            805

<210> SEQ ID NO 33
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
tctagagcta gcaccatgga ctacaaagac catgacggtg attataaaga tcatgacatc      60
gattacaagg atgacgatga caagatggcc cccaagaaga agaggaaggt gggcattcac     120
cgcggggtac ctatggtgga cttgaggaca ctcggttatt cgcaacagca acaggagaaa     180
atcaagccta aggtcaggag caccgtcgcg caacaccacg aggcgcttgt ggggcatggc     240
ttcactcatg cgcatattgt cgcgctttca cagcaccctg cggcgcttgg acgtggct      300 gtcaaatacc aagatatgat tgcggccctg cccgaagcca cgcacgaggc aattgtaggg     360
gtcggtaaac agtggtcggg agcgcgagca cttgaggcgc tgctgactgt ggcgggtgag     420
cttagggggc ctccgctcca gctcgacacc gggcagctgc tgaagatcgc gaagagaggg     480

```
ggagtaacag cggtagaggc agtgcacgcc tggcgcaatg cgctcaccgg ggccccttg      540
aacctgaccc cagaccaggt agtcgcaatc gcgtcacatg acggggggaaa gcaagccctg    600
gaaaccgtgc aaaggttgtt gccggtcctt tgtcaagacc acggccttac accggagcaa    660
gtcgtggcca ttgcaaataa taacggtggc aaacaggctc ttgagacggt tcagagactt    720
ctcccagttc tctgtcaagc ccacgggctg actccgatc aagttgtagc gattgcgtcg     780
aacattggag ggaaacaagc attggagact gtccaacggc ccttcccgt gttgtgtcaa     840
gcccacggtt tgacgcctgc acaagtggtc gccatcgcca acaacaacgg cggtaagcag    900
gcgctggaaa cagtacagcg cctgctgcct gtactgtgcc aggatcatgg actgaccccca   960
gaccaggtag tcgcaatcgc gtcacatgac gggggaaagc aagccctgga accgtgcaa    1020
aggttgttgc cggtcctttg tcaagaccac ggccttacac cggagcaagt cgtggccatt   1080
gcaagcaatg ggggtggcaa acaggctctt gagacggttc agagacttct cccagttctc   1140
tgtcaagccc acgggctgac tcccgatcaa gttgtagcga ttgcgaataa caatggaggg   1200
aaacaagcat tggagactgt ccaacggctc cttcccgtgt tgtgtcaagc ccacggtttg   1260
acgcctgcac aagtggtcgc catcgcctcc aatattggcg gtaagcaggc gctggaaaca   1320
gtacagcgcc tgctgcctgt actgtgccag gatcatggac tgaccccaga ccaggtagtc   1380
gcaatcgcgt cgaacattgg gggaaagcaa gccctggaaa ccgtgcaaag gttgttgccg   1440
gtcctttgtc aagaccacgg ccttacaccg gagcaagtcg tggccattgc aaataataac   1500
ggtggcaaac aggctcttga cggttcag agacttctcc cagttctctg tcaagcccac     1560
gggctgactc ccgatcaagt tgtagcgatt gcgaataaca atggagggaa caagcattg    1620
gagactgtcc aacggctcct tcccgtgttg tgtcaagccc acggtttgac gcctgcacaa   1680
gtggtcgcca tcgccaacaa caacggcggt aagcaggcgc tggaaacagt acagcgcctg   1740
ctgcctgtac tgtgccagga tcatggactg accccagacc aggtagtcgc aatcgcgtca   1800
catgacgggg gaaagcaagc cctggaaacc gtgcaaaggt tgttgccggt cctttgtcaa   1860
gaccacggcc ttacaccgga gcaagtcgtg gccattgcaa gcaacatcgg tggcaaacag   1920
gctcttgaga cggttcagag acttctccca gttctctgtc aagcccacgg gctgactccc   1980
gatcaagttg tagcgattgc gtccaacggt ggagggaaac aagcattgga gactgtccaa   2040
cggctccttc ccgtgttgtg tcaagcccac ggtctgacac ccgaacaggt ggtcgccatt   2100
gcttcccacg acggaggacg gccagccttg gagtccatcg tagcccaatt gtccaggccc   2160
gatcccgcgt tggctgcgtt aacgaatgac catctggtgg cgttggcatg tcttggtgga   2220
cgacccgcgc tcgatgcagt caaaaagggt ctgcctcatg ctcccgcatt gatcaaaaga   2280
accaaccggc ggattcccga gagaacttcc catcgagtcg cgggatcc                2328
```

<210> SEQ ID NO 34
<211> LENGTH: 771
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30
```

-continued

```
Gly Ile His Arg Gly Val Pro Met Val Asp Leu Arg Thr Leu Gly Tyr
         35                  40                  45

Ser Gln Gln Gln Glu Lys Ile Lys Pro Lys Val Arg Ser Thr Val
 50                  55                  60

Ala Gln His His Glu Ala Leu Val Gly His Gly Phe Thr His Ala His
 65                  70                  75                  80

Ile Val Ala Leu Ser Gln His Pro Ala Ala Leu Gly Thr Val Ala Val
                 85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
                115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
                180                 185                 190

Gln Ala Leu Glu Thr Val Gln Arg Leu Leu Pro Val Leu Cys Gln Asp
                195                 200                 205

His Gly Leu Thr Pro Glu Gln Val Val Ala Ile Ala Asn Asn Asn Gly
                210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
                260                 265                 270

Leu Cys Gln Ala His Gly Leu Thr Pro Ala Gln Val Val Ala Ile Ala
                275                 280                 285

Asn Asn Asn Gly Gly Lys Gln Ala Leu Glu Thr Val Gln Arg Leu Leu
290                 295                 300

Pro Val Leu Cys Gln Asp His Gly Leu Thr Pro Asp Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Glu Gln Val
                340                 345                 350

Val Ala Ile Ala Ser Asn Gly Gly Lys Gln Ala Leu Glu Thr Val
                355                 360                 365

Gln Arg Leu Leu Pro Val Leu Cys Gln Ala His Gly Leu Thr Pro Asp
                370                 375                 380

Gln Val Val Ala Ile Ala Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser Asn Ile Gly Gly Lys Gln Ala
                420                 425                 430

Leu Glu Thr Val Gln Arg Leu Leu Pro Val Leu Cys Gln Asp His Gly
                435                 440                 445

Leu Thr Pro Asp Gln Val Val Ala Ile Ala Ser Asn Ile Gly Gly Lys
```

```
            450                 455                 460
Gln Ala Leu Glu Thr Val Gln Arg Leu Leu Pro Val Leu Cys Gln Asp
465                 470                 475                 480
His Gly Leu Thr Pro Glu Gln Val Val Ala Ile Ala Asn Asn Asn Gly
                485                 490                 495
Gly Lys Gln Ala Leu Glu Thr Val Gln Arg Leu Leu Pro Val Leu Cys
            500                 505                 510
Gln Ala His Gly Leu Thr Pro Asp Gln Val Val Ala Ile Ala Asn Asn
        515                 520                 525
Asn Gly Gly Lys Gln Ala Leu Glu Thr Val Gln Arg Leu Leu Pro Val
    530                 535                 540
Leu Cys Gln Ala His Gly Leu Thr Pro Ala Gln Val Val Ala Ile Ala
545                 550                 555                 560
Asn Asn Asn Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser His Asp Gly Gly Lys Gln Ala Leu Glu Thr Val Gln Arg
        595                 600                 605
Leu Leu Pro Val Leu Cys Gln Asp His Gly Leu Thr Pro Glu Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Ala His Gly Leu Thr Pro Asp
                645                 650                 655
Gln Val Val Ala Ile Ala Ser Asn Gly Gly Lys Gln Ala Leu Glu
            660                 665                 670
Thr Val Gln Arg Leu Leu Pro Val Leu Cys Gln Ala His Gly Leu Thr
        675                 680                 685
Pro Glu Gln Val Val Ala Ile Ala Ser His Asp Gly Gly Arg Pro Ala
    690                 695                 700
Leu Glu Ser Ile Val Ala Gln Leu Ser Arg Pro Asp Pro Ala Leu Ala
705                 710                 715                 720
Ala Leu Thr Asn Asp His Leu Val Ala Leu Ala Cys Leu Gly Gly Arg
                725                 730                 735
Pro Ala Leu Asp Ala Val Lys Lys Gly Leu Pro His Ala Pro Ala Leu
            740                 745                 750
Ile Lys Arg Thr Asn Arg Arg Ile Pro Glu Arg Thr Ser His Arg Val
        755                 760                 765
Ala Gly Ser
770

<210> SEQ ID NO 35
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
tctagagcta gcaccatgga ctacaaagac catgacggtg attataaaga tcatgacatc    60
gattacaagg atgacgatga caagatggcc cccaagaaga agaggaaggt gggcattcac   120
cgcggggtac ctatggtgga cttgaggaca ctcggttatt cgcaacagca acaggagaaa   180
```

```
atcaagccta aggtcaggag caccgtcgcg caacaccacg aggcgcttgt ggggcatggc    240
ttcactcatg cgcatattgt cgcgctttca cagcaccctg cggcgcttgg gacggtggct    300
gtcaaatacc aagatatgat tgcggccctg cccgaagcca cgcacgaggc aattgtaggg    360
gtcggtaaac agtggtcggg agcgcgagca cttgaggcgc tgctgactgt ggcgggtgag    420 cttaggggc ctccgctcca gctcgacacc gggcagctgc tgaagatcgc gaagagaggg    480
ggagtaacag cggtagaggc agtgcacgcc tggcgcaatg cgctcaccgg ggcccccttg    540
aacctgaccc cagaccaggt agtcgcaatc gcgtcacatg acggggaaa gcaagccctg    600 gaaaccgtgc aaaggttgtt gccggtcctt tgtcaagacc acggcttac accgagcaa    660 gtcgtggcca ttgcaaataa taacggtggc aaacaggctc ttgagacggt tcagagactt    720
ctcccagttc tctgtcaagc ccacgggctg actcccgatc aagttgtagc gattgcgtcg    780
aacattggag ggaaacaagc attggagact gtccaacggc tccttcccgt gttgtgtcaa    840
gcccacggtt tgacgcctgc acaagtggtc gccatcgcca acaacaacgg cggtaagcag    900
gcgctggaaa cagtacagcg cctgctgcct gtactgtgcc aggatcatgg actgaccca    960 gaccaggtag tcgcaatcgc gtcacatgac gggggaaagc aagccctgga accgtgcaa    1020 aggttgttgc cggtccttttg tcaagaccac ggccttacac cggagcaagt cgtggccatt    1080
gcaagcaatg gggtggcaa acaggctctt gagacggttc agagacttct cccagttctc    1140
tgtcaagccc acgggctgac tcccgatcaa gttgtagcga ttgcgaataa caatggaggg    1200
aaacaagcat ggagactgt ccaacggctc cttcccgtgt tgtgtcaagc ccacggtttg    1260
acgcctgcac aagtggtcgc catcgcctcc aatattggcg taagcaggc gctggaaaca    1320 gtacagcgcc tgctgcctgt actgtgccag gatcatggac tgaccccaga ccaggtagtc    1380
gcaatcgcgt cgaacattgg gggaaagcaa gccctggaaa ccgtgcaaag gttgttgccg    1440
gtcctttgtc aagaccacgg ccttacaccg gagcaagtcg tggccattgc aaataataac    1500
ggtggcaaac aggctcttga gacggttcag agacttctcc cagttctctg tcaagcccac    1560
gggctgactc ccgatcaagt tgtagcgatt gcgaataaca atggagggaa acaagcattg    1620
gagactgtcc aacggctcct tcccgtgttg tgtcaagccc acggtttgac gcctgcacaa    1680
gtggtcgcca tcgccaacaa caacggcggt aagcaggcgc tggaaacagt acagcgcctg    1740
ctgcctgtac tgtgccagga tcatggactg accccagacc aggtagtcgc aatcgcgtca    1800
catgacgggg gaaagcaagc cctggaaacc gtgcaaaggt tgttgccggt cctttgtcaa    1860
gaccacggcc ttacaccgga gcaagtcgtg gccattgcaa gcaacatcgg tggcaaacag    1920
gctcttgaga cggttcagag acttctccca gttctctgtc aagcccacgg gctgactccc    1980
gatcaagttg tagcgattgc gtccaacggt ggagggaaac aagcattgga gactgtccaa    2040
cggctccttc ccgtgttgtg tcaagcccac ggtttgacgc tgcacaagt ggtcgccatc    2100 gccagccatg atggcggtaa gcaggcgctg gaaacagtac agcgcctgct gcctgtactg    2160
tgccaggatc atggactgac acccgaacag gtggtcgcca ttgctaataa taacggagga    2220
cggccagcct ggagtccat cgtagcccaa ttgtccaggc ccgatcccgc gttggctgcg    2280
ttaacgaatg accatctggt ggcgttggca tgtcttggtg gacgacccgc gctcgatgca    2340
gtcaaaaagg gtctgcctca tgctcccgca ttgatcaaaa gaaccaaccg gcggattccc    2400
gagagaactt cccatcgagt cgcgggatcc                                    2430
```

<210> SEQ ID NO 36
<211> LENGTH: 805

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Asn Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Asn Asn Asn Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Ala His Gly Leu Thr Pro Asp
    370                 375                 380

```
Gln Val Val Ala Ile Ala Asn Asn Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Ala Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
            435                 440                 445

Leu Thr Pro Asp Gln Val Val Ala Ile Ala Ser Asn Ile Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Asn Asn Asn Gly
                485                 490                 495

Gly Lys Gln Ala Leu Glu Thr Val Gln Arg Leu Leu Pro Val Leu Cys
                500                 505                 510

Gln Ala His Gly Leu Thr Pro Asp Gln Val Val Ala Ile Ala Asn Asn
            515                 520                 525

Asn Gly Gly Lys Gln Ala Leu Glu Thr Val Gln Arg Leu Leu Pro Val
530                 535                 540

Leu Cys Gln Ala His Gly Leu Thr Pro Ala Gln Val Val Ala Ile Ala
545                 550                 555                 560

Asn Asn Asn Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser His Asp Gly Gly Lys Gln Ala Leu Glu Thr Val Gln Arg
            595                 600                 605

Leu Leu Pro Val Leu Cys Gln Asp His Gly Leu Thr Pro Glu Gln Val
            610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Ser Asn Gly Gly Gly Lys Gln Ala Leu Glu
                660                 665                 670

Thr Val Gln Arg Leu Leu Pro Val Leu Cys Gln Ala His Gly Leu Thr
            675                 680                 685

Pro Ala Gln Val Val Ala Ile Ala Ser His Asp Gly Gly Lys Gln Ala
            690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Asn Asn Asn Gly Gly Arg
                725                 730                 735

Pro Ala Leu Glu Ser Ile Val Ala Gln Leu Ser Arg Pro Asp Pro Ala
                740                 745                 750

Leu Ala Ala Leu Thr Asn Asp His Leu Val Ala Leu Ala Cys Leu Gly
            755                 760                 765

Gly Arg Pro Ala Leu Asp Ala Val Lys Lys Gly Leu Pro His Ala Pro
            770                 775                 780

Ala Leu Ile Lys Arg Thr Asn Arg Arg Ile Pro Glu Arg Thr Ser His
785                 790                 795                 800
```

Arg Val Ala Gly Ser
           805

<210> SEQ ID NO 37
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
tctagagcta gcaccatgga ctacaaagac catgacggtg attataaaga tcatgacatc      60
gattacaagg atgacgatga caagatggcc cccaagaaga gaggaaggt gggcattcac     120
cgcggggtac ctatggtgga cttgaggaca ctcggttatt cgcaacagca acaggagaaa    180
atcaagccta aggtcaggag caccgtcgcg caacaccacg aggcgcttgt ggggcatggc    240
ttcactcatg cgcatattgt cgcgctttca cagcaccctg cggcgcttgg gacggtggct    300
gtcaaatacc aagatatgat tgcggccctg cccgaagcca cgcacgaggc aattgtaggg    360
gtcggtaaac agtggtcggg agcgcgagca cttgaggcgc tgctgactgt ggcgggtgag    420
cttaggggc ctccgctcca gctcgacacc gggcagctgc tgaagatcgc gaagagaggg     480
ggagtaacag cggtagaggc agtgcacgcc tggcgcaatg cgctcaccgg gccccttg      540
aacctgaccc cagaccaggt agtcgcaatc gcgtcaaacg gagggggaaa gcaagccctg    600
gaaaccgtgc aaaggttgtt gccggtcctt tgtcaagacc acggccttac accggagcaa    660
gtcgtggcca ttgcaaataa taacggtggc aaacaggctc ttgagacggt tcagagactt    720
ctcccagttc tctgtcaagc ccacgggctg actcccgatc aagttgtagc gattgcgtcc    780
aacggtggag ggaaacaagc attggagact gtccaacggc tccttccgt gttgtgtcaa     840
gcccacggtt tgacgcctgc acaagtggtc gccatcgcca acaacaacgg cggtaagcag    900
gcgctggaaa cagtacagcg cctgctgcct gtactgtgcc aggatcatgg actgacccca    960
gaccaggtag tcgcaatcgc gtcacatgac ggggaaagc aagccctgga aaccgtgcaa    1020
aggttgttgc cggtcctttg tcaagaccac ggccttacac cggagcaagt cgtggccatt   1080
gcatcccacg acggtggcaa acaggctctt gagacggttc agagacttct cccagttctc    1140
tgtcaagccc acgggctgac tcccgatcaa gttgtagcga ttgcgtcgca tgacggaggg   1200
aaacaagcat ggagactgt ccaacggctc cttcccgtgt tgtgtcaagc ccacggtttg    1260
acgcctgcac aagtggtcgc catcgccagc catgatggcg gtaagcaggc gctggaaaca    1320
gtacagcgcc tgctgcctgt actgtgccag gatcatggac tgaccccaga ccaggtagtc    1380
gcaatcgcgt cgaacattgg gggaaagcaa gccctggaaa ccgtgcaaag gttgttgccg    1440
gtcctttgtc aagaccacgg ccttacaccg gagcaagtcg tggccattgc aaataataac    1500
ggtggcaaac aggctcttga gacggttcag agacttctcc cagttctctg tcaagcccac    1560
gggctgactc ccgatcaagt tgtagcgatt gcgaataaca atggagggaa acaagcattg    1620
gagactgtcc aacggctcct tcccgtgttg tgtcaagccc acgtttgac gcctgcacaa     1680
gtggtcgcca tcgcctccaa tattggcggt aagcaggcgc tggaaacagt acagcgcctg    1740
ctgcctgtac tgtgccagga tcatggactg accccagacc aggtagtcgc aatcgcgtca    1800
aacggagggg aaagcaagc cctggaaacc gtgcaaaggt tgttgccggt cctttgtcaa     1860
gaccacggcc ttacaccgga gcaagtcgtg gccattgcaa ataataacgg tggcaaacag    1920
gctcttgaga cggttcagag acttctccca gttctctgtc aagcccacgg gctgactccc    1980
```

```
gatcaagttg tagcgattgc gtccaacggt ggagggaaac aagcattgga gactgtccaa    2040
cggctccttc ccgtgttgtg tcaagcccac ggtttgacgc ctgcacaagt ggtcgccatc    2100
gcctcgaatg cggcggtaa gcaggcgctg gaaacagtac agcgcctgct gcctgtactg    2160
tgccaggatc atggactgac acccgaacag gtggtcgcca ttgctaataa taacggagga    2220
cggccagcct tggagtccat cgtagcccaa ttgtccaggc ccgatcccgc gttggctgcg    2280
ttaacgaatg accatctggt ggcgttggca tgtcttggtg gacgacccgc gctcgatgca    2340
gtcaaaaagg gtctgcctca tgctcccgca ttgatcaaaa gaaccaaccg gcggattccc    2400
gagagaactt cccatcgagt cgcgggatcc                                     2430
```

<210> SEQ ID NO 38
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65              70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Gly Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Asn Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Gly Gly Gly Lys Gln Ala Leu Glu Thr Val Gln Arg Leu Leu Pro Val
            260                 265                 270
```

-continued

```
Leu Cys Gln Ala His Gly Leu Thr Pro Ala Gln Val Val Ala Ile Ala
            275                 280                 285
Asn Asn Asn Gly Gly Lys Gln Ala Leu Glu Thr Val Gln Arg Leu Leu
        290                 295                 300
Pro Val Leu Cys Gln Asp His Gly Leu Thr Pro Asp Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Glu Gln Val
            340                 345                 350
Val Ala Ile Ala Ser His Asp Gly Gly Lys Gln Ala Leu Glu Thr Val
            355                 360                 365
Gln Arg Leu Leu Pro Val Leu Cys Gln Ala His Gly Leu Thr Pro Asp
    370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Ala Gln Val Val Ala Ile Ala Ser His Asp Gly Gly Lys Gln Ala
            420                 425                 430
Leu Glu Thr Val Gln Arg Leu Leu Pro Val Leu Cys Gln Asp His Gly
        435                 440                 445
Leu Thr Pro Asp Gln Val Val Ala Ile Ala Ser Asn Ile Gly Gly Lys
        450                 455                 460
Gln Ala Leu Glu Thr Val Gln Arg Leu Leu Pro Val Leu Cys Gln Asp
465                 470                 475                 480
His Gly Leu Thr Pro Glu Gln Val Val Ala Ile Ala Asn Asn Asn Gly
                485                 490                 495
Gly Lys Gln Ala Leu Glu Thr Val Gln Arg Leu Leu Pro Val Leu Cys
            500                 505                 510
Gln Ala His Gly Leu Thr Pro Asp Gln Val Val Ala Ile Ala Asn Asn
            515                 520                 525
Asn Gly Gly Lys Gln Ala Leu Glu Thr Val Gln Arg Leu Leu Pro Val
        530                 535                 540
Leu Cys Gln Ala His Gly Leu Thr Pro Ala Gln Val Val Ala Ile Ala
545                 550                 555                 560
Ser Asn Ile Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
            595                 600                 605
Leu Leu Pro Val Leu Cys Gln Asp His Gly Leu Thr Pro Glu Gln Val
    610                 615                 620
Val Ala Ile Ala Asn Asn Asn Gly Gly Lys Gln Ala Leu Glu Thr Val
625                 630                 635                 640
Gln Arg Leu Leu Pro Val Leu Cys Gln Ala His Gly Leu Thr Pro Asp
                645                 650                 655
Gln Val Val Ala Ile Ala Ser Asn Gly Gly Gly Lys Gln Ala Leu Glu
            660                 665                 670
Thr Val Gln Arg Leu Leu Pro Val Leu Cys Gln Ala His Gly Leu Thr
        675                 680                 685
Pro Ala Gln Val Val Ala Ile Ala Ser Asn Gly Gly Gly Lys Gln Ala
```

```
                690             695             700
Leu Glu Thr Val Gln Arg Leu Leu Pro Val Leu Cys Gln Asp His Gly
705                 710                 715                 720

Leu Thr Pro Glu Gln Val Val Ala Ile Ala Asn Asn Gly Gly Arg
                725                 730                 735

Pro Ala Leu Glu Ser Ile Val Ala Gln Leu Ser Arg Pro Asp Pro Ala
                740                 745                 750

Leu Ala Ala Leu Thr Asn Asp His Leu Val Ala Leu Cys Leu Gly
            755                 760                 765

Gly Arg Pro Ala Leu Asp Ala Val Lys Lys Gly Leu Pro His Ala Pro
            770                 775                 780

Ala Leu Ile Lys Arg Thr Asn Arg Arg Ile Pro Glu Arg Thr Ser His
785                 790                 795                 800

Arg Val Ala Gly Ser
                805

<210> SEQ ID NO 39
<211> LENGTH: 2430
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
tctagagcta gcaccatgga ctacaaagac catgacggtg attataaaga tcatgacatc        60
gattacaagg atgacgatga caagatggcc cccaagaaga agaggaaggt gggcattcac       120
cgcggggtac ctatggtgga cttgaggaca ctcggttatt cgcaacagca acaggagaaa       180
atcaagccta aggtcaggag caccgtcgcg caacaccacg aggcgcttgt ggggcatggc       240
ttcactcatg cgcatattgt cgcgctttca cagcaccctg cggcgcttgg acggtggct        300 gtcaaatacc aagatatgat tgcggccctg cccgaagcca cgcacgaggc aattgtaggg       360
gtcggtaaac agtggtcggg agcgcgagca cttgaggcgc tgctgactgt ggcgggtgag       420
cttagggggc ctccgctcca gctcgacacc gggcagctgc tgaagatcgc gaagagaggg       480
ggagtaacag cggtagaggc agtgcacgcc tggcgcaatg cgctcaccgg gccccccttg       540
aacctgaccc cagaccaggt agtcgcaatc gcgaacaata tgggggaaa gcaagccctg       600 gaaaccgtgc aaaggttgtt gccggtcctt tgtcaagacc acggccttac accggagcaa       660
gtcgtggcca ttgcaagcaa tgggggtggc aaacaggctc ttgagacggt tcagagactt       720
ctcccagttc tctgtcaagc ccacgggctg actccgatca agttgtagcg gattgcgaat       780
aacaatggag ggaaacaagc attggagact gtccaacggc tccttcccgt gttgtgtcaa       840
gcccacggtt tgacgcctgc acaagtggtc gccatcgcca gccatgatgg cggtaagcag       900
gcgctggaaa cagtcagcg cctgctgcct gtactgtgcc aggatcatgg actgaccccca       960 gaccaggtag tcgcaatcgc gtcacatgac ggggaaagc aagccctgga aaccgtgcaa      1020
aggttgttgc cggtcctttg tcaagaccac ggccttacac cggagcaagt cgtggccatt      1080
gcatcccacg acggtggcaa acaggctctt gagacggttc agagacttct cccagttctc      1140
tgtcaagccc acgggctgac tccgatcaa gttgtagcga ttgcgtcgca tgacggaggg      1200
aaacaagcat ggagactgt ccaacggctc cttcccgtgt tgtgtcaagc ccacggtttg      1260
acgcctgcac aagtggtcgc catcgcctcc aatattggcg gtaagcaggc gctgaaaaca      1320
gtacagcgcc tgctgcctgt actgtgccag gatcatggac tgaccccaga ccaggtagtc      1380
```

-continued

```
gcaatcgcga acaataatgg gggaaagcaa gccctggaaa ccgtgcaaag gttgttgccg    1440
gtcctttgtc aagaccacgg ccttacaccg gagcaagtcg tggccattgc aaataataac    1500
ggtggcaaac aggctcttga cggttcag agacttctcc cagttctctg tcaagcccac      1560
gggctgactc ccgatcaagt tgtagcgatt gcgtcgaaca ttggagggaa acaagcattg    1620
gagactgtcc aacggctcct tcccgtgttg tgtcaagccc acggtttgac gcctgcacaa    1680
gtggtcgcca tcgcctcgaa tggcggcggt aagcaggcgc tggaaacagt acagcgcctg    1740
ctgcctgtac tgtgccagga tcatggactg accccagacc aggtagtcgc aatcgcgaac    1800
aataatgggg gaaagcaagc cctggaaacc gtgcaaaggt tgttgccggt cctttgtcaa    1860
gaccacggcc ttacaccgga gcaagtcgtg gccattgcaa gcaatggggg tggcaaacag    1920
gctcttgaga cggttcagag acttctccca gttctctgtc aagcccacgg gctgactccc    1980
gatcaagttg tagcgattgc gtccaacggt ggagggaaac aagcattgga gactgtccaa    2040
cggctccttc ccgtgttgtg tcaagcccac ggtttgacgc ctgcacaagt ggtcgccatc    2100
gccaacaaca acggcggtaa gcaggcgctg aaacagtac agcgcctgct gcctgtactg     2160
tgccaggatc atggactgac acccgaacag gtggtcgcca ttgcttccca cgacggagga    2220
cggccagcct tggagtccat cgtagcccaa ttgtccaggc ccgatcccgc gttggctgcg    2280
ttaacgaatg accatctggt ggcgttggca tgtcttggtg gacgaccgcg gctcgatgca    2340
gtcaaaaagg gtctgcctca tgctcccgca ttgatcaaaa gaaccaaccg gcggattccc    2400
gagagaactt cccatcgagt cgcgggatcc                                     2430
```

<210> SEQ ID NO 40
<211> LENGTH: 805
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
```

```
                    165                 170                 175
Leu Thr Pro Asp Gln Val Val Ala Ile Ala Asn Asn Asn Gly Gly Lys
                180                 185                 190

Gln Ala Leu Glu Thr Val Gln Arg Leu Leu Pro Val Leu Cys Gln Asp
            195                 200                 205

His Gly Leu Thr Pro Glu Gln Val Val Ala Ile Ala Ser Asn Gly Gly
        210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Asn Asn
                245                 250                 255

Asn Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Asp
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Asn Asn Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Asn Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590
```

```
Ile Ala Asn Asn Asn Gly Gly Lys Gln Ala Leu Glu Thr Val Gln Arg
        595                 600                 605

Leu Leu Pro Val Leu Cys Gln Asp His Gly Leu Thr Pro Glu Gln Val
    610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Ala His Gly Leu Thr
            675                 680                 685

Pro Ala Gln Val Val Ala Ile Ala Asn Asn Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser His Asp Gly Gly Arg
                725                 730                 735

Pro Ala Leu Glu Ser Ile Val Ala Gln Leu Ser Arg Pro Asp Pro Ala
                740                 745                 750

Leu Ala Ala Leu Thr Asn Asp His Leu Val Ala Leu Ala Cys Leu Gly
                755                 760                 765

Gly Arg Pro Ala Leu Asp Ala Val Lys Lys Gly Leu Pro His Ala Pro
        770                 775                 780

Ala Leu Ile Lys Arg Thr Asn Arg Arg Ile Pro Glu Arg Thr Ser His
785                 790                 795                 800

Arg Val Ala Gly Ser
                805

<210> SEQ ID NO 41
<211> LENGTH: 16
<212> TYPE: DNA
<213> ORGANISM: Homo sapiens

<400> SEQUENCE: 41
gcagtgcttc agccgc                                                        16

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tctagagaag acaagaacct gacc                                               24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-biotin

<400> SEQUENCE: 43
```

```
ggatccggtc tcttaaggcc gtgg                                          24

<210> SEQ ID NO 44
<211> LENGTH: 16
<212> TYPE: DNA
<213> ORGANISM: Homo sapiens

<400> SEQUENCE: 44
gcagtgcttc agccgc                                                   16

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 tctaacatc                                                            9

<210> SEQ ID NO 46
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 tcccacgac                                                            9

<210> SEQ ID NO 47
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 aataataac                                                            9

<210> SEQ ID NO 48
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48 tccaataaa                                                            9

<210> SEQ ID NO 49
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 tctaatggg                                                            9

<210> SEQ ID NO 50
<211> LENGTH: 17
```

```
<212> TYPE: DNA
<213> ORGANISM: Homo sapiens

<400> SEQUENCE: 50
tgcagtgctt cagccgc                                                  17

<210> SEQ ID NO 51
<211> LENGTH: 18
<212> TYPE: DNA
<213> ORGANISM: Homo sapiens

<400> SEQUENCE: 51
tgcagtgctt cagccgct                                                 18

<210> SEQ ID NO 52
<211> LENGTH: 18
<212> TYPE: DNA
<213> ORGANISM: Homo sapiens

<400> SEQUENCE: 52
ttgaagaagt cgtgctgc                                                 18

<210> SEQ ID NO 53
<211> LENGTH: 18
<212> TYPE: DNA
<213> ORGANISM: Homo sapiens

<400> SEQUENCE: 53
tgaagaagtc gtgctgct                                                 18

<210> SEQ ID NO 54
<211> LENGTH: 17
<212> TYPE: DNA
<213> ORGANISM: Homo sapiens

<400> SEQUENCE: 54
tcgagctgaa gggcatc                                                  17

<210> SEQ ID NO 55
<211> LENGTH: 18
<212> TYPE: DNA
<213> ORGANISM: Homo sapiens

<400> SEQUENCE: 55
tcgagctgaa gggcatcg                                                 18

<210> SEQ ID NO 56
<211> LENGTH: 18
<212> TYPE: DNA
<213> ORGANISM: Homo sapiens

<400> SEQUENCE: 56
ttgtgcccca ggatgttg                                                 18

<210> SEQ ID NO 57
<211> LENGTH: 18
<212> TYPE: DNA
<213> ORGANISM: Homo sapiens

<400> SEQUENCE: 57
tgtgccccag gatgttgc                                                 18

<210> SEQ ID NO 58
```

-continued

```
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
tctagagaag acaagaacct gaccccagac caggtagtcg caatcgcgtc gaacattggg      60
ggaaagcaag ccctggaaac cgtgcaaagg ttgttgccgg tcctttgtca agaccacggc     120
cttaagagac cggatcc                                                    137

<210> SEQ ID NO 59
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
tctagagaag acaagaacct gaccccagac caggtagtcg caatcgcgtc acatgacggg      60
ggaaagcaag ccctggaaac cgtgcaaagg ttgttgccgg tcctttgtca agaccacggc     120
cttaagagac cggatcc                                                    137

<210> SEQ ID NO 60
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tctagagaag acaagaacct gaccccagac caggtagtcg caatcgcgtc gaacaaaggg      60
ggaaagcaag ccctggaaac cgtgcaaagg ttgttgccgg tcctttgtca agaccacggc     120
cttaagagac cggatcc                                                    137

<210> SEQ ID NO 61
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
tctagagaag acaagaacct gaccccagac caggtagtcg caatcgcgaa caataatggg      60
ggaaagcaag ccctggaaac cgtgcaaagg ttgttgccgg tcctttgtca agaccacggc     120
cttaagagac cggatcc                                                    137

<210> SEQ ID NO 62
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
tctagagaag acaagaacct gaccccagac caggtagtcg caatcgcgtc aaacggaggg      60
```
ggaaagcaag ccctggaaac cgtgcaaagg ttgttgccgg tcctttgtca agaccacggc    120
cttaagagac cggatcc                                                   137

<210> SEQ ID NO 63
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
tctagagaag acaacttaca ccggagcaag tcgtggccat tgcaagcaac atcggtggca    60
aacaggctct tgagacggtt cagagacttc tcccagttct ctgtcaagcc cacgggctga    120
agagaccgga tcc                                                       133

<210> SEQ ID NO 64
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
tctagagaag acaacttaca ccggagcaag tcgtggccat tgcatcccac gacggtggca    60
aacaggctct tgagacggtt cagagacttc tcccagttct ctgtcaagcc cacgggctga    120
agagaccgga tcc                                                       133

<210> SEQ ID NO 65
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
tctagagaag acaacttaca ccggagcaag tcgtggccat tgcatcaaat aaaggtggca    60
aacaggctct tgagacggtt cagagacttc tcccagttct ctgtcaagcc cacgggctga    120
agagaccgga tcc                                                       133

<210> SEQ ID NO 66
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
tctagagaag acaacttaca ccggagcaag tcgtggccat tgcaaataat aacggtggca    60
aacaggctct tgagacggtt cagagacttc tcccagttct ctgtcaagcc cacgggctga    120
agagaccgga tcc                                                       133

<210> SEQ ID NO 67
<211> LENGTH: 133
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 67
tctagagaag acaacttaca ccggagcaag tcgtggccat tgcaagcaat ggggtggca      60 aacaggctct tgagacggtt cagagacttc tcccagttct ctgtcaagcc cacgggctga    120
agagaccgga tcc                                                       133

<210> SEQ ID NO 68
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
tctagagaag acaactgact cccgatcaag ttgtagcgat tgcgtcgaac attggaggga    60
aacaagcatt ggagactgtc caacggctcc ttcccgtgtt gtgtcaagcc cacggtttga   120
agagaccgga tcc                                                       133

<210> SEQ ID NO 69
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
tctagagaag acaactgact cccgatcaag ttgtagcgat tgcgtcgcat gacggaggga    60
aacaagcatt ggagactgtc caacggctcc ttcccgtgtt gtgtcaagcc cacggtttga   120
agagaccgga tcc                                                       133

<210> SEQ ID NO 70
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
tctagagaag acaactgact cccgatcaag ttgtagcgat tgcgtccaac aagggaggga    60
aacaagcatt ggagactgtc caacggctcc ttcccgtgtt gtgtcaagcc cacggtttga   120
agagaccgga tcc                                                       133

<210> SEQ ID NO 71
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
tctagagaag acaactgact cccgatcaag ttgtagcgat tgcgaataac aatggaggga    60
aacaagcatt ggagactgtc caacggctcc ttcccgtgtt gtgtcaagcc cacggtttga   120
agagaccgga tcc                                                       133

<210> SEQ ID NO 72
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
tctagagaag acaactgact cccgatcaag ttgtagcgat tgcgtccaac ggtggaggga      60
aacaagcatt ggagactgtc caacggctcc ttcccgtgtt gtgtcaagcc cacggtttga     120
agagaccgga tcc                                                        133

<210> SEQ ID NO 73
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
tctagagaag acaattgacg cctgcacaag tggtcgccat cgcctccaat attggcggta      60
agcaggcgct ggaaacagta cagcgcctgc tgcctgtact gtgccaggat catggactga     120
agagaccgga tcc                                                        133

<210> SEQ ID NO 74
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
tctagagaag acaattgacg cctgcacaag tggtcgccat cgccagccat gatggcggta      60
agcaggcgct ggaaacagta cagcgcctgc tgcctgtact gtgccaggat catggactga     120
agagaccgga tcc                                                        133

<210> SEQ ID NO 75
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
tctagagaag acaattgacg cctgcacaag tggtcgccat cgccagcaat aagggcggta      60
agcaggcgct ggaaacagta cagcgcctgc tgcctgtact gtgccaggat catggactga     120
agagaccgga tcc                                                        133

<210> SEQ ID NO 76
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
tctagagaag acaattgacg cctgcacaag tggtcgccat cgccaacaac aacggcggta      60

```
agcaggcgct ggaaacagta cagcgcctgc tgcctgtact gtgccaggat catggactga    120
agagaccgga tcc                                                      133
```

<210> SEQ ID NO 77
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
tctagagaag acaattgacg cctgcacaag tggtcgccat cgcctcgaat ggcggcggta    60
agcaggcgct ggaaacagta cagcgcctgc tgcctgtact gtgccaggat catggactga    120
agagaccgga tcc                                                      133
```

<210> SEQ ID NO 78
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
tctagagaag acaactgacc ccagaccagg tagtcgcaat cgcgtcgaac attggggaa    60 agcaagccct ggaaaccgtg caaaggttgt tgccggtcct ttgtcaagac cacggcctta    120
agagaccgga tcc                                                      133
```

<210> SEQ ID NO 79
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
tctagagaag acaactgacc ccagaccagg tagtcgcaat cgcgtcacat gacggggaa     60 agcaagccct ggaaaccgtg caaaggttgt tgccggtcct ttgtcaagac cacggcctta    120
agagaccgga tcc                                                      133
```

<210> SEQ ID NO 80
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
tctagagaag acaactgacc ccagaccagg tagtcgcaat cgcgtcgaac aaaggggaa    60 agcaagccct ggaaaccgtg caaaggttgt tgccggtcct ttgtcaagac cacggcctta    120
agagaccgga tcc                                                      133
```

<210> SEQ ID NO 81
<211> LENGTH: 133
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 81
tctagagaag acaactgacc ccagaccagg tagtcgcaat cgcgaacaat aatgggggaa    60
agcaagccct ggaaaccgtg caaaggttgt tgccggtcct ttgtcaagac cacggcctta   120
agagaccgga tcc                                                      133

<210> SEQ ID NO 82
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
tctagagaag acaactgacc ccagaccagg tagtcgcaat cgcgtcaaac ggaggggaa    60 agcaagccct ggaaaccgtg caaaggttgt tgccggtcct ttgtcaagac cacggcctta   120
agagaccgga tcc                                                      133

<210> SEQ ID NO 83
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
tctagagaag acaactgact cccgatcaag ttgtagcgat tgcgtcgaac attggaggga    60
aacaagcatt ggagactgtc caacggctcc ttcccgtgtt gtgtcaagcc cacggtctga   120
agagaccgga tcc                                                      133

<210> SEQ ID NO 84
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
tctagagaag acaactgact cccgatcaag ttgtagcgat tgcgtcgcat gacggaggga    60
aacaagcatt ggagactgtc caacggctcc ttcccgtgtt gtgtcaagcc cacggtctga   120
agagaccgga tcc                                                      133

<210> SEQ ID NO 85
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
tctagagaag acaactgact cccgatcaag ttgtagcgat tgcgtccaac aagggaggga    60
aacaagcatt ggagactgtc caacggctcc ttcccgtgtt gtgtcaagcc cacggtctga   120
agagaccgga tcc                                                      133
```

<210> SEQ ID NO 86
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
tctagagaag acaactgact cccgatcaag ttgtagcgat tgcgaataac aatggaggga      60
aacaagcatt ggagactgtc caacggctcc ttcccgtgtt gtgtcaagcc cacggtctga     120
agagaccgga tcc                                                         133

<210> SEQ ID NO 87
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
tctagagaag acaactgact cccgatcaag ttgtagcgat tgcgtccaac ggtggaggga      60
aacaagcatt ggagactgtc caacggctcc ttcccgtgtt gtgtcaagcc cacggtctga     120
agagaccgga tcc                                                         133

<210> SEQ ID NO 88
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
tctagagaag acaactgacc ccagaccagg tagtcgcaat cgcgtcgaac attgggggaa      60
agcaagccct ggaaaccgtg caaaggttgt tgccggtcct ttgtcaagac cacggcctga    120
agagaccgga tcc                                                         133

<210> SEQ ID NO 89
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
tctagagaag acaactgacc ccagaccagg tagtcgcaat cgcgtcacat gacgggggaa      60
agcaagccct ggaaaccgtg caaaggttgt tgccggtcct ttgtcaagac cacggcctga    120
agagaccgga tcc                                                         133

<210> SEQ ID NO 90
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
tctagagaag acaactgacc ccagaccagg tagtcgcaat cgcgtcgaac aaaggggaa    60 agcaagccct ggaaaccgtg caaaggttgt tgccggtcct ttgtcaagac cacggcctga   120
agagaccgga tcc                                                       133

```
<210> SEQ ID NO 91
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
```
tctagagaag acaactgacc ccagaccagg tagtcgcaat cgcgaacaat aatggggaa    60 agcaagccct ggaaaccgtg caaaggttgt tgccggtcct ttgtcaagac cacggcctga   120
agagaccgga tcc                                                       133

```
<210> SEQ ID NO 92
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
```
tctagagaag acaactgacc ccagaccagg tagtcgcaat cgcgtcaaac ggaggggaa    60 agcaagccct ggaaaccgtg caaaggttgt tgccggtcct ttgtcaagac cacggcctga   120
agagaccgga tcc                                                       133

```
<210> SEQ ID NO 93
<211> LENGTH: 36
<212> TYPE: DNA
<213> ORGANISM: Homo sapiens

<400> SEQUENCE: 93
```
tcgccaccat ggtgagcaag ggcgaggagc tgttca                              36

```
<210> SEQ ID NO 94
<211> LENGTH: 36
<212> TYPE: DNA
<213> ORGANISM: Homo sapiens

<400> SEQUENCE: 94
```
tggtgcccat cctggtcgag ctggacggcg acgtaa                              36

```
<210> SEQ ID NO 95
<211> LENGTH: 36
<212> TYPE: DNA
<213> ORGANISM: Homo sapiens

<400> SEQUENCE: 95
```
tctgcaccac cggcaagctg cccgtgccct ggccca                              36

```
<210> SEQ ID NO 96
<211> LENGTH: 36
<212> TYPE: DNA
<213> ORGANISM: Homo sapiens

<400> SEQUENCE: 96
```
tggagtacaa ctacaacagc cacaacgtct atatca                              36

<210> SEQ ID NO 97
<211> LENGTH: 38
<212> TYPE: DNA
<213> ORGANISM: Homo sapiens

<400> SEQUENCE: 97
ttcagcgtgt ccggcgaggg cgagggcgat gccaccta                           38

<210> SEQ ID NO 98
<211> LENGTH: 38
<212> TYPE: DNA
<213> ORGANISM: Homo sapiens

<400> SEQUENCE: 98
tgccacctac ggcaagctga ccctgaagtt catctgca                           38

<210> SEQ ID NO 99
<211> LENGTH: 38
<212> TYPE: DNA
<213> ORGANISM: Homo sapiens

<400> SEQUENCE: 99
tggcccaccc tcgtgaccac cctgacctac ggcgtgca                           38

<210> SEQ ID NO 100
<211> LENGTH: 38
<212> TYPE: DNA
<213> ORGANISM: Homo sapiens

<400> SEQUENCE: 100
ttcaagatcc gccacaacat cgaggacggc agcgtgca                           38

<210> SEQ ID NO 101
<211> LENGTH: 40
<212> TYPE: DNA
<213> ORGANISM: Homo sapiens

<400> SEQUENCE: 101
tagaggatcc accggtcgcc accatggtga gcaagggcga                         40

<210> SEQ ID NO 102
<211> LENGTH: 40
<212> TYPE: DNA
<213> ORGANISM: Homo sapiens

<400> SEQUENCE: 102
tccggcgagg gcgagggcga tgccacctac ggcaagctga                         40

<210> SEQ ID NO 103
<211> LENGTH: 40
<212> TYPE: DNA
<213> ORGANISM: Homo sapiens

<400> SEQUENCE: 103
tgacctacgg cgtgcagtgc ttcagccgct accccgacca                         40

<210> SEQ ID NO 104
<211> LENGTH: 40
<212> TYPE: DNA
<213> ORGANISM: Homo sapiens

<400> SEQUENCE: 104

```
tccgccacaa catcgaggac ggcagcgtgc agctcgccga                    40

<210> SEQ ID NO 105
<211> LENGTH: 42
<212> TYPE: DNA
<213> ORGANISM: Homo sapiens

<400> SEQUENCE: 105
tcctggtcga gctggacggc gacgtaaacg gccacaagtt ca                 42

<210> SEQ ID NO 106
<211> LENGTH: 42
<212> TYPE: DNA
<213> ORGANISM: Homo sapiens

<400> SEQUENCE: 106
tcagccgcta ccccgaccac atgaagcagc acgacttctt ca                 42

<210> SEQ ID NO 107
<211> LENGTH: 42
<212> TYPE: DNA
<213> ORGANISM: Homo sapiens

<400> SEQUENCE: 107
tcttcaagtc cgccatgccc gaaggctacg tccaggagcg ca                 42

<210> SEQ ID NO 108
<211> LENGTH: 42
<212> TYPE: DNA
<213> ORGANISM: Homo sapiens

<400> SEQUENCE: 108
tcaaggagga cggcaacatc ctggggcaca agctggagta ca                 42

<210> SEQ ID NO 109
<211> LENGTH: 42
<212> TYPE: DNA
<213> ORGANISM: Homo sapiens

<400> SEQUENCE: 109
tcaaggtgaa cttcaagatc cgccacaaca tcgaggacgg ca                 42

<210> SEQ ID NO 110
<211> LENGTH: 44
<212> TYPE: DNA
<213> ORGANISM: Homo sapiens

<400> SEQUENCE: 110
tccaccggtc gccaccatgg tgagcaaggg cgaggagctg ttca               44

<210> SEQ ID NO 111
<211> LENGTH: 44
<212> TYPE: DNA
<213> ORGANISM: Homo sapiens

<400> SEQUENCE: 111
ttcagcgtgt ccggcgaggg cgagggcgat gccacctacg gcaa               44

<210> SEQ ID NO 112
<211> LENGTH: 44
<212> TYPE: DNA
<213> ORGANISM: Homo sapiens

<400> SEQUENCE: 112
```
ttcagccgct accccgacca catgaagcag cacgacttct tcaa                    44

<210> SEQ ID NO 113
<211> LENGTH: 44
<212> TYPE: DNA
<213> ORGANISM: Homo sapiens

<400> SEQUENCE: 113
tacaacagcc acaacgtcta tatcatggcc gacaagcaga agaa                    44

<210> SEQ ID NO 114
<211> LENGTH: 46
<212> TYPE: DNA
<213> ORGANISM: Homo sapiens

<400> SEQUENCE: 114
tggtgcccat cctggtcgag ctggacggcg acgtaaacgg ccacaa                  46

<210> SEQ ID NO 115
<211> LENGTH: 46
<212> TYPE: DNA
<213> ORGANISM: Homo sapiens

<400> SEQUENCE: 115
tgcccgaagg ctacgtccag gagcgcacca tcttcttcaa ggacga                  46

<210> SEQ ID NO 116
<211> LENGTH: 46
<212> TYPE: DNA
<213> ORGANISM: Homo sapiens

<400> SEQUENCE: 116
tgaaccgcat cgagctgaag ggcatcgact caaggagga cggcaa                   46

<210> SEQ ID NO 117
<211> LENGTH: 46
<212> TYPE: DNA
<213> ORGANISM: Homo sapiens

<400> SEQUENCE: 117
tcaagatccg ccacaacatc gaggacggca gcgtgcagct cgccga                  46

<210> SEQ ID NO 118
<211> LENGTH: 48
<212> TYPE: DNA
<213> ORGANISM: Homo sapiens

<400> SEQUENCE: 118
tgttcaccgg ggtggtgccc atcctggtcg agctggacgg cgacgtaa                48

<210> SEQ ID NO 119
<211> LENGTH: 48
<212> TYPE: DNA
<213> ORGANISM: Homo sapiens

<400> SEQUENCE: 119
tgcccatcct ggtcgagctg gacggcgacg taaacggcca caagttca                48

<210> SEQ ID NO 120
<211> LENGTH: 48
<212> TYPE: DNA
<213> ORGANISM: Homo sapiens

```
<400> SEQUENCE: 120
tgtccggcga gggcgagggc gatgccacct acggcaagct gaccctga                  48

<210> SEQ ID NO 121
<211> LENGTH: 48
<212> TYPE: DNA
<213> ORGANISM: Homo sapiens

<400> SEQUENCE: 121
tcatctgcac caccggcaag ctgcccgtgc cctggcccac cctcgtga                  48

<210> SEQ ID NO 122
<211> LENGTH: 48
<212> TYPE: DNA
<213> ORGANISM: Homo sapiens

<400> SEQUENCE: 122
tctatatcat ggccgacaag cagaagaacg gcatcaaggt gaacttca                  48

<210> SEQ ID NO 123
<211> LENGTH: 50
<212> TYPE: DNA
<213> ORGANISM: Homo sapiens

<400> SEQUENCE: 123
tacggcgtgc agtgcttcag ccgctacccc gaccacatga agcagcacga                50

<210> SEQ ID NO 124
<211> LENGTH: 50
<212> TYPE: DNA
<213> ORGANISM: Homo sapiens

<400> SEQUENCE: 124
taccccgacc acatgaagca gcacgacttc ttcaagtccg ccatgcccga                50

<210> SEQ ID NO 125
<211> LENGTH: 50
<212> TYPE: DNA
<213> ORGANISM: Homo sapiens

<400> SEQUENCE: 125
tccgccatgc ccgaaggcta cgtccaggag cgcaccatct tcttcaagga                50

<210> SEQ ID NO 126
<211> LENGTH: 50
<212> TYPE: DNA
<213> ORGANISM: Homo sapiens

<400> SEQUENCE: 126
ttcaaggagg acggcaacat cctggggcac aagctggagt acaactacaa                50

<210> SEQ ID NO 127
<211> LENGTH: 50
<212> TYPE: DNA
<213> ORGANISM: Homo sapiens

<400> SEQUENCE: 127
tacaactaca acagccacaa cgtctatatc atggccgaca agcagaagaa                50

<210> SEQ ID NO 128
<211> LENGTH: 52
<212> TYPE: DNA
<213> ORGANISM: Homo sapiens
```

<400> SEQUENCE: 128
tcaccggggt ggtgcccatc ctggtcgagc tggacggcga cgtaaacggc ca          52

<210> SEQ ID NO 129
<211> LENGTH: 52
<212> TYPE: DNA
<213> ORGANISM: Homo sapiens

<400> SEQUENCE: 129
taaacggcca caagttcagc gtgtccggcg agggcgaggg cgatgccacc ta          52

<210> SEQ ID NO 130
<211> LENGTH: 52
<212> TYPE: DNA
<213> ORGANISM: Homo sapiens

<400> SEQUENCE: 130
tgcagtgctt cagccgctac cccgaccaca tgaagcagca cgacttcttc aa          52

<210> SEQ ID NO 131
<211> LENGTH: 54
<212> TYPE: DNA
<213> ORGANISM: Homo sapiens

<400> SEQUENCE: 131
tcagcgtgtc cggcgagggc gagggcgatg ccacctacgg caagctgacc ctga        54

<210> SEQ ID NO 132
<211> LENGTH: 54
<212> TYPE: DNA
<213> ORGANISM: Homo sapiens

<400> SEQUENCE: 132
tgaagttcat ctgcaccacc ggcaagctgc ccgtgccctg gcccaccctc gtga        54

<210> SEQ ID NO 133
<211> LENGTH: 54
<212> TYPE: DNA
<213> ORGANISM: Homo sapiens

<400> SEQUENCE: 133
tcgtgaccac cctgacctac ggcgtgcagt gcttcagccg ctaccccgac caca        54

<210> SEQ ID NO 134
<211> LENGTH: 54
<212> TYPE: DNA
<213> ORGANISM: Homo sapiens

<400> SEQUENCE: 134
tcatggccga caagcagaag aacggcatca aggtgaactt caagatccgc caca        54

<210> SEQ ID NO 135
<211> LENGTH: 56
<212> TYPE: DNA
<213> ORGANISM: Homo sapiens

<400> SEQUENCE: 135
ttcaccgggg tggtgcccat cctggtcgag ctggacggcg acgtaaacgg ccacaa      56

<210> SEQ ID NO 136
<211> LENGTH: 56
<212> TYPE: DNA

<213> ORGANISM: Homo sapiens

<400> SEQUENCE: 136
tgcaccaccg gcaagctgcc cgtgccctgg cccacccctcg tgaccaccct gaccta    56

<210> SEQ ID NO 137
<211> LENGTH: 56
<212> TYPE: DNA
<213> ORGANISM: Homo sapiens

<400> SEQUENCE: 137
ttcaagtccg ccatgcccga aggctacgtc caggagcgca ccatcttctt caagga    56

<210> SEQ ID NO 138
<211> LENGTH: 56
<212> TYPE: DNA
<213> ORGANISM: Homo sapiens

<400> SEQUENCE: 138
tatatcatgg ccgacaagca gaagaacggc atcaaggtga acttcaagat ccgcca    56

<210> SEQ ID NO 139
<211> LENGTH: 58
<212> TYPE: DNA
<213> ORGANISM: Homo sapiens

<400> SEQUENCE: 139
ttcatctgca ccaccggcaa gctgcccgtg ccctggccca ccctcgtgac caccctga    58

<210> SEQ ID NO 140
<211> LENGTH: 58
<212> TYPE: DNA
<213> ORGANISM: Homo sapiens

<400> SEQUENCE: 140
tgaagttcga gggcgacacc ctggtgaacc gcatcgagct gaagggcatc gacttcaa    58

<210> SEQ ID NO 141
<211> LENGTH: 52
<212> TYPE: DNA
<213> ORGANISM: Homo sapiens

<400> SEQUENCE: 141
tacctattat tactttatgg ggcagcagcc tggaaaagta cttggggacc aa    52

<210> SEQ ID NO 142
<211> LENGTH: 52
<212> TYPE: DNA
<213> ORGANISM: Homo sapiens

<400> SEQUENCE: 142
tgtgtcttgg gatgagtggg tcagtgttct ggtgctcaca ggatggctgg ca    52

<210> SEQ ID NO 143
<211> LENGTH: 51
<212> TYPE: DNA
<213> ORGANISM: Homo sapiens

<400> SEQUENCE: 143
tcctgtggct cctgccgctg ctgctttcca cggcagctgt gggctccggg a    51

<210> SEQ ID NO 144
<211> LENGTH: 52

<212> TYPE: DNA
<213> ORGANISM: Homo sapiens

<400> SEQUENCE: 144
tatgtacgcc tccctgggct cgggtccggt cgccccttg cccgcttctg ta         52

<210> SEQ ID NO 145
<211> LENGTH: 54
<212> TYPE: DNA
<213> ORGANISM: Homo sapiens

<400> SEQUENCE: 145
tgaattggga tgctgttttt aggtattcta ttcaaattta ttttactgtc ttta       54

<210> SEQ ID NO 146
<211> LENGTH: 52
<212> TYPE: DNA
<213> ORGANISM: Homo sapiens

<400> SEQUENCE: 146
tccctcacca tgagtagcgc tatgttggtg acttgcctcc cggaccccag ca         52

<210> SEQ ID NO 147
<211> LENGTH: 52
<212> TYPE: DNA
<213> ORGANISM: Homo sapiens

<400> SEQUENCE: 147
tgtgcgatct ccaagcactg aggggcagaa actcccggat cgggcgctgc ca         52

<210> SEQ ID NO 148
<211> LENGTH: 52
<212> TYPE: DNA
<213> ORGANISM: Homo sapiens

<400> SEQUENCE: 148
ttttcaagtg aagacaaaat ggcctcgccg gctgacagct gtatccagtt ca         52

<210> SEQ ID NO 149
<211> LENGTH: 53
<212> TYPE: DNA
<213> ORGANISM: Homo sapiens

<400> SEQUENCE: 149
tacaattgaa caatgcctca gctatacatt tacatcagat tattgggagc cta        53

<210> SEQ ID NO 150
<211> LENGTH: 52
<212> TYPE: DNA
<213> ORGANISM: Homo sapiens

<400> SEQUENCE: 150
tccgaagctg acagatgggt attctttgac gggggtagg ggcggaacct ga          52

<210> SEQ ID NO 151
<211> LENGTH: 52
<212> TYPE: DNA
<213> ORGANISM: Homo sapiens

<400> SEQUENCE: 151
ttagacttag gtaagtaatg caatatggta gactggggag aactacaaac ta         52

<210> SEQ ID NO 152

```
<211> LENGTH: 52
<212> TYPE: DNA
<213> ORGANISM: Homo sapiens

<400> SEQUENCE: 152
tctgcaataa aaatggcct ccaacaaaac tacattggta agttaatgaa aa                52

<210> SEQ ID NO 153
<211> LENGTH: 52
<212> TYPE: DNA
<213> ORGANISM: Homo sapiens

<400> SEQUENCE: 153
tggagctttc agcggtgggg gagcgggtgt tcgcggccga agccctcctg aa                52

<210> SEQ ID NO 154
<211> LENGTH: 55
<212> TYPE: DNA
<213> ORGANISM: Homo sapiens

<400> SEQUENCE: 154
tggaacacca gctcctgtgc tgcgaagtgg aaaccatccg ccgcgcgtac cccga             55

<210> SEQ ID NO 155
<211> LENGTH: 52
<212> TYPE: DNA
<213> ORGANISM: Homo sapiens

<400> SEQUENCE: 155
tgcttagcgt cctgcgacag tacaacatcc agaagaagga gattgtggtg aa                52

<210> SEQ ID NO 156
<211> LENGTH: 52
<212> TYPE: DNA
<213> ORGANISM: Homo sapiens

<400> SEQUENCE: 156
tgctgcaggt accccggatc ccctgacttg cgagggacgc attcgggccg ca                52

<210> SEQ ID NO 157
<211> LENGTH: 49
<212> TYPE: DNA
<213> ORGANISM: Homo sapiens

<400> SEQUENCE: 157
tcccttgatc tgagaatggc tacctctcga tatgagccag tggctgaaa                    49

<210> SEQ ID NO 158
<211> LENGTH: 52
<212> TYPE: DNA
<213> ORGANISM: Homo sapiens

<400> SEQUENCE: 158
tggcgtcggg cctgggctcc ccgtccccct gctcggcggg cagtgaggag ga                52

<210> SEQ ID NO 159
<211> LENGTH: 52
<212> TYPE: DNA
<213> ORGANISM: Homo sapiens

<400> SEQUENCE: 159
tgtgttggaa gaagatggca gatccaggaa tgatgagtct ttttggcgag ga                52
```

```
<210> SEQ ID NO 160
<211> LENGTH: 51
<212> TYPE: DNA
<213> ORGANISM: Homo sapiens

<400> SEQUENCE: 160
tccagcgtgg acaatggcta ctcaaggttt gtgtcattaa atctttagtt a            51

<210> SEQ ID NO 161
<211> LENGTH: 54
<212> TYPE: DNA
<213> ORGANISM: Homo sapiens

<400> SEQUENCE: 161
taatatcaca atgagttcag cttatggag ccaagaaaaa gtcacttcac ccta          54

<210> SEQ ID NO 162
<211> LENGTH: 50
<212> TYPE: DNA
<213> ORGANISM: Homo sapiens

<400> SEQUENCE: 162
tcacacggag gacgcgatgg ctcccaagaa acgcccagaa acccagaaga              50

<210> SEQ ID NO 163
<211> LENGTH: 49
<212> TYPE: DNA
<213> ORGANISM: Homo sapiens

<400> SEQUENCE: 163
tccggccggc gccatgaagt gagaagggg ctggggtcg cgctcgcta                 49

<210> SEQ ID NO 164
<211> LENGTH: 55
<212> TYPE: DNA
<213> ORGANISM: Homo sapiens

<400> SEQUENCE: 164
tccgggatcg ccatgggaac tcaatagaaa atcctcatct tctcactttg tttca        55

<210> SEQ ID NO 165
<211> LENGTH: 53
<212> TYPE: DNA
<213> ORGANISM: Homo sapiens

<400> SEQUENCE: 165
tggcgtccac gggtgagtat ggtggaactg cggtcgcgcc ggcggtagcc gga          53

<210> SEQ ID NO 166
<211> LENGTH: 53
<212> TYPE: DNA
<213> ORGANISM: Homo sapiens

<400> SEQUENCE: 166
tgacccaggc aggacacatg caggccaaaa aacgctattt catcctgctc tca          53

<210> SEQ ID NO 167
<211> LENGTH: 52
<212> TYPE: DNA
<213> ORGANISM: Homo sapiens

<400> SEQUENCE: 167
ttcctcccag ggggatgtcc tgcgcctcag ggtccggtgg tggcctgcgg ca           52
```

<210> SEQ ID NO 168
<211> LENGTH: 52
<212> TYPE: DNA
<213> ORGANISM: Homo sapiens

<400> SEQUENCE: 168
tgcttttaga ataatcatgg gccagactgg gaagaaatct gagaagggac ca        52

<210> SEQ ID NO 169
<211> LENGTH: 52
<212> TYPE: DNA
<213> ORGANISM: Homo sapiens

<400> SEQUENCE: 169
taggcgccaa ggccatgtcc gactcgtggg tcccgaactc cgcctcgggc ca        52

<210> SEQ ID NO 170
<211> LENGTH: 52
<212> TYPE: DNA
<213> ORGANISM: Homo sapiens

<400> SEQUENCE: 170
tgaagggaca tcaccttttc gcttttttcca agatggctca agattcagta ga       52

<210> SEQ ID NO 171
<211> LENGTH: 53
<212> TYPE: DNA
<213> ORGANISM: Homo sapiens

<400> SEQUENCE: 171
tgccccggca tggcgacacc ggacgcgggg ctccctgggg ctgagggcgt gga       53

<210> SEQ ID NO 172
<211> LENGTH: 50
<212> TYPE: DNA
<213> ORGANISM: Homo sapiens

<400> SEQUENCE: 172
ttcgcgcacc tcatggaatc ccttctgcag cacctggatc gcttttccga           50

<210> SEQ ID NO 173
<211> LENGTH: 50
<212> TYPE: DNA
<213> ORGANISM: Homo sapiens

<400> SEQUENCE: 173
tcggccacca tgtcccgcca gaccacctct gtgggctcca gctgcctgga           50

<210> SEQ ID NO 174
<211> LENGTH: 54
<212> TYPE: DNA
<213> ORGANISM: Homo sapiens

<400> SEQUENCE: 174
tccccagaac agcactatgg gcttctcttc cgagctgtgc agcccccagg gcca      54

<210> SEQ ID NO 175
<211> LENGTH: 51
<212> TYPE: DNA
<213> ORGANISM: Homo sapiens

<400> SEQUENCE: 175
tctgctcccc accgaggacc tctgcatgca ggcatgaatc ccaggagcct a         51

<210> SEQ ID NO 176
<211> LENGTH: 53
<212> TYPE: DNA
<213> ORGANISM: Homo sapiens

<400> SEQUENCE: 176
tgtaccgagc acttcggctc ctcgcgcgct cgcgtcccct cgtgcgggct cca        53

<210> SEQ ID NO 177
<211> LENGTH: 54
<212> TYPE: DNA
<213> ORGANISM: Homo sapiens

<400> SEQUENCE: 177
tctccaaggc accatgaatg ccatcgtggc tctctgccac ttctgcgagc tcca       54

<210> SEQ ID NO 178
<211> LENGTH: 56
<212> TYPE: DNA
<213> ORGANISM: Homo sapiens

<400> SEQUENCE: 178
tccggaggcc atgccggcgt tggcgcgcga cggcggccag ctgccgctgc tcggta     56

<210> SEQ ID NO 179
<211> LENGTH: 55
<212> TYPE: DNA
<213> ORGANISM: Homo sapiens

<400> SEQUENCE: 179
tgcagcgggg cgccgcgctg tgcctgcgac tgtggctctg cctgggactc ctgga      55

<210> SEQ ID NO 180
<211> LENGTH: 49
<212> TYPE: DNA
<213> ORGANISM: Homo sapiens

<400> SEQUENCE: 180
tcaccatggc cgaggcgcct caggtggtgg agatcgaccc ggacttcga             49

<210> SEQ ID NO 181
<211> LENGTH: 54
<212> TYPE: DNA
<213> ORGANISM: Homo sapiens

<400> SEQUENCE: 181
tctccgctcg aagtggagct ggacccggag ttcgagcccc agagccgtcc gcga       54

<210> SEQ ID NO 182
<211> LENGTH: 52
<212> TYPE: DNA
<213> ORGANISM: Homo sapiens

<400> SEQUENCE: 182
tcctctgaga cgccatgttc aactcgatga ccccaccacc aatcagtagc ta         52

<210> SEQ ID NO 183
<211> LENGTH: 52
<212> TYPE: DNA
<213> ORGANISM: Homo sapiens

<400> SEQUENCE: 183
tggcgcagac gcagggcacc cggaggaaag tctgttacta ctacgacggt ga    52

<210> SEQ ID NO 184
<211> LENGTH: 54
<212> TYPE: DNA
<213> ORGANISM: Homo sapiens

<400> SEQUENCE: 184
tgcgctcacc tccctgcggc ctcctgaggt ggtttggtgg ccccctcctc gcga    54

<210> SEQ ID NO 185
<211> LENGTH: 52
<212> TYPE: DNA
<213> ORGANISM: Homo sapiens

<400> SEQUENCE: 185
tcctcaacta tgacctcaac cggccaggat tccaccacaa ccaggcagcg aa    52

<210> SEQ ID NO 186
<211> LENGTH: 52
<212> TYPE: DNA
<213> ORGANISM: Homo sapiens

<400> SEQUENCE: 186
tgagcgcacg cggtgagggc gcgggcagc cgtccacttc agcccaggga ca    52

<210> SEQ ID NO 187
<211> LENGTH: 53
<212> TYPE: DNA
<213> ORGANISM: Homo sapiens

<400> SEQUENCE: 187
tccgtgctcc tccaccccccg ctggatcgag cccaccgtca tgtttctcta cga    53

<210> SEQ ID NO 188
<211> LENGTH: 49
<212> TYPE: DNA
<213> ORGANISM: Homo sapiens

<400> SEQUENCE: 188
tgggcacggt gatggccacc actggggccc tgggcaacta ctacgtgga    49

<210> SEQ ID NO 189
<211> LENGTH: 54
<212> TYPE: DNA
<213> ORGANISM: Homo sapiens

<400> SEQUENCE: 189
tccagcagat catgtcatga cgacttcgct gctcctgcat ccacgctggc cgga    54

<210> SEQ ID NO 190
<211> LENGTH: 52
<212> TYPE: DNA
<213> ORGANISM: Homo sapiens

<400> SEQUENCE: 190
ttgacgagtg cggccagagc gcagccagca tgtacctgcc gggctgcgcc ta    52

<210> SEQ ID NO 191
<211> LENGTH: 53
<212> TYPE: DNA
<213> ORGANISM: Homo sapiens

<400> SEQUENCE: 191
tgcgggcaga cggcggggc gccggtggcg ccccggcctc ttcctcctcc tca        53

<210> SEQ ID NO 192
<211> LENGTH: 52
<212> TYPE: DNA
<213> ORGANISM: Homo sapiens

<400> SEQUENCE: 192
tctgaaaaag actctgcatg ggaatggcct gccttacgat gacagaaatg ga        52

<210> SEQ ID NO 193
<211> LENGTH: 55
<212> TYPE: DNA
<213> ORGANISM: Homo sapiens

<400> SEQUENCE: 193
taccgcgatg agaggcgctc gcggcgcctg ggattttctc tgcgttctgc tccta     55

<210> SEQ ID NO 194
<211> LENGTH: 52
<212> TYPE: DNA
<213> ORGANISM: Homo sapiens

<400> SEQUENCE: 194
tgaaaatgac tgaatataaa cttgtggtag ttggagctgg tggcgtaggc aa        52

<210> SEQ ID NO 195
<211> LENGTH: 52
<212> TYPE: DNA
<213> ORGANISM: Homo sapiens

<400> SEQUENCE: 195
tagggtcccc ggcgccaggc cacccggccg tcagcagcat gcagggtaag ga        52

<210> SEQ ID NO 196
<211> LENGTH: 52
<212> TYPE: DNA
<213> ORGANISM: Homo sapiens

<400> SEQUENCE: 196
tccaagcgcg aaaaccccgg atggtgagga gcaggtactg gcccggcagc ga        52

<210> SEQ ID NO 197
<211> LENGTH: 52
<212> TYPE: DNA
<213> ORGANISM: Homo sapiens

<400> SEQUENCE: 197
ttattattac atggctttgc cttactgagg cttcatcttg tcctctggtc ca        52

<210> SEQ ID NO 198
<211> LENGTH: 52
<212> TYPE: DNA
<213> ORGANISM: Homo sapiens

<400> SEQUENCE: 198
tctggcgcca aaatgtcgtt cgtggcaggg gttattcggc ggctggacga ga        52

<210> SEQ ID NO 199
<211> LENGTH: 52
<212> TYPE: DNA
<213> ORGANISM: Homo sapiens

<400> SEQUENCE: 199
tgaggaggtt tcgacatggc ggtgcagccg aaggagacgc tgcagttgga ga    52

<210> SEQ ID NO 200
<211> LENGTH: 54
<212> TYPE: DNA
<213> ORGANISM: Homo sapiens

<400> SEQUENCE: 200
tcactgtcgg cggccatgac accgctcgtc tcccgcctga gtcgtctgtg ggta    54

<210> SEQ ID NO 201
<211> LENGTH: 52
<212> TYPE: DNA
<213> ORGANISM: Homo sapiens

<400> SEQUENCE: 201
tgcttagacg ctggattttt tcgggtagt ggaaaaccag gtaagcaccg aa    52

<210> SEQ ID NO 202
<211> LENGTH: 52
<212> TYPE: DNA
<213> ORGANISM: Homo sapiens

<400> SEQUENCE: 202
tcccgcaggg agcggacatg gactacgact cgtaccagca ctatttctac ga    52

<210> SEQ ID NO 203
<211> LENGTH: 50
<212> TYPE: DNA
<213> ORGANISM: Homo sapiens

<400> SEQUENCE: 203
tgccgagctg ctccacgtcc accatgccgg gcatgatctg caagaaccca    50

<210> SEQ ID NO 204
<211> LENGTH: 48
<212> TYPE: DNA
<213> ORGANISM: Homo sapiens

<400> SEQUENCE: 204
tgaggagccg gaccgatgtg gaaactgctg cccgccgcgg gcccggca    48

<210> SEQ ID NO 205
<211> LENGTH: 52
<212> TYPE: DNA
<213> ORGANISM: Homo sapiens

<400> SEQUENCE: 205
tctttactga taatgtcaag ttcatgttac cctcccaacc aaggagcatt ca    52

<210> SEQ ID NO 206
<211> LENGTH: 48
<212> TYPE: DNA
<213> ORGANISM: Homo sapiens

<400> SEQUENCE: 206
tggagggcca ctgagccccg ctacccgccc cacagccttt cctaccca    48

<210> SEQ ID NO 207
<211> LENGTH: 52
<212> TYPE: DNA
<213> ORGANISM: Homo sapiens

```
<400> SEQUENCE: 207
tcggcgcatg aaggaggtac tcctcatttt cgttctctct ctctgtgccc ca          52

<210> SEQ ID NO 208
<211> LENGTH: 52
<212> TYPE: DNA
<213> ORGANISM: Homo sapiens

<400> SEQUENCE: 208
ttgcgctcgg ggcggccatg tcggccggcg aggtcgagcg cctagtgtcg ga          52

<210> SEQ ID NO 209
<211> LENGTH: 52
<212> TYPE: DNA
<213> ORGANISM: Homo sapiens

<400> SEQUENCE: 209
tctgcaggac accatgcggc ttccgggtgc gatgccagct ctggccctca aa          52

<210> SEQ ID NO 210
<211> LENGTH: 52
<212> TYPE: DNA
<213> ORGANISM: Homo sapiens

<400> SEQUENCE: 210
tgagtactcc gcctctaccc cggctgaagc ccgcccccgc cgccacctat ta          52

<210> SEQ ID NO 211
<211> LENGTH: 54
<212> TYPE: DNA
<213> ORGANISM: Homo sapiens

<400> SEQUENCE: 211
tcgggtgttg catccatgga gcgagctgag agctcgaggt gagcggggct cgca        54

<210> SEQ ID NO 212
<211> LENGTH: 48
<212> TYPE: DNA
<213> ORGANISM: Homo sapiens

<400> SEQUENCE: 212
tggaactgct taatagaaac aggcttgtaa ttgtgagtcc gcgctgca              48

<210> SEQ ID NO 213
<211> LENGTH: 51
<212> TYPE: DNA
<213> ORGANISM: Homo sapiens

<400> SEQUENCE: 213
tcccagacat gacagccatc atcaaagaga tcgttagcag aaacaaaagg a           51

<210> SEQ ID NO 214
<211> LENGTH: 53
<212> TYPE: DNA
<213> ORGANISM: Homo sapiens

<400> SEQUENCE: 214
tggcatggcc agcaacagca gctcctgccc gacacctggg ggcgggcacc tca         53

<210> SEQ ID NO 215
<211> LENGTH: 52
<212> TYPE: DNA
```

<213> ORGANISM: Homo sapiens

<400> SEQUENCE: 215
tgctgggtga aagggctgtg ggctgcgttt tagagaagcg ttgggtactg ga        52

<210> SEQ ID NO 216
<211> LENGTH: 52
<212> TYPE: DNA
<213> ORGANISM: Homo sapiens

<400> SEQUENCE: 216
tgcgggacgt gcgggagcgg ctgcaggcgt gggagcgcgc gttccgacgg ca        52

<210> SEQ ID NO 217
<211> LENGTH: 52
<212> TYPE: DNA
<213> ORGANISM: Homo sapiens

<400> SEQUENCE: 217
tcagaataca gttatggcca cccaggtaat ggggcagtct tctggaggag ga        52

<210> SEQ ID NO 218
<211> LENGTH: 53
<212> TYPE: DNA
<213> ORGANISM: Homo sapiens

<400> SEQUENCE: 218
tgagttctgc cggccgccgg ctcccgcagg ggccagggcg aagttggcgc cga       53

<210> SEQ ID NO 219
<211> LENGTH: 52
<212> TYPE: DNA
<213> ORGANISM: Homo sapiens

<400> SEQUENCE: 219
ttctttattt ccagcaatgt ctcaggctgt gcagacaaac ggaactcaac ca        52

<210> SEQ ID NO 220
<211> LENGTH: 52
<212> TYPE: DNA
<213> ORGANISM: Homo sapiens

<400> SEQUENCE: 220
ttcaggagga agcgatggct tcagacagca tatttgagtc atttccttcg ta        52

<210> SEQ ID NO 221
<211> LENGTH: 52
<212> TYPE: DNA
<213> ORGANISM: Homo sapiens

<400> SEQUENCE: 221
tctccttgag gcgccggttg ccggccacaa cccttggcgg agcctgcctg ca        52

<210> SEQ ID NO 222
<211> LENGTH: 54
<212> TYPE: DNA
<213> ORGANISM: Homo sapiens

<400> SEQUENCE: 222
tgttgctgag gtgacttcag tgggactggg agttggtgcc tgcggccctc cgga      54

<210> SEQ ID NO 223
<211> LENGTH: 53

<212> TYPE: DNA
<213> ORGANISM: Homo sapiens

<400> SEQUENCE: 223
tcaggaacga gatggcggtt ctctggaggc tgagtgccgt ttgcggtgcc cta        53

<210> SEQ ID NO 224
<211> LENGTH: 52
<212> TYPE: DNA
<213> ORGANISM: Homo sapiens

<400> SEQUENCE: 224
tgcagaggac aaaagcatgt cttcccttcc tgggtgcatt ggtttggatg ca         52

<210> SEQ ID NO 225
<211> LENGTH: 54
<212> TYPE: DNA
<213> ORGANISM: Homo sapiens

<400> SEQUENCE: 225
ttacgcggcg gggctgtcgc cgtacgcgga caagggcaag tgcggcctcc cgga       54

<210> SEQ ID NO 226
<211> LENGTH: 52
<212> TYPE: DNA
<213> ORGANISM: Homo sapiens

<400> SEQUENCE: 226
tttggtaaga acatgtcgtc catcttgcca ttcacgccgc cagttgtgaa ga         52

<210> SEQ ID NO 227
<211> LENGTH: 53
<212> TYPE: DNA
<213> ORGANISM: Homo sapiens

<400> SEQUENCE: 227
tggtgacggc ggcaacatgt ctgtggcttt cgcggccccg aggcagcgag gca        53

<210> SEQ ID NO 228
<211> LENGTH: 48
<212> TYPE: DNA
<213> ORGANISM: Homo sapiens

<400> SEQUENCE: 228
tggcgcctca gaagcacggc ggtgggggag ggggcggctc ggggccca              48

<210> SEQ ID NO 229
<211> LENGTH: 52
<212> TYPE: DNA
<213> ORGANISM: Homo sapiens

<400> SEQUENCE: 229
tcatgtctca tgcggccgaa ccagctcggg atggcgtaga ggccagcgcg ga         52

<210> SEQ ID NO 230
<211> LENGTH: 53
<212> TYPE: DNA
<213> ORGANISM: Homo sapiens

<400> SEQUENCE: 230 tcggggctg ctcaggggcc tgtggccgct gcacatcgtc ctgtggacgc gta         53

<210> SEQ ID NO 231

```
<211> LENGTH: 53
<212> TYPE: DNA
<213> ORGANISM: Homo sapiens

<400> SEQUENCE: 231
ttccgcccgc ccaggatgga ggcgcccgcc agcgcgcaga ccccgcaccc gca        53

<210> SEQ ID NO 232
<211> LENGTH: 53
<212> TYPE: DNA
<213> ORGANISM: Homo sapiens

<400> SEQUENCE: 232
ttgccgtccc aagcaatgga tgatttgatg ctgtccccgg acgatattga aca        53

<210> SEQ ID NO 233
<211> LENGTH: 52
<212> TYPE: DNA
<213> ORGANISM: Homo sapiens

<400> SEQUENCE: 233
tcctggtcca ccatggccaa accaacaagc aaagattcag cttgaagga ga          52

<210> SEQ ID NO 234
<211> LENGTH: 52
<212> TYPE: DNA
<213> ORGANISM: Homo sapiens

<400> SEQUENCE: 234
tctggatcgc ggagggaatg ccccggaggg cggagaactg ggacgaggcc ga         52

<210> SEQ ID NO 235
<211> LENGTH: 52
<212> TYPE: DNA
<213> ORGANISM: Homo sapiens

<400> SEQUENCE: 235
tgggccagag atggcggcgg ccgacggggc tttgccggag gcggcggctt ta         52

<210> SEQ ID NO 236
<211> LENGTH: 55
<212> TYPE: DNA
<213> ORGANISM: Homo sapiens

<400> SEQUENCE: 236
tgcccagaca agcaacatgg ctcggaaacg cgcggccggc ggggagccgc gggga      55

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-biotin

<400> SEQUENCE: 237
tctagagaag acaagaacct gacc                                        24

<210> SEQ ID NO 238
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 238
ggatccggtc tcttaaggcc gtgg                                          24

<210> SEQ ID NO 239
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gacggtggct gtcaaatacc aagatatg                                      28

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
tctcctccag ttcacttttg actagttggg                                    30

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
agtaacagcg gtagaggcag                                               20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
attgggctac gatggactcc                                               20

<210> SEQ ID NO 243
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ttaattcaat atattcatga ggcac                                         25

<210> SEQ ID NO 244
<211> LENGTH: 5656
<212> TYPE: DNA
<213> ORGANISM: Artificial Sequence
<220> FEATURE:
<223> OTHER INFORMATION: Description of Artificial Sequence: Synthetic

```
      polynucleotide
<220> FEATURE:
<221> NAME/KEY: modified_base
<222> LOCATION: (901)..(910)
<223> OTHER INFORMATION: a, c, t, g, unknown or other

<400> SEQUENCE: 244
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttgcg atgtacgggc cagatatacg cgttgacatt     240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
nnnnnnnnnn ggatcccaac tagtcaaaag tgaactggag gagaagaaat ctgaacttcg    960
tcataaattg aaatatgtgc ctcatgaata tattgaatta attgaaattg ccagaaattc   1020
cactcaggat agaattcttg aaatgaaggt aatggaattt tttatgaaag tttatggata   1080
tagaggtaaa catttgggtg gatcaaggaa accggacgga gcaatttata ctgtcggatc   1140
tcctattgat tacggtgtga tcgtggatac taaagcttat agcggaggtt ataatctgcc   1200
aattggccaa gcagatgaaa tgcaacgata tgtcgaagaa aatcaaacac gaaacaaaca   1260 tatcaacccct aatgaatggt ggaaagtcta tccatcttct gtaacggaat ttaagttttt   1320
atttgtgagt ggtcacttta aaggaaacta caaagctcag cttacacgat taaatcatat   1380
cactaattgt aatggagctg ttcttagtgt agaagagctt ttaattggtg agaaatgat    1440 taaagccggc acattaacct tagaggaagt cagacgaaaa tttaataacg gcagataaa    1500 ctttttaaggg cccttcgaag gtaagcctat ccctaaccct ctcctcggtc tcgattctac   1560
gcgtaccggt catcatcacc atcaccattg agtttaaacc cgctgatcag cctcgactgt   1620
gccttctagt tgccagccat ctgttgtttg cccctcccc gtgccttcct tgaccctgga    1680
aggtgccact cccactgtcc tttcctaata aaatgaggaa attgcatcgc attgtctgag   1740
taggtgtcat tctattctgg ggggtggggt ggggcaggac agcaagggg aggattggga    1800 agacaatagc aggcatgctg gggatgcggt gggctctatg gcttctgagg cggaaagaac   1860
cagctggggc tctaggggt atccccacgc gccctgtagc ggcgcattaa gcgcggcggg   1920
tgtggtggtt acgcgcagcg tgaccgctac acttgccagc gccctagcgc ccgctccttt   1980
cgctttcttc ccttccttc tcgccacgtt cgccggcttt cccgtcaag ctctaaatcg   2040 gggcatccct ttagggttcc gatttagtgc tttacggcac ctcgacccca aaaaacttga   2100
ttagggtgat ggttcacgta gtgggccatc gccctgatag acggtttttc gccctttgac   2160
```

```
gttggagtcc acgttcttta atagtggact cttgttccaa actggaacaa cactcaaccc    2220
tatctcggtc tattcttttg atttataagg gattttgggg atttcggcct attggttaaa    2280
aaatgagctg atttaacaaa aatttaacgc gaattaattc tgtggaatgt gtgtcagtta    2340
gggtgtggaa agtccccagg ctccccaggc aggcagaagt atgcaaagca tgcatctcaa    2400
ttagtcagca accaggtgtg gaaagtcccc aggctcccca gcaggcagaa gtatgcaaag    2460
catgcatctc aattagtcag caaccatagt cccgcccta actccgccca tcccgcccct     2520
aactccgccc agttccgccc attctccgcc ccatggctga ctaattttt ttatttatgc     2580
agaggccgag gccgcctctg cctctgagct attccagaag tagtgaggag cttttttgg     2640
aggcctaggc ttttgcaaaa agctcccggg agcttgtata tccattttcg gatctgatca    2700
gcacgtgttg acaattaatc atcggcatag tatatcggca tagtataata cgacaaggtg    2760
aggaactaaa ccatggccaa gcctttgtct caagaagaat ccaccctcat tgaaagagca    2820
acggctacaa tcaacagcat ccccatctct gaagactaca cgtcgccag cgcagctctc     2880
tctagcgacg gccgcatctt cactggtgtc aatgtatatc attttactgg gggaccttgt    2940
gcagaactcg tggtgctggg cactgctgct gctgcggcag ctggcaacct gacttgtatc    3000
gtcgcgatcg gaaatgagaa cagggggcatc ttgagcccct gcggacggtg tcgacaggtg    3060
cttctcgatc tgcatcctgg gatcaaagcg atagtgaagg acagtgatgg acagccgacg    3120
gcagttggga ttcgtgaatt gctgccctct ggttatgtgt gggagggcta agcacttcgt    3180
ggccgaggag caggactgac acgtgctacg agatttcgat tccaccgccg ccttctatga    3240
aaggttgggc ttcggaatcg ttttccggga cgccggctgg atgatcctcc agcgcgggga    3300
tctcatgctg gagttcttcg cccaccccaa cttgtttatt gcagcttata atggttacaa    3360
ataaagcaat agcatcacaa atttcacaaa taaagcattt ttttcactgc attctagttg    3420
tggtttgtcc aaactcatca atgtatctta tcatgtctgt ataccgtcga cctctagcta    3480
gagcttggcg taatcatggt catagctgtt tcctgtgtga aattgttatc cgctcacaat    3540
tccacacaac atacgagccg gaagcataaa gtgtaaagcc tggggtgcct aatgagtgag    3600
ctaactcaca ttaattgcgt tgcgctcact gcccgctttc cagtcgggaa acctgtcgtg    3660
ccagctgcat taatgaatcg gccaacgcgc ggggagaggc ggtttgcgta ttgggcgctc    3720
ttccgcttcc tcgctcactg actcgctgcg ctcggtcgtt cggctgcggc gagcggtatc    3780
agctcactca aaggcggtaa tacggttatc cacagaatca ggggataacg caggaaagaa    3840
catgtgagca aaaggccagc aaaaggccag gaaccgtaaa aaggccgcgt tgctggcgtt    3900
tttccatagg ctccgccccc ctgacgagca tcacaaaaat cgacgctcaa gtcagaggtg    3960
gcgaaacccg acaggactat aaagatacca ggcgtttccc cctggaagct ccctcgtgcg    4020
ctctcctgtt ccgaccctgc cgcttaccgg atacctgtcc gcctttctcc cttcgggaag    4080
cgtggcgctt tctcaatgct cacgctgtag gtatctcagt tcggtgtagg tcgttcgctc    4140
caagctgggc tgtgtgcacg aaccccccgt tcagcccgac cgctgcgcct tatccggtaa    4200
ctatcgtctt gagtccaacc cggtaagaca cgacttatcg ccactggcag cagccactgg    4260
taacaggatt agcagagcga ggtatgtagg cggtgctaca gagttcttga agtggtggcc    4320
taactacggc tacactagaa ggacagtatt tggtatctgc gctctgctga agccagttac    4380
cttcggaaaa agagttggta gctcttgatc cggcaaacaa accaccgctg gtagcggtgg    4440
tttttttgtt tgcaagcagc agattacgcg cagaaaaaaa ggatctcaag aagatccttt    4500
```

```
gatcttttct acggggtctg acgctcagtg gaacgaaaac tcacgttaag ggattttggt    4560
catgagatta tcaaaaagga tcttcaccta gatccttta  aattaaaaat gaagttttaa    4620
atcaatctaa agtatatatg agtaaacttg gtctgacagt taccaatgct taatcagtga    4680
ggcacctatc tcagcgatct gtctatttcg ttcatccata gttgcctgac tccccgtcgt    4740
gtagataact acgatacggg agggcttacc atctggcccc agtgctgcaa tgataccgcg    4800
agacccacgc tcaccggctc cagatttatc agcaataaac cagccagccg aagggccga    4860 gcgcagaagt ggtcctgcaa ctttatccgc ctccatccag tctattaatt gttgccggga    4920
agctagagta agtagttcgc cagttaatag tttgcgcaac gttgttgcca ttgctacagg    4980
catcgtggtg tcacgctcgt cgtttggtat ggcttcattc agctccggtt cccaacgatc    5040
aaggcgagtt acatgatccc ccatgttgtg caaaaaagcg gttagctcct tcggtcctcc    5100
gatcgttgtc agaagtaagt tggccgcagt gttatcactc atggttatgg cagcactgca    5160
taattctctt actgtcatgc catccgtaag atgcttttct gtgactggtg agtactcaac    5220
caagtcattc tgagaatagt gtatgcggcg accgagttgc tcttgcccgg cgtcaatacg    5280
ggataatacc gcgccacata gcagaacttt aaaagtgctc atcattggaa aacgttcttc    5340
ggggcgaaaa ctctcaagga tcttaccgct gttgagatcc agttcgatgt aacccactcg    5400
tgcacccaac tgatcttcag catcttttac tttcaccagc gtttctgggt gagcaaaaac    5460
aggaaggcaa aatgccgcaa aaaagggaat aagggcgaca cggaaatgtt gaatactcat    5520
actcttcctt tttcaatatt attgaagcat ttatcagggt tattgtctca tgagcggata    5580
catatttgaa tgtatttaga aaaataaaca ataggggtt  ccgcgcacat ttccccgaaa    5640
agtgccacct gacgtc                                                    5656
```

<210> SEQ ID NO 245
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245

```
gctagcacca tggactacaa agaccatgac ggtgattata agatcatga  catcgattac     60 aaggatgacg atgacaagat ggccccccaag aagaagagga aggtgggcat tcaccgcggg   120
gtacctatgg tggacttgag gacactcggt tattcgcaac agcaacagga gaaaatcaag   180
cctaaggtca ggagcaccgt cgcgcaacac cacgaggcgc ttgtggggca tggcttcact   240
catgcgcata ttgtcgcgct ttcacagcac cctgcggcgc ttgggacggt ggctgtcaaa   300
taccaagata tgattgcggc cctgcccgaa gccacgcacg aggcaattgt aggggtcggt   360
aaacagtggt cggagcgcg  agcacttgag gcgctgctga ctgtggcggg tgagcttagg   420
gggcctccgc tccagctcga caccgggcag ctgctgaaga tcgcgaagag agggggagta   480
acagcggtag aggcagtgca cgcctggcgc aatgcgctca ccggggcccc cttgaacctg   540
accccagacc aggtagtcgc aatcgcgtcg aacattgggg gaaagcaagc cctggaaacc   600
gtgcaaaggt tgttgccggt cctttgtcaa gaccacggcc ttacaccgga gcaagtcgtg   660
gccattgcaa gcaatggggg tggcaaacag gctcttgaga cggttcagag acttctccca   720
gttctctgtc aagcccacgg gctgactccc gatcaagttg tagcgattgc gaataacaat   780
ggagggaaac aagcattgga gactgtccaa cggctccttc ccgtgttgtg tcaagcccac   840
```

```
ggtttgacgc ctgcacaagt ggtcgccatc gcctcgaatg gcggcggtaa gcaggcgctg    900
gaaacagtac agcgcctgct gcctgtactg tgccaggatc atggactgac cccagaccag    960
gtagtcgcaa tcgcgtcgaa cattgggga aagcaagccc tggaaaccgt gcaaaggttg    1020
ttgccggtcc tttgtcaaga ccacggcctt acaccggagc aagtcgtggc cattgcatcc   1080
cacgacggtg caaacaggc tcttgagacg gttcagagac ttctcccagt tctctgtcaa    1140
gcccacgggc tgactcccga tcaagttgta gcgattgcga ataacaatgg agggaaacaa   1200
gcattggaga ctgtccaacg gctccttccc gtgttgtgtc aagcccacgg tttgacgcct   1260
gcacaagtgg tcgccatcgc cagccatgat ggcggtaagc aggcgctgga aacagtacag   1320
cgcctgctgc ctgtactgtg ccaggatcat ggactgaccc cagaccaggt agtcgcaatc    1380
gcgtcacatg acgggggaaa gcaagccctg aaaccgtgc aaaggttgtt gccggtcctt    1440
tgtcaagacc acggccttac accggagcaa gtcgtggcca ttgcaagcaa tggggtggc    1500
aaacaggctc ttgagacggt tcagagactt ctcccagttc tctgtcaagc ccacgggctg    1560
actcccgatc aagttgtagc gattgcgtcg catgacggag gaaacaagc attggagact    1620
gtccaacggc tccttcccgt gttgtgtcaa gcccacggtt tgacgcctgc acaagtggtc    1680
gccatcgcca gccatgatgg cggtaagcag gcgctggaaa cagtacagcg cctgctgcct    1740
gtactgtgcc aggatcatgg actgacccca gaccaggtag tcgcaatcgc gtcacatgac    1800
ggggggaaagc aagccctgga aaccgtgcaa aggttgttgc cggtcctttg tcaagaccac   1860
ggccttacac cggagcaagt cgtggccatt gcaagcaatg ggggtggcaa acaggctctt    1920
gagacggttc agagacttct cccagttctc tgtcaagccc acgggctgac tcccgatcaa    1980
gttgtagcga ttgcgaataa caatggaggg aacaagcat ggagactgt ccaacggctc     2040
cttcccgtgt tgtgtcaagc ccacggtttg acgcctgcac aagtggtcgc catcgccaac    2100
aacaacggcg gtaagcaggc gctggaaaca gtacagcgcc tgctgcctgt actgtgccag    2160
gatcatggac tgacacccga acaggtggtc gccattgcta ataataacgg aggacggcca    2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc ctcatgctcc cgcattgatc aaaagaacca accggcggat tcccgagaga    2400
acttcccatc gagtcgcggg atcc                                           2424
```

<210> SEQ ID NO 246
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                       85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
            115                 120                 125

Leu Glu Ala Leu Leu Thr Val Ala Gly Glu Leu Arg Gly Pro Pro Leu
        130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
                180                 185                 190

Gly Gly Lys Gln Ala Leu Glu Thr Val Gln Arg Leu Leu Pro Val Leu
            195                 200                 205

Cys Gln Asp His Gly Leu Thr Pro Glu Gln Val Val Ala Ile Ala Ser
        210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
                260                 265                 270

Leu Pro Val Leu Cys Gln Ala His Gly Leu Thr Pro Ala Gln Val Val
            275                 280                 285

Ala Ile Ala Ser Asn Gly Gly Lys Gln Ala Leu Glu Thr Val Gln
        290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser His Asp Gly Gly Lys Gln Ala Leu
        355                 360                 365

Glu Thr Val Gln Arg Leu Leu Pro Val Leu Cys Gln Ala His Gly Leu
370                 375                 380

Thr Pro Asp Gln Val Val Ala Ile Ala Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser His Asp Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Ser His Asp
450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

-continued

Asn Gly Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
        515                 520                 525

Ala Ser His Asp Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
        580                 585                 590

Val Val Ala Ile Ala Ser His Asp Gly Gly Lys Gln Ala Leu Glu Thr
        595                 600                 605

Val Gln Arg Leu Leu Pro Val Leu Cys Gln Asp His Gly Leu Thr Pro
610                 615                 620

Glu Gln Val Val Ala Ile Ala Ser Asn Gly Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Asn Asn Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 247
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
gctagcacca tggactacaa agaccatgac ggtgattata aagatcatga catcgattac      60
aaggatgacg atgacaagat ggcccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240

```
catgcgcata ttgtcgcgct ttcacagcac cctgcggcgc ttgggacggt ggctgtcaaa      300
taccaagata tgattgcggc cctgcccgaa gccacgcacg aggcaattgt aggggtcggt      360
aaacagtggt cgggagcgcg agcacttgag gcgctgctga ctgtggcggg tgagcttagg      420
gggcctccgc tccagctcga caccgggcag ctgctgaaga tcgcgaagag aggggagta      480
acagcggtag aggcagtgca cgcctggcgc aatgcgctca ccggggcccc cttgaacctg      540
accccagacc aggtagtcgc aatcgcgtcg aacattgggg gaaagcaagc cctggaaacc      600
gtgcaaaggt tgttgccggt cctttgtcaa gaccacggcc ttacaccgga gcaagtcgtg      660
gccattgcat cccacgacgg tggcaaacag gctcttgaga cggttcagag acttctccca      720
gttctctgtc aagcccacgg gctgactccc gatcaagttg tagcgattgc gtcgaacatt      780
ggagggaaac aagcattgga gactgtccaa cggctccttc ccgtgttgtg tcaagcccac      840
ggtttgacgc ctgcacaagt ggtcgccatc gccaacaaca acggcggtaa gcaggcgctg      900
gaaacagtac agcgcctgct gcctgtactg tgccaggatc atggactgac cccagaccag      960
gtagtcgcaa tcgcgtcgaa cattggggga aagcaagccc tggaaaccgt gcaaaggttg     1020
ttgccggtcc tttgtcaaga ccacggcctt acaccggagc aagtcgtggc cattgcaagc     1080
aacatcggtg gcaaacaggc tcttgagacg gttcagagac ttctcccagt tctctgtcaa     1140
gcccacgggc tgactcccga tcaagttgta gcgattgcga taacaatgg agggaaacaa      1200
gcattggaga ctgtccaacg gctccttccc gtgttgtgtc aagcccacgg tttgacgcct     1260
gcacaagtgg tcgccatcgc cagccatgat ggcggtaagc aggcgctgga aacagtacag     1320
cgcctgctgc ctgtactgtg ccaggatcat ggactgaccc cagaccaggt agtcgcaatc     1380
gcgaacaata tgggggaaa gcaagccctg aaaccgtgc aaaggttgtt gccggtcctt      1440
tgtcaagacc acgccttac accggagcaa gtcgtgcca ttgcaaataa taacggtggc      1500
aaacaggctc ttgagacggt tcagagactt ctcccagttc tctgtcaagc ccacgggctg     1560
actcccgatc aagttgtagc gattgcgaat aacaatggag ggaaacaagc attggagact     1620
gtccaacggc tccttcccgt gttgtgtcaa gcccacggtt tgacgcctgc acaagtggtc     1680
gccatcgcca gccatgatgg cggtaagcag gcgctggaaa cagtacagcg cctgctgcct     1740
gtactgtgcc aggatcatgg actgaccca gaccaggtag tcgcaatcgc gtcgaacatt     1800
gggggaaagc aagcccctgga aaccgtgcaa aggttgttgc cggtcctttg tcaagaccac     1860
ggccttacac cggagcaagt cgtggccatt gcaagcaaca tcggtggcaa acaggctctt     1920
gagacggttc agagacttct cccagttctc tgtcaagccc acgggctgac tcccgatcaa     1980
gttgtagcga ttgcgtcgaa cattggaggg aaacaagcat ggagactgt ccaacggctc      2040
cttcccgtgt tgtgtcaagc ccacggtttg acgcctgcac aagtggtcgc catcgccaac     2100
aacaacggcg gtaagcaggc gctggaaaca gtacagcgcc tgctgcctgt actgtgccag     2160
gatcatggac tgacacccga acaggtggtc gccattgcta ataataacgg aggacggcca     2220
gccttggagt ccatcgtagc ccaattgtcc aggcccgatc ccgcgttggc tgcgttaacg     2280
aatgaccatc tggtggcgtt ggcatgtctt ggtggacgac ccgcgctcga tgcagtcaaa     2340
aagggtctgc ctcatgctcc cgcattgatc aaaagaacca accggcggat tcccgagaga     2400
acttcccatc gagtcgcggg atcc                                              2424
```

<210> SEQ ID NO 248
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
            115                 120                 125

Leu Glu Ala Leu Leu Thr Val Ala Gly Glu Leu Arg Gly Pro Pro Leu
130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
                180                 185                 190

Gly Gly Lys Gln Ala Leu Glu Thr Val Gln Arg Leu Leu Pro Val Leu
            195                 200                 205

Cys Gln Asp His Gly Leu Thr Pro Glu Gln Val Val Ala Ile Ala Ser
210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
                260                 265                 270

Leu Pro Val Leu Cys Gln Ala His Gly Leu Thr Pro Ala Gln Val Val
            275                 280                 285

Ala Ile Ala Asn Asn Asn Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
                340                 345                 350

Glu Gln Val Val Ala Ile Ala Ser Asn Ile Gly Gly Lys Gln Ala Leu
            355                 360                 365

Glu Thr Val Gln Arg Leu Leu Pro Val Leu Cys Gln Ala His Gly Leu
370                 375                 380

Thr Pro Asp Gln Val Val Ala Ile Ala Asn Asn Asn Gly Gly Lys Gln
```

```
                385                 390                 395                 400
Ala Leu Glu Thr Val Gln Arg Leu Leu Pro Val Leu Cys Gln Ala His
                    405                 410                 415

Gly Leu Thr Pro Ala Gln Val Val Ala Ile Ala Ser His Asp Gly Gly
                420                 425                 430

Lys Gln Ala Leu Glu Thr Val Gln Arg Leu Leu Pro Val Leu Cys Gln
                    435                 440                 445

Asp His Gly Leu Thr Pro Asp Gln Val Val Ala Ile Ala Asn Asn Asn
            450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
                    485                 490                 495

Asn Asn Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
            515                 520                 525

Ala Asn Asn Asn Gly Gly Lys Gln Ala Leu Glu Thr Val Gln Arg Leu
530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                    565                 570                 575

Arg Leu Leu Pro Val Leu Cys Gln Asp His Gly Leu Thr Pro Asp Gln
                580                 585                 590

Val Val Ala Ile Ala Ser Asn Ile Gly Gly Lys Gln Ala Leu Glu Thr
            595                 600                 605

Val Gln Arg Leu Leu Pro Val Leu Cys Gln Asp His Gly Leu Thr Pro
610                 615                 620

Glu Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
                    645                 650                 655

Thr Pro Asp Gln Val Val Ala Ile Ala Ser Asn Ile Gly Gly Lys Gln
                660                 665                 670

Ala Leu Glu Thr Val Gln Arg Leu Leu Pro Val Leu Cys Gln Ala His
            675                 680                 685

Gly Leu Thr Pro Ala Gln Val Val Ala Ile Ala Asn Asn Asn Gly Gly
690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                    725                 730                 735

Gly Gly Arg Pro Ala Leu Glu Ser Ile Val Ala Gln Leu Ser Arg Pro
                740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805
```

<210> SEQ ID NO 249
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249

| | | | | |
|---|---|---|---|---|
| gctagcacca | tggactacaa | agaccatgac | ggtgattata | aagatcatga catcgattac | 60 |
| aaggatgacg | atgacaagat | ggcccccaag | aagaagagga | aggtgggcat tcaccgcggg | 120 |
| gtacctatgg | tggacttgag | gacactcggt | tattcgcaac | agcaacagga gaaaatcaag | 180 |
| cctaaggtca | ggagcaccgt | cgcgcaacac | cacgaggcgc | ttgtggggca tggcttcact | 240 |
| catgcgcata | ttgtcgcgct | ttcacagcac | cctgcggcgc | ttgggacggt ggctgtcaaa | 300 |
| taccaagata | tgattgcggc | cctgcccgaa | gccacgcacg | aggcaattgt aggggtcggt | 360 |
| aaacagtggt | cgggagcgcg | agcacttgag | gcgctgctga | ctgtggcggg tgagcttagg | 420 |
| gggcctccgc | tccagctcga | caccgggcag | ctgctgaaga | tcgcgaagag aggggagta | 480 |
| acagcggtag | aggcagtgca | cgcctggcgc | aatgcgctca | ccggggcccc cttgaacctg | 540 |
| accccagacc | aggtagtcgc | aatcgcgtca | catgacgggg | aaagcaagc cctggaaacc | 600 |
| gtgcaaaggt | tgttgccggt | cctttgtcaa | gaccacggcc | ttacaccgga gcaagtcgtg | 660 |
| gccattgcat | cccacgacgg | tggcaaacag | gctcttgaga | cggttcagag acttctccca | 720 |
| gttctctgtc | aagcccacgg | gctgactccc | gatcaagttg | tagcgattgc gaataacaat | 780 |
| ggagggaaac | aagcattgga | gactgtccaa | cggctccttc | ccgtgttgtg tcaagcccac | 840 |
| ggtttgacgc | ctgcacaagt | ggtcgccatc | gcctccaata | ttggcggtaa gcaggcgctg | 900 |
| gaaacagtac | agcgcctgct | gcctgtactg | tgccaggatc | atggactgac cccagaccag | 960 |
| gtagtcgcaa | tcgcgtcgaa | cattggggga | aagcaagccc | tggaaaccgt gcaaaggttg | 1020 |
| ttgccggtcc | tttgtcaaga | ccacggcctt | acaccggagc | aagtcgtggc cattgcaaat | 1080 |
| aataacggtg | gcaaacaggc | tcttgagacg | gttcagagac | ttctcccagt tctctgtcaa | 1140 |
| gcccacgggc | tgactcccga | tcaagttgta | gcgattgcgt | cgcatgacgg agggaaacaa | 1200 |
| gcattggaga | ctgtccaacg | gctccttccc | gtgttgtgtc | aagcccacgg tttgacgcct | 1260 |
| gcacaagtgg | tcgccatcgc | ctcgaatggc | ggcgtaagc | aggcgctgga aacagtacag | 1320 |
| cgcctgctgc | ctgtactgtg | ccaggatcat | ggactgaccc | cagaccaggt agtcgcaatc | 1380 |
| gcgaacaata | tgggggaaa | gcaagccctg | gaaaccgtgc | aaaggttgtt gccggtcctt | 1440 |
| tgtcaagacc | acggccttac | accggagcaa | gtcgtggcca | ttgcaagcaa catcggtggc | 1500 |
| aaacaggctc | ttgagacggt | tcagagactt | ctcccagttc | tctgtcaagc ccacgggctg | 1560 |
| actcccgatc | aagttgtagc | gattgcgtcg | catgacggag | ggaaacaagc attggagact | 1620 |
| gtccaacggc | tccttcccgt | gttgtgtcaa | gcccacggtt | tgacgcctgc acaagtggtc | 1680 |
| gccatcgcct | ccaatattgg | cggtaagcag | gcgctggaaa | cagtacagcg cctgctgcct | 1740 |
| gtactgtgcc | aggatcatgg | actgacccca | gaccaggtag | tcgcaatcgc gaacaataat | 1800 |
| gggggaaagc | aagccctgga | aaccgtgcaa | aggttgttgc | cggtcctttg tcaagaccac | 1860 |
| ggccttacac | cggagcaagt | cgtggccatt | gcaagcaaca | tcggtggcaa acaggctctt | 1920 |
| gagacggttc | agagacttct | cccagttctc | tgtcaagccc | acgggctgac tcccgatcaa | 1980 |
| gttgtagcga | ttgcgtccaa | cggtggaggg | aaacaagcat | tggagactgt ccaacggctc | 2040 |

-continued

```
cttcccgtgt tgtgtcaagc ccacggtttg acgcctgcac aagtggtcgc catcgccaac     2100
aacaacggcg gtaagcaggc gctggaaaca gtacagcgcc tgctgcctgt actgtgccag     2160
gatcatggac tgacacccga acaggtggtc gccattgcta ataataacgg aggacggcca     2220
gccttggagt ccatcgtagc ccaattgtcc aggcccgatc ccgcgttggc tgcgttaacg     2280
aatgaccatc tggtggcgtt ggcatgtctt ggtggacgac ccgcgctcga tgcagtcaaa     2340
aagggtctgc ctcatgctcc cgcattgatc aaaagaacca accggcggat tcccgagaga     2400
acttcccatc gagtcgcggg atcc                                            2424
```

<210> SEQ ID NO 250
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285
```

```
Ala Ile Ala Ser Asn Ile Gly Gly Lys Gln Ala Leu Glu Thr Val Gln
        290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
                340                 345                 350

Glu Gln Val Val Ala Ile Ala Asn Asn Asn Gly Gly Lys Gln Ala Leu
        355                 360                 365

Glu Thr Val Gln Arg Leu Leu Pro Val Leu Cys Gln Ala His Gly Leu
370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Gly Gly Gly
                420                 425                 430

Lys Gln Ala Leu Glu Thr Val Gln Arg Leu Leu Pro Val Leu Cys Gln
                435                 440                 445

Asp His Gly Leu Thr Pro Asp Gln Val Val Ala Ile Ala Asn Asn Asn
        450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Ile Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
        515                 520                 525

Ala Ser His Asp Gly Gly Lys Gln Ala Leu Glu Thr Val Gln Arg Leu
530                 535                 540

Leu Pro Val Leu Cys Gln Ala His Gly Leu Thr Pro Ala Gln Val Val
545                 550                 555                 560

Ala Ile Ala Ser Asn Ile Gly Gly Lys Gln Ala Leu Glu Thr Val Gln
                565                 570                 575

Arg Leu Leu Pro Val Leu Cys Gln Asp His Gly Leu Thr Pro Asp Gln
                580                 585                 590

Val Val Ala Ile Ala Asn Asn Asn Gly Gly Lys Gln Ala Leu Glu Thr
        595                 600                 605

Val Gln Arg Leu Leu Pro Val Leu Cys Gln Asp His Gly Leu Thr Pro
610                 615                 620

Glu Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Gly Gly Gly Lys Gln
                660                 665                 670

Ala Leu Glu Thr Val Gln Arg Leu Leu Pro Val Leu Cys Gln Ala His
                675                 680                 685

Gly Leu Thr Pro Ala Gln Val Val Ala Ile Ala Asn Asn Asn Gly Gly
        690                 695                 700
```

```
Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 251
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
```

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgtca | catgacgggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcaa | gcaacatcgg | tggcaaacag | gctcttgaga | cggttcagag | acttctccca | 720 |
| gttctctgtc | aagcccacgg | gctgactccc | gatcaagttg | tagcgattgc | gaataacaat | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccaacaaca | acggcggtaa | gcaggcgctg | 900 |
| gaaacagtac | agcgcctgct | gcctgtactg | tgccaggatc | atggactgac | cccagaccag | 960 |
| gtagtcgcaa | tcgcgtcaaa | cggagggggga | aagcaagccc | tggaaaccgt | gcaaaggttg | 1020 |
| ttgccggtcc | tttgtcaaga | ccacggcctt | acaccggagc | aagtcgtggc | cattgcaagc | 1080 |
| aatgggggtg | gcaaacaggc | tcttgagacg | gttcagagac | ttctcccagt | tctctgtcaa | 1140 |
| gcccacgggc | tgactcccga | tcaagttgta | gcgattgcgt | cgcatgacgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | cagccatgat | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgaacaata | tgggggaaa | gcaagccctg | gaaaccgtgc | aaaggttgtt | gccggtcctt | 1440 |

```
tgtcaagacc acggccttac accggagcaa gtcgtggcca ttgcatccca cgacggtggc   1500
aaacaggctc ttgagacggt tcagagactt ctcccagttc tctgtcaagc ccacgggctg   1560
actcccgatc aagttgtagc gattgcgtcg catgacggag ggaaacaagc attggagact   1620
gtccaacggc tccttcccgt gttgtgtcaa gcccacggtt tgacgcctgc acaagtggtc   1680
gccatcgcca gccatgatgg cggtaagcag gcgctggaaa cagtacagcg cctgctgcct   1740
gtactgtgcc aggatcatgg actgacccca gaccaggtag tcgcaatcgc gtcacatgac   1800
gggggaaagc aagccctgga aaccgtgcaa aggttgttgc cggtcctttg tcaagaccac   1860
ggccttacac cggagcaagt cgtggccatt gcaagcaatg ggggtggcaa acaggctctt   1920
gagacggttc agagacttct cccagttctc tgtcaagccc acgggctgac tcccgatcaa   1980
gttgtagcga ttgcgtcgaa cattggaggg aaacaagcat ggagactgt ccaacggctc   2040 cttcccgtgt tgtgtcaagc ccacggtttg acgcctgcac aagtggtcgc catcgccagc   2100
catgatggcg gtaagcaggc gctggaaaca gtacagcgcc tgctgcctgt actgtgccag   2160
gatcatggac tgacacccga acaggtggtc gccattgctt cccacgacgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                         2424
```

<210> SEQ ID NO 252
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175
```

```
Pro Leu Asn Leu Thr Pro Asp Gln Val Val Ala Ile Ala Ser His Asp
                180                 185                 190

Gly Gly Lys Gln Ala Leu Glu Thr Val Gln Arg Leu Leu Pro Val Leu
            195                 200                 205

Cys Gln Asp His Gly Leu Thr Pro Glu Gln Val Val Ala Ile Ala Ser
        210                 215                 220

Asn Ile Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Asn Asn Asn Gly Gly Lys Gln Ala Leu Glu Thr Val Gln
        290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser Asn Gly Gly Lys Gln Ala Leu
        355                 360                 365

Glu Thr Val Gln Arg Leu Leu Pro Val Leu Cys Gln Ala His Gly Leu
        370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser His Asp Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Asn Asn Asn
450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

His Asp Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser His Asp Gly Gly Lys Gln Ala Leu Glu Thr Val Gln Arg Leu
        530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
```

```
                    595                 600                 605
Val Gln Arg Leu Leu Pro Val Leu Cys Gln Asp His Gly Leu Thr Pro
        610                 615                 620

Glu Gln Val Val Ala Ile Ala Ser Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Ile Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser His Asp Gly Gly
690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser His Asp
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 253
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
gctagcacca tggactacaa agaccatgac ggtgattata agatcatga catcgattac       60 aaggatgacg atgacaagat ggccccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag agggggagta    480
acagcggtag aggcagtgca cgcctggcgc aatgcgctca ccggggcccc cttgaacctg    540
accccagacc aggtagtcgc aatcgcgtca acggagggg gaaagcaagc cctggaaacc    600
gtgcaaaggt tgttgccggt cctttgtcaa gaccacggcc ttacaccgga gcaagtcgtg    660
gccattgcaa gcaacatcgg tggcaaacag gctcttgaga cggttcagag acttctccca    720
gttctctgtc aagcccacgg gctgactccc gatcaagttg tagcgattgc gaataacaat    780
ggagggaaac aagcattgga gactgtccaa cggctccttc ccgtgttgtg tcaagcccac    840
```

```
ggtttgacgc ctgcacaagt ggtcgccatc gcctccaata ttggcggtaa gcaggcgctg    900
gaaacagtac agcgcctgct gcctgtactg tgccaggatc atggactgac cccagaccag    960
gtagtcgcaa tcgcgtcaca tgacggggga agcaagcccc tggaaaccgt gcaaaggttg   1020
ttgccggtcc tttgtcaaga ccacggcctt acaccggagc aagtcgtggc cattgcaagc   1080 aatggggtg gcaaacaggc tcttgagacg gttcagagac ttctcccagt tctctgtcaa   1140
gcccacgggc tgactcccga tcaagttgta gcgattgcgt ccaacggtgg agggaaacaa   1200
gcattggaga ctgtccaacg gctccttccc gtgttgtgtc aagcccacgg tttgacgcct   1260
gcacaagtgg tcgccatcgc ctccaatatt ggcggtaagc aggcgctgga aacagtacag   1320
cgcctgctgc ctgtactgtg ccaggatcat ggactgaccc cagaccaggt agtcgcaatc   1380
gcgaacaata tgggggaaa gcaagccctg gaaaccgtgc aaaggttgtt gccggtcctt   1440
tgtcaagacc acggccttac accggagcaa gtcgtggcca ttgcaaataa taacggtggc   1500
aaacaggctc ttgagacggt tcagagactt ctcccagttc tctgtcaagc ccacgggctg   1560
actcccgatc aagttgtagc gattgcgtcc aacggtggag ggaaacaagc attggagact   1620
gtccaacggc tccttcccgt gttgtgtcaa gcccacggtt tgacgcctgc acaagtggtc   1680
gccatcgcct ccaatattgg cggtaagcag gcgctggaaa cagtacagcg cctgctgcct   1740
gtactgtgcc aggatcatgg actgaccca gaccaggtag tcgcaatcgc gtcgaacatt   1800 ggggaaagc aagccctgga aaccgtgcaa aggttgttgc cggtcctttg tcaagaccac   1860
ggccttacac cggagcaagt cgtggccatt gcaaataata acggtggcaa acaggctctt   1920
gagacggttc agagacttct cccagttctc tgtcaagccc acgggctgac tcccgatcaa   1980
gttgtagcga ttgcgtccaa cggtggaggg aaacaagcat tggagactgt ccaacggctc   2040
cttcccgtgt tgtgtcaagc cacggtttg acgcctgcac aagtggtcgc catcgcctcc   2100
aatattggcg gtaagcaggc gctggaaaca gtacagcgcc tgctgcctgt actgtgccag   2160
gatcatggac tgacacccga acaggtggtc gccattgctt ctaacatcgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 254
<211> LENGTH: 808
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 254

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Gln Glu Lys Ile Lys Pro Lys Val Arg
    50                  55                  60

Ser Thr Val Ala Gln His His Glu Ala Leu Val Gly His Gly Phe Thr

```
                65                  70                  75                  80
          His Ala His Ile Val Ala Leu Ser Gln His Pro Ala Ala Leu Gly Thr
                          85                  90                  95

Val Ala Val Lys Tyr Gln Asp Met Ile Ala Ala Leu Pro Glu Ala Thr
                          100                 105                 110

His Glu Ala Ile Val Gly Val Gly Lys Gln Trp Ser Gly Ala Arg Ala
                          115                 120                 125

Leu Glu Ala Leu Leu Thr Val Ala Gly Glu Leu Arg Gly Pro Pro Leu
                  130                 135                 140

Gln Leu Asp Thr Gly Gln Leu Leu Lys Ile Ala Lys Arg Gly Gly Val
          145                 150                 155                 160

Thr Ala Val Glu Ala Val His Ala Trp Arg Asn Ala Leu Thr Gly Ala
                          165                 170                 175

Pro Leu Asn Leu Thr Pro Asp Gln Val Val Ala Ile Ala Ser Asn Gly
                          180                 185                 190

Gly Gly Lys Gln Ala Leu Glu Thr Val Gln Arg Leu Leu Pro Val Leu
                  195                 200                 205

Cys Gln Asp His Gly Leu Thr Pro Glu Gln Val Val Ala Ile Ala Ser
                  210                 215                 220

Asn Ile Gly Gly Lys Gln Ala Leu Glu Thr Val Gln Arg Leu Leu Pro
          225                 230                 235                 240

Val Leu Cys Gln Ala His Gly Leu Thr Pro Asp Gln Val Val Ala Ile
                          245                 250                 255

Ala Asn Asn Asn Gly Gly Lys Gln Ala Leu Glu Thr Val Gln Arg Leu
                          260                 265                 270

Leu Pro Val Leu Cys Gln Ala His Gly Leu Thr Pro Ala Gln Val Val
                  275                 280                 285

Ala Ile Ala Ser Asn Ile Gly Gly Lys Gln Ala Leu Glu Thr Val Gln
                  290                 295                 300

Arg Leu Leu Pro Val Leu Cys Gln Asp His Gly Leu Thr Pro Asp Gln
          305                 310                 315                 320

Val Val Ala Ile Ala Ser His Asp Gly Gly Lys Gln Ala Leu Glu Thr
                          325                 330                 335

Val Gln Arg Leu Leu Pro Val Leu Cys Gln Asp His Gly Leu Thr Pro
                          340                 345                 350

Glu Gln Val Val Ala Ile Ala Ser Asn Gly Gly Gly Lys Gln Ala Leu
                          355                 360                 365

Glu Thr Val Gln Arg Leu Leu Pro Val Leu Cys Gln Ala His Gly Leu
                  370                 375                 380

Thr Pro Asp Gln Val Val Ala Ile Ala Ser Asn Gly Gly Gly Lys Gln
          385                 390                 395                 400

Ala Leu Glu Thr Val Gln Arg Leu Leu Pro Val Leu Cys Gln Ala His
                          405                 410                 415

Gly Leu Thr Pro Ala Gln Val Val Ala Ile Ala Ser Asn Ile Gly Gly
                          420                 425                 430

Lys Gln Ala Leu Glu Thr Val Gln Arg Leu Leu Pro Val Leu Cys Gln
                  435                 440                 445

Asp His Gly Leu Thr Pro Asp Gln Val Val Ala Ile Ala Asn Asn Asn
                  450                 455                 460

Gly Gly Lys Gln Ala Leu Glu Thr Val Gln Arg Leu Leu Pro Val Leu
          465                 470                 475                 480

Cys Gln Asp His Gly Leu Thr Pro Glu Gln Val Val Ala Ile Ala Asn
                          485                 490                 495
```

```
Asn Asn Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
            515                 520                 525

Ala Ser Asn Gly Gly Lys Gln Ala Leu Glu Thr Val Gln Arg Leu
        530                 535                 540

Leu Pro Val Leu Cys Gln Ala His Gly Leu Thr Pro Ala Gln Val Val
545                 550                 555                 560

Ala Ile Ala Ser Asn Ile Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Ile Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Asn Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser Asn Ile Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Ile
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805
```

<210> SEQ ID NO 255
<211> LENGTH: 2424
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255

```
gctagcacca tggactacaa agaccatgac ggtgattata aagatcatga catcgattac      60
aaggatgacg atgacaagat ggcccccaag aagaagagga aggtgggcat tcaccgcggg     120
gtacctatgg tggacttgag acactcggt tattcgcaac agcaacagga gaaaatcaag      180
cctaaggtca ggagcaccgt cgcgcaacac cacgaggcgc ttgtgggca tggcttcact      240
```

```
catgcgcata ttgtcgcgct tcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag agggggagta    480
acagcggtag aggcagtgca cgcctggcgc aatgcgctca ccggggcccc cttgaacctg    540
accccagacc aggtagtcgc aatcgcgtcg aacattgggg gaaagcaagc cctggaaacc    600
gtgcaaaggt tgttgccggt cctttgtcaa gaccacggcc ttacaccgga gcaagtcgtg    660
gccattgcaa ataatacgg tggcaaacag gctcttgaga cggttcagag acttctccca    720
gttctctgtc aagcccacgg gctgactccc gatcaagttg tagcgattgc gtccaacggt    780
ggagggaaac aagcattgga gactgtccaa cggctccttc ccgtgttgtg tcaagcccac    840
ggtttgacgc ctgcacaagt ggtcgccatc gcctcgaatg gcggcggtaa gcaggcgctg    900
gaaacagtac agcgcctgct gcctgtactg tgccaggatc atggactgac ccagaccag    960 gtagtcgcaa tcgcgtcaaa cggagggga aagcaagccc tggaaccgt gcaaaggttg   1020 ttgccggtcc tttgtcaaga ccacggcctt acaccggagc aagtcgtggc cattgcaaat   1080
aataacggtg gcaaacaggc tcttgagacg gttcagagac ttctcccagt tctctgtcaa   1140
gcccacgggc tgactccga tcaagttgta gcgattgcgt ccaacggtgg agggaaacaa   1200
gcattggaga ctgtccaacg gctccttccc gtgttgtgtc aagcccacgg tttgacgcct   1260
gcacaagtgg tcgccatcgc ctccaatatt ggcggtaagc aggcgctgga aacagtacag   1320
cgcctgctgc ctgtactgtg ccaggatcat ggactgaccc cagaccaggt agtcgcaatc   1380
gcgaacaata tgggggaaa gcaagccctg gaaaccgtgc aaaggttgtt gccggtcctt   1440
tgtcaagacc acggccttac accggagcaa gtcgtggcca ttgcaagcaa tggggtggc   1500 aaacaggctc ttgagacggt tcagagactt ctcccagttc tctgtcaagc ccacgggctg   1560
actcccgatc aagttgtagc gattgcgtcc aacggtggag ggaaacaagc attggagact   1620
gtccaacggc tccttcccgt gttgtgtcaa gcccacggtt tgacgcctgc acaagtggtc   1680
gccatcgcca ccatgatgg cggtaagcag gcgctgaaa cagtacagcg cctgctgcct   1740
gtactgtgcc aggatcatgg actgaccca gaccaggtag tcgcaatcgc gtcaaacgga   1800 gggaaagc aagccctgga aaccgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac tcccgatcaa   1980
gttgtagcga ttgcgtcgca tgacggaggg aaacaagcat ggagactgt ccaacggctc   2040 cttcccgtgt tgtgtcaagc ccacggtttg acgcctgcac aagtggtcgc catcgccagc   2100
catgatggcg gtaagcaggc gctgaaaca gtacagcgcc tgctgcctgt actgtgccag   2160
gatcatggac tgacaccga acaggtggtc gccattgctt cccacgacgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 256
<211> LENGTH: 808
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 256

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
            35                  40                  45

Leu Gly Tyr Ser Gln Gln Gln Glu Lys Ile Lys Pro Lys Val Arg
        50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
            115                 120                 125

Leu Glu Ala Leu Leu Thr Val Ala Gly Glu Leu Arg Gly Pro Pro Leu
130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser Asn Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Asn Asn Gly Gly Lys Gln Ala Leu
            355                 360                 365

Glu Thr Val Gln Arg Leu Leu Pro Val Leu Cys Gln Ala His Gly Leu
370                 375                 380
```

```
Thr Pro Asp Gln Val Val Ala Ile Ala Ser Asn Gly Gly Lys Gln
385                 390                 395                 400

Ala Leu Glu Thr Val Gln Arg Leu Leu Pro Val Leu Cys Gln Ala His
        405                 410                 415

Gly Leu Thr Pro Ala Gln Val Val Ala Ile Ala Ser Asn Ile Gly Gly
            420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Asn Asn Asn
        450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Gly Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Ser Asn Gly Gly Gly Lys Gln Ala Leu Glu Thr Val Gln Arg Leu
530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Gly Gly Gly Lys Gln Ala Leu Glu Thr
            595                 600                 605

Val Gln Arg Leu Leu Pro Val Leu Cys Gln Asp His Gly Leu Thr Pro
        610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
            645                 650                 655

Thr Pro Asp Gln Val Val Ala Ile Ala Ser His Asp Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser His Asp Gly Gly
        690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser His Asp
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
        770                 775                 780

His Ala Pro Ala Leu Ile Lys Arg Thr Asn Arg Arg Ile Pro Glu Arg
785                 790                 795                 800

Thr Ser His Arg Val Ala Gly Ser
```

<210> SEQ ID NO 257
<211> LENGTH: 2322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 257

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | agggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgtca | catgacgggg | gaaagcaagc | cctgaaaacc | 600 |
| gtgcaaaggt | tgttgccggt | cctttgtcaa | gaccacggcc | ttacaccgga | gcaagtcgtg | 660 |
| gccattgcat | cccacgacgg | tgcaaacag | gctcttgaga | cggttcagag | acttctccca | 720 |
| gttctctgtc | aagcccacgg | gctgactccc | gatcaagttg | tagcgattgc | gaataacaat | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccaacaaca | acgcggtaa | gcaggcgctg | 900 |
| gaaacagtac | agcgcctgct | gcctgtactg | tgccaggatc | atggactgac | cccagaccag | 960 |
| gtagtcgcaa | tcgcgtcaca | tgacggggga | aagcaagccc | tggaaaccgt | gcaaaggttg | 1020 |
| ttgccggtcc | tttgtcaaga | ccacggcctt | acaccggagc | aagtcgtggc | cattgcatcc | 1080 |
| cacgacggtg | caaacaggc | tcttgagacg | gttcagagac | ttctcccagt | tctctgtcaa | 1140 |
| gcccacgggc | tgactcccga | tcaagttgta | gcgattgcga | ataacaatgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | caacaacaac | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgtcacatg | acggggaaa | gcaagccctg | gaaaccgtgc | aaaggttgtt | gccggtcctt | 1440 |
| tgtcaagacc | acggccttac | accggagcaa | gtcgtggcca | ttgcaaataa | taacggtggc | 1500 |
| aaacaggctc | ttgagacggt | tcagagactt | ctcccagttc | tctgtcaagc | cacgggctg | 1560 |
| actcccgatc | aagttgtagc | gattgcgtcg | catgacggag | ggaaacaagc | attggagact | 1620 |
| gtccaacggc | tccttcccgt | gttgtgtcaa | gcccacggtt | tgacgcctgc | acaagtggtc | 1680 |
| gccatcgcca | gccatgatgg | cggtaagcag | gcgctggaaa | cagtacagcg | cctgctgcct | 1740 |
| gtactgtgcc | aggatcatgg | actgacccca | gaccaggtag | tcgcaatcgc | gtcgaacatt | 1800 |
| gggggaaagc | aagccctgga | aaccgtgcaa | aggttgttgc | cggtcctttg | tcaagaccac | 1860 |
| ggccttacac | cggagcaagt | cgtggccatt | gcaagcaatg | ggggtggcaa | acaggctctt | 1920 |
| gagacggttc | agagacttct | cccagttctc | tgtcaagccc | acgggctgac | tcccgatcaa | 1980 |

```
gttgtagcga ttgcgaataa caatggaggg aaacaagcat tggagactgt ccaacggctc   2040
cttcccgtgt tgtgtcaagc ccacggtctg acacccgaac aggtggtcgc cattgcttct   2100
aacatcggag gacggccagc cttggagtcc atcgtagccc aattgtccag gcccgatccc   2160
gcgttggctg cgttaacgaa tgaccatctg gtggcgttgg catgtcttgg tggacgaccc   2220
gcgctcgatg cagtcaaaaa gggtctgcct catgctcccg cattgatcaa agaaccaac    2280 cggcggattc ccgagagaac ttcccatcga gtcgcgggat cc                      2322
```

<210> SEQ ID NO 258
<211> LENGTH: 774
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Asn Asn Asn Gly Gly Lys Gln Ala Leu Glu Thr Val Gln
    290                 295                 300
```

```
Arg Leu Leu Pro Val Leu Cys Gln Asp His Gly Leu Thr Pro Asp Gln
305                 310                 315                 320

Val Val Ala Ile Ala Ser His Asp Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser His Asp Gly Gly Lys Gln Ala Leu
        355                 360                 365

Glu Thr Val Gln Arg Leu Leu Pro Val Leu Cys Gln Ala His Gly Leu
370                 375                 380

Thr Pro Asp Gln Val Val Ala Ile Ala Asn Asn Gly Gly Lys Gln
385                 390                 395                 400

Ala Leu Glu Thr Val Gln Arg Leu Leu Pro Val Leu Cys Gln Ala His
            405                 410                 415

Gly Leu Thr Pro Ala Gln Val Val Ala Ile Ala Asn Asn Gly Gly
                420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser His Asp
450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Ser His Asp Gly Gly Lys Gln Ala Leu Glu Thr Val Gln Arg Leu
        530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Ile Gly Gly Lys Gln Ala Leu Glu Thr
        595                 600                 605

Val Gln Arg Leu Leu Pro Val Leu Cys Gln Asp His Gly Leu Thr Pro
610                 615                 620

Glu Gln Val Val Ala Ile Ala Ser Asn Gly Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Glu Gln Val Val Ala Ile Ala Ser Asn Ile Gly Gly
690                 695                 700

Arg Pro Ala Leu Glu Ser Ile Val Ala Gln Leu Ser Arg Pro Asp Pro
705                 710                 715                 720
```

Ala Leu Ala Ala Leu Thr Asn Asp His Leu Val Ala Leu Ala Cys Leu
                725                 730                 735

Gly Gly Arg Pro Ala Leu Asp Ala Val Lys Lys Gly Leu Pro His Ala
            740                 745                 750

Pro Ala Leu Ile Lys Arg Thr Asn Arg Arg Ile Pro Glu Arg Thr Ser
        755                 760                 765

His Arg Val Ala Gly Ser
    770

```
<210> SEQ ID NO 259
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
```

| | |
|---|---|
| gctagcacca tggactacaa agaccatgac ggtgattata aagatcatga catcgattac | 60 |
| aaggatgacg atgacaagat ggcccccaag aagaagagga aggtgggcat tcaccgcggg | 120 |
| gtacctatgg tggacttgag gacactcggt tattcgcaac agcaacagga gaaaatcaag | 180 |
| cctaaggtca ggagcaccgt cgcgcaacac cacgaggcgc ttgtggggca tggcttcact | 240 |
| catgcgcata ttgtcgcgct ttcacagcac cctgcggcgc ttgggacggt ggctgtcaaa | 300 |
| taccaagata tgattgcggc cctgcccgaa gccacgcacg aggcaattgt aggggtcggt | 360 |
| aaacagtggt cgggagcgcg agcacttgag gcgctgctga ctgtggcggg tgagcttagg | 420 |
| gggcctccgc tccagctcga caccgggcag ctgctgaaga tcgcgaagag aggggagta | 480 |
| acagcggtag aggcagtgca cgcctggcgc aatgcgctca ccggggcccc cttgaacctg | 540 |
| accccagacc aggtagtcgc aatcgcgtcg aacattgggg aaagcaagc cctggaaacc | 600 |
| gtgcaaaggt tgttgccggt cctttgtcaa gaccacggcc ttacaccgga gcaagtcgtg | 660 |
| gccattgcaa ataataacgg tggcaaacag gctcttgaga cggttcagag acttctccca | 720 |
| gttctctgtc aagcccacgg gctgactccc gatcaagttg tagcgattgc gtcgcatgac | 780 |
| ggagggaaac aagcattgga gactgtccaa cggctccttc ccgtgttgtg tcaagcccac | 840 |
| ggttttgacgc ctgcacaagt ggtcgccatc gccaacaaca acggcggtaa gcaggcgctg | 900 |
| gaaacagtac agcgcctgct gcctgtactg tgccaggatc atggactgac ccagaccag | 960 |
| gtagtcgcaa tcgcgtcgaa cattggggga aagcaagccc tggaaaccgt gcaaaggttg | 1020 |
| ttgccggtcc tttgtcaaga ccacggcctt acaccggagc aagtcgtggc cattgcaaat | 1080 |
| aataacggtg gcaaacaggc tcttgagacg gttcagagac ttctcccagt tctctgtcaa | 1140 |
| gcccacgggc tgactcccga tcaagttgta gcgattgcgt cgcatgacgg agggaaacaa | 1200 |
| gcattggaga ctgtccaacg gctccttccc gtgttgtgtc aagcccacgg tttgacgcct | 1260 |
| gcacaagtgg tcgccatcgc caacaacaac ggcggtaagc aggcgctgga aacagtacag | 1320 |
| cgcctgctgc ctgtactgtg ccaggatcat ggactgaccc agaccaggt agtcgcaatc | 1380 |
| gcgtcacatg acggggggaaa gcaagccctg aaaccgtgc aaaggttgtt gccggtcctt | 1440 |
| tgtcaagacc acgccttac accggagcaa gtcgtggcca ttgcaaataa taacggtggc | 1500 |
| aaacaggctc ttgagacggt tcagagactt ctcccagttc tctgtcaagc ccacgggctg | 1560 |
| actcccgatc aagttgtagc gattgcgtcg aacattggag ggaaacaagc attggagact | 1620 |
| gtccaacggc tccttcccgt gttgtgtcaa gcccacggtt tgacgcctgc acaagtggtc | 1680 |

-continued

```
gccatcgcca gccatgatgg cggtaagcag gcgctggaaa cagtacagcg cctgctgcct   1740
gtactgtgcc aggatcatgg actgacccca gaccaggtag tcgcaatcgc gtcacatgac   1800
gggggaaagc aagccctgga aaccgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac acccgaacag   1980
gtggtcgcca ttgcttccca cgacggagga cggccagcct tggagtccat cgtagcccaa   2040
ttgtccaggc ccgatcccgc gttggctgcg ttaacgaatg accatctggt ggcgttggca   2100
tgtcttggtg gacgacccgc gctcgatgca gtcaaaaagg gtctgcctca tgctcccgca   2160
ttgatcaaaa gaaccaaccg gcggattccc gagagaactt cccatcgagt cgcgggatcc   2220
```

<210> SEQ ID NO 260
<211> LENGTH: 740
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser His Asp Gly Gly Lys Gln Ala Leu Glu Thr Val Gln Arg Leu
            260                 265                 270
```

```
Leu Pro Val Leu Cys Gln Ala His Gly Leu Thr Pro Ala Gln Val Val
            275                 280                 285

Ala Ile Ala Asn Asn Asn Gly Gly Lys Gln Ala Leu Glu Thr Val Gln
            290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Asn Asn Asn Gly Gly Lys Gln Ala Leu
            355                 360                 365

Glu Thr Val Gln Arg Leu Leu Pro Val Leu Cys Gln Ala His Gly Leu
            370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Asn Asn Asn Gly Gly
            420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser His Asp
            450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Ser Asn Ile Gly Gly Lys Gln Ala Leu Glu Thr Val Gln Arg Leu
            530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
            610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Glu Gln Val Val Ala Ile Ala Ser His Asp Gly Gly Arg Pro
            660                 665                 670

Ala Leu Glu Ser Ile Val Ala Gln Leu Ser Arg Pro Asp Pro Ala Leu
            675                 680                 685
```

```
Ala Ala Leu Thr Asn Asp His Leu Val Ala Leu Ala Cys Leu Gly Gly
    690                 695                 700

Arg Pro Ala Leu Asp Ala Val Lys Lys Gly Leu Pro His Ala Pro Ala
705                 710                 715                 720

Leu Ile Lys Arg Thr Asn Arg Arg Ile Pro Glu Arg Thr Ser His Arg
            725                 730                 735

Val Ala Gly Ser
        740

<210> SEQ ID NO 261
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
```

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgtcg | aacattgggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcaa | ataatacgg | tggcaaacag | gctcttgaga | cggttcagag | acttctccca | 720 |
| gttctctgtc | aagcccacgg | gctgactccc | gatcaagttg | tagcgattgc | gaataacaat | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccagccatg | atggcggtaa | gcaggcgctg | 900 |
| gaaacagtac | agcgcctgct | gcctgtactg | tgccaggatc | atggactgac | ccagaccag | 960 |
| gtagtcgcaa | tcgcgaacaa | taatggggga | aagcaagccc | tggaaaccgt | gcaaaggttg | 1020 |
| ttgccggtcc | tttgtcaaga | ccacggcctt | acaccggagc | aagtcgtggc | cattgcatcc | 1080 |
| cacgacggtg | gcaaacaggc | tcttgagacg | ttcagagac | ttctcccagt | tctctgtcaa | 1140 |
| gcccacgggc | tgactcccga | tcaagttgta | gcgattgcgt | cgcatgacgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | ctccaatatt | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgtcgaaca | ttgggggaaa | gcaagccctg | gaaaccgtgc | aaaggttgtt | gccggtcctt | 1440 |
| tgtcaagacc | acggccttac | accggagcaa | gtcgtggcca | ttgcaaataa | taacggtggc | 1500 |
| aaacaggctc | ttgagacggt | tcagagactt | ctcccagttc | tctgtcaagc | ccacgggctg | 1560 |
| actcccgatc | aagttgtagc | gattgcgaat | aacaatggag | ggaaacaagc | attggagact | 1620 |
| gtccaacggc | tccttcccgt | gttgtgtcaa | gcccacggtt | tgacgcctgc | acaagtggtc | 1680 |

```
gccatcgcca gccatgatgg cggtaagcag gcgctggaaa cagtacagcg cctgctgcct    1740
gtactgtgcc aggatcatgg actgacccca gaccaggtag tcgcaatcgc gtcacatgac    1800
gggggaaagc aagccctgga aaccgtgcaa aggttgttgc cggtcctttg tcaagaccac    1860
ggccttacac cggagcaagt cgtggccatt gcaagcaaca tcggtggcaa acaggctctt    1920
gagacggttc agagacttct cccagttctc tgtcaagccc acgggctgac tcccgatcaa    1980
gttgtagcga ttgcgtccaa cggtggaggg aaacaagcat ggagactgt ccaacggctc     2040 cttcccgtgt tgtgtcaagc ccacggtttg acgcctgcac aagtggtcgc catcgccaac    2100
aacaacggcg gtaagcaggc gctggaaaca gtacagcgcc tgctgcctgt actgtgccag    2160
gatcatggac tgacacccga acaggtggtc gccattgctt ctaatggggg aggacggcca    2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc ctcatgctcc cgcattgatc aaaagaacca accggcggat tcccgagaga    2400
acttcccatc gagtcgcggg atcc                                           2424
```

<210> SEQ ID NO 262
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 262

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220
```

-continued

```
Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
            245                 250                 255

Ala Asn Asn Asn Gly Gly Lys Gln Ala Leu Glu Thr Val Gln Arg Leu
        260                 265                 270

Leu Pro Val Leu Cys Gln Ala His Gly Leu Thr Pro Ala Gln Val Val
    275                 280                 285

Ala Ile Ala Ser His Asp Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Asn Asn Gly Gly Lys Gln Ala Leu Glu Thr
            325                 330                 335

Val Gln Arg Leu Leu Pro Val Leu Cys Gln Asp His Gly Leu Thr Pro
            340                 345                 350

Glu Gln Val Val Ala Ile Ala Ser His Asp Gly Gly Lys Gln Ala Leu
            355                 360                 365

Glu Thr Val Gln Arg Leu Leu Pro Val Leu Cys Gln Ala His Gly Leu
370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
            405                 410                 415

Gly Leu Thr Pro Ala Gln Val Val Ala Ile Ala Ser Asn Ile Gly Gly
            420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser Asn Ile
    450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
            485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Asn Asn Asn Gly Gly Lys Gln Ala Leu Glu Thr Val Gln Arg Leu
530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
            565                 570                 575

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
            610                 615                 620

Glu Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
```

```
              645                 650                 655
Thr Pro Asp Gln Val Ala Ile Ala Ser Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Ala Ile Ala Asn Asn Gly Gly
        690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Ala Ile Ala Ser Asn Gly
                725                 730                 735

Gly Gly Arg Pro Ala Leu Glu Ser Ile Val Ala Gln Leu Ser Arg Pro
                740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
        770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805
```

<210> SEQ ID NO 263
<211> LENGTH: 2424
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 263

```
gctagcacca tggactacaa agaccatgac ggtgattata aagatcatga catcgattac      60
aaggatgacg atgacaagat ggccccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggg ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag aggggggagta    480
acagcggtag aggcagtgca cgcctggcgc aatgcgctca ccggggcccc cttgaacctg    540
accccagacc aggtagtcgc aatcgcgaac aataatgggg gaaagcaagc cctggaaacc    600
gtgcaaaggt tgttgccggt cctttgtcaa gaccacggcc ttacaccgga gcaagtcgtg    660
gccattgcaa ataataacgg tggcaaacag gctcttgaga cggttcagag acttctccca    720
gttctctgtc aagcccacgg gctgactccc gatcaagttg tagcgattgc gtcgcatgac    780
ggagggaaac aagcattgga gactgtccaa cggctccttc ccgtgttgtg tcaagcccac    840
ggtttgacgc ctgcacaagt ggtcgccatc gccagccatg atggcggtaa gcaggcgctg    900
gaaacagtac agcgcctgct gcctgtactg tgccaggatc atggactgac cccagaccag    960
gtagtcgcaa tcgcgtcaca tgacggggga aagcaagccc tggaaaccgt gcaaaggttg   1020
ttgccggtcc tttgtcaaga ccacggcctt acaccggagc aagtcgtggc cattgcaaat   1080
```

```
aataacggtg gcaaacaggc tcttgagacg gttcagagac ttctcccagt tctctgtcaa    1140
gcccacgggc tgactcccga tcaagttgta gcgattgcgt cgaacattgg agggaaacaa    1200
gcattggaga ctgtccaacg gctccttccc gtgttgtgtc aagcccacgg tttgacgcct    1260
gcacaagtgg tcgccatcgc caacaacaac ggcggtaagc aggcgctgga acagtacag    1320
cgcctgctgc ctgtactgtg ccaggatcat ggactgaccc cagaccaggt agtcgcaatc    1380
gcgaacaata tgggggaaa gcaagccctg gaaaccgtgc aaaggttgtt gccggtcctt    1440
tgtcaagacc acggccttac accggagcaa gtcgtggcca ttgcatccca cgacggtggc    1500
aaacaggctc ttgagacggt tcagagactt ctcccagttc tctgtcaagc ccacgggctg    1560
actcccgatc aagttgtagc gattgcgaat aacaatggag ggaaacaagc attggagact    1620
gtccaacggc tccttcccgt gttgtgtcaa gcccacggtt tgacgcctgc acaagtggtc    1680
gccatcgcca acaacaacgg cggtaagcag gcgctggaaa cagtacagcg cctgctgcct    1740
gtactgtgcc aggatcatgg actgacccca gaccaggtag tcgcaatcgc gtcgaacatt    1800
gggggaaagc aagccctgga aaccgtgcaa aggttgttgc cggtcctttg tcaagaccac    1860
ggccttacac cggagcaagt cgtggccatt gcaaataata acggtggcaa acaggctctt    1920
gagacggttc agagacttct cccagttctc tgtcaagccc acgggctgac tcccgatcaa    1980
gttgtagcga ttgcgtccaa cggtggaggg aaacaagcat ggagactgt ccaacggctc    2040
cttcccgtgt tgtgtcaagc ccacggtttg acgcctgcac aagtggtcgc catcgcctcg    2100
aatggcggcg gtaagcaggc gctggaaaca gtacagcgcc tgctgcctgt actgtgccag    2160
gatcatggac tgacacccga acaggtggtc gccattgctt cccacgacgg aggacggcca    2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc ctcatgctcc cgcattgatc aaaagaacca accggcggat tcccgagaga    2400
acttcccatc gagtcgcggg atcc                                           2424
```

<210> SEQ ID NO 264
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala

```
            115                 120                 125
Leu Glu Ala Leu Leu Thr Val Ala Gly Glu Leu Arg Gly Pro Pro Leu
            130                 135                 140
Gln Leu Asp Thr Gly Gln Leu Leu Lys Ile Ala Lys Arg Gly Gly Val
145                 150                 155                 160
Thr Ala Val Glu Ala Val His Ala Trp Arg Asn Ala Leu Thr Gly Ala
                165                 170                 175
Pro Leu Asn Leu Thr Pro Asp Gln Val Val Ala Ile Ala Asn Asn Asn
                180                 185                 190
Gly Gly Lys Gln Ala Leu Glu Thr Val Gln Arg Leu Leu Pro Val Leu
            195                 200                 205
Cys Gln Asp His Gly Leu Thr Pro Glu Gln Val Val Ala Ile Ala Asn
            210                 215                 220
Asn Asn Gly Gly Lys Gln Ala Leu Glu Thr Val Gln Arg Leu Leu Pro
225                 230                 235                 240
Val Leu Cys Gln Ala His Gly Leu Thr Pro Asp Gln Val Val Ala Ile
                245                 250                 255
Ala Ser His Asp Gly Gly Lys Gln Ala Leu Glu Thr Val Gln Arg Leu
                260                 265                 270
Leu Pro Val Leu Cys Gln Ala His Gly Leu Thr Pro Ala Gln Val Val
            275                 280                 285
Ala Ile Ala Ser His Asp Gly Gly Lys Gln Ala Leu Glu Thr Val Gln
            290                 295                 300
Arg Leu Leu Pro Val Leu Cys Gln Asp His Gly Leu Thr Pro Asp Gln
305                 310                 315                 320
Val Val Ala Ile Ala Ser His Asp Gly Gly Lys Gln Ala Leu Glu Thr
                325                 330                 335
Val Gln Arg Leu Leu Pro Val Leu Cys Gln Asp His Gly Leu Thr Pro
                340                 345                 350
Glu Gln Val Val Ala Ile Ala Asn Asn Asn Gly Gly Lys Gln Ala Leu
            355                 360                 365
Glu Thr Val Gln Arg Leu Leu Pro Val Leu Cys Gln Ala His Gly Leu
            370                 375                 380
Thr Pro Asp Gln Val Val Ala Ile Ala Ser Asn Ile Gly Gly Lys Gln
385                 390                 395                 400
Ala Leu Glu Thr Val Gln Arg Leu Leu Pro Val Leu Cys Gln Ala His
                405                 410                 415
Gly Leu Thr Pro Ala Gln Val Val Ala Ile Ala Asn Asn Asn Gly Gly
                420                 425                 430
Lys Gln Ala Leu Glu Thr Val Gln Arg Leu Leu Pro Val Leu Cys Gln
            435                 440                 445
Asp His Gly Leu Thr Pro Asp Gln Val Val Ala Ile Ala Asn Asn Asn
            450                 455                 460
Gly Gly Lys Gln Ala Leu Glu Thr Val Gln Arg Leu Leu Pro Val Leu
465                 470                 475                 480
Cys Gln Asp His Gly Leu Thr Pro Glu Gln Val Val Ala Ile Ala Ser
                485                 490                 495
His Asp Gly Gly Lys Gln Ala Leu Glu Thr Val Gln Arg Leu Leu Pro
                500                 505                 510
Val Leu Cys Gln Ala His Gly Leu Thr Pro Asp Gln Val Val Ala Ile
            515                 520                 525
Ala Asn Asn Asn Gly Gly Lys Gln Ala Leu Glu Thr Val Gln Arg Leu
            530                 535                 540
```

Leu Pro Val Leu Cys Gln Ala His Gly Leu Thr Pro Ala Gln Val Val
545                 550                 555                 560

Ala Ile Ala Asn Asn Asn Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Ile Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Asn Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser Asn Gly Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser His Asp
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 265
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
gctagcacca tggactacaa agaccatgac ggtgattata agatcatga catcgattac      60 aaggatgacg atgacaagat ggcccccaag aagaagagga aggtgggcat tcaccgcggg     120
gtacctatgg tggacttgag acactcggt tattcgcaac agcaacagga gaaaatcaag     180
cctaaggtca ggagcaccgt cgcgcaacac cacgaggcgc ttgtggggca tggcttcact     240
catgcgcata ttgtcgcgct ttcacagcac cctgcgcgc ttgggacggt ggctgtcaaa     300
taccaagata tgattgcggc cctgcccgaa gccacgcacg aggcaattgt aggggtcggt     360
aaacagtggt cgggagcgcg agcacttgag gcgctgctga ctgtggcggg tgagcttagg     420
gggcctccgc tccagctcga caccgggcag ctgctgaaga tcgcgaagag aggggagta     480

| acagcggtag aggcagtgca cgcctggcgc aatgcgctca ccggggcccc cttgaacctg | 540 |
| acccagacc aggtagtcgc aatcgcgaac aataatgggg gaaagcaagc cctggaaacc | 600 |
| gtgcaaaggt tgttgccggt cctttgtcaa gaccacggcc ttacaccgga gcaagtcgtg | 660 |
| gccattgcaa gcaacatcgg tggcaaacag gctcttgaga cggttcagag acttctccca | 720 |
| gttctctgtc aagcccacgg gctgactccc gatcaagttg tagcgattgc gtcgaacatt | 780 |
| ggagggaaac aagcattgga gactgtccaa cggctccttc ccgtgttgtg tcaagcccac | 840 |
| ggtttgacgc ctgcacaagt ggtcgccatc gccaacaaca acggcggtaa gcaggcgctg | 900 |
| gaaacagtac agcgcctgct gcctgtactg tgccaggatc atggactgac cccagaccag | 960 |
| gtagtcgcaa tcgcgaacaa taatggggga aagcaagccc tggaaaccgt gcaaaggttg | 1020 |
| ttgccggtcc tttgtcaaga ccacggcctt acaccggagc aagtcgtggc cattgcaaat | 1080 |
| aataacggtg gcaaacaggc tcttgagacg gttcagagac ttctcccagt tctctgtcaa | 1140 |
| gcccacgggc tgactcccga tcaagttgta gcgattgcgt cgaacattgg agggaaacaa | 1200 |
| gcattggaga ctgtccaacg gctccttccc gtgttgtgtc aagcccacgg tttgacgcct | 1260 |
| gcacaagtgg tcgccatcgc cagccatgat ggcggtaagc aggcgctgga aacagtacag | 1320 |
| cgcctgctgc ctgtactgtg ccaggatcat ggactgaccc cagaccaggt agtcgcaatc | 1380 |
| gcgtcgaaca ttgggggaaa gcaagccctg aaaccgtgc aaaggttgtt gccggtcctt | 1440 |
| tgtcaagacc acgccttac accggagcaa gtcgtggcca ttgcaagcaa tgggggtggc | 1500 |
| aaacaggctc ttgagacggt tcagagactt ctcccagttc tctgtcaagc ccacgggctg | 1560 |
| actcccgatc aagttgtagc gattgcgtcg catgacggag ggaaacaagc attggagact | 1620 |
| gtccaacggc tccttcccgt gttgtgtcaa gcccacggtt tgacgcctgc acaagtggtc | 1680 |
| gccatcgcct ccaatattgg cggtaagcag gcgctggaaa cagtacagcg cctgctgcct | 1740 |
| gtactgtgcc aggatcatgg actgacccca gaccaggtag tcgcaatcgc gtcacatgac | 1800 |
| gggggaaagc aagcccctgga aaccgtgcaa aggttgttgc cggtcctttg tcaagaccac | 1860 |
| ggccttacac cggagcaagt cgtggccatt gcatcccacg acggtggcaa acaggctctt | 1920 |
| gagacggttc agagacttct cccagttctc tgtcaagccc acgggctgac tcccgatcaa | 1980 |
| gttgtagcga ttgcgtccaa cggtggaggg aaacaagcat ggagactgt ccaacggctc | 2040 |
| cttcccgtgt tgtgtcaagc ccacggtttg acgcctgcac aagtggtcgc catcgcctcg | 2100 |
| aatggcggcg gtaagcaggc gctggaaaca gtacagcgcc tgctgcctgt actgtgccag | 2160 |
| gatcatggac tgacacccga acaggtggtc gccattgctt ctaatggggg aggacggcca | 2220 |
| gccttggagt ccatcgtagc ccaattgtcc aggcccgatc ccgcgttggc tgcgttaacg | 2280 |
| aatgaccatc tggtggcgtt ggcatgtctt ggtggacgac ccgcgctcga tgcagtcaaa | 2340 |
| aagggtctgc ctcatgctcc cgcattgatc aaaagaacca accggcggat tcccgagaga | 2400 |
| acttcccatc gagtcgcggg atcc | 2424 |

<210> SEQ ID NO 266
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 266

Ala Ser Thr Met Asp Tyr Lys Asp His Asp Gly Asp Tyr Lys Asp His
1               5                   10                  15

```
Asp Ile Asp Tyr Lys Asp Asp Asp Lys Met Ala Pro Lys Lys Lys
         20                  25                  30

Arg Lys Val Gly Ile His Arg Gly Val Pro Met Val Asp Leu Arg Thr
         35                  40                  45

Leu Gly Tyr Ser Gln Gln Gln Glu Lys Ile Lys Pro Lys Val Arg
 50                  55                  60

Ser Thr Val Ala Gln His His Glu Ala Leu Val Gly His Gly Phe Thr
 65                  70                  75                  80

His Ala His Ile Val Ala Leu Ser Gln His Pro Ala Ala Leu Gly Thr
             85                  90                  95

Val Ala Val Lys Tyr Gln Asp Met Ile Ala Ala Leu Pro Glu Ala Thr
             100                 105                 110

His Glu Ala Ile Val Gly Val Gly Lys Gln Trp Ser Gly Ala Arg Ala
             115                 120                 125

Leu Glu Ala Leu Leu Thr Val Ala Gly Glu Leu Arg Gly Pro Pro Leu
 130                 135                 140

Gln Leu Asp Thr Gly Gln Leu Leu Lys Ile Ala Lys Arg Gly Gly Val
 145                 150                 155                 160

Thr Ala Val Glu Ala Val His Ala Trp Arg Asn Ala Leu Thr Gly Ala
             165                 170                 175

Pro Leu Asn Leu Thr Pro Asp Gln Val Val Ala Ile Ala Asn Asn Asn
             180                 185                 190

Gly Gly Lys Gln Ala Leu Glu Thr Val Gln Arg Leu Leu Pro Val Leu
             195                 200                 205

Cys Gln Asp His Gly Leu Thr Pro Glu Gln Val Val Ala Ile Ala Ser
 210                 215                 220

Asn Ile Gly Gly Lys Gln Ala Leu Glu Thr Val Gln Arg Leu Leu Pro
225                  230                 235                 240

Val Leu Cys Gln Ala His Gly Leu Thr Pro Asp Gln Val Val Ala Ile
             245                 250                 255

Ala Ser Asn Ile Gly Gly Lys Gln Ala Leu Glu Thr Val Gln Arg Leu
             260                 265                 270

Leu Pro Val Leu Cys Gln Ala His Gly Leu Thr Pro Ala Gln Val Val
             275                 280                 285

Ala Ile Ala Asn Asn Asn Gly Gly Lys Gln Ala Leu Glu Thr Val Gln
             290                 295                 300

Arg Leu Leu Pro Val Leu Cys Gln Asp His Gly Leu Thr Pro Asp Gln
305                  310                 315                 320

Val Val Ala Ile Ala Asn Asn Gly Gly Lys Gln Ala Leu Glu Thr
             325                 330                 335

Val Gln Arg Leu Leu Pro Val Leu Cys Gln Asp His Gly Leu Thr Pro
             340                 345                 350

Glu Gln Val Val Ala Ile Ala Asn Asn Asn Gly Gly Lys Gln Ala Leu
             355                 360                 365

Glu Thr Val Gln Arg Leu Leu Pro Val Leu Cys Gln Ala His Gly Leu
             370                 375                 380

Thr Pro Asp Gln Val Val Ala Ile Ala Ser Asn Ile Gly Gly Lys Gln
385                  390                 395                 400

Ala Leu Glu Thr Val Gln Arg Leu Leu Pro Val Leu Cys Gln Ala His
             405                 410                 415

Gly Leu Thr Pro Ala Gln Val Val Ala Ile Ala Ser His Asp Gly Gly
             420                 425                 430
```

```
Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser Asn Ile
450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
            485                 490                 495

Asn Gly Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
            515                 520                 525

Ala Ser His Asp Gly Gly Lys Gln Ala Leu Glu Thr Val Gln Arg Leu
530                 535                 540

Leu Pro Val Leu Cys Gln Ala His Gly Leu Thr Pro Ala Gln Val Val
545                 550                 555                 560

Ala Ile Ala Ser Asn Ile Gly Gly Lys Gln Ala Leu Glu Thr Val Gln
            565                 570                 575

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
            610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
            645                 650                 655

Thr Pro Asp Gln Val Val Ala Ile Ala Ser Asn Gly Gly Gly Lys Gln
            660                 665                 670

Ala Leu Glu Thr Val Gln Arg Leu Leu Pro Val Leu Cys Gln Ala His
            675                 680                 685

Gly Leu Thr Pro Ala Gln Val Val Ala Ile Ala Ser Asn Gly Gly Gly
690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Gly
            725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
            805
```

<210> SEQ ID NO 267
<211> LENGTH: 2322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 267

```
gctagcacca tggactacaa agaccatgac ggtgattata aagatcatga catcgattac      60
aaggatgacg atgacaagat ggcccccaag aagaagagga aggtgggcat tcaccgcggg     120
gtacctatgg tggacttgag gacactcggt tattcgcaac agcaacagga gaaaatcaag     180
cctaaggtca ggagcaccgt cgcgcaacac cacgaggcgc ttgtggggca tggcttcact     240
catgcgcata ttgtcgcgct ttcacagcac cctgcggcgc ttgggacggt ggctgtcaaa     300
taccaagata tgattgcggc cctgcccgaa gccacgcacg aggcaattgt aggggtcggt     360
aaacagtggt cgggagcgcg agcacttgag gcgctgctga ctgtggcggg tgagcttagg     420
gggcctccgc tccagctcga caccgggcag ctgctgaaga tcgcgaagag aggggagta     480
acagcggtag aggcagtgca cgcctggcgc aatgcgctca ccggggcccc cttgaacctg     540
acccccagacc aggtagtcgc aatcgcgtca catgacgggg aaagcaagc cctggaaacc     600
gtgcaaaggt tgttgccggt cctttgtcaa gaccacggcc ttacaccgga gcaagtcgtg     660
gccattgcaa gcaatggggg tggcaaacag gctcttgaga cggttcagag acttctccca     720
gttctctgtc aagcccacgg gctgactccc gatcaagttg tagcgattgc gtcgaacatt     780
ggagggaaac aagcattgga gactgtccaa cggctccttc ccgtgttgtg tcaagcccac     840
ggtttgacgc ctgcacaagt ggtcgccatc gccagccatg atggcggtaa gcaggcgctg     900
gaaacagtac agcgcctgct gcctgtactg tgccaggatc atggactgac cccagaccag     960
gtagtcgcaa tcgcgtcaaa cggagggggga aagcaagccc tggaaaccgt gcaaaggttg    1020
ttgccggtcc tttgtcaaga ccacggcctt acaccggagc aagtcgtggc cattgcaaat    1080
aataacggtg gcaaacaggc tcttgagacg gttcagagac ttctcccagt tctctgtcaa    1140
gcccacgggc tgactcccga tcaagttgta gcgattgcgt cgaacattgg agggaaacaa    1200
gcattggaga ctgtccaacg gctccttccc gtgttgtgtc aagcccacgg tttgacgcct    1260
gcacaagtgg tcgccatcgc ctccaatatt ggcggtaagc aggcgctgga aacagtacag    1320
cgcctgctgc ctgtactgtg ccaggatcat ggactgaccc cagaccaggt agtcgcaatc    1380
gcgtcaaacg gagggggaaa gcaagccctg aaaccgtgc aaaggttgtt gccggtcctt    1440
tgtcaagacc acgccttac accggagcaa gtcgtggcca ttgcatccca cgacggtggc    1500
aaacaggctc ttgagacggt tcagagactt ctcccagttc tctgtcaagc ccacgggctg    1560
actcccgatc aagttgtagc gattgcgtcc aacggtggag ggaaacaagc attggagact    1620
gtccaacggc tccttcccgt gttgtgtcaa gcccacggtt tgacgcctgc acaagtggtc    1680
gccatcgcct cgaatggcgg cggtaagcag gcgctggaaa cagtacagcg cctgctgcct    1740
gtactgtgcc aggatcatgg actgacccca gaccaggtag tcgcaatcgc gaacaataat    1800
gggggaaagc aagccctgga aaccgtgcaa aggttgttgc cggtcctttg tcaagaccac    1860
ggccttacac cggagcaagt cgtggccatt gcaagcaaca tcgtggcaa acaggctctt    1920
gagacggttc agagacttct cccagttctc tgtcaagccc acgggctgac tccgatcaa    1980
gttgtagcga ttgcgaataa caatggaggg aaacaagcat ggagactgt ccaacggctc    2040
cttcccgtgt tgtgtcaagc ccacggtctg acacccgaac aggtggtcgc cattgcttcc    2100
cacgacggag acggccagc cttggagtcc atcgtagccc aattgtccag gcccgatccc    2160
gcgttggctc gcgttaacga atgaccatctg gtggcgttgg catgtcttgg tggacgaccc    2220
gcgctcgatg cagtcaaaaa gggtctgcct catgctcccg cattgatcaa agaaccaac    2280
```
cggcggattc cgagagaac ttcccatcga gtcgcgggat cc                2322

<210> SEQ ID NO 268
<211> LENGTH: 774
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser His Asp Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Asp His Gly Leu Thr Pro
            340                 345                 350
```

```
Glu Gln Val Val Ala Ile Ala Asn Asn Asn Gly Gly Lys Gln Ala Leu
            355                 360                 365
Glu Thr Val Gln Arg Leu Leu Pro Val Leu Cys Gln Ala His Gly Leu
            370                 375                 380
Thr Pro Asp Gln Val Val Ala Ile Ala Ser Asn Ile Gly Gly Lys Gln
385                 390                 395                 400
Ala Leu Glu Thr Val Gln Arg Leu Leu Pro Val Leu Cys Gln Ala His
                405                 410                 415
Gly Leu Thr Pro Ala Gln Val Val Ala Ile Ala Ser Asn Ile Gly Gly
            420                 425                 430
Lys Gln Ala Leu Glu Thr Val Gln Arg Leu Leu Pro Val Leu Cys Gln
            435                 440                 445
Asp His Gly Leu Thr Pro Asp Gln Val Val Ala Ile Ala Ser Asn Gly
            450                 455                 460
Gly Gly Lys Gln Ala Leu Glu Thr Val Gln Arg Leu Leu Pro Val Leu
465                 470                 475                 480
Cys Gln Asp His Gly Leu Thr Pro Glu Gln Val Val Ala Ile Ala Ser
                485                 490                 495
His Asp Gly Gly Lys Gln Ala Leu Glu Thr Val Gln Arg Leu Leu Pro
            500                 505                 510
Val Leu Cys Gln Ala His Gly Leu Thr Pro Asp Gln Val Val Ala Ile
            515                 520                 525
Ala Ser Asn Gly Gly Gly Lys Gln Ala Leu Glu Thr Val Gln Arg Leu
            530                 535                 540
Leu Pro Val Leu Cys Gln Ala His Gly Leu Thr Pro Ala Gln Val Val
545                 550                 555                 560
Ala Ile Ala Ser Asn Gly Gly Gly Lys Gln Ala Leu Glu Thr Val Gln
                565                 570                 575
Arg Leu Leu Pro Val Leu Cys Gln Asp His Gly Leu Thr Pro Asp Gln
            580                 585                 590
Val Val Ala Ile Ala Asn Asn Asn Gly Gly Lys Gln Ala Leu Glu Thr
            595                 600                 605
Val Gln Arg Leu Leu Pro Val Leu Cys Gln Asp His Gly Leu Thr Pro
            610                 615                 620
Glu Gln Val Val Ala Ile Ala Ser Asn Ile Gly Gly Lys Gln Ala Leu
625                 630                 635                 640
Glu Thr Val Gln Arg Leu Leu Pro Val Leu Cys Gln Ala His Gly Leu
                645                 650                 655
Thr Pro Asp Gln Val Val Ala Ile Ala Asn Asn Asn Gly Gly Lys Gln
            660                 665                 670
Ala Leu Glu Thr Val Gln Arg Leu Leu Pro Val Leu Cys Gln Ala His
            675                 680                 685
Gly Leu Thr Pro Glu Gln Val Val Ala Ile Ala Ser His Asp Gly Gly
            690                 695                 700
Arg Pro Ala Leu Glu Ser Ile Val Ala Gln Leu Ser Arg Pro Asp Pro
705                 710                 715                 720
Ala Leu Ala Ala Leu Thr Asn Asp His Leu Val Ala Leu Ala Cys Leu
                725                 730                 735
Gly Gly Arg Pro Ala Leu Asp Ala Val Lys Lys Gly Leu Pro His Ala
            740                 745                 750
Pro Ala Leu Ile Lys Arg Thr Asn Arg Arg Ile Pro Glu Arg Thr Ser
            755                 760                 765
```

His Arg Val Ala Gly Ser
    770

<210> SEQ ID NO 269
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

```
gctagcacca tggactacaa agaccatgac ggtgattata agatcatga catcgattac      60
aaggatgacg atgacaagat ggcccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag aggggagta     480
acagcggtag aggcagtgca cgcctggcgc aatgcgctca cggggcccc cttgaacctg     540
acccagacc aggtagtcgc aatcgcgtca catgacgggg aaagcaagc cctggaaacc      600
gtgcaaaggt tgttgccggt cctttgtcaa gaccacggcc ttacaccgga gcaagtcgtg    660
gccattgcaa ataataacgg tggcaaacag gctcttgaga cggttcagag acttctccca    720
gttctctgtc aagcccacgg gctgactccc gatcaagttg tagcgattgc gaataacaat    780
ggagggaaac aagcattgga gactgtccaa cggctccttc ccgtgttgtg tcaagcccac    840
ggtttgacgc ctgcacaagt ggtcgccatc gccagccatg atggcggtaa gcaggcgctg    900
gaaacagtac agcgcctgct gcctgtactg tgccaggatc atggactgac ccagaccag    960
gtagtcgcaa tcgcgtcaca tgacggggga agcaagccc tggaaaccgt gcaaaggttg    1020
ttgccggtcc tttgtcaaga ccacggcctt acaccggagc aagtcgtggc cattgcaagc   1080
aacatcggtg gcaaacaggc tcttgagacg gttcagagac ttctcccagt tctctgtcaa   1140
gcccacgggc tgactcccga tcaagttgta gcgattgcgt cgcatgacgg agggaaacaa   1200
gcattggaga ctgtccaacg gctccttccc gtgttgtgtc aagcccacgg tttgacgcct   1260
gcacaagtgg tcgccatcgc cagccatgat ggcggtaagc aggcgctgga aacagtacag   1320
cgcctgctgc ctgtactgtg ccaggatcat ggactgaccc agaccaggt agtcgcaatc    1380
gcgtcgaaca ttgggggaaa gcaagccctg gaaccgtgc aaaggttgtt gccggtcctt    1440
tgtcaagacc acggccttac accggagcaa gtcgtggcca ttgcaagcaa tggggtggc    1500
aaacaggctc ttgagacggt tcagagactt ctcccagttc tctgtcaagc ccacgggctg   1560
actcccgatc aagttgtagc gattgcgaat aacaatggag gaaacaagc attggagact    1620
gtccaacggc tccttcccgt gttgtgtcaa gcccacggtt tgacgcctgc acaagtggtc   1680
gccatcgcct cgaatggcgg cggtaagcag gcgctggaaa cagtacagcg cctgctgcct   1740
gtactgtgcc aggatcatgg actgacccca gaccaggtag tcgcaatcgc gtcacatgac   1800
gggggaaagc aagccctgga aaccgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac acccgaacag   1980
```

```
gtggtcgcca ttgcttccca cgacggagga cggccagcct tggagtccat cgtagcccaa    2040
ttgtccaggc ccgatcccgc gttggctgcg ttaacgaatg accatctggt ggcgttggca    2100
tgtcttggtg gacgacccgc gctcgatgca gtcaaaaagg gtctgcctca tgctcccgca    2160
ttgatcaaaa gaaccaaccg gcggattccc gagagaactt cccatcgagt cgcgggatcc    2220
```

<210> SEQ ID NO 270
<211> LENGTH: 740
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser His Asp Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320
```

-continued

Val Val Ala Ile Ala Ser His Asp Gly Gly Lys Gln Ala Leu Glu Thr
             325                 330                 335

Val Gln Arg Leu Leu Pro Val Leu Cys Gln Asp His Gly Leu Thr Pro
             340                 345                 350

Glu Gln Val Val Ala Ile Ala Ser Asn Ile Gly Gly Lys Gln Ala Leu
             355                 360                 365

Glu Thr Val Gln Arg Leu Leu Pro Val Leu Cys Gln Ala His Gly Leu
             370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
             405                 410                 415

Gly Leu Thr Pro Ala Gln Val Val Ala Ile Ala Ser His Asp Gly Gly
             420                 425                 430

Lys Gln Ala Leu Glu Thr Val Gln Arg Leu Leu Pro Val Leu Cys Gln
             435                 440                 445

Asp His Gly Leu Thr Pro Asp Gln Val Val Ala Ile Ala Ser Asn Ile
             450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
             485                 490                 495

Asn Gly Gly Gly Lys Gln Ala Leu Glu Thr Val Gln Arg Leu Leu Pro
             500                 505                 510

Val Leu Cys Gln Ala His Gly Leu Thr Pro Asp Gln Val Val Ala Ile
             515                 520                 525

Ala Asn Asn Asn Gly Gly Lys Gln Ala Leu Glu Thr Val Gln Arg Leu
             530                 535                 540

Leu Pro Val Leu Cys Gln Ala His Gly Leu Thr Pro Ala Gln Val Val
545                 550                 555                 560

Ala Ile Ala Ser Asn Gly Gly Lys Gln Ala Leu Glu Thr Val Gln
             565                 570                 575

Arg Leu Leu Pro Val Leu Cys Gln Asp His Gly Leu Thr Pro Asp Gln
             580                 585                 590

Val Val Ala Ile Ala Ser His Asp Gly Gly Lys Gln Ala Leu Glu Thr
             595                 600                 605

Val Gln Arg Leu Leu Pro Val Leu Cys Gln Asp His Gly Leu Thr Pro
             610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
             645                 650                 655

Thr Pro Glu Gln Val Val Ala Ile Ala Ser His Asp Gly Gly Arg Pro
             660                 665                 670

Ala Leu Glu Ser Ile Val Ala Gln Leu Ser Arg Pro Asp Pro Ala Leu
             675                 680                 685

Ala Ala Leu Thr Asn Asp His Leu Val Ala Leu Ala Cys Leu Gly Gly
             690                 695                 700

Arg Pro Ala Leu Asp Ala Val Lys Lys Gly Leu Pro His Ala Pro Ala
705                 710                 715                 720

Leu Ile Lys Arg Thr Asn Arg Arg Ile Pro Glu Arg Thr Ser His Arg
             725                 730                 735

Val Ala Gly Ser
    740

<210> SEQ ID NO 271
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271

```
gctagcacca tggactacaa agaccatgac ggtgattata agatcatga catcgattac      60
aaggatgacg atgacaagat ggcccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag aggggagta    480
acagcggtag aggcagtgca cgcctggcgc aatgcgctca ccggggcccc cttgaacctg    540
accccagacc aggtagtcgc aatcgcgtca catgacgggg gaaagcaagc cctggaaacc    600
gtgcaaaggt tgttgccggt cctttgtcaa gaccacggcc ttacaccgga gcaagtcgtg    660
gccattgcat cccacgacgg tggcaaacag gctcttgaga cggttcagag acttctccca    720
gttctctgtc aagcccacgg gctgactccc gatcaagttg tagcgattgc gtcgaacatt    780
ggagggaaac aagcattgga gactgtccaa cggctccttc ccgtgttgtg tcaagcccac    840
ggtttgacgc ctgcacaagt ggtcgccatc gccaacaaca acggcggtaa gcaggcgctg    900
gaaacagtac agcgcctgct gcctgtactg tgccaggatc atggactgac ccagaccag    960
gtagtcgcaa tcgcgaacaa taatggggga agcaagccc tggaaaccgt gcaaaggttg   1020
ttgccggtcc tttgtcaaga ccacggcctt acaccggagc aagtcgtggc cattgcatcc   1080
cacgacggtg gcaaacaggc tcttgagacg gttcagagac ttctcccagt tctctgtcaa   1140
gcccacgggc tgactcccga tcaagttgta gcgattgcgt cgaacattgg agggaaacaa   1200
gcattggaga ctgtccaacg gctccttccc gtgttgtgtc aagcccacgg tttgacgcct   1260
gcacaagtgg tcgccatcgc caacaacaac ggcggtaagc aggcgctgga aacagtacag   1320
cgcctgctgc ctgtactgtg ccaggatcat ggactgaccc agaccaggt agtcgcaatc   1380
gcgtcacatg acgggggaaa gcaagccctg gaaaccgtgc aaaggttgtt gccggtcctt   1440
tgtcaagacc acggccttac accggagcaa gtcgtggcca ttgcaagcaa tgggggtggc   1500
aaacaggctc ttgagacggt tcagagactt ctcccagttc tctgtcaagc ccacgggctg   1560
actcccgatc aagttgtagc gattgcgaat aacaatggag ggaaacaagc attggagact   1620
gtccaacggc tccttcccgt gttgtgtcaa gcccacggtt tgacgcctgc acaagtggtc   1680
gccatcgcca caacaacgg cggtaagcag gcgctggaaa cagtacagcg cctgctgcct   1740
gtactgtgcc aggatcatgg actgacccca gaccaggtag tcgcaatcgc gtcgaacatt   1800
gggggaaagc aagccctgga aaccgtgcaa aggttgttgc cggtcctttg tcaagaccac   1860
ggccttacac cggagcaagt cgtggccatt gcaaataata acgtggcaa acaggctctt   1920
gagacggttc agagacttct cccagttctc tgtcaagccc acgggctgac tcccgatcaa   1980
```

```
gttgtagcga ttgcgtcgca tgacggaggg aaacaagcat tggagactgt ccaacggctc    2040
cttcccgtgt tgtgtcaagc ccacggtttg acgcctgcac aagtggtcgc catcgccagc    2100
catgatggcg gtaagcaggc gctggaaaca gtacagcgcc tgctgcctgt actgtgccag    2160
gatcatggac tgcacccga acaggtggtc gccattgctt cccacgacgg aggacggcca     2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc ctcatgctcc cgcattgatc aaaagaacca accggcggat tcccgagaga    2400
acttcccatc gagtcgcggg atcc                                           2424

<210> SEQ ID NO 272
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272
```

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
            260                 265                 270

```
Leu Pro Val Leu Cys Gln Ala His Gly Leu Thr Pro Ala Gln Val Val
            275                 280                 285

Ala Ile Ala Asn Asn Asn Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Asn Asn Asn Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser His Asp Gly Gly Lys Gln Ala Leu
            355                 360                 365

Glu Thr Val Gln Arg Leu Leu Pro Val Leu Cys Gln Ala His Gly Leu
370                 375                 380

Thr Pro Asp Gln Val Val Ala Ile Ala Ser Asn Ile Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Asn Asn Asn Gly Gly
            420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser His Asp
            450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Gly Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Asn Asn Asn Gly Gly Lys Gln Ala Leu Glu Thr Val Gln Arg Leu
            530                 535                 540

Leu Pro Val Leu Cys Gln Ala His Gly Leu Thr Pro Ala Gln Val Val
545                 550                 555                 560

Ala Ile Ala Asn Asn Asn Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Ile Gly Gly Lys Gln Ala Leu Glu Thr
            595                 600                 605

Val Gln Arg Leu Leu Pro Val Leu Cys Gln Asp His Gly Leu Thr Pro
610                 615                 620

Glu Gln Val Val Ala Ile Ala Asn Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser His Asp Gly Gly Lys Gln
            660                 665                 670

Ala Leu Glu Thr Val Gln Arg Leu Leu Pro Val Leu Cys Gln Ala His
            675                 680                 685

Gly Leu Thr Pro Ala Gln Val Val Ala Ile Ala Ser His Asp Gly Gly
```

```
                690                  695                  700
Lys Gln Ala Leu Glu Thr Val Gln Arg Leu Leu Pro Val Leu Cys Gln
705                 710                  715                  720

Asp His Gly Leu Thr Pro Glu Gln Val Val Ala Ile Ala Ser His Asp
                725                  730                  735

Gly Gly Arg Pro Ala Leu Glu Ser Ile Val Ala Gln Leu Ser Arg Pro
            740                  745                  750

Asp Pro Ala Leu Ala Ala Leu Thr Asn Asp His Leu Val Ala Leu Ala
        755                  760                  765

Cys Leu Gly Gly Arg Pro Ala Leu Asp Ala Val Lys Lys Gly Leu Pro
770                 775                  780

His Ala Pro Ala Leu Ile Lys Arg Thr Asn Arg Arg Ile Pro Glu Arg
785                 790                  795                  800

Thr Ser His Arg Val Ala Gly Ser
                805
```

<210> SEQ ID NO 273
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273

```
gctagcacca tggactacaa agaccatgac ggtgattata agatcatga catcgattac      60
aaggatgacg atgacaagat ggcccccaag aagaagagga aggtgggcat tcaccgcggg    120
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag agggggagta    480
acagcggtag aggcagtgca cgcctggcgc aatgcgctca ccggggcccc cttgaacctg    540
accccagacc aggtagtcgc aatcgcgtca catgacgggg gaaagcaagc cctggaaacc    600
gtgcaaaggt tgttgccggt cctttgtcaa gaccacggcc ttacaccgga gcaagtcgtg    660
gccattgcaa gcaatggggg tgcaaacag ctcttgaga cggttcagag acttctccca    720
gttctctgtc aagcccacgg gctgactccc gatcaagttg tagcgattgc gaataacaat    780
ggagggaaac aagcattgga gactgtccaa cggctccttc ccgtgttgtg tcaagcccac    840
ggtttgacgc ctgcacaagt ggtcgccatc gcctccaata ttggcggtaa gcaggcgctg    900
gaaacagtac agcgcctgct gcctgtactg tgccaggatc atggactgac cccagaccag    960
gtagtcgcaa tcgcgtcgaa cattggggga agcaagccc tggaaaccgt gcaaaggttg    1020
ttgccggtcc tttgtcaaga ccacggcctt acaccggagc aagtcgtggc cattgcaagc    1080
aacatcggtg gcaaacaggc tcttgagacg gttcagagac ttctcccagt tctctgtcaa    1140
gcccacgggc tgactcccga tcaagttgta gcgattgcgt cgaacattgg agggaaacaa    1200
gcattggaga ctgtccaacg gctccttccc gtgttgtgtc aagcccacgg tttgacgcct    1260
gcacaagtgt cgccatcgc ctccaatatt ggcggtaagc aggcgctgga aacagtacag    1320
cgcctgctgc ctgtactgtg ccaggatcat ggactgaccc cagaccaggt agtcgcaatc    1380
```

```
gcgaacaata atgggggaaa gcaagccctg gaaaccgtgc aaaggttgtt gccggtcctt      1440
tgtcaagacc acggccttac accggagcaa gtcgtggcca ttgcaagcaa catcggtggc      1500
aaacaggctc ttgagacggt tcagagactt ctcccagttc tctgtcaagc ccacgggctg      1560
actcccgatc aagttgtagc gattgcgtcg catgacggag ggaaacaagc attggagact      1620
gtccaacggc tccttcccgt gttgtgtcaa gcccacggtt tgacgcctgc acaagtggtc      1680
gccatcgcct cgaatggcgg cggtaagcag gcgctggaaa cagtacagcg cctgctgcct      1740
gtactgtgcc aggatcatgg actgacccca gaccaggtag tcgcaatcgc gtcacatgac      1800 ggggggaaagc aagccctgga aaccgtgcaa aggttgttgc cggtcctttg tcaagaccac      1860
ggccttacac cggagcaagt cgtggccatt gcaagcaatg ggggtggcaa acaggctctt      1920
gagacggttc agagacttct cccagttctc tgtcaagccc acgggctgac tcccgatcaa      1980
gttgtagcga ttgcgaataa caatggaggg aaacaagcat ggagactgt ccaacggctc       2040 cttcccgtgt tgtgtcaagc ccacggtttg acgcctgcac aagtggtcgc catcgccagc      2100
catgatggcg gtaagcaggc gctggaaaca gtacagcgcc tgctgcctgt actgtgccag      2160
gatcatggac tgacacccga acaggtggtc gccattgctt ctaacatcgg aggacggcca      2220
gccttggagt ccatcgtagc ccaattgtcc aggcccgatc ccgcgttggc tgcgttaacg      2280
aatgaccatc tggtggcgtt ggcatgtctt ggtggacgac ccgcgctcga tgcagtcaaa      2340
aagggtctgc ctcatgctcc cgcattgatc aaaagaacca accggcggat tcccgagaga      2400
acttcccatc gagtcgcggg atcc                                             2424
```

<210> SEQ ID NO 274
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 274

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
```

```
                    165                 170                 175
Pro Leu Asn Leu Thr Pro Asp Gln Val Val Ala Ile Ala Ser His Asp
                180                 185                 190

Gly Gly Lys Gln Ala Leu Glu Thr Val Gln Arg Leu Leu Pro Val Leu
            195                 200                 205

Cys Gln Asp His Gly Leu Thr Pro Glu Gln Val Val Ala Ile Ala Ser
        210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
                260                 265                 270

Leu Pro Val Leu Cys Gln Ala His Gly Leu Thr Pro Ala Gln Val Val
            275                 280                 285

Ala Ile Ala Ser Asn Ile Gly Gly Lys Gln Ala Leu Glu Thr Val Gln
        290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser Asn Ile Gly Gly Lys Gln Ala Leu
        355                 360                 365

Glu Thr Val Gln Arg Leu Leu Pro Val Leu Cys Gln Ala His Gly Leu
    370                 375                 380

Thr Pro Asp Gln Val Val Ala Ile Ala Ser Asn Ile Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Ile Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Asn Asn Asn
    450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Ile Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser His Asp Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser Asn Gly Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590
```

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
        610                 615                 620

Glu Gln Val Val Ala Ile Ala Ser Asn Gly Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser His Asp Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Ile
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 275
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275
gctagcacca tggactacaa agaccatgac ggtgattata aagatcatga catcgattac      60
aaggatgacg atgacaagat ggcccccaag aagaagagga aggtgggcat tcaccgcggg     120
gtacctatgg tggacttgag acactcggt tattcgcaac agcaacagga gaaaatcaag     180
cctaaggtca ggagcaccgt cgcgcaacac cacgaggcgc ttgtggggca tggcttcact     240
catgcgcata ttgtcgcgct ttcacagcac cctgcggcgc ttgggacggt ggctgtcaaa     300
taccaagata tgattgcggc cctgcccgaa gccacgcacg aggcaattgt aggggtcggt     360
aaacagtggt cgggagcgcg agcacttgag gcgctgctga ctgtggcggg tgagcttagg     420
gggcctccgc tccagctcga caccgggcag ctgctgaaga tcgcgaagag aggggagta     480 acagcggtag aggcagtgca cgcctggcgc aatgcgctca ccggggcccc cttgaacctg     540
accccagacc aggtagtcgc aatcgcgtca catgacgggg gaaagcaagc cctggaaacc     600
gtgcaaaggt tgttgccggt cctttgtcaa gaccacggcc ttacaccgga gcaagtcgtg     660
gccattgcat cccacgacgg tggcaaacag gctcttgaga cggttcagag acttctccca     720
gttctctgtc aagcccacgg gctgactccc gatcaagttg tagcgattgc gtcgaacatt     780

```
ggagggaaac aagcattgga gactgtccaa cggctccttc ccgtgttgtg tcaagcccac    840
ggtttgacgc ctgcacaagt ggtcgccatc gcctcgaatg gcggcggtaa gcaggcgctg    900
gaaacagtac agcgcctgct gcctgtactg tgccaggatc atggactgac cccagaccag    960
gtagtcgcaa tcgcgtcaaa cggagggggda agcaagccc tggaaaccgt gcaaaggttg   1020
ttgccggtcc tttgtcaaga ccacggcctt acaccggagc aagtcgtggc cattgcaagc   1080 aatggggtg gcaaacaggc tcttgagacg gttcagagac ttctcccagt tctctgtcaa   1140
gcccacgggc tgactcccga tcaagttgta gcgattgcgt cgcatgacgg agggaaacaa   1200
gcattggaga ctgtccaacg gctccttccc gtgttgtgtc aagcccacgg tttgacgcct   1260
gcacaagtgg tcgccatcgc ctcgaatggc ggcggtaagc aggcgctgga aacagtacag   1320
cgcctgctgc ctgtactgtg ccaggatcat ggactgaccc cagaccaggt agtcgcaatc   1380
gcgaacaata tgggggaaaa gcaagccctg gaaaccgtgc aaaggttgtt gccggtcctt   1440
tgtcaagacc acgccttac accggagcaa gtcgtggcca ttgcaagcaa tggggggtggc   1500 aaacaggctc ttgagacggt tcagagactt ctcccagttc tctgtcaagc ccacgggctg   1560
actcccgatc aagttgtagc gattgcgtcg catgacggag ggaaacaagc attggagact   1620
gtccaacggc tccttcccgt gttgtgtcaa gcccacggtt tgacgcctgc acaagtggtc   1680
gccatcgcct ccaatattgg cggtaagcag gcgctggaaa cagtacagcg cctgctgcct   1740
gtactgtgcc aggatcatgg actgacccca gaccaggtag tcgcaatcgc gtcaaacgga   1800 ggggaaagc aagccctgga aaccgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac tcccgatcaa   1980
gttgtagcga ttgcgaataa caatggaggg aaacaagcat ggagactgt caacggctc   2040 cttcccgtgt tgtgtcaagc ccacggtttg acgcctgcac aagtggtcgc catcgcctcg   2100
aatggcggcg gtaagcaggc gctggaaaca gtacagcgcc tgctgcctgt actgtgccag   2160
gatcatggac tgcacccga caggtggtc gccattgctt ctaacatcgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 276
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Gln Glu Lys Ile Lys Pro Lys Val Arg
    50                  55                  60

-continued

Ser Thr Val Ala Gln His His Glu Ala Leu Val Gly His Gly Phe Thr
 65                  70                  75                  80

His Ala His Ile Val Ala Leu Ser Gln His Pro Ala Ala Leu Gly Thr
                 85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser Asn Gly Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser Asn Gly Gly Gly Lys Gln Ala Leu
        355                 360                 365

Glu Thr Val Gln Arg Leu Leu Pro Val Leu Cys Gln Ala His Gly Leu
370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Gly Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Asn Asn Asn
450                 455                 460

Gly Gly Lys Gln Ala Leu Glu Thr Val Gln Arg Leu Leu Pro Val Leu
465                 470                 475                 480

| | | | | | | | | | | | |
|---|---|---|---|---|---|---|---|---|---|---|---|
|Cys|Gln|Asp|His|Gly|Leu|Thr|Pro|Glu|Gln|Val|Val|Ala|Ile|Ala|Ser|
| | | | |485| | | |490| | | |495| | | |

Asn Gly Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
            515                 520                 525

Ala Ser His Asp Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser Asn Ile Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Gly Gly Gly Lys Gln Ala Leu Glu Thr
            595                 600                 605

Val Gln Arg Leu Leu Pro Val Leu Cys Gln Asp His Gly Leu Thr Pro
610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser Asn Gly Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Ile
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
            770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 277
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
gctagcacca tggactacaa agaccatgac ggtgattata aagatcatga catcgattac      60
aaggatgacg atgacaagat ggcccccaag aagaagagga aggtgggcat tcaccgcggg     120
gtacctatgg tggacttgag gacactcggt tattcgcaac agcaacagga gaaaatcaag    180

```
cctaaggtca ggagcaccgt cgcgcaacac cacgaggcgc ttgtgggca tggcttcact    240 catgcgcata ttgtcgcgct ttcacagcac cctgcgcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag aggggagta    480 acagcggtag aggcagtgca cgcctggcgc aatgcgctca ccggggcccc cttgaacctg    540
accccagacc aggtagtcgc aatcgcgaac aataatgggg gaaagcaagc cctggaaacc    600
gtgcaaaggt tgttgccggt cctttgtcaa gaccacggcc ttacaccgga gcaagtcgtg    660
gccattgcaa gcaacatcgg tggcaaacag gctcttgaga cggttcagag acttctccca    720
gttctctgtc aagcccacgg gctgactccc gatcaagttg tagcgattgc gtcgaacatt    780
ggagggaaac aagcattgga gactgtccaa cggctccttc ccgtgttgtg tcaagcccac    840
ggtttgacgc ctgcacaagt ggtcgccatc gcctccaata ttggcggtaa gcaggcgctg    900
gaaacagtac agcgcctgct gcctgtactg tgccaggatc atggactgac cccagaccag    960
gtagtcgcaa tcgcgtcgaa cattggggga aagcaagccc tggaaaccgt gcaaaggttg    1020
ttgccggtcc tttgtcaaga ccacggcctt acaccggagc aagtcgtggc cattgcaagc    1080 aatggggtg gcaaacaggc tcttgagacg gttcagagac ttctcccagt tctctgtcaa    1140
gcccacgggc tgactcccga tcaagttgta gcgattgcga taacaatgg agggaaacaa    1200 gcattggaga ctgtccaacg gctccttccc gtgttgtgtc aagcccacgg tttgacgcct    1260
gcacaagtgg tcgccatcgc ctccaatatt ggcggtaagc aggcgctgga aacagtacag    1320
cgcctgctgc ctgtactgtg ccaggatcat ggactgaccc cagaccaggt agtcgcaatc    1380
gcgtcacatg acgggggaaa gcaagccctg gaaaccgtgc aaaggttgtt gccggtcctt    1440
tgtcaagacc acggcttac accggagcaa gtcgtggcca ttgcaagcaa tgggggtggc    1500
aaacaggctc ttgagacggt tcagagactt ctcccagttc tctgtcaagc ccacgggctg    1560
actcccgatc aagttgtagc gattgcgaat aacaatggag ggaaacaagc attggagact    1620
gtccaacggc tccttcccgt gttgtgtcaa gcccacggtt tgacgcctgc acaagtggtc    1680
gccatcgcct ccaatattgg cggtaagcag gcgctggaaa cagtacagcg cctgctgcct    1740
gtactgtgcc aggatcatgg actgacccca gaccaggtag tcgcaatcgc gtcgaacatt    1800
gggggaaagc aagccctgga aaccgtgcaa aggttgttgc cggtcctttg tcaagaccac    1860
ggccttacac cggagcaagt cgtggccatt gcaagcaatg gggtggcaa acaggctctt    1920 gagacggttc agagacttct cccagttctc tgtcaagccc acgggctgac tcccgatcaa    1980
gttgtagcga ttgcgtcgaa cattggaggg aaacaagcat ggagactgt ccaacggctc    2040 cttcccgtgt tgtgtcaagc ccacggtttg acgcctgcac aagtggtcgc catcgcctcg    2100
aatggcggcg gtaagcaggc gctggaaaca gtacagcgcc tgctgcctgt actgtgccag    2160
gatcatggac tgacacccga acaggtggtc gccattgctt ctaacatcgg aggacggcca    2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc tcatgctccc cgcattgatc aaaagaacca accggcggat tcccgagaga    2400
acttcccatc gagtcgcggg atcc                                          2424
```

<210> SEQ ID NO 278

<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 278

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Asn Asn Asn
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

Asn Ile Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser Asn Ile Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser Asn Gly Gly Gly Lys Gln Ala Leu
        355                 360                 365

Glu Thr Val Gln Arg Leu Leu Pro Val Leu Cys Gln Ala His Gly Leu
```

-continued

```
                370                 375                 380
Thr Pro Asp Gln Val Val Ala Ile Ala Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Ile Gly Gly
                420                 425                 430

Lys Gln Ala Leu Glu Thr Val Gln Arg Leu Leu Pro Val Leu Cys Gln
                435                 440                 445

Asp His Gly Leu Thr Pro Asp Gln Val Val Ala Ile Ala Ser His Asp
                450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Gly Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
                515                 520                 525

Ala Asn Asn Asn Gly Gly Lys Gln Ala Leu Glu Thr Val Gln Arg Leu
                530                 535                 540

Leu Pro Val Leu Cys Gln Ala His Gly Leu Thr Pro Ala Gln Val Val
545                 550                 555                 560

Ala Ile Ala Ser Asn Ile Gly Gly Lys Gln Ala Leu Glu Thr Val Gln
                565                 570                 575

Arg Leu Leu Pro Val Leu Cys Gln Asp His Gly Leu Thr Pro Asp Gln
                580                 585                 590

Val Val Ala Ile Ala Ser Asn Ile Gly Gly Lys Gln Ala Leu Glu Thr
                595                 600                 605

Val Gln Arg Leu Leu Pro Val Leu Cys Gln Asp His Gly Leu Thr Pro
                610                 615                 620

Glu Gln Val Val Ala Ile Ala Ser Asn Gly Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Ile Gly Gly Lys Gln
                660                 665                 670

Ala Leu Glu Thr Val Gln Arg Leu Leu Pro Val Leu Cys Gln Ala His
                675                 680                 685

Gly Leu Thr Pro Ala Gln Val Val Ala Ile Ala Ser Asn Gly Gly Gly
                690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Ile
                725                 730                 735

Gly Gly Arg Pro Ala Leu Glu Ser Ile Val Ala Gln Leu Ser Arg Pro
                740                 745                 750

Asp Pro Ala Leu Ala Ala Leu Thr Asn Asp His Leu Val Ala Leu Ala
                755                 760                 765

Cys Leu Gly Gly Arg Pro Ala Leu Asp Ala Val Lys Lys Gly Leu Pro
                770                 775                 780

His Ala Pro Ala Leu Ile Lys Arg Thr Asn Arg Arg Ile Pro Glu Arg
785                 790                 795                 800
```

Thr Ser His Arg Val Ala Gly Ser
            805

<210> SEQ ID NO 279
<211> LENGTH: 2322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcgcgc | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggggagta | 480 |
| acagcggtag | aggcagtgca | cgcctggcgc | aatgcgctca | ccggggcccc | cttgaacctg | 540 |
| accccagacc | aggtagtcgc | aatcgcgtca | aacggagggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcaa | ataataacgg | tggcaaacag | gctcttgaga | cggttcagag | acttctccca | 720 |
| gttctctgtc | aagcccacgg | gctgactccc | gatcaagttg | tagcgattgc | gtcgcatgac | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccagccatg | atggcggtaa | gcaggcgctg | 900 |
| gaaacagtac | agcgcctgct | gcctgtactg | tgccaggatc | atggactgac | cccagaccag | 960 |
| gtagtcgcaa | tcgcgtcaaa | cggaggggga | aagcaagccc | tggaaaccgt | gcaaaggttg | 1020 |
| ttgccggtcc | tttgtcaaga | ccacggcctt | acaccggagc | aagtcgtggc | cattgcaagc | 1080 |
| aacatcggtg | gcaaacaggc | tcttgagacg | gttcagagac | ttctcccagt | tctctgtcaa | 1140 |
| gcccacgggc | tgactcccga | tcaagttgta | gcgattgcgt | cgcatgacgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | caacaacaac | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgtcacatg | acggggggaaa | gcaagccctg | gaaaccgtgc | aaaggttgtt | gccggtcctt | 1440 |
| tgtcaagacc | acggccttac | accggagcaa | gtcgtggcca | ttgcatccca | cgacggtggc | 1500 |
| aaacaggctc | ttgagacggt | tcagagactt | ctcccagttc | tctgtcaagc | ccacgggctg | 1560 |
| actcccgatc | aagttgtagc | gattgcgtcg | aacattggag | ggaaacaagc | attggagact | 1620 |
| gtccaacggc | tccttcccgt | gttgtgtcaa | gcccacggtt | tgacgcctgc | acaagtggtc | 1680 |
| gccatcgcca | gccatgatgg | cggtaagcag | gcgctgaaa | cagtacagcg | cctgctgcct | 1740 |
| gtactgtgcc | aggatcatgg | actgaccccca | gaccaggtag | tcgcaatcgc | gtcacatgac | 1800 |
| gggggaaagc | aagccctgga | aaccgtgcaa | aggttgttgc | cggtcctttg | tcaagaccac | 1860 |
| ggccttacac | cggagcaagt | cgtggccatt | gcaagcaaca | tcgtggcaa | acaggctctt | 1920 |

```
gagacggttc agagacttct cccagttctc tgtcaagccc acgggctgac tcccgatcaa    1980
gttgtagcga ttgcgaataa caatggaggg aaacaagcat tggagactgt ccaacggctc    2040
cttcccgtgt tgtgtcaagc ccacggtctg acacccgaac aggtggtcgc cattgcttcc    2100
cacgacggag gacggccagc cttggagtcc atcgtagccc aattgtccag gcccgatccc    2160
gcgttggctg cgttaacgaa tgaccatctg gtggcgttgg catgtcttgg tggacgaccc    2220
gcgctcgatg cagtcaaaaa gggtctgcct catgctcccg cattgatcaa aagaaccaac    2280
cggcggattc ccgagagaac ttcccatcga gtcgcgggat cc                       2322
```

<210> SEQ ID NO 280
<211> LENGTH: 774
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 280

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Gly
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser His Asp Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285
```

```
Ala Ile Ala Ser His Asp Gly Gly Lys Gln Ala Leu Glu Thr Val Gln
    290                 295                 300
Arg Leu Leu Pro Val Leu Cys Gln Asp His Gly Leu Thr Pro Asp Gln
305                 310                 315                 320
Val Val Ala Ile Ala Ser Asn Gly Gly Gly Lys Gln Ala Leu Glu Thr
                325                 330                 335
Val Gln Arg Leu Leu Pro Val Leu Cys Gln Asp His Gly Leu Thr Pro
            340                 345                 350
Glu Gln Val Val Ala Ile Ala Ser Asn Ile Gly Gly Lys Gln Ala Leu
        355                 360                 365
Glu Thr Val Gln Arg Leu Leu Pro Val Leu Cys Gln Ala His Gly Leu
    370                 375                 380
Thr Pro Asp Gln Val Val Ala Ile Ala Ser His Asp Gly Gly Lys Gln
385                 390                 395                 400
Ala Leu Glu Thr Val Gln Arg Leu Leu Pro Val Leu Cys Gln Ala His
                405                 410                 415
Gly Leu Thr Pro Ala Gln Val Val Ala Ile Ala Asn Asn Asn Gly Gly
            420                 425                 430
Lys Gln Ala Leu Glu Thr Val Gln Arg Leu Leu Pro Val Leu Cys Gln
        435                 440                 445
Asp His Gly Leu Thr Pro Asp Gln Val Val Ala Ile Ala Ser His Asp
    450                 455                 460
Gly Gly Lys Gln Ala Leu Glu Thr Val Gln Arg Leu Leu Pro Val Leu
465                 470                 475                 480
Cys Gln Asp His Gly Leu Thr Pro Glu Gln Val Val Ala Ile Ala Ser
                485                 490                 495
His Asp Gly Gly Lys Gln Ala Leu Glu Thr Val Gln Arg Leu Leu Pro
            500                 505                 510
Val Leu Cys Gln Ala His Gly Leu Thr Pro Asp Gln Val Val Ala Ile
        515                 520                 525
Ala Ser Asn Ile Gly Gly Lys Gln Ala Leu Glu Thr Val Gln Arg Leu
    530                 535                 540
Leu Pro Val Leu Cys Gln Ala His Gly Leu Thr Pro Ala Gln Val Val
545                 550                 555                 560
Ala Ile Ala Ser His Asp Gly Gly Lys Gln Ala Leu Glu Thr Val Gln
                565                 570                 575
Arg Leu Leu Pro Val Leu Cys Gln Asp His Gly Leu Thr Pro Asp Gln
            580                 585                 590
Val Val Ala Ile Ala Ser His Asp Gly Gly Lys Gln Ala Leu Glu Thr
        595                 600                 605
Val Gln Arg Leu Leu Pro Val Leu Cys Gln Asp His Gly Leu Thr Pro
    610                 615                 620
Glu Gln Val Val Ala Ile Ala Ser Asn Ile Gly Gly Lys Gln Ala Leu
625                 630                 635                 640
Glu Thr Val Gln Arg Leu Leu Pro Val Leu Cys Gln Ala His Gly Leu
                645                 650                 655
Thr Pro Asp Gln Val Val Ala Ile Ala Asn Asn Asn Gly Gly Lys Gln
            660                 665                 670
Ala Leu Glu Thr Val Gln Arg Leu Leu Pro Val Leu Cys Gln Ala His
        675                 680                 685
Gly Leu Thr Pro Glu Gln Val Val Ala Ile Ala Ser His Asp Gly Gly
    690                 695                 700
Arg Pro Ala Leu Glu Ser Ile Val Ala Gln Leu Ser Arg Pro Asp Pro
```

```
            705                 710                 715                 720
Ala Leu Ala Ala Leu Thr Asn Asp His Leu Val Ala Leu Ala Cys Leu
                    725                 730                 735
Gly Gly Arg Pro Ala Leu Asp Ala Val Lys Lys Gly Leu Pro His Ala
                740                 745                 750
Pro Ala Leu Ile Lys Arg Thr Asn Arg Arg Ile Pro Glu Arg Thr Ser
            755                 760                 765
His Arg Val Ala Gly Ser
        770

<210> SEQ ID NO 281
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
```

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgaac | aataatgggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcat | cccacgacgg | tgcaaaacag | gctcttgaga | cggttcagag | acttctccca | 720 |
| gttctctgtc | aagcccacgg | gctgactccc | gatcaagttg | tagcgattgc | gtccaacggt | 780 |
| ggagggaaac | aagcattgga | gactgtccaa | cggctccttc | ccgtgttgtg | tcaagcccac | 840 |
| ggtttgacgc | ctgcacaagt | ggtcgccatc | gcctcgaatg | gcggcggtaa | gcaggcgctg | 900 |
| gaaacagtac | agcgcctgct | gcctgtactg | tgccaggatc | atggactgac | cccagaccag | 960 |
| gtagtcgcaa | tcgcgtcgaa | cattggggga | agcaagccc | tggaaaccgt | gcaaaggttg | 1020 |
| ttgccggtcc | tttgtcaaga | ccacggcctt | acaccggagc | aagtcgtggc | cattgcaaat | 1080 |
| aataacggtg | gcaaacaggc | tcttgagacg | gttcagagac | ttctcccagt | tctctgtcaa | 1140 |
| gcccacgggc | tgactcccga | tcaagttgta | gcgattgcgt | cgaacattgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | cagccatgat | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgaacaata | tgggggaaa | gcaagccctg | aaaccgtgc | aaaggttgtt | gccggtcctt | 1440 |
| tgtcaagacc | acggccttac | accggagcaa | gtcgtggcca | ttgcatccca | cgacggtggc | 1500 |
| aaacaggctc | ttgagacggt | tcagagactt | ctcccagttc | tctgtcaagc | ccacgggctg | 1560 |
| actcccgatc | aagttgtagc | gattgcgtcc | aacggtggag | ggaaacaagc | attggagact | 1620 |

```
gtccaacggc tccttcccgt gttgtgtcaa gcccacggtt tgacgcctgc acaagtggtc   1680
gccatcgcca acaacaacgg cggtaagcag gcgctggaaa cagtacagcg cctgctgcct   1740
gtactgtgcc aggatcatgg actgacccca gaccaggtag tcgcaatcgc gaacaataat   1800
gggggaaagc aagccctgga aaccgtgcaa aggttgttgc cggtcctttg tcaagaccac   1860
ggccttacac cggagcaagt cgtggccatt gcaagcaaca tcggtggcaa acaggctctt   1920
gagacggttc agagacttct cccagttctc tgtcaagccc acgggctgac tcccgatcaa   1980
gttgtagcga ttgcgtccaa cggtggaggg aaacaagcat ggagactgt ccaacggctc    2040
cttcccgtgt tgtgtcaagc ccacggtttg acgcctgcac aagtggtcgc catcgcctcg   2100
aatggcggcg gtaagcaggc gctggaaaca gtacagcgcc tgctgcctgt actgtgccag   2160
gatcatggac tgacacccga acaggtggtc gccattgctt ctaatggggg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 282
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Asn Asn Asn
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
```

```
                210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Ser Asn Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Asn Asn Asn Gly Gly Lys Gln Ala Leu
                355                 360                 365

Glu Thr Val Gln Arg Leu Leu Pro Val Leu Cys Gln Ala His Gly Leu
370                 375                 380

Thr Pro Asp Gln Val Val Ala Ile Ala Ser Asn Ile Gly Gly Lys Gln
385                 390                 395                 400

Ala Leu Glu Thr Val Gln Arg Leu Leu Pro Val Leu Cys Gln Ala His
            405                 410                 415

Gly Leu Thr Pro Ala Gln Val Val Ala Ile Ala Ser His Asp Gly Gly
        420                 425                 430

Lys Gln Ala Leu Glu Thr Val Gln Arg Leu Leu Pro Val Leu Cys Gln
    435                 440                 445

Asp His Gly Leu Thr Pro Asp Gln Val Val Ala Ile Ala Asn Asn Asn
450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

His Asp Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser Asn Gly Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Asn Asn Asn Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Asn Asn Asn Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Ser Asn Ile Gly Gly Lys Gln Ala Leu
625                 630                 635                 640
```

```
Glu Thr Val Gln Arg Leu Leu Pro Val Leu Cys Gln Ala His Gly Leu
                645                 650                 655
Thr Pro Asp Gln Val Val Ala Ile Ala Ser Asn Gly Gly Lys Gln
        660                 665                 670
Ala Leu Glu Thr Val Gln Arg Leu Leu Pro Val Leu Cys Gln Ala His
    675                 680                 685
Gly Leu Thr Pro Ala Gln Val Val Ala Ile Ala Ser Asn Gly Gly Gly
690                 695                 700
Lys Gln Ala Leu Glu Thr Val Gln Arg Leu Leu Pro Val Leu Cys Gln
705                 710                 715                 720
Asp His Gly Leu Thr Pro Glu Gln Val Val Ala Ile Ala Ser Asn Gly
                725                 730                 735
Gly Gly Arg Pro Ala Leu Glu Ser Ile Val Ala Gln Leu Ser Arg Pro
            740                 745                 750
Asp Pro Ala Leu Ala Ala Leu Thr Asn Asp His Leu Val Ala Leu Ala
        755                 760                 765
Cys Leu Gly Gly Arg Pro Ala Leu Asp Ala Val Lys Lys Gly Leu Pro
    770                 775                 780
His Ala Pro Ala Leu Ile Lys Arg Thr Asn Arg Arg Ile Pro Glu Arg
785                 790                 795                 800
Thr Ser His Arg Val Ala Gly Ser
                805
```

<210> SEQ ID NO 283
<211> LENGTH: 2424
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283

```
gctagcacca tggactacaa agaccatgac ggtgattata aagatcatga catcgattac      60
aaggatgacg atgacaagat ggccccccaag aagaagagga aggtgggcat tcaccgcggg    120
gtacctatgg tggacttgag acactcggt tattcgcaac agcaacagga gaaaatcaag      180
cctaaggtca ggagcaccgt cgcgcaacac cacgaggcgc ttgtggggca tggcttcact    240
catgcgcata ttgtcgcgct ttcacagcac cctgcgcgc ttgggacggt ggctgtcaaa     300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag agggggagta    480
acagcggtag aggcagtgca cgcctggcgc aatgcgctca ccggggcccc cttgaacctg    540
accccagacc aggtagtcgc aatcgcgtca acggagggg gaaagcaagc cctggaaacc    600
gtgcaaaggt tgttgccggt cctttgtcaa gaccacggcc ttacaccgga gcaagtcgtg    660
gccattgcat cccacgacgg tggcaaacag gctcttgaga cggttcagag acttctccca    720
gttctctgtc aagcccacgg gctgactccc gatcaagttg tagcgattgc gaataacaat    780
ggagggaaac aagcattgga gactgtccaa cggctccttc ccgtgttgtg tcaagcccac    840
ggtttgacgc ctgcacaagt ggtcgccatc gccaacaaca acggcggtaa gcaggcgctg    900
gaaacagtac agcgcctgct gcctgtactg tgccaggatc atggactgac ccagaccag    960
gtagtcgcaa tcgcgtcaaa cggagggga aagcaagccc tggaaaccgt gcaaaggttg   1020
```

```
ttgccggtcc tttgtcaaga ccacggcctt acaccggagc aagtcgtggc cattgcaaat    1080
aataacggtg caaacaggc tcttgagacg gttcagagac ttctcccagt tctctgtcaa    1140
gcccacgggc tgactcccga tcaagttgta gcgattgcgt cgcatgacgg agggaaacaa    1200
gcattggaga ctgtccaacg gctccttccc gtgttgtgtc aagcccacgg tttgacgcct    1260
gcacaagtgg tcgccatcgc ctcgaatggc ggcggtaagc aggcgctgga acagtacag    1320
cgcctgctgc ctgtactgtg ccaggatcat ggactgaccc cagaccaggt agtcgcaatc    1380
gcgtcaaacg gagggggaaa gcaagccctg gaaaccgtgc aaaggttgtt gccggtcctt    1440
tgtcaagacc acggccttac accggagcaa gtcgtggcca ttgcaagcaa catcggtggc    1500
aaacaggctc ttgagacggt tcagagactt ctcccagttc tctgtcaagc ccacgggctg    1560
actcccgatc aagttgtagc gattgcgtcg catgacggag ggaaacaagc attggagact    1620
gtccaacggc tccttcccgt gttgtgtcaa gcccacggtt tgacgcctgc acaagtggtc    1680
gccatcgcca gccatgatgg cggtaagcag gcgctggaaa cagtacagcg cctgctgcct    1740
gtactgtgcc aggatcatgg actgacccca gaccaggtag tcgcaatcgc gtcaaacgga    1800
gggggaaagc aagccctgga aaccgtgcaa aggttgttgc cggtcctttg tcaagaccac    1860
ggccttacac cggagcaagt cgtggccatt gcaataata cggtggcaa acaggctctt    1920
gagacggttc agagacttct cccagttctc tgtcaagccc acgggctgac tcccgatcaa    1980
gttgtagcga ttgcgaataa caatggaggg aaacaagcat ggagactgt ccaacggctc    2040
cttcccgtgt tgtgtcaagc ccacggtttg acgcctgcac aagtggtcgc catcgcctcg    2100
aatggcggcg gtaagcaggc gctggaaaca gtacagcgcc tgctgcctgt actgtgccag    2160
gatcatggac tgacacccga acaggtggtc gccattgctt ctaatggggg aggacggcca    2220
gccttggagt ccatcgtagc ccaattgtcc aggcccgatc ccgcgttggc tgcgttaacg    2280
aatgaccatc tggtggcgtt ggcatgtctt ggtggacgac ccgcgctcga tgcagtcaaa    2340
aagggtctgc ctcatgctcc cgcattgatc aaaagaacca accggcggat tcccgagaga    2400
acttcccatc gagtcgcggg atcc                                           2424
```

<210> SEQ ID NO 284
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 284

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110
```

-continued

His Glu Ala Ile Val Gly Val Gly Lys Gln Trp Ser Gly Ala Arg Ala
            115                 120                 125

Leu Glu Ala Leu Leu Thr Val Ala Gly Glu Leu Arg Gly Pro Pro Leu
        130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Gly
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Asn Asn Asn Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Asn Asn Asn Gly Gly Lys Gln Ala Leu
        355                 360                 365

Glu Thr Val Gln Arg Leu Leu Pro Val Leu Cys Gln Ala His Gly Leu
    370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Gly Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Ser Asn Gly
    450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Ile Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

| | | | | | | | | | | | | |
|---|---|---|---|---|---|---|---|---|---|---|---|---|
|Ala|Ser|His|Asp|Gly|Gly|Lys|Gln|Ala|Leu|Glu|Thr|Val|Gln|Arg|Leu|
| |530| | | |535| | | |540| | | | | | |

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Gly Gly Lys Gln Ala Leu Glu Thr
        595                 600                 605

Val Gln Arg Leu Leu Pro Val Leu Cys Gln Asp His Gly Leu Thr Pro
610                 615                 620

Glu Gln Val Val Ala Ile Ala Asn Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Asn Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser Asn Gly Gly Gly
690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Gly
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 285
<211> LENGTH: 2322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285
gctagcacca tggactacaa agaccatgac ggtgattata agatcatga catcgattac      60 aaggatgacg atgacaagat ggccccccaag aagaagagga aggtgggcat tcaccgcggg    120
gtacctatgg tggacttgag acactcggt tattcgcaac agcaacagga gaaaatcaag     180
cctaaggtca ggagcaccgt cgcgcaacac cacgaggcgc ttgtgggggca tggcttcact     240 catgcgcata ttgtcgcgct ttcacagcac cctgcggcgc ttgggacggt ggctgtcaaa     300
taccaagata tgattgcggc cctgcccgaa gccacgcacg aggcaattgt aggggtcggt     360
aaacagtggt cgggagcgcg agcacttgag gcgctgctga ctgtggcggg tgagcttagg     420

```
gggcctccgc tccagctcga caccgggcag ctgctgaaga tcgcgaagag aggggagta      480 acagcggtag aggcagtgca cgcctggcgc aatgcgctca ccggggcccc cttgaacctg     540
accccagacc aggtagtcgc aatcgcgtca catgacgggg gaaagcaagc cctggaaacc    600
gtgcaaaggt tgttgccggt cctttgtcaa gaccacggcc ttacaccgga gcaagtcgtg    660
gccattgcat cccacgacgg tggcaaacag gctcttgaga cggttcagag acttctccca    720
gttctctgtc aagcccacgg gctgactccc gatcaagttg tagcgattgc gtcgcatgac    780
ggagggaaac aagcattgga gactgtccaa cggctccttc ccgtgttgtg tcaagcccac    840
ggtttgacgc ctgcacaagt ggtcgccatc gcctccaata ttggcggtaa gcaggcgctg    900
gaaacagtac agcgcctgct gcctgtactg tgccaggatc atggactgac cccagaccag    960
gtagtcgcaa tcgcgaacaa taatggggga aagcaagccc tggaaaccgt gcaaaggttg    1020
ttgccggtcc tttgtcaaga ccacggcctt acaccggagc aagtcgtggc cattgcaagc    1080
aacatcggtg caaacaggc tcttgagacg gttcagagac ttctcccagt tctctgtcaa    1140
gcccacgggc tgactcccga tcaagttgta gcgattgcgt cgcatgacgg agggaaacaa    1200
gcattggaga ctgtccaacg gctccttccc gtgttgtgtc aagcccacgg tttgacgcct    1260
gcacaagtgg tcgccatcgc ctccaatatt ggcggtaagc aggcgctgga aacagtacag    1320
cgcctgctgc ctgtactgtg ccaggatcat ggactgaccc cagaccaggt agtcgcaatc    1380
gcgtcaaacg gaggggaaa gcaagccctg gaaaccgtgc aaaggttgtt gccggtcctt    1440
tgtcaagacc acggccttac accggagcaa gtcgtggcca ttgcaaataa taacggtggc    1500
aaacaggctc ttgagacggt tcagagactt ctcccagttc tctgtcaagc ccacgggctg    1560
actcccgatc aagttgtagc gattgcgtcg acattggag ggaaacaagc attggagact    1620
gtccaacggc tccttcccgt gttgtgtcaa gcccacggtt tgacgcctgc acaagtggtc    1680
gccatcgcca gccatgatgg cggtaagcag gcgctggaaa cagtacagcg cctgctgcct    1740
gtactgtgcc aggatcatgg actgaccca gaccaggtag tcgcaatcgc gtcgaacatt    1800
gggggaaagc aagccctgga accgtgcaa aggttgttgc cggtcctttg tcaagaccac    1860
ggccttacac cggagcaagt cgtggccatt gcaaataata acgtggcaa acaggctctt    1920 gagacggttc agagacttct cccagttctc tgtcaagccc acgggctgac tcccgatcaa    1980
gttgtagcga ttgcgtcgca tgacggaggg aaacaagcat ggagactgt ccaacggctc    2040 cttcccgtgt tgtgtcaagc ccacggtctg acacccgaac aggtggtcgc cattgcttcc    2100
cacgacggag gacggccagc cttggagtcc atcgtagccc aattgtccag gcccgatccc    2160
gcgttggctg cgttaacgaa tgaccatctg gtggcgttgg catgtcttgg tggacgaccc    2220
gcgctcgatg cagtcaaaaa gggtctgcct catgctcccg cattgatcaa agaaccaac    2280 cggcggattc ccgagagaac ttcccatcga gtcgcgggat cc                       2322
```

<210> SEQ ID NO 286
<211> LENGTH: 774
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Ala Ser Thr Met Asp Tyr Lys Asp His Asp Gly Asp Tyr Lys Asp His
1               5                   10                  15

Asp Ile Asp Tyr Lys Asp Asp Asp Asp Lys Met Ala Pro Lys Lys Lys

-continued

```
                    20                  25                  30
Arg Lys Val Gly Ile His Arg Gly Val Pro Met Val Asp Leu Arg Thr
                35                  40                  45
Leu Gly Tyr Ser Gln Gln Gln Glu Lys Ile Lys Pro Lys Val Arg
         50                  55                  60
Ser Thr Val Ala Gln His His Glu Ala Leu Val Gly His Gly Phe Thr
 65                  70                  75                  80
His Ala His Ile Val Ala Leu Ser Gln His Pro Ala Ala Leu Gly Thr
                85                  90                  95
Val Ala Val Lys Tyr Gln Asp Met Ile Ala Ala Leu Pro Glu Ala Thr
                100                 105                 110
His Glu Ala Ile Val Gly Val Gly Lys Gln Trp Ser Gly Ala Arg Ala
                115                 120                 125
Leu Glu Ala Leu Leu Thr Val Ala Gly Glu Leu Arg Gly Pro Pro Leu
                130                 135                 140
Gln Leu Asp Thr Gly Gln Leu Leu Lys Ile Ala Lys Arg Gly Gly Val
145                 150                 155                 160
Thr Ala Val Glu Ala Val His Ala Trp Arg Asn Ala Leu Thr Gly Ala
                165                 170                 175
Pro Leu Asn Leu Thr Pro Asp Gln Val Val Ala Ile Ala Ser His Asp
                180                 185                 190
Gly Gly Lys Gln Ala Leu Glu Thr Val Gln Arg Leu Leu Pro Val Leu
                195                 200                 205
Cys Gln Asp His Gly Leu Thr Pro Glu Gln Val Val Ala Ile Ala Ser
                210                 215                 220
His Asp Gly Gly Lys Gln Ala Leu Glu Thr Val Gln Arg Leu Leu Pro
225                 230                 235                 240
Val Leu Cys Gln Ala His Gly Leu Thr Pro Asp Gln Val Val Ala Ile
                245                 250                 255
Ala Ser His Asp Gly Gly Lys Gln Ala Leu Glu Thr Val Gln Arg Leu
                260                 265                 270
Leu Pro Val Leu Cys Gln Ala His Gly Leu Thr Pro Ala Gln Val Val
                275                 280                 285
Ala Ile Ala Ser Asn Ile Gly Gly Lys Gln Ala Leu Glu Thr Val Gln
                290                 295                 300
Arg Leu Leu Pro Val Leu Cys Gln Asp His Gly Leu Thr Pro Asp Gln
305                 310                 315                 320
Val Val Ala Ile Ala Asn Asn Asn Gly Gly Lys Gln Ala Leu Glu Thr
                325                 330                 335
Val Gln Arg Leu Leu Pro Val Leu Cys Gln Asp His Gly Leu Thr Pro
                340                 345                 350
Glu Gln Val Val Ala Ile Ala Ser Asn Ile Gly Gly Lys Gln Ala Leu
                355                 360                 365
Glu Thr Val Gln Arg Leu Leu Pro Val Leu Cys Gln Ala His Gly Leu
                370                 375                 380
Thr Pro Asp Gln Val Val Ala Ile Ala Ser His Asp Gly Gly Lys Gln
385                 390                 395                 400
Ala Leu Glu Thr Val Gln Arg Leu Leu Pro Val Leu Cys Gln Ala His
                405                 410                 415
Gly Leu Thr Pro Ala Gln Val Val Ala Ile Ala Ser Asn Ile Gly Gly
                420                 425                 430
Lys Gln Ala Leu Glu Thr Val Gln Arg Leu Leu Pro Val Leu Cys Gln
                435                 440                 445
```

Asp His Gly Leu Thr Pro Asp Gln Val Val Ala Ile Ala Ser Asn Gly
        450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser Asn Ile Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Ile Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Asn Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser His Asp Gly Gly Lys Gln
            660                 665                 670

Ala Leu Glu Thr Val Gln Arg Leu Leu Pro Val Leu Cys Gln Ala His
        675                 680                 685

Gly Leu Thr Pro Glu Gln Val Val Ala Ile Ala Ser His Asp Gly Gly
    690                 695                 700

Arg Pro Ala Leu Glu Ser Ile Val Ala Gln Leu Ser Arg Pro Asp Pro
705                 710                 715                 720

Ala Leu Ala Ala Leu Thr Asn Asp His Leu Val Ala Leu Ala Cys Leu
                725                 730                 735

Gly Gly Arg Pro Ala Leu Asp Ala Val Lys Lys Gly Leu Pro His Ala
            740                 745                 750

Pro Ala Leu Ile Lys Arg Thr Asn Arg Arg Ile Pro Glu Arg Thr Ser
        755                 760                 765

His Arg Val Ala Gly Ser
    770

<210> SEQ ID NO 287
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287
gctagcacca tggactacaa agaccatgac ggtgattata agatcatga catcgattac    60 aaggatgacg atgacaagat ggccccccaag aagaagagga aggtgggcat tcaccgcggg   120

```
gtacctatgg tggacttgag acactcggt tattcgcaac agcaacagga gaaaatcaag      180
cctaaggtca ggagcaccgt cgcgcaacac cacgaggcgc ttgtggggca tggcttcact      240
catgcgcata ttgtcgcgct ttcacagcac cctgcggcgc ttgggacggt ggctgtcaaa      300
taccaagata tgattgcggc cctgcccgaa gccacgcacg aggcaattgt aggggtcggt      360
aaacagtggt cgggagcgcg agcacttgag gcgctgctga ctgtggcggg tgagcttagg      420
gggcctccgc tccagctcga caccgggcag ctgctgaaga tcgcgaagag agggggagta      480
acagcggtag aggcagtgca cgcctggcgc aatgcgctca ccggggcccc cttgaacctg      540
accccagacc aggtagtcgc aatcgcgtca catgacgggg gaaagcaagc cctggaaacc      600
gtgcaaaggt tgttgccggt cctttgtcaa gaccacggcc ttacaccgga gcaagtcgtg      660
gccattgcat cccacgacgg tggcaaacag gctcttgaga cggttcagag acttctccca      720
gttctctgtc aagcccacgg gctgactccc gatcaagttg tagcgattgc gtccaacggt      780
ggagggaaac aagcattgga gactgtccaa cggctccttc ccgtgttgtg tcaagcccac      840
ggtttgacgc ctgcacaagt ggtcgccatc gcctcgaatg cggcggtaa gcaggcgctg      900 gaaacagtac agcgcctgct gcctgtactg tgccaggatc atggactgac cccagaccag      960
gtagtcgcaa tcgcgtcaaa cggagggggaa aagcaagccc tggaaccgt gcaaaggttg     1020 ttgccggtcc tttgtcaaga ccacggcctt acaccggagc aagtcgtggc cattgcaagc     1080 aatggggtg gcaaacaggc tcttgagacg gttcagagac ttctcccagt tctctgtcaa     1140
gcccacgggc tgactcccga tcaagttgta gcgattgcga taacaatgg agggaaacaa     1200 gcattggaga ctgtccaacg gctccttccc gtgttgtgtc aagcccacgg tttgacgcct     1260
gcacaagtgg tcgccatcgc ctcgaatggc ggcggtaagc aggcgctgga aacagtacag     1320
cgcctgctgc ctgtactgtg ccaggatcat ggactgaccc cagaccaggt agtcgcaatc     1380
gcgtcaaacg gaggggaaa gcaagccctg aaaccgtgc aaaggttgtt gccggtcctt     1440
tgtcaagacc acggccttac accggagcaa gtcgtggcca ttgcaagcaa tggggtggc     1500 aaacaggctc ttgagacggt tcagagactt ctcccagttc tctgtcaagc ccacgggctg     1560
actcccgatc aagttgtagc gattgcgtcg catgacggag ggaaacaagc attggagact     1620
gtccaacggc tccttcccgt gttgtgtcaa gcccacggtt tgacgcctgc acaagtggtc     1680
gccatcgcct cgaatggcgg cggtaagcag gcgctggaaa cagtacagcg cctgctgcct     1740
gtactgtgcc aggatcatgg actgacccca gaccaggtag tcgcaatcgc gaacaataat     1800 ggggaaagc aagccctgga aaccgtgcaa aggttgttgc cggtcctttg tcaagaccac     1860
ggccttacac cggagcaagt cgtggccatt gcatcccacg acggtggcaa acaggctctt     1920
gagacggttc agagacttct cccagttctc tgtcaagccc acgggctgac tcccgatcaa     1980
gttgtagcga ttgcgtccaa cggtggaggg aaacaagcat tggagactgt ccaacggctc     2040
cttcccgtgt tgtgtcaagc ccacggtttg acgcctgcac aagtggtcgc catcgcctcc     2100
aatattggcg gtaagcaggc gctggaaaca gtacagcgcc tgctgcctgt actgtgccag     2160
gatcatggac tgacacccga acaggtggtc gccattgctt ctaacatcgg aggacggcca     2220
gccttggagt ccatcgtagc ccaattgtcc aggcccgatc ccgcgttggc tgcgttaacg     2280
aatgaccatc tggtggcgtt ggcatgtctt ggtggacgac ccgcgctcga tgcagtcaaa     2340
aagggtctgc ctcatgctcc cgcattgatc aaaagaacca accggcggat tcccgagaga     2400
acttcccatc gagtcgcggg atcc                                            2424
```

<210> SEQ ID NO 288
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Gly Gly Lys Gln Ala Leu Glu Thr Val Gln Arg Leu
            260                 265                 270

Leu Pro Val Leu Cys Gln Ala His Gly Leu Thr Pro Ala Gln Val Val
    275                 280                 285

Ala Ile Ala Ser Asn Gly Gly Lys Gln Ala Leu Glu Thr Val Gln
290                 295                 300

Arg Leu Leu Pro Val Leu Cys Gln Asp His Gly Leu Thr Pro Asp Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser Asn Gly Gly Gly Lys Gln Ala Leu
        355                 360                 365
```

```
Glu Thr Val Gln Arg Leu Leu Pro Val Leu Cys Gln Ala His Gly Leu
    370                 375                 380

Thr Pro Asp Gln Val Val Ala Ile Ala Asn Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Gly Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Ser Asn Gly
    450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Gly Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser His Asp Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser Asn Gly Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Asn Asn Asn Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Gly Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Ser Asn Ile Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser Asn Ile
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
```

Thr Ser His Arg Val Ala Gly Ser
            805

<210> SEQ ID NO 289
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcgcgcg | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgtca | acggaggggg | aaagcaagc | cctggaaacc | 600 |
| gtgcaaaggt | tgttgccggt | cctttgtcaa | gaccacggcc | ttacaccgga | gcaagtcgtg | 660 |
| gccattgcaa | ataataacgg | tggcaaacag | gctcttgaga | cggttcagag | acttctccca | 720 |
| gttctctgtc | aagcccacgg | gctgactccc | gatcaagttg | tagcgattgc | gtcgcatgac | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccagccatg | atggcggtaa | gcaggcgctg | 900 |
| gaaacagtac | agcgcctgct | gcctgtactg | tgccaggatc | atggactgac | cccagaccag | 960 |
| gtagtcgcaa | tcgcgaacaa | taatggggga | aagcaagccc | tggaaaccgt | gcaaaggttg | 1020 |
| ttgccggtcc | tttgtcaaga | ccacggcctt | acaccggagc | aagtcgtggc | cattgcaagc | 1080 |
| aatgggggtg | gcaaacaggc | tcttgagacg | gttcagagac | ttctcccagt | tctctgtcaa | 1140 |
| gcccacgggc | tgactcccga | tcaagttgta | gcgattgcgt | cgcatgacgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | cagccatgat | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgtcacatg | acgggggaaa | gcaagccctg | gaaaccgtgc | aaaggttgtt | gccggtcctt | 1440 |
| tgtcaagacc | acggccttac | accggagcaa | gtcgtggcca | ttgcaagcaa | catcggtggc | 1500 |
| aaacaggctc | ttgagacggt | tcagagactt | ctcccagttc | tctgtcaagc | ccacgggctg | 1560 |
| actcccgatc | aagttgtagc | gattgcgtcg | aacattggag | ggaaacaagc | attggagact | 1620 |
| gtccaacggc | tccttcccgt | gttgtgtcaa | gcccacggtt | tgacgcctgc | acaagtggtc | 1680 |
| gccatcgcca | caacaacgg | cggtaagcag | gcgctggaaa | cagtacagcg | cctgctgcct | 1740 |
| gtactgtgcc | aggatcatgg | actgacccca | gaccaggtag | tcgcaatcgc | gtcacatgac | 1800 |
| ggggggaaagc | aagccctgga | aaccgtgcaa | aggttgttgc | cggtcctttg | tcaagaccac | 1860 |
| ggccttacac | cggagcaagt | cgtggccatt | gcaagcaaca | tcggtggcaa | acaggctctt | 1920 |

```
gagacggttc agagacttct cccagttctc tgtcaagccc acgggctgac tcccgatcaa   1980
gttgtagcga ttgcgtcgaa cattggaggg aaacaagcat tggagactgt ccaacggctc   2040
cttcccgtgt tgtgtcaagc ccacggtttg acgcctgcac aagtggtcgc catcgcctcg   2100
aatggcggcg gtaagcaggc gctggaaaca gtacagcgcc tgctgcctgt actgtgccag   2160
gatcatggac tgacacccga acaggtggtc gccattgcta ataataacgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat cccgagaga   2400 acttcccatc gagtcgcggg atcc                                           2424
```

<210> SEQ ID NO 290
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Gly
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Asn
    210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser His Asp Gly Gly Lys Gln Ala Leu Glu Thr Val Gln Arg Leu
```

```
                260                 265                 270
Leu Pro Val Leu Cys Gln Ala His Gly Leu Thr Pro Ala Gln Val Val
        275                 280                 285

Ala Ile Ala Ser His Asp Gly Lys Gln Ala Leu Glu Thr Val Gln
        290                 295                 300

Arg Leu Leu Pro Val Leu Cys Gln Asp His Gly Leu Thr Pro Asp Gln
305                 310                 315                 320

Val Val Ala Ile Ala Asn Asn Asn Gly Gly Lys Gln Ala Leu Glu Thr
                325                 330                 335

Val Gln Arg Leu Leu Pro Val Leu Cys Gln Asp His Gly Leu Thr Pro
                340                 345                 350

Glu Gln Val Val Ala Ile Ala Ser Asn Gly Gly Lys Gln Ala Leu
            355                 360                 365

Glu Thr Val Gln Arg Leu Leu Pro Val Leu Cys Gln Ala His Gly Leu
            370                 375                 380

Thr Pro Asp Gln Val Val Ala Ile Ala Ser His Asp Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser His Asp Gly Gly
                420                 425                 430

Lys Gln Ala Leu Glu Thr Val Gln Arg Leu Leu Pro Val Leu Cys Gln
            435                 440                 445

Asp His Gly Leu Thr Pro Asp Gln Val Val Ala Ile Ala Ser His Asp
            450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                485                 490                 495

Asn Ile Gly Gly Lys Gln Ala Leu Glu Thr Val Gln Arg Leu Leu Pro
                500                 505                 510

Val Leu Cys Gln Ala His Gly Leu Thr Pro Asp Gln Val Val Ala Ile
            515                 520                 525

Ala Ser Asn Ile Gly Gly Lys Gln Ala Leu Glu Thr Val Gln Arg Leu
            530                 535                 540

Leu Pro Val Leu Cys Gln Ala His Gly Leu Thr Pro Ala Gln Val Val
545                 550                 555                 560

Ala Ile Ala Asn Asn Asn Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
            610                 615                 620

Glu Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Ile Gly Gly Lys Gln
                660                 665                 670

Ala Leu Glu Thr Val Gln Arg Leu Leu Pro Val Leu Cys Gln Ala His
            675                 680                 685
```

Gly Leu Thr Pro Ala Gln Val Val Ala Ile Ala Ser Asn Gly Gly
            690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 291
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | aggggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgaac | aataatgggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcaa | gcaatggggg | tggcaaacag | gctcttgaga | cggttcagag | acttctccca | 720 |
| gttctctgtc | aagcccacgg | gctgactccc | gatcaagttg | tagcgattgc | gtccaacggt | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccagccatg | atggcggtaa | gcaggcgctg | 900 |
| gaaacagtac | agcgcctgct | gcctgtactg | tgccaggatc | atggactgac | ccagaccag | 960 |
| gtagtcgcaa | tcgcgtcgaa | cattggggga | aagcaagccc | tggaaaccgt | gcaaaggttg | 1020 |
| ttgccggtcc | tttgtcaaga | ccacggcctt | acaccggagc | aagtcgtggc | cattgcaagc | 1080 |
| aacatcggtg | gcaaacaggc | tcttgagacg | gttcagagac | ttctcccagt | tctctgtcaa | 1140 |
| gcccacgggc | tgactcccga | tcaagttgta | gcgattgcgt | ccaacggtgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | ctccaatatt | ggcggtaagc | aggcgctgga | aacagtacag | 1320 |

```
cgcctgctgc ctgtactgtg ccaggatcat ggactgaccc cagaccaggt agtcgcaatc   1380
gcgtcaaacg gagggggaaa gcaagccctg gaaaccgtgc aaaggttgtt gccggtcctt   1440
tgtcaagacc acggccttac accggagcaa gtcgtggcca ttgcatccca cgacggtggc   1500
aaacaggctc ttgagacggt tcagagactt ctcccagttc tctgtcaagc ccacgggctg   1560
actcccgatc aagttgtagc gattgcgaat aacaatggag ggaaacaagc attggagact   1620
gtccaacggc tccttcccgt gttgtgtcaa gcccacggtt tgacgcctgc acaagtggtc   1680
gccatcgcct cgaatggcgg cggtaagcag gcgctggaaa cagtacagcg cctgctgcct   1740
gtactgtgcc aggatcatgg actgacccca gaccaggtag tcgcaatcgc gtcacatgac   1800
gggggaaagc aagccctgga accgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac tcccgatcaa   1980
gttgtagcga ttgcgaataa caatggaggg aaacaagcat ggagactgt ccaacggctc   2040 cttcccgtgt tgtgtcaagc ccacggtttg acgcctgcac aagtggtcgc catcgccaac   2100
aacaacggcg gtaagcaggc gctggaaaca gtacagcgcc tgctgcctgt actgtgccag   2160
gatcatggac tgacacccga acaggtggtc gccattgcta ataataacgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 292
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

```
Ala Ser Thr Met Asp Tyr Lys Asp His Asp Gly Asp Tyr Lys Asp His
1               5                  10                  15

Asp Ile Asp Tyr Lys Asp Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160
```

```
Thr Ala Val Glu Ala Val His Ala Trp Arg Asn Ala Leu Thr Gly Ala
            165                 170                 175
Pro Leu Asn Leu Thr Pro Asp Gln Val Val Ala Ile Ala Asn Asn Asn
            180                 185                 190
Gly Gly Lys Gln Ala Leu Glu Thr Val Gln Arg Leu Leu Pro Val Leu
            195                 200                 205
Cys Gln Asp His Gly Leu Thr Pro Glu Gln Val Val Ala Ile Ala Ser
            210                 215                 220
Asn Gly Gly Lys Gln Ala Leu Glu Thr Val Gln Arg Leu Leu Pro
225                 230                 235                 240
Val Leu Cys Gln Ala His Gly Leu Thr Pro Asp Gln Val Val Ala Ile
            245                 250                 255
Ala Ser Asn Gly Gly Lys Gln Ala Leu Glu Thr Val Gln Arg Leu
            260                 265                 270
Leu Pro Val Leu Cys Gln Ala His Gly Leu Thr Pro Ala Gln Val Val
            275                 280                 285
Ala Ile Ala Ser His Asp Gly Gly Lys Gln Ala Leu Glu Thr Val Gln
            290                 295                 300
Arg Leu Leu Pro Val Leu Cys Gln Asp His Gly Leu Thr Pro Asp Gln
305                 310                 315                 320
Val Val Ala Ile Ala Ser Asn Ile Gly Gly Lys Gln Ala Leu Glu Thr
            325                 330                 335
Val Gln Arg Leu Leu Pro Val Leu Cys Gln Asp His Gly Leu Thr Pro
            340                 345                 350
Glu Gln Val Val Ala Ile Ala Ser Asn Ile Gly Gly Lys Gln Ala Leu
            355                 360                 365
Glu Thr Val Gln Arg Leu Leu Pro Val Leu Cys Gln Ala His Gly Leu
            370                 375                 380
Thr Pro Asp Gln Val Val Ala Ile Ala Ser Asn Gly Gly Gly Lys Gln
385                 390                 395                 400
Ala Leu Glu Thr Val Gln Arg Leu Leu Pro Val Leu Cys Gln Ala His
            405                 410                 415
Gly Leu Thr Pro Ala Gln Val Val Ala Ile Ala Ser Asn Ile Gly Gly
            420                 425                 430
Lys Gln Ala Leu Glu Thr Val Gln Arg Leu Leu Pro Val Leu Cys Gln
            435                 440                 445
Asp His Gly Leu Thr Pro Asp Gln Val Val Ala Ile Ala Ser Asn Gly
            450                 455                 460
Gly Gly Lys Gln Ala Leu Glu Thr Val Gln Arg Leu Leu Pro Val Leu
465                 470                 475                 480
Cys Gln Asp His Gly Leu Thr Pro Glu Gln Val Val Ala Ile Ala Ser
            485                 490                 495
His Asp Gly Gly Lys Gln Ala Leu Glu Thr Val Gln Arg Leu Leu Pro
            500                 505                 510
Val Leu Cys Gln Ala His Gly Leu Thr Pro Asp Gln Val Val Ala Ile
            515                 520                 525
Ala Asn Asn Asn Gly Gly Lys Gln Ala Leu Glu Thr Val Gln Arg Leu
            530                 535                 540
Leu Pro Val Leu Cys Gln Ala His Gly Leu Thr Pro Ala Gln Val Val
545                 550                 555                 560
Ala Ile Ala Ser Asn Gly Gly Gly Lys Gln Ala Leu Glu Thr Val Gln
            565                 570                 575
```

```
Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
    610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Asn Asn Asn Gly Gly Lys Gln
            660                 665                 670

Ala Leu Glu Thr Val Gln Arg Leu Leu Pro Val Leu Cys Gln Ala His
            675                 680                 685

Gly Leu Thr Pro Ala Gln Val Val Ala Ile Ala Asn Asn Asn Gly Gly
            690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
    770                 775                 780

His Ala Pro Ala Leu Ile Lys Arg Thr Asn Arg Arg Ile Pro Glu Arg
785                 790                 795                 800

Thr Ser His Arg Val Ala Gly Ser
                805

<210> SEQ ID NO 293
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
gctagcacca tggactacaa agaccatgac ggtgattata aagatcatga catcgattac    60
aaggatgacg atgacaagat ggcccccaag aagaagagga aggtgggcat tcaccgcggg   120
gtacctatgg tggacttgag acactcggt tattcgcaac agcaacagga gaaaatcaag    180
cctaaggtca ggagcaccgt cgcgcaacac cacgaggcgc ttgtggggca tggcttcact   240
catgcgcata ttgtcgcgct ttcacagcac cctgcggcgc ttgggacggt ggctgtcaaa   300
taccaagata tgattgcggc cctgcccgaa gccacgcacg aggcaattgt aggggtcggt   360
aaacagtggt cgggagcgcg agcacttgag gcgctgctga ctgtggcggg tgagcttagg   420
gggcctccgc tccagctcga caccgggcag ctgctgaaga tcgcgaagag aggggggagta  480 acagcggtag aggcagtgca cgcctggcgc aatgcgctca ccggggcccc cttgaacctg   540
accccagacc aggtagtcgc aatcgcgaac aataatgggg gaaagcaagc cctggaaacc   600
gtgcaaaggt tgttgccggt cctttgtcaa gaccacggcc ttacaccgga gcaagtcgtg   660
gccattgcaa ataataacgg tggcaaacag gctcttgaga cggttcagag acttctccca   720
```

```
gttctctgtc aagcccacgg gctgactccc gatcaagttg tagcgattgc gaataacaat      780
ggagggaaac aagcattgga gactgtccaa cggctccttc ccgtgttgtg tcaagcccac      840
ggtttgacgc ctgcacaagt ggtcgccatc gccagccatg atggcggtaa gcaggcgctg      900
gaaacagtac agcgcctgct gcctgtactg tgccaggatc atggactgac cccagaccag      960
gtagtcgcaa tcgcgtcaca tgacggggga agcaagccc tggaaaccgt gcaaaggttg     1020
ttgccggtcc tttgtcaaga ccacggcctt acaccggagc aagtcgtggc cattgcaagc     1080
aacatcggtg caaacaggc tcttgagacg gttcagagac ttctcccagt tctctgtcaa     1140
gcccacgggc tgactcccga tcaagttgta gcgattgcga ataacaatgg agggaaacaa     1200
gcattggaga ctgtccaacg gctccttccc gtgttgtgtc aagcccacgg tttgacgcct     1260
gcacaagtgg tcgccatcgc ctccaatatt ggcggtaagc aggcgctgga aacagtacag     1320
cgcctgctgc ctgtactgtg ccaggatcat ggactgaccc cagaccaggt agtcgcaatc     1380
gcgaacaata tgggggaaa gcaagccctg gaaaccgtgc aaaggttgtt gccggtcctt     1440
tgtcaagacc acggccttac accggagcaa gtcgtggcca ttgcaagcaa catcggtggc     1500
aaacaggctc ttgagacggt tcagagactt ctcccagttc tctgtcaagc ccacgggctg     1560
actcccgatc aagttgtagc gattgcgtcc aacggtggag ggaaacaagc attggagact     1620
gtccaacggt ccttcccgt gttgtgtcaa gcccacggtt tgacgcctgc acaagtggtc     1680
gccatcgcca caacaacgg cggtaagcag gcgctggaaa cagtacagcg cctgctgcct     1740
gtactgtgcc aggatcatgg actgacccca gaccaggtag tcgcaatcgc gaacaataat     1800
gggggaaagc aagccctgga accgtgcaa aggttgttgc cggtcctttg tcaagaccac     1860
ggccttacac cggagcaagt cgtggccatt gcatcccacg acggtggcaa acaggctctt     1920
gagacggttc agagacttct cccagttctc tgtcaagccc acgggctgac tcccgatcaa     1980
gttgtagcga ttgcgaataa caatggaggg aaacaagcat ggagactgt ccaacggctc     2040
cttcccgtgt tgtgtcaagc ccacggtttg acgcctgcac aagtggtcgc catcgccaac     2100
aacaacggcg gtaagcaggc gctggaaaca gtacagcgcc tgctgcctgt actgtgccag     2160
gatcatggac tgacacccga acaggtggtc gccattgctt cccacgacgg aggacggcca     2220
gccttggagt ccatcgtagc ccaattgtcc aggcccgatc ccgcgttggc tgcgttaacg     2280
aatgaccatc tggtggcgtt ggcatgtctt ggtggacgac ccgcgctcga tgcagtcaaa     2340
aagggtctgc ctcatgctcc cgcattgatc aaaagaacca accggcggat tcccgagaga     2400
acttcccatc gagtcgcggg atcc                                           2424
```

<210> SEQ ID NO 294
<211> LENGTH: 808
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
                20                  25                  30

Arg Lys Val Gly Ile His Arg Gly Val Pro Met Val Asp Leu Arg Thr
            35                  40                  45

```
Leu Gly Tyr Ser Gln Gln Gln Glu Lys Ile Lys Pro Lys Val Arg
        50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
                115                 120                 125

Leu Glu Ala Leu Leu Thr Val Ala Gly Glu Leu Arg Gly Pro Pro Leu
130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Asn Asn Asn
                180                 185                 190

Gly Gly Lys Gln Ala Leu Glu Thr Val Gln Arg Leu Leu Pro Val Leu
                195                 200                 205

Cys Gln Asp His Gly Leu Thr Pro Glu Gln Val Val Ala Ile Ala Asn
210                 215                 220

Asn Asn Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Asn Asn Asn Gly Gly Lys Gln Ala Leu Glu Thr Val Gln Arg Leu
                260                 265                 270

Leu Pro Val Leu Cys Gln Ala His Gly Leu Thr Pro Ala Gln Val Val
                275                 280                 285

Ala Ile Ala Ser His Asp Gly Gly Lys Gln Ala Leu Glu Thr Val Gln
                290                 295                 300

Arg Leu Leu Pro Val Leu Cys Gln Asp His Gly Leu Thr Pro Asp Gln
305                 310                 315                 320

Val Val Ala Ile Ala Ser His Asp Gly Gly Lys Gln Ala Leu Glu Thr
                325                 330                 335

Val Gln Arg Leu Leu Pro Val Leu Cys Gln Asp His Gly Leu Thr Pro
                340                 345                 350

Glu Gln Val Val Ala Ile Ala Ser Asn Ile Gly Gly Lys Gln Ala Leu
                355                 360                 365

Glu Thr Val Gln Arg Leu Leu Pro Val Leu Cys Gln Ala His Gly Leu
370                 375                 380

Thr Pro Asp Gln Val Val Ala Ile Ala Asn Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Ile Gly Gly
                420                 425                 430

Lys Gln Ala Leu Glu Thr Val Gln Arg Leu Leu Pro Val Leu Cys Gln
                435                 440                 445

Asp His Gly Leu Thr Pro Asp Gln Val Val Ala Ile Ala Asn Asn Asn
450                 455                 460

Gly Gly Lys Gln Ala Leu Glu Thr Val Gln Arg Leu Leu Pro Val Leu
```

| | | | | | | | 465 | | | 470 | | | 475 | | | 480 | |
|---|---|---|---|---|---|---|---|---|---|---|---|---|---|---|---|---|---|

Cys Gln Asp His Gly Leu Thr Pro Glu Gln Val Val Ala Ile Ala Ser
                          485                        490                    495

Asn Ile Gly Gly Lys Gln Ala Leu Glu Thr Val Gln Arg Leu Leu Pro
                    500                      505                        510

Val Leu Cys Gln Ala His Gly Leu Thr Pro Asp Gln Val Val Ala Ile
                515                      520                    525

Ala Ser Asn Gly Gly Lys Gln Ala Leu Glu Thr Val Gln Arg Leu
530                         535                      540

Leu Pro Val Leu Cys Gln Ala His Gly Leu Thr Pro Ala Gln Val Val
545                 550                  555                560

Ala Ile Ala Asn Asn Asn Gly Gly Lys Gln Ala Leu Glu Thr Val Gln
                565                      570                    575

Arg Leu Leu Pro Val Leu Cys Gln Asp His Gly Leu Thr Pro Asp Gln
                  580                      585                    590

Val Val Ala Ile Ala Asn Asn Asn Gly Gly Lys Gln Ala Leu Glu Thr
              595                      600                    605

Val Gln Arg Leu Leu Pro Val Leu Cys Gln Asp His Gly Leu Thr Pro
610                 615                  620

Glu Gln Val Val Ala Ile Ala Ser His Asp Gly Gly Lys Gln Ala Leu
625                 630                  635                640

Glu Thr Val Gln Arg Leu Leu Pro Val Leu Cys Gln Ala His Gly Leu
                645                      650                    655

Thr Pro Asp Gln Val Val Ala Ile Ala Asn Asn Asn Gly Gly Lys Gln
              660                      665                    670

Ala Leu Glu Thr Val Gln Arg Leu Leu Pro Val Leu Cys Gln Ala His
              675                      680                    685

Gly Leu Thr Pro Ala Gln Val Val Ala Ile Ala Asn Asn Asn Gly Gly
              690                      695                    700

Lys Gln Ala Leu Glu Thr Val Gln Arg Leu Leu Pro Val Leu Cys Gln
705                 710                  715                720

Asp His Gly Leu Thr Pro Glu Gln Val Val Ala Ile Ala Ser His Asp
                725                      730                    735

Gly Gly Arg Pro Ala Leu Glu Ser Ile Val Ala Gln Leu Ser Arg Pro
              740                      745                    750

Asp Pro Ala Leu Ala Ala Leu Thr Asn Asp His Leu Val Ala Leu Ala
              755                      760                    765

Cys Leu Gly Gly Arg Pro Ala Leu Asp Ala Val Lys Lys Gly Leu Pro
770                 775                  780

His Ala Pro Ala Leu Ile Lys Arg Thr Asn Arg Arg Ile Pro Glu Arg
785                 790                  795                800

Thr Ser His Arg Val Ala Gly Ser
              805

<210> SEQ ID NO 295
<211> LENGTH: 2424
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 295
gctagcacca tggactacaa agaccatgac ggtgattata aagatcatga catcgattac    60
aaggatgacg atgacaagat ggccccccaag aagaagagga aggtgggcat tcaccgcggg   120

```
gtacctatgg tggacttgag gacactcggt tattcgcaac agcaacagga gaaaatcaag    180
cctaaggtca ggagcaccgt cgcgcaacac cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag agggggagta    480
acagcggtag aggcagtgca cgcctggcgc aatgcgctca ccggggcccc cttgaacctg    540
accccagacc aggtagtcgc aatcgcgtcg aacattgggg gaaagcaagc cctggaaacc    600
gtgcaaaggt tgttgccggt cctttgtcaa gaccacggcc ttacaccgga gcaagtcgtg    660
gccattgcaa gcaacatcgg tggcaaacag gctcttgaga cggttcagag acttctccca    720
gttctctgtc aagcccacgg gctgactccc gatcaagttg tagcgattgc gtcgaacatt    780
ggagggaaac aagcattgga gactgtccaa cggctccttc ccgtgttgtg tcaagcccac    840
ggtttgacgc ctgcacaagt ggtcgccatc gccaacaaca cggcggtaa gcaggcgctg    900 gaaacagtac agcgcctgct gcctgtactg tgccaggatc atggactgac cccagaccag    960
gtagtcgcaa tcgcgtcaca tgacggggga aagcaagccc tggaaaccgt gcaaaggttg   1020
ttgccggtcc tttgtcaaga ccacggcctt acaccggagc aagtcgtggc cattgcatcc   1080
cacgacggtg gcaaacaggc tcttgagacg gttcagagac ttctcccagt tctctgtcaa   1140
gcccacgggc tgactcccga tcaagttgta gcgattgcga ataacaatgg agggaaacaa   1200
gcattggaga ctgtccaacg gctccttccc gtgttgtgtc aagcccacgg tttgacgcct   1260
gcacaagtgg tcgccatcgc cagccatgat ggcggtaagc aggcgctgga aacagtacag   1320
cgcctgctgc ctgtactgtg ccaggatcat ggactgaccc cagaccaggt agtcgcaatc   1380
gcgtcacatg acggggggaaa gcaagccctg gaaaccgtgc aaaggttgtt gccggtcctt   1440
tgtcaagacc acggccttac accggagcaa gtcgtggcca ttgcaaataa taacggtggc   1500
aaacaggctc ttgagacggt tcagagactt ctcccagttc tctgtcaagc ccacgggctg   1560
actcccgatc aagttgtagc gattgcgtcg catgacggag gaaacaagc attggagact   1620 gtccaacggc tccttcccgt gttgtgtcaa gcccacggtt tgacgcctgc acaagtggtc   1680
gccatcgcca gccatgatgg cggtaagcag gcgctggaaa cagtacagcg cctgctgcct   1740
gtactgtgcc aggatcatgg actgacccca gaccaggtag tcgcaatcgc gtcaaacgga   1800
gggggaaagc aagccctgga aaccgtgcaa aggttgttgc cggtcctttg tcaagaccac   1860
ggccttacac cggagcaagt cgtggccatt gcatcccacg acggtggcaa acaggctctt   1920
gagacggttc agagacttct cccagttctc tgtcaagccc acgggctgac tcccgatcaa   1980
gttgtagcga ttgcgtcgca tgacggaggg aaacaagcat ggagactgt ccaacggctc   2040 cttcccgtgt tgtgtcaagc ccacggtttg acgcctgcac aagtggtcgc catcgccaac   2100
aacaacggcg gtaagcaggc gctggaaaca gtacagcgcc tgctgcctgt actgtgccag   2160
gatcatggac tgacacccga acaggtggtc gccattgcta ataataacgg aggacggcca   2220
gccttggagt ccatcgtagc ccaattgtcc aggcccgatc ccgcgttggc tgcgttaacg   2280
aatgaccatc tggtggcgtt ggcatgtctt ggtggacgac ccgcgctcga tgcagtcaaa   2340
aagggtctgc ctcatgctcc cgcattgatc aaaagaacca accggcggat tcccgagaga   2400
acttcccatc gagtcgcggg atcc                                          2424
```

<210> SEQ ID NO 296
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 296

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys
            20                  25                  30

Arg Lys Val Gly Ile His Arg Gly Val Pro Met Val Asp Leu Arg Thr
            35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Ser Asn Ile
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

Asn Ile Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255

Ala Ser Asn Ile Gly Gly Lys Gln Ala Leu Glu Thr Val Gln Arg Leu
            260                 265                 270

Leu Pro Val Leu Cys Gln Ala His Gly Leu Thr Pro Ala Gln Val Val
        275                 280                 285

Ala Ile Ala Asn Asn Asn Gly Gly Lys Gln Ala Leu Glu Thr Val Gln
    290                 295                 300

Arg Leu Leu Pro Val Leu Cys Gln Asp His Gly Leu Thr Pro Asp Gln
305                 310                 315                 320

Val Val Ala Ile Ala Ser His Asp Gly Gly Lys Gln Ala Leu Glu Thr
                325                 330                 335

Val Gln Arg Leu Leu Pro Val Leu Cys Gln Asp His Gly Leu Thr Pro
            340                 345                 350

Glu Gln Val Val Ala Ile Ala Ser His Asp Gly Gly Lys Gln Ala Leu
        355                 360                 365
```

-continued

```
Glu Thr Val Gln Arg Leu Leu Pro Val Leu Cys Gln Ala His Gly Leu
    370                 375                 380

Thr Pro Asp Gln Val Val Ala Ile Ala Asn Asn Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser His Asp Gly Gly
            420                 425                 430

Lys Gln Ala Leu Glu Thr Val Gln Arg Leu Leu Pro Val Leu Cys Gln
        435                 440                 445

Asp His Gly Leu Thr Pro Asp Gln Val Val Ala Ile Ala Ser His Asp
    450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Asn
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Asp Gln Val Val Ala Ile
        515                 520                 525

Ala Ser His Asp Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                565                 570                 575

Arg Leu Leu Pro Val Leu Cys Gln Asp His Gly Leu Thr Pro Asp Gln
            580                 585                 590

Val Val Ala Ile Ala Ser Asn Gly Gly Lys Gln Ala Leu Glu Thr
        595                 600                 605

Val Gln Arg Leu Leu Pro Val Leu Cys Gln Asp His Gly Leu Thr Pro
    610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser His Asp Gly Gly Lys Gln
            660                 665                 670

Ala Leu Glu Thr Val Gln Arg Leu Leu Pro Val Leu Cys Gln Ala His
        675                 680                 685

Gly Leu Thr Pro Ala Gln Val Val Ala Ile Ala Asn Asn Gly Gly
    690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Asn Asn Asn
                725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Leu Asp Ala Val Lys Lys Gly Leu Pro
    770                 775                 780
```

His Ala Pro Ala Leu Ile Lys Arg Thr Asn Arg Arg Ile Pro Glu Arg
785                 790                 795                 800

Thr Ser His Arg Val Ala Gly Ser
            805

<210> SEQ ID NO 297
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297

| | | | | | |
|---|---|---|---|---|---|
| gctagcacca | tggactacaa | agaccatgac | ggtgattata | aagatcatga | catcgattac | 60 |
| aaggatgacg | atgacaagat | ggcccccaag | aagaagagga | aggtgggcat | tcaccgcggg | 120 |
| gtacctatgg | tggacttgag | gacactcggt | tattcgcaac | agcaacagga | gaaaatcaag | 180 |
| cctaaggtca | ggagcaccgt | cgcgcaacac | cacgaggcgc | ttgtggggca | tggcttcact | 240 |
| catgcgcata | ttgtcgcgct | ttcacagcac | cctgcggcgc | ttgggacggt | ggctgtcaaa | 300 |
| taccaagata | tgattgcggc | cctgcccgaa | gccacgcacg | aggcaattgt | agggtcggt | 360 |
| aaacagtggt | cgggagcgcg | agcacttgag | gcgctgctga | ctgtggcggg | tgagcttagg | 420 |
| gggcctccgc | tccagctcga | caccgggcag | ctgctgaaga | tcgcgaagag | aggggagta | 480 |
| acagcggtag | aggcagtgca | cgcctggcgc | aatgcgctca | ccggggcccc | cttgaacctg | 540 |
| accccagacc | aggtagtcgc | aatcgcgaac | aataatgggg | gaaagcaagc | cctggaaacc | 600 |
| gtgcaaaggt | tgttgccggt | cctttgtcaa | gaccacggcc | ttacaccgga | gcaagtcgtg | 660 |
| gccattgcat | cccacgacgg | tgcaaaacag | gctcttgaga | cggttcagag | acttctccca | 720 |
| gttctctgtc | aagcccacgg | gctgactccc | gatcaagttg | tagcgattgc | gtcgcatgac | 780 |
| ggagggaaac | aagcattgga | gactgtccaa | cggctccttc | ccgtgttgtg | tcaagcccac | 840 |
| ggtttgacgc | ctgcacaagt | ggtcgccatc | gccagccatg | atggcggtaa | gcaggcgctg | 900 |
| gaaacagtac | agcgcctgct | gcctgtactg | tgccaggatc | atggactgac | cccagaccag | 960 |
| gtagtcgcaa | tcgcgtcgaa | cattggggga | aagcaagccc | tggaaaccgt | gcaaaggttg | 1020 |
| ttgccggtcc | tttgtcaaga | ccacggcctt | acaccggagc | aagtcgtggc | cattgcaaat | 1080 |
| aataacggtg | gcaaacaggc | tcttgagacg | gttcagagac | ttctcccagt | tctctgtcaa | 1140 |
| gcccacgggc | tgactcccga | tcaagttgta | gcgattgcgt | cgaacattgg | agggaaacaa | 1200 |
| gcattggaga | ctgtccaacg | gctccttccc | gtgttgtgtc | aagcccacgg | tttgacgcct | 1260 |
| gcacaagtgg | tcgccatcgc | cagccatgat | ggcggtaagc | aggcgctgga | aacagtacag | 1320 |
| cgcctgctgc | ctgtactgtg | ccaggatcat | ggactgaccc | cagaccaggt | agtcgcaatc | 1380 |
| gcgtcgaaca | ttgggggaaa | gcaagccctg | gaaaccgtgc | aaaggttgtt | gccggtcctt | 1440 |
| tgtcaagacc | acggccttac | accggagcaa | gtcgtggcca | ttgcaagcaa | catcggtggc | 1500 |
| aaacaggctc | ttgagacggt | tcagagactt | ctcccagttc | tctgtcaagc | ccacgggctg | 1560 |
| actcccgatc | aagttgtagc | gattgcgaat | aacaatggag | ggaaacaagc | attggagact | 1620 |
| gtccaacggc | tccttcccgt | gttgtgtcaa | gcccacggtt | tgacgcctgc | acaagtggtc | 1680 |
| gccatcgcca | gccatgatgg | cggtaagcag | gcgctggaaa | cagtacagcg | cctgctgcct | 1740 |
| gtactgtgcc | aggatcatgg | actgacccca | gaccaggtag | tcgcaatcgc | gtcgaacatt | 1800 |
| gggggaaagc | aagccctgga | aaccgtgcaa | aggttgttgc | cggtcctttg | tcaagaccac | 1860 |

-continued

```
ggccttacac cggagcaagt cgtggccatt gcaagcaaca tcggtggcaa acaggctctt      1920
gagacggttc agagacttct cccagttctc tgtcaagccc acgggctgac tcccgatcaa      1980
gttgtagcga ttgcgtcgca tgacggaggg aaacaagcat tggagactgt ccaacggctc      2040
cttcccgtgt tgtgtcaagc ccacggtttg acgcctgcac aagtggtcgc catcgcctcc      2100
aatattggcg gtaagcaggc gctggaaaca gtacagcgcc tgctgcctgt actgtgccag      2160
gatcatggac tgcacccga acaggtggtc gccattgctt ctaatggggg aggacggcca      2220
gccttggagt ccatcgtagc ccaattgtcc aggcccgatc cgcgttggc tgcgttaacg       2280 aatgaccatc tggtggcgtt ggcatgtctt ggtggacgac ccgcgctcga tgcagtcaaa      2340
aagggtctgc ctcatgctcc cgcattgatc aaaagaacca accggcggat tcccgagaga      2400
acttcccatc gagtcgcggg atcc                                             2424
```

<210> SEQ ID NO 298
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 298

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Asp Gln Val Val Ala Ile Ala Asn Asn Asn
            180                 185                 190

Gly Gly Lys Gln Ala Leu Glu Thr Val Gln Arg Leu Leu Pro Val Leu
        195                 200                 205

Cys Gln Asp His Gly Leu Thr Pro Glu Gln Val Val Ala Ile Ala Ser
    210                 215                 220

His Asp Gly Gly Lys Gln Ala Leu Glu Thr Val Gln Arg Leu Leu Pro
225                 230                 235                 240

Val Leu Cys Gln Ala His Gly Leu Thr Pro Asp Gln Val Val Ala Ile
                245                 250                 255
```

-continued

Ala Ser His Asp Gly Gly Lys Gln Ala Leu Glu Thr Val Gln Arg Leu
         260                 265                 270

Leu Pro Val Leu Cys Gln Ala His Gly Leu Thr Pro Ala Gln Val Val
     275                 280                 285

Ala Ile Ala Ser His Asp Gly Gly Lys Gln Ala Leu Glu Thr Val Gln
 290                 295                 300

Arg Leu Leu Pro Val Leu Cys Gln Asp His Gly Leu Thr Pro Asp Gln
305                 310                 315                 320

Val Val Ala Ile Ala Ser Asn Ile Gly Gly Lys Gln Ala Leu Glu Thr
                 325                 330                 335

Val Gln Arg Leu Leu Pro Val Leu Cys Gln Asp His Gly Leu Thr Pro
             340                 345                 350

Glu Gln Val Val Ala Ile Ala Asn Asn Asn Gly Gly Lys Gln Ala Leu
         355                 360                 365

Glu Thr Val Gln Arg Leu Leu Pro Val Leu Cys Gln Ala His Gly Leu
     370                 375                 380

Thr Pro Asp Gln Val Val Ala Ile Ala Ser Asn Ile Gly Gly Lys Gln
385                 390                 395                 400

Ala Leu Glu Thr Val Gln Arg Leu Leu Pro Val Leu Cys Gln Ala His
                 405                 410                 415

Gly Leu Thr Pro Ala Gln Val Val Ala Ile Ala Ser His Asp Gly Gly
             420                 425                 430

Lys Gln Ala Leu Glu Thr Val Gln Arg Leu Leu Pro Val Leu Cys Gln
         435                 440                 445

Asp His Gly Leu Thr Pro Asp Gln Val Val Ala Ile Ala Ser Asn Ile
     450                 455                 460

Gly Gly Lys Gln Ala Leu Glu Thr Val Gln Arg Leu Leu Pro Val Leu
465                 470                 475                 480

Cys Gln Asp His Gly Leu Thr Pro Glu Gln Val Val Ala Ile Ala Ser
                 485                 490                 495

Asn Ile Gly Gly Lys Gln Ala Leu Glu Thr Val Gln Arg Leu Leu Pro
             500                 505                 510

Val Leu Cys Gln Ala His Gly Leu Thr Pro Asp Gln Val Val Ala Ile
         515                 520                 525

Ala Asn Asn Asn Gly Gly Lys Gln Ala Leu Glu Thr Val Gln Arg Leu
     530                 535                 540

Leu Pro Val Leu Cys Gln Ala His Gly Leu Thr Pro Ala Gln Val Val
545                 550                 555                 560

Ala Ile Ala Ser His Asp Gly Gly Lys Gln Ala Leu Glu Thr Val Gln
                 565                 570                 575

Arg Leu Leu Pro Val Leu Cys Gln Asp His Gly Leu Thr Pro Asp Gln
             580                 585                 590

Val Val Ala Ile Ala Ser Asn Ile Gly Gly Lys Gln Ala Leu Glu Thr
         595                 600                 605

Val Gln Arg Leu Leu Pro Val Leu Cys Gln Asp His Gly Leu Thr Pro
     610                 615                 620

Glu Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
                 645                 650                 655

Thr Pro Asp Gln Val Val Ala Ile Ala Ser His Asp Gly Gly Lys Gln
             660                 665                 670

Ala Leu Glu Thr Val Gln Arg Leu Leu Pro Val Leu Cys Gln Ala His

```
            675                 680                 685
Gly Leu Thr Pro Ala Gln Val Val Ala Ile Ala Ser Asn Ile Gly Gly
        690                 695                 700
Lys Gln Ala Leu Glu Thr Val Gln Arg Leu Leu Pro Val Leu Cys Gln
705                 710                 715                 720
Asp His Gly Leu Thr Pro Glu Gln Val Val Ala Ile Ala Ser Asn Gly
                725                 730                 735
Gly Gly Arg Pro Ala Leu Glu Ser Ile Val Ala Gln Leu Ser Arg Pro
            740                 745                 750
Asp Pro Ala Leu Ala Ala Leu Thr Asn Asp His Leu Val Ala Leu Ala
                755                 760                 765
Cys Leu Gly Gly Arg Pro Ala Leu Asp Ala Val Lys Lys Gly Leu Pro
        770                 775                 780
His Ala Pro Ala Leu Ile Lys Arg Thr Asn Arg Arg Ile Pro Glu Arg
785                 790                 795                 800
Thr Ser His Arg Val Ala Gly Ser
                805

<210> SEQ ID NO 299
<211> LENGTH: 2424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299
gctagcacca tggactacaa agaccatgac ggtgattata aagatcatga catcgattac     60
aaggatgacg atgacaagat ggccccccaag aagaagagga aggtgggcat tcaccgcggg    120
gtacctatgg tggacttgag acactcggt tattcgcaac agcaacagga gaaaatcaag     180
cctaaggtca ggagcaccgt cgcgcaaaca cacgaggcgc ttgtggggca tggcttcact    240
catgcgcata ttgtcgcgct ttcacagcac cctgcggcgc ttgggacggt ggctgtcaaa    300
taccaagata tgattgcggc cctgcccgaa gccacgcacg aggcaattgt aggggtcggt    360
aaacagtggt cgggagcgcg agcacttgag gcgctgctga ctgtggcggg tgagcttagg    420
gggcctccgc tccagctcga caccgggcag ctgctgaaga tcgcgaagag aggggagta    480 acagcggtag aggcagtgca cgcctggcgc aatgcgctca ccggggcccc cttgaacctg    540
accccagacc aggtagtcgc aatcgcgtca catgacgggg aaagcaagc cctggaaacc     600 gtgcaaaggt tgttgccggt cctttgtcaa gaccacggcc ttacaccgga gcaagtcgtg    660
gccattgcat cccacgacgg tggcaaacag gctcttgaga cggttcagag acttctccca    720
gttctctgtc aagcccacgg gctgactccc gatcaagttg tagcgattgc gtcgcatgac    780
ggagggaaac aagcattgga gactgtccaa cggctccttc ccgtgttgtg tcaagcccac    840
ggtttgacgc ctgcacaagt ggtcgccatc gccagccatg atggcggtaa gcaggcgctg    900
gaaacagtac agcgcctgct gcctgtactg tgccaggatc atggactgac ccagaccag    960 gtagtcgcaa tcgcgaacaa taatggggga aagcaagccc tggaaaccgt gcaaaggttg   1020
ttgccggtcc tttgtcaaga ccacggcctt acaccggagc agtcgtggc cattgcatcc   1080 cacgacggtg gcaaacaggc tcttgagacg gttcagagac ttctcccagt tctctgtcaa   1140
gcccacgggc tgactcccga tcaagttgta gcgattgcga taacaatgg agggaaacaa   1200 gcattggaga ctgtccaacg gctccttccc gtgttgtgtc aagcccacgg tttgacgcct   1260
```

-continued

```
gcacaagtgg tcgccatcgc caacaacaac ggcggtaagc aggcgctgga acagtacag     1320 cgcctgctgc ctgtactgtg ccaggatcat ggactgaccc cagaccaggt agtcgcaatc     1380
gcgtcacatg acggggggaaa gcaagccctg gaaaccgtgc aaaggttgtt gccggtcctt     1440
tgtcaagacc acggccttac accggagcaa gtcgtggcca ttgcaagcaa tgggggtggc     1500
aaacaggctc ttgagacggt tcagagactt ctcccagttc tctgtcaagc ccacgggctg     1560
actcccgatc aagttgtagc gattgcgtcg catgacggag ggaaacaagc attggagact     1620
gtccaacggc tccttcccgt gttgtgtcaa gcccacggtt tgacgcctgc acaagtggtc     1680
gccatcgcca gccatgatgg cggtaagcag gcgctggaaa cagtacagcg cctgctgcct     1740
gtactgtgcc aggatcatgg actgacccca gaccaggtag tcgcaatcgc gtcacatgac     1800
gggggaaagc aagccctgga aaccgtgcaa aggttgttgc cggtcctttg tcaagaccac     1860
ggccttacac cggagcaagt cgtggccatt gcatcccacg acggtggcaa acaggctctt     1920
gagacggttc agagacttct cccagttctc tgtcaagccc acgggctgac tcccgatcaa     1980
gttgtagcga ttgcgaataa caatggaggg aaacaagcat ggagactgt ccaacggctc     2040 cttcccgtgt tgtgtcaagc ccacggtttg acgcctgcac aagtggtcgc atcgccagc     2100 catgatggcg gtaagcaggc gctggaaaca gtacagcgcc tgctgcctgt actgtgccag     2160
gatcatggac tgacacccga acaggtggtc gccattgctt cccacgacgg aggacggcca     2220
gccttggagt ccatcgtagc ccaattgtcc aggcccgatc ccgcgttggc tgcgttaacg     2280
aatgaccatc tggtggcgtt ggcatgtctt ggtggacgac ccgcgctcga tgcagtcaaa     2340
aagggtctgc ctcatgctcc cgcattgatc aaaagaacca accggcggat tcccgagaga     2400
acttcccatc gagtcgcggg atcc                                            2424
```

<210> SEQ ID NO 300
<211> LENGTH: 808
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

```
Ala Ser Thr Met Asp Tyr Lys Asp His Asp Gly Asp Tyr Lys Asp His
1               5                   10                  15

Asp Ile Asp Tyr Lys Asp Asp Asp Lys Met Ala Pro Lys Lys Lys
            20                  25                  30

Arg Lys Val Gly Ile His Arg Gly Val Pro Met Val Asp Leu Arg Thr
        35                  40                  45

Leu Gly Tyr Ser Gln Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
```

```
                145                 150                 155                 160
            Thr Ala Val Glu Ala Val His Ala Trp Arg Asn Ala Leu Thr Gly Ala
                            165                 170                 175
            Pro Leu Asn Leu Thr Pro Asp Gln Val Val Ala Ile Ala Ser His Asp
                            180                 185                 190
            Gly Gly Lys Gln Ala Leu Glu Thr Val Gln Arg Leu Leu Pro Val Leu
                            195                 200                 205
            Cys Gln Asp His Gly Leu Thr Pro Glu Gln Val Val Ala Ile Ala Ser
                            210                 215                 220
            His Asp Gly Gly Lys Gln Ala Leu Glu Thr Val Gln Arg Leu Leu Pro
            225                 230                 235                 240
            Val Leu Cys Gln Ala His Gly Leu Thr Pro Asp Gln Val Val Ala Ile
                            245                 250                 255
            Ala Ser His Asp Gly Gly Lys Gln Ala Leu Glu Thr Val Gln Arg Leu
                            260                 265                 270
            Leu Pro Val Leu Cys Gln Ala His Gly Leu Thr Pro Ala Gln Val Val
                            275                 280                 285
            Ala Ile Ala Ser His Asp Gly Gly Lys Gln Ala Leu Glu Thr Val Gln
                            290                 295                 300
            Arg Leu Leu Pro Val Leu Cys Gln Asp His Gly Leu Thr Pro Asp Gln
            305                 310                 315                 320
            Val Val Ala Ile Ala Asn Asn Asn Gly Gly Lys Gln Ala Leu Glu Thr
                            325                 330                 335
            Val Gln Arg Leu Leu Pro Val Leu Cys Gln Asp His Gly Leu Thr Pro
                            340                 345                 350
            Glu Gln Val Val Ala Ile Ala Ser His Asp Gly Gly Lys Gln Ala Leu
                            355                 360                 365
            Glu Thr Val Gln Arg Leu Leu Pro Val Leu Cys Gln Ala His Gly Leu
                            370                 375                 380
            Thr Pro Asp Gln Val Val Ala Ile Ala Asn Asn Asn Gly Gly Lys Gln
            385                 390                 395                 400
            Ala Leu Glu Thr Val Gln Arg Leu Leu Pro Val Leu Cys Gln Ala His
                            405                 410                 415
            Gly Leu Thr Pro Ala Gln Val Val Ala Ile Ala Asn Asn Asn Gly Gly
                            420                 425                 430
            Lys Gln Ala Leu Glu Thr Val Gln Arg Leu Leu Pro Val Leu Cys Gln
                            435                 440                 445
            Asp His Gly Leu Thr Pro Asp Gln Val Val Ala Ile Ala Ser His Asp
            450                 455                 460
            Gly Gly Lys Gln Ala Leu Glu Thr Val Gln Arg Leu Leu Pro Val Leu
            465                 470                 475                 480
            Cys Gln Asp His Gly Leu Thr Pro Glu Gln Val Val Ala Ile Ala Ser
                            485                 490                 495
            Asn Gly Gly Lys Gln Ala Leu Glu Thr Val Gln Arg Leu Leu Pro
                            500                 505                 510
            Val Leu Cys Gln Ala His Gly Leu Thr Pro Asp Gln Val Val Ala Ile
                            515                 520                 525
            Ala Ser His Asp Gly Gly Lys Gln Ala Leu Glu Thr Val Gln Arg Leu
                            530                 535                 540
            Leu Pro Val Leu Cys Gln Ala His Gly Leu Thr Pro Ala Gln Val Val
            545                 550                 555                 560
            Ala Ile Ala Ser His Asp Gly Gly Lys Gln Ala Leu Glu Thr Val Gln
                            565                 570                 575
```

Arg Leu Leu Pro Val Leu Cys Gln Asp His Gly Leu Thr Pro Asp Gln
            580                 585                 590

Val Val Ala Ile Ala Ser His Asp Gly Gly Lys Gln Ala Leu Glu Thr
            595                 600                 605

Val Gln Arg Leu Leu Pro Val Leu Cys Gln Asp His Gly Leu Thr Pro
            610                 615                 620

Glu Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
            645                 650                 655

Thr Pro Asp Gln Val Val Ala Ile Ala Asn Asn Asn Gly Gly Lys Gln
            660                 665                 670

Ala Leu Glu Thr Val Gln Arg Leu Leu Pro Val Leu Cys Gln Ala His
            675                 680                 685

Gly Leu Thr Pro Ala Gln Val Val Ala Ile Ala Ser His Asp Gly Gly
            690                 695                 700

Lys Gln Ala Leu Glu Thr Val Gln Arg Leu Leu Pro Val Leu Cys Gln
705                 710                 715                 720

Asp His Gly Leu Thr Pro Glu Gln Val Val Ala Ile Ala Ser His Asp
            725                 730                 735

Gly Gly Arg Pro Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Leu Asp Ala Val Lys Lys Gly Leu Pro
            770                 775                 780

His Ala Pro Ala Leu Ile Lys Arg Thr Asn Arg Arg Ile Pro Glu Arg
785                 790                 795                 800

Thr Ser His Arg Val Ala Gly Ser
            805

<210> SEQ ID NO 301
<211> LENGTH: 88
<212> TYPE: DNA
<213> ORGANISM: Homo sapiens

<400> SEQUENCE: 301
ttcccagact cagtgggaag agctccctca ccatgagtag cgctatgttg gtgacttgcc    60
tcccggaccc cagcagcagc ttccgtga                                      88

<210> SEQ ID NO 302
<211> LENGTH: 80
<212> TYPE: DNA
<213> ORGANISM: Homo sapiens

<400> SEQUENCE: 302
ttcccagact cagtgggaag agctccctca ccatgagtag cgctatgttg cctcccggac    60
cccagcagca gcttccgtga                                               80

<210> SEQ ID NO 303
<211> LENGTH: 57
<212> TYPE: DNA
<213> ORGANISM: Homo sapiens

<400> SEQUENCE: 303
ttcccagact cagtgggaag agctccctca cccggacccc agcagcagct tccgtga       57

<210> SEQ ID NO 304
<211> LENGTH: 88
<212> TYPE: DNA
<213> ORGANISM: Homo sapiens

<400> SEQUENCE: 304
ggcgtgggag agtggatttc cgaagctgac agatgggtat tctttgacgg ggggtagggg    60
cggaacctga gaggcgtaag gcgttgtg                                       88

<210> SEQ ID NO 305
<211> LENGTH: 71
<212> TYPE: DNA
<213> ORGANISM: Homo sapiens

<400> SEQUENCE: 305
ggcgtgggag agtggatttc cgaagctgac agatgggtag ggcggaacc tgagaggcgt     60 aaggcgttgt g                                                         71

<210> SEQ ID NO 306
<211> LENGTH: 65
<212> TYPE: DNA
<213> ORGANISM: Homo sapiens

<400> SEQUENCE: 306
ggcgtgggag agtggatttc cgaagctgac agagggcgg aacctgagag gcgtaaggcg     60
ttgtg                                                                65

<210> SEQ ID NO 307
<211> LENGTH: 61
<212> TYPE: DNA
<213> ORGANISM: Homo sapiens

<400> SEQUENCE: 307
ggcgtgggag agtggatttc cgaagctgac agatggaacc tgagaggcgt aaggcgttgt    60
g                                                                    61

<210> SEQ ID NO 308
<211> LENGTH: 50
<212> TYPE: DNA
<213> ORGANISM: Homo sapiens

<400> SEQUENCE: 308
ggcgtgggag agtggatttc cgaagctgac agatgggta aggcgttgtg                50

<210> SEQ ID NO 309
<211> LENGTH: 49
<212> TYPE: DNA
<213> ORGANISM: Homo sapiens

<400> SEQUENCE: 309
ggcgtgggag agtggatttc cgaagctgac agatgggtaa ggcgttgtg                49

<210> SEQ ID NO 310
<211> LENGTH: 60
<212> TYPE: DNA
<213> ORGANISM: Homo sapiens

<400> SEQUENCE: 310
agtggatttc cgaagctgac agatgtggaa gaagaggctg gtcatgaggt caggagttcc    60

<210> SEQ ID NO 311
<211> LENGTH: 60
<212> TYPE: DNA
<213> ORGANISM: Homo sapiens

<400> SEQUENCE: 311
cgctcaggag gccttcaccc tctgctctgg gtaaaggaac tggaatatgc cttgaggggg    60

<210> SEQ ID NO 312
<211> LENGTH: 88
<212> TYPE: DNA
<213> ORGANISM: Homo sapiens

<400> SEQUENCE: 312
cctgagctgt ggtttggagg agccgtgtgt tggaagaaga tggcagatcc aggaatgatg    60 agtcttttg gcgaggatgg gaatattt                                        88

<210> SEQ ID NO 313
<211> LENGTH: 79
<212> TYPE: DNA
<213> ORGANISM: Homo sapiens

<400> SEQUENCE: 313
cctgagctgt ggtttggagg agccgtgtgt tggaagaaga tcagaatgat gagtcttttt    60
ggcgaggatg ggaatattt                                                 79

<210> SEQ ID NO 314
<211> LENGTH: 78
<212> TYPE: DNA
<213> ORGANISM: Homo sapiens

<400> SEQUENCE: 314
cctgagctgt ggtttggagg agccgtgtgt tggaagaaga tggaatgatg agtcttttg    60 gcgaggatgg gaatattt                                                  78

<210> SEQ ID NO 315
<211> LENGTH: 60
<212> TYPE: DNA
<213> ORGANISM: Homo sapiens

<400> SEQUENCE: 315
cctgagctgt ggtttggagg agccgtgtgt tggaagaaga tggcgaggat gggaatattt    60

<210> SEQ ID NO 316
<211> LENGTH: 41
<212> TYPE: DNA
<213> ORGANISM: Homo sapiens

<400> SEQUENCE: 316
taaagaaata tggaatgaca taaaatccag taaatcctat g                        41

<210> SEQ ID NO 317
<211> LENGTH: 88
<212> TYPE: DNA
<213> ORGANISM: Homo sapiens

<400> SEQUENCE: 317
gagggggggg aagatggcgg acgtgcttag cgtcctgcga cagtacaaca tccagaagaa    60
ggagattgtg gtgaagggag acgaagtg                                       88

<210> SEQ ID NO 318
<211> LENGTH: 81
<212> TYPE: DNA
<213> ORGANISM: Homo sapiens

<400> SEQUENCE: 318
gagggggggg aagatggcgg acgtgcttag cgtcctgcga cagtacagaa gaaggagatt    60
gtggtgaagg gagacgaagt g                                              81

<210> SEQ ID NO 319
<211> LENGTH: 80
<212> TYPE: DNA
<213> ORGANISM: Homo sapiens

<400> SEQUENCE: 319
gagggggggg aagatggcgg acgtgcttag cgtcctgcga cagtacaacg aaggagattg    60
tggtgaaggg agacgaagtg                                                80

<210> SEQ ID NO 320
<211> LENGTH: 80
<212> TYPE: DNA
<213> ORGANISM: Homo sapiens

<400> SEQUENCE: 320
gagggggggg aagatggcgg acgtgcttag cgtcctgcga catccagaag aaggagattg    60
tggtgaaggg agacgaagtg                                                80

<210> SEQ ID NO 321
<211> LENGTH: 76
<212> TYPE: DNA
<213> ORGANISM: Homo sapiens

<400> SEQUENCE: 321
gagggggggg aagatggcgg acgtgcttag cgtcctgcga cagaagaagg agattgtggt    60
gaagggagac gaagtg                                                    76

<210> SEQ ID NO 322
<211> LENGTH: 68
<212> TYPE: DNA
<213> ORGANISM: Homo sapiens

<400> SEQUENCE: 322
gagggggggg aagatggcgg acgtgcttag cgtcctgcga cagtattgtg gtgaagggag    60
acgaagtg                                                             68

<210> SEQ ID NO 323
<211> LENGTH: 66
<212> TYPE: DNA
<213> ORGANISM: Homo sapiens

<400> SEQUENCE: 323
gagggggggg aagatggcgg acgtgcttag cgtcctgcga cagttgtggt gaagggagac    60
gaagtg                                                               66

<210> SEQ ID NO 324
<211> LENGTH: 88
<212> TYPE: DNA
<213> ORGANISM: Homo sapiens

<400> SEQUENCE: 324

```
gagggggggg aagatggcgg acgtgcttag cgtcctgcga cagtacaaca acatccagaa    60
gaaggagatt gtggtgaagg gagacgaa                                       88

<210> SEQ ID NO 325
<211> LENGTH: 56
<212> TYPE: DNA
<213> ORGANISM: Homo sapiens

<400> SEQUENCE: 325
agggcgaggc gacaagagaa gaaggaggca ggattgtggt gaagggagac gaagtg        56

<210> SEQ ID NO 326
<211> LENGTH: 88
<212> TYPE: DNA
<213> ORGANISM: Homo sapiens

<400> SEQUENCE: 326
ttagtatttt gaagttaata tcacaatgag ttcaggctta tggagccaag aaaaagtcac    60
ttcaccctac tgggaagagc ggattttt                                       88

<210> SEQ ID NO 327
<211> LENGTH: 79
<212> TYPE: DNA
<213> ORGANISM: Homo sapiens

<400> SEQUENCE: 327
ttagtatttt gaagttaata tcacaatgag ttcaggctta tggaaagtca cttcacccta    60
ctgggaagag cggattttt                                                 79

<210> SEQ ID NO 328
<211> LENGTH: 59
<212> TYPE: DNA
<213> ORGANISM: Homo sapiens

<400> SEQUENCE: 328
ttagtatttt gaagttaata tcacaagtca cttcacccta ctgggaagag cggattttt     59

<210> SEQ ID NO 329
<211> LENGTH: 47
<212> TYPE: DNA
<213> ORGANISM: Homo sapiens

<400> SEQUENCE: 329
ttagtatttt gaagttaata tcaccctact gggaagagcg gattttt                  47

<210> SEQ ID NO 330
<211> LENGTH: 40
<212> TYPE: DNA
<213> ORGANISM: Homo sapiens

<400> SEQUENCE: 330
ttagtatttt gaagttccct actgggaaga gcggattttt                          40

<210> SEQ ID NO 331
<211> LENGTH: 36
<212> TYPE: DNA
<213> ORGANISM: Homo sapiens

<400> SEQUENCE: 331
taagtcactt caccctactg ggaagagcgg attttt                              36
```

```
<210> SEQ ID NO 332
<211> LENGTH: 33
<212> TYPE: DNA
<213> ORGANISM: Homo sapiens

<400> SEQUENCE: 332
ttagtatttc cctactggga agagcggatt ttt                          33

<210> SEQ ID NO 333
<211> LENGTH: 31
<212> TYPE: DNA
<213> ORGANISM: Homo sapiens

<400> SEQUENCE: 333 ttagtattttt gaagttgaag agcggatttt t                           31

<210> SEQ ID NO 334
<211> LENGTH: 22
<212> TYPE: DNA
<213> ORGANISM: Homo sapiens

<400> SEQUENCE: 334 ttagtattttt gaacggattt tt                                     22

<210> SEQ ID NO 335
<211> LENGTH: 4
<212> TYPE: DNA
<213> ORGANISM: Homo sapiens

<400> SEQUENCE: 335 ttag                                                          4

<210> SEQ ID NO 336
<211> LENGTH: 116
<212> TYPE: DNA
<213> ORGANISM: Homo sapiens

<400> SEQUENCE: 336
taatatcaca atgagttctc aggggcacac caggccccag gggaacacca ggccctgggt    60
aagcatgcag tcccaggtgg acatcaggtg ccaggaggaa aagtcacttc acccta       116

<210> SEQ ID NO 337
<211> LENGTH: 88
<212> TYPE: DNA
<213> ORGANISM: Homo sapiens

<400> SEQUENCE: 337
tccacacagc ctgtggcaca gacgtggagg gccactgagc cccgctaccc gccccacagc    60
ctttcctacc cagtgcagat cgcccgga                                     88

<210> SEQ ID NO 338
<211> LENGTH: 87
<212> TYPE: DNA
<213> ORGANISM: Homo sapiens

<400> SEQUENCE: 338
tccacacagc ctgtggcaca gacgtggagg gccactgagc cccgctaccg ccccacagcc    60
tttcctaccc agtgcagatc gcccgga                                      87

<210> SEQ ID NO 339
<211> LENGTH: 81
<212> TYPE: DNA
```

```
<213> ORGANISM: Homo sapiens

<400> SEQUENCE: 339
tccacacagc ctgtggcaca gacgtggagg gccactgagc ccgccccac agcctttcct    60 acccagtgca gatcgcccgg a                                             81

<210> SEQ ID NO 340
<211> LENGTH: 76
<212> TYPE: DNA
<213> ORGANISM: Homo sapiens

<400> SEQUENCE: 340
tccacacagc ctgtggcaca gacgtggagg gccactgagc ccacagcct ttcctaccca    60 gtgcagatcg cccgga                                                   76

<210> SEQ ID NO 341
<211> LENGTH: 19
<212> TYPE: DNA
<213> ORGANISM: Homo sapiens

<400> SEQUENCE: 341
tccacacaga tcgcccgga                                                19

<210> SEQ ID NO 342
<211> LENGTH: 38
<212> TYPE: DNA
<213> ORGANISM: Homo sapiens

<400> SEQUENCE: 342
cccccaccac ctttcctacc cagtgcagat cgcccgga                           38

<210> SEQ ID NO 343
<211> LENGTH: 33
<212> TYPE: DNA
<213> ORGANISM: Homo sapiens

<400> SEQUENCE: 343
gcttattgcg gcctttctcc tgggagccag gct                                33

<210> SEQ ID NO 344
<211> LENGTH: 88
<212> TYPE: DNA
<213> ORGANISM: Homo sapiens

<400> SEQUENCE: 344
tccacacagc ctgtggcaca gacgtggagg gccactgagc ccgctacca cccgccccac    60 agcctttcct acccagtgca gatcgccc                                      88

<210> SEQ ID NO 345
<211> LENGTH: 88
<212> TYPE: DNA
<213> ORGANISM: Homo sapiens

<400> SEQUENCE: 345
tttctcttac aggcaaatgt tctgaaaaag actctgcatg ggaatggcct gccttacgat    60
gacagaaatg gagggaacat ccacctct                                      88

<210> SEQ ID NO 346
<211> LENGTH: 84
<212> TYPE: DNA
<213> ORGANISM: Homo sapiens
```

```
<400> SEQUENCE: 346
tttctcttac aggcaaatgt tctgaaaaag actctgcatg gggcctgcct tacgatgaca    60
gaaatggagg gaacatccac ctct                                          84

<210> SEQ ID NO 347
<211> LENGTH: 83
<212> TYPE: DNA
<213> ORGANISM: Homo sapiens

<400> SEQUENCE: 347
tttctcttac aggcaaatgt tctgaaaaag actctgcatg ggcctgcctt acgatgacag    60
aaatggaggg aacatccacc tct                                           83

<210> SEQ ID NO 348
<211> LENGTH: 82
<212> TYPE: DNA
<213> ORGANISM: Homo sapiens

<400> SEQUENCE: 348
tttctcttac aggcaaatgt tctgaaaaag actctgcatg ggaatggtta cgatgacaga    60
aatggaggga acatccacct ct                                            82

<210> SEQ ID NO 349
<211> LENGTH: 80
<212> TYPE: DNA
<213> ORGANISM: Homo sapiens

<400> SEQUENCE: 349
tttctcttac aggcaaatgt tctgaaaaag actctgcagc ctgccttacg atgacagaaa    60
tggagggaac atccacctct                                               80

<210> SEQ ID NO 350
<211> LENGTH: 73
<212> TYPE: DNA
<213> ORGANISM: Homo sapiens

<400> SEQUENCE: 350
tttctcttac aggcaaatgt tctgaaaaag actctgcctt acgatgacag aaatggaggg    60
aacatccacc tct                                                      73

<210> SEQ ID NO 351
<211> LENGTH: 64
<212> TYPE: DNA
<213> ORGANISM: Homo sapiens

<400> SEQUENCE: 351
tttctcttac aggcaaatgt tctgaaaaag actctgcatg ggaatggagg gaacatccac    60
ctct                                                                64

<210> SEQ ID NO 352
<211> LENGTH: 63
<212> TYPE: DNA
<213> ORGANISM: Homo sapiens

<400> SEQUENCE: 352
tttctcttac aggcaaatgt tctgaaaaag acgatgacag aaatggaggg aacatccacc    60
tct                                                                 63
```

<210> SEQ ID NO 353
<211> LENGTH: 62
<212> TYPE: DNA
<213> ORGANISM: Homo sapiens

<400> SEQUENCE: 353
tttctcttac aggcaaatgt tctgaaaaag actctgcaga aatggaggga acatccacct    60
ct    62

<210> SEQ ID NO 354
<211> LENGTH: 35
<212> TYPE: DNA
<213> ORGANISM: Homo sapiens

<400> SEQUENCE: 354
tttctcttac aggcatggag ggaacatcca cctct    35

<210> SEQ ID NO 355
<211> LENGTH: 34
<212> TYPE: DNA
<213> ORGANISM: Homo sapiens

<400> SEQUENCE: 355
tacgatgaca gaaatggagg gaacatccac ctct    34

<210> SEQ ID NO 356
<211> LENGTH: 84
<212> TYPE: DNA
<213> ORGANISM: Homo sapiens

<400> SEQUENCE: 356
tttctcttac aggcaaatgt tctgaaaaag actctgcatg gagtaagtct tacgatgaca    60
gaaatggagg gaacatccac ctct    84

<210> SEQ ID NO 357
<211> LENGTH: 60
<212> TYPE: DNA
<213> ORGANISM: Homo sapiens

<400> SEQUENCE: 357
cggaggtttg ctgcaaacag agaaatttcg atgacagaaa tggagggaac atccacctct    60

<210> SEQ ID NO 358
<211> LENGTH: 88
<212> TYPE: DNA
<213> ORGANISM: Homo sapiens

<400> SEQUENCE: 358
cgggaggcga gccgatgccg agctgctcca cgtccaccat gccgggcatg atctgcaaga    60
acccagacct cgagtttgac tcgctaca    88

<210> SEQ ID NO 359
<211> LENGTH: 82
<212> TYPE: DNA
<213> ORGANISM: Homo sapiens

<400> SEQUENCE: 359
cgggaggcga gccgatgccg agctgctcca cgtcctcccc catgatctgc aggaacccag    60
acctcgagtt tgactcgcta ca    82

```
<210> SEQ ID NO 360
<211> LENGTH: 80
<212> TYPE: DNA
<213> ORGANISM: Homo sapiens

<400> SEQUENCE: 360
cgggaggcga gccgatgccg agctgctcca cgtccgggca tgatctgcaa gaacccagac      60
ctcgagtttg actcgctaca                                                  80

<210> SEQ ID NO 361
<211> LENGTH: 78
<212> TYPE: DNA
<213> ORGANISM: Homo sapiens

<400> SEQUENCE: 361
cgggaggcga gccgatgccg agctgctcca cgtccaccat atctgcaaga acccagacct      60
cgagtttgac tcgctaca                                                    78

<210> SEQ ID NO 362
<211> LENGTH: 77
<212> TYPE: DNA
<213> ORGANISM: Homo sapiens

<400> SEQUENCE: 362
cgggaggcga gccgatgccg agctgctcca cgtccaccat gctgcaagaa cccagacctc      60
gagtttgact cgctaca                                                     77

<210> SEQ ID NO 363
<211> LENGTH: 76
<212> TYPE: DNA
<213> ORGANISM: Homo sapiens

<400> SEQUENCE: 363
cgggaggcga gccgatgccg agctgctcca cgtccatgat ctgcaagaac ccagacctcg      60
agtttgactc gctaca                                                      76

<210> SEQ ID NO 364
<211> LENGTH: 70
<212> TYPE: DNA
<213> ORGANISM: Homo sapiens

<400> SEQUENCE: 364
cgggaggcga gccgatgccg agctgctcca cgtccaccaa gaacccagac ctcgagtttg      60
actcgctaca                                                             70

<210> SEQ ID NO 365
<211> LENGTH: 69
<212> TYPE: DNA
<213> ORGANISM: Homo sapiens

<400> SEQUENCE: 365
cgggaggcga gccgatgccg agctgctcat gatctgcaag aacccagacc tcgagtttga      60
ctcgctaca                                                              69

<210> SEQ ID NO 366
<211> LENGTH: 46
<212> TYPE: DNA
<213> ORGANISM: Homo sapiens

<400> SEQUENCE: 366
```
aaggaagcac ccccggtctt aaagacctcg agtttgactc gctaca                46

<210> SEQ ID NO 367
<211> LENGTH: 60
<212> TYPE: DNA
<213> ORGANISM: Homo sapiens

<400> SEQUENCE: 367
agtgttggag gtcggcgccg gcccccgggc atgatctgca agaacccaga cctcgagttt   60

<210> SEQ ID NO 368
<211> LENGTH: 34
<212> TYPE: DNA
<213> ORGANISM: Homo sapiens

<400> SEQUENCE: 368
aaggaagcac ccccggtatt aaacgaagat gact                              34

<210> SEQ ID NO 369
<211> LENGTH: 222
<212> TYPE: DNA
<213> ORGANISM: Homo sapiens

<400> SEQUENCE: 369
gaggcgagcc gatgcccgtg atctgggtca cggctgctcc agcttggagg agaggcggct   60 ctccggcga ccctcctcgc gcgggcgccc ctgccattcc cgggaacagg ggctcagccc  120
cctttgttag tgctcgtatg tcttggcctg gggagcattt tggaggcagt gctaggggca  180
gagaggtcct gtttccccca agtcttgatc tgcaagaacc ca                    222

<210> SEQ ID NO 370
<211> LENGTH: 88
<212> TYPE: DNA
<213> ORGANISM: Homo sapiens

<400> SEQUENCE: 370
tgcacgtcgg ccccagccct gaggagccgg accgatgtgg aaactgctgc ccgccgcggg   60
cccggcagga ggtaagggca gaagggaa                                     88

<210> SEQ ID NO 371
<211> LENGTH: 83
<212> TYPE: DNA
<213> ORGANISM: Homo sapiens

<400> SEQUENCE: 371
tgcacgtcgg ccccagccct gaggagccgg accgatgtgg gctgcccgcc gcgggcccgg   60
caggaggtaa gggcagaagg gaa                                          83

<210> SEQ ID NO 372
<211> LENGTH: 81
<212> TYPE: DNA
<213> ORGANISM: Homo sapiens

<400> SEQUENCE: 372
tgcacgtcgg ccccagccct gaggagccgg accgatgtgc tgcccgccgc gggcccggca   60
ggaggtaagg gcagaaggga a                                            81

<210> SEQ ID NO 373
<211> LENGTH: 75
<212> TYPE: DNA
<213> ORGANISM: Homo sapiens

<400> SEQUENCE: 373
tgcacgtcgg ccccagccct gaggagccgg accgatgtgg aaactggccc ggcaggaggt    60
aagggcagaa gggaa    75

<210> SEQ ID NO 374
<211> LENGTH: 71
<212> TYPE: DNA
<213> ORGANISM: Homo sapiens

<400> SEQUENCE: 374
tgcacgtcgg ccccagccct gaggagccgg accgatgtgg actcccggca ggaggtaagg    60
gcagaaggga a    71

<210> SEQ ID NO 375
<211> LENGTH: 69
<212> TYPE: DNA
<213> ORGANISM: Homo sapiens

<400> SEQUENCE: 375
tgcacgtcgg ccccagccct gaggagccgg accgatgtgg acccggcagg aggtaagggc    60
agaagggaa    69

<210> SEQ ID NO 376
<211> LENGTH: 60
<212> TYPE: DNA
<213> ORGANISM: Homo sapiens

<400> SEQUENCE: 376
tgcacgtcgg ccccagccct gaggagccgg accgatgcag gaggtaaggg cagaagggaa    60

<210> SEQ ID NO 377
<211> LENGTH: 60
<212> TYPE: DNA
<213> ORGANISM: Homo sapiens

<400> SEQUENCE: 377
tgcacgtcgg ccccagccct gaggagccgg accgatgtgg aaagtaaggg cagaagggaa    60

<210> SEQ ID NO 378
<211> LENGTH: 58
<212> TYPE: DNA
<213> ORGANISM: Homo sapiens

<400> SEQUENCE: 378
tgcacgtcgg ccccagccct gaggagccgg accggcagga ggtaagggca gaagggaa    58

<210> SEQ ID NO 379
<211> LENGTH: 53
<212> TYPE: DNA
<213> ORGANISM: Homo sapiens

<400> SEQUENCE: 379
tgcacgtcgg ccccagccct gaggagccgg aaggaggtaa gggcagaagg gaa    53

<210> SEQ ID NO 380
<211> LENGTH: 49
<212> TYPE: DNA
<213> ORGANISM: Homo sapiens

<400> SEQUENCE: 380

```
tgcacgtcgg ccccgcgcgg gcccggcagg aggtaagggc agaagggaa        49
```

<210> SEQ ID NO 381
<211> LENGTH: 43
<212> TYPE: DNA
<213> ORGANISM: Homo sapiens

<400> SEQUENCE: 381

```
tgcacgtcgg ccccagccgg caggaggtaa gggcagaagg gaa              43
```

<210> SEQ ID NO 382
<211> LENGTH: 52
<212> TYPE: DNA
<213> ORGANISM: Homo sapiens

<400> SEQUENCE: 382

```
gctcccggga gcgcgcacgt cccggagccc atgcctgcgg gtgattcctg cg    52
```

<210> SEQ ID NO 383
<211> LENGTH: 88
<212> TYPE: DNA
<213> ORGANISM: Homo sapiens

<400> SEQUENCE: 383

```
tcgcgaagtg gaatttgccc agacaagcaa catggctcgg aaacgcgcgg ccggcgggga    60
gccgcgggga cgcgaactgc gcagccag                                      88
```

<210> SEQ ID NO 384
<211> LENGTH: 86
<212> TYPE: DNA
<213> ORGANISM: Homo sapiens

<400> SEQUENCE: 384

```
tcgcgaagtg gaatttgccc agacaagcaa catggctcgg aggaacggcc ggcggggagc    60
cgcggggacg cgaactgcgc agccag                                        86
```

<210> SEQ ID NO 385
<211> LENGTH: 76
<212> TYPE: DNA
<213> ORGANISM: Homo sapiens

<400> SEQUENCE: 385

```
tcgcgaagtg gaatttgccc agacaagcaa catggctcgg aaaggggagc cgcggggacg    60
cgaactgcgc agccag                                                  76
```

<210> SEQ ID NO 386
<211> LENGTH: 73
<212> TYPE: DNA
<213> ORGANISM: Homo sapiens

<400> SEQUENCE: 386

```
tcgcgaagtg gaatttgccc agacaagcaa catggccggc ggggagccgc ggggacgcga    60
actgcgcagc cag                                                     73
```

<210> SEQ ID NO 387
<211> LENGTH: 71
<212> TYPE: DNA
<213> ORGANISM: Homo sapiens

<400> SEQUENCE: 387

```
tcgcgaagtg gaatttgccc agacaagcaa catggctcgg ggagccgcgg ggacgcgaac    60
```

```
tgcgcagcca g                                                           71

<210> SEQ ID NO 388
<211> LENGTH: 69
<212> TYPE: DNA
<213> ORGANISM: Homo sapiens

<400> SEQUENCE: 388
tcgcgaagtg gaatttgccc agacaagcaa catggcgggg agccgcgggg acgcgaactg    60
cgcagccag                                                            69

<210> SEQ ID NO 389
<211> LENGTH: 53
<212> TYPE: DNA
<213> ORGANISM: Homo sapiens

<400> SEQUENCE: 389
tcgcgaagtg gaatttgccc agacaagcaa catgttgcga actgcgcagc cag           53

<210> SEQ ID NO 390
<211> LENGTH: 49
<212> TYPE: DNA
<213> ORGANISM: Homo sapiens

<400> SEQUENCE: 390
tcgcgaagtg gaatttgccc agacaagcaa catggctcgg cgcagccag                49

<210> SEQ ID NO 391
<211> LENGTH: 12
<212> TYPE: DNA
<213> ORGANISM: Homo sapiens

<400> SEQUENCE: 391
tcgcgcagcc ag                                                          12

<210> SEQ ID NO 392
<211> LENGTH: 31
<212> TYPE: DNA
<213> ORGANISM: Homo sapiens

<400> SEQUENCE: 392
tcgcgaagtg gaatccaagg ccaagagcaa g                                     31

<210> SEQ ID NO 393
<211> LENGTH: 88
<212> TYPE: DNA
<213> ORGANISM: Homo sapiens

<400> SEQUENCE: 393
gtcgaccccg ctgcacagtc cggccggcgc catgaagtga aagggggct gggggtcgcg      60 ctcgctagcg ggcgcggggg gtcttgaa                                         88

<210> SEQ ID NO 394
<211> LENGTH: 81
<212> TYPE: DNA
<213> ORGANISM: Homo sapiens

<400> SEQUENCE: 394
gtcgaccccg ctgcacagtc cggccggcgc catgaagtgg ctgggggtc gcgctcgcta      60 gcgggcgcgg ggggtcttga a                                                81
```

<210> SEQ ID NO 395
<211> LENGTH: 77
<212> TYPE: DNA
<213> ORGANISM: Homo sapiens

<400> SEQUENCE: 395 gtcgacccecg ctgcacagtc cggccggcgc catgaagctg ggggtcgcgc tcgctagcgg    60
gcgcgggggg tcttgaa                                                    77

<210> SEQ ID NO 396
<211> LENGTH: 57
<212> TYPE: DNA
<213> ORGANISM: Homo sapiens

<400> SEQUENCE: 396 gtcgacccecg ctgcacagtc cggccggcgc tcgctagcgg gcgcgggggg tcttgaa       57

<210> SEQ ID NO 397
<211> LENGTH: 49
<212> TYPE: DNA
<213> ORGANISM: Homo sapiens

<400> SEQUENCE: 397 gtcgacccecg ctgcacagtc cggccggcgc catgaagtgg ggtcttgaa                49

<210> SEQ ID NO 398
<211> LENGTH: 43
<212> TYPE: DNA
<213> ORGANISM: Homo sapiens

<400> SEQUENCE: 398
ggcctctcgc tgaatattca tgatgggggtc atcggtgggc gcg                      43

<210> SEQ ID NO 399
<211> LENGTH: 53
<212> TYPE: DNA
<213> ORGANISM: Homo sapiens

<400> SEQUENCE: 399 gtcgacccecg ctgcacagtc cggccggcgc catgaagggt aaggggtgg gac            53

<210> SEQ ID NO 400
<211> LENGTH: 65
<212> TYPE: DNA
<213> ORGANISM: Homo sapiens

<400> SEQUENCE: 400 gtcgacccecg ctgcacagtc cggccggcgc catgaagtgc gtccggggtg ggacggggggc    60 agccg                                                                 65

<210> SEQ ID NO 401
<211> LENGTH: 60
<212> TYPE: DNA
<213> ORGANISM: Homo sapiens

<400> SEQUENCE: 401 gtcgacccecg ctgcacagtc cggccggcgc catgaagtgg cagccgcagg gagcagcagt    60

<210> SEQ ID NO 402
<211> LENGTH: 51
<212> TYPE: DNA
<213> ORGANISM: Homo sapiens

<400> SEQUENCE: 402
atggtctcgt aatataggtg gagcgagccc tcgagggggg tcttgaagat g     51

<210> SEQ ID NO 403
<211> LENGTH: 33
<212> TYPE: DNA
<213> ORGANISM: Homo sapiens

<400> SEQUENCE: 403
gtcgaccccg ctgctgagga cctgagggtt acc     33

<210> SEQ ID NO 404
<211> LENGTH: 42
<212> TYPE: DNA
<213> ORGANISM: Homo sapiens

<400> SEQUENCE: 404
ggcctctcgc tgaatattca gctcctgagg acctgagggt ta     42

<210> SEQ ID NO 405
<211> LENGTH: 44
<212> TYPE: DNA
<213> ORGANISM: Homo sapiens

<400> SEQUENCE: 405
gtcgaccccg ctgcacagtc cggcccgtca cccttctctg ggct     44

<210> SEQ ID NO 406
<211> LENGTH: 40
<212> TYPE: DNA
<213> ORGANISM: Homo sapiens

<400> SEQUENCE: 406
gtcgaccccg ctgcacagtc cggccgctcg acgaccgggc     40

<210> SEQ ID NO 407
<211> LENGTH: 46
<212> TYPE: DNA
<213> ORGANISM: Homo sapiens

<400> SEQUENCE: 407
gtcgaccccg ctgcacagtc cggccggcga ccgggcactg tggagg     46

<210> SEQ ID NO 408
<211> LENGTH: 39
<212> TYPE: DNA
<213> ORGANISM: Homo sapiens

<400> SEQUENCE: 408
gtcgaccccg ctgcacagtc cggccgggca ctgtggagg     39

<210> SEQ ID NO 409
<211> LENGTH: 19
<212> TYPE: DNA
<213> ORGANISM: Homo sapiens

<400> SEQUENCE: 409
gtcgacccag cagcccctg     19

<210> SEQ ID NO 410
<211> LENGTH: 19
<212> TYPE: DNA

<213> ORGANISM: Homo sapiens

<400> SEQUENCE: 410
gtcgaccccc ctgccgcca                                                19

<210> SEQ ID NO 411
<211> LENGTH: 43
<212> TYPE: DNA
<213> ORGANISM: Homo sapiens

<400> SEQUENCE: 411
ggcctctcgc tgaatattca tgagccgcca ggctcaacgt gga                     43

<210> SEQ ID NO 412
<211> LENGTH: 18
<212> TYPE: DNA
<213> ORGANISM: Homo sapiens

<400> SEQUENCE: 412
tatgtacgcc tccctggg                                                 18

<210> SEQ ID NO 413
<211> LENGTH: 18
<212> TYPE: DNA
<213> ORGANISM: Homo sapiens

<400> SEQUENCE: 413
tacagaagcg ggcaaagg                                                 18

<210> SEQ ID NO 414
<211> LENGTH: 18
<212> TYPE: DNA
<213> ORGANISM: Homo sapiens

<400> SEQUENCE: 414
tccgaagctg acagatgg                                                 18

<210> SEQ ID NO 415
<211> LENGTH: 18
<212> TYPE: DNA
<213> ORGANISM: Homo sapiens

<400> SEQUENCE: 415
tcaggttccg cccctacc                                                 18

<210> SEQ ID NO 416
<211> LENGTH: 18
<212> TYPE: DNA
<213> ORGANISM: Homo sapiens

<400> SEQUENCE: 416
ttagacttag gtaagtaa                                                 18

<210> SEQ ID NO 417
<211> LENGTH: 18
<212> TYPE: DNA
<213> ORGANISM: Homo sapiens

<400> SEQUENCE: 417
tagtttgtag ttctcccc                                                 18

<210> SEQ ID NO 418
<211> LENGTH: 17

```
<212> TYPE: DNA
<213> ORGANISM: Homo sapiens

<400> SEQUENCE: 418
tccggccggc gccatga                                          17

<210> SEQ ID NO 419
<211> LENGTH: 16
<212> TYPE: DNA
<213> ORGANISM: Homo sapiens

<400> SEQUENCE: 419
tagcgagcgc gacccc                                           16

<210> SEQ ID NO 420
<211> LENGTH: 18
<212> TYPE: DNA
<213> ORGANISM: Homo sapiens

<400> SEQUENCE: 420
taggcgccaa ggccatgt                                         18

<210> SEQ ID NO 421
<211> LENGTH: 18
<212> TYPE: DNA
<213> ORGANISM: Homo sapiens

<400> SEQUENCE: 421
tggcccgagg cggagttc                                         18

<210> SEQ ID NO 422
<211> LENGTH: 18
<212> TYPE: DNA
<213> ORGANISM: Homo sapiens

<400> SEQUENCE: 422
tgaagggaca tcaccttt                                         18

<210> SEQ ID NO 423
<211> LENGTH: 17
<212> TYPE: DNA
<213> ORGANISM: Homo sapiens

<400> SEQUENCE: 423
tctactgaat cttgagc                                          17

<210> SEQ ID NO 424
<211> LENGTH: 16
<212> TYPE: DNA
<213> ORGANISM: Homo sapiens

<400> SEQUENCE: 424
tcggccacca tgtccc                                           16

<210> SEQ ID NO 425
<211> LENGTH: 18
<212> TYPE: DNA
<213> ORGANISM: Homo sapiens

<400> SEQUENCE: 425
tccaggcagc tggagccc                                         18

<210> SEQ ID NO 426
```

```
<211> LENGTH: 18
<212> TYPE: DNA
<213> ORGANISM: Homo sapiens

<400> SEQUENCE: 426
tctgaaaaag actctgca                                                 18

<210> SEQ ID NO 427
<211> LENGTH: 18
<212> TYPE: DNA
<213> ORGANISM: Homo sapiens

<400> SEQUENCE: 427
tccatttctg tcatcgta                                                 18

<210> SEQ ID NO 428
<211> LENGTH: 18
<212> TYPE: DNA
<213> ORGANISM: Homo sapiens

<400> SEQUENCE: 428
tgaaaatgac tgaatata                                                 18

<210> SEQ ID NO 429
<211> LENGTH: 17
<212> TYPE: DNA
<213> ORGANISM: Homo sapiens

<400> SEQUENCE: 429
ttgcctacgc caccagc                                                  17

<210> SEQ ID NO 430
<211> LENGTH: 18
<212> TYPE: DNA
<213> ORGANISM: Homo sapiens

<400> SEQUENCE: 430
tgcttagacg ctggattt                                                 18

<210> SEQ ID NO 431
<211> LENGTH: 18
<212> TYPE: DNA
<213> ORGANISM: Homo sapiens

<400> SEQUENCE: 431
ttcggtgctt acctggtt                                                 18

<210> SEQ ID NO 432
<211> LENGTH: 17
<212> TYPE: DNA
<213> ORGANISM: Homo sapiens

<400> SEQUENCE: 432
tcccagacat gacagcc                                                  17

<210> SEQ ID NO 433
<211> LENGTH: 18
<212> TYPE: DNA
<213> ORGANISM: Homo sapiens

<400> SEQUENCE: 433 tcctttgtt tctgctaa                                                  18
```

```
<210> SEQ ID NO 434
<211> LENGTH: 18
<212> TYPE: DNA
<213> ORGANISM: Homo sapiens

<400> SEQUENCE: 434
ttgccgtccc aagcaatg                                                 18

<210> SEQ ID NO 435
<211> LENGTH: 18
<212> TYPE: DNA
<213> ORGANISM: Homo sapiens

<400> SEQUENCE: 435
tgttcaatat cgtccggg                                                 18

<210> SEQ ID NO 436
<211> LENGTH: 18
<212> TYPE: DNA
<213> ORGANISM: Homo sapiens

<400> SEQUENCE: 436
tgggccagag atggcggc                                                 18

<210> SEQ ID NO 437
<211> LENGTH: 18
<212> TYPE: DNA
<213> ORGANISM: Homo sapiens

<400> SEQUENCE: 437
taaagccgcc gcctccgg                                                 18

<210> SEQ ID NO 438
<211> LENGTH: 18
<212> TYPE: DNA
<213> ORGANISM: Homo sapiens

<400> SEQUENCE: 438
tgcccagaca agcaacat                                                 18

<210> SEQ ID NO 439
<211> LENGTH: 18
<212> TYPE: DNA
<213> ORGANISM: Homo sapiens

<400> SEQUENCE: 439
tccccgcggc tccccgcc                                                 18
```

METHODS OF TRANSCRIPTION ACTIVATOR LIKE EFFECTOR ASSEMBLY

CLAIM OF PRIORITY

This application is a continuation of U.S. patent application Ser. No. 14/232,067, filed on Jun. 5, 2014, which claims priority to International Patent Application No. PCT/US2012/046451, filed on Jul. 12, 2012, which claims the benefit of U.S. Provisional Patent Application Ser. No. 61/508,366, filed on Jul. 15, 2011, and 61/601,409, filed on Feb. 21, 2012, and 61/610,212, filed on Mar. 13, 2012. The entire contents of the foregoing applications are hereby incorporated by reference.

STATEMENT AS TO FEDERALLY SPONSORED RESEARCH

This invention was made with government support under grant number DP1 OD006862 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 11, 2012, is named 2953936W.txt and is 459,673 bytes in size.

TECHNICAL FIELD

This invention relates to methods of producing nucleic acids encoding peptides and polypeptides encoding multiple transcription-like activator effector (TALE) repeat domains and the proteins themselves.

BACKGROUND

TALE proteins of plant pathogenic bacteria in the genus *Xanthomonas* play important roles in disease, or trigger defense, by binding host DNA and activating effector-specific host genes (see, e.g., Gu et al., 2005, Nature 435:1122; Yang et al., 2006 Proc. Natl. Acad. Sci. USA 103:10503; Kay et al., 2007, Science 318:648; Sugio et al., 2007, Proc. Natl. Acad. Sci. USA 104:10720; and Romer et al., 2007, Science 318:645). Specificity for nucleic acid sequences depends on an effector-variable number of imperfect, typically ~33-35 amino acid repeats (Schornack et al., 2006, J. Plant Physiol. 163:256). Each repeat binds to one nucleotide in the target sequence, and the specificity of each repeat for its nucleotide is largely context-independent, allowing for the development of custom sequence-specific TALE proteins (Moscou et al., 2009, Science 326:1501; Boch et al., 2009, Science 326:1509-1512).

SUMMARY

This application is based, at least in part, on the development of rapid, simple, and easily automatable methods for assembling nucleic acids encoding custom TALE repeat array proteins.

Accordingly, this disclosure features a process that includes: (a) providing a first nucleic acid having a sequence encoding a first set comprising one or more (e.g., two or more, three or more, four or more, five or more, six or more, one to six, two to six, three to six, four to six, five or six, one two to five, three to five, four or five, one to four, two to four, three or four, one to three, two or three, one or two, one, two, three, four, five, or six) transcription activator-like effector (TALE) repeat domains and/or one or more portions of one or more TALE repeat domains; (b) contacting the first nucleic acid with a first enzyme, wherein the first enzyme creates a first ligatable end; (c) providing a second nucleic acid having a sequence encoding a second set comprising one or more (e.g., two or more, three or more, four or more, five or more, six or more, one to six, two to six, three to six, four to six, five or six, one two to five, three to five, four or five, one to four, two to four, three or four, one to three, two or three, one or two, one, two, three, four, five, or six) TALE repeat domains and/or one or more portions of one or more TALE repeat domains; (d) contacting the second nucleic acid with a second enzyme, wherein the second enzyme creates a second ligatable end, and wherein the first and second ligatable ends are compatible; and (e) ligating the first and second nucleic acids through the first and second ligatable ends to produce a first ligated nucleic acid, wherein the first ligated nucleic acid is linked to a solid support, and wherein the first ligated nucleic acid encodes a polypeptide comprising said first and second sets.

In some embodiments, the methods include linking the first nucleic acid to a solid support prior to (b) contacting the first nucleic acid with the first enzyme or prior to (e) ligating the first and second nucleic acids. In some embodiments, the methods include linking the first ligated nucleic acid to a solid support.

In some embodiments, the first set is N-terminal to the second set in the polypeptide. In some embodiments, the second set is N-terminal to the first set in the polypeptide.

In some embodiments, the first and second enzymes are a first and second restriction endonuclease, wherein the first restriction endonuclease cleaves at a site within the first nucleic acid and creates a first cut end, and the second restriction endonuclease cleaves at a site within the second nucleic acid and creates a second cut end, and wherein the first and second ligatable ends are the first and second cut ends. When restriction endonucleases are used, the first ligated nucleic acid cannot include a restriction site recognized by the first restriction endonuclease.

The process can further include: (f) contacting the first ligated nucleic acid with a third enzyme, wherein the third enzyme creates a third ligatable end; (g) providing a third nucleic acid comprising a sequence encoding a third set comprising one or more (e.g., two or more, three or more, four or more, five or more, six or more, one to six, two to six, three to six, four to six, five or six, one two to five, three to five, four or five, one to four, two to four, three or four, one to three, two or three, one or two, one, two, three, four, five, or six) TALE repeat domains and/or one or more portions of one or more TALE repeat domains; (h) contacting the third nucleic acid with a fourth enzyme, wherein the fourth enzyme creates a fourth ligatable end, and wherein the third and fourth ligatable ends are compatible; and (i) ligating the first ligated and third nucleic acids through the third and fourth ligatable ends to produce a second ligated nucleic acid linked to the solid support, wherein the second ligated nucleic acid encodes a polypeptide comprising said first, second, and third sets.

In some embodiments, the third and fourth enzymes are a third and fourth restriction endonuclease, wherein the third restriction endonuclease cleaves at a site within the first ligated nucleic acid and creates a third cut end, and the fourth restriction endonuclease cleaves at a site within the third nucleic acid and creates a fourth cut end, and wherein the third and fourth ligatable ends are the third and fourth cut ends.

In some embodiments, the ligated nucleic acid does not include a restriction site recognized by the first endonuclease, and the first and third restriction endonucleases are the same. In some embodiments, the second and fourth restriction endonucleases are the same.

The process can further include: (j) contacting the second ligated nucleic acid with a fifth enzyme, wherein the fifth enzyme creates a fifth ligatable end; (k) providing a fourth nucleic acid having a sequence encoding a fourth set comprising one or more (e.g., two or more, three or more, four or more, five or more, six or more, one to six, two to six, three to six, four to six, five or six, one two to five, three to five, four or five, one to four, two to four, three or four, one to three, two or three, one or two, one, two, three, four, five, or six) TALE repeat domains and/or one or more portions of one or more TALE repeat domains; (l) contacting the fourth nucleic acid with a sixth enzyme, wherein the sixth enzyme creates a sixth ligatable end, and wherein the fifth and sixth ligatable ends are compatible; and (m) ligating the second ligated and fourth nucleic acids through the fifth and sixth ligatable ends to produce a third ligated nucleic acid linked to the solid support, wherein the third ligated nucleic acid encodes a polypeptide comprising said first, second, third, and fourth sets. One of ordinary skill would recognize that the process can be repeated with similar additional steps. Such methods are included within this disclosure.

In some embodiments, the fifth and sixth enzymes are a fifth and sixth restriction endonuclease, wherein the fifth restriction endonuclease cleaves at a site within the second ligated nucleic acid and creates a fifth cut end, and the sixth restriction endonuclease cleaves at a site within the fourth nucleic acid and creates a sixth cut end, and wherein the fifth and sixth ligatable ends are the fifth and sixth cut ends.

In some embodiments, the second ligated nucleic acid does not include a restriction site recognized by the first endonuclease, and the first, third, and fifth restriction endonucleases are the same.

In some embodiments, the second, fourth, and sixth restriction endonucleases are the same.

In some embodiments, the solid support and linked nucleic acid are isolated, e.g., following any of the above steps (a)-(m).

In some embodiments, the second, third, or fourth set comprises one to four TALE repeat domains.

In some embodiments, the ligatable ends include an overhang of 1-10 nucleotides. In some embodiments, the ligatable ends are blunt ends. In some embodiments, an overhang can be generated using an exonuclease and polymerase in the presence of one or more nucleotides.

In some embodiments, an enzyme or restriction endonuclease used in the above processes is a type IIS restriction endonuclease.

The processes can further comprise unlinking a ligated nucleic acid from the solid support and inserting the ligated nucleic acid (or a processed derivative thereof comprising the TALE repeat array coding sequences) into a vector, e.g., an expression vector. The expression vector can include a sequence encoding an effector domain (e.g., a nuclease domain) configured to create a sequence encoding a fusion protein of the polypeptide and the effector domain. The expression vector can be inserted into a cell to affect the cell directly or for expression of the polypeptide or fusion protein. When the polypeptide or fusion protein is to be expressed, the processes can further include expressing and purifying the polypeptide or fusion protein.

In another aspect, this disclosure features TALE proteins that bind to a target nucleotide sequence (e.g., a "half site") disclosed herein (e.g., in Table 6 or 7), TALE nucleases that include the TALE proteins, pairs of TALE proteins (e.g., TALENs) that bind to the target sites disclosed herein (e.g., in Table 6 or 7), and nucleic acids that encode any of the above. In some embodiments, the TALE proteins, TALE nucleases, and pairs of TALE proteins (e.g., TALENs) are those disclosed in Example 7. The nucleic acids encoding the TALE proteins, TALE nucleases, and pairs of TALE proteins (e.g., TALENs) can be those disclosed in Example 7 or other sequences that encode the proteins disclosed in Example 7. The disclosure also includes vectors and cells that include the nucleic acids encoding the TALE proteins, TALE nucleases, or pairs of TALE proteins (e.g., TALENs) disclosed herein and methods of expressing the TALE proteins, TALE nucleases, or pairs of TALE proteins (e.g., TALENs) that include culturing the cells. The methods of expressing the TALE proteins, TALE nucleases, or pairs of TALE proteins (e.g., TALENs) can also include isolating the TALE proteins, TALE nucleases, or pairs of TALE proteins (e.g., TALENs) from the cell culture.

In another aspect, the invention features a set, archive, or library of nucleic acids (e.g., plasmids) that include sequences encoding one or more TALE domains. In some embodiments, the set, archive, or library includes sequences encoding one, two, three, and/or four (or more than four (e.g., five, six, or more)) TALE repeat domains. In some embodiments, the set, library, or archive of nucleic acids includes sequences encoding TALE repeat domains that bind to nucleotide sequences having one, two, three, four (or more than four (e.g., five, six, or more)) nucleotides. In some embodiments, the set, library, or archive includes restriction sites (e.g., sites for type IIS restriction endonucleases) surrounding the sequences encoding the TALE repeat domains.

The methods described herein provide several advantages, including avoiding extensive PCR amplification of the TALE repeats, thereby avoiding the introduction of mutations from PCR errors. Further, TALE repeat arrays of any desired length can be constructed, and the methods can be easily multiplexed and/or automated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 depicts the sequence of the pUC57-ΔBsaI plasmid. This plasmid is identical to plasmid pUC57 except for mutation of a single base (in bold, underlined and lowercase) that destroys a BsaI restriction site.

FIG. 4A depicts the polypeptide sequences of exemplary TALE repeats of type α/ε, β, γ, and δ. Polymorphic residues characteristic of each type are indicated in bold and italic. The hypervariable triplet SNI for binding to A is indicated in underscore.

FIG. 4B depicts the polynucleotide sequences of the exemplary TALE repeats of FIG. 4A.

FIGS. 5A-5B depict the common sequence of expression plasmids pJDS70, pJDS71, pJDS74, pJDS76, and pJDS78. The region of the variable sequences is depicted as XXXXXXXXX (underlined and bold).

FIG. 8 is a depiction of the sequences of insertion-deletion mutants of eGFP induced by TALE nucleases. Deleted bases are indicated by dashes and inserted bases indicated by double underlining; the TALEN target half-sites are single underlined. The net number of bases inserted or deleted is shown to the right.

FIG. 9 is a depiction of an electrophoresis gel of assembled DNA fragments encoding 17-mer TALE array preparations.

FIGS. 11A-11B depict the nucleotide (11A) and polypeptide (11B) sequence of engineered DR-TALE-0003.

FIGS. 12A-12B depict the nucleotide (12A) and polypeptide (12B) sequence of engineered DR-TALE-0006.

FIGS. 13A-13B depict the nucleotide (13A) and polypeptide (13B) sequence of engineered DR-TALE-0005.

FIGS. 14A-14B depict the nucleotide (14A) and polypeptide (14B) sequence of engineered DR-TALE-0010.

FIGS. 15A-15B depict the nucleotide (15A) and polypeptide (15B) sequence of engineered DR-TALE-0023.

FIGS. 16A-16B depict the nucleotide (16A) and polypeptide (16B) sequence of engineered DR-TALE-0025.

FIGS. 17A-17B depict the nucleotide (17A) and polypeptide (17B) sequence of engineered DR-TALE-0020.

FIGS. 18A-18B depict the nucleotide (18A) and polypeptide (18B) sequence of engineered DR-TALE-0022.

Figure 21E:
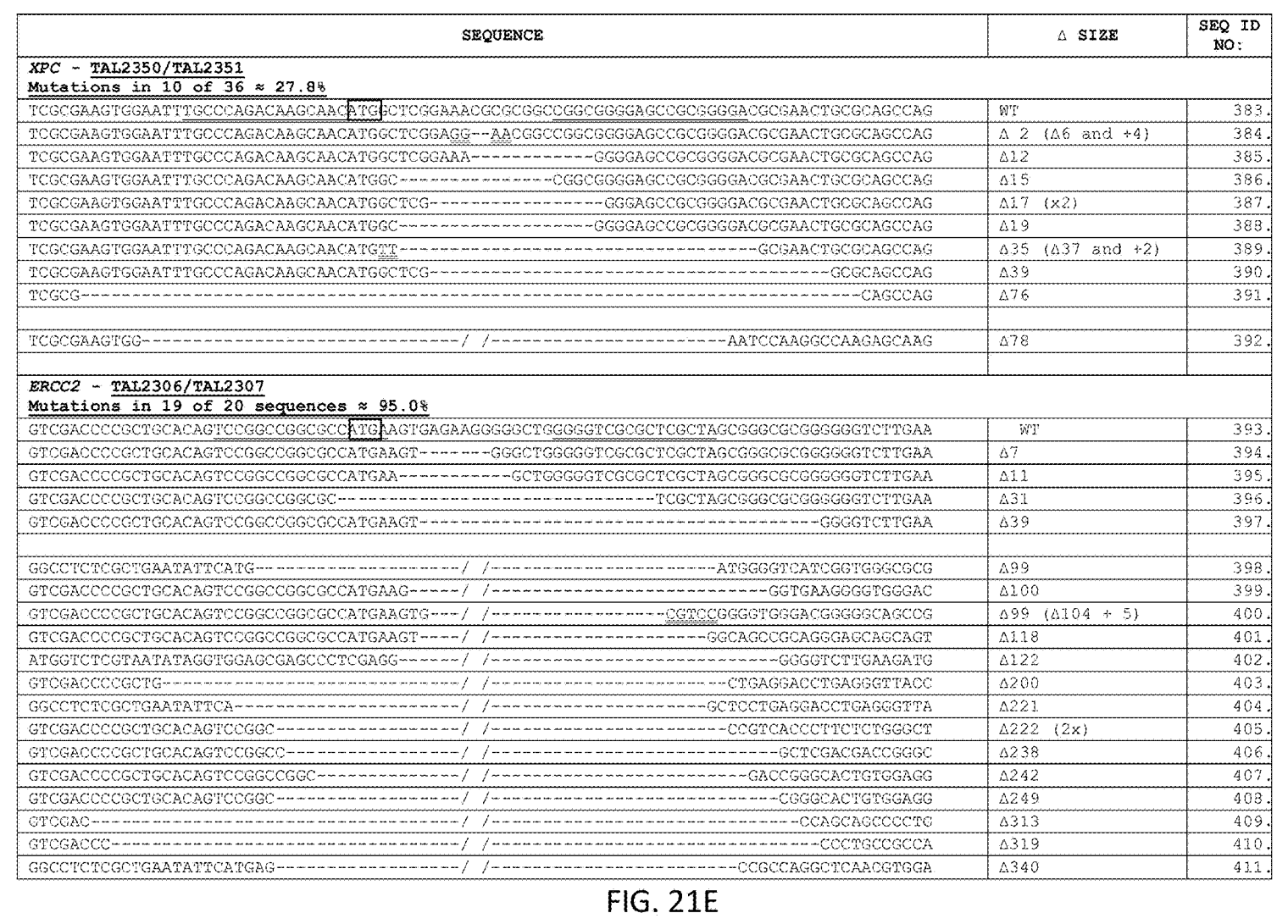

FIGS. 21A-E depict DNA sequences and frequencies of assembled TALEN-induced mutations at endogenous human genes. For each endogenous gene target, the wild-type (WT) sequence is shown at the top with the TALEN target half-sites underlined and the translation start codon of the gene (ATG) indicated by a box. Deletions are indicated by dashes and insertions by lowercase letters and double underlining. The sizes of the insertions (+) or deletions (Δ) are indicated to the right of each mutated site. The number of times that each mutant was isolated is shown in parentheses. Mutation frequencies are calculated as the number of mutants identified divided by the total number of sequences analyzed. Note that for several of the genes, we also identified larger deletions that extend beyond the sequences of the TALEN target sites.

DETAILED DESCRIPTION

The methods described herein can be used to assemble engineered proteins containing TALE repeat domains for binding to specific sequences of interest. Assembling long arrays (e.g., 12 or more) of TALE repeat domain repeats can be challenging because the repeats differ only at a small number of amino acids within their highly conserved ~33-35 amino acid consensus sequence. PCR assembly can lead to the introduction of unwanted mutations. Hierarchical assembly methods that involve one or more passages of intermediate plasmid constructs in *E. coli* can also be problematic because the highly repetitive nature of these constructs can make them unstable and prone to recombination and because the need to passage these intermediate constructs makes these approaches difficult to automate.

TAL Effectors

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the "repeat variable-diresidue" (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet e.g., encompassing residues 11, 12, and 13.

Each DNA binding repeat can include an RVD that determines recognition of a base pair in the target DNA sequence, wherein each DNA binding repeat is responsible for recognizing one base pair in the target DNA sequence, and wherein the RVD comprises, but is not limited to, one or more of the following: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins are useful in research and biotechnology as targeted chimeric nucleases that can facilitate homologous recombination in genome engineering (e.g., to add or enhance traits useful for biofuels or biorenewables in plants). These proteins also are useful as, for example, transcription factors, and especially for therapeutic applications requiring a very high level of specificity such as therapeutics against pathogens (e.g., viruses) as non-limiting examples.

Assembly Methods

Figure 1:
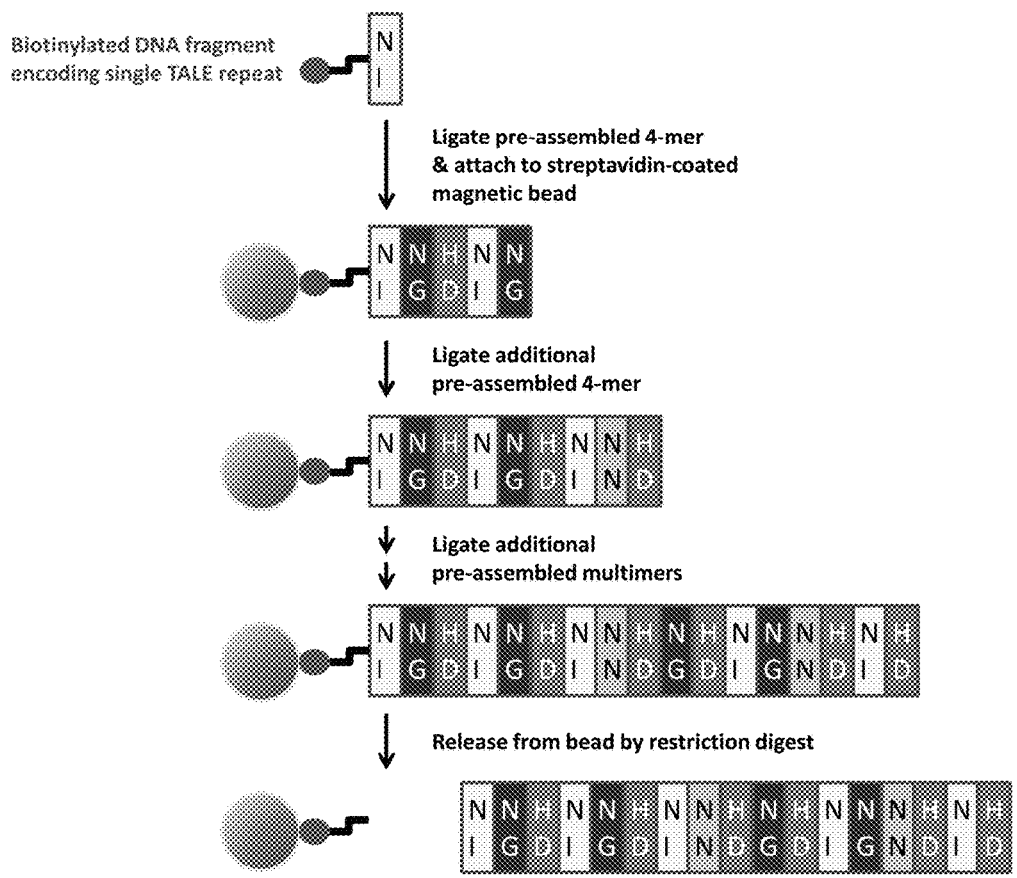
FIG. 1 is a schematic depiction of an exemplary method of assembling a nucleic acid encoding a TALE protein.

An example of the methods described herein of assembling a TALE repeat domain array is shown in FIG. 1 and includes the following steps: (1) provision a single biotinylated PCR product encoding one single N-terminal TALE repeat domain (a one-mer) with a linker suitable for attachment to a solid support (in the example shown here, a magnetic streptavidin coated bead is used but other solid supports can also be utilized as well as other ways of tethering the initial DNA fragment to the solid support); (2) creation of an overhang at the 3' end of the one-mer DNA (e.g., using a Type IIS restriction enzyme); (3) ligation of a second fragment containing four TALE repeat domain (i.e., a pre-assembled four-mer), creating a five-mer; (4) attachment of the five-mer to the solid support; (5) ligation of additional pre-assembled TALE repeat domains to create a long array, e.g., a piece or pieces of DNA encoding one, two, three, or four TALE repeat domains depending upon the length of the desired final array, and (6) release of the extended DNA encoding the TALE repeats from the solid support (e.g., by using a Type IIS restriction enzyme whose site is built in at the 5' end of the initial biotinylated DNA product). The final fragment can then be prepared for ligation to an appropriate expression plasmid.

Alternatively, the method can proceed as follows: (1) attachment of a single biotinylated PCR product encoding one single N-terminal TALE repeat domains to a solid support (in the example shown here, a magnetic streptavidin coated bead is used but other solid supports such as the streptavidin-coated wells of a multi-well plate can also be utilized as well as other ways of tethering the initial DNA fragment to the solid support), (2) creation of an overhang at the 3' end of the anchored DNA (e.g., using a Type IIS restriction enzyme), (3) ligation of a second fragment containing four TALE repeat domain, (4) additional cycles of steps (2) and (3) to create a long array, (5) in the final cycle performing ligation of a piece of DNA encoding one, two, three, or four TALE repeat domains depending upon the length of the desired final array, and (6) release of the extended DNA encoding the TALE repeats from the solid support (e.g., by using a Type IIS restriction enzyme whose site is built in at the 5' end of the initial biotinylated DNA product).

Figure 22:
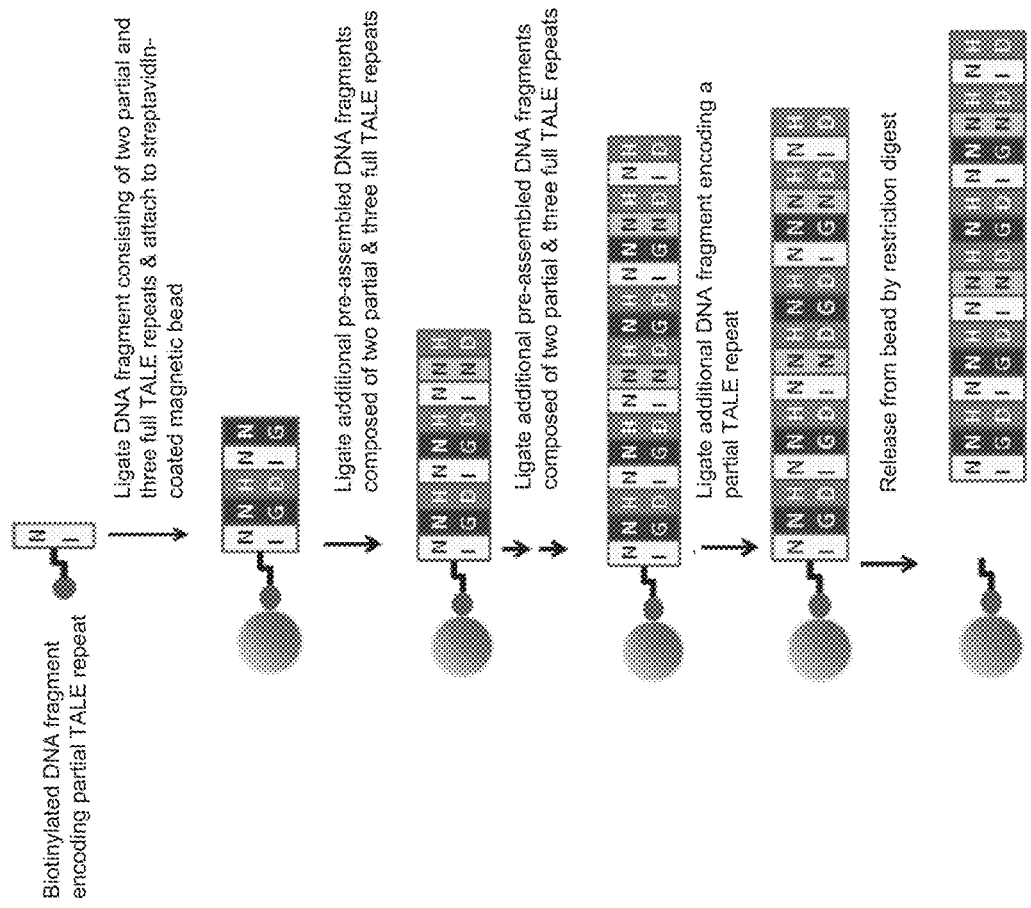
FIG. 22 is a schematic depiction of an exemplary method of assembling a nucleic acid encoding a TALE protein containing TALE repeat domains or portions of TALE repeat domains.

Another example of a method of assembling a TALE repeat domain array based on the methods described herein is shown in FIG. 22 and includes the following steps: (1) provision a single biotinylated PCR product encoding a portion of one single N-terminal TALE repeat domain (a partial one-mer) with a linker suitable for attachment to a solid support (in the example shown here, a magnetic streptavidin coated bead is used but other solid supports can also be utilized as well as other ways of tethering the initial DNA fragment to the solid support); (2) creation of an overhang at the 3' end of the partial one-mer DNA (e.g., using a Type IIS restriction enzyme); (3) ligation of a second fragment containing consisting of two partial and three full TALE repeats; (4) attachment of the second fragment to the solid support; (5) ligation of additional pre-assembled TALE repeat domains or portions of TALE repeat domains to create a long array, e.g., a piece or pieces of DNA encoding one, two, three, or four TALE repeat domains (or portions of TALE repeat domains) depending upon the length of the desired final array, and (6) release of the extended DNA encoding the TALE repeats from the solid support (e.g., by using a Type IIS restriction enzyme whose site is built in at the 5' end of the initial biotinylated DNA product). The final fragment can then be prepared for ligation to an appropriate expression plasmid.

The initial nucleic acid encoding one or more TALE repeat domains (or portions) is linked to a solid support. The initial nucleic acid can be prepared by any means (e.g., chemical synthesis, PCR, or cleavage from a plasmid). Additionally, the nucleic acid can be linked to the solid support by any means, e.g., covalently or noncovalently.

In some embodiments, the nucleic acid is linked noncovalently by using a nucleic acid modified with one member of a binding pair and incorporating the other member of the binding pair on the solid support. A member of a binding pair is meant to be one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X/anti-dansyl, Fluorescein/anti-fluorescein, lucifer yellow/anti-lucifer yellow, peptide/anti-peptide, ligand/receptor and rhodamine/anti-rhodamine), biotin/avidin (or biotin/streptavidin) and calmodulin binding protein (CBP)/calmodulin. Other suitable binding pairs include polypeptides such as the FLAG-peptide (Hopp et al., 1988, BioTechnology, 6:1204 10); the KT3 epitope peptide (Martin et al., Science 255:192 194 (1992)); tubulin epitope peptide (Skinner et al., J. Biol. Chem. 266:15163-66 (1991)); and the T7 gene 10 protein peptide tag (Lutz-Freyerinuth et al., Proc. Natl. Acad. Sci. USA, 87:6393 97 (1990)) and the antibodies each thereto.

Figure 2:
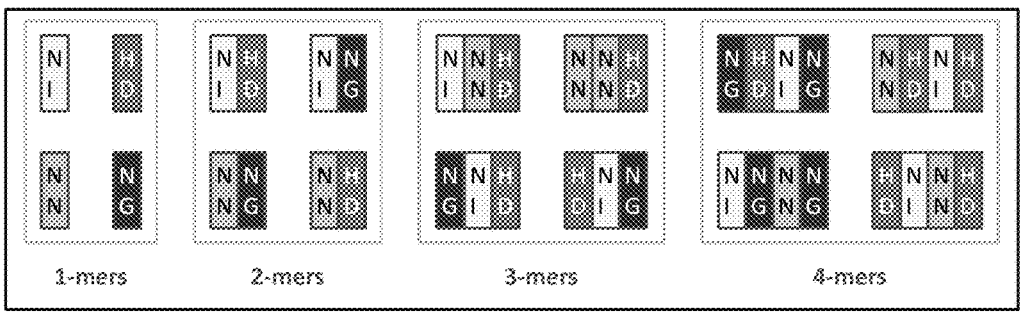
FIG. 2 is a schematic depiction of exemplary archives of nucleic acids encoding single (one-mer), two-mer, three-mer, and four-mer TALE repeat domains.

In some embodiments, the individual nucleic acids encoding one or more TALE repeat domains are present in an archive or library of plasmids (see FIG. 2). Although nucleic acids encoding one to four TALE repeat domains are shown, the library of plasmids can contain nucleic acids encoding more than four (e.g., five, six, or more) TALE repeat domains. Alternatively, as shown FIG. 22, the nucleic acids encoding parts or portions of one or more TALE repeat domains can also be joined together to create final DNA fragments encoding the desired full-length arrays of TALE repeat domains. Numerous TALE repeat domain sequences with binding specificity for specific nucleotides or sets of nucleotides are known in the art, and one of ordinary skill can design and prepare a library of plasmids based on these known sequences and the disclosures herein.

As used herein, a solid support refers to any solid or semisolid or insoluble support to which the nucleic acid can be linked. Such materials include any materials that are used as supports for chemical and biological molecule syntheses and analyses, such as, but not limited to: polystyrene, polycarbonate, polypropylene, nylon, glass, dextran, chitin, sand, pumice, agarose, polysaccharides, dendrimers, buckyballs, polyacryl-amide, silicon, rubber, and other materials used as supports for solid phase syntheses, affinity separations and purifications, hybridization reactions, immunoassays and other such applications. The solid support can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5-10 mm range or smaller. Such particles, referred collectively herein as "beads," are often, but not necessarily, spherical. Such reference, however, does not constrain the geometry of the matrix, which can be any shape, including random shapes, needles, fibers, and elongated. Roughly spherical "beads," particularly microspheres that can be used in the liquid phase, also are contemplated. The "beads" can include additional components, such as magnetic or paramagnetic particles (see, e.g., Dynabeads (Dynal, Oslo, Norway)) for separation using magnets, as long as the additional components do not interfere with the methods described herein.

The ligatable ends can be produced by cutting with a restriction endonuclease (e.g., a type II or type IIS restriction endonuclease) or by "chewing back" the end using an enzyme (or enzymes) with exonuclease and polymerase activities in the presence of one or more nucleotides (see, Aslanidis et al., 1990, Nucl. Acids Res., 18:6069-74). Suitable enzymes are known to those of ordinary skill in the art. When restriction endonucleases are used, the nucleic acids can be designed to include restriction sites for the enzymes at suitable locations.

Following a ligation reaction, any unligated ends with 5' or 3' overhangs can be "blunted" by use of a polymerase, e.g., a DNA polymerase with both 3'→5' exonuclease activity and 5'→3' polymerase activity. This blunting step can reduce the appearance of undesired or partial assembly products. Alternatively, these ends can be capped using either a "hairpin" oligo bearing a compatible overhang (Briggs et al., 2012, Nucleic Acids Res, PMID: 22740649) or by short double-stranded DNAs bearing a compatible overhang on one end and a blunt end on the other.

To prepare the ligated nucleic acid for further downstream processing, it can be useful to select nucleic acids of the expected size, to reduce the presence of minor products created by incomplete ligations. Methods of selecting nucleic acids by size are known in the art, and include gel electrophoresis (e.g., slab gel electrophoresis or capillary gel electrophoresis (see, e.g., Caruso et al., 2003, Electrophoresis, 24:1-2:78-85)), liquid chromatography (e.g., size exclusion chromatography or reverse phase chromatography (see, e.g., Huber et al., 1995, Anal. Chem., 67:578-585)), and lab-on-a-chip systems (e.g., LabChip® XT system, Caliper Life Sciences, Hopkinton, Mass.). In some embodiments, a size exclusion step can be performed using an automated system, e.g., an automated gel electrophoresis system (e.g., a Pippin Prep™ automated DNA size selection system, Sage Science, Beverly, Mass.).

Automation

The methods disclosed herein can be performed manually or implemented in laboratory automation hardware (e.g., SciClone G3 Liquid Handling Workstation, Caliper Life Sciences, Hopkinton, Mass.) controlled by a compatible software package (e.g., Maestro™ liquid handling software) programmed according to the new methods described herein or a new software package designed and implemented to carry out the specific method steps described herein. When performed by laboratory automation hardware, the methods can be implemented by computer programs using standard programming techniques following the method steps described herein.

Examples of automated laboratory system robots include the Sciclone™ G3 liquid handling workstation (Caliper Life Sciences, Hopkinton, Mass.), Biomek® FX liquid handling system (Beckman-Coulter, Fullerton, Calif.), TekBench™ automated liquid handling platform (TekCel, Hopkinton, Mass.), and Freedom EVO® automation platform (Tecan Trading AG, Switzerland).

The programs can be designed to execute on a programmable computer including at least one processor, at least one data storage system (including volatile and non-volatile memory and/or storage elements, e.g., RAM and ROM), at least one communications port that provides access for devices such as a computer keyboard, telephone, or a wireless, hand-held device, such as a PDA, and optionally at least one output device, such as a monitor, printer, or website. The central computer also includes a clock and a communications port that provides control of the lab automation hardware. These are all implemented using known techniques, software, and devices. The system also includes a database that includes data, e.g., data describing the procedure of one or more method steps described herein.

Program code is applied to data input by a user (e.g., location of samples to be processed, timing and frequency of manipulations, amounts of liquid dispensed or aspirated, transfer of samples from one location in the system to another) and data in the database, to perform the functions described herein. The system can also generate inquiries and provide messages to the user. The output information is applied to instruments, e.g., robots, that manipulate, heat, agitate, etc. the vessels that contain the reactants as described herein. In addition, the system can include one or more output devices such as a telephone, printer, or a monitor, or a web page on a computer monitor with access to a website to provide to the user information regarding the synthesis and/or its progress.

Each program embodying the new methods is preferably implemented in a high level procedural or object-oriented programming language to communicate with a computer system. However, the programs can also be implemented in assembly or machine language if desired. In any case, the language can be a compiled or interpreted language.

Each such computer program is preferably stored on a storage medium or device (e.g., RAM, ROM, optical, magnetic) readable by a general or special purpose programmable computer, for configuring and operating the computer when the storage media or device is read by the computer to perform the procedures described herein. The system can also be considered to be implemented as a computer- or machine-readable storage medium (electronic apparatus readable medium), configured with a program, whereby the storage medium so configured causes a computer or machine to operate in a specific and predefined manner to perform the functions described herein.

The new methods can be implemented using various means of data storage. The files can be transferred physically on recordable media or electronically, e.g., by email on a dedicated intranet, or on the Internet. The files can be encrypted using standard encryption software from such companies as RSA Security (Bedford, Mass.) and Baltimore®. The files can be stored in various formats, e.g., spreadsheets or databases.

As used herein, the term "electronic apparatus" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; electronic appliances such as a personal digital assistants (PDAs), cellular telephones, "smartphones," pagers and the like; and local and distributed processing systems.

As used herein, "stored" refers to a process for encoding information on an electronic apparatus readable medium. Those skilled in the art can readily adopt any of the presently known methods for recording information on known media to generate manufactures comprising the sequence information.

A variety of software programs and formats can be used to store method data on an electronic apparatus readable medium. For example, the data and machine instructions can be incorporated in the system of the software provided with the automated system, represented in a word processing text file, formatted in commercially-available software such as WordPerfect® and Microsoft® Word®, or represented in the form of an ASCII file, stored in a database application, such as Microsoft Access®, Microsoft SQL Server®, Sybase®, Oracle®, or the like, as well as in other forms. Any number of data processor structuring formats (e.g., text file or database) can be employed to obtain or create a medium having recorded thereon the relevant data and machine instructions to implement the methods described herein.

By providing information in electronic apparatus readable form, the programmable computer can communicate with and control the lab automation hardware to perform the methods described herein. One skilled in the art can input data in electronic apparatus readable form (or a form that is converted to electronic apparatus readable form) to describe the completion of various method steps by the lab automation hardware.

Polypeptide Expression Systems

In order to use the engineered proteins of the present invention, it is typically necessary to express the engineered proteins from a nucleic acid that encodes them. This can be performed in a variety of ways. For example, the nucleic acid encoding the engineered TALE repeat protein is typically cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the engineered TALE protein or production of protein. The nucleic acid encoding the engineered TALE repeat protein is also typically cloned into an expression vector, for administration to a plant cell, animal cell, preferably a mammalian cell or a human cell, fungal cell, bacterial cell, or protozoan cell.

To obtain expression of a cloned gene or nucleic acid, the engineered TALE repeat protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered TALE repeat protein are available in, e.g., E. coli, Bacillus sp., and Salmonella (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of the engineered TALE repeat protein nucleic acid depends on the particular application. For example, a strong constitutive promoter is typically used for expression and purification of the engineered TALE repeat protein. In contrast, when the engineered TALE repeat protein is to be administered in vivo for gene regulation, either a constitutive or an inducible promoter can be used, depending on the particular use of the engineered TALE repeat protein. In addition, a preferred promoter for administration of the engineered TALE repeat protein can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the TALE repeat protein signals required, e.g., for efficient polyadenylation of the transcript, transcriptional termination, ribosome binding sites, or translation termination. Additional elements of the cassette can include, e.g., enhancers, and heterologous spliced intronic signals.

The particular expression vector used to transport the genetic information into the cell is selected with regard to the intended use of the engineered TALE repeat protein, e.g., expression in plants, animals, bacteria, fungus, protozoa, etc. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the engineered TALE repeat protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the well-known procedures for introducing foreign nucleotide sequences into host cells can be used. These include the use of calcium phosphate transfection, polybrene, protoplast fusion, electroporation, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Characterization of TALE Proteins

Engineered TALE repeat array proteins designed using methods of the present invention can be further characterized to ensure that they have the desired characteristics for their chosen use. For example, TALE repeat array protein can be assayed using a bacterial two-hybrid, bacterial promoter repression, phage-display, or ribosome display system or using an electrophoretic mobility shift assay or "EMSA" (Buratowski & Chodosh, in Current Protocols in Molecular Biology pp. 12.2.1-12.2.7). Equally, any other DNA binding assay known in the art could be used to verify the DNA binding properties of the selected protein.

In one embodiment, a bacterial "two-hybrid" system is used to express and test a TALE repeat protein of the present invention. The bacterial two-hybrid system has an additional advantage, in that the protein expression and the DNA binding "assay" occur within the same cells, thus there is no separate DNA binding assay to set up.

Methods for the use of the bacterial two-hybrid system to express and assay DNA binding proteins are described in Joung et al., 2000, Proc. Natl. Acad. Sci. USA, 97:7382, Wright et al., 2006, Nat. Protoc, 1:1637-52; Maeder et al., 2008, Mol. Cell, 31:294-301; Maeder et al., 2009, Nat. Protoc., 4:1471-1501; and US Patent Application No. 2002/0119498, the contents of which are incorporated herein by reference. Briefly, in a bacterial two-hybrid system, the DNA binding protein is expressed in a bacterial strain bearing the sequence of interest upstream of a weak promoter controlling expression of a reporter gene (e.g., histidine 3 (HIS3), the beta-lactamase antibiotic resistance gene, or the beta-galactosidase (lacZ) gene). Expression of the reporter gene occurs in cells in which the DNA binding protein expressed by the cell binds to the target site sequence. Thus, bacterial cells expressing DNA binding proteins that bind to their target site are identified by detection of an activity related to the reporter gene (e.g., growth on selective media, expression of beta-galactosidase).

In some embodiments, calculations of binding affinity and specificity are also made. This can be done by a variety of methods. The affinity with which the selected TALE repeat array protein binds to the sequence of interest can be measured and quantified in terms of its $K_D$. Any assay system can be used, as long as it gives an accurate measurement of the actual $K_D$ of the TALE repeat array protein. In one embodiment, the $K_D$ for the binding of a TALE repeat array protein to its target is measured using an EMSA In one embodiment, EMSA is used to determine the $K_D$ for binding of the selected TALE repeat array protein both to the sequence of interest (i.e., the specific $K_D$) and to non-specific DNA (i.e., the non-specific $K_D$). Any suitable non-specific or "competitor" double stranded DNA known in the art can be used. In some embodiments, calf thymus DNA or human placental DNA is used. The ratio of the non-specific $K_D$ to the specific KD is the specificity ratio. TALE repeat array proteins that bind with high specificity have a high specificity ratio. This measurement is very useful in deciding which of a group of selected TALE should be used for a given purpose. For example, use of TALE repeat array protein in vivo requires not only high affinity binding but also high-specificity binding.

Construction of Chimeric TALE Proteins

Often, the aim of producing a custom-designed TALE repeat array DNA binding domain is to obtain a TALE repeat array protein that can be used to perform a function. The TALE repeat array DNA binding domain can be used alone, for example to bind to a specific site on a gene and thus block binding of other DNA-binding domains. However, in some embodiments, the TALE repeat array protein will be used in the construction of a chimeric TALE protein containing a TALE repeat array DNA binding domain and an additional domain having some desired specific function (e.g., gene activation) or enzymatic activity i.e., a "functional domain."

Chimeric TALE repeat array proteins designed and produced using the methods described herein can be used to perform any function where it is desired to target, for example, some specific enzymatic activity to a specific DNA sequence, as well as any of the functions already described for other types of synthetic or engineered DNA binding molecules. Engineered TALE repeat array DNA binding domains, can be used in the construction of chimeric proteins useful for the treatment of disease (see, for example, U.S. patent application 2002/0160940, and U.S. Pat. Nos. 6,511,808, 6,013,453 and 6,007,988, and International patent application WO 02/057308), or for otherwise altering the structure or function of a given gene in vivo. The engineered TALE repeat array proteins of the present invention are also useful as research tools, for example, in performing either in vivo or in vitro functional genomics studies (see, for example, U.S. Pat. No. 6,503,717 and U.S. patent application 2002/0164575).

To generate a functional recombinant protein, the engineered TALE repeat array DNA binding domain will typically be fused to at least one "functional" domain. Fusing functional domains to synthetic TALE repeat array proteins to form functional transcription factors involves only routine molecular biology techniques which are commonly practiced by those of skill in the art, see for example, U.S. Pat. Nos. 6,511,808, 6,013,453, 6,007,988, 6,503,717 and U.S. patent application 2002/0160940).

Functional domains can be associated with the engineered TALE repeat array domain at any suitable position, including the C- or N-terminus of the TALE protein. Suitable "functional" domains for addition to the engineered protein made using the methods of the invention are described in U.S. Pat. Nos. 6,511,808, 6,013,453, 6,007,988, and 6,503,717 and U.S. patent application 2002/0160940.

In one embodiment, the functional domain is a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. It is preferred that a nuclear localization domain is routinely incorporated into the final chimeric protein, as the ultimate functions of the chimeric proteins of the present invention will typically require the proteins to be localized in the nucleus. However, it may not be necessary to add a separate nuclear localization domain in cases where the engineered TALE repeat array domain itself, or another functional domain within the final chimeric protein, has intrinsic nuclear translocation function.

In another embodiment, the functional domain is a transcriptional activation domain such that the chimeric protein can be used to activate transcription of the gene of interest. Any transcriptional activation domain known in the art can be used, such as for example, the VP16 domain form herpes simplex virus (Sadowski et al., 1988, Nature, 335:563-564) or the p65 domain from the cellular transcription factor NF-kappaB (Ruben et al., 1991, Science, 251:1490-93).

In yet another embodiment, the functional domain is a transcriptional repression domain such that the chimeric protein can be used to repress transcription of the gene of interest. Any transcriptional repression domain known in the art can be used, such as for example, the KRAB (Kruppel-associated box) domain found in many naturally occurring KRAB proteins (Thiesen et al., 1991, Nucleic Acids Res., 19:3996).

In a further embodiment, the functional domain is a DNA modification domain such as a methyltransferase (or methylase) domain, a de-methylation domain, a deaminase domain, a hydroxylase domain, an acetylation domain, or a deacetylation domain. Many such domains are known in the art and any such domain can be used, depending on the desired function of the resultant chimeric protein. For example, it has been shown that a DNA methylation domain can be fused to a TALE repeat array DNA binding protein and used for targeted methylation of a specific DNA sequence (Xu et al., 1997, Nat. Genet., 17:376-378). The state of methylation of a gene affects its expression and regulation, and furthermore, there are several diseases associated with defects in DNA methylation.

In a still further embodiment the functional domain is a chromatin modification domain such as a histone acetylase or histone de-acetylase (or HDAC) domain. Many such domains are known in the art and any such domain can be used, depending on the desired function of the resultant chimeric protein. Histone deacetylases (such as HDAC1 and HDAC2) are involved in gene repression. Therefore, by targeting HDAC activity to a specific gene of interest using an engineered TALE protein, the expression of the gene of interest can be repressed.

In an alternative embodiment, the functional domain is a nuclease domain, such as a restriction endonuclease (or restriction enzyme) domain. The DNA cleavage activity of a nuclease enzyme can be targeted to a specific target sequence by fusing it to an appropriate engineered TALE repeat array DNA binding domain. In this way, sequence specific chimeric restriction enzyme can be produced. Several nuclease domains are known in the art and any suitable nuclease domain can be used. For example, an endonuclease domain of a type IIS restriction endonuclease (e.g., FokI) can be used, as taught by Kim et al., 1996, Proc. Natl. Acad. Sci. USA, 6:1156-60). In some embodiments, the endonuclease is an engineered FokI variant as described in US 2008/0131962. Such chimeric endonucleases can be used in any situation where cleavage of a specific DNA sequence is desired, such as in laboratory procedures for the construction of recombinant DNA molecules, or in producing double-stranded DNA breaks in genomic DNA in order to promote homologous recombination (Kim et al., 1996, Proc. Natl. Acad. Sci. USA, 6:1156-60; Bibikova et al., 2001, Mol. Cell. Biol., 21:289-297; Porteus & Baltimore, 2003, Science, 300:763; Miller et al., 2011, Nat. Biotechnol., 29:143-148; Cermak et al., 2011, Nucl. Acids Res., 39:e82). Repair of TALE nuclease-induced double-strand breaks (DSB) by error-prone non-homologous end-joining leads to efficient introduction of insertion or deletion mutations at the site of the DSB (Miller et al., 2011, Nat. Biotechnol., 29:143-148; Cermak et al., 2011, Nucl. Acids Res., 39:e82). Alternatively, repair of a DSB by homology-directed repair with an exogenously introduced "donor template" can lead to highly efficient introduction of precise base alterations or insertions at the break site (Bibikova et al., 2003, Science, 300:764; Urnov et al., 2005, Nature, 435:646-651; Porteus et al., 2003, Science, 300:763; Miller et al., 2011, Nat. Biotechnol., 29:143-148).

In some embodiments, the functional domain is an integrase domain, such that the chimeric protein can be used to insert exogenous DNA at a specific location in, for example, the human genome.

Other suitable functional domains include silencer domains, nuclear hormone receptors, resolvase domains oncogene transcription factors (e.g., myc, jun, fos, myb, max, mad, rel, ets, bcl, myb, mos family members etc.), kinases, phosphatases, and any other proteins that modify the structure of DNA and/or the expression of genes. Suitable kinase domains, from kinases involved in transcription regulation are reviewed in Davis, 1995, Mol. Reprod. Dev., 42:459-67. Suitable phosphatase domains are reviewed in, for example, Schonthal & Semin, 1995, Cancer Biol. 6:239-48.

Fusions of TALE repeat arrays to functional domains can be performed by standard recombinant DNA techniques well known to those skilled in the art, and as are described in, for example, basic laboratory texts such as Sambrook et al., Molecular Cloning; A Laboratory Manual 3d ed. (2001), and in U.S. Pat. Nos. 6,511,808, 6,013,453, 6,007,988, and 6,503,717 and U.S. patent application 2002/0160940.

In some embodiments, two or more engineered TALE repeat array proteins are linked together to produce the final DNA binding domain. The linkage of two or more engineered proteins can be performed by covalent or non-covalent means. In the case of covalent linkage, engineered proteins can be covalently linked together using an amino acid linker (see, for example, U.S. patent application 2002/0160940, and International applications WO 02/099084 and WO 01/53480). This linker can be any string of amino acids desired. In one embodiment the linker is a canonical TGEKP linker. Whatever linkers are used, standard recombinant DNA techniques (such as described in, for example, Sambrook et al., Molecular Cloning; A Laboratory Manual 3d ed. (2001)) can be used to produce such linked proteins.

In embodiments where the engineered proteins are used in the generation of chimeric endonuclease, the chimeric protein can possess a dimerization domain as such endonucleases are believed to function as dimers. Any suitable dimerization domain can be used. In one embodiment the endonuclease domain itself possesses dimerization activity. For example, the nuclease domain of FokI which has intrinsic dimerization activity can be used (Kim et al., 1996, Proc. Natl. Acad. Sci., 93:1156-60).

Assays for Determining Regulation of Gene Expression by Engineered Proteins

A variety of assays can be used to determine the level of gene expression regulation by the engineered TALE repeat proteins, see for example U.S. Pat. No. 6,453,242. The activity of a particular engineered TALE repeat protein can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG; $Ca^{2+}$); cytokine and hormone production levels; and neovascularization, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, tumor growth assays, phenotypic assays, and the like.

TALE proteins can be first tested for activity in vitro using cultured cells, e.g., 293 cells, CHO cells, VERO cells, BHK cells, HeLa cells, COS cells, and the like. In some embodiments, human cells are used. The engineered TALE repeat array protein is often first tested using a transient expression system with a reporter gene, and then regulation of the target endogenous gene is tested in cells and in animals, both in vivo and ex vivo. The engineered TALE repeat array protein can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with the engineered TALE repeat array protein and compared to un-treated control samples, to examine the extent of modulation. For regulation of endogenous gene expression, the TALE repeat array protein ideally has a $K_D$ of 200 nM or less, more preferably 100 nM or less, more preferably 50 nM, most preferably 25 nM or less. The effects of the engineered TALE repeat array protein can be measured by examining any of the parameters described above. Any suitable gene expression, phenotypic, or physiological change can be used to assess the influence of the engineered TALE repeat array protein. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for regulation of endogenous gene expression can be performed in vitro. In one in vitro assay format, the engineered TALE repeat array protein regulation of endogenous gene expression in cultured cells is measured by examining protein production using an ELISA assay. The test sample is compared to control cells treated with an empty vector or an unrelated TALE repeat array protein that is targeted to another gene.

In another embodiment, regulation of endogenous gene expression is determined in vitro by measuring the level of target gene mRNA expression. The level of gene expression is measured using amplification, e.g., using RT-PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or beta-galactosidase. The reporter construct is typically co-transfected into a cultured cell. After treatment with the TALE repeat array protein, the amount of reporter gene transcription, translation, or activity is measured according to standard techniques known to those of skill in the art.

Another example of an assay format useful for monitoring regulation of endogenous gene expression is performed in vivo. This assay is particularly useful for examining TALE repeat array proteins that inhibit expression of tumor promoting genes, genes involved in tumor support, such as neovascularization (e.g., VEGF), or that activate tumor suppressor genes such as p53. In this assay, cultured tumor cells expressing the engineered TALE protein are injected subcutaneously into an immune compromised mouse such as an athymic mouse, an irradiated mouse, or a SCID mouse. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals can also be used for examining regulation of endogenous gene expression in vivo. Transgenic animals can express the engineered TALE repeat array protein. Alternatively, animals that transiently express the engineered TALE repeat array protein, or to which the engineered TALE repeat array protein has been administered in a delivery vehicle, can be used. Regulation of endogenous gene expression is tested using any one of the assays described herein.

Use of Engineered TALE Repeat-Containing Proteins in Gene Therapy

The engineered proteins of the present invention can be used to regulate gene expression or alter gene sequence in gene therapy applications in the same. Similar methods have been described for synthetic zinc finger proteins, see for example U.S. Pat. No. 6,511,808, U.S. Pat. No. 6,013,453, U.S. Pat. No. 6,007,988, U.S. Pat. No. 6,503,717, U.S. patent application 2002/0164575, and U.S. patent application 2002/0160940.

Conventional viral and non-viral based gene transfer methods can be used to introduce nucleic acids encoding the engineered TALE repeat array protein into mammalian cells or target tissues. Such methods can be used to administer nucleic acids encoding engineered TALE repeat array proteins to cells in vitro. Preferably, the nucleic acids encoding the engineered TALE repeat array proteins are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, 1992, Science, 256:808-813; Nabel & Felgner, 1993, TIBTECH, 11:211-217; Mitani & Caskey, 1993, TIBTECH, 11:162-166; Dillon, 1993, TIBTECH, 11:167-175; Miller, 1992, Nature, 357:455-460; Van Brunt, 1988, Biotechnology, 6:1149-54; Vigne, 1995, Restorat. Neurol. Neurosci., 8:35-36; Kremer & Perricaudet, 1995, Br. Med. Bull., 51:31-44; Haddada et al., in Current Topics in Microbiology and Immunology Doerfler and Bohm (eds) (1995); and Yu et al., 1994, Gene Ther., 1:13-26.

Methods of non-viral delivery of nucleic acids encoding the engineered TALE repeat array proteins include lipofection, microinjection, biolistics, virosomes, liposomes, immunoliposomes, polycation or lipid:nucleic acid conjugates, naked DNA or RNA, artificial virions, and agent-enhanced uptake of DNA or RNA. Lipofection is described in e.g., U.S. Pat. No. 5,049,386, No. 4,946,787; and No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, 1995, Science, 270:404-410; Blaese et al., 1995, Cancer Gene Ther., 2:291-297; Behr et al., 1994, Bioconjugate Chem. 5:382-389; Remy et al., 1994, Bioconjugate Chem., 5:647-654; Gao et al., Gene Ther., 2:710-722; Ahmad et al., 1992, Cancer Res., 52:4817-20; U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding the engineered TALE repeat array proteins takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of TALE repeat array proteins could include retroviral, lentivirus, adenoviral, adeno-associated, Sendai, and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., 1992, J. Virol., 66:2731-39; Johann et al., 1992, J. Virol., 66:1635-40; Sommerfelt et al., 1990, Virololgy, 176: 58-59; Wilson et al., 1989, J. Virol., 63:2374-78; Miller et al., 1991, J. Virol., 65:2220-24; WO 94/26877).

In applications where transient expression of the engineered TALE repeat array protein is preferred, adenoviral based systems can be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., 1987, Virology 160:38-47; U.S. Pat. No. 4,797,368; WO 93/24641; Kotin, 1994, Hum. Gene Ther., 5:793-801; Muzyczka, 1994, J. Clin. Invest., 94:1351). Construction of recombinant AAV vectors are described in a number of publications, including U.S. Pat. No. 5,173,414; Tratschin et al., 1985, Mol. Cell. Biol. 5:3251-60; Tratschin et al., 1984, Mol. Cell. Biol., 4:2072-81; Hermonat & Muzyczka, 1984, Proc. Natl. Acad. Sci. USA, 81:6466-70; and Samulski et al., 1989, J. Virol., 63:3822-28.

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., 1995, Blood, 85:3048; Kohn et al., 1995, Nat. Med., 1:1017; Malech et al., 1997, Proc. Natl. Acad. Sci. USA, 94:12133-38). PA317/pLASN was the first therapeutic vector used in a gene therapy trial. (Blaese et al., 1995, Science, 270:475-480). Transduction efficiencies of 50% or greater have been observed for MFG-S packaged vectors (Ellem et al., 1997, Immunol Immunother., 44:10-20; Dranoff et al., 1997, Hum. Gene Ther., 1:111-112).

Recombinant adeno-associated virus vectors (rAAV) are a promising alternative gene delivery systems based on the defective and nonpathogenic parvovirus adeno-associated type 2 virus. Typically, the vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., 1998, Lancet, 351:1702-1703; Kearns et al., 1996, Gene Ther., 9:748-55).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., 1998, Hum. Gene Ther. 7:1083-89). Additional examples of the use of adenovirus vectors for gene transfer in clinical trials include Rosenecker et al., 1996, Infection, 24:15-10; Sterman et al., 1998, Hum. Gene Ther., 9:7 1083-89; Welsh et al., 1995, Hum. Gene Ther., 2:205-218; Alvarez et al., 1997, Hum. Gene Ther. 5:597-613; Topf et al., 1998, Gene Ther., 5:507-513; Sterman et al., 1998, Hum. Gene Ther., 7:1083-89.

Packaging cells are used to form virus particles that are capable of infecting a host cell. Such cells include 293 cells, which package adenovirus, and T2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., 1995, Proc. Natl. Acad. Sci. USA, 92:9747-51, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)), followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with nucleic acid (gene or cDNA), encoding the engineered TALE repeat array protein, and re-infused back into the subject organism (e.g., patient). Various cell types suitable for ex vivo transfection are well known to those of skill in the art (see, e.g., Freshney et al., Culture of Animal Cells, A Manual of Basic Technique (5th ed. 2005)) and the references cited therein for a discussion of how to isolate and culture cells from patients).

In one embodiment, stem cells (e.g., universal donor hematopoietic stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004)) are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma and TNF-alpha are known (see Inaba et al., 1992, J. Exp. Med., 176:1693-1702).

Stem cells can be isolated for transduction and differentiation using known methods. For example, stem cells can be isolated from bone marrow cells by panning the bone marrow cells with antibodies which bind unwanted cells, such as CD4+ and CD8+(T cells), CD45+ (panB cells), GR-1 (granulocytes), and lad (differentiated antigen presenting cells) (see Inaba et al., 1992, J. Exp. Med., 176:1693-1702).

Vectors (e.g., retroviruses, adenoviruses, liposomes, etc.) containing nucleic acids encoding the engineered TALE repeat array protein can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Alternatively, stable formulations of the engineered TALE repeat array protein can also be administered.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington: The Science and Practice of Pharmacy, 21st ed., 2005).

Delivery Vehicles

An important factor in the administration of polypeptide compounds, such as the engineered TALE repeat array proteins of the present invention, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as engineered TALE repeat array protein across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, Curr. Opin. Neurobiol., 6:629-634). Another subsequence, the h (hydrophobic) domain of signal peptides, was found to have similar cell membrane translocation characteristics (see, e.g., Lin et al., 1995, J. Biol. Chem., 270:14255-58).

Examples of peptide sequences that can be linked to a protein, for facilitating uptake of the protein into cells, include, but are not limited to: peptide fragments of the tat protein of HIV (Endoh et al., 2010, Methods Mol. Biol., 623:271-281; Schmidt et al., 2010, FEBS Lett., 584:1806-13; Futaki, 2006, Biopolymers, 84:241-249); a 20 residue peptide sequence which corresponds to amino acids 84-103 of the p16 protein (see Fahraeus et al., 1996, Curr. Biol., 6:84); the third helix of the 60-amino acid long homeodomain of Antennapedia (Derossi et al., 1994, J. Biol. Chem., 269:10444); the h region of a signal peptide, such as the Kaposi fibroblast growth factor (K-FGF) h region (Lin et al., supra); or the VP22 translocation domain from HSV (Elliot & O'Hare, 1997, Cell, 88:223-233). See also, e.g., Caron et al., 2001, Mol Ther., 3:310-318; Langel, Cell-Penetrating Peptides: Processes and Applications (CRC Press, Boca Raton Fla. 2002); El-Andaloussi et al., 2005, Curr. Pharm. Des., 11:3597-3611; and Deshayes et al., 2005, Cell. Mol. Life Sci., 62:1839-49. Other suitable chemical moieties that provide enhanced cellular uptake can also be chemically linked to TALE repeat array proteins described herein.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., 1993, J. Biol. Chem., 268:3334-41; Perelle et al., 1993, Infect. Immun., 61:5147-56; Stenmark et al., 1991, J. Cell Biol., 113:1025-32; Donnelly et al., 1993, Proc. Natl. Acad. Sci. USA, 90:3530-34; Carbonetti et al., 1995, Abstr. Annu. Meet. Am. Soc. Microbiol. 95:295; Sebo et al., 1995, Infect. Immun., 63:3851-57; Klimpel et al., 1992, Proc. Natl. Acad. Sci. USA, 89:10277-81; and Novak et al., 1992, J. Biol. Chem., 267:17186-93).

Such subsequences can be used to translocate engineered TALE repeat array proteins across a cell membrane. The engineered TALE repeat array proteins can be conveniently fused to or derivatized with such sequences. Typically, the translocation sequence is provided as part of a fusion protein. Optionally, a linker can be used to link the engineered TALE repeat array protein and the translocation sequence. Any suitable linker can be used, e.g., a peptide linker.

The engineered TALE repeat array protein can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., the engineered TALE repeat array protein.

The liposome fuses with the plasma membrane, thereby releasing the compound into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (e.g., the engineered TALE repeat array protein or a nucleic acid encoding the same) at the target tissue or cell. For systemic or tissue specific delivery, this can be accomplished, for example, in a passive manner wherein the liposome bilayer degrades over time through the action of various agents in the body. Alternatively, active compound release involves using an agent to induce a permeability change in the liposome vesicle. Liposome membranes can be constructed so that they become destabilized when the environment becomes acidic near the liposome membrane (see, e.g., Proc. Natl. Acad. Sci. USA, 84:7851 (1987); Biochemistry, 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise the engineered TALE repeat array protein and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., 1980, Annu. Rev. Biophys. Bioeng., 9:467, U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication. No. WO 91/17424, Deamer & Bangham, 1976, Biochim. Biophys. Acta, 443: 629-634; Fraley, et al., 1979, Proc. Natl. Acad. Sci. USA, 76:3348-52; Hope et al., 1985, Biochim. Biophys. Acta, 812:55-65; Mayer et al., 1986, Biochim. Biophys. Acta, 858:161-168; Williams et al., 1988, Proc. Natl. Acad. Sci. USA, 85:242-246; Liposomes (Ostro (ed.), 1983, Chapter 1); Hope et al., 1986, Chem. Phys. Lip., 40:89; Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or overexpression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., 1990, J. Biol. Chem., 265:16337-42 and Leonetti et al., 1990, Proc. Natl. Acad. Sci. USA, 87:2448-51).

Dosages

For therapeutic applications, the dose of the engineered TALE repeat array protein to be administered to a patient is calculated in a similar way as has been described for zinc finger proteins, see for example U.S. Pat. No. 6,511,808, U.S. Pat. No. 6,492,117, U.S. Pat. No. 6,453,242, U.S. patent application 2002/0164575, and U.S. patent application 2002/0160940. In the context of the present disclosure, the dose should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy, specificity, and $K_D$ of the particular engineered TALE repeat array protein employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

Pharmaceutical Compositions and Administration

Appropriate pharmaceutical compositions for administration of the engineered TALE repeat array proteins of the present invention can be determined as described for zinc finger proteins, see for example U.S. Pat. No. 6,511,808, U.S. Pat. No. 6,492,117, U.S. Pat. No. 6,453,242, U.S. patent application 2002/0164575, and U.S. patent application 2002/0160940. Engineered TALE repeat array proteins, and expression vectors encoding engineered TALE repeat array proteins, can be administered directly to the patient for modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by TALE repeat array protein-mediated gene therapy include pathogenic bacteria, e.g., *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria; infectious fungus, e.g., *Aspergillus, Candida* species; protozoa such as sporozoa (e.g., Plasmodia), rhizopods (e.g., *Entamoeba*) and flagellates (*Trypanosoma, Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing TALE repeat array proteins into ultimate contact with the tissue to be treated. The TALE repeat array proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington: The Science and Practice of Pharmacy, 21st ed., 2005).

The engineered TALE repeat array proteins, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Use of TALE Nucleases

TALE nucleases engineered using the methods described herein can be used to induce mutations in a genomic sequence, e.g., by cleaving at two sites and deleting sequences in between, by cleavage at a single site followed by non-homologous end joining, and/or by cleaving at a site so as to remove or replace one or two or a few nucleotides. In some embodiments, the TALE nuclease is used to induce mutation in an animal, plant, fungal, or bacterial genome. Targeted cleavage can also be used to create gene knockouts (e.g., for functional genomics or target validation) and to facilitate targeted insertion of a sequence into a genome (i.e., gene knock-in); e.g., for purposes of cell engineering or protein overexpression. Insertion can be by means of replacements of chromosomal sequences through homologous recombination or by targeted integration, in which a new sequence (i.e., a sequence not present in the region of interest), flanked by sequences homologous to the region of interest in the chromosome, is used to insert the new sequence at a predetermined target site via homologous recombination. Exogenous DNA can also be inserted into TALE nuclease-induced double stranded breaks without the need for flanking homology sequences (see, Orlando et al., 2010, Nucl. Acids Res., 1-15, doi:10.1093/nar/gkq512).

As demonstrated in Example 3 below, the TALE nucleases produced by the methods described herein were capable of inducing site-specific mutagenesis in mammalian cells. A skilled practitioner will readily appreciate that TALE nucleases produced by the methods described herein would also function to induce efficient site-specific mutagenesis in other cell types and organisms (see, for example, Cade et al., 2012, Nucleic Acids Res., PMID: 22684503 and Moore et al., 2012, PLoS One, PMID: 22655075).

The same methods can also be used to replace a wild-type sequence with a mutant sequence, or to convert one allele to a different allele.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. Non-limiting examples of viruses or viral receptors that can be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors can be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Bimaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tickborne encephalitis viruses. See, e.g., Virology, 3rd Edition (W. K. Joklik, ed. 1988); Fundamental Virology, 4th Edition (Knipe and Howley, eds. 2001), for a description of these and other viruses. Receptors for HIV, for example, include CCR-5 and CXCR-4.

In similar fashion, the genome of an infecting bacterium can be mutagenized by targeted DNA cleavage followed by non-homologous end joining, to block or ameliorate bacterial infections.

The disclosed methods for targeted recombination can be used to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, Fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefelter's syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g., Hunter's disease, Hurler's disease), hemoglobinopathies (e.g., sickle cell diseases, HbC, alpha-thalassemia, beta-thalassemia) and hemophilias.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064. Treated stem cells can be returned to a patient for treatment of various diseases including, but not limited to, SCID and sickle-cell anemia.

In many of these cases, a region of interest comprises a mutation, and the donor polynucleotide comprises the corresponding wild-type sequence. Similarly, a wild-type genomic sequence can be replaced by a mutant sequence, if such is desirable. For example, overexpression of an oncogene can be reversed either by mutating the gene or by replacing its control sequences with sequences that support a lower, non-pathologic level of expression. As another example, the wild-type allele of the ApoAI gene can be replaced by the ApoAI Milano allele, to treat atherosclerosis. Indeed, any pathology dependent upon a particular genomic sequence, in any fashion, can be corrected or alleviated using the methods and compositions disclosed herein.

Targeted cleavage and targeted recombination can also be used to alter non-coding sequences (e.g., sequences encoding microRNAs and long non-coding RNAs, and regulatory sequences such as promoters, enhancers, initiators, terminators, splice sites) to alter the levels of expression of a gene product. Such methods can be used, for example, for therapeutic purposes, functional genomics and/or target validation studies.

The compositions and methods described herein also allow for novel approaches and systems to address immune reactions of a host to allogeneic grafts. In particular, a major problem faced when allogeneic stem cells (or any type of allogeneic cell) are grafted into a host recipient is the high risk of rejection by the host's immune system, primarily mediated through recognition of the Major Histocompatibility Complex (MHC) on the surface of the engrafted cells. The MHC comprises the HLA class I protein(s) that function as heterodimers that are comprised of a common beta subunit and variable alpha subunits. It has been demonstrated that tissue grafts derived from stem cells that are devoid of HLA escape the host's immune response. See, e.g., Coffman et al., 1993, J. Immunol., 151:425-35; Markmann et al., 1992, Transplantation, 54:1085-89; Koller et al., 1990, Science, 248:1227-30. Using the compositions and methods described herein, genes encoding HLA proteins involved in graft rejection can be cleaved, mutagenized or altered by recombination, in either their coding or regulatory sequences, so that their expression is blocked or they express a non-functional product. For example, by inactivating the gene encoding the common beta subunit gene (beta2 microglobulin) using TALE nuclease fusion proteins as described herein, HLA class I can be removed from the cells to rapidly and reliably generate HLA class I null stem cells from any donor, thereby reducing the need for closely matched donor/recipient MHC haplotypes during stem cell grafting.

Inactivation of any gene (e.g., the beta2 microglobulin gene) can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, or by targeted recombination of an irrelevant sequence (i.e., a "stuffer" sequence) into the gene or its regulatory region, so as to disrupt the gene or regulatory region.

Targeted modification of chromatin structure, as disclosed in WO 01/83793, can be used to facilitate the binding of fusion proteins to cellular chromatin.

In additional embodiments, one or more fusions between a TALE binding domain and a recombinase (or functional fragment thereof) can be used, in addition to or instead of the TALE-cleavage domain fusions disclosed herein, to facilitate targeted recombination. See, for example, co-owned U.S. Pat. No. 6,534,261 and Akopian et al. (2003) Proc. Natl. Acad. Sci. USA 100:8688-8691.

In additional embodiments, the disclosed methods and compositions are used to provide fusions of TALE repeat DNA-binding domains with transcriptional activation or repression domains that require dimerization (either homodimerization or heterodimerization) for their activity. In these cases, a fusion polypeptide comprises a TALE repeat DNA-binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

Regulation of Gene Expression in Plants

Engineered TALE repeat array proteins can be used to engineer plants for traits such as increased disease resistance, modification of structural and storage polysaccharides, flavors, proteins, and fatty acids, fruit ripening, yield, color, nutritional characteristics, improved storage capability, and the like. In particular, the engineering of crop species for enhanced oil production, e.g., the modification of the fatty acids produced in oilseeds, is of interest.

Seed oils are composed primarily of triacylglycerols (TAGs), which are glycerol esters of fatty acids. Commercial production of these vegetable oils is accounted for primarily by six major oil crops (soybean, oil palm, rapeseed, sunflower, cotton seed, and peanut). Vegetable oils are used predominantly (90%) for human consumption as margarine, shortening, salad oils, and frying oil. The remaining 10% is used for non-food applications such as lubricants, oleochemicals, biofuels, detergents, and other industrial applications.

The desired characteristics of the oil used in each of these applications varies widely, particularly in terms of the chain length and number of double bonds present in the fatty acids making up the TAGs. These properties are manipulated by the plant in order to control membrane fluidity and temperature sensitivity. The same properties can be controlled using TALE repeat array proteins to produce oils with improved characteristics for food and industrial uses.

The primary fatty acids in the TAGs of oilseed crops are 16 to 18 carbons in length and contain 0 to 3 double bonds. Palmitic acid (16:0 [16 carbons: 0 double bonds]), oleic acid (18:1), linoleic acid (18:2), and linolenic acid (18:3) predominate. The number of double bonds, or degree of saturation, determines the melting temperature, reactivity, cooking performance, and health attributes of the resulting oil.

The enzyme responsible for the conversion of oleic acid (18:1) into linoleic acid (18:2) (which is then the precursor for 18:3 formation) is delta-12-oleate desaturase, also referred to as omega-6 desaturase. A block at this step in the fatty acid desaturation pathway should result in the accumulation of oleic acid at the expense of polyunsaturates.

In one embodiment engineered TALE repeat array proteins are used to regulate expression of the FAD2-1 gene in soybeans. Two genes encoding microsomal delta-6 desaturases have been cloned recently from soybean, and are referred to as FAD2-1 and FAD2-2 (Heppard et al., 1996, Plant Physiol. 110:311-319). FAD2-1 (delta-12 desaturase) appears to control the bulk of oleic acid desaturation in the soybean seed. Engineered TALE repeat array proteins can thus be used to modulate gene expression of FAD2-1 in plants. Specifically, engineered TALE repeat array proteins can be used to inhibit expression of the FAD2-1 gene in soybean in order to increase the accumulation of oleic acid (18:1) in the oil seed. Moreover, engineered TALE proteins can be used to modulate expression of any other plant gene, such as delta-9 desaturase, delta-12 desaturases from other plants, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, polygalacturonase, EPSP synthase, plant viral genes, plant fungal pathogen genes, and plant bacterial pathogen genes.

Recombinant DNA vectors suitable for transformation of plant cells are also used to deliver protein (e.g., engineered TALE repeat array protein)-encoding nucleic acids to plant cells. Techniques for transforming a wide variety of higher plant species are well known and described in the technical and scientific literature (see, e.g., Weising et al., 1988, Ann. Rev. Genet., 22:421-477). A DNA sequence coding for the desired TALE repeat array protein is combined with transcriptional and translational initiation regulatory sequences which will direct the transcription of the TALE protein in the intended tissues of the transformed plant.

For example, a plant promoter fragment can be employed which will direct expression of the engineered TALE repeat array protein in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35 S transcription initiation region, the 1'- or 2'-promoter derived from T-DNA of *Agrobacterium tumefaciens*, and other transcription initiation regions from various plant genes known to those of skill.

Alternatively, the plant promoter can direct expression of the engineered TALE repeat array protein in a specific tissue or can be otherwise under more precise environmental or developmental control. Such promoters are referred to here as "inducible" promoters. Examples of environmental conditions that can affect transcription by inducible promoters include anaerobic conditions or the presence of light.

Examples of promoters under developmental control include promoters that initiate transcription only in certain tissues, such as fruit, seeds, or flowers. For example, the use of a polygalacturonase promoter can direct expression of the TALE repeat array protein in the fruit, a CHS-A (chalcone synthase A from *petunia*) promoter can direct expression of the TALE repeat array protein in the flower of a plant.

The vector comprising the TALE repeat array protein sequences will typically comprise a marker gene which confers a selectable phenotype on plant cells. For example, the marker can encode biocide resistance, particularly antibiotic resistance, such as resistance to kanamycin, G418, bleomycin, hygromycin, or herbicide resistance, such as resistance to chlorosulfuron or Basta.

Such DNA constructs can be introduced into the genome of the desired plant host by a variety of conventional techniques. For example, the DNA construct can be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., 1984, EMBO J., 3:2717-22. Electroporation techniques are described in Fromm et al. 1985, Proc. Natl. Acad. Sci. USA, 82:5824. Biolistic transformation techniques are described in Klein et al., 1987, Nature, 327:70-73.

*Agrobacterium tumefaciens*-meditated transformation techniques are well described in the scientific literature (see, e.g., Horsch et al., 1984, Science, 233:496-498; and Fraley et al., 1983, Proc. Natl. Acad. Sci. USA, 80:4803).

Transformed plant cells which are derived by any of the above transformation techniques can be cultured to regenerate a whole plant which possesses the transformed genotype and thus the desired TALE repeat array protein-controlled phenotype. Such regeneration techniques rely on manipulation of certain phytohormones in a tissue culture growth medium, typically relying on a biocide and/or herbicide marker which has been introduced together with the TALE repeat array protein nucleotide sequences. Plant regeneration from cultured protoplasts is described in Evans et al., Protoplasts Isolation and Culture, Handbook of Plant Cell Culture, pp. 124-176 (1983); and Binding, Regeneration of Plants, Plant Protoplasts, pp. 21-73 (1985). Regeneration can also be obtained from plant callus, explants, organs, or parts thereof. Such regeneration techniques are described generally in Klee et al., 1987, Ann. Rev. Plant Phys., 38:467-486.

Functional Genomics Assays

Engineered TALE repeat array proteins also have use for assays to determine the phenotypic consequences and function of gene expression. Recent advances in analytical techniques, coupled with focused mass sequencing efforts have created the opportunity to identify and characterize many more molecular targets than were previously available. This new information about genes and their functions will improve basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. Many differentially expressed genes correlate with a given physiological phenomenon, but demonstrating a causative relationship between an individual differentially expressed gene and the phenomenon is labor intensive. Until now, simple methods for assigning function to differentially expressed genes have not kept pace with the ability to monitor differential gene expression.

The engineered TALE repeat array proteins described herein can be used to rapidly analyze the function of a differentially expressed gene. Engineered TALE proteins can be readily used to up or down-regulate or knockout any endogenous target gene, or to knock in an endogenous or endogenous gene. Very little sequence information is required to create a gene-specific DNA binding domain. This makes the engineered TALE repeat array technology ideal for analysis of long lists of poorly characterized differentially expressed genes. One can simply build a TALE repeat array protein-based DNA binding domain for each candidate gene, create chimeric up and down-regulating artificial transcription factors and test the consequence of up or down-regulation on the phenotype under study (e.g., transformation or response to a cytokine) by switching the candidate genes on or off one at a time in a model system.

Additionally, greater experimental control can be imparted by engineered TALE repeat array proteins than can be achieved by more conventional methods. This is because the production and/or function of engineered TALE repeat array proteins can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any endogenous gene of interest or any transgene by placing the function and/or expression of a engineered TALE repeat array protein under small molecule control.

Transgenic Animals

A further application of engineered TALE repeat array proteins is manipulating gene expression in animal models. As with cell lines, the introduction of a heterologous gene into or knockout of an endogenous in a transgenic animal, such as a transgenic mouse or zebrafish, is a fairly straightforward process. Thus, transgenic or transient expression of an engineered TALE repeat array protein in an animal can be readily performed.

By transgenically or transiently expressing a suitable engineered TALE repeat array protein fused to an activation domain, a target gene of interest can be over-expressed. Similarly, by transgenically or transiently expressing a suitable engineered TALE repeat array protein fused to a repressor or silencer domain, the expression of a target gene of interest can be down-regulated, or even switched off to create "functional knockout". Knock-in or knockout mutations by insertion or deletion of a target gene of interest can be prepared using TALE nucleases.

Two common issues often prevent the successful application of the standard transgenic and knockout technology; embryonic lethality and developmental compensation. Embryonic lethality results when the gene plays an essential role in development. Developmental compensation is the substitution of a related gene product for the gene product being knocked out, and often results in a lack of a phenotype in a knockout mouse when the ablation of that gene's function would otherwise cause a physiological change.

Expression of transgenic engineered TALE repeat array proteins can be temporally controlled, for example using small molecule regulated systems as described in the previous section. Thus, by switching on expression of an engineered TALE repeat array protein at a desired stage in development, a gene can be over-expressed or "functionally knocked-out" in the adult (or at a late stage in development), thus avoiding the problems of embryonic lethality and developmental compensation.

EXAMPLES

Example 1. Assembly of TALE Repeat Arrays Using Streptavidin Coated Magnetic Beads An archive of DNA plasmids (~850 different plasmids) encoding one, two, three, or four TALE repeat domains was created for assembly of nucleic acids encoding multiple TALE arrays of any desired length. The plasmids were created by cloning synthetic arrays of one, two, three or four TALE repeat domains into the pUC57-ΔBsaI backbone (FIG. 3). The TALE repeats were of the arrangement α, βγδε, βγδ, βγ', βγ, δε', and ε, and included hypervariable triplet residues at each position to bind to the nucleotides as shown in Table 1. Polypeptide and nucleotide sequences of the TALE repeat types are shown in FIGS. 4A and 4B, respectively. The polypeptide and polynucleotide sequences were varied slightly among the four types to reduce the possibility of recombination-mediated mutations due to long sequences of exact repeats.

TABLE 1

| Nucleotide binding code of TALE triplets | |
|---|---|
| Triplet | Bound Nucleotide |
| SNI | A |
| SHD | C |
| NNN | G |
| SNK | G |
| SNG | T |

A 16-mer TALE repeat array targeted to the eGFP gene was created by in vitro assembly of 16 TALE repeats designed to bind the target sequence GCAGTGCTTCAGC-CGC (SEQ ID NO: 41). In the first step, a plasmid carrying an α-type TALE repeat with an NNN triplet (G) was amplified by PCR using a biotinylated forward primer Biotin-TCTAGAGAAGACAAGAACCTGACC (SEQ ID NO: 42) and a reverse primer GGATCCGGTCTCT-TAAGGCCGTGG (SEQ ID NO: 43). The amplified fragment (50 µl) was purified using a QIA Quick PCR purification kit (QIAGEN), eluted in 40 µl 0.1× elution buffer (as provided in the QIA Quick PCR purification kit), and digested with BsaI HF (New England Biolabs (NEB)) in NEB Buffer 4 for 15 minutes at 50° C. (40 µl elution, 5 µl NEBuffer 4, 5 µl BsaI HF). The digested fragment was purified using a QIA Quick PCR purification kit and eluted in 0.1× elution buffer (50 µl).

A plasmid containing a four TALE repeat domain subarray unit (βγδε) coding for repeats that each harbor one of the following variable amino acids SHD, SNI, NNN, and SNG (designed to bind the sequence 5'-CAGT-3') was digested with BbsI (NEB) in NEBuffer 2 for 2 hours at 37° C. in 100 µl (50 µl plasmid [~200 ng/µl], 10 µl NEBuffer 2, 10 µl BbsI, 30 µl water). To the 100 µl digest was added 25 µl NEBuffer 4, 2.5 µl 100λ BSA (NEB), 107.5 µl water, and 5 µl XbaI (NEB), and the digest was incubated for 5 minutes at 37° C. To the mixture, 5 µl of BamHI HF was then added for a 5 minute digest at 37° C., and then 5 µl SalI HF (NEB) was added for an additional 5 minute digest at 37° C. The resulting fragment was purified using a QIA Quick PCR purification kit (QIAGEN) and eluted in 180 µl 0.1× elution buffer.

For the initial ligation, 2 µl of the alpha unit digest was mixed with 2.5 µl of T4 DNA ligase (400 U/µl, NEB) and 27 µl Quick Ligase Buffer (QLB) (NEB). To this 31.5 µl mixture was added 22.5 µl of the first digested subarray, and the mixture was ligated for 15 minutes at room temperature. Magnetic beads were prepared by washing 5 µl of Dynabeads MyOne Streptavidin C1 (Invitrogen) three times with 50 µl 1× B&W Buffer (5.0 mM Tris-HCl [pH 7.5], 0.5 mM EDTA, 1.0 M NaCl, 0.005% Tween 20) and resuspending in 54 µl B&W Buffer. The ligated mixture was added to the washed beads and incubated for 15 minutes at room temperature (with mixing every five minutes). The mixture was then placed on a SPRIplate 96-well Ring magnet for 3 minutes. The supernatant was then aspirated, and 100 µl 1× B&W Buffer was added to wash, with mixing by moving the beads 31 times from side to side within the tube using a DynaMag-96 Side magnet (Invitrogen). The B&W Buffer was then aspirated, and 100 µl 1×BSA was added, with mixing, then aspirated. The ligated, bead-bound nucleic acids (αβγδc) were resuspended in 50 µl BsaI HF mix (5 µl NEBuffer 4, 2 µl BsaI HF, 43 µl water).

The digest was incubated at 50° C. for 10 minutes, and 50 µl 1× B&W buffer was added. The digest was placed on a magnet for 3 minutes, and the supernatant was aspirated.

The beads were washed with 100 μl 1× B&W Buffer and 100 μl 1×BSA as above. To the washed beads were added a digested plasmid containing a four TALE repeat domain sub-array unit (βγδε) coding for repeats that each harbor one of the following variable amino acids NNN, SHD, SNG, and SNG (designed to bind the DNA sequence 5'-GCTT-3') (22.5 μl) and 27.5 μl ligase mix (25 μl Quick Ligase Buffer, 2 μl DNA ligase). The beads were resuspended by pipetting up and down, and the mixture was incubated for 15 minutes at room temperature with mixing every five minutes. To the ligation was added 50 μl 1× B&W Buffer, and the mixture was placed on the magnet for 3 minutes. The supernatant was aspirated, and the beads were washed with 100 μl 1× B&W Buffer and 100 μl 1×BSA as above. The ligated, bead-bound nucleic acids (αβγδεβγδε) were resuspended in 50 μl BsaI HF mix (5 μl NEBuffer 4, 2 μl BsaI HF, 43 μl water). Two more TALE repeat sub-array units were ligated sequentially as above, the first a four TALE repeat sub-array unit (βγδε) coding for repeats that each harbor one of the following variable amino acids SHD, SNI, NNN, and SHD (designed to bind the DNA sequence 5'-CAGC-3') and the second a three TALE repeat sub-array unit (βγδ) coding for repeats that each harbor one of the following variable amino acids SHD, NNN, and SHD (designed to bind the DNA sequence 5'-CGC-3'). The final TALE repeat array contained subunits of the format αβγδεβγδεβγδεβγδ with individual TALE repeats designed to bind the target DNA sequence 5'-GCAGTGCTTCAGCCGC-3' (SEQ ID NO: 44).

Following the final ligation step, the construct was digested with BsaI HF for eventual cloning into an expression vector and the beads were washed with 1× B&W Buffer and 1×BSA. The washed beads were resuspended in 50 μl BbsI mix (5 μl NEBuffer 2, 5 μl BbsI, 40 μl water) and incubated at 37° C. for 2 hours with agitation at 1500 rpm to cleave the biotinylated 5' end and release the assembled TALE repeat array from the magnetic beads. The digested mixture was purified by MinElute column purified (QIAGEN) and ligated into a BsmBI-digested TALE expression vector. The ligated mixture was transformed into chemically competent XL1 Blue cells and plated on LB/Carb$^{100}$ plates overnight.

The expression vectors each harbor the following elements: a T7 promoter, a nuclear localization signal, a FLAG tag, amino acids 153 to 288 from the TALE13 protein (numbering as defined by Miller et al., 2011, Nat. Biotechnol., 29:143-148), two adjacent BsmBI restriction sites into which a DNA fragment encoding a TALE repeat array can be cloned, a 0.5 TALE repeat, amino acids 715 to 777 from the C-terminal end of the TALE13 protein (numbering as defined by Miller et al., 2011, Nat. Biotechnol., 29:143-148), and the wild-type FokI cleavage domain.

The plasmids differ in the identity of the C-terminal 0.5 TALE repeat. Plasmid pJDS70 encodes a 0.5 TALE repeat with a SNI RVD (for recognition of an A nucleotide), plasmid pJDS71 encodes a 0.5 TALE repeat with a SHD RVD (for recognition of a C nucleotide), plasmid pJDS74 encodes a 0.5 TALE repeat with a NNN RVD (for recognition of a G nucleotide), plasmid pJDS76 encodes a 0.5 TALE repeat with a SNK RVD (for recognition of a G nucleotide), and plasmid pJDS78 encodes a 0.5 TALE repeat with a NG RVD (for recognition of a T nucleotide). All plasmids share the common sequence shown in FIGS. 5A-5B and differ at just nine nucleotide positions marked as) XXXXXXXXX (underlined and bold). The sequence of these 9 bps and plasmid names are also shown below in Table 2.

TABLE 2

DNA sequences of expression vectors

| Plasmid name | Sequence of variable 9 bps | SEQ ID NO: | RVD of C-terminal 0.5 TALE repeat |
|---|---|---|---|
| pJDS70 | TCTAACATC | 45 | SNI (for binding to an A nucleotide) |
| pJDS71 | TCCCACGAC | 46 | SHD (for binding to a C nucleotide) |
| pJDS74 | AATAATAAC | 47 | NNN (for binding to a G nucleotide) |
| pJDS76 | TCCAATAAA | 48 | SNK (for binding to a G nucleotide) |
| pJDS78 | TCTAATGGG | 49 | SNG (for binding to a T nucleotide) |

This example demonstrates the construction of TALE repeat arrays on an immobilized substrate using preassembled TALE repeat sub-array units. The above method, up to the cloning step, can be performed in one day.

Example 2. Assembly of TALE Repeat Arrays Using a Streptavidin Coated Plate

TALE repeats are assembled using the archive of DNA plasmids (~850 different plasmids) as described in Example 1. A 16-mer TALE repeat array was created by in vitro assembly of 16 TALE repeats designed to bind a target sequence. In the first step, a plasmid carrying an α-type TALE repeat with an NNN triplet (G) was amplified by PCR using a biotinylated forward primer Biotin-TCTAGA-GAAGACAAGAACCTGACC (SEQ ID NO: 42) and a reverse primer GGATCCGGTCTCTTAAGGCCGTGG (SEQ ID NO: 43). The amplified fragment (50 μl) was purified using a QIA Quick PCR purification kit (QIAGEN), eluted in 40 μl 0.1× elution buffer (as provided in the QIA Quick PCR purification kit), and digested with BsaI HF (New England Biolabs (NEB)) in NEB Buffer 4 for 15 minutes at 50° C. (40 μl elution, 5 μl NEBuffer 4, 5 μl BsaI HF). The digested fragment was purified using a QIA Quick PCR purification kit and eluted in 0.1× elution buffer (50 μl).

A plasmid containing a four TALE repeat domain sub-array unit (βγδε) coding for repeats that each harbor one of the following variable amino acids SHD, SNI, NNN, and SNG (designed to bind the sequence 5'-CAGT-3') was digested with BbsI (NEB) in NEBuffer 2 for 2 hours at 37° C. in 100 μl (50 μl plasmid [~200 ng/μl], 10 μl NEBuffer 2, 10 μl BbsI, 30 μl water). To the 100 μl digest was added 25 μl NEBuffer 4, 2.5 μl 100×BSA (NEB), 107.5 μl water, and 5 μl XbaI (NEB), and the digest was incubated for 5 minutes at 37° C. To the mixture, 5 μl of BamHI HF was then added for a 5 minute digest at 37° C., and then 5 μl SalI HF (NEB) was added for an additional 5 minute digest at 37° C. The resulting fragment was purified using a QIA Quick PCR purification kit (QIAGEN) and eluted in 180 μl 0.1× elution buffer.

For the initial ligation, 2 μl of the alpha unit digest was mixed with 2.5 μl of T4 DNA ligase (400 U/μl; NEB) and 27 μl Quick Ligase Buffer (QLB) (NEB). To this 31.5 μl mixture was added 22.5 μl of the first digested subarray, and the mixture was ligated for 15 minutes at room temperature. The ligation mixture was then mixed with 2× B&@ buffer (Invitrogen) and added to a well in a 96-well plate coated with streptavidin (Thermo Scientific) and incubated at room temperature for 15 min. The supernatant was aspirated. Each well in the 96 well plate was washed with 200 µl of 1× Bovine Serum Albumin (BSA) by pipetting up and down 10 times before discarding the 1×BSA. This was repeated for a total of two washes with 1×BSA. Then 50 µl BsaI HF mix (5 µl NEBuffer 4, 2 µl BsaI HF, 43 µl water) was added to the ligated, nucleic acids (αβγδ) bound to the streptavidin-coated well.

The digest was incubated at 50° C. for 10 minutes and then the supernatant was aspirated. The wells were then washed with 200 µl 1× B&W Buffer and 200 µl 1×BSA twice by pipetting up and down ten times before removal of each supernatant. 22.5 µl of digested plasmid encoding a four TALE repeat domain sub-array unit (βγδε) coding for repeats that each harbor one of the following variable amino acids NNN, SHD, SNG, and SNI and 27.5 µl ligase mix (25 µl Quick Ligase Buffer, 2 µl DNA ligase) were added to the well. The supernatant was mixed by pipetting up and down, and the mixture was incubated for 15 minutes at room temperature. The supernatant was removed and the well was washed with 1× B&W and 1×BSA as above. Then 50 µl BsaI HF mix (5 µl NEBuffer 4, 2 µl BsaI HF, 43 µl water) was added to the ligated nucleic acids (αβγδεβγδε) bound to the well. Two more TALE repeat sub-array units were ligated sequentially as above, the first a four TALE repeat sub-array unit (βγδε) coding for repeats that each harbor one of the following variable amino acids SHD, SNI, NNN, and SNG and the second a three TALE repeat sub-array unit (βββ) coding for repeats that each harbor one of the following variable amino acids SHD, SNI, NNN, and SHD. The final TALE repeat array contained subunits of the format αβγδεβγδεβγδεβγδ with individual TALE repeats designed to bind a target DNA sequence.

Following the final ligation step, the fragments in the well were digested with BsaI HF for eventual cloning into an expression vector. The well was then washed with 1× B&W Buffer and twice with 1×BSA. Then 50 µl BbsI mix (5 µl NEBuffer 2, 5 µl BbsI, 40 µl water) was added to the well and incubated at 37° C. for 2 hours to cleave the biotinylated 5' end and release the assembled TALE repeat array from the well. The digested mixture was purified, ligated, and transformed as described in Example 1.

Example 3. Site-Specific Mutagenesis Using TALE Nucleases

Figure 6:
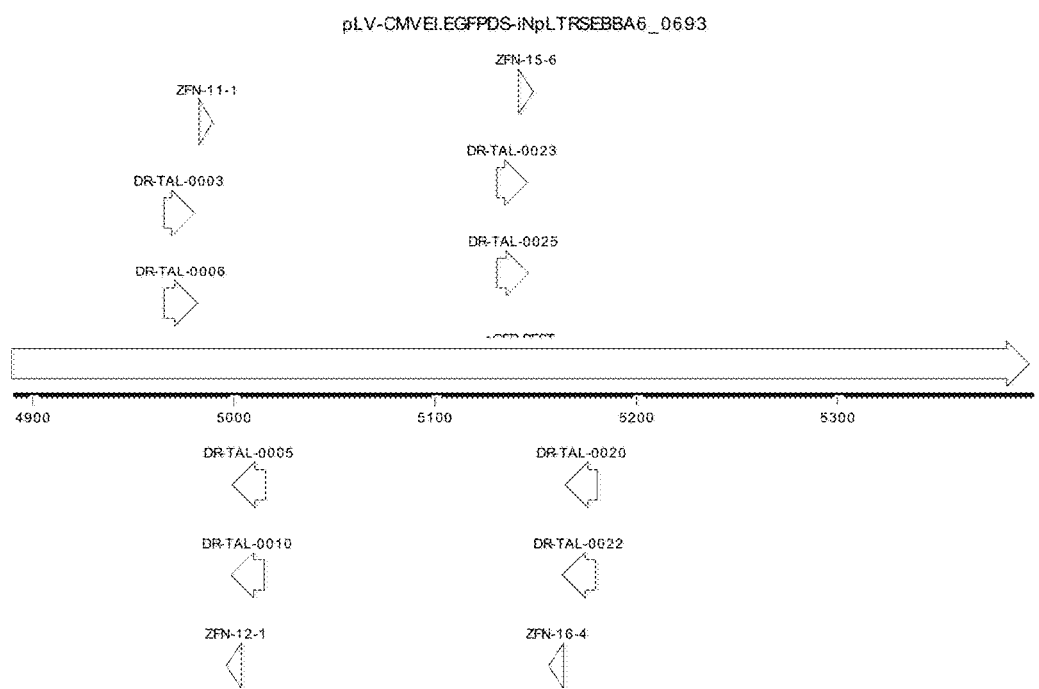
FIG. 6 is a schematic diagram of the enhanced green fluorescent protein (eGFP) gene and the location of the binding sites for synthetic TALE proteins described herein.

To demonstrate the effectiveness of TALE repeat domains created by the methods described herein, TALE repeat arrays were constructed and cloned into TALE nuclease expression vectors (as described in Example 1) to produce plasmids encoding TALE nuclease monomers targeted to the eGFP coding sequences shown in FIG. 6 and Table 3. Nucleic acid and polypeptide sequences of the TALE nuclease monomers are shown in FIGS. 11A-18B.

TABLE 3

TALE nuclease monomer target sequences

| TALE Fragment | Target Sequence | Length of target sequence | SEQ ID NO: | Site | Position (half-site) | Plasmid name |
| --- | --- | --- | --- | --- | --- | --- |
| DR-TALE-0003 | TGCAGTGCTTCAGCCGC | 17 | 50 | eGFP223 | left | SQT70 |
| DR-TALE-0006 | TGCAGTGCTTCAGCCGCT | 18 | 51 | eGFP223 | left | SQT114 |
| DR-TALE-0005 | TTGAAGAAGTCGTGCTGC | 18 | 52 | eGFP223 | right | SQT72 |
| DR-TALE-0010 | TGAAGAAGTCGTGCTGCT | 18 | 53 | eGFP223 | right | SQT56 |
| DR-TALE-0023 | TCGAGCTGAAGGGCATC | 17 | 54 | eGFP382 | left | SQT84 |
| DR-TALE-0025 | TCGAGCTGAAGGGCATCG | 18 | 55 | eGFP382 | left | SQT120 |
| DR-TALE-0020 | TTGTGCCCCAGGATGTTG | 18 | 56 | eGFP382 | right | SQT135 |
| DR-TALE-0022 | TGTGCCCCAGGATGTTGC | 18 | 57 | eGFP382 | right | SQT118 |

Figure 7:
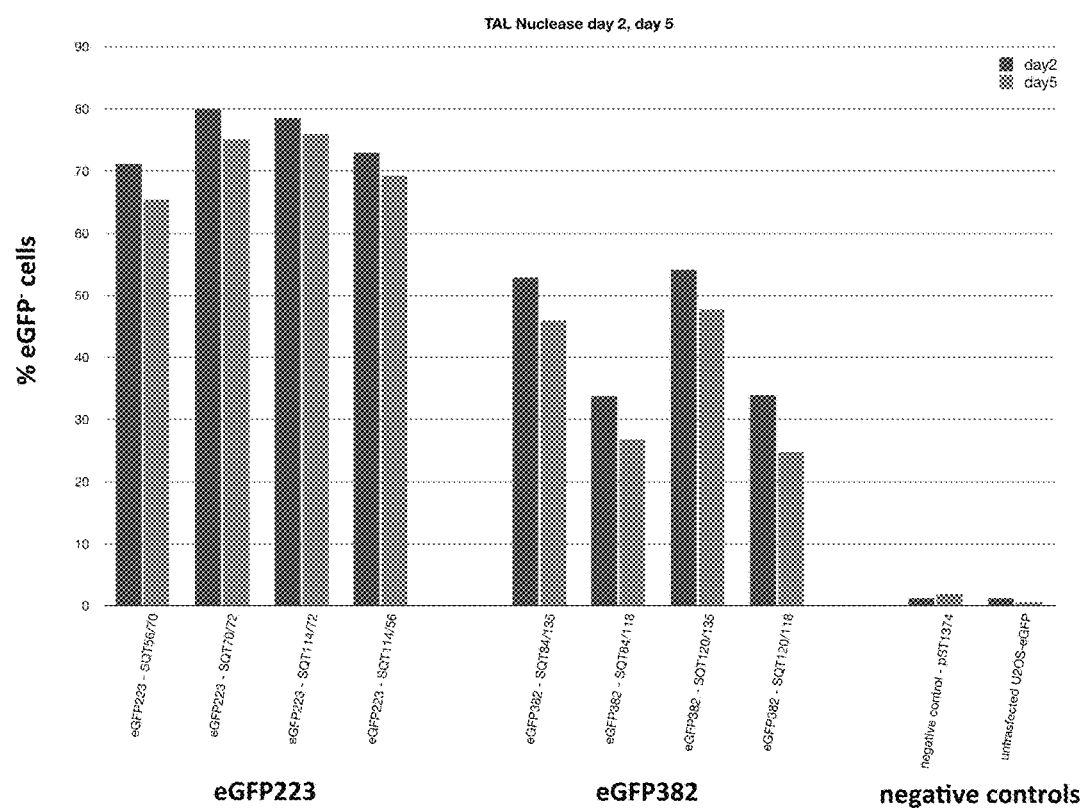
FIG. 7 is a bar graph depicting the % of TALE nuclease-modified, eGFP-negative cells at 2 and 5 days following transfection with plasmids encoding TALE nucleases designed to bind and cleave the eGFP reporter gene.

4E5 U2OS-eGFP cells were nucleofected with 400 ng plasmid DNA in solution SE with program DN-100 using Nucleofector™ non-viral transfection (Lonza, Walkersville, Md.). The cells were analyzed by flow cytometry at days 2 and 5 (FIG. 7). Non-homologous end joining (NHEJ)-mediated mutagenic repair of TALE nuclease-induced double-stranded breaks led to disruption of eGFP expression (eGFP-negative cells). All eight TALE nuclease pairs tested induced a high percentage of eGFP-negative (eGFP−) cells (y-axis). The percentage of eGFP– cells declined only modestly between day 2 and 5 suggesting that the alterations were stably induced.

A subset of mutated eGFP genes were amplified from cells and sequenced. The resulting mutations are shown in FIG. 8. Sequences targeted by the TALE nucleases encoded by expression plasmids SQT70/SQT56 in human USOS-eGFP cells are underlined in the wild-type (WT) sequence shown at the top of FIG. 8. Insertion and deletion mutations induced by the TALE nuclease pair are shown below with deleted bases indicated by dashes and inserted bases indicated by double underlining. The net number of bases inserted or deleted is shown to the right. All mutations were isolated once unless otherwise indicated in brackets. The overall frequency of mutagenesis (46%) is also indicated.

Example 4. Automated Assembly of TALE Repeat Arrays

Figure 10:
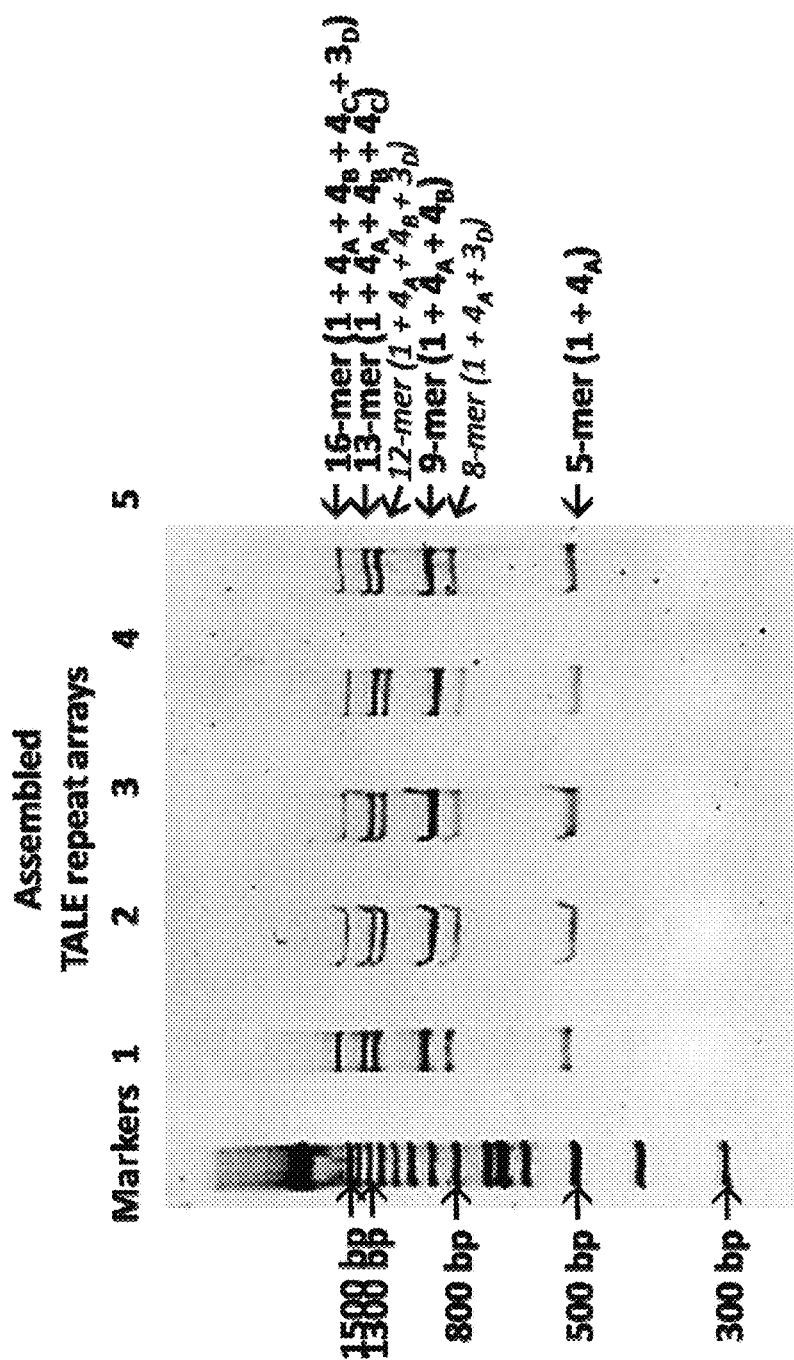
FIG. 10 is a depiction of an electrophoresis gel of 16-mer TALE array preparations.

The assembly method described in Example 1 has been automated so as to be performed using a Sciclone™ G3 liquid handling workstation (Caliper Life Sciences, Hopkinton, Mass.) in 96-well plates. All of the steps were automated except digestion of the nucleic acids prior to ligation and linking to the beads and the steps following release of the assembled TALE repeat array from the magnetic beads. The automated steps were performed essentially as when done manually with minor variations in the number of resuspension and mixing motions. The results of assembly of two 17-mers are shown in FIG. 9. A major product of the expected size can be seen, corresponding to the 17-mer. Additional minor 13-mer, 9-mer, and 5-mer products can also be seen, likely produced by carry forward of incompletely ligated products. A similar result can be seen in FIG. 10, which shows the results of assembly of 16-mers from an N-terminal 1-mer sub-array (1), three 4-mer subarrays ($4_A$, $4_B$, $4_C$), and a C-terminal 3-mer subarray ($3_D$).

This example demonstrates that the methods described herein can be automated for rapid and reproducible synthesis of nucleic acids encoding TALE repeat arrays.

Example 5. Assembly Methods

TALE repeat arrays were created using an architecture in which four distinct TALE repeat backbones that differ slightly in their amino acid and DNA sequences occur in a repeated pattern. The first, amino-terminal TALE repeat in an array was designated as the α unit. This was followed by β, γ, and δ units and then an ε unit that is essentially identical to the α unit except for the different positioning of a Type IIS restriction site on the 5' end (required to enable creation of a unique overhang on the α unit needed for cloning). The ε unit was then followed again by repeats of β, γ, δ, and ε units. Due to constraints related to creation of a 3' end required for cloning, slightly modified DNA sequences were required for TALE repeat arrays that end with a carboxy-terminal γ or ε unit. We designated these variant units as γ* and ε*.

For each type of TALE repeat unit (i.e.—α, β, γ, δ, ε, γ*, and ε*), we commercially synthesized (Genscript) a series of four plasmids, each harboring one of the five repeat variable di-residues (RVDs) that specifies one of the four DNA bases (NI=A; HD=C; NN=G; NG=T, NK=G). Full DNA sequences of these plasmids are provided in Table 4 and FIG. 3. For all 35 of these plasmids, the sequence encoding the TALE repeat domain is flanked on the 5' end by unique XbaI and BbsI restriction sites and on the 3' end by unique BsaI and BamHI restriction sites. Additionally, the overhangs generated by digestion of any plasmids encoding units designed to be adjacent to one another (e.g.—β and γ, or δ and ε) with BsaI and BbsI are complementary. Using these 35 different plasmids and serial ligation via the BsaI and BbsI restriction sites, we assembled an archive of all possible combinations of βγ, βγδε, βγδ, βγ*, and δε* repeats. In total, this archive consisted of 825 different plasmids encoding 5 α's, 5 β's, 25 βγ combinations, 625 βγδε combinations, 125 βγδ combinations, 25 βγ* combinations, and 25 δε* combinations (Table 5). These 825 plasmids plus ten of the original 35 plasmids encoding single TALE repeats (five α and five β plasmids) are required to practice the methods. With this archive of 835 plasmids listed in Table 5, the methods can be used to construct TALE repeat arrays of any desired length and composition.

TABLE 4

DNA sequences encoding individual TALE repeats

| TAL ID# | Unit Archi- tecture | RVD | Tar- get Base | DNA Sequence (Cloned between XbaI/BamHI in pUC57-ΔBsaI) | SEQ ID NO: |
|---|---|---|---|---|---|
| 6 | α | NI | A | TCTAGAGAAGACAAGAACCTGACC CCAGACCAGGTAGTCGCAATCGCG TCGAACATTGGGGGAAAGCAAGCC CTGGAAACCGTGCAAAGGTTGTTG CCGGTCCTTTGTCAAGACCACGGC CTTAAGAGACCGGATCC | 58 |
| 7 | α | HD | C | TCTAGAGAAGACAAGAACCTGACC CCAGACCAGGTAGTCGCAATCGCG TCACATGACGGGGAAAGCAAGCC CTGGAAACCGTGCAAAGGTTGTTG CCGGTCCTTTGTCAAGACCACGGC CTTAAGAGACCGGATCC | 59 |
| 8 | α | NK | G | TCTAGAGAAGACAAGAACCTGACC CCAGACCAGGTAGTCGCAATCGCG TCGAACAAAGGGGGAAAGCAAGCC CTGGAAACCGTGCAAAGGTTGTTG CCGGTCCTTTGTCAAGACCACGGC CTTAAGAGACCGGATCC | 60 |

TABLE 4-continued

DNA sequences encoding individual TALE repeats

| TAL ID# | Unit Archi-tecture | RVD | Tar-get Base | DNA Sequence (Cloned between XbaI/BamHI in pUC57-ΔBsaI) | SEQ ID NO: |
|---|---|---|---|---|---|
| 9 | α | NN | G | TCTAGAGAAGACAAGAACCTGACC CCAGACCAGGTAGTCGCAATCGCG AACAATAATGGGGGAAAGCAAGCC CTGGAAACCGTGCAAAGGTTGTTG CCGGTCCTTTGTCAAGACCACGGC CTTAAGAGACCGGATCC | 61 |
| 10 | α | NG | T | TCTAGAGAAGACAAGAACCTGACC CCAGACCAGGTAGTCGCAATCGCG TCAAACGGAGGGGAAAGCAAGCC CTGGAAACCGTGCAAAGGTTGTTG CCGGTCCTTTGTCAAGACCACGGC CTTAAGAGACCGGATCC | 62 |
| 11 | β | NI | A | TCTAGAGAAGACAACTTACACCGG AGCAAGTCGTGGCCATTGCAAGCA ACATCGGTGGCAAACAGGCTCTTG AGACGGTTCAGAGACTTCTCCCAG TTCTCTGTCAAGCCCACGGGCTGA AGAGACCGGATCC | 63 |
| 12 | β | HD | C | TCTAGAGAAGACAACTTACACCGG AGCAAGTCGTGGCCATTGCATCCC ACGACGGTGGCAAACAGGCTCTTG AGACGGTTCAGAGACTTCTCCCAG TTCTCTGTCAAGCCCACGGGCTGA AGAGACCGGATCC | 64 |
| 13 | β | NK | G | TCTAGAGAAGACAACTTACACCGG AGCAAGTCGTGGCCATTGCATCAA ATAAAGGTGGCAAACAGGCTCTTG AGACGGTTCAGAGACTTCTCCCAG TTCTCTGTCAAGCCCACGGGCTGA AGAGACCGGATCC | 65 |
| 14 | β | NN | G | TCTAGAGAAGACAACTTACACCGG AGCAAGTCGTGGCCATTGCAAATA ATAACGGTGGCAAACAGGCTCTTG AGACGGTTCAGAGACTTCTCCCAG TTCTCTGTCAAGCCCACGGGCTGA AGAGACCGGATCC | 66 |
| 15 | β | NG | T | TCTAGAGAAGACAACTTACACCGG AGCAAGTCGTGGCCATTGCAAGCA ATGGGGGTGGCAAACAGGCTCTTG AGACGGTTCAGAGACTTCTCCCAG TTCTCTGTCAAGCCCACGGGCTGA AGAGACCGGATCC | 67 |
| 16 | γ | NI | A | TCTAGAGAAGACAACTGACTCCCG ATCAAGTTGTAGCGATTGCGTCGA ACATTGGAGGGAAACAAGCATTGG AGACTGTCCAACGGCTCCTTCCCG TGTTGTGTCAAGCCCACGGTTTGA AGAGACCGGATCC | 68 |
| 17 | γ | HD | C | TCTAGAGAAGACAACTGACTCCCG ATCAAGTTGTAGCGATTGCGTCGC ATGACGGAGGGAAACAAGCATTGG AGACTGTCCAACGGCTCCTTCCCG TGTTGTGTCAAGCCCACGGTTTGA AGAGACCGGATCC | 69 |
| 18 | γ | NK | G | TCTAGAGAAGACAACTGACTCCCG ATCAAGTTGTAGCGATTGCGTCCA ACAAGGGAGGGAAACAAGCATTGG AGACTGTCCAACGGCTCCTTCCCG TGTTGTGTCAAGCCCACGGTTTGA AGAGACCGGATCC | 70 |

TABLE 4-continued

DNA sequences encoding individual TALE repeats

| TAL ID# | Unit Archi- tecture | RVD | Tar- get Base | DNA Sequence (Cloned between XbaI/BamHI in pUC57-ΔBsaI) | SEQ ID NO: |
|---|---|---|---|---|---|
| 19 | γ | NN | G | TCTAGAGAAGACAACTGACTCCCG ATCAAGTTGTAGCGATTGCGAATA ACAATGGAGGGAAACAAGCATTGG AGACTGTCCAACGGCTCCTTCCCG TGTTGTGTCAAGCCCACGGTTTGA AGAGACCGGATCC | 71 |
| 20 | γ | NG | T | TCTAGAGAAGACAACTGACTCCCG ATCAAGTTGTAGCGATTGCGTCCA ACGGTGGAGGGAAACAAGCATTGG AGACTGTCCAACGGCTCCTTCCCG TGTTGTGTCAAGCCCACGGTTTGA AGAGACCGGATCC | 72 |
| 21 | δ | NI | A | TCTAGAGAAGACAATTGACGCCTG CACAAGTGGTCGCCATCGCCTCCA ATATTGGCGGTAAGCAGGCGCTGG AAACAGTACAGCGCCTGCTGCCTG TACTGTGCCAGGATCATGGACTGA AGAGACCGGATCC | 73 |
| 22 | δ | HD | C | TCTAGAGAAGACAATTGACGCCTG CACAAGTGGTCGCCATCGCCAGCC ATGATGGCGGTAAGCAGGCGCTGG AAACAGTACAGCGCCTGCTGCCTG TACTGTGCCAGGATCATGGACTGA cAGAGACCGGATCC | 74 |
| 23 | δ | NK | G | TCTAGAGAAGACAATTGACGCCTG CACAAGTGGTCGCCATCGCCAGCA ATAAGGGCGGTAAGCAGGCGCTGG AAACAGTACAGCGCCTGCTGCCTG TACTGTGCCAGGATCATGGACTGA AGAGACCGGATCC | 75 |
| 24 | δ | NN | G | TCTAGAGAAGACAATTGACGCCTG CACAAGTGGTCGCCATCGCCAACA ACAACGGCGGTAAGCAGGCGCTGG AAACAGTACAGCGCCTGCTGCCTG TACTGTGCCAGGATCATGGACTGA AGAGACCGGATCC | 76 |
| 25 | δ | NG | T | TCTAGAGAAGACAATTGACGCCTG CACAAGTGGTCGCCATCGCCTCGA ATGGCGGCGGTAAGCAGGCGCTGG AAACAGTACAGCGCCTGCTGCCTG TACTGTGCCAGGATCATGGACTGA AGAGACCGGATCC | 77 |
| 26 | ε | NI | A | TCTAGAGAAGACAACTGACCCCAG ACCAGGTAGTCGCAATCGCGTCGA ACATTGGGGAAAGCAAGCCCTGG AAACCGTGCAAAGGTTGTTGCCGG TCCTTTGTCAAGACCACGGCCTTA AGAGACCGGATCC | 78 |
| 27 | ε | HD | C | TCTAGAGAAGACAACTGACCCCAG ACCAGGTAGTCGCAATCGCGTCAC ATGACGGGGAAAGCAAGCCCTGG AAACCGTGCAAAGGTTGTTGCCGG TCCTTTGTCAAGACCACGGCCTTA AGAGACCGGATCC | 79 |
| 28 | ε | NK | G | TCTAGAGAAGACAACTGACCCCAG ACCAGGTAGTCGCAATCGCGTCGA ACAAAGGGGGAAAGCAAGCCCTGG AAACCGTGCAAAGGTTGTTGCCGG TCCTTTGTCAAGACCACGGCCTTA AGAGACCGGATCC | 80 |

TABLE 4-continued

DNA sequences encoding individual TALE repeats

| TAL ID# | Unit Architecture | RVD | Target Base | DNA Sequence (Cloned between XbaI/BamHI in pUC57-ΔBsaI) | SEQ ID NO: |
|---|---|---|---|---|---|
| 29 | ε | NN | G | TCTAGAGAAGACAACTGACCCCAG ACCAGGTAGTCGCAATCGCGAACA ATAATGGGGGAAAGCAAGCCCTGG AAACCGTGCAAAGGTTGTTGCCGG TCCTTTGTCAAGACCACGGCCTTA AGAGACCGGATCC | 81 |
| 30 | ε | NG | T | TCTAGAGAAGACAACTGACCCCAG ACCAGGTAGTCGCAATCGCGTCAA ACGGAGGGGAAAGCAAGCCCTGG AAACCGTGCAAAGGTTGTTGCCGG TCCTTTGTCAAGACCACGGCCTTA AGAGACCGGATCC | 82 |
| 31 | γ' | NI | A | TCTAGAGAAGACAACTGACTCCCG ATCAAGTTGTAGCGATTGCGTCGA ACATTGGAGGGAAACAAGCATTGG AGACTGTCCAACGGCTCCTTCCCG TGTTGTGTCAAGCCCACGGTCTGA AGAGACCGGATCC | 83 |
| 32 | γ' | HD | C | TCTAGAGAAGACAACTGACTCCCG ATCAAGTTGTAGCGATTGCGTCGC ATGACGGAGGGAAACAAGCATTGG AGACTGTCCAACGGCTCCTTCCCG TGTTGTGTCAAGCCCACGGTCTGA AGAGACCGGATCC | 84 |
| 33 | γ' | NK | G | TCTAGAGAAGACAACTGACTCCCG ATCAAGTTGTAGCGATTGCGTCCA ACAAGGGAGGGAAACAAGCATTGG AGACTGTCCAACGGCTCCTTCCCG TGTTGTGTCAAGCCCACGGTCTGA AGAGACCGGATCC | 85 |
| 34 | γ' | NN | G | TCTAGAGAAGACAACTGACTCCCG ATCAAGTTGTAGCGATTGCGAATA ACAATGGAGGGAAACAAGCATTGG AGACTGTCCAACGGCTCCTTCCCG TGTTGTGTCAAGCCCACGGTCTGA AGAGACCGGATCC | 86 |
| 35 | γ' | NG | T | TCTAGAGAAGACAACTGACTCCCG ATCAAGTTGTAGCGATTGCGTCCA ACGGTGGAGGGAAACAAGCATTGG AGACTGTCCAACGGCTCCTTCCCG TGTTGTGTCAAGCCCACGGTCTGA AGAGACCGGATCC | 87 |
| 36 | ε' | NI | A | TCTAGAGAAGACAACTGACCCCAG ACCAGGTAGTCGCAATCGCGTCGA ACATTGGGGGAAAGCAAGCCCTGG AAACCGTGCAAAGGTTGTTGCCGG TCCTTTGTCAAGACCACGGCCTGA AGAGACCGGATCC | 88 |
| 37 | ε' | HD | C | TCTAGAGAAGACAACTGACCCCAG ACCAGGTAGTCGCAATCGCGTCAC ATGACGGGGAAAGCAAGCCCTGG AAACCGTGCAAAGGTTGTTGCCGG TCCTTTGTCAAGACCACGGCCTGA AGAGACCGGATCC | 89 |
| 38 | ε' | NK | G | TCTAGAGAAGACAACTGACCCCAG ACCAGGTAGTCGCAATCGCGTCGA ACAAAGGGGGAAAGCAAGCCCTGG AAACCGTGCAAAGGTTGTTGCCGG TCCTTTGTCAAGACCACGGCCTGA AGAGACCGGATCC | 90 |

TABLE 4-continued

DNA sequences encoding individual TALE repeats

| TAL ID# | Unit Architecture | RVD | Target Base | DNA Sequence (Cloned between XbaI/BamHI in pUC57-ΔBsaI) | SEQ ID NO: |
|---|---|---|---|---|---|
| 39 | ε' | NN | G | TCTAGAGAAGACAACTGACCCCAG ACCAGGTAGTCGCAATCGCGAACA ATAATGGGGGAAAGCAAGCCCTGG AAACCGTGCAAAGGTTGTTGCCGG TCCTTTGTCAAGACCACGGCCTGA AGAGACCGGATCC | 91 |
| 40 | ε' | NG | T | TCTAGAGAAGACAACTGACCCCAG ACCAGGTAGTCGCAATCGCGTCAA ACGGAGGGGAAAGCAAGCCCTGG AAACCGTGCAAAGGTTGTTGCCGG TCCTTTGTCAAGACCACGGCCTGA AGAGACCGGATCC | 92 |

TABLE 5

Archive of 835 plasmids encoding pre-assembled TALE repeat units

| Plasmid ID | DNA Target | RVDs | Unit Architecture |
|---|---|---|---|
| TAL006 | A | NI | α |
| TAL007 | C | HD | α |
| TAL008 | G | NK | α |
| TAL009 | G | NN | α |
| TAL010 | T | NG | α |
| TAL011/016/021/026 | AAAA | NI/NI/NI/NI | βγδε |
| TAL011/016/021/027 | AAAC | NI/NI/NI/HD | βγδε |
| TAL011/016/021/028 | AAAG | NI/NI/NI/NK | βγδε |
| TAL011/016/021/029 | AAAG | NI/NI/NI/NN | βγδε |
| TAL011/016/021/030 | AAAT | NI/NI/NI/NG | βγδε |
| TAL011/016/022/026 | AACA | NI/NI/HD/NI | βγδε |
| TAL011/016/022/027 | AACC | NI/NI/HD/HD | βγδε |
| TAL011/016/022/028 | AACG | NI/NI/HD/NK | βγδε |
| TAL011/016/022/029 | AACG | NI/NI/HD/NN | βγδε |
| TAL011/016/022/030 | AACT | NI/NI/HD/NG | βγδε |
| TAL011/016/023/026 | AAGA | NI/NI/NK/NI | βγδε |
| TAL011/016/023/027 | AAGC | NI/NI/NK/HD | βγδε |
| TAL011/016/023/028 | AAGG | NI/NI/NK/NK | βγδε |
| TAL011/016/023/029 | AAGG | NI/NI/NK/NN | βγδε |
| TAL011/016/023/030 | AAGT | NI/NI/NK/NG | βγδε |
| TAL011/016/024/026 | AAGA | NI/NI/NN/NI | βγδε |
| TAL011/016/024/027 | AAGC | NI/NI/NN/HD | βγδε |
| TAL011/016/024/028 | AAGG | NI/NI/NN/NK | βγδε |
| TAL011/016/024/029 | AAGG | NI/NI/NN/NN | βγδε |
| TAL011/016/024/030 | AAGT | NI/NI/NN/NG | βγδε |
| TAL011/016/025/026 | AATA | NI/NI/NG/NI | βγδε |
| TAL011/016/025/027 | AATC | NI/NI/NG/HD | βγδε |
| TAL011/016/025/028 | AATG | NI/NI/NG/NK | βγδε |
| TAL011/016/025/029 | AATG | NI/NI/NG/NN | βγδε |
| TAL011/016/025/030 | AATT | NI/NI/NG/NG | βγδε |
| TAL011/017/021/026 | ACAA | NI/HD/NI/NI | βγδε |
| TAL011/017/021/027 | ACAC | NI/HD/NI/HD | βγδε |
| TAL011/017/021/028 | ACAG | NI/HD/NI/NK | βγδε |
| TAL011/017/021/029 | ACAG | NI/HD/NI/NN | βγδε |
| TAL011/017/021/030 | ACAT | NI/HD/NI/NG | βγδε |
| TAL011/017/022/026 | ACCA | NI/HD/HD/NI | βγδε |
| TAL011/017/022/027 | ACCC | NI/HD/HD/HD | βγδε |
| TAL011/017/022/028 | ACCG | NI/HD/HD/NK | βγδε |
| TAL011/017/022/029 | ACCG | NI/HD/HD/NN | βγδε |
| TAL011/017/022/030 | ACCT | NI/HD/HD/NG | βγδε |
| TAL011/017/023/026 | ACGA | NI/HD/NK/NI | βγδε |
| TAL011/017/023/027 | ACGC | NI/HD/NK/HD | βγδε |
| TAL011/017/023/028 | ACGG | NI/HD/NK/NK | βγδε |
| TAL011/017/023/029 | ACGG | NI/HD/NK/NN | βγδε |
| TAL011/017/023/030 | ACGT | NI/HD/NK/NG | βγδε |
| TAL011/017/024/026 | ACGA | NI/HD/NN/NI | βγδε |
| TAL011/017/024/027 | ACGC | NI/HD/NN/HD | βγδε |
| TAL011/017/024/028 | ACGG | NI/HD/NN/NK | βγδε |
| TAL011/017/024/029 | ACGG | NI/HD/NN/NN | βγδε |
| TAL011/017/024/030 | ACGT | NI/HD/NN/NG | βγδε |
| TAL011/017/025/026 | ACTA | NI/HD/NG/NI | βγδε |
| TAL011/017/025/027 | ACTC | NI/HD/NG/HD | βγδε |
| TAL011/017/025/028 | ACTG | NI/HD/NG/NK | βγδε |
| TAL011/017/025/029 | ACTG | NI/HD/NG/NN | βγδε |
| TAL011/017/025/030 | ACTT | NI/HD/NG/NG | βγδε |
| TAL011/018/021/026 | AGAA | NI/NK/NI/NI | βγδε |
| TAL011/018/021/027 | AGAC | NI/NK/NI/HD | βγδε |
| TAL011/018/021/028 | AGAG | NI/NK/NI/NK | βγδε |
| TAL011/018/021/029 | AGAG | NI/NK/NI/NN | βγδε |
| TAL011/018/021/030 | AGAT | NI/NK/NI/NG | βγδε |
| TAL011/018/022/026 | AGCA | NI/NK/HD/NI | βγδε |
| TAL011/018/022/027 | AGCC | NI/NK/HD/HD | βγδε |
| TAL011/018/022/028 | AGCG | NI/NK/HD/NK | βγδε |
| TAL011/018/022/029 | AGCG | NI/NK/HD/NN | βγδε |
| TAL011/018/022/030 | AGCT | NI/NK/HD/NG | βγδε |
| TAL011/018/023/026 | AGGA | NI/NK/NK/NI | βγδε |
| TAL011/018/023/027 | AGGC | NI/NK/NK/HD | βγδε |
| TAL011/018/023/028 | AGGG | NI/NK/NK/NK | βγδε |
| TAL011/018/023/029 | AGGG | NI/NK/NK/NN | βγδε |
| TAL011/018/023/030 | AGGT | NI/NK/NK/NG | βγδε |
| TAL011/018/024/026 | AGGA | NI/NK/NN/NI | βγδε |
| TAL011/018/024/027 | AGGC | NI/NK/NN/HD | βγδε |
| TAL011/018/024/028 | AGGG | NI/NK/NN/NK | βγδε |
| TAL011/018/024/029 | AGGG | NI/NK/NN/NN | βγδε |
| TAL011/018/024/030 | AGGT | NI/NK/NN/NG | βγδε |
| TAL011/018/025/026 | AGTA | NI/NK/NG/NI | βγδε |
| TAL011/018/025/027 | AGTC | NI/NK/NG/HD | βγδε |
| TAL011/018/025/028 | AGTG | NI/NK/NG/NK | βγδε |
| TAL011/018/025/029 | AGTG | NI/NK/NG/NN | βγδε |
| TAL011/018/025/030 | AGTT | NI/NK/NG/NG | βγδε |
| TAL011/019/021/026 | AGAA | NI/NN/NI/NI | βγδε |
| TAL011/019/021/027 | AGAC | NI/NN/NI/HD | βγδε |
| TAL011/019/021/028 | AGAG | NI/NN/NI/NK | βγδε |
| TAL011/019/021/029 | AGAG | NI/NN/NI/NN | βγδε |
| TAL011/019/021/030 | AGAT | NI/NN/NI/NG | βγδε |
| TAL011/019/022/026 | AGCA | NI/NN/HD/NI | βγδε |
| TAL011/019/022/027 | AGCC | NI/NN/HD/HD | βγδε |
| TAL011/019/022/028 | AGCG | NI/NN/HD/NK | βγδε |
| TAL011/019/022/029 | AGCG | NI/NN/HD/NN | βγδε |
| TAL011/019/022/030 | AGCT | NI/NN/HD/NG | βγδε |
| TAL011/019/023/026 | AGGA | NI/NN/NK/NI | βγδε |
| TAL011/019/023/027 | AGGC | NI/NN/NK/HD | βγδε |
| TAL011/019/023/028 | AGGG | NI/NN/NK/NK | βγδε |
| TAL011/019/023/029 | AGGG | NI/NN/NK/NN | βγδε |
| TAL011/019/023/030 | AGGT | NI/NN/NK/NG | βγδε |
| TAL011/019/024/026 | AGGA | NI/NN/NN/NI | βγδε |

TABLE 5-continued

Archive of 835 plasmids encoding pre-assembled TALE repeat units

| Plasmid ID | DNA Target | RVDs | Unit Architecture |
|---|---|---|---|
| TAL011/019/024/027 | AGGC | NI/NN/NN/HD | βγδε |
| TAL011/019/024/028 | AGGG | NI/NN/NN/NK | βγδε |
| TAL011/019/024/029 | AGGG | NI/NN/NN/NN | βγδε |
| TAL011/019/024/030 | AGGT | NI/NN/NN/NG | βγδε |
| TAL011/019/025/026 | AGTA | NI/NN/NG/NI | βγδε |
| TAL011/019/025/027 | AGTC | NI/NN/NG/HD | βγδε |
| TAL011/019/025/028 | AGTG | NI/NN/NG/NK | βγδε |
| TAL011/019/025/029 | AGTG | NI/NN/NG/NN | βγδε |
| TAL011/019/025/030 | AGTT | NI/NN/NG/NG | βγδε |
| TAL011/020/021/026 | ATAA | NI/NG/NI/NI | βγδε |
| TAL011/020/021/027 | ATAC | NI/NG/NI/HD | βγδε |
| TAL011/020/021/028 | ATAG | NI/NG/NI/NK | βγδε |
| TAL011/020/021/029 | ATAG | NI/NG/NI/NN | βγδε |
| TAL011/020/021/030 | ATAT | NI/NG/NI/NG | βγδε |
| TAL011/020/022/026 | ATCA | NI/NG/HD/NI | βγδε |
| TAL011/020/022/027 | ATCC | NI/NG/HD/HD | βγδε |
| TAL011/020/022/028 | ATCG | NI/NG/HD/NK | βγδε |
| TAL011/020/022/029 | ATCG | NI/NG/HD/NN | βγδε |
| TAL011/020/022/030 | ATCT | NI/NG/HD/NG | βγδε |
| TAL011/020/023/026 | ATGA | NI/NG/NK/NI | βγδε |
| TAL011/020/023/027 | ATGC | NI/NG/NK/HD | βγδε |
| TAL011/020/023/028 | ATGG | NI/NG/NK/NK | βγδε |
| TAL011/020/023/029 | ATGG | NI/NG/NK/NN | βγδε |
| TAL011/020/023/030 | ATGT | NI/NG/NK/NG | βγδε |
| TAL011/020/024/026 | ATGA | NI/NG/NN/NI | βγδε |
| TAL011/020/024/027 | ATGC | NI/NG/NN/HD | βγδε |
| TAL011/020/024/028 | ATGG | NI/NG/NN/NK | βγδε |
| TAL011/020/024/029 | ATGG | NI/NG/NN/NN | βγδε |
| TAL011/020/024/030 | ATGT | NI/NG/NN/NG | βγδε |
| TAL011/020/025/026 | ATTA | NI/NG/NG/NI | βγδε |
| TAL011/020/025/027 | ATTC | NI/NG/NG/HD | βγδε |
| TAL011/020/025/028 | ATTG | NI/NG/NG/NK | βγδε |
| TAL011/020/025/029 | ATTG | NI/NG/NG/NN | βγδε |
| TAL011/020/025/030 | ATTT | NI/NG/NG/NG | βγδε |
| TAL012/016/021/026 | CAAA | HD/NI/NI/NI | βγδε |
| TAL012/016/021/027 | CAAC | HD/NI/NI/HD | βγδε |
| TAL012/016/021/028 | CAAG | HD/NI/NI/NK | βγδε |
| TAL012/016/021/029 | CAAG | HD/NI/NI/NN | βγδε |
| TAL012/016/021/030 | CAAT | HD/NI/NI/NG | βγδε |
| TAL012/016/022/026 | CACA | HD/NI/HD/NI | βγδε |
| TAL012/016/022/027 | CACC | HD/NI/HD/HD | βγδε |
| TAL012/016/022/028 | CACG | HD/NI/HD/NK | βγδε |
| TAL012/016/022/029 | CACG | HD/NI/HD/NN | βγδε |
| TAL012/016/022/030 | CACT | HD/NI/HD/NG | βγδε |
| TAL012/016/023/026 | CAGA | HD/NI/NK/NI | βγδε |
| TAL012/016/023/027 | CAGC | HD/NI/NK/HD | βγδε |
| TAL012/016/023/028 | CAGG | HD/NI/NK/NK | βγδε |
| TAL012/016/023/029 | CAGG | HD/NI/NK/NN | βγδε |
| TAL012/016/023/030 | CAGT | HD/NI/NK/NG | βγδε |
| TAL012/016/024/026 | CAGA | HD/NI/NN/NI | βγδε |
| TAL012/016/024/027 | CAGC | HD/NI/NN/HD | βγδε |
| TAL012/016/024/028 | CAGG | HD/NI/NN/NK | βγδε |
| TAL012/016/024/029 | CAGG | HD/NI/NN/NN | βγδε |
| TAL012/016/024/030 | CAGT | HD/NI/NN/NG | βγδε |
| TAL012/016/025/026 | CATA | HD/NI/NG/NI | βγδε |
| TAL012/016/025/027 | CATC | HD/NI/NG/HD | βγδε |
| TAL012/016/025/028 | CATG | HD/NI/NG/NK | βγδε |
| TAL012/016/025/029 | CATG | HD/NI/NG/NN | βγδε |
| TAL012/016/025/030 | CATT | HD/NI/NG/NG | βγδε |
| TAL012/017/021/026 | CCAA | HD/HD/NI/NI | βγδε |
| TAL012/017/021/027 | CCAC | HD/HD/NI/HD | βγδε |
| TAL012/017/021/028 | CCAG | HD/HD/NI/NK | βγδε |
| TAL012/017/021/029 | CCAG | HD/HD/NI/NN | βγδε |
| TAL012/017/021/030 | CCAT | HD/HD/NI/NG | βγδε |
| TAL012/017/022/026 | CCCA | HD/HD/HD/NI | βγδε |
| TAL012/017/022/027 | CCCC | HD/HD/HD/HD | βγδε |
| TAL012/017/022/028 | CCCG | HD/HD/HD/NK | βγδε |
| TAL012/017/022/029 | CCCG | HD/HD/HD/NN | βγδε |
| TAL012/017/022/030 | CCCT | HD/HD/HD/NG | βγδε |
| TAL012/017/023/026 | CCGA | HD/HD/NK/NI | βγδε |
| TAL012/017/023/027 | CCGC | HD/HD/NK/HD | βγδε |
| TAL012/017/023/028 | CCGG | HD/HD/NK/NK | βγδε |
| TAL012/017/023/029 | CCGG | HD/HD/NK/NN | βγδε |
| TAL012/017/023/030 | CCGT | HD/HD/NK/NG | βγδε |
| TAL012/017/024/026 | CCGA | HD/HD/NN/NI | βγδε |
| TAL012/017/024/027 | CCGC | HD/HD/NN/HD | βγδε |
| TAL012/017/024/028 | CCGG | HD/HD/NN/NK | βγδε |
| TAL012/017/024/029 | CCGG | HD/HD/NN/NN | βγδε |
| TAL012/017/024/030 | CCGT | HD/HD/NN/NG | βγδε |
| TAL012/017/025/026 | CCTA | HD/HD/NG/NI | βγδε |
| TAL012/017/025/027 | CCTC | HD/HD/NG/HD | βγδε |
| TAL012/017/025/028 | CCTG | HD/HD/NG/NK | βγδε |
| TAL012/017/025/029 | CCTG | HD/HD/NG/NN | βγδε |
| TAL012/017/025/030 | CCTT | HD/HD/NG/NG | βγδε |
| TAL012/018/021/026 | CGAA | HD/NK/NI/NI | βγδε |
| TAL012/018/021/027 | CGAC | HD/NK/NI/HD | βγδε |
| TAL012/018/021/028 | CGAG | HD/NK/NI/NK | βγδε |
| TAL012/018/021/029 | CGAG | HD/NK/NI/NN | βγδε |
| TAL012/018/021/030 | CGAT | HD/NK/NI/NG | βγδε |
| TAL012/018/022/026 | CGCA | HD/NK/HD/NI | βγδε |
| TAL012/018/022/027 | CGCC | HD/NK/HD/HD | βγδε |
| TAL012/018/022/028 | CGCG | HD/NK/HD/NK | βγδε |
| TAL012/018/022/029 | CGCG | HD/NK/HD/NN | βγδε |
| TAL012/018/022/030 | CGCT | HD/NK/HD/NG | βγδε |
| TAL012/018/023/026 | CGGA | HD/NK/NK/NI | βγδε |
| TAL012/018/023/027 | CGGC | HD/NK/NK/HD | βγδε |
| TAL012/018/023/028 | CGGG | HD/NK/NK/NK | βγδε |
| TAL012/018/023/029 | CGGG | HD/NK/NK/NN | βγδε |
| TAL012/018/023/030 | CGGT | HD/NK/NK/NG | βγδε |
| TAL012/018/024/026 | CGGA | HD/NK/NN/NI | βγδε |
| TAL012/018/024/027 | CGGC | HD/NK/NN/HD | βγδε |
| TAL012/018/024/028 | CGGG | HD/NK/NN/NK | βγδε |
| TAL012/018/024/029 | CGGG | HD/NK/NN/NN | βγδε |
| TAL012/018/024/030 | CGGT | HD/NK/NN/NG | βγδε |
| TAL012/018/025/026 | CGTA | HD/NK/NG/NI | βγδε |
| TAL012/018/025/027 | CGTC | HD/NK/NG/HD | βγδε |
| TAL012/018/025/028 | CGTG | HD/NK/NG/NK | βγδε |
| TAL012/018/025/029 | CGTG | HD/NK/NG/NN | βγδε |
| TAL012/018/025/030 | CGTT | HD/NK/NG/NG | βγδε |
| TAL012/019/021/026 | CGAA | HD/NN/NI/NI | βγδε |
| TAL012/019/021/027 | CGAC | HD/NN/NI/HD | βγδε |
| TAL012/019/021/028 | CGAG | HD/NN/NI/NK | βγδε |
| TAL012/019/021/029 | CGAG | HD/NN/NI/NN | βγδε |
| TAL012/019/021/030 | CGAT | HD/NN/NI/NG | βγδε |
| TAL012/019/022/026 | CGCA | HD/NN/HD/NI | βγδε |
| TAL012/019/022/027 | CGCC | HD/NN/HD/HD | βγδε |
| TAL012/019/022/028 | CGCG | HD/NN/HD/NK | βγδε |
| TAL012/019/022/029 | CGCG | HD/NN/HD/NN | βγδε |
| TAL012/019/022/030 | CGCT | HD/NN/HD/NG | βγδε |
| TAL012/019/023/026 | CGGA | HD/NN/NK/NI | βγδε |
| TAL012/019/023/027 | CGGC | HD/NN/NK/HD | βγδε |
| TAL012/019/023/028 | CGGG | HD/NN/NK/NK | βγδε |
| TAL012/019/023/029 | CGGG | HD/NN/NK/NN | βγδε |
| TAL012/019/023/030 | CGGT | HD/NN/NK/NG | βγδε |
| TAL012/019/024/026 | CGGA | HD/NN/NN/NI | βγδε |
| TAL012/019/024/027 | CGGC | HD/NN/NN/HD | βγδε |
| TAL012/019/024/028 | CGGG | HD/NN/NN/NK | βγδε |
| TAL012/019/024/029 | CGGG | HD/NN/NN/NN | βγδε |
| TAL012/019/024/030 | CGGT | HD/NN/NN/NG | βγδε |
| TAL012/019/025/026 | CGTA | HD/NN/NG/NI | βγδε |
| TAL012/019/025/027 | CGTC | HD/NN/NG/HD | βγδε |
| TAL012/019/025/028 | CGTG | HD/NN/NG/NK | βγδε |
| TAL012/019/025/029 | CGTG | HD/NN/NG/NN | βγδε |
| TAL012/019/025/030 | CGTT | HD/NN/NG/NG | βγδε |
| TAL012/020/021/026 | CTAA | HD/NG/NI/NI | βγδε |
| TAL012/020/021/027 | CTAC | HD/NG/NI/HD | βγδε |
| TAL012/020/021/028 | CTAG | HD/NG/NI/NK | βγδε |
| TAL012/020/021/029 | CTAG | HD/NG/NI/NN | βγδε |
| TAL012/020/021/030 | CTAT | HD/NG/NI/NG | βγδε |
| TAL012/020/022/026 | CTCA | HD/NG/HD/NI | βγδε |
| TAL012/020/022/027 | CTCC | HD/NG/HD/HD | βγδε |
| TAL012/020/022/028 | CTCG | HD/NG/HD/NK | βγδε |
| TAL012/020/022/029 | CTCG | HD/NG/HD/NN | βγδε |
| TAL012/020/022/030 | CTCT | HD/NG/HD/NG | βγδε |
| TAL012/020/023/026 | CTGA | HD/NG/NK/NI | βγδε |
| TAL012/020/023/027 | CTGC | HD/NG/NK/HD | βγδε |
| TAL012/020/023/028 | CTGG | HD/NG/NK/NK | βγδε |
| TAL012/020/023/029 | CTGG | HD/NG/NK/NN | βγδε |
| TAL012/020/023/030 | CTGT | HD/NG/NK/NG | βγδε |
| TAL012/020/024/026 | CTGA | HD/NG/NN/NI | βγδε |

TABLE 5-continued

Archive of 835 plasmids encoding pre-assembled TALE repeat units

| Plasmid ID | DNA Target | RVDs | Unit Architecture |
|---|---|---|---|
| TAL012/020/024/027 | CTGC | HD/NG/NN/HD | βγδε |
| TAL012/020/024/028 | CTGG | HD/NG/NN/NK | βγδε |
| TAL012/020/024/029 | CTGG | HD/NG/NN/NN | βγδε |
| TAL012/020/024/030 | CTGT | HD/NG/NN/NG | βγδε |
| TAL012/020/025/026 | CTTA | HD/NG/NG/NI | βγδε |
| TAL012/020/025/027 | CTTC | HD/NG/NG/HD | βγδε |
| TAL012/020/025/028 | CTTG | HD/NG/NG/NK | βγδε |
| TAL012/020/025/029 | CTTG | HD/NG/NG/NN | βγδε |
| TAL012/020/025/030 | CTTT | HD/NG/NG/NG | βγδε |
| TAL013/016/021/026 | GAAA | NK/NI/NI/NI | βγδε |
| TAL013/016/021/027 | GAAC | NK/NI/NI/HD | βγδε |
| TAL013/016/021/028 | GAAG | NK/NI/NI/NK | βγδε |
| TAL013/016/021/029 | GAAG | NK/NI/NI/NN | βγδε |
| TAL013/016/021/030 | GAAT | NK/NI/NI/NG | βγδε |
| TAL013/016/022/026 | GACA | NK/NI/HD/NI | βγδε |
| TAL013/016/022/027 | GACC | NK/NI/HD/HD | βγδε |
| TAL013/016/022/028 | GACG | NK/NI/HD/NK | βγδε |
| TAL013/016/022/029 | GACG | NK/NI/HD/NN | βγδε |
| TAL013/016/022/030 | GACT | NK/NI/HD/NG | βγδε |
| TAL013/016/023/026 | GAGA | NK/NI/NK/NI | βγδε |
| TAL013/016/023/027 | GAGC | NK/NI/NK/HD | βγδε |
| TAL013/016/023/028 | GAGG | NK/NI/NK/NK | βγδε |
| TAL013/016/023/029 | GAGG | NK/NI/NK/NN | βγδε |
| TAL013/016/023/030 | GAGT | NK/NI/NK/NG | βγδε |
| TAL013/016/024/026 | GAGA | NK/NI/NN/NI | βγδε |
| TAL013/016/024/027 | GAGC | NK/NI/NN/HD | βγδε |
| TAL013/016/024/028 | GAGG | NK/NI/NN/NK | βγδε |
| TAL013/016/024/029 | GAGG | NK/NI/NN/NN | βγδε |
| TAL013/016/024/030 | GAGT | NK/NI/NN/NG | βγδε |
| TAL013/016/025/026 | GATA | NK/NI/NG/NI | βγδε |
| TAL013/016/025/027 | GATC | NK/NI/NG/HD | βγδε |
| TAL013/016/025/028 | GATG | NK/NI/NG/NK | βγδε |
| TAL013/016/025/029 | GATG | NK/NI/NG/NN | βγδε |
| TAL013/016/025/030 | GATT | NK/NI/NG/NG | βγδε |
| TAL013/017/021/026 | GCAA | NK/HD/NI/NI | βγδε |
| TAL013/017/021/027 | GCAC | NK/HD/NI/HD | βγδε |
| TAL013/017/021/028 | GCAG | NK/HD/NI/NK | βγδε |
| TAL013/017/021/029 | GCAG | NK/HD/NI/NN | βγδε |
| TAL013/017/021/030 | GCAT | NK/HD/NI/NG | βγδε |
| TAL013/017/022/026 | GCCA | NK/HD/HD/NI | βγδε |
| TAL013/017/022/027 | GCCC | NK/HD/HD/HD | βγδε |
| TAL013/017/022/028 | GCCG | NK/HD/HD/NK | βγδε |
| TAL013/017/022/029 | GCCG | NK/HD/HD/NN | βγδε |
| TAL013/017/022/030 | GCCT | NK/HD/HD/NG | βγδε |
| TAL013/017/023/026 | GCGA | NK/HD/NK/NI | βγδε |
| TAL013/017/023/027 | GCGC | NK/HD/NK/HD | βγδε |
| TAL013/017/023/028 | GCGG | NK/HD/NK/NK | βγδε |
| TAL013/017/023/029 | GCGG | NK/HD/NK/NN | βγδε |
| TAL013/017/023/030 | GCGT | NK/HD/NK/NG | βγδε |
| TAL013/017/024/026 | GCGA | NK/HD/NN/NI | βγδε |
| TAL013/017/024/027 | GCGC | NK/HD/NN/HD | βγδε |
| TAL013/017/024/028 | GCGG | NK/HD/NN/NK | βγδε |
| TAL013/017/024/029 | GCGG | NK/HD/NN/NN | βγδε |
| TAL013/017/024/030 | GCGT | NK/HD/NN/NG | βγδε |
| TAL013/017/025/026 | GCTA | NK/HD/NG/NI | βγδε |
| TAL013/017/025/027 | GCTC | NK/HD/NG/HD | βγδε |
| TAL013/017/025/028 | GCTG | NK/HD/NG/NK | βγδε |
| TAL013/017/025/029 | GCTG | NK/HD/NG/NN | βγδε |
| TAL013/017/025/030 | GCTT | NK/HD/NG/NG | βγδε |
| TAL013/018/021/026 | GGAA | NK/NK/NI/NI | βγδε |
| TAL013/018/021/027 | GGAC | NK/NK/NI/HD | βγδε |
| TAL013/018/021/028 | GGAG | NK/NK/NI/NK | βγδε |
| TAL013/018/021/029 | GGAG | NK/NK/NI/NN | βγδε |
| TAL013/018/021/030 | GGAT | NK/NK/NI/NG | βγδε |
| TAL013/018/022/026 | GGCA | NK/NK/HD/NI | βγδε |
| TAL013/018/022/027 | GGCC | NK/NK/HD/HD | βγδε |
| TAL013/018/022/028 | GGCG | NK/NK/HD/NK | βγδε |
| TAL013/018/022/029 | GGCG | NK/NK/HD/NN | βγδε |
| TAL013/018/022/030 | GGCT | NK/NK/HD/NG | βγδε |
| TAL013/018/023/026 | GGGA | NK/NK/NK/NI | βγδε |
| TAL013/018/023/027 | GGGC | NK/NK/NK/HD | βγδε |
| TAL013/018/023/028 | GGGG | NK/NK/NK/NK | βγδε |
| TAL013/018/023/029 | GGGG | NK/NK/NK/NN | βγδε |
| TAL013/018/023/030 | GGGT | NK/NK/NK/NG | βγδε |
| TAL013/018/024/026 | GGGA | NK/NK/NN/NI | βγδε |
| TAL013/018/024/027 | GGGC | NK/NK/NN/HD | βγδε |
| TAL013/018/024/028 | GGGG | NK/NK/NN/NK | βγδε |
| TAL013/018/024/029 | GGGG | NK/NK/NN/NN | βγδε |
| TAL013/018/024/030 | GGGT | NK/NK/NN/NG | βγδε |
| TAL013/018/025/026 | GGTA | NK/NK/NG/NI | βγδε |
| TAL013/018/025/027 | GGTC | NK/NK/NG/HD | βγδε |
| TAL013/018/025/028 | GGTG | NK/NK/NG/NK | βγδε |
| TAL013/018/025/029 | GGTG | NK/NK/NG/NN | βγδε |
| TAL013/018/025/030 | GGTT | NK/NK/NG/NG | βγδε |
| TAL013/019/021/026 | GGAA | NK/NN/NI/NI | βγδε |
| TAL013/019/021/027 | GGAC | NK/NN/NI/HD | βγδε |
| TAL013/019/021/028 | GGAG | NK/NN/NI/NK | βγδε |
| TAL013/019/021/029 | GGAG | NK/NN/NI/NN | βγδε |
| TAL013/019/021/030 | GGAT | NK/NN/NI/NG | βγδε |
| TAL013/019/022/026 | GGCA | NK/NN/HD/NI | βγδε |
| TAL013/019/022/027 | GGCC | NK/NN/HD/HD | βγδε |
| TAL013/019/022/028 | GGCG | NK/NN/HD/NK | βγδε |
| TAL013/019/022/029 | GGCG | NK/NN/HD/NN | βγδε |
| TAL013/019/022/030 | GGCT | NK/NN/HD/NG | βγδε |
| TAL013/019/023/026 | GGGA | NK/NN/NK/NI | βγδε |
| TAL013/019/023/027 | GGGC | NK/NN/NK/HD | βγδε |
| TAL013/019/023/028 | GGGG | NK/NN/NK/NK | βγδε |
| TAL013/019/023/029 | GGGG | NK/NN/NK/NN | βγδε |
| TAL013/019/023/030 | GGGT | NK/NN/NK/NG | βγδε |
| TAL013/019/024/026 | GGGA | NK/NN/NN/NI | βγδε |
| TAL013/019/024/027 | GGGC | NK/NN/NN/HD | βγδε |
| TAL013/019/024/028 | GGGG | NK/NN/NN/NK | βγδε |
| TAL013/019/024/029 | GGGG | NK/NN/NN/NN | βγδε |
| TAL013/019/024/030 | GGGT | NK/NN/NN/NG | βγδε |
| TAL013/019/025/026 | GGTA | NK/NN/NG/NI | βγδε |
| TAL013/019/025/027 | GGTC | NK/NN/NG/HD | βγδε |
| TAL013/019/025/028 | GGTG | NK/NN/NG/NK | βγδε |
| TAL013/019/025/029 | GGTG | NK/NN/NG/NN | βγδε |
| TAL013/019/025/030 | GGTT | NK/NN/NG/NG | βγδε |
| TAL013/020/021/026 | GTAA | NK/NG/NI/NI | βγδε |
| TAL013/020/021/027 | GTAC | NK/NG/NI/HD | βγδε |
| TAL013/020/021/028 | GTAG | NK/NG/NI/NK | βγδε |
| TAL013/020/021/029 | GTAG | NK/NG/NI/NN | βγδε |
| TAL013/020/021/030 | GTAT | NK/NG/NI/NG | βγδε |
| TAL013/020/022/026 | GTCA | NK/NG/HD/NI | βγδε |
| TAL013/020/022/027 | GTCC | NK/NG/HD/HD | βγδε |
| TAL013/020/022/028 | GTCG | NK/NG/HD/NK | βγδε |
| TAL013/020/022/029 | GTCG | NK/NG/HD/NN | βγδε |
| TAL013/020/022/030 | GTCT | NK/NG/HD/NG | βγδε |
| TAL013/020/023/026 | GTGA | NK/NG/NK/NI | βγδε |
| TAL013/020/023/027 | GTGC | NK/NG/NK/HD | βγδε |
| TAL013/020/023/028 | GTGG | NK/NG/NK/NK | βγδε |
| TAL013/020/023/029 | GTGG | NK/NG/NK/NN | βγδε |
| TAL013/020/023/030 | GTGT | NK/NG/NK/NG | βγδε |
| TAL013/020/024/026 | GTGA | NK/NG/NN/NI | βγδε |
| TAL013/020/024/027 | GTGC | NK/NG/NN/HD | βγδε |
| TAL013/020/024/028 | GTGG | NK/NG/NN/NK | βγδε |
| TAL013/020/024/029 | GTGG | NK/NG/NN/NN | βγδε |
| TAL013/020/024/030 | GTGT | NK/NG/NN/NG | βγδε |
| TAL013/020/025/026 | GTTA | NK/NG/NG/NI | βγδε |
| TAL013/020/025/027 | GTTC | NK/NG/NG/HD | βγδε |
| TAL013/020/025/028 | GTTG | NK/NG/NG/NK | βγδε |
| TAL013/020/025/029 | GTTG | NK/NG/NG/NN | βγδε |
| TAL013/020/025/030 | GTTT | NK/NG/NG/NG | βγδε |
| TAL014/016/021/026 | GAAA | NN/NI/NI/NI | βγδε |
| TAL014/016/021/027 | GAAC | NN/NI/NI/HD | βγδε |
| TAL014/016/021/028 | GAAG | NN/NI/NI/NK | βγδε |
| TAL014/016/021/029 | GAAG | NN/NI/NI/NN | βγδε |
| TAL014/016/021/030 | GAAT | NN/NI/NI/NG | βγδε |
| TAL014/016/022/026 | GACA | NN/NI/HD/NI | βγδε |
| TAL014/016/022/027 | GACC | NN/NI/HD/HD | βγδε |
| TAL014/016/022/028 | GACG | NN/NI/HD/NK | βγδε |
| TAL014/016/022/029 | GACG | NN/NI/HD/NN | βγδε |
| TAL014/016/022/030 | GACT | NN/NI/HD/NG | βγδε |
| TAL014/016/023/026 | GAGA | NN/NI/NK/NI | βγδε |
| TAL014/016/023/027 | GAGC | NN/NI/NK/HD | βγδε |
| TAL014/016/023/028 | GAGG | NN/NI/NK/NK | βγδε |
| TAL014/016/023/029 | GAGG | NN/NI/NK/NN | βγδε |
| TAL014/016/023/030 | GAGT | NN/NI/NK/NG | βγδε |
| TAL014/016/024/026 | GAGA | NN/NI/NN/NI | βγδε |

TABLE 5-continued

Archive of 835 plasmids encoding pre-assembled TALE repeat units

| Plasmid ID | DNA Target | RVDs | Unit Architecture |
|---|---|---|---|
| TAL014/016/024/027 | GAGC | NN/NI/NN/HD | βγδε |
| TAL014/016/024/028 | GAGG | NN/NI/NN/NK | βγδε |
| TAL014/016/024/029 | GAGG | NN/NI/NN/NN | βγδε |
| TAL014/016/024/030 | GAGT | NN/NI/NN/NG | βγδε |
| TAL014/016/025/026 | GATA | NN/NI/NG/NI | βγδε |
| TAL014/016/025/027 | GATC | NN/NI/NG/HD | βγδε |
| TAL014/016/025/028 | GATG | NN/NI/NG/NK | βγδε |
| TAL014/016/025/029 | GATG | NN/NI/NG/NN | βγδε |
| TAL014/016/025/030 | GATT | NN/NI/NG/NG | βγδε |
| TAL014/017/021/026 | GCAA | NN/HD/NI/NI | βγδε |
| TAL014/017/021/027 | GCAC | NN/HD/NI/HD | βγδε |
| TAL014/017/021/028 | GCAG | NN/HD/NI/NK | βγδε |
| TAL014/017/021/029 | GCAG | NN/HD/NI/NN | βγδε |
| TAL014/017/021/030 | GCAT | NN/HD/NI/NG | βγδε |
| TAL014/017/022/026 | GCCA | NN/HD/HD/NI | βγδε |
| TAL014/017/022/027 | GCCC | NN/HD/HD/HD | βγδε |
| TAL014/017/022/028 | GCCG | NN/HD/HD/NK | βγδε |
| TAL014/017/022/029 | GCCG | NN/HD/HD/NN | βγδε |
| TAL014/017/022/030 | GCCT | NN/HD/HD/NG | βγδε |
| TAL014/017/023/026 | GCGA | NN/HD/NK/NI | βγδε |
| TAL014/017/023/027 | GCGC | NN/HD/NK/HD | βγδε |
| TAL014/017/023/028 | GCGG | NN/HD/NK/NK | βγδε |
| TAL014/017/023/029 | GCGG | NN/HD/NK/NN | βγδε |
| TAL014/017/023/030 | GCGT | NN/HD/NK/NG | βγδε |
| TAL014/017/024/026 | GCGA | NN/HD/NN/NI | βγδε |
| TAL014/017/024/027 | GCGC | NN/HD/NN/HD | βγδε |
| TAL014/017/024/028 | GCGG | NN/HD/NN/NK | βγδε |
| TAL014/017/024/029 | GCGG | NN/HD/NN/NN | βγδε |
| TAL014/017/024/030 | GCGT | NN/HD/NN/NG | βγδε |
| TAL014/017/025/026 | GCTA | NN/HD/NG/NI | βγδε |
| TAL014/017/025/027 | GCTC | NN/HD/NG/HD | βγδε |
| TAL014/017/025/028 | GCTG | NN/HD/NG/NK | βγδε |
| TAL014/017/025/029 | GCTG | NN/HD/NG/NN | βγδε |
| TAL014/017/025/030 | GCTT | NN/HD/NG/NG | βγδε |
| TAL014/018/021/026 | GGAA | NN/NK/NI/NI | βγδε |
| TAL014/018/021/027 | GGAC | NN/NK/NI/HD | βγδε |
| TAL014/018/021/028 | GGAG | NN/NK/NI/NK | βγδε |
| TAL014/018/021/029 | GGAG | NN/NK/NI/NN | βγδε |
| TAL014/018/021/030 | GGAT | NN/NK/NI/NG | βγδε |
| TAL014/018/022/026 | GGCA | NN/NK/HD/NI | βγδε |
| TAL014/018/022/027 | GGCC | NN/NK/HD/HD | βγδε |
| TAL014/018/022/028 | GGCG | NN/NK/HD/NK | βγδε |
| TAL014/018/022/029 | GGCG | NN/NK/HD/NN | βγδε |
| TAL014/018/022/030 | GGCT | NN/NK/HD/NG | βγδε |
| TAL014/018/023/026 | GGGA | NN/NK/NK/NI | βγδε |
| TAL014/018/023/027 | GGGC | NN/NK/NK/HD | βγδε |
| TAL014/018/023/028 | GGGG | NN/NK/NK/NK | βγδε |
| TAL014/018/023/029 | GGGG | NN/NK/NK/NN | βγδε |
| TAL014/018/023/030 | GGGT | NN/NK/NK/NG | βγδε |
| TAL014/018/024/026 | GGGA | NN/NK/NN/NI | βγδε |
| TAL014/018/024/027 | GGGC | NN/NK/NN/HD | βγδε |
| TAL014/018/024/028 | GGGG | NN/NK/NN/NK | βγδε |
| TAL014/018/024/029 | GGGG | NN/NK/NN/NN | βγδε |
| TAL014/018/024/030 | GGGT | NN/NK/NN/NG | βγδε |
| TAL014/018/025/026 | GGTA | NN/NK/NG/NI | βγδε |
| TAL014/018/025/027 | GGTC | NN/NK/NG/HD | βγδε |
| TAL014/018/025/028 | GGTG | NN/NK/NG/NK | βγδε |
| TAL014/018/025/029 | GGTG | NN/NK/NG/NN | βγδε |
| TAL014/018/025/030 | GGTT | NN/NK/NG/NG | βγδε |
| TAL014/019/021/026 | GGAA | NN/NN/NI/NI | βγδε |
| TAL014/019/021/027 | GGAC | NN/NN/NI/HD | βγδε |
| TAL014/019/021/028 | GGAG | NN/NN/NI/NK | βγδε |
| TAL014/019/021/029 | GGAG | NN/NN/NI/NN | βγδε |
| TAL014/019/021/030 | GGAT | NN/NN/NI/NG | βγδε |
| TAL014/019/022/026 | GGCA | NN/NN/HD/NI | βγδε |
| TAL014/019/022/027 | GGCC | NN/NN/HD/HD | βγδε |
| TAL014/019/022/028 | GGCG | NN/NN/HD/NK | βγδε |
| TAL014/019/022/029 | GGCG | NN/NN/HD/NN | βγδε |
| TAL014/019/022/030 | GGCT | NN/NN/HD/NG | βγδε |
| TAL014/019/023/026 | GGGA | NN/NN/NK/NI | βγδε |
| TAL014/019/023/027 | GGGC | NN/NN/NK/HD | βγδε |
| TAL014/019/023/028 | GGGG | NN/NN/NK/NK | βγδε |
| TAL014/019/023/029 | GGGG | NN/NN/NK/NN | βγδε |
| TAL014/019/023/030 | GGGT | NN/NN/NK/NG | βγδε |
| TAL014/019/024/026 | GGGA | NN/NN/NN/NI | βγδε |
| TAL014/019/024/027 | GGGC | NN/NN/NN/HD | βγδε |
| TAL014/019/024/028 | GGGG | NN/NN/NN/NK | βγδε |
| TAL014/019/024/029 | GGGG | NN/NN/NN/NN | βγδε |
| TAL014/019/024/030 | GGGT | NN/NN/NN/NG | βγδε |
| TAL014/019/025/026 | GGTA | NN/NN/NG/NI | βγδε |
| TAL014/019/025/027 | GGTC | NN/NN/NG/HD | βγδε |
| TAL014/019/025/028 | GGTG | NN/NN/NG/NK | βγδε |
| TAL014/019/025/029 | GGTG | NN/NN/NG/NN | βγδε |
| TAL014/019/025/030 | GGTT | NN/NN/NG/NG | βγδε |
| TAL014/020/021/026 | GTAA | NN/NG/NI/NI | βγδε |
| TAL014/020/021/027 | GTAC | NN/NG/NI/HD | βγδε |
| TAL014/020/021/028 | GTAG | NN/NG/NI/NK | βγδε |
| TAL014/020/021/029 | GTAG | NN/NG/NI/NN | βγδε |
| TAL014/020/021/030 | GTAT | NN/NG/NI/NG | βγδε |
| TAL014/020/022/026 | GTCA | NN/NG/HD/NI | βγδε |
| TAL014/020/022/027 | GTCC | NN/NG/HD/HD | βγδε |
| TAL014/020/022/028 | GTCG | NN/NG/HD/NK | βγδε |
| TAL014/020/022/029 | GTCG | NN/NG/HD/NN | βγδε |
| TAL014/020/022/030 | GTCT | NN/NG/HD/NG | βγδε |
| TAL014/020/023/026 | GTGA | NN/NG/NK/NI | βγδε |
| TAL014/020/023/027 | GTGC | NN/NG/NK/HD | βγδε |
| TAL014/020/023/028 | GTGG | NN/NG/NK/NK | βγδε |
| TAL014/020/023/029 | GTGG | NN/NG/NK/NN | βγδε |
| TAL014/020/023/030 | GTGT | NN/NG/NK/NG | βγδε |
| TAL014/020/024/026 | GTGA | NN/NG/NN/NI | βγδε |
| TAL014/020/024/027 | GTGC | NN/NG/NN/HD | βγδε |
| TAL014/020/024/028 | GTGG | NN/NG/NN/NK | βγδε |
| TAL014/020/024/029 | GTGG | NN/NG/NN/NN | βγδε |
| TAL014/020/024/030 | GTGT | NN/NG/NN/NG | βγδε |
| TAL014/020/025/026 | GTTA | NN/NG/NG/NI | βγδε |
| TAL014/020/025/027 | GTTC | NN/NG/NG/HD | βγδε |
| TAL014/020/025/028 | GTTG | NN/NG/NG/NK | βγδε |
| TAL014/020/025/029 | GTTG | NN/NG/NG/NN | βγδε |
| TAL014/020/025/030 | GTTT | NN/NG/NG/NG | βγδε |
| TAL015/016/021/026 | TAAA | NG/NI/NI/NI | βγδε |
| TAL015/016/021/027 | TAAC | NG/NI/NI/HD | βγδε |
| TAL015/016/021/028 | TAAG | NG/NI/NI/NK | βγδε |
| TAL015/016/021/029 | TAAG | NG/NI/NI/NN | βγδε |
| TAL015/016/021/030 | TAAT | NG/NI/NI/NG | βγδε |
| TAL015/016/022/026 | TACA | NG/NI/HD/NI | βγδε |
| TAL015/016/022/027 | TACC | NG/NI/HD/HD | βγδε |
| TAL015/016/022/028 | TACG | NG/NI/HD/NK | βγδε |
| TAL015/016/022/029 | TACG | NG/NI/HD/NN | βγδε |
| TAL015/016/022/030 | TACT | NG/NI/HD/NG | βγδε |
| TAL015/016/023/026 | TAGA | NG/NI/NK/NI | βγδε |
| TAL015/016/023/027 | TAGC | NG/NI/NK/HD | βγδε |
| TAL015/016/023/028 | TAGG | NG/NI/NK/NK | βγδε |
| TAL015/016/023/029 | TAGG | NG/NI/NK/NN | βγδε |
| TAL015/016/023/030 | TAGT | NG/NI/NK/NG | βγδε |
| TAL015/016/024/026 | TAGA | NG/NI/NN/NI | βγδε |
| TAL015/016/024/027 | TAGC | NG/NI/NN/HD | βγδε |
| TAL015/016/024/028 | TAGG | NG/NI/NN/NK | βγδε |
| TAL015/016/024/029 | TAGG | NG/NI/NN/NN | βγδε |
| TAL015/016/024/030 | TAGT | NG/NI/NN/NG | βγδε |
| TAL015/016/025/026 | TATA | NG/NI/NG/NI | βγδε |
| TAL015/016/025/027 | TATC | NG/NI/NG/HD | βγδε |
| TAL015/016/025/028 | TATG | NG/NI/NG/NK | βγδε |
| TAL015/016/025/029 | TATG | NG/NI/NG/NN | βγδε |
| TAL015/016/025/030 | TATT | NG/NI/NG/NG | βγδε |
| TAL015/017/021/026 | TCAA | NG/HD/NI/NI | βγδε |
| TAL015/017/021/027 | TCAC | NG/HD/NI/HD | βγδε |
| TAL015/017/021/028 | TCAG | NG/HD/NI/NK | βγδε |
| TAL015/017/021/029 | TCAG | NG/HD/NI/NN | βγδε |
| TAL015/017/021/030 | TCAT | NG/HD/NI/NG | βγδε |
| TAL015/017/022/026 | TCCA | NG/HD/HD/NI | βγδε |
| TAL015/017/022/027 | TCCC | NG/HD/HD/HD | βγδε |
| TAL015/017/022/028 | TCCG | NG/HD/HD/NK | βγδε |
| TAL015/017/022/029 | TCCG | NG/HD/HD/NN | βγδε |
| TAL015/017/022/030 | TCCT | NG/HD/HD/NG | βγδε |
| TAL015/017/023/026 | TCGA | NG/HD/NK/NI | βγδε |
| TAL015/017/023/027 | TCGC | NG/HD/NK/HD | βγδε |
| TAL015/017/023/028 | TCGG | NG/HD/NK/NK | βγδε |
| TAL015/017/023/029 | TCGG | NG/HD/NK/NN | βγδε |
| TAL015/017/023/030 | TCGT | NG/HD/NK/NG | βγδε |
| TAL015/017/024/026 | TCGA | NG/HD/NN/NI | βγδε |

TABLE 5-continued

Archive of 835 plasmids encoding pre-assembled TALE repeat units

| Plasmid ID | DNA Target | RVDs | Unit Architecture |
|---|---|---|---|
| TAL015/017/024/027 | TCGC | NG/HD/NN/HD | βγδε |
| TAL015/017/024/028 | TCGG | NG/HD/NN/NK | βγδε |
| TAL015/017/024/029 | TCGG | NG/HD/NN/NN | βγδε |
| TAL015/017/024/030 | TCGT | NG/HD/NN/NG | βγδε |
| TAL015/017/025/026 | TCTA | NG/HD/NG/NI | βγδε |
| TAL015/017/025/027 | TCTC | NG/HD/NG/HD | βγδε |
| TAL015/017/025/028 | TCTG | NG/HD/NG/NK | βγδε |
| TAL015/017/025/029 | TCTG | NG/HD/NG/NN | βγδε |
| TAL015/017/025/030 | TCTT | NG/HD/NG/NG | βγδε |
| TAL015/018/021/026 | TGAA | NG/NK/NI/NI | βγδε |
| TAL015/018/021/027 | TGAC | NG/NK/NI/HD | βγδε |
| TAL015/018/021/028 | TGAG | NG/NK/NI/NK | βγδε |
| TAL015/018/021/029 | TGAG | NG/NK/NI/NN | βγδε |
| TAL015/018/021/030 | TGAT | NG/NK/NI/NG | βγδε |
| TAL015/018/022/026 | TGCA | NG/NK/HD/NI | βγδε |
| TAL015/018/022/027 | TGCC | NG/NK/HD/HD | βγδε |
| TAL015/018/022/028 | TGCG | NG/NK/HD/NK | βγδε |
| TAL015/018/022/029 | TGCG | NG/NK/HD/NN | βγδε |
| TAL015/018/022/030 | TGCT | NG/NK/HD/NG | βγδε |
| TAL015/018/023/026 | TGGA | NG/NK/NK/NI | βγδε |
| TAL015/018/023/027 | TGGC | NG/NK/NK/HD | βγδε |
| TAL015/018/023/028 | TGGG | NG/NK/NK/NK | βγδε |
| TAL015/018/023/029 | TGGG | NG/NK/NK/NN | βγδε |
| TAL015/018/023/030 | TGGT | NG/NK/NK/NG | βγδε |
| TAL015/018/024/026 | TGGA | NG/NK/NN/NI | βγδε |
| TAL015/018/024/027 | TGGC | NG/NK/NN/HD | βγδε |
| TAL015/018/024/028 | TGGG | NG/NK/NN/NK | βγδε |
| TAL015/018/024/029 | TGGG | NG/NK/NN/NN | βγδε |
| TAL015/018/024/030 | TGGT | NG/NK/NN/NG | βγδε |
| TAL015/018/025/026 | TGTA | NG/NK/NG/NI | βγδε |
| TAL015/018/025/027 | TGTC | NG/NK/NG/HD | βγδε |
| TAL015/018/025/028 | TGTG | NG/NK/NG/NK | βγδε |
| TAL015/018/025/029 | TGTG | NG/NK/NG/NN | βγδε |
| TAL015/018/025/030 | TGTT | NG/NK/NG/NG | βγδε |
| TAL015/019/021/026 | TGAA | NG/NN/NI/NI | βγδε |
| TAL015/019/021/027 | TGAC | NG/NN/NI/HD | βγδε |
| TAL015/019/021/028 | TGAG | NG/NN/NI/NK | βγδε |
| TAL015/019/021/029 | TGAG | NG/NN/NI/NN | βγδε |
| TAL015/019/021/030 | TGAT | NG/NN/NI/NG | βγδε |
| TAL015/019/022/026 | TGCA | NG/NN/HD/NI | βγδε |
| TAL015/019/022/027 | TGCC | NG/NN/HD/HD | βγδε |
| TAL015/019/022/028 | TGCG | NG/NN/HD/NK | βγδε |
| TAL015/019/022/029 | TGCG | NG/NN/HD/NN | βγδε |
| TAL015/019/022/030 | TGCT | NG/NN/HD/NG | βγδε |
| TAL015/019/023/026 | TGGA | NG/NN/NK/NI | βγδε |
| TAL015/019/023/027 | TGGC | NG/NN/NK/HD | βγδε |
| TAL015/019/023/028 | TGGG | NG/NN/NK/NK | βγδε |
| TAL015/019/023/029 | TGGG | NG/NN/NK/NN | βγδε |
| TAL015/019/023/030 | TGGT | NG/NN/NK/NG | βγδε |
| TAL015/019/024/026 | TGGA | NG/NN/NN/NI | βγδε |
| TAL015/019/024/027 | TGGC | NG/NN/NN/HD | βγδε |
| TAL015/019/024/028 | TGGG | NG/NN/NN/NK | βγδε |
| TAL015/019/024/029 | TGGG | NG/NN/NN/NN | βγδε |
| TAL015/019/024/030 | TGGT | NG/NN/NN/NG | βγδε |
| TAL015/019/025/026 | TGTA | NG/NN/NG/NI | βγδε |
| TAL015/019/025/027 | TGTC | NG/NN/NG/HD | βγδε |
| TAL015/019/025/028 | TGTG | NG/NN/NG/NK | βγδε |
| TAL015/019/025/029 | TGTG | NG/NN/NG/NN | βγδε |
| TAL015/019/025/030 | TGTT | NG/NN/NG/NG | βγδε |
| TAL015/020/021/026 | TTAA | NG/NG/NI/NI | βγδε |
| TAL015/020/021/027 | TTAC | NG/NG/NI/HD | βγδε |
| TAL015/020/021/028 | TTAG | NG/NG/NI/NK | βγδε |
| TAL015/020/021/029 | TTAG | NG/NG/NI/NN | βγδε |
| TAL015/020/021/030 | TTAT | NG/NG/NI/NG | βγδε |
| TAL015/020/022/026 | TTCA | NG/NG/HD/NI | βγδε |
| TAL015/020/022/027 | TTCC | NG/NG/HD/HD | βγδε |
| TAL015/020/022/028 | TTCG | NG/NG/HD/NK | βγδε |
| TAL015/020/022/029 | TTCG | NG/NG/HD/NN | βγδε |
| TAL015/020/022/030 | TTCT | NG/NG/HD/NG | βγδε |
| TAL015/020/023/026 | TTGA | NG/NG/NK/NI | βγδε |
| TAL015/020/023/027 | TTGC | NG/NG/NK/HD | βγδε |
| TAL015/020/023/028 | TTGG | NG/NG/NK/NK | βγδε |
| TAL015/020/023/029 | TTGG | NG/NG/NK/NN | βγδε |
| TAL015/020/023/030 | TTGT | NG/NG/NK/NG | βγδε |
| TAL015/020/024/026 | TTGA | NG/NG/NN/NI | βγδε |
| TAL015/020/024/027 | TTGC | NG/NG/NN/HD | βγδε |
| TAL015/020/024/028 | TTGG | NG/NG/NN/NK | βγδε |
| TAL015/020/024/029 | TTGG | NG/NG/NN/NN | βγδε |
| TAL015/020/024/030 | TTGT | NG/NG/NN/NG | βγδε |
| TAL015/020/025/026 | TTTA | NG/NG/NG/NI | βγδε |
| TAL015/020/025/027 | TTTC | NG/NG/NG/HD | βγδε |
| TAL015/020/025/028 | TTTG | NG/NG/NG/NK | βγδε |
| TAL015/020/025/029 | TTTG | NG/NG/NG/NN | βγδε |
| TAL015/020/025/030 | TTTT | NG/NG/NG/NG | βγδε |
| TAL011/016 | AA | NI/NI | βγ |
| TAL011/017 | AC | NI/HD | βγ |
| TAL011/018 | AG | NI/NK | βγ |
| TAL011/019 | AG | NI/NN | βγ |
| TAL011/020 | AT | NI/NG | βγ |
| TAL012/016 | CA | HD/NI | βγ |
| TAL012/017 | CC | HD/HD | βγ |
| TAL012/018 | CG | HD/NK | βγ |
| TAL012/019 | CG | HD/NN | βγ |
| TAL012/020 | CT | HD/NG | βγ |
| TAL013/016 | GA | NK/NI | βγ |
| TAL013/017 | GC | NK/HD | βγ |
| TAL013/018 | GG | NK/NK | βγ |
| TAL013/019 | GG | NK/NN | βγ |
| TAL013/020 | GT | NK/NG | βγ |
| TAL014/016 | GA | NN/NI | βγ |
| TAL014/017 | GC | NN/HD | βγ |
| TAL014/018 | GG | NN/NK | βγ |
| TAL014/019 | GG | NN/NN | βγ |
| TAL014/020 | GT | NN/NG | βγ |
| TAL015/016 | TA | NG/NI | βγ |
| TAL015/017 | TC | NG/HD | βγ |
| TAL015/018 | TG | NG/NK | βγ |
| TAL015/019 | TG | NG/NN | βγ |
| TAL015/020 | TT | NG/NG | βγ |
| TAL011/016/021 | AAA | NI/NI/NI | βγδ |
| TAL011/016/022 | AAC | NI/NI/HD | βγδ |
| TAL011/016/023 | AAG | NI/NI/NK | βγδ |
| TAL011/016/024 | AAG | NI/NI/NN | βγδ |
| TAL011/016/025 | AAT | NI/NI/NG | βγδ |
| TAL011/017/021 | ACA | NI/HD/NI | βγδ |
| TAL011/017/022 | ACC | NI/HD/HD | βγδ |
| TAL011/017/023 | ACG | NI/HD/NK | βγδ |
| TAL011/017/024 | ACG | NI/HD/NN | βγδ |
| TAL011/017/025 | ACT | NI/HD/NG | βγδ |
| TAL011/018/021 | AGA | NI/NK/NI | βγδ |
| TAL011/018/022 | AGC | NI/NK/HD | βγδ |
| TAL011/018/023 | AGG | NI/NK/NK | βγδ |
| TAL011/018/024 | AGG | NI/NK/NN | βγδ |
| TAL011/018/025 | AGT | NI/NK/NG | βγδ |
| TAL011/019/021 | AGA | NI/NN/NI | βγδ |
| TAL011/019/022 | AGC | NI/NN/HD | βγδ |
| TAL011/019/023 | AGG | NI/NN/NK | βγδ |
| TAL011/019/024 | AGG | NI/NN/NN | βγδ |
| TAL011/019/025 | AGT | NI/NN/NG | βγδ |
| TAL011/020/021 | ATA | NI/NG/NI | βγδ |
| TAL011/020/022 | ATC | NI/NG/HD | βγδ |
| TAL011/020/023 | ATG | NI/NG/NK | βγδ |
| TAL011/020/024 | ATG | NI/NG/NN | βγδ |
| TAL011/020/025 | ATT | NI/NG/NG | βγδ |
| TAL012/016/021 | CAA | HD/NI/NI | βγδ |
| TAL012/016/022 | CAC | HD/NI/HD | βγδ |
| TAL012/016/023 | CAG | HD/NI/NK | βγδ |
| TAL012/016/024 | CAG | HD/NI/NN | βγδ |
| TAL012/016/025 | CAT | HD/NI/NG | βγδ |
| TAL012/017/021 | CCA | HD/HD/NI | βγδ |
| TAL012/017/022 | CCC | HD/HD/HD | βγδ |
| TAL012/017/023 | CCG | HD/HD/NK | βγδ |
| TAL012/017/024 | CCG | HD/HD/NN | βγδ |
| TAL012/017/025 | CCT | HD/HD/NG | βγδ |
| TAL012/018/021 | CGA | HD/NK/NI | βγδ |
| TAL012/018/022 | CGC | HD/NK/HD | βγδ |
| TAL012/018/023 | CGG | HD/NK/NK | βγδ |
| TAL012/018/024 | CGG | HD/NK/NN | βγδ |
| TAL012/018/025 | CGT | HD/NK/NG | βγδ |
| TAL012/019/021 | CGA | HD/NN/NI | βγδ |

TABLE 5-continued

Archive of 835 plasmids encoding pre-assembled TALE repeat units

| Plasmid ID | DNA Target | RVDs | Unit Architecture |
|---|---|---|---|
| TAL012/019/022 | CGC | HD/NN/HD | βγδ |
| TAL012/019/023 | CGG | HD/NN/NK | βγδ |
| TAL012/019/024 | CGG | HD/NN/NN | βγδ |
| TAL012/019/025 | CGT | HD/NN/NG | βγδ |
| TAL012/020/021 | CTA | HD/NG/NI | βγδ |
| TAL012/020/022 | CTC | HD/NG/HD | βγδ |
| TAL012/020/023 | CTG | HD/NG/NK | βγδ |
| TAL012/020/024 | CTG | HD/NG/NN | βγδ |
| TAL012/020/025 | CTT | HD/NG/NG | βγδ |
| TAL013/016/021 | GAA | NK/NI/NI | βγδ |
| TAL013/016/022 | GAC | NK/NI/HD | βγδ |
| TAL013/016/023 | GAG | NK/NI/NK | βγδ |
| TAL013/016/024 | GAG | NK/NI/NN | βγδ |
| TAL013/016/025 | GAT | NK/NI/NG | βγδ |
| TAL013/017/021 | GCA | NK/HD/NI | βγδ |
| TAL013/017/022 | GCC | NK/HD/HD | βγδ |
| TAL013/017/023 | GCG | NK/HD/NK | βγδ |
| TAL013/017/024 | GCG | NK/HD/NN | βγδ |
| TAL013/017/025 | GCT | NK/HD/NG | βγδ |
| TAL013/018/021 | GGA | NK/NK/NI | βγδ |
| TAL013/018/022 | GGC | NK/NK/HD | βγδ |
| TAL013/018/023 | GGG | NK/NK/NK | βγδ |
| TAL013/018/024 | GGG | NK/NK/NN | βγδ |
| TAL013/018/025 | GGT | NK/NK/NG | βγδ |
| TAL013/019/021 | GGA | NK/NN/NI | βγδ |
| TAL013/019/022 | GGC | NK/NN/HD | βγδ |
| TAL013/019/023 | GGG | NK/NN/NK | βγδ |
| TAL013/019/024 | GGG | NK/NN/NN | βγδ |
| TAL013/019/025 | GGT | NK/NN/NG | βγδ |
| TAL013/020/021 | GTA | NK/NG/NI | βγδ |
| TAL013/020/022 | GTC | NK/NG/HD | βγδ |
| TAL013/020/023 | GTG | NK/NG/NK | βγδ |
| TAL013/020/024 | GTG | NK/NG/NN | βγδ |
| TAL013/020/025 | GTT | NK/NG/NG | βγδ |
| TAL014/016/021 | GAA | NN/NI/NI | βγδ |
| TAL014/016/022 | GAC | NN/NI/HD | βγδ |
| TAL014/016/023 | GAG | NN/NI/NK | βγδ |
| TAL014/016/024 | GAG | NN/NI/NN | βγδ |
| TAL014/016/025 | GAT | NN/NI/NG | βγδ |
| TAL014/017/021 | GCA | NN/HD/NI | βγδ |
| TAL014/017/022 | GCC | NN/HD/HD | βγδ |
| TAL014/017/023 | GCG | NN/HD/NK | βγδ |
| TAL014/017/024 | GCG | NN/HD/NN | βγδ |
| TAL014/017/025 | GCT | NN/HD/NG | βγδ |
| TAL014/018/021 | GGA | NN/NK/NI | βγδ |
| TAL014/018/022 | GGC | NN/NK/HD | βγδ |
| TAL014/018/023 | GGG | NN/NK/NK | βγδ |
| TAL014/018/024 | GGG | NN/NK/NN | βγδ |
| TAL014/018/025 | GGT | NN/NK/NG | βγδ |
| TAL014/019/021 | GGA | NN/NN/NI | βγδ |
| TAL014/019/022 | GGC | NN/NN/HD | βγδ |
| TAL014/019/023 | GGG | NN/NN/NK | βγδ |
| TAL014/019/024 | GGG | NN/NN/NN | βγδ |
| TAL014/019/025 | GGT | NN/NN/NG | βγδ |
| TAL014/020/021 | GTA | NN/NG/NI | βγδ |
| TAL014/020/022 | GTC | NN/NG/HD | βγδ |
| TAL014/020/023 | GTG | NN/NG/NK | βγδ |
| TAL014/020/024 | GTG | NN/NG/NN | βγδ |
| TAL014/020/025 | GTT | NN/NG/NG | βγδ |
| TAL015/016/021 | TAA | NG/NI/NI | βγδ |
| TAL015/016/022 | TAC | NG/NI/HD | βγδ |
| TAL015/016/023 | TAG | NG/NI/NK | βγδ |
| TAL015/016/024 | TAG | NG/NI/NN | βγδ |
| TAL015/016/025 | TAT | NG/NI/NG | βγδ |
| TAL015/017/021 | TCA | NG/HD/NI | βγδ |
| TAL015/017/022 | TCC | NG/HD/HD | βγδ |
| TAL015/017/023 | TCG | NG/HD/NK | βγδ |
| TAL015/017/024 | TCG | NG/HD/NN | βγδ |
| TAL015/017/025 | TCT | NG/HD/NG | βγδ |
| TAL015/018/021 | TGA | NG/NK/NI | βγδ |
| TAL015/018/022 | TGC | NG/NK/HD | βγδ |
| TAL015/018/023 | TGG | NG/NK/NK | βγδ |
| TAL015/018/024 | TGG | NG/NK/NN | βγδ |
| TAL015/018/025 | TGT | NG/NK/NG | βγδ |
| TAL015/019/021 | TGA | NG/NN/NI | βγδ |
| TAL015/019/022 | TGC | NG/NN/HD | βγδ |
| TAL015/019/023 | TGG | NG/NN/NK | βγδ |
| TAL015/019/024 | TGG | NG/NN/NN | βγδ |
| TAL015/019/025 | TGT | NG/NN/NG | βγδ |
| TAL015/020/021 | TTA | NG/NG/NI | βγδ |
| TAL015/020/022 | TTC | NG/NG/HD | βγδ |
| TAL015/020/023 | TTG | NG/NG/NK | βγδ |
| TAL015/020/024 | TTG | NG/NG/NN | βγδ |
| TAL015/020/025 | TTT | NG/NG/NG | βγδ |
| TAL011/031 | AA | NI/NI | βγ' |
| TAL011/032 | AC | NI/HD | βγ' |
| TAL011/033 | AG | NI/NK | βγ' |
| TAL011/034 | AG | NI/NN | βγ' |
| TAL011/035 | AT | NI/NG | βγ' |
| TAL012/031 | CA | HD/NI | βγ' |
| TAL012/032 | CC | HD/HD | βγ' |
| TAL012/033 | CG | HD/NK | βγ' |
| TAL012/034 | CG | HD/NN | βγ' |
| TAL012/035 | CT | HD/NG | βγ' |
| TAL013/031 | GA | NK/NI | βγ' |
| TAL013/032 | GC | NK/HD | βγ' |
| TAL013/033 | GG | NK/NK | βγ' |
| TAL013/034 | GG | NK/NN | βγ' |
| TAL013/035 | GT | NK/NG | βγ' |
| TAL014/031 | GA | NN/NI | βγ' |
| TAL014/032 | GC | NN/HD | βγ' |
| TAL014/033 | GG | NN/NK | βγ' |
| TAL014/034 | GG | NN/NN | βγ' |
| TAL014/035 | GT | NN/NG | βγ' |
| TAL015/031 | TA | NG/NI | βγ' |
| TAL015/032 | TC | NG/HD | βγ' |
| TAL015/033 | TG | NG/NK | βγ' |
| TAL015/034 | TG | NG/NN | βγ' |
| TAL015/035 | TT | NG/NG | βγ' |
| TAL021/036 | AA | NI/NI | δε' |
| TAL021/037 | AC | NI/HD | δε' |
| TAL021/038 | AG | NI/NK | δε' |
| TAL021/039 | AG | NI/NN | δε' |
| TAL021/040 | AT | NI/NG | δε' |
| TAL022/036 | CA | HD/NI | δε' |
| TAL022/037 | CC | HD/HD | δε' |
| TAL022/038 | CG | HD/NK | δε' |
| TAL022/039 | CG | HD/NN | δε' |
| TAL022/040 | CT | HD/NG | δε' |
| TAL023/036 | GA | NK/NI | δε' |
| TAL023/037 | GC | NK/HD | δε' |
| TAL023/038 | GG | NK/NK | δε' |
| TAL023/039 | GG | NK/NN | δε' |
| TAL023/040 | GT | NK/NG | δε' |
| TAL024/036 | GA | NN/NI | δε' |
| TAL024/037 | GC | NN/HD | δε' |
| TAL024/038 | GG | NN/NK | δε' |
| TAL024/039 | GG | NN/NN | δε' |
| TAL024/040 | GT | NN/NG | δε' |
| TAL025/036 | TA | NG/NI | δε' |
| TAL025/037 | TC | NG/HD | δε' |
| TAL025/038 | TG | NG/NK | δε' |
| TAL025/039 | TG | NG/NN | δε' |
| TAL025/040 | TT | NG/NG | δε' |
| TAL011 | A | NI | β |
| TAL012 | C | HD | β |
| TAL013 | G | NK | β |
| TAL014 | G | NN | β |
| TAL015 | T | NG | β |

To prepare DNA fragments encoding α units for use in assembly, 20 rounds of PCR were performed with each α unit plasmid as a template using primers oJS2581 (5'-Biotin-TCTAGAGAAGACAAGAACCTGACC-3' (SEQ ID NO:237)) and oJS2582 (5'-GGATCCGGTCTCTTAAGGC-CGTGG-3' (SEQ ID NO:238)). The resulting PCR products were biotinylated on the 5' end. Each α PCR product was then digested with 40 units of BsaI-HF restriction enzyme to generate 4 bp overhangs, purified using the QIAquick PCR purification kit (QIAGEN) according to manufacturer's instructions except that the final product was eluted in 50 µl of 0.1×EB.

To prepare DNA fragments encoding β, βγδε, βγδ, βγ, βγ*, and δε* repeats, 10 µg of each of these plasmids was digested with 50 units of BbsI restriction enzyme in NEBuffer 2 for 2 hours at 37° C. followed by serial restriction digests performed in NEBuffer 4 at 37° C. using 100 units each of XbaI, BamHI-HF, and SalI-HF enzymes that were added at 5 minute intervals. The latter set of restriction digestions were designed to cleave the plasmid backbone to ensure that this larger DNA fragment does not interfere with subsequent ligations performed during the assembly process. These restriction digest reactions were then purified using the QIAquick PCR purification kit (QIAGEN) according to manufacturer's instructions except that the final product was eluted in 180 µl of 0.1×EB.

All assembly steps were performed using a Sciclone G3 liquid handling workstation (Caliper) in 96-well plates and using a SPRIplate 96-ring magnet (Beckman Coulter Genomics) and a DynaMag-96 Side magnet (Life Technologies). In the first assembly step, a biotinylated α unit fragment was ligated to the first βγδε fragment and then the resulting αβγδε fragments are bound to Dynabeads MyOne C1 streptavidin-coated magnetic beads (Life Technologies) in 2× B&W Buffer (Life Technologies). Beads were then drawn to the side of the well by placing the plate on the magnet and then washed with 100 µl B&W buffer with 0.005% Tween 20 (Sigma) and again with 100 µl 0.1 mg/ml bovine serum albumin (BSA) (New England Biolabs). Additional βγδε fragments were ligated by removing the plate from the magnet, resuspending the beads in solution in each well, digesting the bead bound fragment with BsaI-HF restriction enzyme, placing the plate on the magnet, washing with 100 µl B&W/Tween20 followed by 100 µl of 0.1 mg/ml BSA, and then ligating the next fragment. This process was repeated multiple times with additional βγδε units to extend the bead-bound fragment. The last fragment to be ligated was always a β, βγ*, βγδ, or δε* unit to enable cloning of the full-length fragment into expression vectors (note that fragments that end with a δε* unit are always preceded by ligation of a βγ unit).

The final full-length bead-bound fragment was digested with 40 units of BsaI-HF restriction enzyme followed by 25 units of BbsI restriction enzyme (New England Biolabs). Digestion with BbsI released the fragment from the beads and generated a unique 5' overhang for cloning of the fragment. Digestion with BsaI-HF resulted in creation of a unique 3' overhang for cloning.

DNA fragments encoding the assembled TALE repeat arrays were subcloned into one of four TALEN expression vectors. Each of these vectors included a CMV promoter, a translational start codon optimized for mammalian cell expression, a triple FLAG epitope tag, a nuclear localization signal, amino acids 153 to 288 from the TALE 13 protein (Miller et al., 2011, Nat. Biotechnol., 29:143-148), two unique and closely positioned Type IIS BsmBI restriction sites, a 0.5 TALE repeat domain encoding one of four possible RVDs (NI, HD, NN, or NG for recognition of an A, C, or T nucleotide, respectively), amino acids 715 to 777 from the TALE 13 protein, and the wild-type FokI cleavage domain. All DNA fragments possessed overhangs that enable directional cloning into any of the four TALEN expression vectors that has been digested with BsmBI.

To prepare a TALEN expression vector for subcloning, 5 µg of plasmid DNA were digested with 50 units of BsmBI restriction enzyme (New England Biolabs) in NEBuffer 3 for 8 hours at 55 degrees C. Digested DNA was purified using 90 µl of Ampure XP beads (Agencourt) according to manufacturer's instructions and diluted to a final concentration of 5 ng/µl in 1 mM TrisHCl. The assembled TALE repeat arrays were ligated into TALEN expression vectors using 400 U of T4 DNA Ligase (New England Biolabs). Ligation products were transformed into chemically competent XL-1 Blue cells. Six colonies were picked for each ligation and plasmid DNA isolated by an alkaline lysis miniprep procedure. Simultaneously, the same six colonies were screened by PCR using primers oSQT34 (5'-GACG-GTGGCTGTCAAATACCAAGATATG-3' (SEQ ID NO:239)) and oSQT35 (5'-TCTCCTCCAGTTCACTTTT-GACTAGTTGGG-3' (SEQ ID NO:240)). PCR products were analyzed on a QIAxcel capillary electrophoresis system (Qiagen). Miniprep DNA from clones that contained correctly sized PCR products were sent for DNA sequence confirmation with primers oSQT1 (5'-AGTAACAGCGG-TAGAGGCAG-3' (SEQ ID NO:241)), oSQT3 (5'-AT-TGGGCTACGATGGACTCC-3' (SEQ ID NO:242)), and oJS2980 (5-TTAATTCAATATATTCATGAGGCAC-3' (SEQ ID NO:243)).

Because the final fragment ligated can encode one, two, or three TALE repeats, the methods disclosed herein can be used to assemble arrays consisting of any desired number of TALE repeats. Assembled DNA fragments encoding the final full-length TALE repeat array are released from the beads by restriction enzyme digestion and can be directly cloned into a desired expression vector of choice.

The methods can be efficiently practiced in 96-well format using a robotic liquid handling workstation. With automation, DNA fragments encoding 96 different TALE repeat arrays of variable lengths can be assembled in less than one day. Medium-throughput assembly of fragments can be performed in one to two days using multi-channel pipets and 96-well plates. Fragments assembled using either approach can then be cloned into expression vectors (e.g., for expression as a TALEN) to generate sequence-verified plasmids in less than one week. Using the automated assembly approach, sequence-verified TALE repeat array expression plasmids can be made quickly and inexpensively.

Example 6. Large-Scale Testing of Assembled TALENs Using a Human Cell-Based Reporter Assay To perform a large-scale test of the robustness of TALENs for genome editing in human cells, the method described in Example 5 was used to construct a series of plasmids encoding 48 TALEN pairs targeted to different sites scattered throughout the EGFP reporter gene. Monomers in each of the TALEN pairs contained the same number of repeats (ranging from 8.5 to 19.5 in number), and these pairs were targeted to sites possessing a fixed length "spacer" sequence (16 bps) between the "half-sites" bound by each TALEN monomer (Table 6).

TABLE 6

EGFP reporter gene sequences targeted by 48 pairs of TALENs

| TALEN pair # | Position within EGFP of the first nucleotide in the binding site | Target site (half-sites in CAPS, spacer in lowercase) | SEQ ID NO: | # of repeat domains in Left TALEN | # of repeat domains in Right TALEN |
|---|---|---|---|---|---|
| 1 | -8 | TCGCCACCATggtgagcaaggg cgagGAGCTGTTCA | 93 | 8.5 | 8.5 |
| 2 | 35 | TGGTGCCCATcctggtcgagct ggacGGCGACGTAA | 94 | 8.5 | 8.5 |
| 3 | 143 | TCTGCACCACcggcaagctgcc cgtgCCCTGGCCCA | 95 | 8.5 | 8.5 |
| 4 | 425 | TGGAGTACAActacaacagcca caacGTCTATATCA | 96 | 8.5 | 8.5 |
| 5 | 82 | TTCAGCGTGTCcggcgagggcg agggcGATGCCACCTA | 97 | 9.5 | 9.5 |
| 6 | 111 | TGCCACCTACGgcaagctgacc ctgaaaGTTCATCTGCA | 98 | 9.5 | 9.5 |
| 7 | 172 | TGGCCCACCCTcgtgaccaccc tgaccTACGGCGTGCA | 99 | 9.5 | 9.5 |
| 8 | 496 | TTCAAGATCCGccacaacatcg aggacGGCAGCGTGCA | 100 | 9.5 | 9.5 |
| 9 | -23 | TAGAGGATCCACcggtcgccac catggtGAGCAAGGGCGA | 101 | 10.5 | 10.5 |
| 10 | 91 | TCCGGCGAGGGCgagggcgatg ccacctACGGCAAGCTGA | 102 | 10.5 | 10.5 |
| 11 | 194 | TGACCTACGGCGtgcagtgctt cagccgCTACCCCGACCA | 103 | 10.5 | 10.5 |
| 12 | 503 | TCCGCCACAACAtcgaggacgg cagcgtGCAGCTCGCCGA | 104 | 10.5 | 10.5 |
| 13 | 44 | TCCTGGTCGAGCTggacggcga cgtaaacGGCCACAAGTTCA | 105 | 11.5 | 11.5 |
| 14 | 215 | TCAGCCGCTACCCcgaccacat gaagcagCACGACTTCTTCA | 106 | 11.5 | 11.5 |
| 15 | 251 | TCTTCAAGTCCGCcatgcccga aggctacGTCCAGGAGCGCA | 107 | 11.5 | 11.5 |
| 16 | 392 | TCAAGGAGGACGGcaacatcct ggggcacAAGCTGGAGTACA | 108 | 11.5 | 11.5 |
| 17 | 485 | TCAAGGTGAACTTcaagatccg ccacaacATCGAGGACGGCA | 109 | 11.5 | 11.5 |
| 18 | -16 | TCCACCGGTCGCCAccatggtg agcaagggCGAGGAGCTGTTCA | 110 | 12.5 | 12.5 |
| 19 | 82 | TTCAGCGTGTCCGGcgagggcg agggcgatGCCACCTACGGCAA | 111 | 12.5 | 12.5 |
| 20 | 214 | TTCAGCCGCTACCCcgaccaca tgaagcagACGACTTCTTCAA | 112 | 12.5 | 12.5 |
| 21 | 436 | TACAACAGCCACAAcgtctata tcatggccGACAAGCAGAAGAA | 113 | 12.5 | 12.5 |
| 22 | 35 | TGGTGCCCATCCTGGtcgagct ggacggcgaCGTAAACGGCCAC AA | 114 | 13.5 | 13.5 |

TABLE 6-continued

EGFP reporter gene sequences targeted by 48 pairs of TALENs

| TALEN pair # | Position within EGFP of the first nucleotide in the binding site | Target site (half-sites in CAPS, spacer in lowercase) | SEQ ID NO: | # of repeat domains in Left TALEN | # of repeat domains in Right TALEN |
|---|---|---|---|---|---|
| 23 | 266 | TGCCCGAAGGCTACGtccaggagcgcaccatCTTCTTCAAGGACGA | 115 | 13.5 | 13.5 |
| 24 | 362 | TGAACCGCATCGAGCtgaagggcatcgacttCAAGGAGGACGGCAA | 116 | 13.5 | 13.5 |
| 25 | 497 | TCAAGATCCGCCACAacatcgaggacggcagCGTGCAGCTCGCCGA | 117 | 13.5 | 13.5 |
| 26 | 23 | TGTTCACCGGGGTGGTgcccatcctggtcgagCTGGACGGCGACGTAA | 118 | 14.5 | 14.5 |
| 27 | 38 | TGCCCATCCTGGTCGAgctggacggcgacgtaAACGGCCACAAGTTCA | 119 | 14.5 | 14.5 |
| 28 | 89 | TGTCCGGCGAGGGCGAgggcgatgccacctacGGCAAGCTGACCCTGA | 120 | 14.5 | 14.5 |
| 29 | 140 | TCATCTGCACCACCGGcaagctgcccgtgcccTGGCCCACCCTCGTGA | 121 | 14.5 | 14.5 |
| 30 | 452 | TCTATATCATGGCCGAcaagcagaagaacggcATCAAGGTGAACTTCA | 122 | 14.5 | 14.5 |
| 31 | 199 | TACGGCGTGCAGTGCTTcagccgctaccccgacCACATGAAGCAGCACGA | 123 | 15.5 | 15.5 |
| 32 | 223 | TACCCCGACCACATGAAgcagcacgacttcttcAAGTCCGCCATGCCCGA | 124 | 15.5 | 15.5 |
| 33 | 259 | TCCGCCATGCCCGAAGGctacgtccaggagcgcACCATCTTCTTCAAGGA | 125 | 15.5 | 15.5 |
| 34 | 391 | TTCAAGGAGGACGGCAAcatcctggggcacaagCTGGAGTACAACTACAA | 126 | 15.5 | 15.5 |
| 35 | 430 | TACAACTACAACAGCCAcaacgtctatatcatgGCCGACAAGCAGAAGAA | 127 | 15.5 | 15.5 |
| 36 | 26 | TCACCGGGGTGGTGCCCAtcctggtcgagctggaCGGCGACGTAAACGGCCA | 128 | 16.5 | 16.5 |
| 37 | 68 | TAAACGGCCACAAGTTCAgcgtgtccggcgagggCGAGGGCGATGCCACCTA | 129 | 16.5 | 16.5 |
| 38 | 206 | TGCAGTGCTTCAGCCGCTacccgaccacatgaaGCAGCACGACTTCTTCAA | 130 | 16.5 | 16.5 |
| 39 | 83 | TCAGCGTGTCCGGCGAGGGCgagggcgatgccaccTACGGCAAGCTGACCCTGA | 131 | 17.5 | 17.5 |

TABLE 6-continued

EGFP reporter gene sequences targeted by 48 pairs of TALENs

| TALEN pair # | Position within EGFP of the first nucleotide in the binding site | Target site (half-sites in CAPS, spacer in lowercase) | SEQ ID NO: | # of repeat domains in Left TALEN | # of repeat domains in Right TALEN |
|---|---|---|---|---|---|
| 40 | 134 | TGAAGTTCATCTGCACCACcgg caagctgcccgtgCCCTGGCCC ACCCTCGTGA | 132 | 17.5 | 17.5 |
| 41 | 182 | TCGTGACCACCCTGACCTAcgg cgtgcagtgcttcAGCCGCTAC CCCGACCACA | 133 | 17.5 | 17.5 |
| 42 | 458 | TCATGGCCGACAAGCAGAAgaa cggcatcaaggtgAACTTCAAG ATCCGCCACA | 134 | 17.5 | 17.5 |
| 43 | 25 | TTCACCGGGGTGGTGCCCATcc tggtcgagctggacGGCGACGT AAACGGCCACAA | 135 | 18.5 | 18.5 |
| 44 | 145 | TGCACCACCGGCAAGCTGCCcg tgccctggcccaccCTCGTGAC CACCCTGACCTA | 136 | 18.5 | 18.5 |
| 45 | 253 | TTCAAGTCCGCCATGCCCGAag gctacgtccaggagCGCACCAT CTTCTTCAAGGA | 137 | 18.5 | 18.5 |
| 46 | 454 | TATATCATGGCCGACAAGCAga agaacggcatcaagGTGAACTT CAAGATCCGCCA | 138 | 18.5 | 18.5 |
| 47 | 139 | TTCATCTGCACCACCGGCAAGc tgcccgtgccctggcCCACCCT CGTGACCACCCTGA | 139 | 19.5 | 19.5 |
| 48 | 338 | TGAAGTTCGAGGGCGACACCCt ggtgaaccgcatcgaGCTGAAG GGCATCGACTTCAA | 140 | 19.5 | 19.5 |

Figures 19A, 19B:
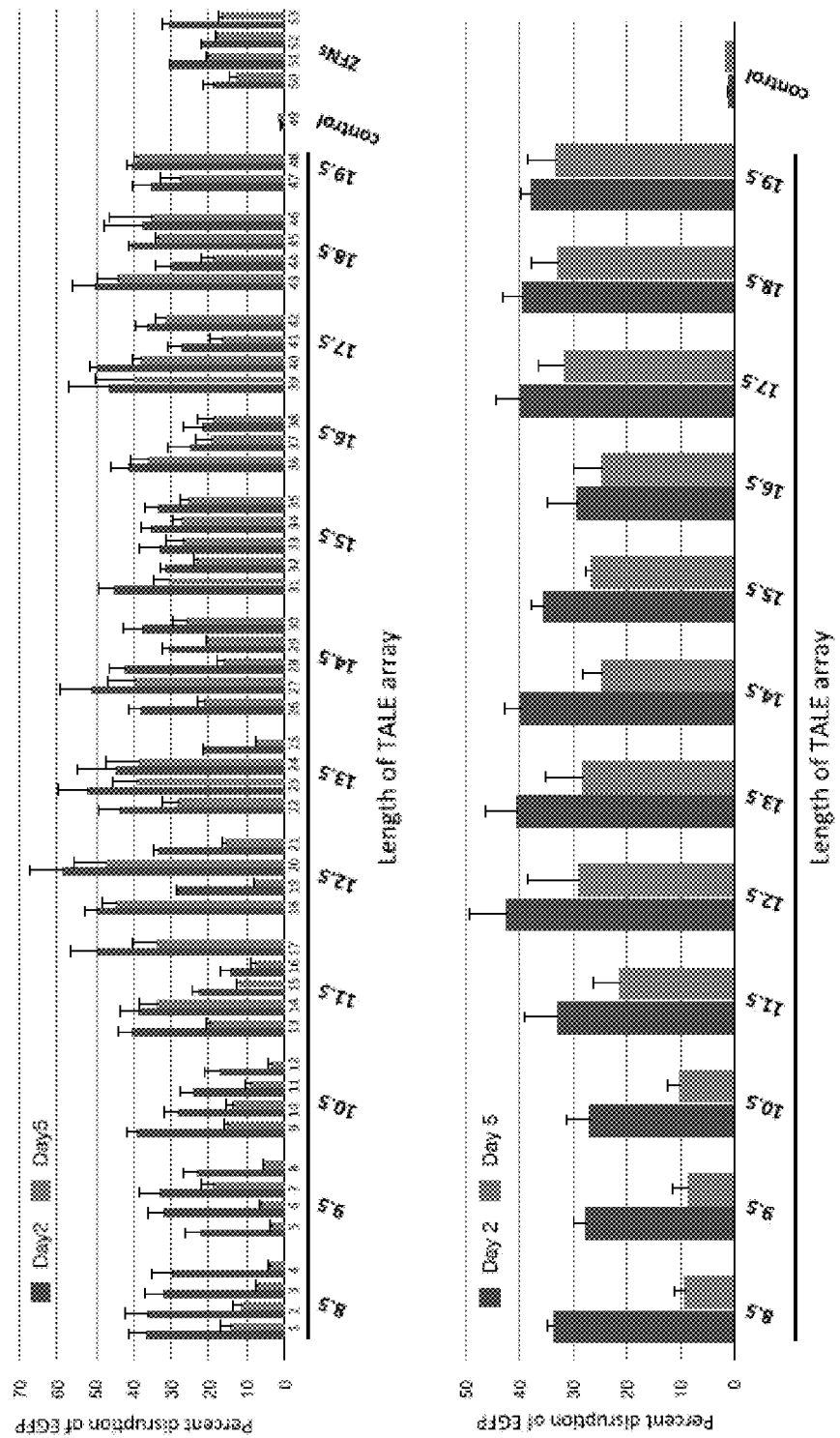
FIG. 19A is a bar graph depicting activities of 48 TALEN pairs and four ZFN pairs in the EGFP gene-disruption assay. Percentages of EGFP-negative cells as measured 2 and 5 days following transfection of U2OS cells bearing a chromosomally integrated EGFP reporter gene with nuclease-encoding plasmids are shown. Mean percent disruption of EGFP and standard error of the mean from three independent transfections are shown.
FIG. 19B is a bar graph depicting mean EGFP-disruption activities from FIG. 19A, grouped by length of the TALENs.

Each of the 48 TALEN pairs was tested in human cells for its ability to disrupt the coding sequence of a chromosomally integrated EGFP reporter gene. In this assay, NHEJ-mediated repair of TALEN-induced breaks within the EGFP coding sequence led to loss of EGFP expression, which was quantitatively assessed using flow cytometry 2 and 5 days following transfection. (To ensure that activities of each active TALEN pair could be detected, we only targeted sites located at or upstream of nucleotide position 503 in the gene, a position we had previously shown would disrupt EGFP function when mutated with a zinc finger nuclease (ZFN) (Maeder et al., 2008, Mol. Cell 31:294-301).) Strikingly, all 48 TALEN pairs showed significant EGFP gene-disruption activities in this assay (FIG. 19A). The net percentage of EGFP-disrupted cells induced by TALENs on day 2 post-transfection ranged from 9.4% to 68.0%, levels comparable to the percentage disruption observed with four EGFP-targeted ZFN pairs originally made by the Oligomerized Pool Engineering (OPEN) method (FIG. 19A). These results demonstrate that TALENs containing as few as 8.5 TALE repeats possess significant nuclease activities and provide a large-scale demonstration of the robustness of TALENs in human cells.

Figure 20A:
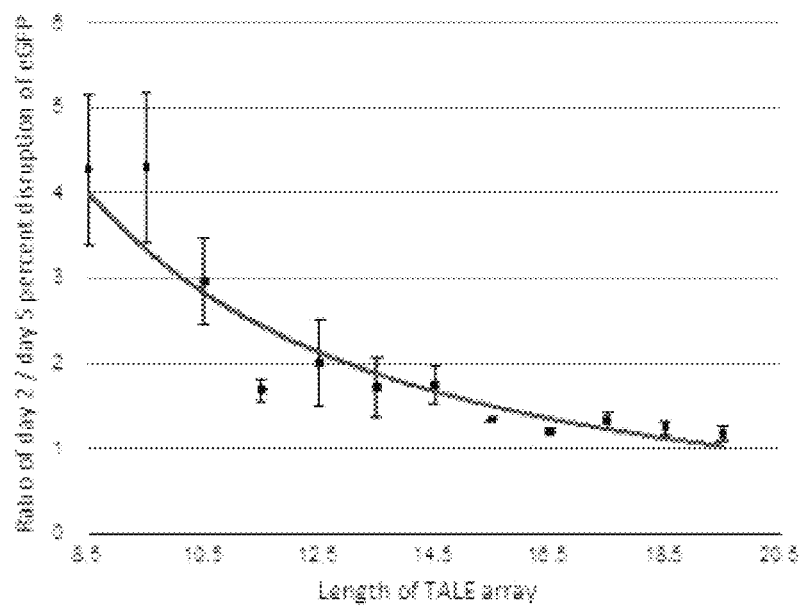
FIG. 20A is a graph depicting the ratio of mean percent EGFP disruption values from day 2 to day 5. Ratios were calculated for groups of each length TALEN using the data from FIG. 19B. Values greater than 1 indicate a decrease in the average of EGFP-disrupted cells at day 5 relative to day 2.
Figure 20B:
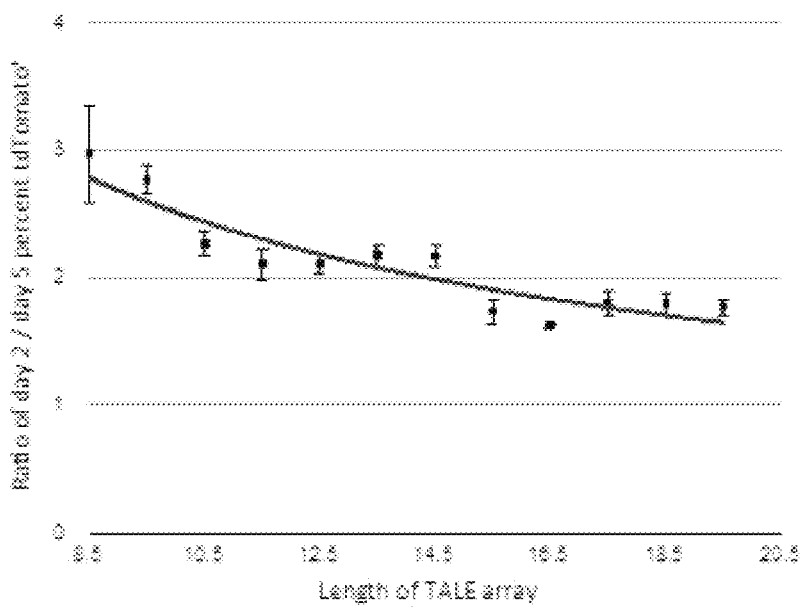
FIG. 20B is a graph depicting the ratio of mean tdTomato-positive cells from day 2 to day 5 grouped by various lengths of TALENs. tdTomato-encoding control plasmids were transfected together with nuclease-encoding plasmids on day 0.

Interestingly, re-quantification of the percentage of EGFP-negative cells at day 5 post-transfection revealed that cells expressing shorter-length TALENs (such as those composed of 8.5 to 10.5 repeats) showed significant reductions in the percentage of EGFP-disrupted cells whereas those expressing longer TALENs did not (FIGS. 19A-B and 20A). One potential explanation for this effect is cellular toxicity associated with expression of shorter-length TALENs. Consistent with this hypothesis, in cells transfected with plasmids encoding shorter-length TALENs, greater reductions in the percentage of tdTomato-positive cells were observed from day 2 to day 5 post-transfection (FIG. 20D) (a tdTomato-encoding plasmid was co-transfected together with the TALEN expression plasmids on day 0). Taken together, our results suggest that although shorter-length TALENs are as active as longer-length TALENs, the former can cause greater cytotoxicity in human cells.

Our EGFP experiments also provided an opportunity to assess four of five computationally-derived design guidelines (Cermak et al., 2011, Nucleic Acids Res., 39:e82). The guidelines proposed by Cermak are as follows:

1. The nucleotide just 5' to the first nucleotide of the half-site should be a thymine.

2. The first nucleotide of the half-site should not be a thymine.

3. The second nucleotide of the half-site should not be an adenosine.

4. The 3' most nucleotide in the target half-site should be a thymine.

5. The composition of each nucleotide within the target half-site should not vary from the observed percentage composition of naturally occurring binding sites by more than 2 standard deviations. The percentage composition of all naturally occurring TALE binding sites is: A=31±16%, C=37±13%, G=9±8%, T=22±10%. Hence, the nucleotide composition of potential TALE binding sites should be: A=0% to 63%, C=11% to 63%, G=0% to 25% and T=2% to 42%.

These guidelines have been implemented in the TALE-NT webserver (boglabx.plp.iastate.edu/TALENT/TALENT/) to assist users in identifying potential TALEN target sites. All 48 of the sequences we targeted in EGFP did not meet one or more of these guidelines (however, note that all of our sites did meet the requirement for a 5' T). The ~100% success rate observed for these 48 sites demonstrates that TALENs can be readily obtained for target sequences that do not follow these guidelines. In addition, for each of the four design guidelines, we did not find any statistically significant correlation between guideline violation and the level of TALEN-induced mutagenesis on either day 2 or day 5 post-transfection. We also failed to find a significant correlation between the total number of guideline violations and the level of mutagenic TALEN activity. Thus, our results show that failure to meet four of the five previously described design guidelines when identifying potential TALEN target sites does not appear to adversely affect success rates or nuclease efficiencies.

Example 7. High-Throughput Alteration of Endogenous Human Genes Using Assembled TALENs Having established the robustness of the TALEN platform with a chromosomally integrated reporter gene, it was next determined whether this high success rate would also be observed with endogenous genes in human cells. To test this, the assembly method described in Example 5 was used to engineer TALEN pairs targeted to 96 different human genes: 78 genes implicated in human cancer (Vogelstein and Kinzler, 2004, Nat. Med., 10:789-799) and 18 genes involved in epigenetic regulation of gene expression (Table 7). For each gene, a TALEN pair was designed to cleave near the amino-terminal end of the protein coding sequence, although in a small number of cases the presence of repetitive sequences led us to target alternate sites in neighboring downstream exons or introns (Table 7). Guided by the results with the EGFP TALENs, TALENs composed of 14.5, 15.5, or 16.5 repeats were constructed that cleaved sites with 16, 17, 18, 19 or 21 bp spacer sequences. All of the target sites had a T at the 5' end of each half-site.

TABLE 7

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| ABL1 | 22.5 ± 7.1 | TACCTATTATTACT TTATggggcagcagcctgg aaAAGTACTTGGGG ACCAA | 141. | 16.5 | 17 | 15.5 | Cancer |
| AKT2 | 14.1 ± 7.3 | TGTGTCTTGGGATG AGTGggtcagtgttctggtg CTCACAGGATGGCT GGCA | 142. | 16.5 | 16 | 16.5 | Cancer |
| ALK | 12.7 ± 2.9 | TCCTGTGGCTCCTG CCGCtgctgctttccacggc AGCTGTGGGCTCCG GGA | 143. | 16.5 | 16 | 15.5 | Cancer |
| APC | 48.8 ± 9.8 | TATGTACGCCTCCC TGGGctcgggtccggtcgcc CCTTTGCCCGCTTC TGTA | 144. | 16.5 | 16 | 16.5 | Cancer |
| ATM | 35.5 ± 15.6 | TGAATTGGGATGCT GTTTttaggtattctattcaaa TTTATTTTACTGTCT TTA | 145. | 16.5 | 18 | 16.5 | Cancer |
| AXIN2 | 2.5 ± 0.6 | TCCCTCACCATGAG TAGCgctatgttggtgacttG CCTCCCGGACCCCA GCA | 146. | 16.5 | 16 | 16.5 | Cancer |
| BAX | 14.7 ± 11.6 | TGTGCGATCTCCAA GCACtgaggggcagaaact cCCGGATCGGGCGC TGCCA | 147. | 16.5 | 16 | 16.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| BCL6 | 14.9 ± 5.9 | TTTTCAAGTGAAGA CAAatggcctcgccggct gACAGCTGTATCCA GTTCA | 148. | 16.5 | 16 | 16.5 | Cancer |
| BMPR1A | 50.4 ± 16.4 | TACAATTGAACAAT GCCTcagctatacatttacat CAGATTATTGGGAG CCTA | 149. | 16.5 | 17 | 16.5 | Cancer |
| BRCA1 | 44.5 ± 15.5 | TCCGAAGCTGACAG ATGGgtattctttgacgggg GGTAGGGGCGGAA CCTGA | 150. | 16.5 | 16 | 16.5 | Cancer |
| BRCA2 | 41.6 ± 10.5 | TTAGACTTAGGTAA GTAAtgcaatatggtagact GGGGAGAACTACA AACTA | 151. | 16.5 | 16 | 16.5 | Cancer |
| CBX3 | 35.2 ± 22.6 | TCTGCAATAAAAAA TGGCctccaacaaaactaca TTGGTAAGTTAATG AAAA | 152. | 16.5 | 16 | 16.5 | Epigenetic |
| CBX8 | 13.5 ± 3.4 | TGGAGCTTTCAGCG GTGGgggagcgggtgttcg cgGCCGAAGCCCTC CTGAA | 153. | 16.5 | 17 | 15.5 | Epigenetic |
| CCND1 | 40.5 ± 2.2 | TGGAACACCAGCTC CTGTgctgcgaagtggaaac catCCGCCGCGCGTA CCCCGA | 154. | 16.5 | 19 | 16.5 | Cancer |
| CDC73 | 36.3 ± 7.7 | TGCTTAGCGTCCTG CGACagtacaacatccagaa GAAGGAGATTGTG GTGAA | 155. | 16.5 | 16 | 16.5 | Cancer |
| CDH1 | none | TGCTGCAGGTACCC CGGAtcccctgacttgcgag GGACGCATTCGGGC CGCA | 156. | 16.5 | 16 | 16.5 | Cancer |
| CDK4 | 21.5 ± 17.4 | TCCCTTGATCTGAG AAtggctacctctcgataTG AGCCAGTGGCTGA AA | 157. | 14.5 | 16 | 15.5 | Cancer |
| CHD4 | 9.6 ± 0.1 | TGGCGTCGGGCCTG GGCtccccgtcccctgctc GGCGGGCAGTGAG GAGGA | 158. | 15.5 | 17 | 16.5 | Epigenetic |
| CHD7 | 11.4 ± 2.7 | TGTGTTGGAAGAAG ATGGcagatccaggaatgat GAGTCTTTTTGGCG AGGA | 159. | 16.5 | 16 | 16.5 | Epigenetic |
| CTNNB1 | 26.0 ± 8.1 | TCCAGCGTGGACAA TGGctactcaaggtttgtgTC ATTAAATCTTTAGT TA | 160. | 15.5 | 16 | 16.5 | Cancer |
| CYLD | 24.7 ± 2.3 | TAATATCACAATGA GTTCaggcttatggagccaa gaAAAAGTCACTTC ACCCTA | 161. | 16.5 | 18 | 16.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| DDB2 | 15.8 ± 7.2 | TCACACGGAGGAC GCGatggctcccaagaaac GCCCAGAAACCCA GAAGA | 162. | 14.5 | 16 | 16.5 | Cancer |
| ERCC2 | 55.8 ± 12.7 | TCCGGCCGGCGCCA TGAagtgagaagggggctg GGGGTCGCGCTCGC TA | 163. | 15.5 | 16 | 14.5 | Cancer |
| ERCC5 | none | TCCGGGATCGCCAT GGGAactcaatagaaaatcc tcaTCTTCTCACTTTG TTTCA | 164. | 16.5 | 19 | 16.5 | Cancer |
| EWSR1 | 14.3 ± 8.2 | TGGCGTCCACGGGT GAGTatggtggaactgcggt cGCGCCGGCGGTAG CCGGA | 165. | 16.5 | 17 | 16.5 | Cancer |
| EXT1 | 9.5 ± 3.0 | TGACCCAGGCAGG ACACAtgcaggccaaaaaa cgcTATTTCATCCTG CTCTCA | 166. | 16.5 | 17 | 16.5 | Cancer |
| EXT2 | none | TTCCTCCCAGGGGG ATGTcctgcgcctcagggtc CGGTGGTGGCCTGC GGCA | 167. | 16.5 | 16 | 16.5 | Cancer |
| EZH2 | 41.3 ± 2.6 | TGCTTTTAGAATAA TCATgggccagactgggaa gAAATCTGAGAAGG GACCA | 168. | 16.5 | 16 | 16.5 | Epigenetic |
| FANCA | 9.7 ± 5.0 | TAGGCGCCAAGGC CATGTccgactcgtgggtc ccGAACTCCGCCTC GGGCCA | 169. | 16.5 | 16 | 16.5 | Cancer |
| FANCC | 23.7 ± 17.8 | TGAAGGGACATCA CCTTTtcgcttttccaagatg GCTCAAGATTCAGT AGA | 170. | 16.5 | 17 | 15.5 | Cancer |
| FANCE | none | TGCCCCGGCATGGC GACAccggacgcggggctc ccTGGGGCTGAGGG CGTGGA | 171. | 16.5 | 17 | 16.5 | Cancer |
| FANCF | 46.0 ± 7.7 | TTCGCGCACCTCAT GGaatcccttctgcagcaCC TGGATCGCTTTTCC GA | 172. | 14.5 | 16 | 16.5 | Cancer |
| FANCG | 26.9 ± 16.2 | TCGGCCACCATGTC CCgccagaccacctctgtGG GCTCCAGCTGCCTG GA | 173. | 14.5 | 16 | 16.5 | Cancer |
| FES | 12.6 ± 10.6 | TCCCCAGAACAGCA CTATgggcttctcttccgagc tGTGCAGCCCCCAG GGCCA | 174. | 16.5 | 18 | 16.5 | Cancer |
| FGFR1 | 17.4 ± 6.2 | TCTGCTCCCCACCG AGGAcctctgcatgcaggca TGAATCCCAGGAGC CTA | 175. | 16.5 | 16 | 15.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| FH | 20.9 ± 11.8 | TGTACCGAGCACTT CGGCtcctcgcgcgctcgcg tCCCCTCGTGCGGG CTCCA | 176. | 16.5 | 17 | 16.5 | Cancer |
| FLCN | 11.1 ± 4.4 | TCTCCAAGGCACCA TGAAtgccatcgtggctctct gCCACTTCTGCGAG CTCCA | 177. | 16.5 | 18 | 16.5 | Cancer |
| FLT3 | none | TCCGGAGGCCATGC CGGCgttggcgcgcgacgg cggccaGCTGCCGCTG CTCGGTA | 178. | 16.5 | 21 | 15.5 | Cancer |
| FLT4 | 9.9 ± 5.0 | TGCAGCGGGGCGC CGCGCtgtgcctgcgactgt ggctCTGCCTGGGAC TCCTGGA | 179. | 16.5 | 19 | 16.5 | Cancer |
| FOXO1 | 8.5 ± 1.1 | TCACCATGGCCGAG GCGcctcaggtggtggagaT CGACCCGGACTTCG A | 180. | 15.5 | 16 | 14.5 | Cancer |
| FOXO3 | 7.3 ± 2.3 | TCTCCGCTCGAAGT GGAGctggacccggagttc gagCCCCAGAGCCGT CCGCGA | 181. | 16.5 | 18 | 16.5 | Cancer |
| GLI1 | 21.5 ± 12.4 | TCCTCTGAGACGCC ATGTtcaactcgatgacccc ACCACCAATCAGTA GCTA | 182. | 16.5 | 16 | 16.5 | Cancer |
| HDAC1 | 10.8 ± 3.0 | TGGCGCAGACGCA GGGCaccccggaggaaagtc tgTTACTACTACGAC GGTGA | 183. | 15.5 | 17 | 16.5 | Epigenetic |
| HDAC2 | 4.2 ± 0.9 | TGCGCTCACCTCCC TGCGgcctcctgaggtggttt gGTGGCCCCCTCCT CGCGA | 184. | 16.5 | 18 | 16.5 | Epigenetic |
| HDAC6 | 21.4 ± 2.1 | TCCTCAACTATGAC CTCAaccggccaggattcca CCACAACCAGGCA GCGAA | 185. | 16.5 | 16 | 16.5 | Epigenetic |
| HMGA2 | 3.0 ± 1.5 | TGAGCGCACGCGGT GAGGgcgcggggcagccg tcCACTTCAGCCCAG GGACA | 186. | 16.5 | 16 | 16.5 | Cancer |
| HOXA13 | 7.6 ± 3.1 | TCCGTGCTCCTCCA CCCCcgctggatcgagccca cCGTCATGTTTCTCT ACGA | 187. | 16.5 | 17 | 16.5 | Cancer |
| HOXA9 | 6.4 ± 2.7 | TGGGCACGGTGATG GCcaccactggggccctgG GCAACTACTACGTG GA | 188. | 14.5 | 16 | 15.5 | Cancer |
| HOXC13 | 10.5 ± 0.3 | TCCAGCAGATCATG TCATgacgacttcgctgctcc tGCATCCACGCTGG CCGGA | 189. | 16.5 | 18 | 16.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| HOXD1 1 | none | TTGACGAGTGCGGC CAGagcgcagccagcatgta CCTGCCGGGCTGCG CCTA | 190. | 15.5 | 17 | 16.5 | Cancer |
| HOXD1 3 | none | TGCGGGCAGACGG CGGGGgcgccggtggcgc cccgGCCTCTTCCTCC TCCTCA | 191. | 16.5 | 17 | 16.5 | Cancer |
| JAK2 | 44.9 ± 16.9 | TCTGAAAAAGACTC TGCAtgggaatggcctgcct TACGATGACAGAA ATGGA | 192. | 16.5 | 16 | 16.5 | Cancer |
| KIT | none | TACCGCGATGAGA GGCGCtcgcggcgcctgg gattttCTCTGCGTTCT GCTCCTA | 193. | 16.5 | 19 | 16.5 | Cancer |
| KRAS | 9.4 ± 0.9 | TGAAAATGACTGA ATATAaacttgtggtagttg gaGCTGGTGGCGTA GGCAA | 194. | 16.5 | 17 | 15.5 | Cancer |
| MAP2K 4 | 11.9 ± 7.1 | TAGGGTCCCCGGCG CCAGgccacccggccgtca gCAGCATGCAGGGT AAGGA | 195. | 16.5 | 16 | 16.5 | Cancer |
| MDM2 | 33.0 ± 20.2 | TCCAAGCGCGAAA ACCCCggatggtgaggag caggTACTGGCCCGG CAGCGA | 196. | 16.5 | 17 | 15.5 | Cancer |
| MET | 40.4 ± 10.7 | TTATTATTACATGG CTTTgccttactgaggcttcA TCTTGTCCTCTGGT CCA | 197. | 16.5 | 16 | 16.5 | Cancer |
| MLH1 | 44.9 ± 6.3 | TCTGGCGCCAAAAT GTCGttcgtggcaggggtta TTCGGCGGCTGGAC GAGA | 198. | 16.5 | 16 | 16.5 | Cancer |
| MSH2 | 27.5 ± 10.4 | TGAGGAGGTTTCGA CATGgcggtgcagccgaag gAGACGCTGCAGTT GGAGA | 199. | 16.5 | 16 | 16.5 | Cancer |
| MUTY H | 24.9 ± 8.4 | TCACTGTCGGCGGC CATGacaccgctcgtctccc gcCTGAGTCGTCTGT GGGTA | 200. | 16.5 | 18 | 16.5 | Cancer |
| MYC | 13.4 ± 4.0 | TGCTTAGACGCTGG ATTTttttcgggtagtggaaA ACCAGGTAAGCAC CGAA | 201. | 16.5 | 16 | 16.5 | Cancer |
| MYCL1 | 17.3 ± 0.6 | TCCCGCAGGGAGC GGACAtggactacgactcg taCCAGCACTATTTC TACGA | 202. | 16.5 | 16 | 16.5 | Cancer |
| MYCN | 16.3 ± 11.6 | TGCCGAGCTGCTCC ACgtccaccatgccgggcA TGATCTGCAAGAAC CCA | 203. | 14.5 | 16 | 16.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| NBN | 46.3 ± 15.5 | TGAGGAGCCGGAC CGAtgtggaaaactgctgccC GCCGCGGGCCCGG CA | 204. | 14.5 | 16 | 14.5 | Cancer |
| NCOR1 | 29.6 ± 13.1 | TCTTTACTGATAAT GTCAagttcatgttaccctcC CAACCAAGGAGCA TTCA | 205. | 16.5 | 16 | 16.5 | Epigenetic |
| NCOR2 | 3.3 ± 0.6 | TGGAGGGCCACTG AGCcccgctacccgccca CAGCCTTTCCTACC CA | 206. | 14.5 | 16 | 14.5 | Epigenetic |
| NTRK1 | none | TCGGCGCATGAAG GAGGTactcctcatttttcgtt CTCTCTCTCTGTGC CCCA | 207. | 16.5 | 16 | 16.5 | Cancer |
| PDGFRA | 16.0 ± 4.3 | TTGCGCTCGGGGCG GCCAtgtcggccggcgagg tCGAGCGCCTAGTG TCGGA | 208. | 16.5 | 16 | 16.5 | Cancer |
| PDGFRB | 16.0 ± 3.2 | TCTGCAGGACACCA TGCGgcttccgggtgcgatg CCAGCTCTGGCCCT CAAA | 209. | 16.5 | 16 | 16.5 | Cancer |
| PHF8 | 22.2 ± 6.1 | TGAGTACTCCGCCT CTACcccggctgaagcccg cCCCCGCCGCCACC TATTA | 210. | 16.5 | 16 | 16.5 | Epigenetic |
| PMS2 | 26.9 ± 9.5 | TCGGGTGTTGCATC CATGgagcgagctgagagc tcgAGGTGAGCGGG GCTCGCA | 211. | 16.5 | 18 | 16.5 | Cancer |
| PTCH1 | 27.5 ± 15.9 | TGGAACTGCTTAAT AGaaacaggcttgtaattGT GAGTCCGCGCTGCA | 212. | 14.5 | 16 | 14.5 | Cancer |
| PTEN | 31.5 ± 11.7 | TCCCAGACATGACA GCCatcatcaaagagatcgT TAGCAGAAACAAA AGGA | 213. | 15.5 | 16 | 16.5 | Cancer |
| RARA | 13.4 ± 6.1 | TGGCATGGCCAGCA ACAGcagctcctgcccgac acCTGGGGGCGGGC ACCTCA | 214. | 16.5 | 17 | 16.5 | Cancer |
| RBBP5 | 15.7 ± 9.5 | TGCTGGGTGAGAA GGGCtgtggctgcgtttaga GAAGCGTTGGGTAC TGGA | 215. | 15.5 | 17 | 16.5 | Epigenetic |
| RECQL4 | 22.1 ± 16.2 | TGCGGGACGTGCG GGAGCggctgcaggcgtg ggaGCGCGCGTTCCG ACGGCA | 216. | 16.5 | 16 | 16.5 | Cancer |
| REST | none | TCAGAATACAGTTA TGGCcacccaggtaatggg gCAGTCTTCTGGAG GAGGA | 217. | 16.5 | 16 | 16.5 | Epigenetic |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| RET | 5.4 ± 1.8 | TGAGTTCTGCCGGC CGCCggctcccgcaggggc caGGGCGAAGTTGG CGCCGA | 218. | 16.5 | 17 | 16.5 | Cancer |
| RNF2 | none | TTCTTTATTTCCAG CAATgtctcaggctgtgcag ACAAACGGAACTC AACCA | 219. | 16.5 | 16 | 16.5 | Epigenetic |
| RUNX1 | 25.1 ± 6.9 | TTCAGGAGGAAGC GATGGcttcagacagcatat tTGAGTCATTTCCTT CGTA | 220. | 16.5 | 16 | 16.5 | Epigenetic |
| SDHB | 36.4 ± 19.2 | TCTCCTTGAGGCGC CGGTgccggccacaaccct TGGCGGAGCCTGCC TGCA | 221. | 16.5 | 16 | 16.5 | Cancer |
| SDHC | 13.7 ± 3.4 | TGTTGCTGAGGTGA CTTCagtgggactgggagtt ggtGCCTGCGGCCCT CCGGA | 222. | 16.5 | 19 | 15.5 | Cancer |
| SDHD | 42.0 ± 7.8 | TCAGGAACGAGAT GGCGGttctctggaggctga gtGCCGTTTGCGGTG CCCTA | 223. | 16.5 | 17 | 16.5 | Cancer |
| SETDB1 | 33.5 ± 6.1 | TGCAGAGGACAAA AGCATgtcttcccttcctgg gTGCATTGGTTTGG ATGCA | 224. | 16.5 | 16 | 16.5 | Epigenetic |
| SIRT6 | 43.3 ± 3.1 | TTACGCGGCGGGGC TGTCgccgtacgcggacaa gggCAAGTGCGGCC TCCCGGA | 225. | 16.5 | 18 | 16.5 | Epigenetic |
| SMAD2 | 3.9 ± 1.6 | TTTGGTAAGAACAT GTCGtccatcttgccattcac GCCGCCAGTTGTGA AGA | 226. | 16.5 | 17 | 15.5 | Cancer |
| SS18 | 31.4 ± 7.9 | TGGTGACGGCGGC AACATgtctgtggctttcgc ggCCCCGAGGCAGC GAGGCA | 227. | 16.5 | 17 | 16.5 | Cancer |
| SUZ12 | 13.1 ± 0.4 | TGGCGCCTCAGAAG CAcggcggtggggaggg GGCGGCTCGGGGC CCA | 228. | 14.5 | 16 | 14.5 | Epigenetic |
| TFE3 | 17.3 ± 2.4 | TCATGTCTCATGCG GCCGaaccagctcgggatg gCGTAGAGGCCAGC GCGGA | 229. | 16.5 | 16 | 16.5 | Cancer |
| TGFBR2 | none | TCGGGGCTGCTCA GGGGcctgtggccgctgca caTCGTCCTGTGGAC GCGTA | 230. | 16.5 | 17 | 16.5 | Cancer |
| TLX3 | none | TTCCGCCCGCCCAG GATGgaggcgcccgccag cgcGCAGACCCCGC ACCCGCA | 231. | 16.5 | 17 | 16.5 | Cancer |

TABLE 7-continued

Endogenous human gene sequences targeted by 96 pairs of TALENs

| Target gene name | % NHEJ | Target site (half-sites in CAPS, spacer in lowercase, ATG underlined) | SEQ ID NO: | Length of LEFT half site (include 5' T) | Length of spacer | Length of RIGHT half site (include 5' T) | Gene Type |
|---|---|---|---|---|---|---|---|
| TP53 | 19.9 ± 3.6 | TTGCCGTCCCAAGC AATGgatgatttgatgctgtc CCCGGACGATATTG AACA | 232. | 16.5 | 17 | 16.5 | Cancer |
| TSC2 | 30.7 ± 22.7 | TCCTGGTCCACCAT GGCcaaaccaacaagcaaa gATTCAGGCTTGAA GGAGA | 233. | 15.5 | 17 | 16.5 | Cancer |
| VHL | 19.4 ± 1.1 | TCTGGATCGCGGAG GGAAtgccccggagggcg gaGAACTGGGACGA GGCCGA | 234. | 16.5 | 16 | 16.5 | Cancer |
| XPA | 12.9 ± 2.2 | TGGGCCAGAGATG GCGGCggccgacggggct ttgCGGAGGCGGCG GCTTTA | 235. | 16.5 | 16 | 16.5 | Cancer |
| XPC | 31.4 ± 4.2 | TGCCCAGACAAGC AACATggctcggaaacgc gcggccGGCGGGGAG CCGCGGGGA | 236. | 16.5 | 19 | 16.5 | Cancer |

The abilities of the 96 TALEN pairs to introduce NHEJ-mediated insertion or deletion (indel) mutations at their intended endogenous gene targets were tested in cultured human cells using a slightly modified version of a previously described T7 Endonuclease I (T7EI) assay (Mussolino et al., 2011, Nucleic Acids Res., 39:9283-93; Kim et al., 2009, Genome Res., 19:1279-88). With this T7EI assay, 83 of the 96 TALEN pairs showed evidence of NHEJ-mediated mutagenesis at their intended endogenous gene target sites, an overall success rate of ~86% (Table 7). The efficiencies of TALEN-induced mutagenesis we observed ranged from 2.5% to 55.8% with a mean of 22.5%. To provide molecular confirmation of the mutations we identified by T7EI assay, we sequenced target loci for 11 different TALEN pairs that induced varying efficiencies of mutagenesis (FIGS. 21A-D). As expected, this sequencing revealed indels at the expected target gene sites with frequencies similar to those determined by the T7EI assays.

The nucleotide and amino acid sequences for 14 of the 96 pairs of TALENs targeted to the endogenous human genes in Table 7 are presented below. Each TALEN monomer is presented as follows:

(1) A header with information presented in the format: Gene target_Left or Right monomer_Target DNA site shown 5' to 3'_TALE repeat monomers and 0.5 repeat plasmid used with code as shown in Table 4.

(2) DNA sequence encoding the N-terminal part of the TALE required for activity, the TALE repeat array, the C-terminal 0.5 TALE repeat domain, and the C-terminal 63 amino acids required for activity from a NheI site to a BamHI site. This sequence is present in the "Vector Sequence" plasmid shown below, taking the place of the underlined X's flanked by NheI and BamHI sites (3) Amino acid sequences the N-terminal part of the TALE required for activity, the TALE repeat array, the C-terminal 0.5 TALE repeat domain, and the C-terminal 63 amino acids required for activity shown from the start of translation (located just 3' to the NheI site and including an N-terminal FLAG epitope tag) to a Gly-Ser sequence (encoded by the BamHI site) that serves as a linker from the TALE repeat array to the FokI cleavage domain.

VECTOR SEQUENCE

SEQ ID NO: 244
GACGGATCGGGAGATCTCCCGATCCCCTATGGTCGACTCTCAGTACAATC

TGCTCTGATGCCGCATAGTTAAGCCAGTATCTGCTCCCTGCTTGTGTGTT

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGACTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCTGGCTAACTAGAGAACCCACTGCTTACTG

-continued

GCTTATCGAAATTAATACGACTCACTATAGGGAGACCCAAGCTGGCTAGC

XXXXXXXXXXGGATCCCAACTAGTCAAAAGTGAACTGGAGGAGAAGAAAT

CTGAACTTCGTCATAAATTGAAATATGTGCCTCATGAATATATTGAATTA

ATTGAAATTGCCAGAAATTCCACTCAGGATAGAATTCTTGAAATGAAGGT

AATGGAATTTTTTATGAAAGTTTATGGATATAGAGGTAAACATTTGGGTG

GATCAAGGAAACCGGACGGAGCAATTTATACTGTCGGATCTCCTATTGAT

TACGGTGTGATCGTGGATACTAAAGCTTATAGCGGAGGTTATAATCTGCC

AATTGGCCAAGCAGATGAAATGCAACGATATGTCGAAGAAAATCAAACAC

GAAACAAACATATCAACCCTAATGAATGGTGGAAAGTCTATCCATCTTCT

GTAACGGAATTTAAGTTTTTATTTGTGAGTGGTCACTTTAAAGGAAACTA

CAAAGCTCAGCTTACACGATTAAATCATATCACTAATTGTAATGGAGCTG

TTCTTAGTGTAGAAGAGCTTTTAATTGGTGGAGAAATGATTAAAGCCGGC

ACATTAACCTTAGAGGAAGTCAGACGGAAATTTAATAACGGCGAGATAAA

CTTTTAAGGGCCCTTCGAAGGTAAGCCTATCCCTAACCCTCTCCTCGGTC

TCGATTCTACGCGTACCGGTCATCATCACCATCACCATTGAGTTTAAACC

CGCTGATCAGCCTCGACTGTGCCTTCTAGTTGCCAGCCATCTGTTGTTTG

CCCCTCCCCCGTGCCTTCCTTGACCCTGGAAGGTGCCACTCCCACTGTCC

TTTCCTAATAAAATGAGGAAATTGCATCGCATTGTCTGAGTAGGTGTCAT

TCTATTCTGGGGGGTGGGGTGGGGCAGGACAGCAAGGGGGAGGATTGGGA

AGACAATAGCAGGCATGCTGGGGATGCGGTGGGCTCTATGGCTTCTGAGG

CGGAAAGAACCAGCTGGGGCTCTAGGGGGTATCCCCACGCGCCCTGTAGC

GGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGCATCCCT

TTAGGGTTCCGATTTAGTGCTTTACGGCACCTCGACCCCAAAAAACTTGA

TTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAA

ACTGGAACAACACTCAACCCTATCTCGGTCTATTCTTTTGATTTATAAGG

GATTTTGGGGATTTCGGCCTATTGGTTAAAAAATGAGCTGATTTAACAAA

AATTTAACGCGAATTAATTCTGTGGAATGTGTGTCAGTTAGGGTGTGGAA

AGTCCCCAGGCTCCCCAGGCAGGCAGAAGTATGCAAAGCATGCATCTCAA

TTAGTCAGCAACCAGGTGTGGAAAGTCCCCAGGCTCCCCAGCAGGCAGAA

GTATGCAAAGCATGCATCTCAATTAGTCAGCAACCATAGTCCCGCCCCTA

ACTCCGCCCATCCCGCCCCTAACTCCGCCCAGTTCCGCCCATTCTCCGCC

CCATGGCTGACTAATTTTTTTTATTTATGCAGAGGCCGAGGCCGCCTCTG

CCTCTGAGCTATTCCAGAAGTAGTGAGGAGGCTTTTTTGGAGGCCTAGGC

TTTTGCAAAAAGCTCCCGGGAGCTTGTATATCCATTTTCGGATCTGATCA

GCACGTGTTGACAATTAATCATCGGCATAGTATATCGGCATAGTATAATA

CGACAAGGTGAGGAACTAAACCATGGCCAAGCCTTTGTCTCAAGAAGAAT

CCACCCTCATTGAAAGAGCAACGGCTACAATCAACAGCATCCCCATCTCT

GAAGACTACAGCGTCGCCAGCGCAGCTCTCTCTAGCGACGGCCGCATCTT

CACTGGTGTCAATGTATATCATTTTACTGGGGGACCTTGTGCAGAACTCG

TGGTGCTGGGCACTGCTGCTGCTGCGGCAGCTGGCAACCTGACTTGTATC

GTCGCGATCGGAAATGAGAACAGGGGCATCTTGAGCCCCTGCGGACGGTG

TCGACAGGTGCTTCTCGATCTGCATCCTGGGATCAAAGCGATAGTGAAGG

ACAGTGATGGACAGCCGACGGCAGTTGGGATTCGTGAATTGCTGCCCTCT

GGTTATGTGTGGGAGGGCTAAGCACTTCGTGGCCGAGGAGCAGGACTGAC

ACGTGCTACGAGATTTCGATTCCACCGCCGCCTTCTATGAAAGGTTGGGC

TTCGGAATCGTTTTCCGGGACGCCGGCTGGATGATCCTCCAGCGCGGGGA

TCTCATGCTGGAGTTCTTCGCCCACCCCAACTTGTTTATTGCAGCTTATA

ATGGTTACAAATAAAGCAATAGCATCACAAATTTCACAAATAAAGCATTT

TTTTCACTGCATTCTAGTTGTGGTTTGTCCAAACTCATCAATGTATCTTA

TCATGTCTGTATACCGTCGACCTCTAGCTAGAGCTTGGCGTAATCATGGT

CATAGCTGTTTCCTGTGTGAAATTGTTATCCGCTCACAATTCCACACAAC

ATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAA

ACCTGTCGTGCCAGCTGCATTAATGAATCGGCCAACGCGCGGGGAGAGGC

GGTTTGCGTATTGGGCGCTCTTCCGCTTCCTCGCTCACTGACTCGCTGCG

CTCGGTCGTTCGGCTGCGGCGAGCGGTATCAGCTCACTCAAAGGCGGTAA

TACGGTTATCCACAGAATCAGGGGATAACGCAGGAAAGAACATGTGAGCA

AAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAA

GTCAGAGGTGGCGAAACCCGACAGGACTATAAAGATACCAGGCGTTTCCC

CCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCAATGCT

CACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAA

CTATCGTCTTGAGTCCAACCCGGTAAGACACGACTTATCGCCACTGGCAG

CAGCCACTGGTAACAGGATTAGCAGAGCGAGGTATGTAGGCGGTGCTACA

GAGTTCTTGAAGTGGTGGCCTAACTACGGCTACACTAGAAGGACAGTATT

TGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTT

GATCTTTTCTACGGGGTCTGACGCTCAGTGGAACGAAAACTCACGTTAAG

GGATTTTGGTCATGAGATTATCAAAAAGGATCTTCACCTAGATCCTTTTA

AATTAAAAATGAAGTTTTAAATCAATCTAAAGTATATATGAGTAAACTTG

GTCTGACAGTTACCAATGCTTAATCAGTGAGGCACCTATCTCAGCGATCT

GTCTATTTCGTTCATCCATAGTTGCCTGACTCCCCGTCGTGTAGATAACT

ACGATACGGGAGGGCTTACCATCTGGCCCCAGTGCTGCAATGATACCGCG

AGACCCACGCTCACCGGCTCCAGATTTATCAGCAATAAACCAGCCAGCCG

GAAGGGCCGAGCGCAGAAGTGGTCCTGCAACTTTATCCGCCTCCATCCAG

-continued

TCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGT
CGTTTGGTATGGCTTCATTCAGCTCCGGTTCCCAACGATCAAGGCGAGTT
ACATGATCCCCATGTTGTGCAAAAAAGCGGTTAGCTCCTTCGGTCCTCC
GATCGTTGTCAGAAGTAAGTTGGCCGCAGTGTTATCACTCATGGTTATGG
CAGCACTGCATAATTCTCTTACTGTCATGCCATCCGTAAGATGCTTTTCT
GTGACTGGTGAGTACTCAACCAAGTCATTCTGAGAATAGTGTATGCGGCG
ACCGAGTTGCTCTTGCCCGGCGTCAATACGGGATAATACCGCGCCACATA

-continued

GCAGAACTTTAAAAGTGCTCATCATTGGAAAACGTTCTTCGGGGCGAAAA
CTCTCAAGGATCTTACCGCTGTTGAGATCCAGTTCGATGTAACCCACTCG
TGCACCCAACTGATCTTCAGCATCTTTTACTTTCACCAGCGTTTCTGGGT
GAGCAAAAACAGGAAGGCAAAATGCCGCAAAAAAGGGAATAAGGGCGACA
CGGAAATGTTGAATACTCATACTCTTCCTTTTTCAATATTATTGAAGCAT
TTATCAGGGTTATTGTCTCATGAGCGGATACATATTTGAATGTATTTAGA
AAAATAAACAAATAGGGGTTCCGCGCACATTTCCCCGAAAAGTGCCACCT
GACGTC

| TALE REPEAT SEQUENCES | | | | |
|---|---|---|---|---|
| Target | SEQEUNCE | SEQ ID NO: | SEQUENCE | SEQ ID NO: |
| >APC_Left_ TATGTACGCC TCCCTGGG_T AL/006/015 /019/025/0 26/012/019 /022/027/0 15/017/022 /027/015/0 19/024/JDS 74/ ('TATGTACG CCCTCCCTGGG' disclosed as SEQ ID NO: 412) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCCGCTCCAGCTCGACACCGGG AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCGAACATT GGGGGAAAGCAAGCCCTGGAAACCGTGCAAAG GTTGTTGCCGGTCCTTTGTCAAGACCACGGCC TTACACCGGAGCAAGTCGTGGCCATTGCAAGC AATGGGGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCTCGAATGGCGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCATCCCACGACGG TGGCAAACAGGCTCTTGAGACGGTTCAGAGAC TTCTCCCAGTTCTCTGTCAAGCCCACGGGCTG ACTCCCGATCAAGTTGTAGCGATTGCGAATAA CAATGGAGGGAAACAAGCATTGGAGACTGTCC AACGGCTCCTTCCCGTGTTGTGTCAAGCCCAC GGTTTGACGCCTGCACAAGTGGTCGCCATCGC CAGCCATGATGGCGGTAAGCAGGCGCTGGAAA CAGTACAGCGCCTGCTGCCTGTACTGTGCCAG GATCATGGACTGACCCCAGACCAGGTAGTCGC AATCGCGTCACATGACGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGCATGACGGAG GGAAACAAGCATTGGAGACTGTCCAACGGCTC CTTCCCGTGTTGTGTCAAGCCCACGGTTTGAC GCCTGCACAAGTGGTCGCCATCGCCAGCCATG ATGCGGTAAGCAGGCGCTGGAAACAGTACAG CGCCTGCTGCCTGTACTGTGCCAGGATCATGG | 245. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASNGGGKQALETVQRLLPVLCQDHGLTPEQVVAI ASNGGGKQALETVQRLLPVLCQAHGLTPDQVVAIANN NGGKQALETVQRLLPVLCQDHGLTPAQVVAIASNGGG KQALETVQRLLPVLCQDHGLTPDQVVAIASNIGGKQA LETVQRLLPVLCQDHGLTPEQVVAIASHDGGKQALET VQRLLPVLCQAHGLTPDQVVAIANNNGGKQALETVQR LLPVLCQAHGLTPAQVVAIASHDGGKQALETVQRLLP VLCQDHGLTPDQVVAIASHDGGKQALETVQRLLPVLC QDHGLTPEQVVAIASNGGGKQALETVQRLLPVLCQAH GLTPDQVVAIASHDGGKQALETVQRLLPVLCQAHGLT PAQVVAIASHDGGKQALETVQRLLPVLCQDHGLTPDQ VVAIASHDGGKQALETVQRLLPVLCQDHGLTPEQVVA IASNGGGKQALETVQRLLPVLCQAHGLTPDQVVAIAN NGGKQALETVQRLLPVLCQAHGLTPAQVVAIANNNG GKQALETVQRLLPVLCQDHGLTPEQVVAIANNNGGRP ALESIVAQLSRPDPALAALTNDHLVALACLGGRPALD AVKKGLPHAPALIKRTNRRIPERTSHRVAGS | 246. |

TALE REPEAT SEQUENCES

| Target | SEQEUNCE | SEQ ID NO: | SEQUENCE | SEQ ID NO: |
|---|---|---|---|---|
| | ACTGACCCCAGACCAGGTAGTCGCAATCGCGT<br>CACATGACGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAATGGGGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGAATAACAATGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTAATAATAAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >APC_Right<br>_TACAGAAGC<br>GGGCAAAGG_<br>TAL/006/01<br>2/016/024/<br>026/011/01<br>9/022/029/<br>014/019/02<br>2/026/011/<br>016/024/JD<br>S74/<br>('TACAGAAG<br>CGGGCAAAGG'<br>disclosed<br>as SEQ ID<br>NO: 413) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCGAACATT<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCATCC<br>CACGACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGAACATTGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCGAACATTGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAGCAACATCGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGAATAA<br>CAATGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGAACAATAATGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAATAATAACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGAATAACAATGGAG<br>GGAAACAAGCATTGGAGACTGTCCAACGGCTC | 247. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNIGGKQALETVQRLLPVLCQDHGLTPEQVVAI<br>ASHDGGKQALETVQRLLPVLCQAHGLTPDQVVAIASN<br>IGGKQALETVQRLLPVLCQAHGLTPAQVVAIANNNGG<br>KQALETVQRLLPVLCQDHGLTPDQVVAIASNIGGKQA<br>LETVQRLLPVLCQAHGLTPEQVVAIASNIGGKQALET<br>VQRLLPVLCQAHGLTPDQVVAIANNNGGKQALETVQR<br>LLPVLCQAHGLTPAQVVAIASHDGGKQALETVQRLLP<br>VLCQDHGLTPDQVVAIANNNGGKQALETVQRLLPVLC<br>QDHGLTPEQVVAIANNNGGKQALETVQRLLPVLCQAH<br>GLTPDQVVAIANNNGGKQALETVQRLLPVLCQAHGLT<br>PAQVVAIASHDGGKQALETVQRLLPVLCQDHGLTPDQ<br>VVAIASNIGGKQALETVQRLLPVLCQDHGLTPEQVVA<br>IASNIGGKQALETVQRLLPVLCQAHGLTPDQVVAIAS<br>NIGGKQALETVQRLLPVLCQAHGLTPAQVVAIANNNG<br>GKQALETVQRLLPVLCQDHGLTPEQVVAIANNNGGRP<br>ALESIVAQLSRPDPALAALTNDHLVALACLGGRPALD<br>AVKKGLPHAPALIKRTNRRIPERTSHRVAGS | 248. |

TALE REPEAT SEQUENCES

| Target | SEQUENCE | SEQ ID NO: | SEQUENCE | SEQ ID NO: |
|---|---|---|---|---|
| | CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CGAACATTGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAACATCGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCGAACATTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTAATAATAAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >BRCA1_Left_TCCGAAGC<br>TGACAGATGG<br>_TAL/007/0<br>12/019/021<br>/026/014/0<br>17/025/029<br>/011/017/0<br>21/029/011<br>/020/024/J<br>DS74/<br>('TCCGAAGC<br>TGACAGATGG'<br>disclosed<br>as SEQ ID<br>NO: 414) | GCTAGCaccATGGACTACAAAGACCATGACGG<br>TGATTATAAAGATCATGACATCGATTACGGA<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCACATGAC<br>GGGGGAAAGCAAGCCCTGGAAACCGTCAAAG<br>GTTGTTGCCGGTCCTTTGTCAAGACCACGGCC<br>TTACACCGGAGCAAGTCGTGGCCATTGCATCC<br>CACGACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGAATAACAATGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCTCCAATATTGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCGAACATTGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGCA<br>TGACGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CTCGAATGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGAACAATAATGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAGCAACATCGGTGGCAAAC | 249. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASHDGGKQALETVQRLLPVLCQDHGLTPEQVVAI<br>ASHDGGKQALETVQRLLPVLCQAHGLTPDQVVAIANN<br>NGGKQALETVQRLLPVLCQAHGLTPAQVVAIASNIGG<br>KQALETVQRLLPVLCQDHGLTPDQVVAIASNIGGKQA<br>LETVQRLLPVLCQDHGLTPEQVVAIANNNGGKQALET<br>VQRLLPVLCQDHGLTPDQVVAIASHDGGKQALETVQR<br>LLPVLCQAHGLTPAQVVAIASNGGGKQALETVQRLLP<br>VLCQDHGLTPDQVVAIANNNGGKQALETVQRLLPVLC<br>QDHGLTPEQVVAIASNIGGKQALETVQRLLPVLCQAH<br>GLTPDQVVAIASNIGGKQALETVQRLLPVLCQDHGLTPDQ<br>VVAIANNNGGKQALETVQRLLPVLCQDHGLTPEQVVA<br>IASNIGGKQALETVQRLLPVLCQAHGLTPDQVVAIAS<br>NGGGKQALETVQRLLPVLCQAHGLTPAQVVAIANNNG<br>GKQALETVQRLLPVLCQDHGLTPEQVVAIANNNGGRP<br>ALESIVAQLSRPDPALAALTNDHLVALACLGGRPALD<br>AVKKGLPHAPALIKRTNRRIPERTSHRVAGS | 250. |

TALE REPEAT SEQUENCES

| Target | SEQEUNCE | SEQ ID NO: | SEQUENCE | SEQ ID NO: |
|---|---|---|---|---|
| | AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCTCCAATA<br>TTGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGA<br>ACAATAATGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAACATCGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCCAACGGTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTAATAATAAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >BRCA1_Right_TCAGGTT<br>CCGCCCCTAC<br>C_TAL/007/<br>011/019/02<br>4/030/015/<br>017/022/02<br>9/012/017/<br>022/027/01<br>5/016/022/<br>JDS71/<br>('TCAGGTTC<br>CGCCCCTACC'<br>disclosed<br>as SEQ ID<br>N: 415) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>AGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCACATGAC<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCAAGC<br>AACATCGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGAATAACAATGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCAAACGAGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCATTGCAAGCAATGGGGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGCA<br>TGACGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC | 251. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASHDGGKQALETVQRLLPVLCQDHGLTPEQVVAI<br>ASNIGGKQALETVQRLLPVLCQAHGLTPDQVVAIANN<br>NGGKQALETVQRLLPVLCQAHGLTPAQVVAIANNNGG<br>KQALETVQRLLPVLCQDHGLTPDQVVAIASNGGGKQA<br>LETVQRLLPVLCQDHGLTPEQVVAIASNGGGKQALET<br>VQRLLPVLCQAHGLTPDQVVAIASHDGGKQALETVQR<br>LLPVLCQAHGLTPAQVVAIASHDGGKQALETVQRLLP<br>VLCQDHGLTPDQVVAIANNNGGKQALETVQRLLPVLC<br>QDHGLTPEQVVAIASHDGGKQALETVQRLLPVLCQAH<br>GLTPDQVVAIASHDGKQALETVQRLLPVLCQAHGLT<br>PAQVVAIASHDGGKQALETVQRLLPVLCQDHGLTPDQ<br>VVAIASHDGKQALETVQRLLPVLCQDHGLTPEQVVA<br>IASNGGGKQALETVQRLLPVLCQAHGLTPDQVVAIAS<br>NIGGKQALETVQRLLPVLCQAHGLTPAQVVAIASHDG<br>GKQALETVQRLLPVLCQDHGLTPEQVVAIASHDGGRP<br>ALESIVAQLSRPDPALAALTNDHLVALACLGGRPALD<br>AVKKGLPHAPALIKRTNRRIPERTSHRVAGS | 252. |

TALE REPEAT SEQUENCES

| Target | SEQEUNCE | SEQ ID NO: | SEQUENCE | SEQ ID NO: |
|---|---|---|---|---|
| | AATCGCGAACAATAATGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCATCCCACGACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CACATGACGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAATGGGGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCGAACATTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAGCCATGATGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCCCACGAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >BRCA2_Left_TTAGACTT AGGTAAGTAA _TAL/010/0 11/019/021 /027/015/0 20/021/029 /014/020/0 21/026/014 /020/021/J DS70/ ('TTAGACTT AGGTAAGTAA' disclosed as SEQ ID NO: 416) | GCTAGCaccATGGACTACAAAGACCATGACGG TGATTATAAAGATCATGACATCGATTACGACG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCAAACGGA GGGGGAAAGCAAGCCCTGGAAACCGTGCAAAG GTTGTTGCCGGTCCTTTGTCAAGACCACGGCC TTACACCGGAGCAAGTCGTGGCCATTGCAAGC AACATCGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCTCCAATATTGGCGGTAAGCAGGC GCTGGAAACAGTACAGCGCCTGCTGCCTGTAC TGTGCCAGGATCATGGACTGACCCCAGACCAG GTAGTCGCAATCGCGTCACATGACGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAATGGGGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCCAA CGGTGGAGGGAAACAAGCATTGGAGACTGTCC AACGGCTCCTTCCCGTGTTGTGTCAAGCCCAC | 253. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASNGGGKQALETVQRLLPVLCQDHGLTPEQVVAI ASNGGKQALETVQRLLPVLCQAHGLTPDQVVAIANN NGGKQALETVQRLLPVLCQAHGLTPAQVVAIASNIGG KQALETVQRLLPVLCQDHGLTPDQVVAIASHDGGKQA LETVQRLLPVLCQDHGLTPEQVVAIASNGGGKQALET VQRLLPVLCQAHGLTPDQVVAIASNGGGKQALETVQR LLPVLCQAHGLTPAQVVAIASNIGGKQALETVQRLLP VLCQDHGLTPDQVVAIANNGGKQALETVQRLLPVLC QDHGLTPEQVVAIANNNGGKQALETVQRLLPVLCQAH GLTPDQVVAIASNGGGKQALETVQRLLPVLCQAHGLT PAQVVAIASNIGGKQALETVQRLLPVLCQDHGLTPDQ VVAIASNIGGKQALETVQRLLPVLCQDHGLTPEQVVA IANNNGGKQALETVQRLLPVLCQAHGLTPDQVVAIAS NGGGKQALETVQRLLPVLCQAHGLTPAQVVAIASNIG GKQALETVQRLLPVLCQDHGLTPEQVVAIASNIGGRP ALESIVAQLSRPDPALAALTNDHLVALACLGGRPALD AVKKGLPHAPALIKRTNRRIPERTSHRVAGS | 254. |

TALE REPEAT SEQUENCES

| Target | SEQEUNCE | SEQ ID NO: | SEQUENCE | SEQ ID NO: |
|---|---|---|---|---|
| | GGTTTGACGCCTGCACAAGTGGTCGCCATCGC<br>CTCCAATATTGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGAACAATAATGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAATAATAACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCCAACGGTGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCTCCAATA<br>TTGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CGAACATTGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAATAATAACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCCAACGGTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCTCCAATATTGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCTAACATC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >BRCA2_Rig<br>ht_TAGTTTG<br>TAGTTCTCCC<br>C_TAL/006/<br>014/020/02<br>5/030/014/<br>020/021/02<br>9/015/020/<br>022/030/01<br>2/017/022/<br>JDS71/<br>('TAGTTTGT<br>AGTTCTCCCC'<br>disclosed<br>as SEQ ID<br>NO: 417) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCGAACATT<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCAAAT<br>AATAACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCCAACGGTGGAGGGAAACAAGCATTGGA<br>GACTGTCAACGGCTCCTTCCCGTGTTGTGTC<br>AAGCCCACGGTTTGACGCCTGCACAAGTGGTC<br>GCCATCGCCTCGAATGGCGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCAAACGAGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC | 255. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNIGGKQALETVQRLLPVLCQDHGLTPEQVVAI<br>ANNNGGKQALETVQRLLPVLCQAHGLTPDQVVAIASN<br>GGGKQALETVQRLLPVLCQAHGLTPAQVVAIASNGGG<br>KQALETVQRLLPVLCQDHGLTPDQVVAIASNGGGKQA<br>LETVQRLLPVLCQDHGLTPEQVVAIANNNGGKQALET<br>VQRLLPVLCQAHGLTPDQVVAIASNGGGKQALETVQR<br>LLPVLCQAHGLTPAQVVAIASNIGGKQALETVQRLLP<br>VLCQDHGLTPDQVVAIANNNGGKQALETVQRLLPVLC<br>QDHGLTPEQVVAIASNGGGKQALETVQRLLPVLCQAH<br>GLTPDQVVAIASNGGGKQALETVQRLLPVLCQAHGLT<br>PAQVVAIASHDGGKQALETVQRLLPVLCQDHGLTPDQ<br>VVAIASNGGGKQALETVQRLLPVLCQDHGLTPEQVVA<br>IASHDGGKQALETVQRLLPVLCQAHGLTPDQVVAIAS<br>HDGGKQALETVQRLLPVLCQAHGLTPAQVVAIASHDG<br>GKQALETVQRLLPVLCQDHGLTPEQVVAIASHDGGRP<br>ALESIVAQLSRPDPALAALTNDHLVALACLGGRPALD<br>AVKKGLPHAPALIKRTNRRIPERTSHRVAGS | 256. |

TALE REPEAT SEQUENCES

| Target | SEQEUNCE | SEQ ID NO: | SEQUENCE | SEQ ID NO: |
|---|---|---|---|---|
| | TTCTCCCAGTTCTCTGTCAAGCCCACGGGCTG ACTCCCGATCAAGTTGTAGCGATTGCGTCCAA CGGTGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGAACAATAATGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCCAACGGTGGAG GGAAACAAGCATTGGAGACTGTCCAACGGCTC CTTCCCGTGTTGTGTCAAGCCCACGGTTTGAC GCCTGCACAAGTGGTCGCCATCGCCAGCCATG ATGGCGGTAAGCAGGCGCTGGAAACAGTACAG CGCCTGCTGCCTGTACTGTGCCAGGATCATGG ACTGACCCCAGACCAGGTAGTCGCAATCGCGT CAAACGGAGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACTCCCGATCAAGTTG TAGCGATTGCGTCGCATGACGGAGGGAAACAA GCATTGGAGACTGTCCAACGGCTCCTTCCCGT GTTGTGTCAAGCCCACGGTTTGACGCCTGCAC AAGTGGTCGCCATCGCCAGCCATGATGGCGGT AAGCAGGCGCTGGAAACAGTACAGCGCCTGCT GCCTGTACTGTGCCAGGATCATGGACTGACAC CCGAACAGGTGGTCGCCATTGCTTCCCACGAC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | | |
| >ERCC2_Left_TCCGGCCG GCGCCATGA_ TAL/007/01 2/019/024/ 027/012/01 9/024/027/ 014/017/02 2/026/015/ 034/JDS70/ ('TCCGGCCG GCGCCATGA' disclosed as SEQ ID NO: 418) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCGCACGCACGAGGCAATTGA GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCATCC CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCAACAACAACGGCGGTAAGCAGGC GCTGGAAACAGTACAGCGCCTGCTGCCTGTAC TGTGCCAGGATCATGGACTGACCCCAGACCAG GTAGTCGCAATCGCGTCACATGACGGGGGAAA | 257. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASHDGGKQALETVQRLLPVLCQDHGLTPEQVVAI ASHDGGKQALETVQRLLPVLCQAHGLTPDQVVAIANN NGGKQALETVQRLLPVLCQAHGLTPAQVVAIANNNGG KQALETVQRLLPVLCQDHGLTPDQVVAIASHDGGKQA LETVQRLLPVLCQDHGLTPEQVVAIASHDGGKQALET VQRLLPVLCQAHGLTPDQVVAIANNNGGKQALETVQR LLPVLCQAHGLTPAQVVAIANNNGGKQALETVQRLLP VLCQDHGLTPDQVVAIASHDGGKQALETVQRLLPVLC QDHGLTPEQVVAIANNNGGKQALETVQRLLPVLCQAH GLTPDQVVAIASHDGGKQALETVQRLLPVLCQAHGLT PAQVVAIASHDGGKQALETVQRLLPVLCQDHGLTPDQ VVAIASNIGGKQALETVQRLLPVLCQDHGLTPEQVVA IASNGGGKQALETVQRLLPVLCQAHGLTPDQVVAIAN NNGGKQALETVQRLLPVLCQAHGLTPEQVVAIASNIG GRPALESIVAQLSRPDDPALAALTNDHLVALACLGGRP ALDAVKKGLPHAPALIKRTNRRIPERTSHRVAGS | 258. |

TALE REPEAT SEQUENCES

| Target | SEQEUNCE | SEQ ID NO: | SEQUENCE | SEQ ID NO: |
|---|---|---|---|---|
| | GCAAGCCCTGGAAACCGTGCAAAGGTTGTTGC<br>CGGTCCTTTGTCAAGACCACGGCCTTACACCG<br>GAGCAAGTCGTGGCCATTGCATCCCACGACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGAATAA<br>CAATGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAACAACAACGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCACATGACGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAATAATAACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CGAACATTGGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAATGGGGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGAATAACAATGGAGGGAAACAA<br>GCATTGGAGACTGTCCAACGGCTCCTTCCCGT<br>GTTGTGTCAAGCCCACGGTCTGACACCCGAAC<br>AGGTGGTCGCCATTGCTTCTAACATCGGAGGA<br>CGGCCAGCCTTGGAGTCCATCGTAGCCCAATT<br>GTCCAGGCCCGATCCCGCGTTGGCTGCGTTAA<br>CGAATGACCATCTGGTGGCGTTGGCATGTCTT<br>GGTGGACGACCCGCGCTCGATGCAGTCAAAAA<br>GGGTCTGCCTCATGCTCCCGCATTGATCAAAA<br>GAACCAACCGGCGGATTCCCGAGAGAACTTCC<br>CATCGAGTCGCGGGATCC | | | |
| >ERCC2_Right_TAGCGAG<br>CGCGACCCC_<br>TAL/006/01<br>4/017/024/<br>026/014/01<br>7/024/027/<br>014/016/02<br>2/027/012/<br>JDS71/<br>('TAGCGAGC<br>GCGACCCC'<br>disclosed<br>as SEQ ID<br>NO: 419) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>ACAGTGGCAGTGAAGTACAGATGATCGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCGAACATT<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCAAAT<br>AATAACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGCATGACGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG | 259. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNIGGKQALETVQRLLPVLCQDHGLTPEQVVAI<br>ANNNGGKQALETVQRLLPVLCQAHGLTPDQVVAIASH<br>DGGKQALETVQRLLPVLCQAHGLTPAQVVAIANNNGG<br>KQALETVQRLLPVLCQDHGLTPDQVVAIASNIGGKQA<br>LETVQRLLPVLCQDHGLTPEQVVAIANNNGGKQALET<br>VQRLLPVLCQAHGLTPDQVVAIASHDGGKQALETVQR<br>LLPVLCQAHGLTPAQVVAIANNNGGKQALETVQRLLP<br>VLCQDHGLTPDQVVAIASHDGGKQALETVQRLLPVLC<br>QDHGLTPEQVVAIANNNGGKQALETVQRLLPVLCQAH<br>GLTPDQVVAIASNIGGKQALETVQRLLPVLCQAHGLT<br>PAQVVAIASHDGGKQALETVQRLLPVLCQDHGLTPDQ<br>VVAIASHDGGKQALETVQRLLPVLCQDHGLTPEQVVA<br>IASHDGGKQALETVQRLLPVLCQAHGLTPEQVVAIAS<br>HDGGRPALESIVAQLSRPDPALAALTNDHLVALACLG<br>GRPALDAVKKGLPHAPALIKRTNRRIPERTSHRVAGS | 260. |

TALE REPEAT SEQUENCES

| Target | SEQEUNCE | SEQ ID NO: | SEQUENCE | SEQ ID NO: |
|---|---|---|---|---|
| | GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCAAATAATAACGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGCA TGACGGAGGGAAACAAGCATTGGAGACTGTCC AACGGCTCCTTCCCGTGTTGTGTCAAGCCCAC GGTTTGACGCCTGCACAAGTGGTCGCCATCGC CAACAACAACGGCGGTAAGCAGGCGCTGGAAA CAGTACAGCGCCTGCTGCCTGTACTGTGCCAG GATCATGGACTGACCCCAGACCAGGTAGTCGC AATCGCGTCACATGACGGGGAAAGCAAGCCC TGGAAACCGTGCAAAGGTTGTTGCCGGTCCTT TGTCAAGACCACGGCCTTACACCGGAGCAAGT CGTGGCCATTGCAAATAATAACGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGAACATTGGAG GGAAACAAGCATTGGAGACTGTCCAACGGCTC CTTCCCGTGTTGTGTCAAGCCCACGGTTTGAC GCCTGCACAAGTGGTCGCCATCGCCAGCCATG ATGGCGGTAAGCAGGCGCTGGAAACAGTACAG CGCCTGCTGCCTGTACTGTGCCAGGATCATGG ACTGACCCCAGACCAGGTAGTCGCAATCGCGT CACATGACGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACACCCGAACAGGTGG TCGCCATTGCTTCCCACGACGGAGGACGGCCA GCCTTGGAGTCCATCGTAGCCCAATTGTCCAG GCCCGATCCCGCGTTGGCTGCGTTAACGAATG ACCATCTGGTGGCGTTGGCATGTCTTGGTGGA CGACCCGCGCTCGATGCAGTCAAAAAGGGTCT GCCTCATGCTCCCGCATTGATCAAAAGAACCA ACCGGCGGATTCCCGAGAGAACTTCCCATCGA GTCGCGGGATCC | | | |
| >FANCA_Left_TAGGCGCC AAGGCCATGT _TAL/006/0 14/019/022 /029/012/0 17/021/026 /014/019/0 22/027/011 /020/024/J DS78/ ('TAGGCGCC AAGGCCATGT' disclosed as SEQ ID NO: 420) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCGTGGCGCAA TGCGCTCACCGGGGCCCCCTTGAACCTGACCC CAGACCAGGTAGTCGCAATCGCGTCGAACATT GGGGGAAAGCAAGCCCTGGAAACCGTGCAAAG GTTGTTGCCGGTCCTTTGTCAAGACCACGGCC TTACACCGGAGCAAGTCGTGGCCATTGCAAAT AATAACGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACAATAATGGGGA AAGCAAGCCCTGGAAACCGTGCAAAGGTTGTTGC | 261. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASNIGGKQALETVQRLLPVLCQDHGLTPEQVVAI ANNNGGKQALETVQRLLPVLCQAHGLTPDQVVAIANN NGGKQALETVQRLLPVLCQDHGLTPDQVVAIASHDGG KQALETVQRLLPVLCQDHGLTPDQVVAIANNNGGKQA LETVQRLLPVLCQDHGLTPEQVVAIASHDGGKQALET VQRLLPVLCQAHGLTPDQVVAIASHDGGKQALETVQR LLPVLCQDHGLTPAQVVAIASNIGGKQALETVQRLLP VLCQDHGLTPEQVVAIANNNGGKQALETVQRLLPVLCQAH GLTPDQVVAIANNNGGKQALETVQRLLPVLCQAHGLT PAQVVAIASHDGGKQALETVQRLLPVLCQDHGLTPDQ VVAIASHDGGKQALETVQRLLPVLCQDHGLTPEQVVA IASNIGGKQALETVQRLLPVLCQAHGLTPDQVVAIAS NGGGKQALETVQRLLPVLCQAHGLTPAQVVAIANNNG GKQALETVQRLLPVLCQDHGLTPEQVVAIASNGGGRP ALESIVAQLSRPDPALAALTNDHLVALACLGGRPALD AVKKGLPHAPALIKRTNRRIPERTSHRVAGS | 262. |

TALE REPEAT SEQUENCES

| Target | SEQEUNCE | SEQ ID NO: | SEQUENCE | SEQ ID NO: |
|---|---|---|---|---|
| | CGGTCCTTTGTCAAGACCACGGCCTTACACCG<br>GAGCAAGTCGTGGCCATTGCATCCCACGACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGCA<br>TGACGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CTCCAATATTGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCGAACATTGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAATAATAACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGAATAACAATGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CACATGACGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAACATCGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCCAACGGTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCTAATGGG<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCGAGAGA<br>ACTTCCCATCGAGTCGCGGGATCC | | | |
| >FANCA_Right_TGGCCCG AGGCGGAGTT C_TAL/009/ 014/017/02 2/027/014/ 016/024/02 9/012/019/ 024/026/01 4/020/025/ JDS71/ ('TGGCCCGA GGCGGAGTTC' disclosed as SEQ ID NO: 421) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTGG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGCCCCCTTGAACCTGACCC CAGACCAGGTAGTCGCAATCGCGAACAATAAT GGGGGAAAGCAAGCCCTGGAAACCGTGCAAAG GTTGTTGCCGGTCCTTTGTCAAGACCACGGCC TTACACCGGAGCAAGTCGTGGCCATTGCAAAT AATAACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGCATGACGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC | 263. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIANNNGGKQALETVQRLLPVLCQAHGLTPDQVVAI ANNNGGKQALETVQRLLPVLCQAHGLTPDQVVAIASH DGGKQALETVQRLLPVLCQAHGLTPAQVVAIASHDGG KQALETVQRLLPVLCQDHGLTPDQVVAIASHDGGKQA LETVQRLLPVLCQDHGLTPEQVVAIANNNGGKQALET VQRLLPVLCQAHGLTPDQVVAIASNIGGKQALETVQR LLPVLCQAHGLTPAQVVAIANNNGGKQALETVQRLLP VLCQDHGLTPDQVVAIANNNGGKQALETVQRLLPVLC QDHGLTPEQVVAIASHDGGKQALETVQRLLPVLCQAH GLTPDQVVAIANNNGGKQALETVQRLLPVLCQAHGLT PAQVVAIANNNGGKQALETVQRLLPVLCQDHGLTPDQ VVAIASNIGGKQALETVQRLLPVLCQDHGLTPEQVVA IANNNGGKQALETVQRLLPVLCQAHGLTPDQVVAIAS NGGGKQALETVQRLLPVLCQAHGLTPAQVVAIASNGG GKQALETVQRLLPVLCQDHGLTPEQVVAIASHDGGRP ALESIVAQLSRPDPALAALTNDHLVALACLGGRPALD AVKKGLPHAPALIKRTNRRIPERTSHRVAGS | 264. |

TALE REPEAT SEQUENCES

| Target | SEQEUNCE | SEQ ID NO: | SEQUENCE | SEQ ID NO: |
|---|---|---|---|---|
| | GCTGGAAACAGTACAGCGCCTGCTGCCTGTAC<br>TGTGCCAGGATCATGGACTGACCCCAGACCAG<br>GTAGTCGCAATCGCGTCACATGACGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGAA<br>CATTGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAACAACAACGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGAACAATAATGGGGAAAGCAAGCCT<br>TGGAAACCGTGCAAAGGTTGTTGCCGGTCCTT<br>TGTCAAGACCACGGCCTTACACCGGAGCAAGT<br>CGTGGCCATTGCATCCCACGACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGAATAACAATGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAACAACA<br>ACGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CGAACATTGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAATAATAACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCCAACGGTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCTCGAATGGCGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCCCACGAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >FANCC_Left_TGAAGGGACATCACCTTT_TAL/009/011/016/024/029/014/016/022/026/015/017/021/027/012/020/025/JDS78/ ('TGAAGGGACATCACCTTT' disclosed as SEQ ID NO: 422) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGAACAATAAT<br>GGGGGAAAGCAAGCCCTGGAAACCGTGCAAAG<br>GTTGTTGCCGGTCCTTTGTCAAGACCACGCC<br>TTACACCGGAGCAAGTCGTGGCCATTGCAAGC<br>AACATCGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT | 265. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIANNNGGKQALETVQRLLPVLCQDHGLTPEQVVAI<br>ASNIGGKQALETVQRLLPVLCQAHGLTPDQVVAIASN<br>IGGKQALETVQRLLPVLCQAHGLTPAQVVAIANNNGG<br>KQALETVQRLLPVLCQDHGLTPDQVVAIANNNGGKQA<br>LETVQRLLPVLCQDHGLTPEQVVAIANNNGGKQALET<br>VQRLLPVLCQAHGLTPDQVVAIASNIGGKQALETVQR<br>LLPVLCQAHGLTPAQVVAIASHDGGKQALETVQRLLP<br>VLCQDHGLTPDQVVAIASNIGGKQALETVQRLLPVLC<br>QDHGLTPEQVVAIASNGGGKQALETVQRLLPVLCQAH<br>GLTPDQVVAIASHDGGKQALETVQRLLPVLCQAHGLT<br>PAQVVAIASNIGGKQALETVQRLLPVLCQDHGLTPDQ<br>VVAIASHDGGKQALETVQRLLPVLCQAHGLTPEQVVA<br>IASHDGGKQALETVQRLLPVLCQAHGLTPDQVVAIAS<br>NGGGKQALETVQRLLPVLCQDHGLTPAQVVAIASNGG<br>GKQALETVQRLLPVLCQDHGLTPEQVVAIASNGGGRP<br>ALESIVAQLSRPDPALAALTNDHLVALACLGGRPALD<br>AVKKGLPHAPALIKRTNRRIPERTSHRVAGS | 266. |

TALE REPEAT SEQUENCES

| Target | SEQEUNCE | SEQ ID NO: | SEQUENCE | SEQ ID NO: |
|---|---|---|---|---|
| | GCGTCGAACATTGGAGGGAAACAAGCATTGGA<br>GACTGTCCAACGGCTCCTTCCCGTGTTGTGTC<br>AAGCCCACGGTTTGACGCCTGCACAAGTGGT<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGAACAATAATGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGAA<br>CATTGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCGAACATTGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAGCAATGGGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCTCCAATA<br>TTGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CACATGACGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCATCCCACGACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCCAACGGTGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCTCGAATGGCGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCTAATGGG<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >FANCC_Rig<br>ht_TCTACTG<br>AATCTTGAGC<br>_TAL/007/0<br>15/016/022<br>/030/014/0<br>16/021/030<br>/012/020/0<br>25/029/011<br>/034/JDS71<br>/<br>('TCTACTGA<br>ATCTTGAGC'<br>disclosed<br>as SEQ ID<br>NO: 423) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGA<br>AGCTGCTGAAGATCGCAAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCACATGAC<br>GGGGGAAAGCAAGCCCTGGAAACCGTGCAAAG<br>GTTGTTGCCGGTCCTTTGTCAAGACCACGGCC | 267. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASHDGGKQALETVQRLLPVLCQDHGLTPEQVVAI<br>ASNGGGKQALETVQRLLPVLCQAHGLTPDQVVAIASN<br>IGGKQALETVQRLLPVLCQAHGLTPAQVVAIASHDGG<br>KQALETVQRLLPVLCQDHGLTPDQVVAIASNGGGKQA<br>LETVQRLLPVLCQDHGLTPEQVVAIANNNGGKQALET<br>VQRLLPVLCQAHGLTPDQVVAIASNIGGKQALETVQR<br>LLPVLCQAHGLTPAQVVAIASNIGGKQALETVQRLLP<br>VLCQDHGLTPDQVVAIASNGGGKQALETVQRLLPVLC<br>QDHGLTPEQVVAIASHDGGKQALETVQRLLPVLCQAH<br>GLTPDQVVAIASNGGGKQALETVQRLLPVLCQAHGLT<br>PAQVVAIASNGGGKQALETVQRLLPVLCQDHGLTPDQ<br>VVAIANNNGGKQALETVQRLLPVLCQDHGLTPEQVVA<br>IASNIGGKQALETVQRLLPVLCQAHGLTPDQVVAIAN<br>NNGGKQALETVQRLLPVLCQAHGLTPEQVVAIASHDG<br>GRPALESIVAQLSRPDPALAALTNDHLVALACLGGRP | 268. |

TALE REPEAT SEQUENCES

| Target | SEQEUNCE | SEQ ID NO: | SEQUENCE | SEQ ID NO: |
|---|---|---|---|---|
| | TTACACCGGAGCAAGTCGTGGCCATTGCAAGC<br>AATGGGGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGAACATTGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAGCCATGATGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCAAACGGAGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGAA<br>CATTGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CTCCAATATTGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCAAACGGAGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCATCCCACGACGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCCAACGGTGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCTCGAATG<br>GCGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGA<br>ACAATAATGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAACATCGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGAATAACAATGGAGGGAAACAA<br>GCATTGGAGACTGTCCAACGGCTCCTTCCCGT<br>GTTGTGTCAAGCCCACGGTCTGACACCCGAAC<br>AGGTGGTCGCCATTGCTTCCCACGACGGAGGA<br>CGGCCAGCCTTGGAGTCCATCGTAGCCCAATT<br>GTCCAGGCCCGATCCCGCGTTGGCTGCGTTAA<br>CGAATGACCATCTGGTGGCGTTGGCATGTCTT<br>GGTGGACGACCCGCGCTCGATGCAGTCAAAAA<br>GGGTCTGCCTCATGCTCCCGCATTGATCAAAA<br>GAACCAACCGGCGGATTCCCGAGAGAACTTCC<br>CATCGAGTCGCGGGATCC | | ALDAVKKGLPHAPALIKRTNRRIPERTSHRVAGS | |
| >FANCG_Left_TCGGCCAC<br>CATGTCCC_T<br>AL/007/014<br>/019/022/0<br>27/011/017<br>/022/026/0<br>15/019/025<br>/027/012/J<br>DS71/<br>('TCGGCCAC<br>CATGTCCC'<br>disclosed<br>as SEQ ID<br>NO: 424) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>CGGCCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCACATGAC<br>GGGGGAAAGCAAGCCCTGGAAACCGTGCAAAG | 269. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASHDGGKQALETVQRLLPVLCQDHGLTPEQVVAI<br>ANNNGGKQALETVQRLLPVLCQAHGLTPDQVVAIANN<br>NGGGKQALETVQRLLPVLCQDHGLTPDQVVAIASHDGG<br>KQALETVQRLLPVLCQDHGLTPDQVVAIASHDGGKQA<br>LETVQRLLPVLCQDHGLTPEQVVAIASNIGGKQALET<br>VQRLLPVLCQAHGLTPDQVVAIASHDGGKQALETVQR<br>LLPVLCQAHGLTPAQVVAIASHDGGKQALETVQRLLP<br>VLCQDHGLTPDQVVAIASNGGGKQALETVQRLLPVLC<br>QDHGLTPEQVVAIASNGGGKQALETVQRLLPVLCQAH<br>GLTPDQVVAIANNNGGKQALETVQRLLPVLCQAHGLT<br>PAQVVAIASNGGGKQALETVQRLLPVLCQDHGLTPDQ<br>VVAIASHDGGKQALETVQRLLPVLCQDHGLTPEQVVA<br>IASHDGGKQALETVQRLLPVLCQAHGLTPEQVVAIAS<br>HDGGRPALESIVAQLSRPDPALAALTNDHLVALACLG | 270. |

TALE REPEAT SEQUENCES

| Target | SEQEUNCE | SEQ ID NO: | SEQUENCE | SEQ ID NO: |
|---|---|---|---|---|
| | GTTGTTGCCGGTCCTTTGTCAAGACCACGGCC TTACACCGGAGCAAGTCGTGGCCATTGCAAAT AATAACGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC GCTGGAAACAGTACAGCGCCTGCTGCCTGTAC TGTGCCAGGATCATGGACTGACCCCAGACCAG GTAGTCGCAATCGCGTCACATGACGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGCA TGACGGAGGGAAACAAGCATTGGAGACTGTCC AACGGCTCCTTCCCGTGTTGTGTCAAGCCCAC GGTTTGACGCCTGCACAAGTGGTCGCCATCGC CAGCCATGATGGCGGTAAGCAGGCGCTGGAAA CAGTACAGCGCCTGCTGCCTGTACTGTGCCAG GATCATGGACTGACCCCAGACCAGGTAGTCGC AATCGCGTCGAACATTGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGAATAACAATGGAG GGAAACAAGCATTGGAGACTGTCCAACGGCTC CTTCCCGTGTTGTGTCAAGCCCACGGTTTGAC GCCTGCACAAGTGGTCGCCATCGCCTCGAATG GCGGCGGTAAGCAGGCGCTGGAAACAGTACAG CGCCTGCTGCCTGTACTGTGCCAGGATCATGG ACTGACCCCAGACCAGGTAGTCGCAATCGCGT CACATGACGGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACACCCGAACAGGTGG TCGCCATTGCTTCCCACGACGGAGGACGGCCA GCCTTGGAGTCCATCGTAGCCCAATTGTCCAG GCCCGATCCCGCGTTGGCTGCGTTAACGAATG ACCATCTGGTGGCGTTGGCATGTCTTGGTGGA CGACCCGCGCTCGATGCAGTCAAAAAGGGTCT GCCTCATGCTCCCGCATTGATCAAAGAACCA ACCGGCGGATTCCCGAGAGAACTTCCCATCGA GTCGCGGGATCC | | GRPALDAVKKGLPHAPALIKRTNRRIPERTSHRVAGS | |
| >FANCG_Right_TCCAGGC AGCTGGAGCC C_TAL/007/ 012/016/02 4/029/012/ 016/024/02 7/015/019/ 024/026/01 4/017/022/ JDS71/ ('TCCAGGCA GCTGGAGCCC' disclosed as SEQ ID NO: 425) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCATCC | 271. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGVTAVEAVHAWRNALTGAPLNLTPDQV VAIASHDGGKQALETVQRLLPVLCQDHGLTPEQVVAI ASHDGGKQALETVQRLLPVLCQAHGLTPDQVVAIASN IGGKQALETVQRLLPVLCQAHGLTPAQVVAIANNNGG KQALETVQRLLPVLCQDHGLTPDVVAIANNNGGKQA LETVQRLLPVLCQDHGLTPDQVVAIANNNGGKQALET VQRLLPVLCQAHGLTPDQVVAIASNIGGKQALETVQR LLPVLCQAHGLTPAQVVAIANNNGGKQALETVQRLLP VLCQDHGLTPDQVVAIASHDGGKQALETVQRLLPVLC QDHGLTPEQVVAIASNGGGKQALETVQRLLPVLCQAH GLTPDQVVAIANNNGGKQALETVQRLLPVLCQAHGLT PAQVVAIANNNGGKQALETVQRLLPVLCQDHGLTPDQ VVAIASNIGGKQALETVQRLLPVLCQDHGLTPEQVVA IANNNGGKQALETVQRLLPVLCQAHGLTPDQVVAIAS HDGGKQALETVQRLLPVLCQAHGLTPAQVVAIASHDG GKQALETVQRLLPVLCQDHGLTPEQVVAIASHDGGRP ALESIVAQLSRPDPALAALTNDHLVALACLGGRPALD | 272. |

TALE REPEAT SEQUENCES

| Target | SEQEUNCE | SEQ ID NO: | SEQUENCE | SEQ ID NO: |
|---|---|---|---|---|
| | CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGAACATTGGAGGGAAACAAGCATTGGA GACTGTCCAACGGCTCCTTCCCGTGTTGTGTC AAGCCCACGGTTTGACGCCTGCACAAGTGGTC GCCATCGCCAACAACAACGGCGGTAAGCAGGC GCTGGAAACAGTACAGCGCCTGCTGCCTGTAC TGTGCCAGGATCATGGACTGACCCCAGACCAG GTAGTCGCAATCGCGAACAATAATGGGGGAAA GCAAGCCCTGGAAACCGTGCAAAGGTTGTTGC CGGTCCTTTGTCAAGACCACGGCCTTACACCG GAGCAAGTCGTGGCCATTGCATCCCACGACGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGAA CATTGGAGGGAAACAAGCATTGGAGACTGTCC AACGGCTCCTTCCCGTGTTGTGTCAAGCCCAC GGTTTGACGCCTGCACAAGTGGTCGCCATCGC CAACAACAACGGCGGTAAGCAGGCGCTGGAAA CAGTACAGCGCCTGCTGCCTGTACTGTGCCAG GATCATGGACTGACCCCAGACCAGGTAGTCGC AATCGCGTCACATGACGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGAATAACAATGGAG GGAAACAAGCATTGGAGACTGTCCAACGGCTC CTTCCCGTGTTGTGTCAAGCCCACGGTTTGAC GCCTGCACAAGTGGTCGCCATCGCCAACAACA ACGGCGGTAAGCAGGCGCTGGAAACAGTACAG CGCCTGCTGCCTGTACTGTGCCAGGATCATGG ACTGACCCCAGACCAGGTAGTCGCAATCGCGT CGAACATTGGGGGAAAGCAAGCCCTGGAAACC GTGCAAAGGTTGTTGCCGGTCCTTTGTCAAGA CCACGGCCTTACACCGGAGCAAGTCGTGGCCA TTGCAAATAATAACGGTGGCAAACAGGCTCTT GAGACGGTTCAGAGACTTCTCCCAGTTCTCTG TCAAGCCCACGGGCTGACTCCCGATCAAGTTG TAGCGATTGCGTCGCATGACGGAGGGAAACAA GCATTGGAGACTGTCCAACGGCTCCTTCCCGT GTTGTGTCAAGCCCACGGTTTGACGCCTGCAC AAGTGGTCGCCATCGCCAGCCATGATGGCGGT AAGCAGGCGCTGGAAACAGTACAGCGCCTGCT GCCTGTACTGTGCCAGGATCATGGACTGACAC CCGAACAGGTGGTCGCCATTGCTTCCCACGAC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCGAGAGA ACTTCCCATCGAGTCGCGGGATCC | | AVKKGLPHAPALIKRTNRRIPERTSHRVAGS | |
| >JAK2_Left _TCTGAAAAA GACTCTGCA_ TAL/007/01 5/019/021/ 026/011/01 6/021/029/ 011/017/02 5/027/015/ 019/022/JD S70/ ('TCTGAAAA AGACTCTGCA' disclosed | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC | 273. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASHDGGKQALETVQRLLPVLCQDHGLTPEQVVAI ASNGGGKQALETVQRLLPVLCQAHGLTPDQVVAIANN NGGKQALETVQRLLPVLCQAHGLTPAQVVAIASNIGG KQALETVQRLLPVLCQDHGLTPDQVVAIASNIGGKQA LETVQRLLPVLCQDHGLTPEQVVAIASNIGGKQALET VQRLLPVLCQAHGLTPDQVVAIASNIGGKQALETVQR LLPVLCQAHGLTPAQVVAIASNIGGKQALETVQRLLP VLCQDHGLTPDQVVAIANNNGGKQALETVQRLLPVLC QDHGLTPEQVVAIASNIGGKQALETVQRLLPVLCQAH | 274. |

TALE REPEAT SEQUENCES

| Target | SEQEUNCE | SEQ ID NO: | SEQUENCE | SEQ ID NO: |
|---|---|---|---|---|
| as SEQ ID NO: 426) | AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCAAGC AATGGGGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTC AAGCCCACGGTTTGACGCCTGCACAAGTGGTC GCCATCGCCTCCAATATTGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGAA CATTGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGAACAATAATGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAACATCGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGATGACGGAG GGAAACAAGCATTGGAGACTGTCCAACGGCTC CTTCCCGTGTTGTGTCAAGCCCACGGTTTGAC GCCTGCACAAGTGGTCGCCATCGCCTCGAATG GCGGCGGTAAGCAGGCGCTGGAAACAGTACAG CGCCTGCTGCCTGTACTGTGCCAGGATCATGG ACTGACCCCAGACCAGGTAGTCGCAATCGCGT CACATGACGGGGGAAAGCAAGCCCTGGAAACC GTGCAAAGGTTGTTGCCGGTCCTTTGTCAAGA CCACGGCCTTACACCGGAGCAAGTCGTGGCCA TTGCAAGCAATGGGGGTGGCAAACAGGCTCTT GAGACGGTTCAGAGACTTCTCCCAGTTCTCTG TCAAGCCCACGGGCTGACTCCCGATCAAGTTG TAGCGATTGCGAATAACAATGGAGGGAAACAA GCATTGGAGACTGTCCAACGGCTCCTTCCCGT GTTGTGTCAAGCCCACGGTTTGACGCCTGCAC AAGTGGTCGCCATCGCCAGCCATGATGGCGGT AAGCAGGCGCTGGAAACAGTACAGCGCCTGCT GCCTGTACTGTGCCAGGATCATGGACTGACAC CCGAACAGGTGGTCGCCATTGCTTCTAACATC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | GLTPDQVVAIASHDGGKQALETVQRLLPVLCQAHGLT PAQVVAIASNGGGKQALETVQRLLPVLCQDHGLTPDQ VVAIASHDGGKQALETVQRLLPVLCQDHGLTPEQVVA IASNGGGKQALETVQRLLPVLCQAHGLTPDQVVAIAN NNGGKQALETVQRLLPVLCQDHGLTPAQVVAIASHDG GKQALETVQRLLPVLCQDHGLTPEQVVAIASNIGGRP ALESIVAQLSRPDPALAALTNDHLVALACLGGRPALD AVKKGLPHAPALIKRTNRRIPERTSHRVAGS | |
| >JAK2_Right_TCCATTTC TGTCATCGTA _TAL/007/0 12/016/025 /030/015/0 17/025/029 /015/017/0 21/030/012 /019/025/J | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGTACCTAT GGGTGACTTGAGGACACTCGGTTATTCGCAAC AGCAACAGGAGAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCCGTGAAATACCAAGATATGATTGCGGC | 275. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASHDGGKQALETVQRLLPVLCQDHGLTPEQVVAI ASHDGGKQALETVQRLLPVLCQAHGLTPDQVVAIASN IGGKQALETVQRLLPVLCQAHGLTPAQVVAIASNGGG KQALETVQRLLPVLCQDHGLTPDQVVAIASNGGGKQA LETVQRLLPVLCQDHGLTPEQVVAIASNGGGKQALET | 276. |

TALE REPEAT SEQUENCES

| Target | SEQEUNCE | SEQ ID NO: | SEQUENCE | SEQ ID NO: |
|---|---|---|---|---|
| DS70/ ('TCCATTTC TGTCATCGTA' disclosed as SEQ ID NO: 427) | CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCATCC CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGAACATTGGAGGGAAACAAGCATTGGA GACTGTCCAACGGCTCCTTCCCGTGTTGTGTC AAGCCCACGGTTTGACGCCTGCACAAGTGGTC GCCATCGCCTCGAATGGCGGCGGTAAGCAGGC GCTGGAAACAGTACAGCGCCTGCTGCCTGTAC TGTGCCAGGATCATGGACTGACCCCAGACCAG GTAGTCGCAATCGCGTCAAACGGAGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAATGGGGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGCA TGACGGAGGGAAACAAGCATTGGAGACTGTCC AACGGCTCCTTCCCGTGTTGTGTCAAGCCCAC GGTTTGACGCCTGCACAAGTGGTCGCCATCGC CTCGAATGGCGGCGGTAAGCAGGCGCTGGAAA CAGTACAGCGCCTGCTGCCTGTACTGTGCCAG GATCATGGACTGACCCCAGACCAGGTAGTCGC AATCGCGAACAATAATGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGCATGACGGAG GGAAACAAGCATTGGAGACTGTCCAACGGCTC CTTCCCGTGTTGTGTCAAGCCCACGGTTTGAC GCCTGCACAAGTGGTCGCCATCGCCTCCAATA TTGGCGGTAAGCAGGCGCTGGAAACAGTACAG CGCCTGCTGCCTGTACTGTGCCAGGATCATGG ACTGACCCCAGACCAGGTAGTCGCAATCGCGT CAAACGGAGGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACTCCCGATCAAGTTG TAGCGATTGCGAATAACAATGGAGGGAAACAA GCATTGGAGACTGTCCAACGGCTCCTTCCCGT GTTGTGTCAAGCCCACGGTTTGACGCCTGCAC AAGTGGTCGCCATCGCCTCGAATGGCGGCGGT AAGCAGGCGCTGGAAACAGTACAGCGCCTGCT GCCTGTACTGTGCCAGGATCATGGACTGACAC CCGAACAGGTGGTCGCCATTGCTTCTAACATC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | VQRLLPVLCQAHGLTPDQVVAIASHDGGKQALETVQR LLPVLCQAHGLTPAQVVAIASNGGGKQALETVQRLLP VLCQDHGLTPDQVVAIANNNGGKQALETVQRLLPVLC QDHGLTPEQVVAIASNGGGKQALETVQRLLPVLCQAH GLTPDQVVAIASHDGGKQALETVQRLLPVLCQAHGLT PAQVVAIASNIGGKQALETVQRLLPVLCQDHGLTPDQ VVAIASNGGGKQALETVQRLLPVLCQDHGLTPEQVVA IASHDGGKQALETVQRLLPVLCQAHGLTPDQVVAIAN NNGGKQALETVQRLLPVLCQAHGLTPAQVVAIASNGG GKQALETVQRLLPVLCQDHGLTPEQVVAIASNIGGRP ALESIVAQLSRPDPALAALTNDHLVALACLGGRPALD AVKKGLPHAPALIKRTNRRIPERTSHRVAGS | |
| >KRAS_Left _TGAAAATGA CTGAATATA_ TAL/009/01 1/016/021/ 026/015/01 | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG | 277. | ASTMDYKDHDGDYKDHDIDYKDDDDKMAPKKKRKVGI HRGVPMVDLRTLGYSQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIANNNGGKQALETVQRLLPVLCQDHGLTPEQVVAI | 278. |

TABLE REPEAT SEQUENCES

| Target | SEQEUNCE | SEQ ID NO: | SEQUENCE | SEQ ID NO: |
|---|---|---|---|---|
| 9/021/027/ 015/019/02 1/026/015/ 016/025/JD S70/ ('TGAAAATG ACTGAATATA' disclosed as SEQ ID NO: 428) | AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGAACAATAAT GGGGGAAAGCAAGCCCTGGAAACCGTGCAAAG GTTGTTGCCGGTCCTTTGTCAAGACCACGGCC TTACACCGGAGCAAGTCGTGGCCATTGCAAGC AACATCGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGAACATTGGAGGGAAACAAGCATTGGA GACTGTCCAACGGCTCCTTCCCGTGTTGTGTC AAGCCCACGGTTTGACGCCTGCACAAGTGGTC GCCATCGCCTCCAATATTGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAATGGGGG TGGCAAACAGGCTCTTGAGACGGTTCAGAGAC TTCTCCCAGTTCTCTGTCAAGCCCACGGGCTG ACTCCCGATCAAGTTGTAGCGATTGCGAATAA CAATGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGTCACATGACGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGAATAACAATGGAG GGAAACAAGCATTGGAGACTGTCCAACGGCTC CTTCCCGTGTTGTGTCAAGCCCACGGTTTGAC GCCTGCACAAGTGGTCGCCATCGCCTCCAATA TTGGCGGTAAGCAGGCGCTGGAAACAGTACAG CGCCTGCTGCCTGTACTGTGCCAGGATCATGG ACTGACCCCAGACCAGGTAGTCGCAATCGCGT CGAACATTGGGGGAAAGCAAGCCCTGGAAACC GTGCAAAGGTTGTTGCCGGTCCTTTGTCAAGA CCACGGCCTTACACCGGAGCAAGTCGTGGCCA TTGCAAGCAATGGGGGTGGCAAACAGGCTCTT GAGACGGTTCAGAGACTTCTCCCAGTTCTCTG TCAAGCCCACGGGCTGACTCCCGATCAAGTT TAGCGATTGCGTCGAACATTGGAGGGAAACAA GCATTGGAGACTGTCCAACGGCTCCTTCCCGT GTTGTGTCAAGCCCACGGTTTGACGCCTGCAC AAGTGGTCGCCATCGCCTCGAATGGCGGCGGT AAGCAGGCGCTGGAAACAGTACAGCGCCTGCT GCCTGTACTGTGCCAGGATCATGGACTGACAC CCGAACAGGTGGTCGCCATTGCTTCTAACATC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | ASNIGGKQALETVQRLLPVLCQAHGLTPDQVVAIASN IGGKQALETVQRLLPVLCQAHGLTPAQVVAIASNIGG KQALETVQRLLPVLCQDHGLTPDQVVAIASNIGGKQA LETVQRLLPVLCQDHGLTPEQVVAIASNGGGKQALET VQRLLPVLCQAHGLTPDQVVAIANNNGGKQALETVQR LLPVLCQAHGLTPAQVVAIASNIGGKQALETVQRLLP VLCQDHGLTPDQVVAIASHDGGKQALETVQRLLPVLC QDHGLTPEQVVAIASNGGGKQALETVQRLLPVLCQAH GLTPDQVVAIANNNGGKQALETVQRLLPVLCQAHGLT PAQVVAIASNIGGKQALETVQRLLPVLCQDHGLTPDQ VVAIASNIGGKQALETVQRLLPVLCQDHGLTPEQVVA IASNGGGKQALETVQRLLPVLCQDHGLTPDQVVAIAS NIGGKQALETVQRLLPVLCQAHGLTPAQVVAIASNGG GKQALETVQRLLPVLCQDHGLTPEQVVAIASNIGGRP ALESIVAQLSRPDPALAALTNDHLVALACLGGRPALD AVKKGLPHAPALIKRTNRRIPERTSHRVAGS | |
| >KRAS_Right_TTGCCTAC | GCTAGCaccATGGACTACAAAGACCATGACGG TGATTATAAAGATCATGACATCGATTACAAGG | 279. | ASTMDYKDHDGDYKDHDIDYKDDDDKMAPKKKRKVGI HRGVPMVDLRTLGYSQQQQEKIKPKVRSTVAQHHEAL | 280. |

TALE REPEAT SEQUENCES

| Target | SEQEUNCE | SEQ ID NO: | SEQUENCE | SEQ ID NO: |
|---|---|---|---|---|
| GCCACCAGC_TAL/010/014/017/022/030/011/017/024/027/012/016/022/027/011/034/JDS71/ ('TTGCCTACGCCACCAGC' disclosed as SEQ ID NO: 429) | ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCAAACGGA GGGGGAAAGCAAGCCCTGGAAACCGTGCAAAG GTTGTTGCCGGTCCTTTGTCAAGACCACGGCC TTACACCGGAGCAAGTCGTGGCCATTGCAAAT AATAACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGCATGACGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC GCTGGAAACAGTACAGCGCCTGCTGCCTGTAC TGTGCCAGGATCATGGACTGACCCCAGACCAG GTAGTCGCAATCGCGTCAAACGGAGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGCA TGACGGAGGGAAACAAGCATTGGAGACTGTCC AACGGCTCCTTCCCGTGTTGTGTCAAGCCCAC GGTTTGACGCCTGCACAAGTGGTCGCCATCGC CAACAACGGCGGTAAGCAGGCGCTGGAAA CAGTACAGCGCCTGCTGCCTGTACTGTGCCAG GATCATGGACTGACCCCAGACCAGGTAGTCGC AATCGCGTCACATGACGGGGAAAGCAAGCCC TGGAAACCGTGCAAAGGTTGTTGCCGGTCCTT TGTCAAGACCACGGCCTTACACCGGAGCAAGT CGTGGCCATTGCATCCCACGACGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGAACATTGGAG GGAAACAAGCATTGGAGACTGTCCAACGGCTC CTTCCCGTGTTGTGTCAAGCCCACGGTTTGAC GCCTGCACAAGTGGTCGCCATCGCCAGCCATG ATGGCGGTAAGCAGGCGCTGGAAACAGTACAG CGCCTGCTGCCTGTACTGTGCCAGGATCATGG ACTGACCCCAGACCAGGTAGTCGCAATCGCGT CACATGACGGGGAAAGCAAGCCCTGGAAACC GTGCAAAGGTTGTTGCCGGTCCTTTGTCAAGA CCACGGCCTTACACCGGAGCAAGTCGTGGCCA TTGCAAGCAACATCGGTGGCAAACAGGCTCTT GAGACGGTTCAGAGACTTCTCCCAGTTCTCTG TCAAGCCCACGGGCTGACTCCCGATCAAGTTG TAGCGATTGCGAATAACAATGGAGGGAAACAA GCATTGGAGACTGTCCAACGGCTCCTTCCCGT GTTGTGTCAAGCCCACGGTCTGACACCCGAAC AGGTGGTCGCCATTGCTTCCCACGACGGAGGA CGGCCAGCCTTGGAGTCCATCGTAGCCCAATT GTCCAGGCCCGATCCCGCGTTGGCTGCGTTAA CGAATGACCATCTGGTGGCGTTGGCATGTCTT GGTGGACGACCCGCGCTCGATGCAGTCAAAAA GGGTCTGCCTCATGCTCCCGCATTGATCAAAA GAACCAACCGGCGGATTCCCGAGAGAACTTCC CATCGAGTCGCGGGATCC | | VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASNGGGKQALETVQRLLPVLCQDHGLTPEQVVAI ANNNGGKQALETVQRLLPVLCQAHGLTPDQVVAIASH DGGKQALETVQRLLPVLCQDHGLTPDQVVAIASNGGGKQA LETVQRLLPVLCQDHGLTPEQVVAIASNIGGKQALET VQRLLPVLCQAHGLTPDQVVAIASHDGGKQALETVQR LLPVLCQAHGLTPAQVVAIANNNGGKQALETVQRLLP VLCQDHGLTPDQVVAIASHDGGKQALETVQRLLPVLC QDHGLTPEQVVAIASHDGGKQALETVQRLLPVLCQAH GLTPDQVVAIASNIGGKQALETVQRLLPVLCQAHGLT PAQVVAIASHDGGKQALETVQRLLPVLCQDHGLTPDQ VVAIASHDGGKQALETVQRLLPVLCQDHGLTPEQVVA IASNIGGKQALETVQRLLPVLCQAHGLTPEQVVAIAN NNGGKQALETVQRLLPVLCQAHGLTPEQVVAIASHDG GRPALESIVAQLSRPDPALAALTNDHLVALACLGGRP ALDAVKKGLPHAPALIKRTNRRIPERTSHRVAGS | |

TALE REPEAT SEQUENCES

| Target | SEQUENCE | SEQ ID NO: | SEQUENCE | SEQ ID NO: |
|---|---|---|---|---|
| >MYC_Left_TGCTTAGACG CTGGATTT_TAL/009/012 /020/025/026/014/016 /022/029/012/020/024 /029/011/020/025/JDS78/ ('TGCTTAGACGCTGGATTT' disclosed as SEQ ID NO: 430) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGAACAATAAT GGGGGAAAGCAAGCCCTGGAAACCGTGCAAAG GTTGTTGCCGGTCCTTTGTCAAGACCACGGCC TTACACCGGAGCAAGTCGTGGCCATTGCATCC CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCCAACGGTGGAGGGAAACAAGCATTGGA GACTGTCCAACGGCTCCTTCCCGTGTTGTGTC AAGCCCACGGTTTGACGCCTGCACAAGTGGTC GCCATCGCCTCGAATGGCGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCAAATAATAACGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGAA CATTGGAGGGAAACAAGCATTGGAGACTGTCC AACGGCTCCTTCCCGTGTTGTGTCAAGCCCAC GGTTTGACGCCTGCACAAGTGGTCGCCATCGC CAGCCATGATGGCGGTAAGCAGGCGCTGGAAA CAGTACAGCGCCTGCTGCCTGTACTGTGCCAG GATCATGGACTGACCCCAGACCAGGTAGTCGC AATCGCGAACAATAATGGGGAAAGCAAGCCC TGGAAACCGTGCAAAGGTTGTTGCCGGTCCTT TGTCAAGACCACGGCCTTACACCGGAGCAAGT CGTGGCCATTGCATCCCACGACGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCCAACGGTGGAG GGAAACAAGCATTGGAGACTGTCCAACGGCTC CTTCCCGTGTTGTGTCAAGCCCACGGTTTGAC GCCTGCACAAGTGGTCGCCATCGCCAACAACA ACGGCGGTAAGCAGGCGCTGGAAACAGTACAG CGCCTGCTGCCTGTACTGTGCCAGGATCATGG ACTGACCCCAGACCAGGTAGTCGCAATCGCGA ACAATAATGGGGGAAAGCAAGCCCTGGAAACC GTGCAAAGGTTGTTGCCGGTCCTTTGTCAAGA CCACGGCCTTACACCGGAGCAAGTCGTGGCCA TTGCAAGCAACATCGGTGGCAAACAGGCTCTT GAGACGGTTCAGAGACTTCTCCCAGTTCTCTG TCAAGCCCACGGGCTGACTCCCGATCAAGTTG TAGCGATTGCGTCCAACGGTGGAGGGAAACAA GCATTGGAGACTGTCCAACGGCTCCTTCCCGT GTTGTGTCAAGCCCACGGTTTGACGCCTGCAC AAGTGGTCGCCATCGCCTCGAATGGCGGCGGT AAGCAGGCGCTGGAAACAGTACAGCGCCTGCT GCCTGTACTGTGCCAGGATCATGGACTGACAC CCGAACAGGTGGTCGCCATTGCTTCTAATGGG GGAGGACGGCCAGCCTTGGAGTCCATCGTAGC CCAATTGTCCAGGCCCGATCCCGCGTTGGCTG CGTTAACGAATGACCATCTGGTGGCGTTGGCA | 281. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIANNNGGKQALETVQRLLPVLCQDHGLTPEQVVAI ASHDGGKQALETVQRLLPVLCQAHGLTPDQVVAIASN GGGKQALETVQRLLPVLCQAHGLTPAQVVAIASNGGG KQALETVQRLLPVLCQDHGLTPDQVVAIASNIGGKQA LETVQRLLPVLCQDHGLTPEQVVAIANNNGGKQALET VQRLLPVLCQDHGLTPDQVVAIASNIGGKQALETVQR LLPVLCQAHGLTPAQVVAIASHDGGKQALETVQRLLP VLCQDHGLTPDQVVAIANNNGGKQALETVQRLLPVLC QDHGLTPEQVVAIASHDGGKQALETVQRLLPVLCQAH GLTPDQVVAIASNGGGKQALETVQRLLPVLCQAHGLT PAQVVAIANNNGGKQALETVQRLLPVLCQDHGLTPDQ VVAIANNNGGKQALETVQRLLPVLCQDHGLTPEQVVA IASNIGGKQALETVQRLLPVLCQAHGLTPDQVVAIAS NGGGKQALETVQRLLPVLCQAHGLTPAQVVAIASNGG GKQALETVQRLLPVLCQDHGLTPEQVVAIASNGGGRP ALESIVAQLSRPDPALAALTNDHLVALACLGGRPALD AVKKGLPHAPALIKRTNRRIPERTSHRVAGS | 282. |

TALE REPEAT SEQUENCES

| Target | SEQEUNCE | SEQ ID NO: | SEQUENCE | SEQ ID NO: |
|---|---|---|---|---|
| | TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >MYC_Right<br>_TTCGGTGCT<br>TACCTGGTT_<br>TAL/010/01<br>2/019/024/<br>030/014/01<br>7/025/030/<br>011/017/02<br>2/030/014/<br>019/025/JD<br>S78/<br>('TTCGGTGC<br>TTACCTGGTT'<br>disclosed<br>as SEQ ID<br>NO: 431) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCAAACGGA<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCATCC<br>CACGACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGAATAACAATGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCAAACGAGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGCA<br>TGACGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CTCGAATGGCGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCAAACGGAGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAGCAACATCGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CAAACGGAGGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAATAATAACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGAATAACAATGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCTCGAATGGCGGCGGT<br>AAGCAGGCGCTGGAAACAGTACAGCGCCTGCT<br>GCCTGTACTGTGCCAGGATCATGGACTGACAC | 283. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNGGGKQALETVQRLLPVLCQDHGLTPEQVVAI<br>ASHDGGKQALETVQRLLPVLCQAHGLTPDQVVAIANN<br>NGGKQALETVQRLLPVLCQAHGLTPAQVVAIANNNGG<br>KQALETVQRLLPVLCQDHGLTPDQVVAIASNGGGKQA<br>LETVQRLLPVLCQDHGLTPEQVVAIANNNGGKQALET<br>VQRLLPVLCQAHGLTPDQVVAIASHDGGKQALETVQR<br>LLPVLCQAHGLTPAQVVAIASNGGGKQALETVQRLLP<br>VLCQDHGLTPDQVVAIASNGGGKQALETVQRLLPVLC<br>QDHGLTPEQVVAIASNIGGKQALETVQRLLPVLCQAH<br>GLTPDQVVAIASHDGGKQALETVQRLLPVLCQAHGLT<br>PAQVVAIASHDGGKQALETVQRLLPVLCQDHGLTPDQ<br>VVAIASNGGGKQALETVQRLLPVLCQDHGLTPEQVVA<br>IANNNGGKQALETVQRLLPVLCQAHGLTPDQVVAIAN<br>NNGGKQALETVQRLLPVLCQAHGLTPAQVVAIASNGG<br>GKQALETVQRLLPVLCQDHGLTPEQVVAIASNGGGRP<br>ALESIVAQLSRPDPALAALTNDHLVALACLGGRPALD<br>AVKKGLPHAPALIKRTNRRIPERTSHRVAGS | 284. |

TALE REPEAT SEQUENCES

| Target | SEQEUNCE | SEQ ID NO: | SEQUENCE | SEQ ID NO: |
|---|---|---|---|---|
| | CCGAACAGGTGGTCGCCATTGCTTCTAATGGG GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | | |
| >PTEN_Left _TCCCAGACA TGACAGCC_T AL/007/012 /017/021/0 29/011/017 /021/030/0 14/016/022 /026/014/0 32/JDS71/ ('TCCCAGAC ATGACAGCC' disclosed as SEQ ID NO: 432) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCATCC CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCGCATGACGGAGGGAAACAAGCATTGGA GACTGTCCAACGGCTCCTTCCCGTGTTGTGTC AAGCCCACGGTTTGACGCCTGCACAAGTGGTC GCCATCGCCTCCAATATTGGCGGTAAGCAGGC GCTGGAAACAGTACAGCGCCTGCTGCCTGTAC TGTGCCAGGATCATGGACTGACCCCAGACCAG GTAGTCGCAATCGCGAACAATAATGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCGCA TGACGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGTCAAACGGAGGGGGAAAGCAAGCCC TGGAAACCGTGCAAAGGTTGTTGCCGGTCCTT TGTCAAGACCACGGCCTTACACCGGAGCAAGT CGTGGCCATTGCAAATAATAACGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGAACATTGGAG GGAAACAAGCATTGGAGACTGTCCAACGGCTC CTTCCCGTGTTGTGTCAAGCCCACGGTTTGAC GCCTGCACAAGTGGTCGCCATCGCCAGCCATG ATGGCGGTAAGCAGGCGCTGGAAACAGTACAG CGCCTGCTGCCTGTACTGTGCCAGGATCATGG ACTGACCCCAGACCAGGTAGTCGCAATCGCGT CGAACATTGGGGAAAGCAAGCCCTGGAAACC GTGCAAAGGTTGTTGCCGGTCCTTTGTCAAGA CCACGGCCTTACACCGGAGCAAGTCGTGGCCA TTGCAAATAATAACGGTGGCAAACAGGCTCTT GAGACGGTTCAGAGACTTCTCCCAGTTCTCTG TCAAGCCCACGGGCTGACTCCCGATCAAGTTG TAGCGATTGCGTCGCATGACGGAGGGAAACAA GCATTGGAGACTGTCCAACGGCTCCTTCCCGT | 285. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASHDGGKQALETVQRLLPVLCQDHGLTPEQVVAI ASHDGGKQALETVQRLLPVLCQAHGLTPDQVVAIASH DGGKQALETVQRLLPVLCQAHGLTPAQVVAIASNIGG KQALETVQRLLPVLCQDHGLTPDQVVAIANNNGGKQA LETVQRLLPVLCQDHGLTPEQVVAIASNIGGKQALET VQRLLPVLCQDHGLTPDQVVAIASHDGGKQALETVQR LLPVLCQAHGLTPAQVVAIASNIGGKQALETVQRLLP VLCQDHGLTPDQVVAIASNGGGKQALETVQRLLPVLC QDHGLTPEQVVAIANNNGGKQALETVQRLLPVLCQAH GLTPDQVVAIASNIGGKQALETVQRLLPVLCQAHGLT PAQVVAIASHDGGKQALETVQRLLPVLCQDHGLTPDQ VVAIASNIGGKQALETVQRLLPVLCQDHGLTPEQVVA IANNNGGKQALETVQRLLPVLCQAHGLTPDQVVAIAS HDGGKQALETVQRLLPVLCQAHGLTPEQVVAISHDG GRPALESIVAQLSRPDPALAALTNDHLVALACLGGRP ALDAVKKGLPHAPALIKRTNRRIPERTSHRVAGS | 286. |

TALE REPEAT SEQUENCES

| Target | SEQEUNCE | SEQ ID NO: | SEQUENCE | SEQ ID NO: |
|---|---|---|---|---|
| | GTTGTGTCAAGCCCACGGTCTGACACCCGAAC AGGTGGTCGCCATTGCTTCCCACGACGGAGGA CGGCCAGCCTTGGAGTCCATCGTAGCCCAATT GTCCAGGCCCGATCCCGCGTTGGCTGCGTTAA CGAATGACCATCTGGTGGCGTTGGCATGTCTT GGTGGACGACCCGCGCTCGATGCAGTCAAAAA GGGTCTGCCTCATGCTCCCGCATTGATCAAAA GAACCAACCGGCGGATTCCCGAGAGAACTTCC CATCGAGTCGCGGGATCC | | | |
| >PTEN_Right_TCCTTTTG TTTCTGCTAA _TAL/007/0 12/020/025 /030/015/0 19/025/030 /015/017/0 25/029/012 /020/021/J DS70/ ('TCCTTTTG TTTCTGCTAA' disclosed as SEQ ID NO: 433) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG GTGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGTCACATGAC GGGGGAAAGCAAGCCCTGGAAACCGTGCAAAG GTTGTTGCCGGTCCTTTGTCAAGACCACGGCC TTACACCGGAGCAAGTCGTGGCCATTGCATCC CACGACGGTGGCAAACAGGCTCTTGAGACGGT TCAGAGACTTCTCCCAGTTCTCTGTCAAGCCC ACGGGCTGACTCCCGATCAAGTTGTAGCGATT GCGTCCAACGGTGGAGGGAAACAAGCATTGGA GACTGTCCAACGGCTCCTTCCCGTGTTGTGTC AAGCCCACGGTTTGACGCCTGCACAAGTGGTC GCCATCGCCTCGAATGGCGGCGGTAAGCAGGC GCTGGAAACAGTACAGCGCCTGCTGCCTGTAC TGTGCCAGGATCATGGACTGACCCCAGACCAG GTAGTCGCAATCGCGTCAAACGGAGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAATGGGGG TGGCAAACAGGCTCTTGAGACGGTTCAGAGAC TTCTCCCAGTTCTCTGTCAAGCCCACGGGCTG ACTCCCGATCAAGTTGTAGCGATTGCGAATAA CAATGGAGGGAAACAAGCATTGGAGACTGTCC AACGGCTCCTTCCCGTGTTGTGTCAAGCCCAC GGTTTGACGCCTGCACAAGTGGTCGCCATCGC CTCGAATGGCGGCGGTAAGCAGGCGCTGGAAA CAGTACAGCGCCTGCTGCCTGTACTGTGCCAG GATCATGGACTGACCCCAGACCAGGTAGTCGC AATCGCGTCAAACGGAGGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAATGGGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCGCATGACGGAG GGAAACAAGCATTGGAGACTGTCCAACGGCTC CTTCCCGTGTTGTGTCAAGCCCACGGTTTGAC GCCTGCACAAGTGGTCGCCATCGCCTCGAATG GCGGCGGTAAGCAGGCGCTGGAAACAGTACAG CGCCTGCTGCCTGTACTGTGCCAGGATCATGG ACTGACCCCAGACCAGGTAGTCGCAATCGCGA ACAATAATGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACTCCCGATCAAGTTG TAGCGATTGCGTCCAACGGTGGAGGGAAACAA | 287. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIASHDGGKQALETVQRLLPVLCQDHGLTPEQVVAI ASHDGGKQALETVQRLLPVLCQAHGLTPDQVVAIASN GGGKQALETVQRLLPVLCQAHGLTPAQVVAIASNGGG KQALETVQRLLPVLCQDHGLTPDQVVAIASNGGGKQA LETVQRLLPVLCQDHGLTPEQVVAIASNGGGKQALET VQRLLPVLCQAHGLTPDQVVAIANNNGGKQALETVQR LLPVLCQAHGLTPAQVVAIASNGGGKQALETVQRLLP VLCQDHGLTPDQVVAIASNGGGKQALETVQRLLPVLC QDHGLTPEQVVAIASNGGGKQALETVQRLLPVLCQAH GLTPDQVVAIASHDGGKQALETVQRLLPVLCQAHGLT PAQVVAIASNGGGKQALETVQRLLPVLCQDHGLTPDQ VVAIANNNGGKQALETVQRLLPVLCQDHGLTPEQVVA IASHDGGKQALETVQRLLPVLCQAHGLTPDQVVAIAS NGGGKQALETVQRLLPVLCQAHGLTPAQVVAIASNIG GKQALETVQRLLPVLCQDHGLTPEQVVAIASNIGGRP ALESIVAQLSRPDPALAALTNDHLVALACLGGRPALD AVKKGLPHAPALIKRTNRRIPERTSHRVAGS | 288. |

TALE REPEAT SEQUENCES

| Target | SEQEUNCE | SEQ ID NO: | SEQUENCE | SEQ ID NO: |
|---|---|---|---|---|
| | GCATTGGAGACTGTCCAACGGCTCCTTCCCGT<br>GTTGTGTCAAGCCCACGGTTTGACGCCTGCAC<br>AAGTGGTCGCCATCGCCTCCAATATTGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCTAACATC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >TP53_Left_TTGCCGTCC CAAGCAATG_ TAL/010/01 4/017/022/ 029/015/01 7/022/027/ 011/016/02 4/027/011/ 016/025/JD S74/ ('TTGCCGTC CCAAGCAATG' disclosed as SEQ ID NO: 434) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGA<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCAAACGGA<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCAAAT<br>AATAACGGTGGCAAACAGGCTCTCTTGAGACGGT<br>TCAGAGACTTCTCCCAGTTCTCTGTCAAGCCC<br>ACGGGCTGACTCCCGATCAAGTTGTAGCGATT<br>GCGTCGCATGACGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAGCCATGATGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGAACAATAATGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCAAGCAATGGGGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGCA<br>TGACGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCACATGACGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAGCAACATCGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGTCGAACATTGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAACAACA<br>ACGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CACATGACGGGGAAAGCAAGCCCTGGAAACC<br>GTGCAAAGGTTGTTGCCGGTCCTTTGTCAAGA<br>CCACGGCCTTACACCGGAGCAAGTCGTGGCCA | 289. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNGGGKQALETVQRLLPVLCQDHGLTPEQVVAI<br>ANNNGGKQALETVQRLLPVLCQAHGLTPDQVVAIASH<br>DGGKQALETVQRLLPVLCQDHGLTPDQVVAIASHDGG<br>KQALETVQRLLPVLCQDHGLTPDQVVAIANNNGGKQA<br>LETVQRLLPVLCQDHGLTPEQVVAIASNGGGKQALET<br>VQRLLPVLCQAHGLTPDQVVAIASHDGGKQALETVQR<br>LLPVLCQAHGLTPAQVVAIASHDGGKQALETVQRLLP<br>VLCQDHGLTPDQVVAIASHDGGKQALETVQRLLPVLC<br>QDHGLTPEQVVAIASNIGGKQALETVQRLLPVLCQAH<br>GLTPDQVVAIASNIGGKQALETVQRLLPVLCQAHGLT<br>PAQVVAIANNNGGKQALETVQRLLPVLCQDHGLTPDQ<br>VVAIASHDGGKQALETVQRLLPVLCQDHGLTPEQVVA<br>IASNIGGKQALETVQRLLPVLCQAHGLTPDQVVAIAS<br>NIGGKQALETVQRLLPVLCQAHGLTPAQVVAIASNGG<br>GKQALETVQRLLPVLCQDHGLTPEQVVAIANNNGGRP<br>ALESIVAQLSRPDPALAALTNDHLVALACLGGRPALD<br>AVKKGLPHAPALIKRTNRRIPERTSHRVAGS | 290. |

TALE REPEAT SEQUENCES

| Target | SEQEUNCE | SEQ ID NO: | SEQUENCE | SEQ ID NO: |
|---|---|---|---|---|
| | TTGCAAGCAACATCGGTGGCAAACAGGCTCTT GAGACGGTTCAGAGACTTCTCCCAGTTCTCTG TCAAGCCCACGGGCTGACTCCCGATCAAGTTG TAGCGATTGCGTCGAACATTGGAGGGAAACAA GCATTGGAGACTGTCCAACGGCTCCTTCCCGT GTTGTGTCAAGCCCACGGTTTGACGCCTGCAC AAGTGGTCGCCATCGCCTCGAATGGCGGCGGT AAGCAGGCGCTGGAAACAGTACAGCGCCTGCT GCCTGTACTGTGCCAGGATCATGGACTGACAC CCGAACAGGTGGTCGCCATTGCTAATAATAAC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | | |
| >TP53_Right_TGTTCAAT ATCGTCCGGG_TAL/009/0 15/020/022 /026/011/0 20/021/030 /012/019/0 25/027/012 /019/024/J DS74/ ('TGTTCAAT ATCGTCCGGG' disclosed as SEQ ID NO: 435) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCTGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGAACAATAAT GGGGGAAAGCAAGCCCTGGAAACCGTGCAAAG GTTGTTGCCGGTCCTTTGTCAAGACCACGGCC TTACACCGGAGCAAGTCGTGGCCATTGCAAGC AATGGGGGTGGCAAACAGGCTCTTGAGACGGT TCAGAGACTTCTCCCAGTTCTCTGTCAAGCCC ACGGGCTGACTCCCGATCAAGTTGTAGCGATT GCGTCCAACGGTGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC GCTGGAAACAGTACAGCGCCTGCTGCCTGTAC TGTGCCAGGATCATGGACTGACCCCAGACCAG GTAGTCGCAATCGCGTCGAACATTGGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGTCCAA CGGTGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGTCAAACGGAGGGGGAAAGCAAGCCC TGGAAACCGTGCAAAGGTTGTTGCCGGTCCTT TGTCAAGACCACGGCCTTACACCGGAGCAAGT CGTGGCCATTGCATCCCACGACGGTGGCAAAC AGGCTCTTGAGACGGTTCAGAGACTTCTCCCA GTTCTCTGTCAAGCCCACGGGCTGACTCCCGA TCAAGTTGTAGCGATTGCGAATAACAATGGAG GGAAACAAGCATTGGAGACTGTCCAACGGCTC CTTCCCGTGTTGTGTCAAGCCCACGGTTTGAC GCCTGCACAAGTGGTCGCCATCGCCTCGAATG GCGGCGGTAAGCAGGCGCTGGAAACAGTACAG CGCCTGCTGCCTGTACTGTGCCAGGATCATGG | 291. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIANNNGGKQALETVQRLLPVLCQDHGLTPEQVVAI ASNGGGKQALETVQRLLPVLCQAHGLTPDQVVAIASN GGGKQALETVQRLLPVLCQDHGLTPAQVVAIASHDGG KQALETVQRLLPVLCQDHGLTPDQVVAIASNIGGKQA LETVQRLLPVLCQDHGLTPEQVVAIASNIGGKQALET VQRLLPVLCQAHGLTPDQVVAIASNGGGKQALETVQR LLPVLCQAHGLTPAQVVAIASNIGGKQALETVQRLLP VLCQDHGLTPDQVVAIASNGGGKQALETVQRLLPVLC QDHGLTPEQVVAIASHDGGKQALETVQRLLPVLCQAH GLTPDQVVAIANNNGGKQALETVQRLLPVLCQAHGLT PAQVVAIASNGGGKQALETVQRLLPVLCQDHGLTPDQ VVAIASHDGGKQALETVQRLLPVLCQDHGLTPEQVVA IASHDGGKQALETVQRLLPVLCQAHGLTPDQVVAIAN NGGKQALETVQRLLPVLCQAHGLTPAQVVAIANNNG GKQALETVQRLLPVLCQDHGLTPEQVVAIANNNGGRP ALESIVAQLSRPDPALAALTNDHLVALACLGGRPALD AVKKGLPHAPALIKRTNRRIPERTSHRVAGS | 292. |

TALE REPEAT SEQUENCES

| Target | SEQEUNCE | SEQ ID NO: | SEQUENCE | SEQ ID NO: |
|---|---|---|---|---|
| | ACTGACCCCAGACCAGGTAGTCGCAATCGCGT CACATGACGGGGAAAGCAAGCCCTGGAAACC GTGCAAAGGTTGTTGCCGGTCCTTTGTCAAGA CCACGGCCTTACACCGGAGCAAGTCGTGGCCA TTGCATCCCACGACGGTGGCAAACAGGCTCTT GAGACGGTTCAGAGACTTCTCCCAGTTCTCTG TCAAGCCCACGGGCTGACTCCCGATCAAGTTG TAGCGATTGCGAATAACAATGGAGGGAAACAA GCATTGGAGACTGTCCAACGGCTCCTTCCCGT GTTGTGTCAAGCCCACGGTTTGACGCCTGCAC AAGTGGTCGCCATCGCCAACAACAACGGCGGT AAGCAGGCGCTGGAAACAGTACAGCGCCTGCT GCCTGTACTGTGCCAGGATCATGGACTGACAC CCGAACAGGTGGTCGCCATTGCTAATAATAAC GGAGGACGGCCAGCCTTGGAGTCCATCGTAGC CCAATTGTCCAGGCCCGATCCCGCGTTGGCTG CGTTAACGAATGACCATCTGGTGGCGTTGGCA TGTCTTGGTGGACGACCCGCGCTCGATGCAGT CAAAAAGGGTCTGCCTCATGCTCCCGCATTGA TCAAAAGAACCAACCGGCGGATTCCCGAGAGA ACTTCCCATCGAGTCGCGGGATCC | | | |
| >XPA_Left_ TGGGCCAGAG ATGGCGGC_T AL/009/014 /019/022/0 27/011/019 /021/029/0 11/020/024 /029/012/0 19/024/JDS 71/ ('TGGGCCAG AGATGGCGGC' disclosed as SEQ ID NO: 436) | GCTAGCaccATGGACTACAAAGACCATGACGG TGATTATAAAGATCATGACATCGATTACAAGG ATGACGATGACAAGATGGCCCCCAAGAAGAAG AGGAAGGTGGGCATTCACCGCGGGGTACCTAT GGTGGACTTGAGGACACTCGGTTATTCGCAAC AGCAACAGGAGAAAATCAAGCCTAAGGTCAGG AGCACCGTCGCGCAACACCACGAGGCGCTTGT GGGGCATGGCTTCACTCATGCGCATATTGTCG CGCTTTCACAGCACCCTGCGGCGCTTGGGACG GTGGCTGTCAAATACCAAGATATGATTGCGGC CCTGCCCGAAGCCACGCACGAGGCAATTGTAG GGGTCGGTAAACAGTGGTCGGGAGCGCGAGCA CTTGAGGCGCTGCTGACTGTGGCGGGTGAGCT TAGGGGGCCTCCGCTCCAGCTCGACACCGGGC AGCTGCTGAAGATCGCGAAGAGAGGGGGAGTA ACAGCGGTAGAGGCAGTGCACGCCTGGCGCAA TGCGCTCACCGGGGCCCCCTTGAACCTGACCC CAGACCAGGTAGTCGCAATCGCGAACAATAAT GGGGGAAAGCAAGCCCTGGAAACCGTGCAAAG GTTGTTGCCGGTCCTTTGTCAAGACCACGGCC TTACACCGGAGCAAGTCGTGGCCATTGCAAAT AATAACGGTGGCAAACAGGCTCTTGAGACGGT TCAGAGACTTCTCCCAGTTCTCTGTCAAGCCC ACGGGCTGACTCCCGATCAAGTTGTAGCGATT GCGAATAACAATGGAGGGAAACAAGCATTGGA GACTGTCCAACGGCTCCTTCCCGTGTTGTGTC AAGCCCACGGTTTGACGCCTGCACAAGTGGTC GCCATCGCCAGCCATGATGGCGGTAAGCAGGC GCTGGAAACAGTACAGCGCCTGCTGCCTGTAC TGTGCCAGGATCATGGACTGACCCCAGACCAG GTAGTCGCAATCGCGTCACATGACGGGGAAA GCAAGCCCTGGAAACCGTGCAAAGGTTGTTGC CGGTCCTTTGTCAAGACCACGGCCTTACACCG GAGCAAGTCGTGGCCATTGCAAGCAACATCGG TGGCAAACAGGCTCTTGAGACGGTTCAGAGAC TTCTCCCAGTTCTCTGTCAAGCCCACGGGCTG ACTCCCGATCAAGTTGTAGCGATTGCGAATAA CAATGGAGGGAAACAAGCATTGGAGACTGTCC AACGGCTCCTTCCCGTGTTGTGTCAAGCCCAC GGTTTGACGCCTGCACAAGTGGTCGCCATCGC CTCCAATATTGGCGGTAAGCAGGCGCTGGAAA CAGTACAGCGCCTGCTGCCTGTACTGTGCCAG GATCATGGACTGACCCCAGACCAGGTAGTCGC AATCGCGAACAATAATGGGGAAAGCAAGCCC TGGAAACCGTGCAAAGGTTGTTGCCGGTCCTT TGTCAAGACCACGGCCTTACACCGGAGCAAGT CGTGGCCATTGCAAGCAACATCGGTGGCAAAC AGGCTCTTGAGACGGTTCAGAGACTTCTCCCA GTTCTCTGTCAAGCCCACGGGCTGACTCCCGA TCAAGTTGTAGCGATTGCGTCCAACGGTGGAG GGAAACAAGCATTGGAGACTGTCCAACGGCTC | 293. | ASTMDYKDHDGDYKDHDIDYKDDDDKMAPKKKRKVGI HRGVPMVDLRTLGYSQQQQEKIKPKVRSTVAQHHEAL VGHGFTHAHIVALSQHPAALGTVAVKYQDMIAALPEA THEAIVGVGKQWSGARALEALLTVAGELRGPPLQLDT GQLLKIAKRGGVTAVEAVHAWRNALTGAPLNLTPDQV VAIANNNGGKQALETVQRLLPVLCQDHGLTPEQVVAI ANNNGGKQALETVQRLLPVLCQAHGLTPDQVVAIANN NGGKQALETVQRLLPVLCQDHGLTPDQVVAIASHDGG KQALETVQRLLPVLCQDHGLTPDQVVAIASHDGGKQA LETVQRLLPVLCQDHGLTPEQVVAIASNIGGKQALET VQRLLPVLCQDHGLTPDQVVAIANNNGGKQALETVQR LLPVLCQAHGLTPAQVVAIASNIGGKQALETVQRLLP VLCQDHGLTPDQVVAIANNNGGKQALETVQRLLPVLC QDHGLTPEQVVAIASNIGGKQALETVQRLLPVLCQAH GLTPDQVVAIASNGGGKQALETVQRLLPVLCQAHGLT PAQVVAIANNNGGKQALETVQRLLPVLCQDHGLTPDQ VVAIANNNGGKQALETVQRLLPVLCQDHGLTPEQVVA IASHDGGKQALETVQRLLPVLCQAHGLTPDQVVAIAN NNGGKQALETVQRLLPVLCQAHGLTPAQVVAIANNNG GKQALETVQRLLPVLCQDHGLTPEQVVAIASHDGGRP ALESIVAQLSRPDPALAALTNDHLVALACLGGRPALD AVKKGLPHAPALIKRTNRRIPERTSHRVAGS | 294. |

TALE REPEAT SEQUENCES

| Target | SEQEUNCE | SEQ ID NO: | SEQUENCE | SEQ ID NO: |
|---|---|---|---|---|
| | CTTCCCGTGTTGTGTCAAGCCCACGGTTTGAC<br>GCCTGCACAAGTGGTCGCCATCGCCAACAACA<br>ACGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGA<br>ACAATAATGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCATCCCACGACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGAATAACAATGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCCCACGAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >XPA_Right _TAAAGCCGC CGCCTCCGG_ TAL/006/01 1/016/024/ 027/012/01 9/022/027/ 014/017/02 2/030/012/ 017/024/JD S74/ ('TAAAGCCG CCGCCTCCGG' disclosed as SEQ ID NO: 437) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCGAACATT<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCAAGC<br>AACATCGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGAACATTGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAACAACAACGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCACATGACGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCATCCCACGACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGAATAA<br>CAATGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC<br>AATCGCGTCACATGACGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAATAATAACGGTGGCAAAC | 295. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASNIGGKQALETVQRLLPVLCQDHGLTPEQVVAI<br>ASNIGGKQALETVQRLLPVLCQAHGLTPDQVVAIASN<br>IGGKQALETVQRLLPVLCQAHGLTPAQVVAIANNNGG<br>KQALETVQRLLPVLCQDHGLTPDQVVAIASHDGGKQA<br>LETVQRLLPVLCQDHGLTPEQVVAIASHDGGKQALET<br>VQRLLPVLCQAHGLTPDQVVAIANNNGGKQALETVQR<br>LLPVLCQAHGLTPAQVVAIASHDGGKQALETVQRLLP<br>VLCQDHGLTPDQVVAIASHDGGKQALETVQRLLPVLC<br>QDHGLTPEQVVAIANNNGGKQALETVQRLLPVLCQAH<br>GLTPDQVVAIASHDGGKQALETVQRLLPVLCQAHGLT<br>PAQVVAIASHDGGKQALETVQRLLPVLCQDHGLTPDQ<br>VVAIASNGGGKQALETVQRLLPVLCQDHGLTPEQVVA<br>IASHDGGKQALETVQRLLPVLCQAHGLTPAQVVAIAS<br>HDGGKQALETVQRLLPVLCQDHGLTPEQVVAIANNNG<br>GKQALETVQRLLPVLCQDHGLTPEQVVAIANNNGGRP<br>ALESIVAQLSRPDPALAALTNDHLVALACLGGRPALD<br>AVKKGLPHAPALIKRTNRRIPERTSHRVAGS | 296. |

TALE REPEAT SEQUENCES

| Target | SEQEUNCE | SEQ ID NO: | SEQUENCE | SEQ ID NO: |
|---|---|---|---|---|
| | AGGCTCTTGAGACGGTTCAGAGACTTCTCCCA<br>GTTCTCTGTCAAGCCCACGGGCTGACTCCCGA<br>TCAAGTTGTAGCGATTGCGTCGCATGACGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CAAACGGAGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCATCCCACGACGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCGCATGACGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCAACAACAACGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTAATAATAAC<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >XPC_Left_<br>TGCCCAGACA<br>AGCAACAT_T<br>AL/009/012<br>/017/022/0<br>26/014/016<br>/022/026/0<br>11/019/022<br>/026/011/0<br>17/021/JDS<br>78/<br>('TGCCCAGA<br>CAAGCAACAT'<br>disclosed<br>as SEQ ID<br>NO: 438) | GCTAGCaccATGGACTACAAAGACCATGACGG<br>TGATTATAAAGATCATGACATCGATTACAAGG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGT<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGAACAATAAT<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCATCC<br>CACGACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGCATGACGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAGCCATGATGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGTCGAACATTGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCATTGCAAATAATAACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGTCGAA<br>CATTGGAGGGAAACAAGCATTGGAGACTGTCC<br>AACGGCTCCTTCCCGTGTTGTGTCAAGCCCAC<br>GGTTTGACGCCTGCACAAGTGGTCGCCATCGC<br>CAGCCATGATGGCGGTAAGCAGGCGCTGGAAA<br>CAGTACAGCGCCTGCTGCCTGTACTGTGCCAG<br>GATCATGGACTGACCCCAGACCAGGTAGTCGC | 297. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMTAALPEA<br>THEAIVGVGKQWSGARALEALLTVAGELRGPPLQLDT<br>GQLLKIAKRGGVTAVEAVHAWRNALTGAPLNLTPDQV<br>VAIANNNGGKQALETVQRLLPVLCQDHGLTPEQVVAI<br>ASHDGGKQALETVQRLLPVLCQAHGLTPDQVVAIASH<br>DGGKQALETVQRLLPVLCQAHGLTPAQVVAIASHDGG<br>KQALETVQRLLPVLCQDHGLTPDQVVAIASNIGGKQA<br>LETVQRLLPVLCQDHGLTPEQVVAIANNNGGKQALET<br>VQRLLPVLCQAHGLTPDQVVAIASNIGGKQALETVQR<br>LLPVLCQAHGLTPAQVVAIASHDGGKQALETVQRLLP<br>VLCQDHGLTPDQVVAIASNIGGKQALETVQRLLPVLC<br>QDHGLTPEQVVAIASNIGGKQALETVQRLLPVLCQAH<br>GLTPDQVVAIANNNGGKQALETVQRLLPVLCQAHGLT<br>PAQVVAIASHDGGKQALETVQRLLPVLCQDHGLTPDQ<br>VVAIASNIGGKQALETVQRLLPVLCQDHGLTPEQVVA<br>IASNIGGKQALETVQRLLPVLCQAHGLTPDQVVAIAS<br>HDGGKQALETVQRLLPVLCQAHGLTPAQVVAIASNIG<br>GKQALETVQRLLPVLCQDHGLTPEQVVAIASNGGGRP<br>ALESIVAQLSRPDPALAALTNDHLVALACLGGRPALD<br>AVKKGLPHAPALIKRTNRRIPERTSHRVAGS | 298. |

TALE REPEAT SEQUENCES

| Target | SEQEUNCE | SEQ ID NO: | SEQUENCE | SEQ ID NO: |
|---|---|---|---|---|
| | AATCGCGTCGAACATTGGGGGAAAGCAAGCCC<br>TGGAAACCGTGCAAAGGTTGTTGCCGGTCCTT<br>TGTCAAGACCACGGCCTTACACCGGAGCAAGT<br>CGTGGCCATTGCAAGCAACATCGGTGGCAAAC<br>AGGCTCTTGAGACGGTTCAGAGACTTCTCCCA<br>GTTCTCTGTCAAGCCCACGGGCTGACTCCCGA<br>TCAAGTTGTAGCGATTGCGAATAACAATGGAG<br>GGAAACAAGCATTGGAGACTGTCCAACGGCTC<br>CTTCCCGTGTTGTGTCAAGCCCACGGTTTGAC<br>GCCTGCACAAGTGGTCGCCATCGCCAGCCATG<br>ATGGCGGTAAGCAGGCGCTGGAAACAGTACAG<br>CGCCTGCTGCCTGTACTGTGCCAGGATCATGG<br>ACTGACCCCAGACCAGGTAGTCGCAATCGCGT<br>CGAACATTGGGGAAAGCAAGCCCTGGAAACC<br>GTGCAAAGGTTGTTGCCGGTCCTTTGTCAAGA<br>CCACGGCCTTACACCGGAGCAAGTCGTGGCCA<br>TTGCAAGCAACATCGGTGGCAAACAGGCTCTT<br>GAGACGGTTCAGAGACTTCTCCCAGTTCTCTG<br>TCAAGCCCACGGGCTGACTCCCGATCAAGTTG<br>TAGCGATTGCGTCGCATGACGGAGGGAAACAA<br>GCATTGGAGACTGTCCAACGGCTCCTTCCCGT<br>GTTGTGTCAAGCCCACGGTTTGACGCCTGCAC<br>AAGTGGTCGCCATCGCCTCCAATATTGGCGGT<br>AAGCAGGCGCTGGAAACAGTACAGCGCCTGCT<br>GCCTGTACTGTGCCAGGATCATGGACTGACAC<br>CCGAACAGGTGGTCGCCATTGCTTCTAATGGG<br>GGAGGACGGCCAGCCTTGGAGTCCATCGTAGC<br>CCAATTGTCCAGGCCCGATCCCGCGTTGGCTG<br>CGTTAACGAATGACCATCTGGTGGCGTTGGCA<br>TGTCTTGGTGGACGACCCGCGCTCGATGCAGT<br>CAAAAAGGGTCTGCCTCATGCTCCCGCATTGA<br>TCAAAAGAACCAACCGGCGGATTCCCGAGAGA<br>ACTTCCCATCGAGTCGCGGGATCC | | | |
| >XPC_Right<br>_TCCCCGCGG<br>CTCCCCGCC_<br>TAL/007/01<br>2/017/022/<br>029/012/01<br>9/024/027/<br>015/017/02<br>2/027/012/<br>019/022/JD<br>S71/<br>('TCCCCGCG<br>GCTCCCCGCC'<br>disclosed<br>as SEQ ID<br>NO: 439) | GCTAGCaccATGGACTACAAAGACCATGACGG<br>TGATTATAAAGATCATGACATCGATTACAAG<br>ATGACGATGACAAGATGGCCCCCAAGAAGAAG<br>AGGAAGGTGGGCATTCACCGCGGGGTACCTAT<br>GGTGGACTTGAGGACACTCGGTTATTCGCAAC<br>AGCAACAGGAGAAAATCAAGCCTAAGGTCAGG<br>AGCACCGTCGCGCAACACCACGAGGCGCTTGA<br>GGGGCATGGCTTCACTCATGCGCATATTGTCG<br>CGCTTTCACAGCACCCTGCGGCGCTTGGGACG<br>GTGGCTGTCAAATACCAAGATATGATTGCGGC<br>CCTGCCCGAAGCCACGCACGCAGGCAATTGTAG<br>GGGTCGGTAAACAGTGGTCGGGAGCGCGAGCA<br>CTTGAGGCGCTGCTGACTGTGGCGGGTGAGCT<br>TAGGGGGCCTCCGCTCCAGCTCGACACCGGGC<br>AGCTGCTGAAGATCGCGAAGAGAGGGGGAGTA<br>ACAGCGGTAGAGGCAGTGCACGCCTGGCGCAA<br>TGCGCTCACCGGGGCCCCCTTGAACCTGACCC<br>CAGACCAGGTAGTCGCAATCGCGTCACATGAC<br>GGGGGAAAGCAAGCCCTGGAAACCGTGCAAAG<br>GTTGTTGCCGGTCCTTTGTCAAGACCACGGCC<br>TTACACCGGAGCAAGTCGTGGCCATTGCATCC<br>CACGACGGTGGCAAACAGGCTCTTGAGACGGT<br>TCAGAGACTTCTCCCAGTTCTCTGTCAAGCCC<br>ACGGGCTGACTCCCGATCAAGTTGTAGCGATT<br>GCGTCGCATGACGGAGGGAAACAAGCATTGGA<br>GACTGTCCAACGGCTCCTTCCCGTGTTGTGTC<br>AAGCCCACGGTTTGACGCCTGCACAAGTGGTC<br>GCCATCGCCAGCCATGATGGCGGTAAGCAGGC<br>GCTGGAAACAGTACAGCGCCTGCTGCCTGTAC<br>TGTGCCAGGATCATGGACTGACCCCAGACCAG<br>GTAGTCGCAATCGCGAACAATAATGGGGGAAA<br>GCAAGCCCTGGAAACCGTGCAAAGGTTGTTGC<br>CGGTCCTTTGTCAAGACCACGGCCTTACACCG<br>GAGCAAGTCGTGGCCATTGCATCCCACGACGG<br>TGGCAAACAGGCTCTTGAGACGGTTCAGAGAC<br>TTCTCCCAGTTCTCTGTCAAGCCCACGGGCTG<br>ACTCCCGATCAAGTTGTAGCGATTGCGAATAA<br>CAATGGAGGGAAACAAGCATTGGAGACTGTCC<br>AACGGCTCCTTCCCGTGTTGTGTCAAGCCCAC | 299. | ASTMDYKDHDGDYKDHDIDYKDDDDKMAPKKKRKVGI<br>HRGVPMVDLRTLGYSQQQQEKIKPKVRSTVAQHHEAL<br>VGHGFTHAHIVALSQHPAALGTVAVKYQDMIAALPEA<br>THEAIVGVGKQWSGARALEALLTVAGELRGPPLQLDT<br>GQLLKIAKRGGVTAVEAVHAWRNALTGAPLNLTPDQV<br>VAIASHDGGKQALETVQRLLPVLCQDHGLTPEQVVAI<br>ASHDGGKQALETVQRLLPVLCQAHGLTPDQVVAIASH<br>DGGKQALETVQRLLPVLCQDHGLTPDQVVAIANNGGKQA<br>LETVQRLLPVLCQDHGLTPEQVVAIASHDGGKQALET<br>VQRLLPVLCQAHGLTPDQVVAIANNNGGKQALETVQR<br>LLPVLCQAHGLTPAQVVAIANNNGGKQALETVQRLLP<br>VLCQDHGLTPDQVVAIASHDGGKQALETVQRLLPVLC<br>QDHGLTPEQVVAIASNGGGKQALETVQRLLPVLCQAH<br>GLTPDQVVAIASHDGGKQALETVQRLLPVLCQAHGLT<br>PAQVVAIASHDGGKQALETVQRLLPVLCQDHGLTPDQ<br>VVAIASHDGGKQALETVQRLLPVLCQDHGLTPEQVVA<br>IASHDGGKQALETVQRLLPVLCQAHGLTPDQVVAIAN<br>NGGGKQALETVQRLLPVLCQAHGLTPAQVVAIASHDG<br>GKQALETVQRLLPVLCQDHGLTPEQVVAIASHDGGRP<br>ALESIVAQLSRPDPALAALTNDHLVALACLGGRPALD<br>AVKKGLPHAPALIKRTNRRIPERTSHRVAGS | 300. |

TALE REPEAT SEQUENCES

| Target | SEQEUNCE | SEQ ID NO: | SEQUENCE | SEQ ID NO: |
|--------|----------|------------|----------|------------|
| | GGTTTGACGCCTGCACAAGTGGTCGCCATCGC | | | |
| | CAACAACAACGGCGGTAAGCAGGCGCTGGAAA | | | |
| | CAGTACAGCGCCTGCTGCCTGTACTGTGCCAG | | | |
| | GATCATGGACTGACCCCAGACCAGGTAGTCGC | | | |
| | AATCGCGTCACATGACGGGGAAAGCAAGCCC | | | |
| | TGGAAACCGTGCAAAGGTTGTTGCCGGTCCTT | | | |
| | TGTCAAGACCACGGCCTTACACCGGAGCAAGT | | | |
| | CGTGGCCATTGCAAGCAATGGGGGTGGCAAAC | | | |
| | AGGCTCTTGAGACGGTTCAGAGACTTCTCCCA | | | |
| | GTTCTCTGTCAAGCCCACGGGCTGACTCCCGA | | | |
| | TCAAGTTGTAGCGATTGCGTCGCATGACGGAG | | | |
| | GGAAACAAGCATTGGAGACTGTCCAACGGCTC | | | |
| | CTTCCCGTGTTGTGTCAAGCCCACGGTTTGAC | | | |
| | GCCTGCACAAGTGGTCGCCATCGCCAGCCATG | | | |
| | ATGGCGGTAAGCAGGCGCTGGAAACAGTACAG | | | |
| | CGCCTGCTGCCTGTACTGTGCCAGGATCATGG | | | |
| | ACTGACCCCAGACCAGGTAGTCGCAATCGCGT | | | |
| | CACATGACGGGGAAAGCAAGCCCTGGAAACC | | | |
| | GTGCAAAGGTTGTTGCCGGTCCTTTGTCAAGA | | | |
| | CCACGGCCTTACACCGGAGCAAGTCGTGGCCA | | | |
| | TTGCATCCCACGACGGTGGCAAACAGGCTCTT | | | |
| | GAGACGGTTCAGAGACTTCTCCCAGTTCTCTG | | | |
| | TCAAGCCCACGGGCTGACTCCCGATCAAGTTG | | | |
| | TAGCGATTGCGAATAACAATGGAGGGAAACAA | | | |
| | GCATTGGAGACTGTCCAACGGCTCCTTCCCGT | | | |
| | GTTGTGTCAAGCCCACGGTTTGACGCCTGCAC | | | |
| | AAGTGGTCGCCATCGCCAGCCATGATGGCGGT | | | |
| | AAGCAGGCGCTGGAAACAGTACAGCGCCTGCT | | | |
| | GCCTGTACTGTGCCAGGATCATGGACTGACAC | | | |
| | CCGAACAGGTGGTCGCCATTGCTTCCCACGAC | | | |
| | GGAGGACGGCCAGCCTTGGAGTCCATCGTAGC | | | |
| | CCAATTGTCCAGGCCCGATCCCGCGTTGGCTG | | | |
| | CGTTAACGAATGACCATCTGGTGGCGTTGGCA | | | |
| | TGTCTTGGTGGACGACCCGCGCTCGATGCAGT | | | |
| | CAAAAAGGGTCTGCCTCATGCTCCCGCATTGA | | | |
| | TCAAAAGAACCAACCGGCGGATTCCCGAGAGA | | | |
| | ACTTCCCATCGAGTCGCGGGATCC | | | |

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A process comprising:
   (a) providing a first nucleic acid comprising a nucleotide sequence selected from the group consisting of SEQ ID NOs: 58-62;
   (b) contacting the first nucleic acid with BsaI, thereby creating a ligatable end;
   (c) providing a second nucleic acid comprising βγδε, wherein the second nucleic acid is constructed by:
   (i) contacting a β unit comprising a nucleotide sequence selected from the group consisting of SEQ ID NOs: 63-67 with BsaI to create a ligatable end, and contacting a γ unit comprising a nucleotide sequence selected from the group consisting of SEQ ID NOs: 68-72 with BbsI to create a ligatable end
   (ii) ligating the β unit and the γ unit through their ligatable ends to produce βγ;
   (iii) contacting βγ with BsaI to create a ligatable end, and contacting a δ unit comprising a nucleotide sequence selected from the group consisting of SEQ ID NOs: 73-77 with BbsI to create a ligatable end;
   (iv) ligating βγ and the δ unit through their ligatable ends to produce βγδ;
   (v) contacting βγδ with BsaI to create a ligatable end, and contacting a ε unit comprising a nucleotide sequence selected from the group consisting of SEQ ID NOs: 78-82 with BbsI to create a ligatable end;
   (vi) ligating βγδ and the ε unit through their ligatable ends to produce the second nucleic acid comprising βγδε;
   (d) contacting the second nucleic acid with BbsI, thereby creating a ligatable end;
   (e) ligating the first and second nucleic acids through their ligatable ends to produce a first ligated nucleic acid, and (f) linking the first ligated nucleic acid to a solid support to produce a ligated nucleic acid linked to the solid support.

2. The process of claim 1, further comprising:
(g) contacting the ligated nucleic acid linked to the solid support with BsaI, thereby creating a ligatable end;
(h) providing a third nucleic acid comprising βγδε, constructed as set forth in step (c) above;
(i) contacting the third nucleic acid with BbsI to create a ligatable end; and
(j) ligating the ligated nucleic acid linked to the solid support to the third nucleic acid through their ligatable ends to extend the ligated nucleic acid linked to the solid support, and
(k) optionally repeating steps (g)-(j).

3. The process of claim 2, further comprising:
(l) contacting the ligated nucleic acid linked to the solid support with BsaI, thereby creating a ligatable end;
(m) providing a fourth nucleic acid, wherein the fourth nucleic acid is selected from one of the following nucleic acids:
i. a nucleic acid comprising a β unit,
ii. a nucleic acid comprising βγ', wherein the nucleic acid is constructed by:
 (a) contacting a β unit comprising a nucleotide sequence selected from the group consisting of SEQ ID NOs: 63-67 with BsaI to create a ligatable end, and contacting a γ' unit comprising a nucleotide sequence selected from the group consisting of SEQ ID NOs: 83-87 with BbsI to create a ligatable end;
 (b) ligating the β unit and the γ' unit through their ligatable ends to produce βγ'; or
iii. a nucleic acid comprising βγδ, wherein the nucleic acid is constructed by:
 (a) contacting a β unit comprising a nucleotide sequence selected from the group consisting of SEQ ID NOs: 63-67 with BsaI to create a ligatable end, and contacting a γ unit comprising a nucleotide sequence selected from the group consisting of SEQ ID NOs: 68-72 with BbsI to create a ligatable end;
 (b) ligating the β unit and the γ unit through their ligatable ends to produce βγ;
 (c) contacting βγ with BsaI to create a ligatable end, and contacting a δ unit comprising a nucleotide sequence selected from the group consisting of SEQ ID NOs: 73-77 with BbsI to create a ligatable end;
 (d) ligating βγ and the δ unit through their ligatable ends to produce βγδ;
(n) contacting the fourth nucleic acid with BbsI to create a ligatable end; and
(o) ligating the ligated nucleic acid linked to the solid support to the fourth nucleic acid through their ligatable ends to extend the ligated nucleic acid linked to the solid support.

4. The process of claim 2, further comprising:
(l) contacting the ligated nucleic acid linked to the solid support with BsaI, thereby creating a ligatable end;
(m) providing a fourth nucleic acid comprising βγ, wherein the fourth nucleic acid is constructed by:
 (i) contacting a β unit comprising a nucleotide sequence selected from the group consisting of SEQ ID NOs: 63-67 with BsaI to create a ligatable end, and contacting a γ unit comprising a nucleotide sequence selected from the group consisting of SEQ ID NOs: 68-72 with BbsI to create a ligatable end
 (ii) ligating the β unit and the γ unit through their ligatable ends to produce βγ;
(n) contacting the fourth nucleic acid with BbsI, thereby creating a ligatable end; and
(o) ligating the ligated nucleic acid linked to the solid support to the fourth nucleic acid through their ligatable ends to extend the ligated nucleic acid linked to the solid support.

5. The process of claim 4, further comprising:
(p) contacting the ligated nucleic acid linked to the solid support with BsaI, thereby creating a ligatable end;
(q) providing a fifth nucleic acid comprising a 6E', wherein the fifth nucleic acid is constructed by:
 (i) contacting a δ unit comprising a nucleotide sequence selected from the group consisting of SEQ ID NOs: 73-77 with BsaI to create a ligatable end, and contacting an ε' unit comprising a nucleotide sequence selected from the group consisting of SEQ ID NOs: 88-92 with BbsI to create a ligatable end;
 (ii) ligating the δ unit and the ε' unit through their ligatable ends to produce δε';
(r) contacting the fifth nucleic acid with BbsI, thereby creating an eighth ligatable end; and
(s) ligating the ligated nucleic acid linked to the solid support to the fifth nucleic acid through their ligatable ends to extend the ligated nucleic acid linked to the solid support.

6. The process of claim 1, further comprising unlinking the ligated nucleic acid from the solid support and inserting said ligated nucleic acid into a vector.

7. The process of claim 2, further comprising unlinking the ligated nucleic acid from the solid support and inserting said ligated nucleic acid into a vector.

8. The process of claim 3, further comprising unlinking the ligated nucleic acid from the solid support and inserting said ligated nucleic acid into a vector.

9. The process of claim 6, wherein the vector is an expression vector.

10. The process of claim 9, wherein the expression vector includes a sequence encoding an effector domain, and wherein the ligated nucleic acid is inserted into the vector such that the vector comprises a sequence encoding a fusion protein of a TALE repeat domain and the effector domain.

11. The process of claim 10, wherein the effector domain is a nuclease domain.

12. The process of claim 10, further comprising inserting the expression vector into a cell.

13. The process of claim 12, further comprising expressing the fusion protein.

14. The process of claim 13, further comprising purifying the fusion protein.

* * * * *

UNITED STATES PATENT AND TRADEMARK OFFICE
CERTIFICATE OF CORRECTION

PATENT NO. : 10,273,271 B2
APPLICATION NO. : 15/156574
DATED : April 30, 2019
INVENTOR(S) : J. Keith Joung and Jeffry D. Sander Page 1 of 1

It is certified that error appears in the above-identified patent and that said Letters Patent is hereby corrected as shown below:

In the Claims

In Column 496, Line 18 (approx.), in Claim 5, delete "6E'," and insert -- δε', --

Signed and Sealed this
Thirty-first Day of March, 2020

Andrei Iancu
*Director of the United States Patent and Trademark Office*